(12) United States Patent
Cirpus et al.

(10) Patent No.: US 7,842,852 B2
(45) Date of Patent: Nov. 30, 2010

(54) METHOD FOR INCREASING THE CONTENT OF POLYUNSATURATED LONG-CHAINED FATTY ACIDS IN TRANSGENIC ORGANISMS

(75) Inventors: Petra Cirpus, Mannheim (DE); Jörg Bauer, Ludwigshafen (DE); Xiao Qiu, Saskatoon (CA); Patricia Vrinten, Saskatoon (CA)

(73) Assignee: BASF Plant Science GmbH, Ludwigshafen (DE)

( * ) Notice: Subject to any disclaimer, the term of this patent is extended or adjusted under 35 U.S.C. 154(b) by 739 days.

(21) Appl. No.: 11/632,555

(22) PCT Filed: Jul. 15, 2005

(86) PCT No.: PCT/EP2005/007754

§ 371 (c)(1),
(2), (4) Date: Jan. 16, 2007

(87) PCT Pub. No.: WO2006/008099

PCT Pub. Date: Jan. 26, 2006

(65) Prior Publication Data

US 2008/0076164 A1  Mar. 27, 2008

(30) Foreign Application Priority Data

Jul. 16, 2004 (DE) .................. 10 2004 034 442
Dec. 15, 2004 (DE) .................. 10 2004 060 340

(51) Int. Cl.
*C12N 15/82* (2006.01)
*C07H 21/04* (2006.01)

(52) U.S. Cl. ............... 800/278; 800/281; 536/23.7; 530/350

(58) Field of Classification Search .................. None
See application file for complete search history.

(56) References Cited

U.S. PATENT DOCUMENTS 7,053,267 B2 * 5/2006 Knauf et al. ............ 800/281
7,230,160 B2 * 6/2007 Benning et al. ......... 800/281

FOREIGN PATENT DOCUMENTS

WO  WO-97/37006   10/1997
WO  WO-01/83788   11/2001
WO  WO-03/093482  11/2003
WO  WO-2004/057001  7/2004

OTHER PUBLICATIONS

Six and Dennis, Biochimica et Biophysica Acta, 1488, (2000), pp. 1-19 (cited in IDS).*
Derelle et al, Database Uniprot_15.5, included in Office Action.* BLASTresults.*
Beisson, F., et al., "Arabidopsis Genes Involved in Acyl Lipid Metabolism. A 2003 Census of the Candidates, a Study of the Distribution of Expressed Sequence Tags in Organs, and a Web-Based Database", Plant Physiology, 2003, vol. 132, pp. 681-697.
Derelle, E., et al., "DNA Libraries for Sequencing the Genome of *Ostreococcus Tauri* (Chlorophyta, Prasinophyceae): The Smallest Free-Living Eukaryotic Cell", J. Phycol., 2002, vol. 38, pp. 1150-1156.
Drexler, H., et al., "Metabolic Engineering of Fatty Acids for Breeding of New Oilseed Crops: Strategies, Problems and First Results", Journal of Plant Physiology, 2003, vol. 160, pp. 779-802.
May, C., et al., "A Phospholipase $A_2$ is Transiently Synthesized During Seed Germination and Localized to Lipid Bodies", Biochimica et Biophysica Acta, 1998, vol. 1393, pp. 267-276.
Six, D., et al., "The Expanding Superfamily of Phospholipase $A_2$ Enzymes: Classification and Characterization", Biochimica et Biopysica Acta, 2000, vol. 1488, pp. 1-19.
Xu, X., et al., "Sequence Analysis of the Cloned *glossy8* Gene of Maize Suggests That It May Code for a β-Ketoacyl Reductase Required for the Biosynthesis of Cuticular Waxes", Plant Physiol., 1997, vol. 115, pp. 501-510.

* cited by examiner

*Primary Examiner*—Eileen B O Hara
(74) *Attorney, Agent, or Firm*—Connolly Bove Lodge & Hutz LLP

(57) ABSTRACT

The present invention relates to a method for increasing the content of polyunsaturated long-chain fatty acids in an organism by introducing nucleic acids coding for polypeptides or proteins exhibiting a phospholipase, ketoacyl-CoA reductase and/or dehydratase activity. The present invention also provides nucleic acid sequences coding for polypeptides with enzyme activities of a phospholipase, ketoacyl-CoA reductase and/or dehydratase, and nucleic acid constructs, vectors and organisms containing the nucleic acid sequences according to the present invention. A further part of the present invention relates to oils, lipids and/or fatty acids produced according to the method of the present invention and the use thereof. Furthermore, the present invention relates to unsaturated fatty acids and triglycerides having an increased content of unsaturated fatty acids and the use thereof.

23 Claims, 7 Drawing Sheets

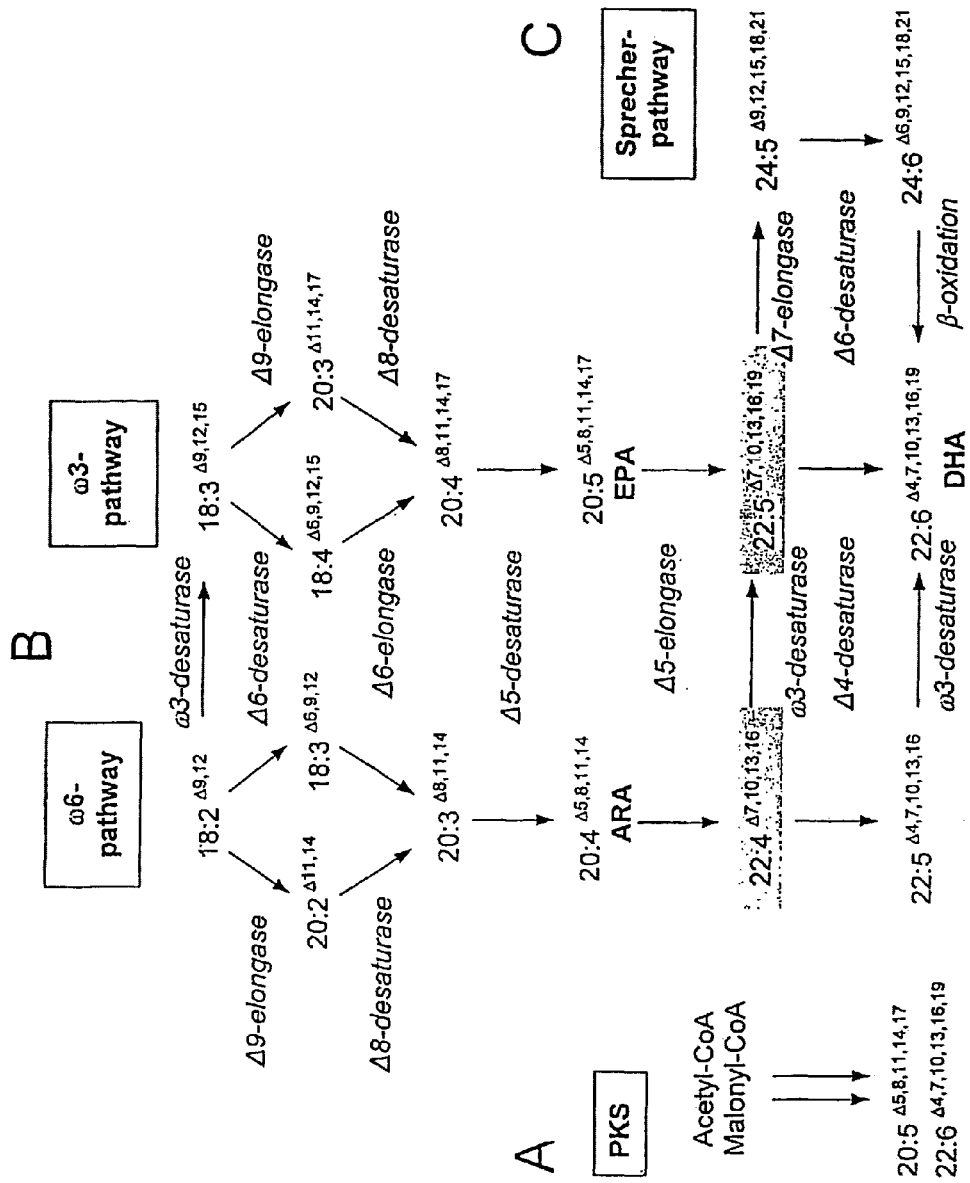
Fig. 1: Different synthesis pathways for the biosynthesis of DHA (docosahexaenoic acid)

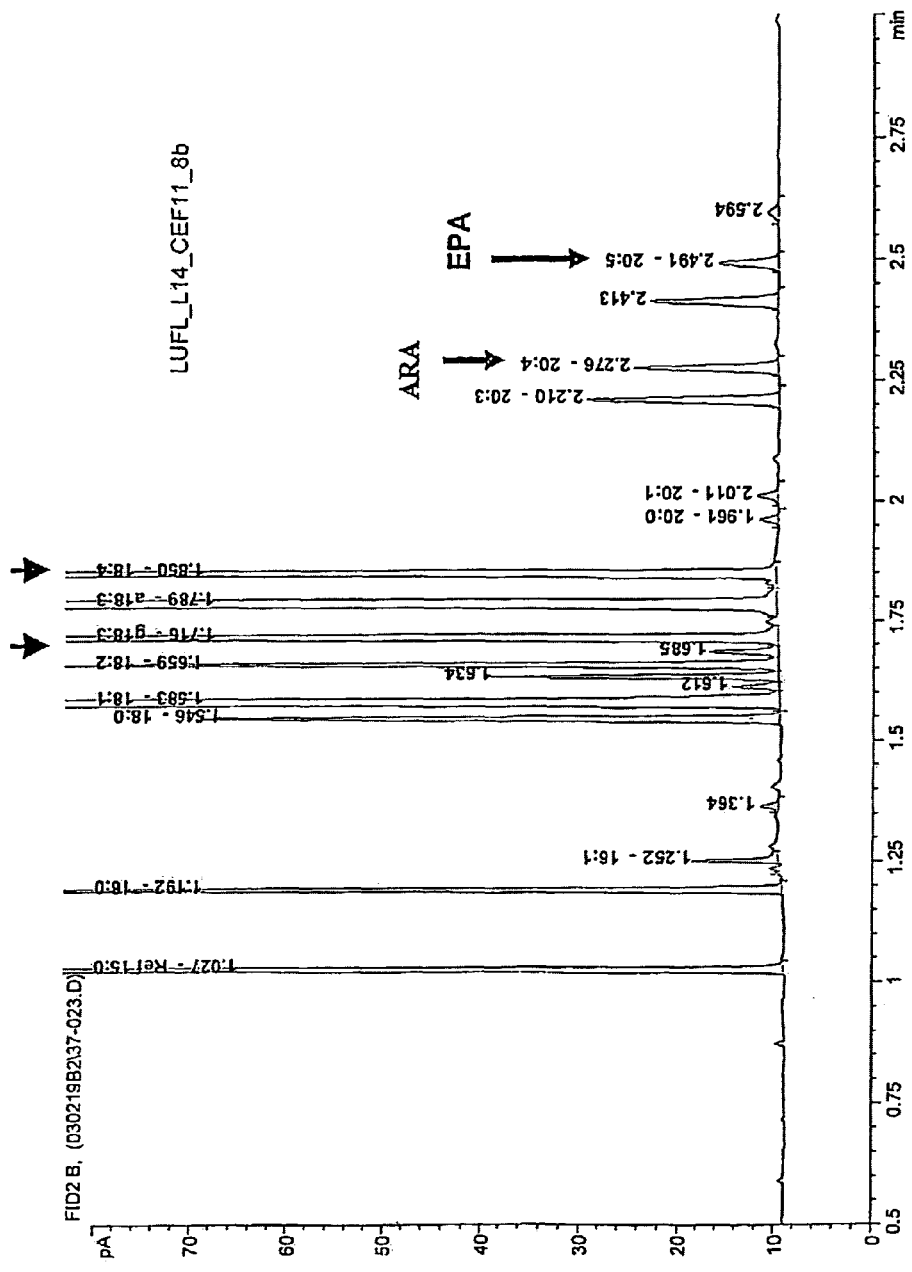
Fig. 2: Gas chromatogram of the fatty acid extract from flax seed transformed with the construct pGPTV-USP_PSE1_d6Des(Pt)_d5Des(Pt).

Fig. 3: Sequence alignment of phospholipase A2 from H. sapiens and the *Ostreococcus* sequence PLA2(Ot).

```
  1 m...gvcssksgaapeaqetefrlrktadgrrlgddstknlsafaedsgm  47
    |   |   .           ||.:. |       |   :        : |
  1 mqffgrlvntfsgvtnlfsnpfrvkevavadytssdrvr.......eegq  43

48 svgserevtrgepiaslrpqtrnqeiskkdfktkkknaiaveddqvlegd  97
    :   :   |    . |  ||  :  :  |.        :  .|  | ..
 44 lilfqntpnrtwdcvlvnp..rnsqsgfrlfq......leleadalv...  82

98 dddvyrfdqsll..nsaraamnededadqnrsllrrqsivkapnqtvakp 145
    . :.:   ||    .    .  |           |:|     |. .||
 83 ..nfhqyssqllpfyesspqvlhtevlqhltdlirnh.....pswsvahl 125

146 pvelserlkryeaepklkanelpvsygpewlappdiqrettvrkpkkysi 195
    ||| |   :.     ||    . |   |         ||         :
126 avelgirecfhhsriiscan...caeneegctplhl....acrkgdgeil 168

196 gnlargdhkleptnltdkdfsdyapgngpwfngpfpsmmassakqmglay 245
    | . |      |    | .||        |   :     |.
169 velvqych.......tqmdvtdy...kg...etvfhyavqgdnsqvlqll 205

246 gkfcvvgvitlfwvpnfllyhrllmngtfqaysrllsailsslfmtrtvl 295
    |:  | |.            ...    |   :  |. |    | | .|
206 grnavagl...........nqvnnqgltplh...lacqlgkqemvrvll 240

296 nmnmelcrmfwrgsivnsqvicsligavgffwqtlviftvgwlsdnrgif 345
    |      |  ) :.) . | |         ::|        |. |
241 lcnarcnimgpngypihsamkfsqkgca.....emii.....smdssqih 280

346 sfliafgvgwfivwrqdqrhekqqrirtv.mgaflalekdakhmaqlmg. 393
    |   :|   : |  ..   :    |  ...    | |.| :
281 skdprygas.plhwaknaemarmllkrgcnvnstssagntalhvavmrnr 329

394 ...spvvrtn....diqymna.apvwaryrpd..elvpwlnnfltqv.wp 432
      .|. |.    |  . |.       | |::  |   |  :| |
330 fdcaivllthganadargehgntplhlamskdnvemikalivfgaevdtp 379

433 .fynkaaselvreiveplmeqsrpsmlkrltfkqldfgenpfmvrsv.sy 480
    : . . | .|  .  .| ..| |  ::   ]   :   | .
380 ndfgetptflaskigrlv...trkailtllrtvgaeycfpp..ihgvpae 424

481 vgkkaedkgmsld.idfawagrsnivlaakthigadiniavkdleiytkl 529
    |  |   ||:       .|:   |     ||     || |    |   :
425 qgsaaphhpfsleraqpppislnnlelqdlmhisr....arkpafilgsm 470

530 rvtlnplvplpsplggvvismterpivefhvelpsgldvlyaaidkwle. 578
    |         ]]| |  :    |::   : :    |    :   |.
```

Fig. 3 (cont.)

```
471 rdekrthdhllcldgggvkgli...iiqlliaiekasgvatkdlfdwvag 517

579 efvagllgdmfiqperlviplsfnfdpivmpdgevkpfkwydhnvlq... 625
    |:|      :    . :       | |   |    :   :  |:    |:
518 tstggilalailhsksmaymrgmyfr...mkdevfrgsrpyesgpleefl 564

626 lrntgv.lkvtvvraenvpsadllsktdpfvkmfvkkhglqvntttimnn 674
    |  |   |.| ||   |       ||        .  |  |     |
565 krefgehtkmtdvrkpkvmltgtlsdrqp.....aelh.lfrnydapetv 608

675 edpvwneifyipvddvdlrvlkvamydhdvdplssddklgatevridtik 724
    :| .|:         .|.||             |    |.|         :
609 reprfnq.......nvnlr...........ppaqpsdql........vwr 632

725 aatadgseqelwldfpeqvkgnvkkppmklllnaqfisfgsd.iaqnmft 773
    ||  . |.    .      .| .       |    :   : | | .
633 aarssgaaptyfrpngrfldggllannptldamteiheynqdlirkgqan 682

774 glgllsvhvi..rgrnlq.pmdsnglsdpyvkvkvpkftldsmdmdkgki 820
    . ||: |    ||. | |.    .  |    .. |   . :: |   :
683 kvkklsivvslgtgrspqvpvtcvdvfrpsnpwelaktvfgakelgk.mv 731

821 lrgkrgkkgkknaeahdytvysskihyknlnpefnamfefspasedtkvs 870
    .       |:    | :       | |  |||:          | || .
732 vdcctdpdgravdrarawcemvg.iqyfrlnpqlgtdimldevs.dtvlv 779

871 ielfdvdstfpmgtkskfmgnlevpistiihhggsmearfkvgnaksgel 920
    |.:  :    :    :  :.|   :  . :|
780 nalwete.vyiyehreefqklihllls...................... 805

921 diafnwqpyt 931
          |
806 .......p... 806
```

Fig. 4: Sequence alignment between KR(Ot) and Ybr159w.

```
  1 mgalsylpipyvralvrdtvvdacvshvlalyglvalltywvpkva....  46
    | : |      | |  :.  . | | |..   |  . .|
  1 mtfmqqlq....eagerfrcingllwvvfgl.gvlkcttlslrflalifd  45

47 vqmmpsqdlkkkyda...qwalvtggstgigrslafalaeqglnvavcal  93
    . ::|. .    ||. |   .:  :|| | |||:  |  :|..| |. . .
 46 lfllpavnf.dkygaktgkycaitgasdgigkefarqmakrgfnlvlisr  94

94 ddehlettcralrekfgatseirkigcnlgdqsgayvetiskaledvdvq 143
    || : |  :.    .|  :  .: :   . |.| .    . :
 95 tqsklealqkeledqhhvvvki..laidiaedkesnyesikelcaqlpit 142

144 vvfnnag...fmltgffdkqpleklnannecnatsamrithvfvrrmla. 189
    |. || |    . | : |  |   | |.: || :  :..
143 vlvnnvgqshsipvpfleteekelrniit.inntatllitqiiapkivet 191

190 .....kk..lrgcvvftssaaacqptpfsamygatkayissfaanigvel 232
         ||   || :.   |      ||| | |  .|.::   .. .:  ||
192 vkaenkksgtrgliltmgsfggliptpllatysgsksflqgwsnslagel 241

233 ksrgidvcavhpspvasnfydkahkldslnffmnfavkpeelptemfrpi 282
    |||  :    | |.  | :  ||         |::       | :
242 skdaidveliisylvtssm.skirr.ssl.....mipnpqqfvkstlrsv 284

283 gr...........vlw.hdvggvai....g.frmllklfdygffatl.i 313
    ||              | | |    |   | : :.    .| |  .: |
285 grrcgsqeryatmtpywahavyqfvitetfgvyskivnsinysfhksiri 334

314 srfahlmgdykknv* 328
                || 
335 ralkkaarqvkke.. 347
```

Fig. 5: Sequence alignment between DH(Ot) and Ydr036c.

```
  1 ......................mstpph......pplrverrgnaqfi  20
                         |.| |       ||.   .|.|
  1 MLRNTLKCAQLSSKYGFKTTTRTFMTTQPQLNVTDAPPVLFTVQDTARVI  50

21 vldrprarnaltsdvierlhrayaagednatlcahvilgan.sgtfcagg  69
    |.||: ||| .:. | :  :  .|   :: .|  .|||||
 51 TLNRPKKLNALNAEMSESMFKTLNEYAKSDTTNLVILKSSNRPRSFCAGG 100

70 dvravremvlknerdaavgffsrefalnarlatltkpsacvwngsvmggg 119
    || |       |   .: ||. |:.|| .:|| ||     .|  ||||
101 DVATVAIFNFNKEFAKSIKFFTDEYSLNFQIATYLKPIVTFMDGITMGGG 150

120 aglscyapvrvstektvfampecaiglwpdvgaswflrrlcggatgt... 166
    ||| : | |:.|| | .||||  || .||||... | |:    |
151 VGLSIHTPFRIATENTKWAMPEMDIGFFPDVGSTFALPRIVTLANSNSQM 200

167 ..wlaltgarvrgkackalglsthhvtceswdav................ 198
     :| ||| | |    |||..|:|. |. ||.
201 ALYLCLTGEVVTGADAYMLGLASHYVSSENLDALQKRLGEISPPFNNDPQ 250

199 ..............cepmvraltvgasaedlaacaaagetsadaa.ed. 231
                  |: :      ||| |   |    | .    ||
251 SAYFFGMVNESIDEFVSPLPKDYVFKYSNEKLNVIEACFNLSKNGTIEDI 300

232 ..gcdeyattargkraieevfgdeslslsgitseiarr......rdaatd 273
     :|  .| ||   :|:   . |. |  . :|| |       ||
301 MNNLRQYEGSAEGKAFAQEI.KTKLLTKSPSSLQIALRLVQENSRDHIES 349

274 dverrffae.....saeslakacptslevtlelmr............... 303
    :.| :        . :|| .     ::  |
350 AIKRDLYTAANMCMNQDSLVEFSEATKHKLIDKQRVPYPWTKKEQLFVSQ 399

304 ....rargkslewsla..tdnalisqfifaddfkrgvd...avlitk... 341
    .   || ||  || .|: :    :.  :   | | |
400 LTSITSPKPSLPMSLLRNTSNVTWTQYPYHSKYQLPTEQEIAAYIEKRTN 449

342 ..vg...............vpppegwaptrspasffs..........rl 363
      |                :|   | .|                   |
450 DDTGAKVTEREVLNHFANVIPSRRGKLGIQSLCKIVCERKCEEVNDGLRW 499

364 * 364

500 K 500
```

Fig. 6: Sequence alignment of the dehydratases from *Ostreococcus tauri*, *Thraustochytrium ssp.* and *Saccharomyces cerevisiae* by ClustalW analysis. Conserved regions are dark.

```
                      *        20         *        40         *
DH(Ot)   : ------------------------------MSTPPHPPLRVERRGNAQFI :  20
DH(Tc)   : -------------------------------------------------- :   -
YDR036C  : MLRNTLKCAQLSSKYGFKTTTRTFMTTQPQLNVTDAPPVLFTVQDTLRVI   :  50

*        60         *        80         *       100
DH(Ot)   : VLDRPRARNALTSDVLERLHRAYAAGEDNALLCAHVILCAN-SGLFCAGG   :  69
DH(Tc)   : --------------MRIIKPKYDEVGSGKAQCVLMHGAG-ERAFCAGG     :  35
YDR036C  : TLNRESKLNAINAEMSESNFRTLNEYAKSDTNLVILKSSNRPRSFCAGG    : 100

*       120         *       140         *
DH(Ot)   : DVRAVREMVLKNERDALVGPFSREFALNARLATLTKES----ACVTHGSV   : 115
DH(Tc)   : DIASVRSSALEGG-SLAEDPFYEEYQLNYRIATAFDRCGIVQVSFIDGII   :  84
YDR036C  : DVATWAIFNENKEFAKSIKEEIDENSLNEQIATYLKEI----VTEMDGII   : 146

160         *       180         *       200
DH(Ot)   : HGGCAGLSCYAPVRVSTEKTVFAMPECAIGIWPDVGASHFLRRICGG---  : 162
DH(Tc)   : HGGCVGLSLHGKIRVATEKTLFAMPETGICLFPDVGGTFALSRISGGP-- : 132
YDR036C  : HGGCAGLSIHTEFRLFTENTKFAHPEMDIGFFPDVGSTEALPRIVTLANS : 196

*       220         *       240         *
DH(Ot)   : --ATGTNLALTGAEVRGKACKALGLETHHVECSWDAVCEPVVRALTVGA  : 210
DH(Tc)   : --SIGVYLALTGTRLGAADCLYAGLITHKVAEENVDKVCEKLA-----AS : 175
YDR036C  : NSQMALYLCLTGEVVTGADAYMLGLASHLVSSENLDALQKRLGEISPPFN : 246

260         *       280         *       300
DH(Ot)   : SAEDLAACAAAGETSADAAEDGCDEYATTARG---KRAIEEVFGDESLSL : 257
DH(Tc)   : KSDPSAIEAVLRBFAADAPPPKNPAMGLEAR----HEAIKKCPSISESVE : 221
YDR036C  : NDPQSAYFFGAVNESIDEFVSPLEKDYVFKYSNEKLNVIEACFNLSKN-- : 294

*       320         *       340         *
DH(Ot)   : SGITSEIARRRDAATPDVERRBFADSAESLARACPTSLEVTLEIRRBARC : 307
DH(Tc)   : VILDRLERMAADELADKDDRAWABASRDAIRKASPTSVCLSFEAVRRHAG : 271
YDR036C  : GTIEDIYNNLRQYEGSAEGKAEKQEIKTKLLTKSPSSLCIALRIVQENSR : 344

360         *       380         *       400
DH(Ot)   : K--SLEWSLATDNALISQFIFAD----IFKRGVDAVLITRVGVPPEG--  : 349
DH(Tc)   : ADVDLAKFLTNEYRLTQRLCVPDG---IFFEGVRAVLVDRDQSEKWKF-- : 316
YDR036C  : D--HIESAIKRDLYTAANMCHNQDSLVEFSFATRHKLIDKQRVFYPWTKK : 392

*       420         *       440         *
DH(Ot)   : WAPTRSPASBESRL----------------------------------  : 363
DH(Tc)   : ASVEDVPADEIESHFQPLPDSHPPGDLSHS------------------  : 346
YDR036C  : EQLFVSQLTSITSPKPSLFMSLLRNTSNVTWTQYPYHSKYQLPTEQEIAA : 442

460         *       480         *       500
DH(Ot)   : ----------------------------------------------  :   -
DH(Tc)   : ----------------------------------------------  :   -
YDR036C  : YIEKRTNDDTGAKVTEREVLNHFANVIPSRRGKLGIQSLCKIVCERKCEE : 492

DH(Ot)   : --------  :   -
DH(Tc)   : --------  :   -
YDR036C  : VNDGLRWK  : 500
```

METHOD FOR INCREASING THE CONTENT OF POLYUNSATURATED LONG-CHAINED FATTY ACIDS IN TRANSGENIC ORGANISMS

RELATED APPLICATIONS

This application is a national stage application (under 35 U.S.C. 371) of PCT/EP2005/007754 filed Jul. 15, 2005, which claims benefit of German application 10 2004 034 442.6 filed Jul. 16, 2004 and German application 10 2004 060 340.5 filed Dec. 15, 2004.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence_Listing_13477_00006. The size of the text file is 603 KB, and the text file was created on Mar. 29, 2010.

The present invention relates to a method for increasing the content of polyunsaturated long-chain fatty acids in an organism by introducing into said organism nucleic acids coding for polypeptides or proteins having a phospholipase, ketoacyl-CoA reductase and/or dehydratase activity. Advantageously, said enzymes originate from *Ostreococcus* or *Thraustochytrium*.

Furthermore, the present invention relates to the nucleic acid sequences, the nucleic acid constructs containing the nucleic acid sequences according to the present invention, the vectors containing the nucleic acid sequences and/or the nucleic acid constructs as well as the transgenic organisms containing the previously mentioned nucleic acid sequences, nucleic acid constructs and/or vectors.

Advantageously, said above mentioned nucleic acid sequences, nucleic acid constructs and/or vectors can be expressed in said organism, optionally together with further nucleic acid sequences coding for polypeptides or proteins of the biosynthesis of the fatty acid or lipid metabolism. Herein, particularly advantageous nucleic acid sequences of the fatty acid or lipid metabolism are nucleic acid sequences coding for an activity of a Δ-9 elongase, Δ-8 desaturase, Δ-6 desaturase, a Δ-5 desaturase, Δ-4 desaturase, Δ-12 desaturase, Δ-5 elongase and/or Δ-6 elongase. Advantageously, said desaturases and elongases originate from organisms like *Thalassiosira, Euglena, Isochrysis, Physcomitrella, Thraustochytrium, Borago, Phytophthora, Crypthecodinium, Oncorhynchus, Primula, Xenopus, Ciona, Arabidopsis, Mortierella, Caenorhabditis, Phaeodactylum, Ceratodon* or *Ostreococcus*.

A further part of the present invention relates to oils, lipids and/or fatty acids produced according to the method of the present invention and to uses thereof. Furthermore, the present invention relates to unsaturated fatty acids and to triglycerides having an increased content of unsaturated fatty acids and to uses thereof.

Fatty acids and triacylglycerides have a variety of uses in food industry, animal nutrition, cosmetics, and in the pharmaceutical field. Depending on whether they are free saturated and unsaturated fatty acids or triacylglycerides having an increased content of saturated or unsaturated fatty acids, they are suitable for the most diverse uses. Polyunsaturated fatty acids like linoleic or linolenic acid are essential for mammals, as they are not capable of producing said substances themselves. Therefore, polyunsaturated ω-3 fatty acids and ω-6 fatty acids are essential components of feeding and food for animals and humans.

Polyunsaturated long-chain ω-3 fatty acids like eicosapentaenoic acid (=EPA, $C20:5^{\Delta5,8,11,14,17}$) or docosahexaenoic acid (=DHA, $C22:6^{\Delta4,7,10,13,16,19}$) are essential components of human food due to their different roles with respect to health, comprising aspects like the development of the infant brain, the functionality of the eye, the synthesis of hormones and other signal substances as well as the prevention of cardiovascular disorders, cancer and diabetes (Poulos, A Lipids 30:1-14, 1995; Horrocks, L A und Yeo Y K Pharmacol Res 40:211-225, 1999). There is thus a need for the production of polyunsaturated long-chain fatty acids.

Due to the composition of human food that is conventional nowadays, the addition of polyunsaturated ω-3 fatty acids, which are preferably present in fish oils, to food is of essential importance. For instance, polyunsaturated fatty acids like docosahexaenoic acid (=DHA, $C22:6^{\Delta4,7,10,13,16,19}$) or eicosapentaenoic acid (=EPA, $C20:5^{\Delta5,8,11,14,17}$) are added to baby food in order to increase the nutritional value. Herein, a positive effect on the development and maintenance of brain functions is assigned to the unsaturated fatty acid DHA.

In the following, polyunsaturated fatty acids will be referred to as PUFA, PUFAs, LCPUFA or LCPUFAs (poly unsaturated fatty acids, PUFA; long chain poly unsaturated fatty acids, LCPUFA).

The different fatty acids and triglycerides are mainly obtained from microorganisms like *Mortierella* or *Schizochytrium* or from oil-producing plants like soy, rape or algae like *Crypthecodinium* or *Phaeodactylum* and others, wherein they usually occur in form of their triacylglycerides (=triglycerides=triglycerols). However, they can also be obtained from animals like, for example, fish. Advantageously, the free fatty acids are produced by saponification. Very long-chain polyunsaturated fatty acids, like DHA, EPA, arachidonic acid (=ARA, $C20:4^{\Delta5,8,11,14}$), dihomo-γ-linolenic acid ($C20:3^{\Delta8,11,14}$) or docosapentaenoic acid (DPA, $C22:5^{\Delta7,10,13,16,19}$) are not synthesized in oil plants like rape, soy, sunflower or safflower. Conventional natural sources for these fatty acids are algae or fish like herring, salmon, sardine, redfish, eel, carp, trout, halibut, mackerel, pike-perch, or tuna.

According to the respective purpose of use, oils having saturated or unsaturated fatty acids are preferred. In human nutrition, for example, lipids having unsaturated fatty acids, in particular polyunsaturated fatty acids, are preferred. Herein, a positive effect on the blood cholesterol level and therefore on the possibility of preventing a heart disease is assigned to the polyunsaturated ω-3 fatty acids. By adding said ω-3 fatty acids to food, the risk of suffering from a heart disease, apoplexia, or high blood pressure can be substantially reduced. Inflammatory, in particular chronically inflammatory processes within the scope of immunological diseases like rheumatoid arthritis can also be positively influenced by ω-3 fatty acids. They are therefore added to food, in particular to dietary food, or are used in drugs. Owing to our conventional food composition, ω-6 fatty acids like arachidonic acid have a rather negative effect on said rheumatoid diseases.

ω-3 and ω-6 fatty acids are precursors of tissue hormones, the so-called eicosanoids like the prostaglandins, which are derived from the dihomo-γ-linolenic acid, the arachidonic acid and the eicosapentaenoic acid, the thromboxanes and leukotrienes, which are derived from arachidonic acid and the eicosapentaenoic acid. Eicosanoids (the so-called $PG_2$ series), which are formed from ω-6 fatty acids, usually enhance inflammatory reactions, whereas eicosanoids (the so-called $PG_3$ series) from ω-3 fatty acids have only a slight inflammatory effect or none at all.

Due to their positive qualities, there have been enough approaches in the past to make genes that are involved in the synthesis of fatty acids or triglycerides available for producing oils having an altered content of unsaturated fatty acids in different organisms. Thus, in WO 91/13972 and in its US equivalent, a Δ-9 desaturase is described. In WO 93/11245, a Δ-15 desaturase, in WO 94/11516 a Δ-12 desaturase is claimed. Further desaturases are, for example, described in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203, or Huang et al., Lipids 34, 1999: 649-659. However, biochemical characterization of the different desaturases has only been taken place insufficiently up to now, as it is very difficult to isolate and characterize the enzymes, which are membrane-bound proteins (McKeon et al., Methods in Enzymol. 71, 1981: 12141-12147, Wang et al., Plant Physiol. Biochem., 26, 1988: 777-792). Normally, characterization of membrane-bound desaturases is done by introducing them into a suitable organism, which is subsequently examined for enzyme activity by educt and product analysis. Δ-6 desaturases are described in WO 93/06712, U.S. Pat. No. 5,614,393, WO 96/21022, WO 00/21557, and WO 99/27111, and their use for production in transgenic organisms is also described, for example, in WO 98/46763, WO 98/46764, and WO 98/46765. Herein, the expression of different desaturases, like in WO 99/64616 or WO 98/46776, and the formation of polyunsaturated fatty acids are also described and claimed. With respect to the efficiency of the expression of desaturases and their influence on the formation of polyunsaturated fatty acids, it has to be noted that by expressing an individual desaturase, as hitherto described, only low contents of unsaturated fatty acids/lipids, like for example γ-linolenic acid and stearidonic acid, were achieved. Furthermore, a mixture of ω-3 and ω-6 fatty acids was normally obtained.

Microorganisms that are particularly suitable for producing PUFAs are microorganism such as microalgae like *Phaeodactylum tricornutum*, *Porphiridium* species, *Thraustochytria* species, *Schizochytria* species or *Crypthecodinium* species, ciliates like *Stylonychia* or *Colpidium*, fungi like *Mortierella*, *Entomophthora*, or *Mucor* and/or mosses like *Physcomitrella*, *Ceratodon*, and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). By strain selection, a number of mutant strains of the respective microorganisms has been developed, which produce a variety of desirable compounds, including PUFAs. However, mutation and selection of strains exhibiting an improved production of a specific molecule like the polyunsaturated fatty acids is a time-consuming and difficult procedure. Therefore, as described in the above, methods of genetic engineering are preferred wherever possible. With the aid of the previously mentioned microorganisms, only limited amounts of the desired polyunsaturated fatty acids like DPA, EPA, or ARA can be produced, however, wherein the latter normally occur in form of fatty acid mixtures of, for example, EPA, DPA, and ARA, depending on the microorganism used.

Different synthesis ways are discussed for the synthesis of arachidonic acid, eicosapentaenoic acid (EPA), and docosahexaenoic acid (DHA) (FIG. 1). Thus, the production of EPA or DHA is performed in marine bacteria like *Vibrio* sp. or *Shewanella* sp. according to the polyketide pathway (Yu, R. et al. Lipids 35:1061-1064, 2000; Takeyama, H. et al. Microbiology 143:2725-2731, 1997).

An alternative strategy proceeds via the alternating activity of desaturases and elongases (Zank, T. K. et al. Plant Journal 31:255-268, 2002; Sakuradani, E. et al. Gene 238:445-453, 1999). A modification of the described pathway via Δ6 desaturase, Δ6 elongase, Δ5 desaturase, Δ5 elongase, Δ4 desaturase is the synthetic pathway in mammals according to Sprecher (Sprecher 2000, Biochim. Biophys. Acta 1486:219-231). Herein, instead of the Δ4 desaturation, a further elongation step to $C_{24}$, a further Δ6 desaturation, and finally a β-oxidation to the $C_{22}$ chain length is performed. The so-called Sprecher synthetic pathway (see FIG. 1) is, however, not suitable for the production in plants and microorganisms, as its regulatory mechanisms are unknown.

According to their desaturation pattern, the polyunsaturated fatty acids can be divided into two large classes, into ω-6 or ω-3 fatty acids, which exhibit different activities in both metabolic and functional sense (FIG. 1).

The fatty acid linoleic acid ($18:2^{\Delta 9,12}$) functions as the starting product for the ω-6 metabolic pathway, while the ω-3 pathway proceeds via linolenic acid ($18:3^{\Delta 9,12,15}$). Herein, linolenic acid is formed by the activity of an ω-3 desaturase (Tocher et al. 1998, Prog. Lipid Res. 37, 73-117; Domergue et al. 2002, Eur. J. Biochem. 269, 4105-4113).

In mammals, and therefore also in humans, there is no corresponding desaturase activity (Δ-12 and ω-3 desaturase), which is why they have to take in said fatty acids (essential fatty acids) with food. Via the sequence of desaturase and elongase reactions, the physiologically important polyunsaturated fatty acids arachidonic acid (=ARA, $20:4^{\Delta 5,8,11,14}$), an ω-6 fatty acid, and the two ω-3 fatty acids eicosapentaenoic (=EPA, $20:5^{\Delta 5,8,11,14,17}$) and docosahexaenoic acid (=DHA, $22:6^{\Delta 4,7,10,13,17,19}$) are then synthesized from said precursors. Herein, the application of ω-3 fatty acids exhibits the previously described therapeutic effect in the treatment of cardiovascular diseases (Shimikawa 2001, World Rev. Nutr. Diet. 88, 100-108), inflammations (Calder 2002, Proc. Nutr. Soc. 61, 345-358), and arthritis (Cleland und James 2000, J. Rheumatol. 27, 2305-2307).

The elongation of fatty acids via elongases by 2 or 4 C atoms is of decisive importance for the production of $C_{20}$ or $C_{22}$ PUFAs. Said process proceeds over 4 steps. The first step provides the condensation of malonyl-CoA to the fatty acid-acyl-CoA by the ketoacyl-CoA synthase (KCS, referred to as elongase in the following). Subsequently, a reduction step (ketoacyl-CoA reductase, KCR), a dehydratation step (dehydratase), and a final reduction step (enoyl-CoA reductase) are performed. It has been postulated that the activity of the elongase influences the specifity and the speed of the entire process (Millar and Kunst, 1997 Plant Journal 12:121-131).

In the past, numerous attempts have been made to obtain elongase genes. Millar and Kunst (1997, Plant Journal 12:121-131) and Millar et al. (1999, Plant Cell 11:825-838) describe the characterization of plant elongases for the synthesis of monounsaturated long-chain fatty acids (C22:1) or for the synthesis of fatty acids having very long chains for wax formation in plants ($C_{28}$-$C_{32}$). Descriptions on the synthesis of arachidonic acid and EPA can be found, for example, in WO 01/59128, WO 00/12720, WO 02/077213, and WO 02/08401. The synthesis of polyunsaturated C24 fatty acids is described, for example, in Tvrdik et al. (2000, JCB 149:707-717) or in WO 02/44320.

Higher plants contain polyunsaturated fatty acids like linoleic acid (C18:2) and linolenic acid (C18:3). ARA, EPA, and DHA are not, or only in traces, present in the seed oil of higher plants (E. Ucciani: Nouveau Dictionnaire des Huiles Végétales. Technique & Documentation—Lavoisier, 1995. ISBN: 2-7430-0009-0). However, it would be advantageous to produce LCPUFAs in higher plants, preferably in oil plants such as rape, flax, sunflower, and soy, as in this manner large amounts of high-quality LCPUFAs could be obtained cost-effectively for the food industry, for animal nutrition, and for pharmaceutical purposes. To this end, genes coding for enzymes of the biosynthesis of LCPUFAs have to be introduced into and expressed in oil plants, advantageously by genetic engineering methods. These are genes coding for, for example, Δ-6 desaturases, Δ-6 elongases, Δ-5 desaturases, or Δ-4 desaturases. Advantageously, said genes can be isolated from microorganisms and lower plants which produce LCPUFAs and integrate them into the membranes or triacylglycerides. Thus, Δ-6 desaturase genes from the moss *Physcomitrella patens* and Δ-6 elongase genes from *P. patens* and from the nematode *C. elegans* could already be isolated.

First transgenic plants containing genes coding for and expressing enzymes of the LCPUFA biosynthesis, and producing LCPUFAs, have been described for the first time, for example, in DE 102 19 203 (Method for producing polyunsaturated fatty acids in plants). However, said plants produce LCPUFAs only in amounts that have to be further optimized for processing the oils contained in the plants.

In order to enable the enrichment of food and feed with said polyunsaturated fatty acids, there is thus a need for a simple, cost-effective method for the production of said polyunsaturated fatty acids, in particular in eukaryotic systems.

BRIEF DESCRIPTION OF THE DRAWINGS

FIG. 1 shows different synthesis pathways for the biosynthesis of DHA (docosahexaenoic acid).

FIG. 2 shows gas chromatogram of the fatty acid extract from flax seed transformed with the construct pGPTV-USP_PSE1_d6Des(Pt)_d5Des(Pt).

FIG. 3 shows sequence alignment of phospholipase A2 from *H. sapiens* (SEQ ID NO: 146) and the *Ostreococcus* sequence PLA2(Ot) (SEQ ID NO: 2).

FIG. 4 shows sequence alignment between KR(Ot) (SEQ ID NO: 4) and Ybr159w (SEQ ID NO: 147).

FIG. 5 shows sequence alignment between DH(Ot) (SEQ ID NO: 6) and Ydr036c (SEQ ID NO: 148).

FIG. 6 shows sequence alignment of the dehydratase from *Ostreococcus tauri* ("DH(Ot)"; SEQ ID NO: 6), *Thraustochytrium* ssp. ("DH(Tc)"; SEQ ID NO: 8) and *Saccharomyces cerevisiae* ("YDR036C"; SEQ ID NO: 148) by ClustalW analysis. Conserved regions are dark.

There are still a number of limiting steps in the fatty acid biosynthesis which impair the increase of the content of polyunsaturated long-chain fatty acids. It could thus be shown in transgenic plants, as have, for example, been described in DE 10 219 203, that the elongation, i.e. the chain extension, from C18 to C20 fatty acids is such a limiting step (FIG. 2). FIG. 2 shows the gas chromatogram of the fatty acid extract from flaxseed, transformed with the construct pGPTV-USP_PSE1_d6Des(Pt)_d5Des(Pt), according to the descriptions from DE 10 219 203. The newly formed products from the activities of the genes are marked with arrows. The synthesis of the final products arachidonic acid (ARA) and eicosapentaenoic acid (EPA) proceeds via γ-linolenic acid (g18:3) or stearidonic acid (18:4) (first step, see also FIG. 1). In the second step, the elongation to form the intermediate products 20:3n-6 and 20:4n-3 is performed (elongation step). In the last step, the intermediate products are then reacted to form ARA and EPA. A strong decrease in the product quantities from the first to the second step can be observed. FIG. 2 shows that after the first step in the aerobic LCPUFA synthesis, the amount of product is drastically reduced by the desaturation of linoleic or linolenic acid (see FIG. 1). This may indicate that the conversion of the elongation of Δ6-desaturated fatty acids is effected to an insufficient extent. Herein, the conversion rate is significantly lower than could be shown in yeast experiments in which the Δ6-desaturated fatty acids had been fed (Zank et al. 2002, Plant Journal 31:255-268).

Thus, the problem was posed to provide further genes or enzymes suitable for the synthesis of LCPUFAs, in particular genes exhibiting a phospholipase A2, ketoacyl-CoA reductase and/or dehydratase activity, to produce polyunsaturated fatty acids and to further optimize the biosynthesis of fatty acids in oils and/or lipids by said genes or enzymes.

It was a further problem to develop a method for producing oils or lipids having a high content of unsaturated fatty acids, advantageously of polyunsaturated fatty acids, in an organism, advantageously in an eukaryotic organism, preferably in a plant or a microorganism. Said problem was solved by the method according to the present invention for producing oils or lipids having a high content of unsaturated fatty acids in transgenic organisms. Said method is characterized in that it comprises the following procedural steps:

a) introducing at least one nucleic acid sequence coding for a phospholipase A2 activity into the organism, or b) introducing at least one nucleic acid sequence coding for a ketoacyl-CoA reductase activity into the organism, or c) introducing at least one nucleic acid sequence coding for a dehydratase activity into the organism, and d) cultivating and harvesting the transgenic organism.

Advantageously, the oils or lipids produced in said method are isolated from the transgenic organism and, optionally, the fatty acids contained in the oils or lipids, advantageously the unsaturated fatty acids, are released from said oils or lipids.

Advantageously, the polyunsaturated fatty acids produced in the method according to the present invention contain at least two, advantageously three, four, five, or six double bonds. Particularly advantageously, the fatty acids contain four, five, or six double bonds. Advantageously, fatty acids produced in said method contain 18, 20 or 22 C atoms in their fatty acid chain, preferably the fatty acids contain 20 or 22 carbon atoms in the fatty acid chain. Said fatty acids produced can be produced in the method as the exclusive product or they can be present in a fatty acid mixture.

The nucleic acid sequences used in the method according to the present invention are isolated nucleic acid sequences coding for polypeptides or proteins having phospholipase A2, ketoacyl-CoA reductase, or dehydratase activity, and advantageously originate from organisms of the genera *Ostreococcus* or *Thraustochytrium*.

Preferred nucleic acid sequences used in the method according to the present invention coding for polypeptides or proteins with phospholipase A2, ketoacyl-CoA reductase or dehydratase activity are selected from the group consisting of:

a) a nucleic acid sequence having the sequence depicted in SEQ ID NO: 1, SEQ ID NO: 3, SEQ ID NO: 5 or SEQ ID NO: 7, or b) nucleic acid sequences that can be derived as a result of the degenerate genetic code from the amino acid sequences depicted in SEQ ID NO: 2, SEQ ID NO: 4, SEQ ID NO: 6 or SEQ ID NO: 8, or c) derivatives of the nucleic acid sequence depicted in SEQ ID NO: 1, SEQ ID NO: 3, SEQ ID NO: 5 or SEQ ID NO: 7 coding for polypeptides or proteins having at least 40% identity on the amino acid level to SEQ ID NO: 2, SEQ ID NO: 4, SEQ ID NO: 6 or SEQ ID NO: 8 and having a phospholipase A2, ketoacyl-CoA reductase or dehydratase activity.

Said nucleic acid sequences used in the method according to the present invention coding for polypeptides or proteins with phospholipase A2, ketoacyl-CoA reductase or dehydratase activity can be advantageously used in the method according to the present invention in combination with nucleic acid sequences coding for polypeptides or proteins having Δ-9 elongase, Δ-6 desaturase, Δ-8 desaturase, Δ-12 desaturase, Δ-6 elongase, Δ-5 desaturase, Δ-5 elongase, ω-3 desaturase and/or Δ-4 desaturase activity. Said nucleic acid sequences used in the method according to the present invention and the proteins encoded thereby lead to an increase of the content of unsaturated fatty acids, preferably to an increase of the content of LCPUFAs, in the transgenic organisms. The term "having a high content" of unsaturated fatty acids or the term "increase" is understood to denote an increase of the unsaturated fatty acids in the oils or lipids or in form of the free fatty acids in the organisms by at least 5, 6, 7, 8, 9 or 10%, advantageously by at least 15, 20, 25, 30, 35, 40, 45 or 50%, preferably by at least 55, 60, 65, 70, 75, 80, 85, 90, 95 or 100%, particularly preferably by at least 105, 110, 115 or 120%, in particular preferably by at least 130, 135, 140, 145 or 150% as compared to the amount of unsaturated fatty acids in the oils or lipids or in form of the free fatty acids in organisms, which is achieved in the method according to the present invention with the used nucleic acid sequences and by the proteins encoded thereby as compared to the non-transgenic original organism, for example a yeast, an alga, a fungus or a plant such as *Arabidopsis* or flax, in comparing in the GC analysis (see Examples). The previously given percent values refer to the increase of unsaturated fatty acids in the oils and lipids or in form of the free fatty acids in the organisms based on the total lipid content in percent by weight. Thus, in the method according to the present invention, the LCPUFAs thus produced are synthesized in the transgenic organisms, advantageously in a transgenic plant, at a content of at least 3 weight %, advantageously of at least 5 weight %, preferably of at least 8 weight %, particularly preferably of at least 10 weight % and in particular preferably of at least 15 weight % based on the total of the fatty acids.

The activity of the phospholipase A2 [=PLA2(Ot)] used in the method according to the present invention is described as hydrolase reaction of the ester bond of the sn-2 position of triacylglycerides (E.C. number 3.1.1.4). Due to the activity, an increase of the LCPUFA content can be attributed to the following reaction mechanism:

The reaction mechanism of LCPUFA is composed of the steps Δ6-desaturation, Δ6-elongation, and Δ5-desaturation (FIG. 1). These steps are performed in different compartments (Domergue et al. 2003, JBC, 278:35115-35126). Herein, the first desaturation step takes place at the sn-2 position of phospholipids, mainly phosphatidylcholine (Domergue et al. 2002, Eur. J. Biochem. 269:4105-4113). For the subsequent elongation step, the fatty acid has to be released from the phosphatidylcholine and has to be made accessible to the elongation complex in form of an acyl-CoA ester. Herein, organisms have a set of acyltransferases in order to be capable of conducting this reaction.

In transgenic plants, said step appears to be limiting, i.e. the endogenously available set of enzymes is not capable of catalyzing the reaction efficiently.

Due to the activity of the PLA2(Ot), more fatty acids are provided for elongation, which leads to an increase in the content of LCPUFA. The PLA2(Ot) exhibits homologies to a phospholipase Δ2 from *Homo sapiens* (see FIG. 3).

Enzymes of the elongation complex are another subject of the present invention. Beside the above mentioned provision of fatty acids for the elongation, the activity of the elongation complex is an important potential for increasing the content of elongated fatty acids.

From the alga *Ostreococcus tauri* and the fungus *Thraustochytrium* ssp., it was possible to identify genes coding for proteins of the elongase complex, whose combination leads to an increase in the content of LCPUFAs in organisms.

The process for the elongation of fatty acids proceeds over 4 steps (Biochemistry and Molecular Biology of Plants, 2000, ed. Buchanan, Gruissem, Jones, ASPP). The first step represents the condensation of malonyl-CoA to the fatty acid-acyl-CoA via the ketoacyl-CoA synthase (KCS, referred to as elongase in the following). Then, a reduction step (ketoacyl-CoA reductase, KCR), a dehydration step (dehydratase), and a final reduction step (enoyl-CoA reductase) are following. It has been postulated that the activity of the elongase influences the specificity and the speed of the entire process (Millar and Kunst, 1997 Plant Journal 12:121-131). It could be shown that the enhanced provision of one of the components of the elongase complex leads to an increase in the amount of elongation product (Beaudoin et al. 2001, JBC, 277:11481-11488).

Surprisingly, the combined expression of the genes for the ketoacyl-CoA reductase [KR(Ot)] and for the dehydratase [DH (Ot)] from the alga *Ostreococcus* leads to an increase or further enhancement of the amount of LCPUFAs in plants. By sequence comparisons it could be shown that the two identified genes have homologies to enzymes with ketoacyl-CoA reductase (ketoacyl-CoA reductase from *Saccharomyces* cerevisiae GenBank Acc. No. NP009717; Ybr159w; SEQ ID NO: 147) or dehydratase activity (dehydratase/enoyl reductase activity of *Saccharomyces cerevisiae* GenBank Acc. No. S61591; Ydr036c; SEQ ID NO: 148) (see FIGS. 4, 5 and 6).

Advantageously used in the method according to the present invention, as has been described in the above, are nucleic acid sequences coding for polypeptides or proteins exhibiting phospholipase A2, ketoacyl-CoA reductase and/or dehydratase activity in combination with nucleic acid sequences coding for polypeptides or proteins exhibiting Δ-9 elongase, Δ-6 desaturase, Δ-8 desaturase, Δ-12 desaturase, Δ-6 elongase, Δ-5 desaturase, Δ-5 elongase or Δ-4 desaturase activity. Herein, the nucleic acid sequences coding for polypeptides or proteins exhibiting Δ-9 elongase, Δ-6 desaturase, Δ-8 desaturase, Δ-12 desaturase, Δ-6 elongase, Δ-5 desaturase, Δ-5 elongase, ω-3 desaturase or Δ-4 desaturase activity are advantageously selected from the group consisting of:

a) a nucleic acid sequence having the sequence depicted in SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142 or SEQ ID NO: 144, or b) nucleic acid sequences which can be derived as a result of the degenerate genetic code from the amino acid sequences depicted in SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143 or SEQ ID NO: 145, or c) derivatives of the nucleic acid sequence depicted in SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142 or SEQ ID NO: 144, which code for polypeptides or proteins having, on the amino acid level, at least 40% identity to SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143 or SEQ ID NO: 145 and exhibiting $\Delta$-9 elongase, $\Delta$-6 desaturase, $\Delta$-8 desaturase, $\Delta$-6 elongase, $\Delta$-5 desaturase, $\Delta$-12 desaturase, $\omega$-3 desaturase, $\Delta$-5 elongase or $\Delta$-4 desaturase activity.

The oils or lipids produced in the method according to the present invention advantageously have a high content of polyunsaturated fatty acids, which advantageously are bound in membrane lipids and/or triacylglycerides. However, the polyunsaturated fatty acids can also be present in the organisms as free fatty acids or bound in form of other fatty acid esters. Herein, they can be present as "pure products" or, however, advantageously in form of mixtures of different fatty acids or mixtures of different glycerides. Herein, the different fatty acids bound in the triacylglycerides can be derived from short-chain fatty acids having 4 to 6 C atoms, medium-chain fatty acids having 8 to 12 C atoms, or long-chain fatty acids having 14 to 24 C atoms. Preferred are the long-chain fatty acids, particularly preferred are the long-chain fatty acids LCPUFAs of $C_{18}$, $C_{20}$ and/or $C_{22}$ fatty acids.

In the method according to the present invention, oils and lipids are advantageously produced in form of their fatty acid esters having polyunsaturated $C_{18}$-, $C_{20}$- and/or $C_{22}$ fatty acid molecules with at least two double bonds in the fatty acid ester, advantageously at least three, four, five or six double bonds in the fatty acid ester, particularly advantageously with at least five or six double bonds in the fatty acid ester. In the method, this advantageously leads to the synthesis of linoleic acid (=LA, $C18:2^{\Delta9,12}$), $\gamma$-linolenic acid (=GLA, $C18:3^{\Delta6,9,12}$), stearidonic acid (=SDA, $C18:4^{\Delta6,9,12,15}$), dihomo-$\gamma$-linolenic acid (=DGLA, $20:3^{\Delta8,11,14}$), $\omega$-3-eicosatetraenoic acid (=ETA, $C20:4^{\Delta5,8,11,14}$), arachidonic acid (ARA, $C20:4^{\Delta5,8,11,14}$), eicosapentaenoic acid (EPA, $C20:5^{\Delta5,8,11,14,17}$), $\omega$-6-docosapentaenoic acid ($C22:5^{\Delta4,7,10,13,16}$), $\omega$-6-docosatetraenoic acid ($C22:4^{\Delta7,10,13,16}$), $\omega$-3-docosapentaenoic acid (=DPA, $C22:5^{\Delta7,10,13,16,19}$), docosahexaenoic acid (=DHA, $C22:6^{\Delta4,7,10,13,16,19}$) or mixtures thereof, preferably to the synthesis of ARA, EPA and/or DHA. Particularly preferred is the production of $\omega$-3 fatty acids such as EPA and/or DHA.

The fatty acid esters having polyunsaturated $C_{18}$, $C_{20}$ and/or $C_{22}$ fatty acid molecules can be isolated from the organisms, which have been used for the production of the fatty acid esters, in form of an oil or a lipid, for example in form of compounds such as sphingolipids, phosphoglycerides, lipids, glycolipids like glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters like the acetyl Coenzyme A esters containing those polyunsaturated fatty acids with at least two, three, four, five or six, preferably five or six, double bonds. Advantageously, they are isolated in form of their diacylglycerides, triacylglycerides and/or in form of phosphatidylcholine, particularly preferably in form of the triacylglycerides. Apart from said esters, the polyunsaturated fatty acids are also contained in the organisms, preferably in the plants, as free fatty acids or bound in other compounds. Normally, the different previously mentioned compounds (fatty acid esters and free fatty acids) are present in the organisms at approximate proportions of 80 to 90 weight % triglycerides, 2 to 5 weight % diglycerides, 5 to 10 weight % monoglycerides, 1 to 5 weight % free fatty acids, 2 to 8 weight % phospholipids, wherein the sum of the different compounds adds up to 100 weight %.

In the method according to the present invention, the produced LCPUFAs are synthesized in the transgenic organisms, preferably in a transgenic plant, in a content of at least 3 weight %, advantageously of at least 5 weight %, preferably of at least 8 weight %, particularly preferably of at least 10 weight %, and in particular preferably of at least 15 weight % based on the total of the fatty acids. Herein, advantageously $C_{18}$, $C_{20}$ and/or $C_{22}$ fatty acids that are present in the host organisms are converted into the corresponding products like DPA or DHA, just to mention two by way of example, by at least 10%, advantageously by at least 20%, particularly advantageously by at least 30%, and in particular advantageously by at least 40%. Advantageously, the fatty acids are produced in bound form. With the aid of the nucleic acids used in the method according to the present invention, said unsaturated fatty acids can be brought at the sn1, sn2 and/or sn3 position/s of the advantageously produced triglycerides. Furthermore, precursors of said fatty acids are advantageously provided in the method according to the present invention. As, in the method according to the present invention, the starter compounds linoleic acid (C18:2) or linolenic acid (C18:3) go through several reaction steps, the final products of the method, like for example arachidonic acid (ARA), eicosapentaenoic acid (EPA), ω-6-docosapentaenoic acid or DHA, do not emerge as absolutely pure products; there will always be small traces of the precursors present in the final product as well. If both linoleic acid and linolenic acid are present in the original organism or in the original plant, the final products like ARA, EPA or DHA will be present as mixtures. Advantageously, the precursors should not amount to more than 20 weight %, preferably not more than 15 weight %, particularly preferably not more than 10 weight %, and in particular preferably not more than 5 weight %, based on the amount of the respective final product. Advantageously, in a transgenic plant, only ARA, EPA or only DHA are bound or produced as free acids as final products in the method according to the present invention. If the compounds ARA, EPA, and DHA are produced simultaneously, they are advantageously produced in a proportion of at least 1:1:2 (EPA:ARA:DHA), advantageously of at least 1:1:3, preferably of 1:1:4, and particularly preferably of 1:1:5.

Fatty acid esters or fatty acid mixtures produced according to the method of the present invention advantageously contain 6 to 15% palmitic acid, 1 to 6% stearic acid; 7 to 85% oleic acid; 0.5 to 8% vaccenic acid, 0.1 to 1% arachinic acid, 7 to 25% saturated fatty acids, 8 to 85% monounsaturated fatty acids and 60 to 85% polyunsaturated fatty acids, in each case based on 100% and on the total fatty acid content of the organisms. As advantageous polyunsaturated fatty acid, preferably at least 0.1; 0.2; 0.3; 0.4; 0.5; 0.6; 0.7; 0.8; 0.9 or 1%, based on the total fatty acid content, of arachidonic acid, EPA and/or DHA, are contained in the fatty acid esters or fatty acid mixtures. Furthermore, the fatty acid esters or fatty acid mixtures produced according to the method of the present invention advantageously contain fatty acids selected from the following group of fatty acids: erucic acid (13-docosaenoic acid), sterculinic acid (9,10-methylene octadec-9-enoic acid), malvalinic acid (8,9-methylene heptadec-8-enoic acid), chaulmoogrinic acid (cyclopentene-dodecanoic acid), furan fatty acid (9,12-epoxy-octadeca-9,11-dienoic acid), vernolic acid (9,10-epoxyoctadec-12-enoic acid), taric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselinic acid (cis-6-octadecenoic acid), 9c,12t-octadecadienoic acid, calendulic acid (8t10t12c-octadecatrienoic acid), catalpic acid (9c11t13c-octadecatrienoic acid), eleostearinic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienoic acid), ricinolic acid (12-hydroxy-9c-octadecenoic acid) and/or coriolic acid (13-hydroxy-9c,11t-octadecadienoic acid). As a rule, the previously mentioned fatty acids are advantageously present in the fatty acid esters or fatty acid mixtures produced according to the method of the present invention only in traces, i.e. they are present, based on the entire fatty acids, by less than 30%, preferably less than 25%, 24%, 23%, 22% or 21%, particularly preferably less than 20%, 15%, 10%, 9%, 8%, 7%, 6% or 5%, and in particular preferably less than 4%, 3%, 2% or 1%. Advantageously, the fatty acid esters or fatty acid mixtures produced according to the method of the present invention contain less than 0.1%, based on the total fatty acids, or no butyric acid, no cholesterol, no clupanodonic acid (=docosapentaenoic acid, $C22:5^{\Delta4,8,12,15,21}$) and no nisinic acid (tetracosahexaenoic acid, $C23:6^{\Delta3,8,12,15,18,21}$).

Chemically pure, polyunsaturated fatty acids or fatty acid compositions can also be synthesized according to the method described in the above. To this end, the fatty acids or the fatty acid compositions are isolated from the organism such as the microorganisms or the plants or the culture medium, in or on which the organisms have been cultivated, or from the organism and the culture medium in a known manner, for example via extraction, distillation, crystallization, chromatography, or by combinations of said methods. These chemically pure fatty acids or fatty acid compositions are advantageous for uses in the fields of food industry, cosmetics industry, and, in particular, pharmaceutical industry.

In principle, all organisms like microorganisms, non-human animals, or plants can be considered as organisms for the production in the method according to the present invention.

In principle, all plants that are capable of synthesizing fatty acids, like all dicotyledonous or monocotyledonous plants, algae or mosses, can be considered as plants. Advantageous plants are selected from the group of the plant classes or families of Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Euglenaceae or Prasinophyceae. Vegetable plants or ornamental plants like *Tagetes* can also be considered.

By way of example, the following plants are to be mentioned, selected from the group: Adelotheciaceae like genera *Physcomitrella*, for example genus and species *Physcomitrella patens*, Anacardiaceae like genera *Pistacia, Mangifera, Anacardium*, for example genus and species *Pistacia vera* [pistache], *Mangifer indica* [mango] or *Anacardium occidentale* [cashew], Asteraceae like genera *Calendula, Carthamus, Centaurea, Cichorium, Cynara, Helianthus, Lactuca, Locusta, Tagetes, Valeriana*, for example genus and species *Calendula officinalis* [pot marigold], *Carthamus tinctorius* [safflower], *Centaurea cyanus* [garden cornflower], *Cichorium intybus* [witloof chicory], *Cynara scolymus* [artichoke], *Helianthus annuus* [common sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [lamb's lettuce], *Tagetes lucida, Tagetes erecta* or *Tagetes tenuifolia* [lemon marigold], Apiaceae like genus *Daucus*, for example genus and species *Daucus carota* [carrot], Betulaceae like genus *Corylus*, for example genera and species *Corylus avellana* or *Corylus* colurna [hazelnut], Boraginaceae like genus *Borago*, for example genus and species *Borago officinalis* [borage], Brassicaceae like genera *Brassica, Camelina, Melanosinapis, Sinapis, Arabidopsis*, for example genera and species *Brassica napus, Brassica rapa* ssp. [tunip], *Sinapis arvensis, Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [wild cabbage] or *Arabidopsis thaliana*, Bromeliaceae such as the genera *Anana, Bromelia* (pineapple), for example genera and species *Ananas comosus, Ananas ananas* or *Bromelia comosa* [pineapple], Caricaceae like the genus *Carica*, for example the genus and species *Carica papaya* [papaya], Cannabaceae like genus *Cannabis*, e.g. genus and species *Cannabis sativa* [hemp], Convolvulaceae like genera *Ipomoea, Convolvulus*, for example genera and species *Ipomoea batatas, Ipomoea pandurata, Convolvulus batatas, Convolvulus tiliaceus, Ipomoea fastigiata, Ipomoea tiliacea, Ipomoea triloba* or *Convolvulus panduratus* [sweet potato], Chenopodiaceae like genus *Beta* like genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugar beet], Crypthecodiniaceae like genus *Crypthecodinium*, for example genus and species *Crypthecodinium cohnii*, Cucurbitaceae like genus *Cucurbita*, for example genera and species *Cucurbita maxima, Cucurbita mixta, Cucurbita pepo* or *Cucurbita moschata* [pumpkin], Cymbellaceae like genera *Amphora, Cymbella, Okedenia, Phaeodactylum, Reimeria*, for example genus and species *Phaeodactylum tricornutum*, Ditrichaceae like genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae like genus *Elaeagnus*, for example genus and species *Olea europaea* [olive], Ericaceae like genus *Kalmia*, for example genera and species *Kalmia latifolia, Kalmia angustifolia, Kalmia microphylla, Kalmia polifolia, Kalmia occidentalis, Cistus chamaerhodendros* or *Kalmia lucida* [Mountain laurel], Euglenaceae like genera *Ascoglena, Astasia, Colacium, Cyclidiopsis, Euglena, Euglenopsis, Hyalaphacus, Khawkinea, Lepocinclis, Phacus, Strombomonas, Trachelomonas*, for example genus and species *Euglena gracilis*; Euphorbiaceae like genera *Manihot, Janipha, Jatropha, Ricinus*, for example genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [ricinus], Fabaceae like the genera *Pisum, Albizia, Cathormion, Feuillea, Inga, Pithecolobium, Acacia, Mimosa, Medicago, Glycine, Dolichos, Phaseolus*, soy, for example genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [acacia], *Medicago sativa, Medicago falcata, Medicago varia* [alfalfa], *Glycine max, Dolichos soja, Glycine gracilis, Glycine hispida, Phaseolus max, Soja hispida* or *Soja max* [soy bean], Funariaceae like genera *Aphanorrhegma, Entosthodon, Funaria, Physcomitrella, Physcomitrium*, for example genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae like genera *Pelargonium, Cocos, Oleum*, for example genera and species *Cocos nucifera, Pelargonium grossularioides* or *Oleum cocois* [coconut], Gramineae like genus *Saccharum*, for example genus and species *Saccharum officinarum*, Juglandaceae like genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae like e.g. the genera *Persea, Laurus*, for example genera and species *Laurus nobilis* [laurel], *Persea americana, Persea gratissima* or *Persea persea* [avocado], Leguminosae like genus *Arachis*, for example genus and species *Arachis hypogaea* [peanut], Linaceae like genera *Linum, Adenolinum*, for example genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigy-* num [flax], Lythrarieae like genus *Punica*, for example genus and species *Punica granatum* [pomegranate], Malvaceae like genus *Gossypium*, for example genera and species *Gossypium hirsutum, Gossypium arboreum, Gossypium barbadense, Gossypium herbaceum* or *Gossypium thurberi* [cotton], Marchantiaceae like genus *Marchantia*, for example genera and species *Marchantia berteroana, Marchantia foliacea, Marchantia macropora*, Musaceae such as the genus *Musa*, for example genera and species *Musa nana, Musa acuminata, Musa paradisiaca, Musa* spp. [banana], Onagraceae like genera *Camissonia, Oenothera*, for example genera and species *Oenothera biennis* or *Camissonia brevipes* [evening primrose or sun cup], Palmae like genus *Elacis*, for example genus and species *Elaeis guineensis* [oil palm], Papaveraceae like genus *Papaver*, for example genera and species *Papaver orientale, Papaver rhoeas, Papaver dubium* [poppy], Pedaliaceae like genus *Sesamum*, for example genus and species *Sesamum indicum* [sesame], Piperaceae like genera *Piper, Artanthe, Peperomia, Steffensia*, for example genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata*. [Cayenne pepper], Poaceae like genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oat], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice]; *Zea mays* [maize], *Triticum aestivum, Triticum durum, Triticum turgidum, Triticum hybernum, Triticum macha, Triticum sativum* or *Triticum vulgare* [wheat], Porphyridiaceae like genera *Chroothece, Flintiella, Petrovanella, Porphyridium, Rhodella, Rhodosorus, Vanhoeffenia*, for example genus and species *Porphyridium cruentum*, Proteaceae like genus *Macadamia*, for example genus and species *Macadamia integrifolia* [macadamia], Prasinophyceae like genera *Nephroselmis, Prasinococcus, Scherffelia, Tetraselmis, Mantoniella, Ostreococcus*, for example genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae like genus *Coffea*, for example genera and species *Coffea* spp., *Coffea arabica, Coffea canephora* or *Coffea liberica* [coffee], Scrophulariaceae like genus *Verbascum*, for example genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [common mullein], Solanaceae like genera *Capsicum, Nicotiana, Solanum, Lycopersicon*, for example genera and species *Capsicum annuum, Capsicum annuum* var. *glabriusculum, Capsicum frutescens* [chili pepper], *Capsicum annuum* [sweet pepper], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant] *Lycopersicon esculentum, Lycopersicon lycopersicum, Lycopersicon pyriforme, Solanum integrifolium* or *Solanum lycopersicum* [tomato], Sterculiaceae like genus *Theobroma*, for example genus and species *Theobroma cacao* [cacao] or Theaceae like genus *Camellia*, for example genus and species *Camellia sinensis* [tea].

Advantageous microorganisms are, for example, fungi selected from the group of the families Chaetomiaceae, Choanephoraceae, Cryptococcaceae, Cunninghamellaceae, Dematiaceae, Moniliaceae, Mortierellaceae, Mucoraceae, Pythiaceae, Sacharomycetaceae, Saprolegniaceae, Schizosacharomycetaceae, Sordariaceae or Tuberculariaceae.

By way of example, the following microorganisms are to be mentioned, which are selected from the group: Choanephoraceae like the genera *Blakeslea, Choanephora*, for example genera and species *Blakeslea trispora, Choanephora cucurbitarum, Choanephora infundibulifera* var. *cucurbitarum*, Mortierellaceae like genus *Mortierella* for example genera and species *Mortierella isabellina, Mortierella polycephala, Mortierella ramanniana, Mortierella vinacea, Mortierella zonata*, Pythiaceae like genera *Pythium, Phytophthora* for example genera and species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae*, Sacharomycetaceae like genera *Hansenula, Pichia, Saccharomyces, Saccharomycodes, Yarrowia* for example genera and species *Hansenula anomala, Hansenula californica, Hansenula canadensis, Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia holstii, Pichia jadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharo-* myces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica, Schizosacharomycetaceae like genera *Schizosaccharomyces* like for example species of *Schizosaccharomyces japonicus* var. *japonicus*, *Schizosaccharomyces japonicus* var. *versatilis*, *Schizosaccharomyces malidevorans*, *Schizosaccharomyces octosporus*, *Schizosaccharomyces pombe* var. *malidevorans*, *Schizosaccharomyces pombe* var. *pombe*, Thraustochytriaceae like genera *Althornia, Aplanochytrium, Japonochytrium, Schizochytrium, Thraustochytrium* like, for example, species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense*.

Further useful microorganisms are, for example, bacteria selected from the group of the families Bacillaceae, Enterobacteriaceae or Rhizobiaceae.

By way of example, the following microorganisms are to be mentioned, selected from the group: Bacillaceae like genus *Bacillus* for example genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriaceae like genera *Citrobacter, Edwardsiella, Enterobacter, Erwinia, Escherichia, Klebsiella, Salmonella* or *Serratia*, for example genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *beta vasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia colimutabile, Escherichia fergusonii, Escherichia hermannii, Escherichia* sp., *Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae like genera *Agrobacterium, Carbophilus, Chelatobacter, Ensifer, Rhizobium, Sinorhizobium* for example genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri, Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense*.

Further advantageous microorganisms for the method according to the present invention are, for example, protists or Diatomeae selected from the group of the families Dinophyceae, Turaniellidae or Oxytrichidae like genera and species: *Crypthecodinium cohnii, Phaeodactylum tricornutum, Stylonychia mytilus, Stylonychia pustulata, Stylonychia putrina, Stylonychia notophora, Stylonychia* sp., *Colpidium campylum* or *Colpidium* sp.

Transgenic organisms like fungi like *Mortierella* or *Thraustochytrium*, yeasts like *Saccharomyces* or *Schizosaccharomyces*, mosses like *Physcomitrella* or *Ceratodon*, non-human animals like *Caenorhabditis*, algae like *Nephroselmis, Pseudoscourfielda, Prasinococcus, Scherffelia, Tetraselmis, Mantoniella, Ostreococcus, Crypthecodinium* or *Phaeodactylum* or plants like dicotyledonous or monocotyledonous plants are advantageously used in the method according to the present invention. Particularly advantageously, organisms belonging to the oil-producing organisms, i.e. which are used for producing oils, are used in the method according to the present invention, such as fungi like *Mortierella* or *Thraustochytrium*, algae like *Nephroselmis, Pseudoscourfielda, Prasinococcus, Scherffelia, Tetraselmis, Mantoniella, Ostreococcus, Crypthecodinium, Phaeodactylum* or plants, in particular plants, preferably oil plants containing large amounts of lipid compounds, like peanut, rape, canola, sunflower, safflower (*Carthamus tinctoria*), poppy, mustard, hemp, *ricinus*, olive, sesame, *calendula, Punica*, evening primrose/sun cup, mullein, thistle, wild roses, hazelnut, almond, macadamia, avocado, laurel, pumpkin, flax, soy, pistache, borage, trees (oil palm, coconut or walnut) or crops like maize, wheat, rye, oat, triticale, rice, barley, cotton, manioc, pepper, marigold, Solanaceae plants like potato, tobacco, eggplant and tomato, *Vicia* species, pea, alfalfa or bush plants (coffee, cacao, tea), *Salix* species like perennial grasses and feed crop products. Plants preferred according to the present invention are oil plants like peanut, rape, canola, sunflower, safflower, poppy, mustard, hemp, *ricinus*, olive, *calendula, Punica*, evening primrose/sun cup, pumpkin, flax, soy, borage, trees (oil palm, coconut). Particularly hemp, thistle or safflower. Particularly preferred are plants like safflower, sunflower, poppy, evening primrose, walnut, flax or hemp.

It is advantageous for the described method according to the present invention to introduce into the organism, in addition to the nucleic acids introduced via procedural steps (a) to (c), further nucleic acids coding for enzymes of the fatty acid or lipid metabolism.

In principle, all genes of the fatty acid or lipid metabolism can advantageously be used in combination with the phospholipase(s) A2, ketoacyl-CoA reductase(s) and/or dehydratase(s) according to the present invention [in the sense of the present application, the plural is meant to include the singular and vice versa] in the method for producing polyunsaturated fatty acids. Advantageously, genes of the fatty acid or lipid metabolism are selected from the group of acyl-CoA dehydrogenase(s), acyl-ACP [=acyl carrier protein] desaturase(s), acyl-ACP thioesterase(s), fatty acid-acyltransferase(s), acyl-CoA:lysophospholipid acyltransferase(s), fatty acid synthase(s), fatty acid hydroxylase(s), acetyl-coenzyme A carboxylase(s), acyl-coenzyme A-oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) in combination with the phospholipase A2, ketoacyl-CoA reductase and/or dehydratase are used. Particularly preferably, genes selected from the group of the ω-3-desaturases, Δ-4 desaturases, Δ-5 desaturases, Δ-6 desaturases, Δ-8 desaturases, Δ-9 desaturases, Δ-12 desaturases, Δ-6 elongases, Δ-5 elongases or Δ-9 elongases in combination with the previously mentioned genes for phospholipase A2, ketoacyl-CoA reductase and/or dehydratase are used, wherein it is possible to use individual genes or several genes in combination.

Due to the enzymatic activity of the nucleic acids used in the method according to the present invention that are coding for polypeptides or proteins exhibiting phospholipase A2, ketoacyl-CoA reductase or dehydratase activity, advantageously in combination with nucleic acid sequences coding for polypeptides or proteins of the fatty acid or lipid metabolism like further polypeptides or proteins exhibiting ω-3, Δ-4, Δ-5, Δ-6, Δ-8, Δ-12 desaturase activity or Δ-5, Δ-6 or Δ-9 elongase activity, most diverse polyunsaturated fatty acids can be produced in the method according to the present invention. Depending on the selection of the organisms used for the method according to the present invention, like the advantageous plants, mixtures of the different polyunsaturated fatty acids or individual polyunsaturated fatty acids like EPA or ARA can be produced in free or bound form. Thus, depending on the fatty acid composition prevailing in the original plant (C18:2 or C18:3 fatty acids), fatty acids will emerge which are derived from C18:2 fatty acids like GLA, DGLA or ARA, or which are derived from C18:3 fatty acids like SDA, ETA or EPA. If linoleic acid (=LA, C18:$2^{\Delta 9,12}$) is the only unsaturated fatty acid present in the plant used for the method, only GLA, DGLA and ARA can emerge as procedural products, which can be present as free fatty acids or in bound form. If α-linolenic acid (=ALA, C18:$3^{\Delta 9,12,15}$) is the only unsaturated fatty acid present in the plant used for the method, such as for example in flax, only SDA, ETA, EPA and/or DHA can emerge as procedural products, which can be present as free fatty acids or in bound form, as has been described above. By modifying the activity of the enzymes involved in the synthesis, like phospholipase A2, ketoacyl-CoA reductase and/or dehydratase, advantageously in combination with the ω-3, Δ-4, Δ-5, Δ-6, Δ-12 desaturase and/or Δ-6, Δ-5 elongase, or the Δ-4, Δ-5, Δ-8, Δ-12 desaturase, and/or Δ-9, Δ-5 elongase, individual products can be exclusively produced in the previously mentioned organisms, advantageously in the previously mentioned plants, in a targeted manner. Due to the activity of Δ-6 desaturase and Δ-6 elongase, for example GLA and DGLA or SDA and ETA will emerge, depending on the original plant and the unsaturated fatty acid. Preferably, DGLA or ETA or mixtures thereof will emerge. If the Δ-5 desaturase, the Δ-5 elongase and the Δ-4 desaturase are additionally introduced into the organisms, advantageously into the plant, thus ARA, EPA and/or DHA will additionally emerge. This also applies to organisms, into which Δ-8 desaturase and Δ-9 elongase had previously been introduced. Advantageously, only ARA, EPA or DHA or mixtures thereof are synthesized, depending on the fatty acid present in the organism or in the plant, which serves as original substance for the synthesis. As all this is about biosynthesis sequences, the respective final products are not present in form of pure substances in the organisms. In any case, there will always be contained small amounts of the precursor compounds in the final product. Said small amounts are less than 20 weight %, advantageously less than 15 weight %, particularly advantageously less than 10 weight %, in particular advantageously less than 5, 4, 3, 2 or 1 weight %, based on the final product DGLA, ETA or mixtures thereof, or ARA, EPA, DHA or mixtures thereof, advantageously EPA or DHA or mixtures thereof.

Beside the production of the starter fatty acids for the phospholipases A2, ketoacyl-CoA reductases or dehydratases of the present invention directly in the organism, the fatty acids can also be fed externally. For reasons of cost-effectiveness, the production in the organism is preferred. Preferred substrates of the phospholipase A2 are phospholipids, more specifically phosphatidylcholines and phosphatidylethanolamines, most preferably phosphatidylcholines with the fatty acids γ-linolenic acid (C18:$3^{\Delta 6,9,12}$), stearidonic acid (C18:$4^{\Delta 6,9,12,15}$) and eicosapentaenoic acid (C20:$5^{\Delta 5,8,11,14,17}$) at the sn-2 position. Preferred substrates of the ketoacyl-CoA reductase or dehydratase are the CoA esters of γ-linolenic acid (C18:$3^{\Delta 6,9,12}$), stearidonic acid (C18:$4^{\Delta 6,9,12,15}$), arachidonic acid (C20:$4^{\Delta 5,8,11,14}$) and eicosapentaenoic acid (C20:$5^{\Delta 5,8,11,14,17}$).

In Order to Increase the Yield of the Described Method for the Production of Oils and/or triglycerides having an advantageously increased content of polyunsaturated fatty acids, it is advantageous to increase the amount of the starter product for the synthesis of fatty acids. This can, for example, be achieved by introducing into the organism a nucleic acid coding for a polypeptide or protein with Δ-12 desaturase activity. This is particularly advantageous in oil-producing organisms such as the family of Brassicaceae like genus *Brassica*, for example rape; the family of the Elaeagnaceae like genus *Elaeagnus*, for example genus and species *Olea europaea* or the family Fabaceae like genus *Glycine*, for example genus and species *Glycine max*, which have a high content of oleic acid. As these organisms have only a low content of linoleic acid (Mikoklajczak et al., Journal of the American Oil Chemical Society, 38, 1961, 678-681), the use of the mentioned Δ-12 desaturases for producing the starter product linoleic acid is advantageous.

Preferably, in the method of the present invention, the previously mentioned nucleic acid sequences or derivatives or homologs thereof coding for polypeptides or proteins exhibiting phospholipase A2, ketoacyl-CoA reductase or dehydratase activity are used, which have retained the enzymatic activity of the proteins encoded by the nucleic acid sequences. Said sequences are cloned, either individually or in combination with the nucleic acid sequences coding for Δ-12 desaturase, Δ-4 desaturase, Δ-5 desaturase, Δ-8 desaturase, Δ-6 desaturase, Δ-5 elongase, Δ-6 elongase, Δ-9 elongase and/or ω-3 desaturase, into expression constructs and are used for introduction into and for expression in organisms. Due to their construction, said expression constructs enable an advantageous optimal synthesis of the polyunsaturated fatty acids produced in the method according to the present invention.

In a preferred embodiment, the method further comprises the step of obtaining a cell or an entire organism containing the nucleic acid sequences used in the method, wherein the cell and/or the organism is transformed with a nucleic acid sequence of the present invention coding for phospholipase A2, ketoacyl-CoA reductase and/or dehydratase, a gene construct or a vector as described in the following, either alone or in combination with further nucleic acid sequences coding for proteins of the fatty acid or lipid metabolism. In a further preferred embodiment, said method further comprises the step of extracting the oils, lipids, or free fatty acids from the organism or from the culture. The culture can be, for example, a fermentation culture, for example in case of the cultivation of microorganisms like, for example, *Mortierella, Thalassiosira, Mantoniella, Ostreococcus, Saccharomyces* or *Thraustochytrium*, or it can be a greenhouse or field culture of a plant. The cell or the organism thus obtained advantageously is a cell of an oil-producing organism like an oleaginous plant, like for example peanut, rape, canola, flax, hemp, soy, safflower, sunflowers or borage.

The term cultivation is understood to denote, for example, in case of plant cells, plant tissues or plant organs the cultivation thereof on or in a growth medium, or in case of the entire plant it means the cultivation on or in a substrate, for example in hydroponics, in potting soil, or on fertile soil.

In the sense of the present invention, "transgenic" or "recombinant", with respect to, for example, a nucleic acid sequence, an expression cassette (=gene construct), or a vector containing the nucleic acid sequence of the present invention, or an organism transformed with the nucleic acid sequence, the expression cassette, or the vector of the present invention, denotes all such constructions created by genetic engineering methods, wherein either a) the nucleic acid sequence of the present invention, or b) a genetic control sequence functionally linked to the nucleic acid sequence of the present invention, for example a promoter, or c) (a) and (b)

are not located in their natural genetic environment or have been modified by genetic engineering methods, wherein the modification can be, by way of example, a substitution, addition, deletion, inversion, or insertion of one or more nucleotide residues. "Natural genetic environment" denotes the natural genomic or chromosomal locus in the original organism or the presence in a genomic library. In case of a genomic library, the natural genetic environment of the nucleic acid sequence is preferably conserved, at least in part. The environment flanks the nucleic acid sequence at least at one side and has a sequence length of at least 50 bp, preferably of at least 500 bp, particularly preferably of at least 1,000 bp, and more particular preferably of at least 5,000 bp. A naturally occurring expression cassette—for example the naturally occurring combination of the natural promoter of the nucleic acid sequences of the present invention with the corresponding phospholipase A2, ketoacyl-CoA reductase or dehydratase genes—turns into a transgenic expression cassette if it is altered by non-natural, synthetic ("artificial") methods, for example a mutagenization. Corresponding methods are described, for example, in U.S. Pat. No. 5,565,350 or WO 00/15815.

In the sense of the present invention, "transgenic organism" or "transgenic plant" is understood to denote, as previously mentioned, that the nucleic acids used in the method are not located at their natural site in the genome of an organism. Herein, the nucleic acids can be expressed homologously or heterologously. However, as has already been mentioned, transgenic also denotes that the nucleic acids of the present invention are located at their natural site in the genome of an organism, but that the sequence has been altered as compared to the natural sequence and/or that the regulatory sequences have been altered as compared to the natural sequences. Preferably, "transgenic" is understood to denote the expression of the nucleic acids of the present invention at a non-natural site in the genome, i.e. a homologous or preferably heterologous expression of the nucleic acids exists. Preferred transgenic organisms are fungi like *Mortierella* or *Phytophthora*, mosses like *Physcomitrella*, algae like *Mantoniella, Euglena* or *Ostreococcus*, Diatomeae like *Thalassiosira* or *Crypthecodinium* or plants like the oil plants.

In principle, all organisms that are capable of synthesizing fatty acids, in particular unsaturated fatty acids, or that are suitable for the expression of recombinant genes are suitable as organisms or host organisms for the nucleic acids, expression cassettes, or vectors used in the method according to the present invention. By way of example, there are to be mentioned plants like *Arabidopsis*, Asteraceae like *Calendula* or cultured plants like soy, peanut, *ricinus*, sunflower, maize, cotton, flax, rape, coconut, oil palm, safflower (*Carthamus tinctorius*) or cocoa bean, microorganisms like fungi, for example the genus *Mortierella, Thraustochytrium, Saprolegnia, Phytophthora* or *Pythium*, bacteria like genus *Escherichia* or *Shewanella*, yeasts like genus *Saccharomyces, Cyanobacteria, ciliates*, algae like *Mantoniella, Euglena* or *Ostreococcus* or protozoa like dinoflagellates like *Thalassiosira* or *Crypthecodinium*. Preferred are organisms that are naturally capable of synthesizing oils in larger amounts, like fungi e.g. *Mortierella alpina, Pythium insidiosum, Phytophthora infestans* or plants like soy, rape, coconut, oil palm, safflower, flax, hemp, *Ricinus, Calendula*, peanut, cocoa bean or sunflower, or yeasts like *Saccharomyces cerevisiae*. Particularly preferred are soy, flax, rape, safflower, sunflower, *Calendula, Mortierella* or *Saccharomyces cerevisiae*. Beside the previously mentioned transgenic organisms, also transgenic animals, preferably non-human animals, are suitable as host organisms, for example *C. elegans, Ciona intestinalis* or *Xenopus laevis*.

Furthermore, utilizable host cells are mentioned in: Goeddel, Gene Expression Technology: Methods in Enzymology 185, Academic Press, San Diego, Calif. (1990).

Suitable expression strains like, for example, those strains comprising a lower protease activity, are described in: Gottesman, S., Gene Expression Technology: Methods in Enzymology 185, Academic Press, San Diego, Calif. (1990) 119-128.

Among the plant hosts are, advantageously, also plant cells and specific tissues, organs and plant parts in all their manifestations, like anthers, fibers, root hairs, stems, embryos, calli, cotyledons, petioles, harvest material, plant tissue, reproductive tissue and cell cultures, which are derived from the actual transgenic plant and/or can be used for generating the transgenic plant.

Advantageously, transgenic plants containing the polyunsaturated fatty acids synthesized in the method according to the present invention can be marketed directly, without the need for isolating the synthesized oils, lipids or fatty acids. In the method according to the present invention, plants are understood to denote entire plants as well as all plant organs or plant parts like leaf, stem, seed, root, tuber, anthers, fibers, root hairs, stalks, embryos, calli, cotyledons, petioles, harvest material, plant tissue, reproductive tissue or cell cultures, which are derived from the transgenic plant and/or can be used for generating the transgenic plant. Herein, seed comprises all seed parts like seed shells, epidermal and seed cells, endosperm or embryonic tissue. However, the compounds produced in the method according to the present invention can also be isolated from the organisms, preferably plants, in form of their oils, fats, lipids and/or free fatty acids. Polyunsaturated fatty acids produced by said method can be obtained by harvesting the organisms either from the culture, in which they grow, or from the field. This can be performed by pressing or extracting the plant parts, preferably the plant seeds. Herein, the oils, fats, lipids and/or free fatty acids can be obtained by so-called cold-rolling or cold pressing without heat supply while pressing. In order to make the plant parts, in particular the seeds, easier to disrupt, they are crushed, steamed or roasted beforehand. The seeds pretreated in this manner can subsequently be pressed or extracted by a solvent like warm hexane. Subsequently, the solvent is removed again. In the case of microorganisms, these are extracted after the harvest, for example, directly without further procedural steps or after lysis they are extracted via different methods known to the person skilled in the art. In this manner, more than 96% of the compounds produced in the method can be isolated. Subsequently, the products thus obtained are further processed, i.e. refined. Herein, for example, the plant slimes and turbidizing substances are first removed. This so-called desliming can be performed enzymatically or, for example, chemico-physically by adding an acid like phosphoric acid. After that the free fatty acids are removed by treatment with a base, for example sodium hydroxide solution. In order to remove the alkaline solution still present in the product, the product obtained is thoroughly washed with water and then dried. In order to remove the dyes still contained in the product, the products are subjected to bleaching, for example with fuller's earth or activated carbon. Finally, the product is deodorized, for example with water vapor.

Preferably, the PUFAs or LCPUFAs produced by said method are $C_{18}$, $C_{20}$ or $C_{22}$ fatty acid molecules, advantageously $C_{20}$ or $C_{22}$ fatty acid molecules having at least two double bonds in the fatty acid molecule, preferably three, four, five, or six double bonds. These $C_{18}$, $C_{20}$ or $C_{22}$ fatty acid molecules can be isolated from the organism as an oil, a lipid, or a free fatty acid. Suitable organisms are, for example, the previously mentioned organisms. Preferred organisms are transgenic plants.

Thus, one embodiment of the present invention are oils, lipids, fatty acids or fractions thereof which have been produced by the method described in the above, particularly preferably oil, lipid or a fatty acid composition, comprising PUFAs and originating from transgenic plants.

As described in the above, these oils, lipids or fatty acids advantageously contain 6 to 15% palmitic acid, 1 to 6% stearic acid; 7 to 85% oleic acid; 0.5 to 8% vaccenic acid, 0.1 to 1% arachinic acid, 7 to 25% saturated fatty acids, 8 to 85% monounsaturated fatty acids and 60 to 85% polyunsaturated fatty acids, in each case related to 100% and based on the total fatty acid content of the organisms. As advantageous polyunsaturated fatty acid, the fatty acid esters or fatty acid mixtures advantageously contain at least 0.1; 0.2; 0.3; 0.4; 0.5; 0.6; 0.7; 0.8; 0.9 or 1% arachidonic acid, EPA and/or DHA, based on the total fatty acid content. Furthermore, the fatty acid esters or fatty acid mixtures produced according to the method of the present invention advantageously contain fatty acids selected from the following group of fatty acids: erucic acid (13-docosaenoic acid), sterculinic acid (9,10-methylene octadec-9-enoic acid), malvalinic acid (8,9-methylene heptadec-8-enoic acid), chaulmoogrinic acid (cyclopentene-dodecanoic acid), furan fatty acid (9,12-epoxy-octadeca-9,11-dienoic acid), vernolic acid (9,10-epoxyoctadec-12-enoic acid), taric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselinic acid (cis-6-octadecenoic acid), 9c,12t-octadecadienoic acid, calendulic acid (8t10t12c-octadecatrienoic acid), catalpic acid (9c11t13c-octadecatrienoic acid), eleostearinic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienoic acid), ricinolic acid (12-hydroxy-9c-octadecenoic acid) and/or coriolic acid (13-hydroxy-9c,11t-octadecadienoic acid). Advantageously, the previously mentioned fatty acids are normally present in the fatty acid esters or fatty acid mixtures produced according to the method of the present invention only in traces, i.e. they are present, as related to the total content of fatty acids, by less than 30%, preferably by less than 25%, 24%, 23%, 22% or 21%, particularly preferably by less than 20%, 15%, 10%, 9%, 8%, 7%, 6% or 5%, especially preferably by less than 4%, 3%, 2% or 1%. Advantageously, the fatty acid esters or fatty acid mixtures produced according to the method of the present invention contain, based on the total content of fatty acids, less than 0.1% or none of butyric acid, no cholesterol, no clupanodonic acid (=docosapentaenoic acid, C22:$5^{\Delta 4,8,12,15,21}$) and no nisinic acid (tetracosahexaenoic acid, C23:$6^{\Delta 3,8,12,15,18,21}$).

Advantageously, the oils, lipids or fatty acids produced in the method according to the present invention contain at least 0.5%, 1%, 2%, 3%, 4% or 5%, advantageously at least 6%, 7%, 8%, 9% or 10%, particularly advantageously at least 11%, 12%, 13%, 14% or 15% ARA or at least 0.5%, 1%, 2%, 3%, 4% or 5%, advantageously at least 6% or 7%, particularly advantageously at least 8%, 9% or 10% EPA and/or DHA, based on the total fatty acid content of the production organism, advantageously of a plant, particularly advantageously of an oil plant like soy, rape, coconut, oil palm, safflower, flax, hemp, *ricinus, Calendula*, peanut, cocoa bean, sunflower or of the previously mentioned further monocotyledonous or dicotyledonous oil plants.

A further embodiment of the present invention is the use of said oils, lipids, fatty acids and/or fatty acid compositions in feed, food, cosmetics, or pharmaceuticals. The oils, lipids, fatty acids or fatty acid mixtures of the present invention can be used in a manner known to the person skilled in the art for mixing with other oils, lipids, fatty acids or fatty acid mixtures of animal origin, like for example fish oils. Said oils, lipids, fatty acids or fatty acid mixtures consisting of plant and animal components can also be used for producing feed, food, cosmetics or pharmaceuticals.

The term "oil", "lipid" or "fat" is understood to denote a fatty acid mixture containing unsaturated, saturated, preferably esterified fatty acid/s. It is preferred that the oil, lipid or fat has a high content of polyunsaturated free or advantageously esterified fatty acid/s, in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. Preferably, the proportion of unsaturated esterified fatty acids is about 30%, more preferred is a proportion of 50%, even more preferred is a proportion of 60%, 70%, 80% or more. For evaluation, for example, the proportion of fatty acid after converting the fatty acids into the methyl esters by transesterification can be gas-chromatographically determined. The oil, lipid or fat can contain various other saturated or unsaturated fatty acids, for example calendulic acid, palmitic, palmitoleic, stearic, oleic acid etc. In particular, depending on the starter organism, the proportion of the different fatty acids in the oil or fat may vary.

The polyunsaturated fatty acids, which are produced in the method and advantageously have at least two double bonds, are, as described in the above, for example sphingolipids, phosphoglycerides, lipids, glycolipids, phospholipids, monoacylglycerol, diacylglycerol, triacylglycerol or other fatty acid esters.

From the polyunsaturated fatty acids, which have been produced in the method according to the present invention in this manner and which advantageously have at least five or six double bonds, the contained polyunsaturated fatty acids can, for example, be released via alkaline treatment, for example aqueous KOH or NaOH, or acidic hydrolysis, advantageously in the presence of an alcohol like methanol or ethanol, or via enzymatic cleavage and they can be isolated, for example, via phase separation and subsequent acidification via e.g. $H_2SO_4$. Releasing the fatty acids can also be performed directly, without the previously described processing.

The nucleic acids used in the method can, after introduction into an organism, advantageously a plant cell or plant, either be located on a separate plasmid or advantageously be integrated into the genome of the host cell. In case of integration into the genome, said integration can take place at random or by such a recombination that will cause substitution of the native gene for the introduced copy, whereby the production of the desired compound is modulated by the cell or by using a gene in trans, so that the gene is functionally linked to a functional expression unit containing at least one sequence ensuring the expression of a gene and at least one sequence ensuring the polyadenylation of a functionally transcribed gene. Preferably, the nucleic acids are introduced into the organisms via multi-expression cassettes or via constructs for multi-parallel expression, advantageously for multi-parallel seed-specific expression, of genes into the plants.

As substrates of the nucleic acids used in the method according to the present invention, which code for polypeptides or proteins exhibiting phospholipase A2, ketoacyl-CoA reductase and/or dehydratase activity and/or the further nucleic acids used, like the nucleic acids coding for polypeptides or proteins of the fatty acid or lipid metabolism, selected from the group of Δ-12 desaturase(s), Δ-9 elongase(s), Δ-8 desaturase(s), Δ-6 desaturase(s), Δ-6 elongase(s), Δ-5 desaturase(s), Δ-5 elongase(s), ω-3 desaturase(s), Δ-4 desaturase(s), acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-Coenzyme A carboxylase(s), acyl-Coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s), $C_{16}$, $C_{18}$, $C_{20}$ or $C_{22}$ fatty acids are advantageously suitable. Preferably, the fatty acids converted as substrates in the method are converted in form of their acyl-CoA esters and/or their phospholipid esters.

For producing the long-chain PUFAs of the present invention, the polyunsaturated $C_{18}$ fatty acids first have to be desaturated by the enzymatic activity of a desaturase and subsequently be elongated by at least two carbon atoms via an elongase. After one elongation cycle, said enzymatic activity will lead to $C_{20}$ fatty acids and after two elongation cycles to $C_{22}$ fatty acids. The activity of the desaturases and elongases used in the method according to the present invention preferably leads to $C_{18}$, $C_{20}$ and/or $C_{22}$ fatty acids, advantageously having at least two double bonds in the fatty acid molecule, preferably having three, four, five or six double bonds, particularly preferably it leads to $C_{20}$ and/or $C_{22}$ fatty acids having at least two double bonds in the fatty acid molecule, preferably having three, four, five or six double bonds, in particular preferably having five or six double bonds in the molecule. After a first desaturation and the elongation have taken place, further desaturation and elongation steps, like for example such a desaturation in the Δ-5- and Δ-4 positions, can be performed. Particularly preferred as products of the method according to the present invention are dihomo-γ-linolenic acid, arachidonic acid, eicosapentaenoic acid, docosapentaenoic acid and/or docosahexaenoic acid. The $C_{20}$ fatty acids having at least two double bonds in the fatty acid can be elongated by means of enzymatic activities in form of the free fatty acid or in form of the esters like phospholipids, glycolipids, sphingolipids, phosphoglycerides, monoacylglycerol, diacylglycerol or triacylglycerol.

The preferred site of biosynthesis of fatty acids, oils, lipids, or fats in the advantageously used plants is, for example, generally in the seed or in cell layers of the seed so that a seed-specific expression of the nucleic acids used in the method is appropriate. It is, however, obvious that the biosynthesis of fatty acids, oils, or lipids does not have to be restricted to the seed tissue, but can also take place in all other parts of the plant—for example in epidermal cells or in the tubers—in a tissue-specific manner.

If microorganisms like yeasts like *Saccharomyces* or *Schizosaccharomyces*, fungi like *Mortierella, Aspergillus, Phytophthora, Entomophthora, Mucor* or *Thraustochytrium* or algae like *Isochrysis, Mantoniella, Euglena, Ostreococcus, Phaeodactylum* or *Crypthecodinium* are used as organisms in the method according to the present invention, said organisms are advantageously cultivated by fermentation.

By the method according to the present invention, the polyunsaturated fatty acids produced can, in principle, be increased in the organisms used in the method in two ways. Preferably, the pool of free polyunsaturated fatty acids and/or the content of the esterified polyunsaturated fatty acids produced via the method can be increased. Advantageously, the pool of esterified polyunsaturated fatty acids is increased in the transgenic organisms by the method according to the present invention.

If microorganisms are used as organisms in the method according to the present invention, they are grown or cultured in a manner known to the person skilled in the art, depending on the host organism. Normally, microorganisms are cultivated in a liquid medium containing a carbon source, mostly in form of sugars, a nitrogen source, mostly in form of organic nitrogen sources like yeast extract or salts like ammonium sulfate, trace elements like iron, manganese, magnesium salts, and optionally vitamins at temperatures between 0° C. and 100° C., preferably between 10° C. and 60° C. under oxygen transfer. Herein, the pH value of the liquid culture medium may or may not be kept at a fixed value, i.e. is regulated during cultivation. Cultivation can be performed batchwise, semi-batchwise or continuously. Nutrients can be added at the beginning of the fermentation or they can be added semi-continuously or continuously during cultivation. The polyunsaturated fatty acids produced can be isolated from the organisms according to methods known to the person skilled in the art, as described in the above, for example via extraction, distillation, crystallization, optionally salt precipitation and/or chromatography. To this end, the organisms can advantageously be disrupted beforehand.

In case the host organisms are microorganisms, the method according to the present invention will advantageously be performed at a temperature between 0° C. and 95°, preferably between 10° C. and 85° C., particularly preferably between 15° C. and 75° C., and especially preferably between 15° C. and 45° C.

Herein, the pH value is advantageously maintained between pH 4 and 12, preferably between pH 6 and 9, particularly preferably between pH 7 and 8.

The method according to the present invention can be performed batchwise, semi-batchwise or continuously. A summary of known cultivation methods can be found in the textbook by Chmiel (Bioprozeßtechnik 1. Einführung in die Bioverfahrenstechnik (Gustav Fischer Verlag, Stuttgart, Germany, 1991)) or in the textbook by Storhas (Bioreaktoren und periphere Einrichtungen (Vieweg Verlag, Braunschweig/Wiesbaden, Germany, 1994)).

The culture medium to be used has to suitably meet the requirements of the respective strains. Descriptions of culture media for different microorganisms are contained in the "Manual of Methods for General Bacteriology" by the American Society for Bacteriology (Washington D.C., USA, 1981).

As has been described in the above, said media suitable for the present invention usually comprise one or more carbon sources, nitrogen sources, inorganic salts, vitamins and/or trace elements.

Preferred carbon sources are sugars like mono-, di- or polysaccharides. Very effective carbon sources are, for example, glucose, fructose, mannose, galactose, ribose, sorbose, ribulose, lactose, maltose, sucrose, raffinose, starch or cellulose. Sugar can also be added to the media via complex compounds like molasses or other by-products of sugar refinement. It can also be advantageous to add mixtures of different carbon sources. Other possible carbon sources are oils and fats like, for example, soy oil, sunflower oil, peanut oil and/or coconut oil, fatty acids like, for example, palmitic acid, stearic acid and/or linoleic acid, alcohols and/or polyalcohols like, for example, glycerol, methanol and/or ethanol and/or organic acids like, for example, acetic acid and/or lactic acid.

Nitrogen sources usually are organic or inorganic nitrogen compounds or materials containing said compounds. Exemplary nitrogen sources comprise ammonia in liquid or gaseous form or ammonium salts like ammonium sulfate, ammonium chloride, ammonium phosphate, ammonium carbonate or ammonium nitrate, nitrates, urea, amino acids or complex nitrogen sources like corn steep liquor, soy flour, soy protein, yeast extract, meat extract and others. The nitrogen sources can be used individually or in form of a mixture.

Inorganic salt compounds that can be contained in the media comprise the chloride, phosphorus or sulfate salts of calcium, magnesium, sodium, cobalt, molybdenum, potassium, manganese, zinc, copper and iron.

As sulfur source for the production of sulfur-containing fine chemicals, in particular of methionine, inorganic sulfur-containing compounds like, for example, sulfates, sulfites, dithionites, tetrathionates, thiosulfates, sulfides, but also organic sulfur compounds like mercaptans and thiols can be used.

As phosphor sources, phosphoric acid, potassium dihydrogen phosphate or dipotassium hydrogen phosphate or the corresponding sodium-containing salts can be used.

Chelating agents can be added to the medium in order to keep the metal ions in solution. Particularly suitable chelating agents comprise dihydroxyphenols like catechol or protocatechuate or organic acids like citric acid.

The fermentation media used according to the present invention for cultivating microorganisms usually also contain other growth factors like vitamins or growth stimulators, among which are, for example, biotin, riboflavin, thiamine, folic acid, nicotinic acid, pantothenate and pyridoxine. Growth factors and salts frequently originate from complex media components like yeast extract, molasses, corn steep liquor and the like. Moreover, suitable precursors can be added to the culture medium. The exact composition of the media compounds strongly depends on the respective experiment and is selected individually for each specific case. Information on media optimization can be obtained from the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, like Standard 1 (Merck) or BHI (Brain heart infusion, DIFCO) and the like.

All media components are sterilized either by heat (20 min at 1.5 bar and 121° C.) or by sterile filtration. The components can either be sterilized together or, if necessary, separately. All media components can be present at the beginning of the cultivation or can optionally be added continuously or batchwise.

Normally, the temperature of the culture lies between 15° C. and 45° C., preferably at 25° C. to 40° C., and can be kept constant or be altered during the experiment. The pH value of the medium should lie within a range from 5 to 8.5, preferably about 7.0. The pH value for cultivation can be controlled during cultivation by adding alkaline compounds like sodium hydroxide, potassium hydroxide, ammonia or ammonia water, or acidic compounds like phosphoric acid or sulfuric acid. In order to control foam formation, anti-foaming agents like, for example, fatty acid polyglycol esters can be used. In order to maintain the stability of plasmids, suitable selectively acting substances can be added to the medium, like for example antibiotics. In order to maintain aerobic conditions, oxygen and oxygen-containing gas mixtures, like for example ambient air, are brought into the culture. The temperature of the culture normally lies between 20° C. and 45° C., and preferably between 25° C. and 40° C. Cultivation is continued until a maximum of the desired product has formed. This goal is normally reached within 10 hours to 160 hours.

The fermentation broths thus obtained, in particular containing polyunsaturated fatty acids, usually have a dry mass of 7.5 to 25 weight %.

Subsequently, the fermentation broth can be further processed. According to the requirements, the biomass can be removed from the fermentation broth completely or partially by separation methods like, for example, centrifugation, filtration, decanting or a combination of said methods, or the entire biomass can remain in the broth. Advantageously, the biomass is processed after separation.

However, the fermentation broth can also be thickened or concentrated, without cell separation, by known methods, like for example with the aid of a rotary evaporator, thin film evaporator, drop film evaporator, by reverse osmosis, or by nanofiltration. Said concentrated fermentation broth can subsequently be processed in order to recover the fatty acids contained therein.

The fatty acids obtained in the method are also suitable as starting material for the chemical synthesis of further valuable products. They can, for example, be used in combination or individually for producing pharmaceuticals, food, animal feed, or cosmetics.

A further object of the present invention are isolated nucleic acid sequences coding for polypeptides or proteins exhibiting phospholipase A2, ketoacyl-CoA reductase and/or dehydratase activity.

An object of the present invention are isolated nucleic acid sequences coding for polypeptides or proteins exhibiting phospholipase A2 activity, selected from the group of:
a) a nucleic acid sequence having the sequence depicted in SEQ ID NO: 1,
b) nucleic acid sequences which can be derived due to the degenerate genetic code from the amino acid sequence depicted in SEQ ID NO: 2, or
c) derivatives of the nucleic acid sequence depicted in SEQ ID NO: 1 coding for polypeptides or proteins having at least 40% identity with SEQ ID NO: 2 on the amino acid level and exhibiting phospholipase A2 activity.

A further object of the present invention are isolated nucleic acid sequences coding for polypeptides or proteins exhibiting ketoacyl-CoA reductase activity, selected from the group of:
a) a nucleic acid sequence having the sequence depicted in SEQ ID NO: 3,
b) nucleic acid sequences which can be derived due to the degenerate genetic code from the amino acid sequence depicted in SEQ ID NO: 4, or
c) derivatives of the nucleic acid sequence depicted in SEQ ID NO: 3 coding for polypeptides or proteins having at least 40% identity with SEQ ID NO: 4 on the amino acid level and exhibiting ketoacyl-CoA reductase activity.

A further object of the present invention are isolated nucleic acid sequences coding for polypeptides or proteins exhibiting dehydratase activity, selected from the group of:
a) a nucleic acid sequence having the sequence depicted in SEQ ID NO: 5 or SEQ ID NO: 7,
b) nucleic acid sequences which can be derived as a result of the degenerate genetic code from the amino acid sequences depicted in SEQ ID NO: 6 or SEQ ID NO: 8, or
c) derivatives of the nucleic acid sequences depicted in SEQ ID NO: 5 or SEQ ID NO: 7 coding for polypeptides or proteins having at least 40% identity with SEQ ID NO: 6 or SEQ ID NO: 8 on the amino acid level and exhibiting dehydratase activity.

A further object of the present invention are gene constructs containing the nucleic acid sequences SEQ ID NO: 1, SEQ ID NO: 3, SEQ ID NO: 5 or SEQ ID NO: 7 of the present invention, wherein the nucleic acid is functionally linked to one or more regulatory signals. In addition, further biosynthesis genes of the fatty acid or lipid metabolism can be contained in the gene construct, which are selected from the group: Δ-4 desaturase(s), Δ-5 desaturase(s), Δ-6 desaturase(s), Δ-8 desaturase(s), Δ-12 desaturase(s), Δ-6 elongase(s), Δ-5 elongase(s), Δ-9 elongase(s), ω-3 desaturase(s), acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s). Advantageously, there are additionally contained biosynthetic genes of the fatty acid or lipid metabolism, selected from the group of Δ-4 desaturase, Δ-5 desaturase, Δ-6 desaturase, Δ-8 desaturase, Δ-9 desaturase, Δ-12 desaturase, Δ-6 elongase, Δ-5 elongase, Δ-9 elongase or ω-3 desaturase.

Mosses and algae are the only known plant systems producing considerable amounts of polyunsaturated fatty acids like arachidonic acid (ARA) and/or eicosapentaenoic acid (EPA) and/or docosahexaenoic acid (DHA). Mosses contain PUFAs in membrane lipids, whereas algae, organisms related to algae, and some fungi also accumulate considerable amounts of PUFAs in the triacylglycerol fraction. Thus, nucleic acid molecules isolated from such strains also accumulating PUFAs in the triacylglycerol fraction are particularly advantageous for the method according to the present invention and therefore for modifying the lipid and PUFA production system in a host.

Therefore, the nucleic acids used in the method according to the present invention advantageously originate from plants like algae, for example, algae of the class of Prasinophyceae, like from genera *Heteromastix, Mammella, Mantoniella, Micromonas, Nephroselmis, Ostreococcus, Prasinocladus, Prasinococcus, Pseudoscourfielda, Pycnococcus, Pyramimonas, Scherffelia* or *Tetraselmis* like genera and species *Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus* sp. *Prasinocladus ascus, Prasinocladus lubricus, Pycnococcus provasolii, Pyramimonas amylifera, Pyramimonas disomata, Pyramimonas obovata, Pyramimonas orientalis, Pyramimonas parkeae, Pyramimonas spinifera, Pyramimonas* sp., *Tetraselmis apiculata, Tetraselmis carteriaformis, Tetraselmis chui, Tetraselmis convolutae, Tetraselmis desikacharyl, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa* fo. *rubens* or *Tetraselmis* sp. or from algae of the family Pythiaceae or the family Euglenaceae like from genera *Ascoglena, Astasia, Colacium, Cyclidiopsis, Euglena, Euglenopsis, Hyalophacus, Khawkinea, Lepocinclis, Phacus, Strombomonas* or

*Trachelomonas* like genera and species *Euglena acus, Euglena geniculata, Euglena gracilis, Euglena mixocylindracea, Euglena rostrifera, Euglena viridis, Colacium stentorium, Trachelomonas cylindrica* or *Trachelomonas volvocina*. Preferably, the nucleic acids used originate from algae of the genera *Euglena, Mantoniella* or *Ostreococcus*.

Further advantageous plants are algae like *Isochrysis* or *Crypthecodinium*, Diatomeae like *Thalassiosira, Crypthecodinium* or *Phaeodactylum*, mosses like *Physcomitrella* or *Ceratodon* as well as higher plants like *Muscarioides, Borago*, Primulaceae like *Aleuritia, Calendula stellata, Osteospermum spinescens* or *Osteospermum hyoseroides*. Also advantageous are microorganisms like fungi such as Phycomycota like *Thraustochytrium, Aspergillus, Phytophthora, Entomophthora, Mucor, Fusarium, Phytophthora* or *Mortierella*, yeasts like *Saccharomyces* as well as bacteria like *Shewanella*.

Also advantageous are *protista, ciliates, dinoflagellates* as well as non-human animals like nematodes like *Caenorhabditis, Ciona, Xenopus*, insects, sea cucumbers or fish, preferably from the order of Salmoniformes like the family of Salmonidae like genus *Salmo*, for example from genera and species *Oncorhynchus mykiss, Trutta trutta* or *Salmo trutta fario*. Advantageously, the isolated nucleic acid sequences of the present invention originate from an animal from the order of vertebrates. Preferably, the nucleic acid sequences originate from the class of Vertebrata; *Euteleostomi, Actinopterygii; Neopterygii; Teleostei; Euteleostei, Protacanthopterygii, Salmoniformes; Salmonidae* or *Oncorhynchus*, respectively, or *Vertebrata, Amphibia, Anura, Pipidae, Xenopus* or *Evertebrata* like *Protochordata, Tunicata, Holothuroidea, Cionidae* like *Amaroucium constellatum, Botryllus schlosseri, Ciona intestinalis, Molgula citrina, Molgula manhattensis, Perophora viridis* or *Styela partita*.

The nucleic acid sequences used in the method coding for proteins exhibiting phospholipase A2, ketoacyl-CoA reductase or dehydratase activity are advantageously introduced individually or preferably in combination with one another or with other nucleic acid sequences coding for proteins exhibiting ω-3 desaturase, Δ-4 desaturase, Δ-5 desaturase, Δ-6 desaturase, Δ-8 desaturase, Δ-12 desaturase, Δ-5 elongase, Δ-6 elongase or Δ-9 elongase activity in an expression cassette (=nucleic acid construct) enabling the expression of the nucleic acids in an organism, advantageously in a plant or a microorganism. The nucleic acid construct may contain more than one nucleic acid sequence of an enzymatic activity, like for example phospholipase A2, ketoacyl-CoA reductase, dehydratase, Δ-12 desaturase, Δ-4 desaturase, Δ-5 desaturase, Δ-6 desaturase, Δ-5 elongase, Δ-6 elongase and/or ω-3 desaturase.

For introduction, the nucleic acids used in the method are advantageously subjected to an amplification and ligation in a known manner. Preferably, this is conducted following the protocol for Pfu-DNA polymerase or for a Pfu/Taq-DNA polymerase mixture. The primers are selected with respect to the sequence to be amplified. Suitably, the primers should be selected in such a way that the amplicon comprises the entire codogenic sequence from the start to the stop codon. Subsequently to amplification, the amplicon is suitably analyzed. Analysis with respect to quality and quantity can, for example, be conducted after gel electrophoretic separation. Subsequently, the amplicon can be purified according to a standard protocol (for example Qiagen). An aliquot of the purified amplicon is then available for subsequent cloning. Suitable cloning vectors are generally known to the person skilled in the art. Among those are, in particular, vectors that can be replicated in microbial systems, i.e. in particular vectors ensuring an efficient cloning in yeasts or fungi and enabling the stable transformation of plants. In particular, there are to be mentioned different binary and co-integrated vector systems suitable for T-DNA-mediated transformation. Normally, such vector systems are characterized in that they contain at least the vir genes required for the transformation mediated by agrobacteria as well as the T-DNA border sequences. Preferably, said vector systems also comprise further cis-regulatory regions like promoters and terminators and/or selection markers, by which it is possible to identify correspondingly transformed organisms. While vir genes and T-DNA sequences are arranged on the same vector in co-integrated vector systems, binary systems are based on at least two vectors, one of which bears vir genes but no T-DNA and the second of which bears T-DNA but no vir gene. Thus, the latter vectors are comparatively small, easy to manipulate and can be replicated both in *E. coli* and in *agrobacterium*. Among those binary vectors are vectors of the series pBIB-HYG, pPZP, pBecks, and pGreen. According to the present invention, the use of Bin19, pBI101, pBinAR, pGPTV, and pCAMBIA is preferred. A survey of binary vectors and uses thereof is provided by Hellens et al., Trends in Plant Science (2000) 5, 446-451. For vector preparation, the vectors can first be linearized with restriction endonuclease/s and then enzymatically modified in a suitable manner. Subsequently, the vector is purified and an aliquot is used for cloning. During cloning, the enzymatically cleaved and, if needed, purified amplicon is cloned with similarly prepared vector fragments using a ligase. Herein, a specific nucleic acid construct or vector or plasmid construct may have one or also several codogenic gene segments. Preferably, the codogenic gene segments in said constructs are functionally linked to regulatory sequences. Among said regulatory sequences are, in particular, plant sequences like the promoters and terminators described in the above. Advantageously, the constructs can be stably propagated in microorganisms, in particular in *Escherichia coli* and *Agrobacterium tumefaciens*, under selective conditions and they enable a transfer of heterologous DNA into plants or microorganisms.

While advantageously using cloning vectors, the nucleic acids used in the method, the nucleic acids according to the present invention, and nucleic acid constructs can be introduced into organisms like microorganisms, or preferably plants, and can therefore be used for plant transformation, just like those published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, p. 15-38; B. Jenes et al., Techniques for Gene Transfer, in: Transgenic Plants, Vol. 1, Engineering and Utilization, Ed.: Kung and R. Wu, Academic Press (1993), p. 128-143; Potrykus, Annu. Rev. Plant Physiol. Plant Molec. Biol. 42 (1991), 205-225)). The nucleic acids used in the method, the nucleic acids and nucleic acid constructs and/or vectors according to the present invention can therefore be used for altering a wide range of organisms by genetic engineering methods, advantageously of plants, so that they become better and/or more efficient producers of PUFAs.

There is a variety of mechanisms enabling an alteration of the phospholipase A2, ketoacyl-CoA reductase or dehydratase protein of the present invention and of further proteins used in the method, like Δ-12 desaturase, Δ-9 elongase, Δ-6 desaturase, Δ-8 desaturase, Δ-6 elongase, Δ-5 desaturase, Δ-5 elongase or Δ-4 desaturase proteins, so that the yield, the production, and/or the efficiency of the production of the advantageously polyunsaturated fatty acids in a plant, preferably in an oil plant or a microorganism, can be directly influenced due to said altered protein. The number or activity of the phospholipase A2, ketoacyl-CoA reductase, dehydratase, Δ-12 desaturase, ω-3 desaturase, Δ-9 elongase, Δ-6 desaturase, Δ-8 desaturase, Δ-6 elongase, Δ-5 desaturase, Δ-5 elongase and/or Δ-4 desaturase proteins and/or genes can be increased, so that larger quantities of the gene products and therefore, to the end, larger quantities of the compounds of the general formula I can be produced. A de novo synthesis in an organism lacking the activity and capability for the biosynthesis of the compounds before introducing the corresponding gene/s is also possible.

Correspondingly, this also applies to the combination with further desaturases or elongases or further enzymes from the fatty acid and lipid metabolism. Herein, the use of various divergent sequences, i.e. sequences different on the DNA sequence level, or the use of promoters for gene expression, which enables a different time-dependent gene expression, for example, depending on the degree of ripeness of a seed or of an oil storage tissue, can be advantageous.

By introducing a phospholipase A2, ketoacyl-CoA reductase, dehydratase, Δ-12 desaturase, ω-3 desaturase, Δ-9 elongase, Δ-6 desaturase, Δ-8 desaturase, Δ-6 elongase, Δ-5 desaturase, Δ-5 elongase and/or Δ-4 desaturase gene into an organism individually or in combination with other genes in a cell, not only the biosynthetic flow toward the final product can be increased, but also the corresponding triacylglycerol composition can be increased or established de novo. Likewise, the number or activity of other genes involved in the import of nutrients that are required for the biosynthesis of one or more fatty acids, oils, polar and/or neutral lipids can be increased, so that the concentration of said precursors, cofactors or intermediate compounds within the cells or within the storage compartment is increased, whereby the cells' capability of producing PUFAs, as described in the following, is further enhanced. By optimizing the activity or increasing the number of one or more phospholipase A2, ketoacyl-CoA reductase, dehydratase, Δ-12 desaturase, ω-3 desaturase, Δ-9 elongase, Δ-6 desaturase, Δ-8 desaturase, Δ-6 elongase, Δ-5 desaturase, Δ-5 elongase and/or Δ-4 desaturase genes that are involved in the biosynthesis of said compounds or by eliminating the activity of one or more genes that are involved in the degradation process of said compounds, it can be possible to increase the yield, the production and/or the efficiency of the production of fatty acid and lipid molecules from organisms and advantageously from plants.

The isolated nucleic acid molecules used in the method according to the present invention code for proteins or for parts thereof, wherein the proteins or the individual protein or parts thereof contain an amino acid sequence that is sufficiently homologous to an amino acid sequence depicted in the sequences SEQ ID NO: 2, SEQ ID NO: 4, SEQ ID NO: 6 or SEQ ID NO: 8, so that the proteins or parts thereof still possess phospholipase A2, ketoacyl-CoA reductase or dehydratase activity. Preferably, the proteins or parts thereof that are encoded by the nucleic acid molecule/s still have their substantial enzymatic activity and the capability of participating in the metabolism of compounds that are required for synthesis of cell membranes or lipid particles in organisms, advantageously in plants, or of participating in the transport of molecules across said membranes. Preferably, the proteins encoded by the nucleic acid molecules are identical to the amino acid sequences depicted in SEQ ID NO: 2, SEQ ID NO: 4, SEQ ID NO: 6 or SEQ ID NO: 8 by at least about 30%, 35%, 40%, 45% or 50%, preferably by at least about 55% or 60%, more preferably by at least about 70%, 80% or 90%, and most preferably by at least about 85%, 86%, 87%, 88%, 89%, 90%, 91%, 92%, 93%, 94%, 95%, 96%, 97%, 98%, 99% or more. In the sense of the present invention, "homology" or "homologous" is synonymous to identity or identical, respectively.

Homology was calculated over the entire amino acid or nucleic acid sequence region. For comparing different sequences, the person skilled in the art has at his disposal a variety of programs based on different algorithms. Herein, the algorithms by Needleman and Wunsch or Smith and Waterman yield particularly reliable results. For the sequence comparisons the program Pile Up (J. Mol. Evolution. (1987) 25:351-360; Higgins et al., (1989) CABIOS 5:151-153) was used or the programs Gap and Best Fit (Needleman and Wunsch (1970) J. Mol. Biol., 48:443-453, and Smith and Waterman Adv., Appl. Math., 2, 482-489 (1981)), which are contained in the GCG Software Package [Genetics Computer Group, 575 Science Drive, Madison, Wis., USA 53711 (1991)]. The sequence homology values, which are given as percent values in the above, were determined with the program GAP over the entire sequence region with the following settings: Gap Weight: 8, Length Weight: 2, Average Match: 2.778 and Average Mismatch: −2.248. Unless stated otherwise, these settings were always used as standard settings for sequence comparisons.

"Substantial enzymatic activity" of the phospholipase A2, ketoacyl-CoA reductase or dehydratase used in the method according to the present invention is understood to denote that, as compared to the proteins/enzymes encoded by the sequence having SEQ ID NO: 1, SEQ ID NO: 3, SEQ ID NO: 5 or SEQ ID NO: 7 or by derivatives thereof, they still exhibit an enzymatic activity of at least 10%, preferably 20%, particularly preferably 30% and in particular preferably 40% and are thus capable of participating in the metabolism of compounds required for the synthesis of fatty acids, fatty acid esters like diacylglycerides and/or triacylglycerides in an organism, advantageously in a plant or plant cell, or of participating in the transmembrane transport of molecules, which is understood to denote $C_{18}$, $C_{20}$ or $C_{22}$ carbon chains in the fatty acid molecule with double bonds at least two, advantageously three, four, five or six positions.

Alternatively, nucleotide sequences that code for a phospholipase A2, ketoacyl-CoA reductase or dehydratase and that advantageously hybridize, under stringent conditions, to a nucleotide sequence as depicted in SEQ ID NO: 1, SEQ ID NO: 3, SEQ ID NO: 5 or SEQ ID NO: 7 can be used in the method of the present invention.

Advantageously, the nucleic acid sequences used in the method are introduced into an expression cassette, which enables the expression of the nucleic acid in organisms like microorganisms or plants.

Herein, the nucleic acid sequences coding for phospholipase A2, ketoacyl-CoA reductase or dehydratase are functionally linked to one or more regulatory signals, advantageously in order to enhance gene expression. These regulatory sequences are supposed to enable targeted expression of the genes and the proteins. Depending on the host organisms, this can denote, for example, that the gene is expressed and/or overexpressed only after induction or that it is expressed and/or overexpressed at once. Said regulatory sequences are, for example, sequences binding to inducers or repressors and thus regulating the expression of the nucleic acid. In addition to said novel regulatory sequences or instead of said sequences, the natural regulation of said sequences can still be present before the actual structure genes and likewise can have been genetically engineered in a manner that the natural regulation has been switched off and the expression of the genes has been increased. However, the expression cassette (=expression construct=gene construct) can also be of a simpler structure, i.e. no additional regulatory signals have been inserted upstream of the nucleic acid sequence or derivatives thereof, and the natural promoter with its regulation has not been removed. Instead, the natural regulatory sequence has been mutated in such a way that no regulation occurs anymore and/or gene expression is increased. These altered promoters can also be inserted individually upstream of the natural gene in form of partial sequences (=promoter having parts of the nucleic acid sequences according to the present invention) in order to increase the activity. Moreover, the gene construct can advantageously contain one or more so-called enhancer sequences functionally linked to the promoter, which enable an enhanced expression of the nucleic acid sequence. Additional advantageous sequences, like further regulatory elements or terminators, can also be inserted at the 3'-end of the DNA sequences. The phospholipase A2, ketoacyl-CoA reductase or dehydratase genes can be contained in the expression cassette (=gene construct) in one or more copies. Advantageously, only one copy of the genes is present in the expression cassette in each case. Said gene construct or the gene constructs can be expressed together in the host organism. Herein, the gene construct or the gene constructs can be inserted into one or more vectors and be present in the cell in a free form or they can be inserted into the genome. For the insertion of further genes into the host genome, it is advantageous if the genes to be expressed are present together in one gene construct.

Herein, the regulatory sequences or factors can preferably positively influence and thereby increase the gene expression of the introduced genes, as has been described in the above. Thus, enhancing the regulatory elements can advantageously be conducted on the transcriptional level by employing strong transcription signals like promoters and/or enhancers. Beside, enhancement of the translation is also possible, however, by, for example, improving the stability of the mRNA.

A further embodiment of the present invention are one or more gene constructs containing one or more sequences that are defined by SEQ ID NO: 1, SEQ ID NO: 3, SEQ ID NO: 5 or SEQ ID NO: 7 or derivatives thereof and that are coding for polypeptides or proteins according to SEQ ID NO: 2, SEQ ID NO: 4, SEQ ID NO: 6 or SEQ ID NO: 8. Herein, the phospholipase A2, ketoacyl-CoA reductase or dehydratase proteins mentioned preferably lead to cleavage of the ester bond of fatty acids at the sn-2 position of phospholipids or to reduction and dehydrogenation of fatty acids, wherein the substrate advantageously has one, two, three, four, five or six double bonds and advantageously has 18, 20 or 22 carbon atoms in the fatty acid molecule. The same applies to homologs, derivatives or analogs thereof, which are functionally linked to one or more regulatory signals, advantageously for increasing gene expression.

Advantageous regulatory sequences for the novel method are, for example, present in promoters such as the cos-, tac-, trp-, tet-, trp-tet-, lpp-, lac-, lpp-lac-, lacIq-, T7-, T5-, T3-, gal-, trc-, ara-, SP6-, λ-PR- or λ-PL promoter and are advantageously used in gram-negative bacteria. Further advantageous regulatory sequences are, for example, present in the gram-positive promoters amy and SPO2, in the yeast or fungus promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters like the promoters described in EP-A-0 388 186 (benzyl-sulfonamide-inducible), Plant J. 2, 1992:397-404 (Gatz et al., tetracyclin-inducible), EP-A-0 335 528 (abscisic acid-inducible) or WO 93/21334 (ethanol- or cyclohexenol-inducible). Further suitable plant promoters are the promoter of cytosolic FBPase or the ST-LSI promoter of potato (Stockhaus et al., EMBO J. 8, 1989, 2445), the phosphoribosyl-pyrophosphate amidotransferase promoter from *Glycine max* (GenBank Accession No. U87999) or the nodes-specific promoter described in EP-A-0 249 676. Particularly suitable promoters are promoters enabling the expression in tissues that are involved in fatty acid biosynthesis. In particular advantageous are seed-specific promoters like the USP promoter according to the embodiment, but also other promoters like the LeB4, DC3, phaseolin or napin promoter. Further particularly advantageous promoters are seed-specific promoters which can be used for monocotyledonous or dicotyledonous plants and are described in U.S. Pat. No. 5,608,152 (napin promoter from rape), WO 98/45461 (oleosin promoter from *Arabidopsis*), U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), wherein these promoters are suitable for dicotyledonous plants. The following promoters are, for example, suitable for monocotyledons: lpt-2 or lpt-1 promoter from barley (WO 95/15389 and WO 95/23230), hordein promoter from barley and e.g. other suitable promoters described in WO 99/16890.

In principle, it is possible to utilize all natural promoters with their regulatory sequences, like those mentioned in the above, for the novel method. It is also possible and advantageous to use, in addition or individually, synthetic promoters, in particular if they mediate seed-specific expression, for example as has been described in WO 99/16890.

In order to achieve a particularly high content of PUFAs, especially in transgenic plants, the PUFA biosynthetic genes should advantageously be expressed seed-specifically in oil plants. To this end, seed-specific promoters can be used, or for example such promoters that are active in the embryo and/or in the endosperm. In principle, seed-specific promoters can be isolated both from dicotyledonous and from monocotyledonous plants. In the following, advantageous preferred promoters are listed: USP (=unknown seed protein) and vicilin (*Vicia faba*) [Bäumlein et al., Mol. Gen. Genet., 1991, 225 (3)], napin (rape) [U.S. Pat. No. 5,608,152], acyl-carrier protein (rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumes promoter B4 (LegB4 promoter) [Bäumlein et al., Plant J., 2, 2, 1992], Lpt2 and lpt1 (barley) [WO 95/15389 and WO 95/23230], seed-specific promoters from rice, maize and wheat [WO 99/16890], Amy32b, Amy 6-6 and aleurain [U.S. Pat. No. 5,677,474], Bce4 (rape) [U.S. Pat. No. 5,530,149], glycinin (soy) [EP 571 741], phosphoenolpyruvate carboxylase (soy) [JP 06/62870], ADR12-2 (soy) [WO 98/08962], isocitrate lyase (rape) [U.S. Pat. No. 5,689,040] or α-amylase (barley) [EP 781 849].

Gene expression in plants can also be facilitated via a chemically inducible promoter (see a survey in Gatz 1997, Annu. Rev. Plant Physiol. Plant Mol. Biol., 48:89-108). Chemically inducible promoters are particularly suitable in case it is desired that gene expression should occur in a time-specific manner. Examples for such promoters are a salicylic acid-inducible promoter (WO 95/19443), a tetracyclin-inducible promoter (Gatz et al. (1992) Plant J. 2, 397-404) and an ethanol-inducible promoter.

In order to ensure a stable integration of the biosynthetic genes into the transgenic plant for several generations, each of the nucleic acids used in the method coding for phospholipase A2, ketoacyl-CoA reductase and/or dehydratase should advantageously be expressed in combination with the nucleic acids coding for Δ-12 desaturase, ω-3 desaturase, Δ-9 elongase, Δ-6 desaturase, Δ-8 desaturase, Δ-6 elongase, Δ-5 desaturase, Δ-5 elongase and/or Δ-4 desaturase under the control of its own, preferably a different promoter, as repetitive sequence motifs can lead to instability of the T-DNA or to recombination events. Herein, the expression cassette is advantageously constructed in such a way that a promoter is followed by a suitable restriction site for the insertion of the nucleic acid to be expressed, advantageously in a polylinker, and, optionally, a terminator is located downstream of the polylinker. This sequence is repeated several times, preferably three, four, or five times, so that up to five genes are brought together in one construct and can thus be introduced into the transgenic plant for expression. Advantageously, said sequence is repeated up to three times. For expression, the nucleic acid sequences are inserted via the suitable restriction site, for example, in the polylinker downstream of the promoter. Advantageously, each nucleic acid sequence has its own promoter and, optionally, its own terminator. Such advantageous constructs are, for example, disclosed in DE 10 102 337 or DE 10 102 338. However, it is also possible to insert several nucleic acid sequences downstream of a promoter and, optionally, upstream of a terminator. Herein, the insertion site or the sequence of the inserted nucleic acids in the expression cassette is not of crucial importance, i.e. a nucleic acid sequence can be inserted at the first or the last site in the expression cassette without thereby significantly influencing the expression. In the expression cassette, different promoters like, for example, the USP, LegB4 or DC3 promoters as well as different terminators can advantageously be used. However, it is also possible to use only one type of promoter in the cassette. This may, however, lead to undesired recombination events.

As has been described in the above, the transcription of the genes introduced should advantageously be terminated by suitable terminators at the 3'-end of the introduced biosynthesis genes (after the stop codon). Herein, for example, the OCS1 terminator can be used. As with the promoters, different termination sequences for each gene should be used herein.

As has been described in the above, the gene construct may also comprise further genes that are supposed to be introduced into the organisms. It is possible and advantageous to introduce into the host organisms regulatory genes like genes for inducers, repressors, or enzymes, which interfere the regulation of one or more genes of a biosynthetic pathway due to their enzymatic activity, and to express them in said organisms. Said genes can be of heterologous or homologous origin. In addition, further biosynthetic genes of the fatty acid or lipid metabolism may be contained advantageously in the nucleic acid construct or gene construct or said genes may be located on a further or on several further nucleic acid constructs. Further biosynthetic genes of the fatty acid or lipid metabolism are advantageously used in the gene construct, which are selected from the group: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-Coenzyme A carboxylase(s), acyl-Coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) or combinations thereof. Particularly advantageous nucleic acid sequences are biosynthetic genes of the fatty acid or lipid metabolism, selected from the group of the acyl-CoA:lysophospholipid acyltransferase, ω-3 desaturase, Δ-4 desaturase, Δ-5 desaturase, Δ-6 desaturase, Δ-8 desaturase, Δ-9 desaturase, Δ-12 desaturase, Δ-5 elongase, Δ-6 elongase and/or Δ-9 elongase.

Herein, the previously mentioned nucleic acids or genes can be cloned in combination with other elongases and desaturases into expression cassettes like the previously mentioned and can be used for the transformation of plants with the aid of *Agrobacterium*.

Herein, the regulatory sequences or factors can, as has been described in the above, preferably positively influence and thereby increase the gene expression of the genes introduced. Thus, enhancing the regulatory elements can advantageously be conducted on the transcriptional level by using strong transcription signals like promoters and/or enhancers. Besides, enhancing the translation is, however, also possible by, for example, improving the stability of the mRNA. In principle, the expression cassettes can be used directly for introduction into the plant or they can be introduced into vectors.

Said advantageous vectors, preferably expression vectors, contain the nucleic acids used in the method that code for the phospholipases A2, ketoacyl-CoA reductases and/or dehydratases and that can advantageously be combined with nucleic acids coding for Δ-12 desaturases, ω-3 desaturases, Δ-9 elongases, Δ-6 desaturases, Δ-8 desaturases, Δ-9 desaturases, Δ-6 elongases, Δ-5 desaturases, Δ-5 elongases or Δ-4 desaturases or a nucleic acid construct containing the nucleic acid used either individually or in combination with further biosynthetic genes of the fatty acid or lipid metabolism, like the acyl-CoA:lysophospholipid acyltransferases, ω-3 desaturases, Δ-4 desaturases, Δ-5 desaturases, Δ-6 desaturases, Δ-8 desaturases, Δ-9 desaturases, Δ-12 desaturases, ω-3 desaturases, Δ-5 elongases, Δ-6 elongases and/or Δ-9 elongases. As used herein, the term "vector" relates to a nucleic acid molecule that is capable of transporting another nucleic acid to which it is bound. One type of vector is a "plasmid", which stands for a circular double-stranded DNA loop into which the additional DNA segments can be ligated. A further type of vector is a viral vector, wherein additional DNA segments can be ligated into the viral genome. Particular vectors can autonomously replicate in a host cell into which they have been introduced (for example, bacterial vectors having a bacterial replication origin). Other vectors are advantageously integrated into the genome of a host cell upon introduction into the host cell and are thereby replicated together with the host genome. In addition, particular vectors are capable of controlling the expression of genes they are functionally linked to. Herein, said vectors are referred to as "expression vectors". Normally, expression vectors that are suitable for DNA recombination techniques do have the form of plasmids. In the present description, "plasmid" and "vector" can be used interchangeably, as the plasmid is the most frequently used form of a vector. However, the present invention is meant to comprise the other forms of expression vectors, like viral vectors having similar functions. Furthermore, the term vector is also supposed to comprise other vectors that are known to the person skilled in the art, like phages, viruses like SV40, CMV or TMV, transposons, IS elements, phasmids, phagemids, cosmids, linear or circular DNA.

The recombinant expression vectors advantageously used in the method comprise the nucleic acids or the gene construct as described in the above in a form that are suitable for expressing the used nucleic acids in a host cell, which means that the recombinant expression vectors comprise one or more regulatory sequences selected on the basis of the host cells to be used for expression, which is/are functionally linked to the nucleic acid sequence to be expressed. In a recombinant expression vector, "functionally linked" means that the relevant nucleotide sequence is bound to the regulatory sequence/s in such a way that the expression of the nucleotide sequence is enabled and that they are bound to each other in such a way that both sequences fulfill the predicted function that had been assigned to the sequence (for example in an in vitro transcription/translation system or in a host cell, when the vector is introduced into the host cell). The term "regulatory sequence" is supposed to comprise promoters, enhancers, and other expression control elements (for example polyadenylation signals). Said regulatory sequences are described, for example, in Goeddel: Gene Expression Technology: Methods in Enzymology 185, Academic Press, San Diego, Calif. (1990), or in: Gruber and Crosby, in: Methods in Plant Molecular Biology and Biotechnology, CRC Press, Boca Raton, Fla., Eds.: Glick and Thompson, Chapter 7, 89-108, including the references cited therein. Regulatory sequences comprise those sequences that regulate the constitutive expression of a nucleotide sequence in many types of host cells as well as those sequences that regulate direct expression of the nucleotide sequence only in specific host cells under specific conditions. One skilled in the art is aware of the fact that designing the expression vector can depend on factors like the selection of the host cell to be transformed, the extent of the expression of the desired protein, and so on.

The recombinant expression vectors used can be designed for the expression of phospholipases A2, ketoacyl-CoA reductases, dehydratases, Δ-12 desaturases, ω-3 desaturases, Δ-9 elongases, Δ-6 desaturases, Δ-8 desaturases, Δ-6 elongases, Δ-5 desaturases, Δ-5 elongases and/or Δ-4 desaturases in prokaryotic or eukaryotic cells. This is advantageous as, for reasons of simplicity, intermediate steps of vector construction are frequently carried out in microorganisms. For instance, the phospholipase A2, ketoacyl-CoA reductase, dehydratase, Δ-12 desaturase, ω-3 desaturase, Δ-9 elongase, Δ-6 desaturase, Δ-8 desaturase, Δ-6 elongase, Δ-5 desaturase, Δ-5 elongase and/or Δ-4 desaturase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., p. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., p. 1-28, Cambridge University Press: Cambridge), in algae (Falciatore et al., 1999, Marine Biotechnology. 1, 3:239-251), ciliates of the types *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, with vectors according to a transformation method as described in WO 98/01572, as well as preferably in cells of multicellular plants (see Schmidt, R. and Willmitzer, L. (1988) "High efficiency *Agrobacterium tumefaciens*—mediated transformation of *Arabidopsis thaliana* leaf and cotyledon explants" Plant Cell Rep.: 583-586; Plant Molecular Biology and Biotechnology, C Press, Boca Raton, Fla., Chapter 6/7, p. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are further discussed in Goeddel, Gene Expression Technology: Methods in Enzymology 185, Academic Press, San Diego, Calif. (1990). Alternatively, the recombinant expression vector can be transcribed and translated in vitro, for example, using T7 promoter regulatory sequences and T7 polymerase.

The expression of proteins in prokaryotes is mostly conducted with vectors containing constitutive or inducible promoters which regulate the expression of fusion or non-fusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass., USA) and pRIT5 (Pharmacia, Piscataway, N.J., USA), wherein glutathione S-transferase (GST), maltose E-binding protein or protein A is fused to the recombinant target protein.

Examples for suitable inducible non-fusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif., USA (1990) 60-89). The target gene expression of the pTrc vector is based on the transcription by host RNA polymerase from a hybrid trp-lac fusion promoter. The target gene expression from the pET 11d vector is based on the transcription of a T7-gn10-lac fusion promoter, which is mediated by a co-expressed viral RNA polymerase (T7 gn1). Said viral polymerase is provided by the host strains BL21 (DE3) or HMS174 (DE3) by a resident λ prophage which contains a T7 gn1 gene under the transcription control of the lacUV 5 promoter.

Other vectors suitable in prokaryotic organisms are known to the person skilled in the art. Said vectors are, for example, present in *E. coli* pLG338, pACYC184, the pBR series like pBR322, the pUC series like pUC18 or pUC19, the M113 mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples for vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif., USA). Vectors and methods for designing vectors suitable for use in other fungi like, for example, the filamentous fungi, comprise those described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., p. 1-28, Cambridge University Press: Cambridge, or in: More Gene Manipulations in Fungi [J. W. Bennet & L. L. Lasure, Ed., p. 396-428: Academic Press: San Diego]. Further suitable yeast vectors are, for example, pAG-1, YEp6, YEp13 or pEMBLYe23.

Alternatively, the phospholipases A2, ketoacyl-CoA reductases and/or dehydratases can advantageously be expressed in combination with the Δ-12 desaturases, ω-3 desaturases, Δ-9 elongases, Δ-6 desaturases, Δ-8 desaturases, Δ-6 elongases, Δ-5 desaturases, Δ-5 elongases and/or Δ-4 desaturases in insect cells using Baculovirus expression vectors. Baculovirus vectors available for the expression of proteins in cultivated insect cells (for example Sf9 cells) comprise the pAc series (Smith et al. (1983) Mol. Cell. Biol., 3:2156-2165) and the pVL series (Lucklow and Summers (1989) Virology 170:31-39).

The vectors mentioned in the above only provide a small survey of possible suitable vectors. Further plasmids are known to the person skilled in the art and are, for example, described in: Cloning Vectors (Eds. Pouwels, P. H., et al., Elsevier, Amsterdam-New York-Oxford, 1985, ISBN 0 444 904018). Further suitable expression systems for prokaryotic and eukaryotic cells are described in chapters 16 and 17 in Sambrook, J., Fritsch, E. F., and Maniatis, T., Molecular Cloning: A Laboratory Manual, $2^{nd}$ edition, Cold Spring Harbor Laboratory, Cold Spring Harbor Laboratory Press, Cold Spring Harbor, N.Y., USA, 1989.

In a further embodiment of the method, the phospholipases A2, ketoacyl-CoA reductases and/or dehydratases can advantageously be expressed in combination with the Δ-12 desaturases, ω-3 desaturases, Δ-9 elongases, Δ-6 desaturases, Δ-8 desaturases, Δ-6 elongases, Δ-5 desaturases, Δ-5 elongases and/or Δ-4 desaturases in unicellular plants (like algae), see Falciatore et al., 1999, Marine Biotechnology 1 (3):239-251 and references cited therein, and in plant cells from higher plants (for example *Spermatophyta*, like field fruits). Examples of plant expression vectors comprise those described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Eds.: Kung and R. Wu, Academic Press, 1993, p. 15-38.

Preferably, a plant expression cassette contains regulatory sequences which can regulate the gene expression in plant cells and are functionally linked, so that each sequence is able to fulfill its function like transcription termination, for example polyadenylation signals. Preferred polyadenylation signals are those originating from *Agrobacterium tumefaciens* T-DNA, like the gene 3 of the Ti plasmid pTiACH5, which is known as octopine synthase (Gielen et al., EMBO J. 3 (1984) 835 ff.) or functional equivalents thereof. All other terminators that are functionally active in plants are also suitable.

As the gene expression in plants very often is not restricted to the transcriptional level, a plant expression cassette preferably contains other functionally linked sequences like translation enhancers, for example the overdrive sequence containing the 5'-untranslated leader sequence from tobacco mosaic virus, which increases the protein/RNA ratio (Gallie et al., 1987, Nucl. Acids Research 15:8693-8711).

As has been described in the above, the gene expression in plants has to be functionally linked to a suitable promoter that conducts gene expression accurately timed and cell- or tissue-specifically. Utilizable promoters are constitutive promoters (Benfey et al., EMBO J. 8 (1989) 2195-2202), like those originating from plant viruses like 35S CAMV (Franck et al., Cell 21 (1980) 285-294), 19S CaMV (see also U.S. Pat. No. 5,352,605 and WO 84/02913), or plant promoters like the promoter of the small subunit from Rubisco, which is described in U.S. Pat. No. 4,962,028.

Other preferred sequences for the use of functional linkage in plant gene expression cassettes are targeting sequences that are required for directing the gene product to its corresponding cell compartment (see a survey in Kermode, Crit. Rev. Plant Sci. 15, 4 (1996) 285-423 and references cited therein), for example to the vacuole, the nucleus, all types of plastids like amyloplasts, chloroplasts, chromoplasts, the extracellular space, the mitochondria, the endoplasmic reticulum, oil bodies, peroxisomes and other compartments of plant cells.

As has been described in the above, the gene expression in plants can also be facilitated via a chemically inducible promoter (see a survey in Gatz 1997, Annu. Rev. Plant Physiol. Plant Mol. Biol., 48:89-108). Chemically inducible promoters are particularly suitable in case it is desired that the gene expression be conducted in a time-specific manner. Examples for such promoters are a salicylic acid-inducible promoter (WO 95/19443), a tetracycline-inducible promoter (Gatz et al. (1992) Plant J. 2, 397-404), and an ethanol-inducible promoter.

Promoters responding to biotic or abiotic stress conditions are also suitable promoters, for example the pathogen-induced PRP1 gene promoter (Ward et al., Plant. Mol. Biol. 22 (1993) 361-366), the heat-inducible hsp80 promoter from tomato (U.S. Pat. No. 5,187,267), the cold-inducible alpha-amylase promoter from potato (WO 96/12814), or the wound-inducible pinII promoter (EP-A-0 375 091).

Such promoters inducing the gene expression in tissues and organs in which the biosynthesis of fatty acids, lipids and oils takes place, in seed cells, like the cells of the endosperm and the developing embryo. Suitable promoters are the napin gene promoter from rape (U.S. Pat. No. 5,608,152), the USP promoter from *Vicia faba* (Baeumlein et al., Mol Gen Genet, 1991, 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein et al., 1992, Plant Journal, 2 (2):233-9), as well as promoters inducing seed-specific expression in monocotyledonous plants like maize, barley, wheat, rye, rice, etc. Suitable notable promoters are the lpt2- or lpt1 gene promoter from barley (WO 95/15389 and WO 95/23230) or the promoters described in WO 99/16890 from the barley hordein gene, the rice glutelin gene, the rice oryzin gene, the rice prolamin gene, the wheat gliadin gene, the wheat glutelin gene, the maize zein gene, the oat glutelin gene, the sorghum casirin gene, the rye secalin gene.

In particular, the multiparallel expression of the phospholipases A2, ketoacyl-CoA reductases and/or dehydratases used in the method can be desired, advantageously in combination with the Δ-12 desaturases, ω-3 desaturases, Δ-9 elongases, Δ-6 desaturases, Δ-8 desaturases, Δ-6 elongases, Δ-5 desaturases, Δ-5 elongases and/or Δ-4 desaturases. The introduction of such expression cassettes can be carried out via a simultaneous transformation of several individual expression constructs or, preferably, by combining several expression cassettes on one construct. Likewise, several vectors can each be transformed with several expression cassettes and transferred to the host cell.

Also particularly suitable are promoters inducing the plastid-specific expression, as plastids are the compartment in which the precursors and several final products of the lipid biosynthesis are synthesized. Suitable promoters, like the viral RNA polymerase promoter, are described in WO 95/16783 and WO 97/06250, and the clpP promoter from *Arabidopsis*, described in WO 99/46394.

Vector DNA can be introduced into prokaryotic or eukaryotic cells via conventional transformation or transfection techniques. The terms "transformation" and "transfection", conjugation and transduction, as used herein, are supposed to comprise a multiplicity of methods known in the art to introduce foreign nucleic acid (for example DNA) into a host cell, including calcium phosphate or calcium chloride co-precipitation, DEAE dextran-mediated transfection, lipofection, natural competence, chemically mediated transfer, electroporation or particle bombardment. Methods suitable for transforming or transfecting host cells including plant cells can be found in Sambrook et al. (Molecular Cloning: A Laboratory Manual., 2$^{nd}$ ed., Cold Spring Harbor Laboratory, Cold Spring Harbor Laboratory Press, Cold Spring Harbor, N.Y., USA, 1989) and other laboratory manuals like Methods in Molecular Biology, 1995, Vol. 44, *Agrobacterium* protocols, Eds: Gartland and Davey, Humana Press, Totowa, N.J., USA.

Host cells that are, in principle, suitable for taking up the nucleic acid of the present invention, the gene product of the present invention, or the vector of the present invention are all prokaryotic or eukaryotic organisms. Advantageously used host organisms are microorganisms like fungi or yeasts or plant cells, preferably plants or parts thereof. Fungi, yeasts, or plants are preferably used, particularly preferably plants, very particularly preferably plants like oil plants that contain large amounts of lipid compounds, like rape, evening primrose/suncup, hemp, thistle, peanut, canola, flax, soy, safflower, sunflower, borage, or plants like maize, wheat, rye, oat, triticale, rice, barley, cotton, manioc, pepper, Tagetes, Solanaceae plants like potato, tobacco, eggplant and tomato, *Vicia* species, pea, alfalfa, bush plants (coffee, cocoa, tea), *Salix* species, trees (oil palm, coconut) as well as perennial grasses and feed field fruit. Particularly preferred plants of the present invention are oil plants like soy, peanut, rape, canola, flax, hemp, suncup, sunflower, safflower, trees (oil palm, coconut).

As has been described in the above, a further object according to the present invention are isolated nucleic acid sequences coding for polypeptides or proteins with phospholipase A2 activity, wherein the phospholipases A2 encoded by the nucleic acid sequences advantageously hydrolyze off bound fatty acids at the sn2 position of the phospholipids.

Preferred nucleic acid sequences coding for polypeptides or proteins exhibiting phospholipase A2 activity are sequences selected from the group of:
a) a nucleic acid sequence having the sequence depicted in SEQ ID NO: 1,
b) nucleic acid sequences that can be derived due to the degenerate genetic code from the amino acid sequence depicted in SEQ ID NO: 2, or
c) derivatives of the nucleic acid sequence depicted in SEQ ID NO: 1 coding for polypeptides or proteins having at least 40% homology with SEQ ID NO: 2 on the amino acid level and exhibiting phospholipase A2 activity.

Further objects of the present invention are the nucleic acid sequences coding for ketoacyl-CoA reductases or dehydratases, which are listed in the following.

Further advantageous isolated nucleic acid sequences are sequences coding for polypeptides or proteins exhibiting ketoacyl-CoA reductase activity, selected from the group of:
a) a nucleic acid sequence having the sequence depicted in SEQ ID NO: 3,
b) nucleic acid sequences that can be derived as a result of the degenerate genetic code from the amino acid sequence depicted in SEQ ID NO: 4, or
c) derivatives of the nucleic acid sequence depicted in SEQ ID NO: 3, which code for polypeptides or proteins having at least 40% homology with SEQ ID NO: 4 on the amino acid level and exhibiting a ketoacyl-CoA reductase activity.

Further advantageous isolated nucleic acid sequences are sequences coding for polypeptides or proteins exhibiting dehydratase activity, selected from the group of:
a) a nucleic acid sequence having the sequence depicted in SEQ ID NO: 5 or SEQ ID NO: 7,
b) nucleic acid sequences that can be derived as a result of the degenerate genetic code from the amino acid sequences depicted in SEQ ID NO: 6 or SEQ ID NO: 8, or
c) derivatives of the nucleic acid sequences depicted in SEQ ID NO: 5 or SEQ ID NO: 7, which code for polypeptides or proteins having at least 40% identity with SEQ ID NO: 6 or SEQ ID NO: 8 on the amino acid level and exhibiting a dehydratase activity.

The above-mentioned nucleic acids according to the present invention advantageously originate from the previously mentioned organisms.

In a preferred embodiment, the term "nucleic acid (molecule)", as used herein, moreover comprises the untranslated sequence located at the 3' end and at the 5' end of the coding gene region: at least 500, preferably 200, particularly preferably 100 nucleotides of the sequence upstream of the 5' end of the coding region and at least 100, preferably 50, particularly preferably 20 nucleotides of the sequence downstream of the 3' end of the coding gene region. An "isolated" nucleic acid molecule is separated from other nucleic acid molecules that are present in the natural source of the nucleic acid. Preferably, an "isolated" nucleic acid has no sequences that naturally flank the nucleic acid in the genomic DNA of the organism the nucleic acid originates from (for example sequences located at the 5' and 3' ends of the nucleic acid). In different embodiments, the isolated phospholipase A2, ketoacyl-CoA reductase or dehydratase molecule can, for example, contain less than about 5 kb, 4 kb, 3 kb, 2 kb, 1 kb, 0.5 kb or 0.1 kb of nucleotide sequences which naturally flank the nucleic acid molecule in the genomic DNA of the cell, which is the origin of the nucleic acid.

The nucleic acid molecules used in the method, for example a nucleic acid molecule having a nucleotide sequence of SEQ ID NO: 1, SEQ ID NO: 3, SEQ ID NO: 5 or SEQ ID NO: 7 or a part thereof, can be isolated using molecular-biological standard techniques and the sequence information provided herein. It is also possible to identify, for example, a homologous sequence or homologous conserved sequence regions on the DNA or amino acid level with the aid of comparative algorithms. These can be used as hybridization probe according to standard hybridization techniques (as for example described in Sambrook et al., Molecular Cloning: A Laboratory Manual. 2$^{nd}$ ed., Cold Spring Harbor Laboratory, Cold Spring Harbor Laboratory Press, Cold Spring Harbor, N.Y., USA, 1989) for isolating further nucleic acid sequences that are useful in the method. Moreover, a nucleic acid molecule comprising an entire sequence of SEQ ID NO: 1, SEQ ID NO: 3, SEQ ID NO: 5 or SEQ ID NO: 7 or a part thereof can be isolated by the polymerase chain reaction, wherein oligonucleotide primers are used on the basis of said sequence or of parts thereof (for instance, a nucleic acid molecule comprising the entire sequence or a part thereof can be isolated by polymerase chain reaction using oligonucleotide primers that have been produced on the basis of said identical sequence). For instance, mRNA can be isolated from cells (for example by the guanidinium thiocyanate extraction method by Chirgwin et al. (1979) Biochemistry 18:5294-5299) and cDNA can be produced using reverse transcriptase (for example Moloney MLV reverse transcriptase, available from Gibco/BRL, Bethesda, Md., USA or AMV reverse transcriptase, available from Seikagaku America, Inc., St. Petersburg, Fla., USA). Synthetic oligonucleotide primers for amplification by polymerase chain reaction can be produced on the basis of one of the sequences depicted in SEQ ID NO: 1, SEQ ID NO: 3, SEQ ID NO: 5 or SEQ ID NO: 7, or with the aid of the amino acid sequences depicted in SEQ ID NO: 2, SEQ ID NO: 4, SEQ ID NO: 6 or SEQ ID NO: 8. A nucleic acid according to the present invention can be amplified using cDNA or, alternatively, genomic DNA as the template and suitable oligonucleotide primers according to standard PCR amplification techniques. The nucleic acid thus amplified can be cloned into a suitable vector and be characterized by DNA sequence analysis. Oligonucleotides corresponding to a desaturase nucleotide sequence can be produced by standard synthesis procedures, for example with an automated DNA synthesizer.

Homologs of the used phospholipase A2, ketoacyl-CoA reductase or dehydratase nucleic acid sequences having the sequence SEQ ID NO: 1, SEQ ID NO: 3, SEQ ID NO: 5 or SEQ ID NO: 7 denote, for example, allelic variants having at least about 30, 35, 40, 45, 50, 55 or 60%, preferably at least about 60, 65 or 70%, more preferably at least about 70 or 80%, 90% or 95%, and even more preferably at least about 85%, 86%, 87%, 88%, 89%, 90%, 91%, 92%, 93%, 94%, 95%, 96%, 97%, 98%, 99% or more identity or homology to one of the nucleotide sequences depicted in SEQ ID NO: 1, SEQ ID NO: 3, SEQ ID NO: 5 or SEQ ID NO: 7 or homologs, derivatives, or analogs, or parts thereof. Furthermore, isolated nucleic acid molecules of a nucleotide sequence that hybridize to one of the nucleotide sequences depicted in SEQ ID NO: 1, SEQ ID NO: 3, SEQ ID NO: 5 or SEQ ID NO: 7 or to a part thereof are, for example, hybridized under stringent conditions. According to the present invention, "a part thereof" is understood to denote herein that at least 25 base pairs (=bp), 50 bp, 75 bp, 100 bp, 125 bp or 150 bp, preferably at least 175 bp, 200 bp, 225 bp, 250 bp, 275 bp or 300 bp, particularly preferably 350 bp, 400 bp, 450 bp, 500 bp or more base pairs are used for hybridization. Advantageously, the entire sequence can also be used. Allelic variants comprise, in particular, functional variants that can be obtained by deletion, insertion or substitution of nucleotides from/in the sequence depicted in SEQ ID NO: 1, SEQ ID NO: 3, SEQ ID NO: 5 or SEQ ID NO: 7, wherein it is intended, however, that the enzymatic activity of the synthesized proteins originating therefrom is advantageously maintained for the insertion of one or more gene/s. Proteins still exhibiting the enzymatic activity of the phospholipase A2, ketoacyl-CoA reductase or dehydratase, i.e. whose activity is substantially not reduced, denotes proteins having at least 10%, preferably 20%, particularly preferably 30%, more particularly preferably 40% of the original enzymatic activity as compared to the protein encoded by SEQ ID NO: 1, SEQ ID NO: 3, SEQ ID NO: 5 or SEQ ID NO: 7. Homology was calculated over the entire amino acid or nucleic acid sequence region. For comparing different sequences, the person skilled in the art has at his disposal a variety of programs based on different algorithms. Herein, the algorithms by Needleman and Wunsch or Smith and Waterman yield particularly reliable results. For the sequence comparisons the program Pile Up was used (J. Mol. Evolution. (1987), 25, 351-360; Higgins et al., CABIOS, 1989: 151-153) or the programs Gap and Best Fit (Needleman and Wunsch, J. Mol. Biol., 48, 443-453 (1970), and Smith and Waterman Adv., Appl. Math., 2, 482-489 (1981)), which are contained in the GCG Software Package [Genetics Computer Group, 575 Science Drive, Madison, Wis., USA 53711 (1991)]. The sequence homology values, given as percent values in the above, were determined with the program GAP over the entire sequence region with the following settings: Gap Weight: 8, Length Weight: 2, Average Match: 2.778 and Average Mismatch: −2.248. Unless stated otherwise, these settings were always used as standard settings for sequence comparisons.

Moreover, the present invention comprises nucleic acid molecules differing from one of the nucleotide sequences shown in SEQ ID NO: 1, SEQ ID NO: 3, SEQ ID NO: 5 or SEQ ID NO: 7 (and parts thereof) due to the degenerate genetic code and therefore encoding the same phospholipase A2, ketoacyl-CoA reductase or dehydratase like the one encoded by the nucleotide sequences shown in SEQ ID NO: 1, SEQ ID NO: 3, SEQ ID NO: 5 or SEQ ID NO: 7.

In addition to the phospholipases A2, ketoacyl-CoA reductases or dehydratases depicted in SEQ ID NO: 1, SEQ ID NO: 3, SEQ ID NO: 5 or SEQ ID NO: 7, the person skilled in the art will realize that DNA sequence polymorphisms leading to alterations in the amino acid sequences of the phospholipase A2, ketoacyl-CoA reductase or dehydratase can exist within a population. Said genetic polymorphisms in the phospholipase A2, ketoacyl-CoA reductase or dehydratase gene can exist between individuals within a population due to natural variation. Said natural variants normally effect a variance of from 1 to 5% in the nucleotide sequence of the phospholipase A2, ketoacyl-CoA reductase or dehydratase gene. All these nucleotide variations and the amino acid polymorphisms resulting therefrom in the phospholipase A2, ketoacyl-CoA reductase or dehydratase, which are the result of natural variation and do not alter the functional activity of the enzymes, are supposed to be contained within the scope of the present invention.

Nucleic acid molecules advantageous for the method according to the present invention can be isolated on the basis of their homology to the phospholipase A2, ketoacyl-CoA reductase or dehydratase nucleic acids disclosed herein using the sequences or a part thereof as hybridization probe according to standard hybridization techniques under stringent hybridization conditions. Herein, for example, isolated nucleic acid molecules can be used that have a length of at least 15 nucleotides and hybridize under stringent conditions to the nucleic acid molecules comprising a nucleotide sequence of SEQ ID NO: 1, SEQ ID NO: 3, SEQ ID NO: 5 or SEQ ID NO: 7. Nucleic acids having at least 25, 50, 100, 250 or more nucleotides can also be used. As used herein, the term "hybridized under stringent conditions" is supposed to denote hybridization and washing conditions under which nucleotide sequences that are at least 60% homologous to each other usually remain hybridized to one another. Preferably, the conditions are such that sequences, which are homologous to one another by at least about 65%, more preferably by at least about 70% and even more preferably by at least about 75% or more, normally remain hybridized to one another. Said stringent conditions are known to the person skilled in the art and can be found in Current Protocols in Molecular Biology, John Wiley & Sons, N.Y., USA (1989), Chapter 6.3.1-6.3.6. A preferred non-limiting example for stringent hybridization conditions are hybridizations in 6× sodium chloride/sodium citrate=SSC at about 45° C., followed by one or more washing steps in 0.2×SSC, 0.1% SDS at 50 to 65° C. It is known to one skilled in the art that these hybridization conditions vary, depending on the type of the nucleic acid and, for example, in case organic solvents are present, with respect to temperature and concentration of the buffer. For instance, under standard hybridization conditions, the temperature will vary, depending on the type of the nucleic acid, within a range of from 42° C. to 58° C. in aqueous buffer at a concentration of 0.1 to 5×SSC (pH 7.2). In case an organic solvent is present in the previously mentioned buffer, for example 50% formamide, the temperature is about 42° C. under standard conditions. Preferably, the hybridization conditions for DNA:DNA hybrids are, for example, 0.1×SSC and 20° C. to 45° C., preferably between 30° C. and 45° C. Preferably, the hybridization conditions for DNA:RNA hybrids are, for example, 0.1×SSC and 30° C. to 55° C., preferably between 45° C. and 55° C. The previously mentioned hybridization temperatures are preferably determined for a nucleic acid of about 100 bp in length and a G+C content of 50% in the absence of formamide. The person skilled in the art knows how the required hybridization conditions can be determined with the aid of textbooks like those previously mentioned or from the following textbooks: Sambrook et al., "Molecular Cloning", Cold Spring Harbor Laboratory, 1989; Hames and Higgins (Hrsgb.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

In order to determine the homology in terms of percentage of two amino acid sequences (for example of one of the sequences of SEQ ID NO: 2, SEQ ID NO: 4, SEQ ID NO: 6 or SEQ ID NO: 8) or of two nucleic acid sequences (for example SEQ ID NO: 1, SEQ ID NO: 3, SEQ ID NO: 5 or SEQ ID NO: 7), the sequences are written one below the other for purposes of optimal comparison (for example, gaps can be inserted into the sequence of a protein or a nucleic acid in order to create an optimal alignment with the other protein or the other nucleic acid). The amino acid residues or nucleotides in the corresponding amino acid positions or nucleotide positions are then compared. If a position within a sequence is occupied by the same amino acid residue of the same nucleotide as the corresponding position in the other sequence, the molecules in this position are homologous (i.e. amino acid or nucleic acid homology, as used herein, corresponds to amino acid or nucleic acid identity). The homology of the two sequences in terms of percentage is a function of the number of identical positions that are shared by the sequences (i.e. % homology=number of identical positions/ total number of positions×100). Thus, the terms homology and identity are considered to be synonymous. The programs or algorithms used are described in the above.

An isolated nucleic acid molecule coding for a phospholipase A2, ketoacyl-CoA reductase or dehydratase, selected from the group of SEQ ID NO: 1, SEQ ID NO: 3, SEQ ID NO: 5 or SEQ ID NO: 7, which is homologous to a protein sequence of SEQ ID NO: 2, SEQ ID NO: 4, SEQ ID NO: 6 or SEQ ID NO: 8, can be generated by introducing one or more nucleotide substitutions, additions or deletions into a nucleotide sequence of SEQ ID NO: 1, SEQ ID NO: 3, SEQ ID NO: 5 or SEQ ID NO: 7, so that one or more amino acid substitutions, additions or deletions are introduced into the encoded protein. Mutations can be introduced into one of the sequences of SEQ ID NO: 1, SEQ ID NO: 3, SEQ ID NO: 5 or SEQ ID NO: 7 by standard techniques like site-specific mutagenesis and PCR-mediated mutagenesis. Preferably, conservative amino acid substitutions are created at one or more of the predicted non-essential amino acid residues. In case of a "conservative amino acid substitution", the amino acid residue is substituted for an amino acid residue having a similar side chain. Families of amino acid residues having similar side chains have been defined in this field of the art. Said families comprise amino acids having alkaline side chains (for example lysine, arginine, histidine), acidic side chains (for example aspartic acid, glutamic acid), uncharged polar side chains (for example glycine, asparagine, glutamine, serine, threonine, tyrosine, cysteine), nonpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted non-essential amino acid residue in a phospholipase A2, ketoacyl-CoA reductase or dehydratase is thus preferably substituted for another amino acid residue from the same family of side chains. In another embodiment, the mutations can alternatively be introduced at random over the entire sequence, or a part thereof, that is encoding the phospholipase A2, ketoacyl-CoA reductase or dehydratase, for example by saturation mutagenesis, and the resulting mutants can be screened for the phospholipase A2, ketoacyl-CoA reductase or dehydratase activity described herein in order to identify mutants that have retained the phospholipase A2, ketoacyl-CoA reductase or dehydratase activity. After mutagenesis of one of the sequences SEQ ID NO: 1, SEQ ID NO: 3, SEQ ID NO: 5 or SEQ ID NO: 7, the encoded protein can be produced recombinantly and the activity of the protein can be determined, for example, using the tests described herein.

Homologs of SEQ ID NO: 1, SEQ ID NO: 3, SEQ ID NO: 5 or SEQ ID NO: 7 also denotes, for example, bacterial, fungal and plant homologs, truncated sequences, single-stranded DNA or RNA of the coding and non-coding DNA sequence.

Homologs of SEQ ID NO: 1, SEQ ID NO: 3, SEQ ID NO: 5 or SEQ ID NO: 7 also denotes derivatives, like for example promoter variants. The promoters upstream of the given nucleotide sequences can be modified by one or more nucleotide substitutions, by insertion/s and/or deletion/s, however, without interfering with the functionality or activity of the promoters. It is furthermore possible that the activity of the promoters is increased by modification of their sequences or that they are entirely substituted by more active promoters, even from heterologous organisms.

The above mentioned nucleic acids and protein molecules exhibiting phospholipase A2, ketoacyl-CoA reductase or dehydratase activity, advantageously in combination with the nucleic acids and protein molecules exhibiting Δ-12 desaturase, ω-3 desaturase, Δ-9 elongase, Δ-6 desaturase, Δ-8 desaturase, Δ-6 elongase, Δ-5 desaturase, Δ-5 elongase and/or Δ-4 desaturase activity, which are involved in the metabolism of lipids and fatty acids, PUFA cofactors, and enzymes or in the transport of lipophilic compounds across membranes, are used in the method according to the present invention for modulating the production of PUFAs in transgenic organisms, advantageously in plants like maize, wheat, rye, oat, Triticale, rice, barley, soy bean, peanut, cotton, *Linum* species like oil flax or fiber flax, *Brassica* species like rape, canola and turnip, pepper, sunflower, borage, evening primrose/suncup and Tagetes, Solanaceae plants like potato, tobacco, eggplant and tomato, *Vicia* species, pea, manioc, alfalfa, bush plants (coffee, cocoa, tea), *Salix* species, trees (oil palm, coconut) and perennial grasses and feed field fruit, either directly (for example in case the overexpression or optimization of a fatty acid biosynthesis protein has a direct influence on the yield, the production and/or the efficiency of the production of the fatty acid from modified organisms) and/or they can have an indirect effect, which anyhow leads to an increase of the yield, the production and/or the efficiency of the production of the PUFAs or leads to a decrease of undesired compounds (for example in case the modulation of the metabolism of lipids and fatty acids, cofactors, and enzymes leads to alterations in the yield, the production and/or the efficiency of the production or of the composition of the desired compounds within the cells, which may in turn influence the production of one or more fatty acids).

The combination of different precursor molecules and biosynthesis enzymes leads to the production of different fatty acid molecules, which has a decisive effect on the composition of the lipids as polyunsaturated fatty acids (=PUFAs) are not only integrated simply into triacylglycerol, but also into membrane lipids.

Particularly suitable for producing PUFAs, for example stearidonic acid, eicosapentaenoic acid and docosahexaenoic acid, are Brassicaceae, Boraginaceae, Primulaceae or Linaceae. Flax (*Linum usitatissimum*) is particularly advantageously suitable for producing PUFAs having the nucleic acid sequences according to the present invention, as described, in combination with further desaturases and elongases.

The lipid synthesis can be divided into two sections: the synthesis of fatty acids and their binding to sn-glycerol-3-phosphate as well as the addition or modification of a polar head group. Conventional lipids used in membranes comprise phospholipids, glycolipids, sphingolipids and phosphoglycerides. The fatty acid synthesis starts with the conversion of acetyl-CoA into malonyl-CoA via the acetyl-CoA carboxylase or into acetyl-ACP by the acetyl-transacylase. After a condensation reaction, these two product molecules join to form acetoacetyl-ACP, which is converted via a series of condensation, reduction and dehydratation reactions, so that a saturated fatty acid molecule having the desired chain length is obtained. The production of the unsaturated fatty acids from said molecules is catalyzed by specific desaturases, i.e. either aerobically by molecular oxygen or anaerobically (with respect to the fatty acid esters in microorganisms see F. C. Neidhardt et al. (1996) *E. coli* and *Salmonella*. ASM Press: Washington, D.C., USA, p. 612-636 and references cited therein; Lengeler et al. (Ed.) (1999) Biology of Procaryotes. Thieme: Stuttgart, New York, and the references cited therein, as well as Magnuson, K., et al. (1993) Microbiological Reviews 57:522-542 and the references cited therein). The fatty acids thus obtained that are bound to phospholipids subsequently have to be transferred again from the phospholipids into the fatty acid CoA ester pool for further elongations. This is enabled by acyl-CoA:lysophospholipid acyltransferases. Furthermore, said enzymes are capable of transferring the elongated fatty acids from the CoA esters to the phospholipids again. Said reaction sequence can optionally be performed through several cycles.

Precursors for the PUFA biosynthesis are, for example, oleic acid, linoleic and linolenic acid. Said $C_{18}$ carbon fatty acids have to be elongated to $C_{20}$ and $C_{22}$ in order to gain fatty acids of the eicosa and docosa chain types. With the aid of the phospholipases A2, ketoacyl-CoA reductases or dehydratases used in the method in combination with further enzymes like desaturases like the $\Delta$-12, $\omega$-3, $\Delta$-4, $\Delta$-5, $\Delta$-6 and $\Delta$-8 desaturases and/or elongases like the $\Delta$-5, $\Delta$-6, $\Delta$-9 elongases, the production of arachidonic acid, eicosapentaenoic acid, docosapentaenoic acid or docosahexaenoic acid, advantageously eicosapentaenoic acid and/or docosahexaenoic acid, can be carried out and can subsequently be used for different purposes in food, feed, cosmetic or pharmaceutical applications. With the enzymes mentioned, it is possible to produce oils or lipids having a high content of $C_{18}$, $C_{20}$ and/or $C_{22}$ fatty acids having at least two, advantageously at least three, four, five or six double bonds in the fatty acid molecule, preferably $C_{20}$ or $C_{22}$ fatty acids having advantageously four, five or six double bonds in the fatty acid molecule. Advantageously, fatty acids such as linoleic acid, $\gamma$-linolenic acid, dihomo-$\gamma$-linolenic acid, arachidonic acid, stearidonic acid, eicosatetraenoic acid or eicosapentaenoic acid, docosapentaenoic acid, docosatetraenoic acid, docosapentaenoic acid, docosahexaenoic acid or mixtures thereof can be produced in the method. Substrates of the enzymes used in the method according to the present invention are $C_{16}$, $C_{18}$ or $C_{20}$ fatty acids like, for example, linoleic acid, $\gamma$-linolenic acid, $\alpha$-linolenic acid, dihomo-$\gamma$-linolenic acid, eicosatetraenoic acid or stearidonic acid. Preferred substrates are linoleic acid, $\gamma$-linolenic acid and/or $\alpha$-linolenic acid, dihomo-$\gamma$-linolenic acid or arachidonic acid, eicosatetraenoic acid or eicosapentaenoic acid. In the method according to the present invention, the synthesized advantageous $C_{20}$ or $C_{22}$ fatty acids having at least two, three, four, five or six double bonds in the fatty acid are present in form of the free fatty acid or in form of its esters, for example in form of its glycerides.

The term "glyceride" is to be understood as a glycerol esterified with one, two or three carboxylic acid residues (mono-, di- or triglyceride). "Glyceride" is also understood to denote a mixture of different glycerides. The glycerides or the glyceride mixture can contain further additives, for example free fatty acids, antioxidants, proteins, carbohydrates, vitamins and/or other substances.

In the sense of the method according to the present invention, a "glyceride" is further understood to denote derivatives derived from glycerol. Beside the fatty acid glycerides described in the above, among those are also glycerophospholipids and glyceroglycolipids. Herein, as preferred glycerophospholipids are to be mentioned e.g. lecithin (phosphatidylcholine), cardiolipin, phosphatidylglycerol, phosphatidylserine and alkylacyl glycerophospholipids. Said glycerides are finally present in the oils or lipids in form of a substance group.

Furthermore, the fatty acids subsequently have to be transported to different modification sites and integrated into the triacylglycerol storage lipid. A further important step in the lipid synthesis is the transfer of fatty acids to the polar head groups, for example by glycerol fatty acid acyltransferase (see Frentzen, 1998, Lipid, 100(4-5):161-166).

For publications on fatty acid biosynthesis in plants, desaturation, lipid metabolism and membrane transport of fat-containing compounds, beta-oxidation, fatty acid modification and cofactors, triacylglycerol storage and assembling, see the following articles, also including the references cited therein: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Eds.: Murata and Somerville, Rockville, American Society of Plant Physiologists, 150-158, Murphy & Ross 1998, Plant Journal. 13(1):1-16.

The PUFAs produced in the method comprise a group of molecules which higher animals are not capable of synthesizing anymore and therefore have to take in with food etc. or which higher animals are no longer capable of producing in sufficient amounts and therefore have to take in additionally, even though said molecules can easily be synthesized by other organisms, like bacteria. Cats, for example, are no longer capable of synthesizing arachidonic acid.

In the sense of the present invention, phospholipids are understood to denote: phosphatidylcholine, phosphatidylethanolamine, phosphatidylserine, phosphatidylglycerol and/or phosphatidylinositol, advantageously phosphatidylcholine. The terms "production" or "productivity" are known in the field of the art and include the concentration of the fermentation product formed during a specific time period and in a specific fermentation volume (for example kg product per hour per liter). Said terms also comprise the productivity within a plant cell or within a plant, i.e. the content of the desired fatty acids produced in the method, based on the content of all fatty acids in said cell or plant. The term "efficiency of the production" comprises the time period required for obtaining a specific amount of product (for example how long a cell will need to maintain a specific throughput rate of a fine chemical). The term "yield" or "product/carbon yield" is known in the field of the art and comprises the efficiency of converting the carbon source into the product (i.e. the fine chemical). This is, for example, usually expressed as kg product per kg carbon source. By increasing the yield or the production of the compound, the amount of obtained molecules or of obtained suitable molecules of said compound is increased in a specific culture volume over a fixed time period. The terms "biosynthesis" or "biosynthetic pathway" are known in the field of the art and comprise the synthesis of a compound, preferably an organic compound, by a cell from intermediate compounds, for example in a process that is strictly regulated and comprises several steps. The terms "degradation" or "degradation pathway" are known in the field of the art and comprise the cleavage of a compound, preferably an organic compound, by a cell into degradation products (more generally expressed, smaller or less complex molecules), for example in a process that is strictly regulated and comprises several steps. The term "metabolism" is known in the field of the art and comprises the entirety of biochemical reactions occurring in an organism. The metabolism of a specific compound (for example the metabolism of a fatty acid) then comprises the entirety of the biosynthesis, modification and degradation pathways of said compound in the cell, which concern said compound.

Further objects of the present invention are transgenic non-human organisms containing the nucleic acids SEQ ID NO: 1, SEQ ID NO: 3, SEQ ID NO: 5 or SEQ ID NO: 7 of the present invention or containing a gene construct or a vector containing said nucleic acid sequences of the present invention. Advantageously, said non-human organism is a microorganism, a non-human animal, or a plant; particularly preferably it is a plant.

The present invention is further illustrated by the following Examples, which are not to be understood as limiting. The content of all the references, patent applications, patents and published patent applications cited within the scope of the present patent application are incorporated herein by reference.

EXAMPLES

Example 1

General Cloning Methods

The cloning methods, like for example restriction cleavages, agarose gel electrophoresis, purification of DNA fragments, transfer of nucleic acids on nitrocellulose and nylon membranes, linkage of DNA fragments, transformation of *Escherichia coli* cells, cultivation of bacteria, and the sequence analysis of recombinant DNA, were conducted as described in Sambrook et al. (1989) (Cold Spring Harbor Laboratory Press: ISBN 0-87969-309-6).

Example 2

Sequence Analysis of Recombinant DNA

The sequencing of recombinant DNA molecules was conducted via a laser fluorescence DNA sequencer by ABI according to the method of Sanger (Sanger et al. (1977) Proc. Natl. Acad. Sci. USA 74, 5463-5467). In order to avoid polymerase errors, the fragments resulting from a polymerase chain reaction were sequenced and verified in constructs to be expressed.

Example 3

Cloning of Genes from *Ostreococcus tauri*

By searching for homologous regions in protein sequences, sequences having corresponding motifs could be identified in an *Ostreococcus tauri* sequence database (genomic sequences). The alignments for screening of homologies in the individual genes were performed with the tBLASTn algorithm (Altschul et al., J. Mol. Biol. 1990, 215: 403-410). These sequences are the following:

| Name of gene | SEQ ID | Amino acids |
|---|---|---|
| PLA2(Ot) | SEQ ID NO: 1 | 930 |
| KR(Ot) | SEQ ID NO: 3 | 327 |
| DH(Ot) | SEQ ID NO: 5 | 363 |

Cloning is performed as follows:

40 ml of an *Ostreococcus tauri* culture in the stationary phase are centrifuged, resuspended in 100 µl aqua bidist. and stored at −20° C. On the basis of the PCR method, the associated genomic DNAs are amplified. The corresponding primer pairs are selected in such a way that they contain the yeast consensus sequence for highly efficient translation (Kozak, Cell 1986, 44:283-292) next to the start codon. The amplification of the Ot DNAs is in each case performed with 1 µl thawed cells, 200 µM dNTPs, 2.5 U Taq polymerase and 100 pmol of each primer in a total volume of 50 µl. The conditions for the PCR are as follows: first denaturation at 95° C. for 5 minutes, followed by 30 cycles at 94° C. for 30 seconds, 55° C. for 1 minute and 72° C. for 2 minutes, as well as a last elongation step at 72° C. for 10 minutes.

Example 4

Cloning of a Dehydratase Gene from *Thraustochytrium* ssp

By comparing the different dehydratase protein sequences found in the present application, conserved nucleic acid regions could be defined (FIG. 6: Phe-Cys-Ala-Gly-Gly-Asp (SEQ ID NO: 149), Phe-Phe-X-X-Glu-Phe-X-Leu-Asn (SEQ ID NO: 150), Thr-X-Phe-Ala-Met-Pro-Glu (SEQ ID NO: 151), Pro-Asp-Val-Gly-X-Thr/Ser-Phe/Trp (SEQ ID NO: 152)). With the aid of said sequences, an EST database of *Thraustochytrium* ssp. was screened for dehydratases.

| Name of gene | cDNA | Coding sequence | Amino acids | SEQ ID NO. |
|---|---|---|---|---|
| DH(Tc) | 1171 bp | 1041 bp | 346 | SEQ ID NO: 7 |

Total RNA from *Thraustochytrium* ssp. was isolated with the aid of the RNAeasy Kit by Qiagen (Valencia, Calif., USA). With the aid of the PolyATract isolation system (Promega), mRNA was isolated from the total RNA. The mRNA was reverse transcribed by the Marathon cDNA amplification kit (BD Biosciences) and adaptors in accordance with the manufacturer's instructions were ligated. The cDNA bank was then used for the PCR for cloning expression plasmids by 5'- and 3'-RACE (rapid amplification of cDNA ends).

Example 5

Cloning of Expression Plasmids for Heterologous Expression in Yeasts

For characterizing the function of the identified genes from *Ostreococcus tauri* and *Thraustochytrium*, the open reading frames of the respective DNAs are cloned downstream of the galactose-inducible GAL1 promoter of pYES2.1/V5-His-TOPO (Invitrogen), wherein pYES2-PLA2(Ot), pYES2-KR(Ot), pYES2-DH(Ot) and pYES2(DH(Tc) are obtained. The following primer sequences are used:

| Gene | Primer sequence | SEQ ID NO: |
|---|---|---|
| PLA2(Ot) | Forward: caccatgggcgtgtgttcctc | SEQ ID NO: 9 |
| | Reverse: tcacgtgtatggttgccagttg | SEQ ID NO: 10 |
| KR(Ot) | Forward: caccatgggcgccctgagctatc | SEQ ID NO: 11 |
| | Reverse: ttacacgttcttcttgtaat | SEQ ID NO: 12 |
| DH(Ot) | Forward: caccatgtccaccccaccccatccac | SEQ ID NO: 13 |
| | Reverse: ttacaagcgagagaagaagg | SEQ ID NO: 14 |
| DH(Tc) | Forward: caccatggtgcgcatcatcaagcc | SEQ ID NO: 15 |
| | Reverse: ctaggagaggctgagatcg | SEQ ID NO: 16 |

The *Saccharomyces cerevisiae* strain 334 is transformed by electroporation (1500 V) with the vectors pYES2-PLA2(Ot), pYES2-KR(Ot), pYES2-DH(Ot) and pYES2-DH(Tc). A yeast transformed with the empty vector pYES2 is used as control. The selection of the transformed yeasts is conducted on complete minimal medium (CMdum) agar plates containing 2% glucose, but no uracil. After selection, three transformants are each selected for further functional expression.

For expressing the Ot genes and the DH(Tc) gene, starter cultures each of 5 ml CMdum liquid medium containing 2% (w/v) raffinose but no uracil are inoculated with the selected transformants first and are incubated for 2 days at 30° C., 200 rpm. 5 ml CMdum liquid medium (without uracil) containing 2% raffinose and 300 µM various fatty acids are then inoculated with the starter cultures adjusted to an $OD_{600}$ of 0.05. Expression is induced by adding 2% (w/v) galactose. The cultures are incubated for another 96 h at 20° C. In order to characterize the genes, the following described procedures can be used:

PLA2(Ot): Lee et al., 2003, Mol. Cells, 16:361-367

KR(Ot): Beaudoin et al. 2001, JBC, 277:11481-11488

DH(Ot) and DH(Tc): Garcia et al. 2004, The Acyl-CoA elongase in *Arabidopsis thaliana*: characterization of a candidate gene presumably encoding the 3-hydroxyacyl-CoA dehydratase. Poster presentation 16th Plant Lipid Symposium, Budapest.

Example 6

Cloning of Expression Plasmids for Seed-Specific Expression in Plants

For transforming plants, a further transformation vector is generated on the basis of the binary plasmid pSUN-USP. To this end, NotI restriction sites are inserted by PCR at the 5' end and 3' end of the coding sequences. The corresponding primer sequences are derived from the 5'- and 3'-regions of PLA2(Ot), KR(Ot), DH(Ot) and DH(Tc).

Composition of the PCR setup (50 µL):

5.00 µL template cDNA 5.00 µL 10× buffer (Advantage Polymerase)+25 mM $MgCl_2$ 5.00 µL 2 mM dNTP 1.25 µL per primer (10 pmol/µL)

0.50 µL Advantage Polymerase (Clontech)

Reaction conditions of the PCR:

| Annealing: | 1 min 55° C. |
|---|---|
| Denaturation: | 1 min 94° C. |
| Elongation: | 2 min 72° C. |
| Number of cycles: | 35 |

The PCR products are incubated for 16 h at 37° C. with the restriction enzyme NotI. The plant expression vector pSUN300-USP is incubated in the same manner. Subsequently, the PCR products and the vector are separated by agarose gel electrophoresis and the corresponding DNA fragments are cut out. Purification of the DNA is performed via the Qiagen Gel Purification Kit, in accordance with the manufacturer's instructions. Subsequently, vector and PCR products are ligated using the Rapid Ligation Kit by Roche. The resulting plasmids pSUN-PLA2(Ot), pSUN-KR(Ot), pSUN-DH(Ot) and pSUN-DH(Tc) are verified by sequencing.

pSUN300 is a derivative of the plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP resulted from pSUN300 by inserting a USP promoter as EcoRI fragment in pSUN300. The polyadenylation signal is that of the octopine synthase gene from the *A. tumefaciens* Ti plasmid (ocs-Terminator, GenBank Accession No. V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982)). The USP promoter corresponds to the nucleotides 1 to 684 (GenBank Accession No. X56240), wherein a part of the non-coding region of the USP gene is contained in the promoter. The promoter fragment of 684 base pairs in size was amplified via a PCR reaction according to standard methods using purchasable T7 standard primer (Stratagene) and a synthesized primer (Primer sequence: 5'-GTCGACCCGCG-GACTAGTGGGCCCTCTAGACCCGGGG-GATCCGGATCTGCTGGCTATGAA-3', SEQ ID NO: 17). Afterwards, the PCR fragment was cut with EcoRI/SalI and inserted into the vector pSUN300 with OCS terminator. The plasmid referred to as pSUN-USP was created. The construct was used for transforming *Arabidopsis thaliana*, rape, tobacco and flaxseed.

Example 7

Expression of PLA2(Ot), KR(Ot), DH(Ot) and DH(Tc) in Yeasts

Yeasts that are transformed with the plasmids pYES2, pYES2-PLA2(Ot), pYES2-KR(Ot), pYES2-DH(Ot) and pYES2-DH(Tc), as seen in Example 5, are analyzed as follows:

The yeast cells from the main cultures are harvested by centrifugation (100×g, 5 min, 20° C.) and washed with 100 mM NaHCO$_3$, pH 8.0 in order to remove residual medium and fatty acids. By acidic methanolysis, fatty acid methyl esters (FAMEs) are produced from the yeast cell sediments. To this end, the cell sediments are incubated with 2 ml 1 N methanolic sulfuric acid and 2% (v/v) dimethoxypropane for 1 h at 80° C. The extraction of the FAMEs is performed by extracting twice with petrol ether (PE). In order to remove non-derivatized fatty acids, the organic phases are each washed once with 2 ml 100 mM NaHCO$_3$, pH 8.0 and 2 ml acqua dist. Subsequently, the PE phases are dried with Na$_2$SO$_4$, evaporated under argon and taken up in 100 µl PE. The samples are separated on a DB-23 capillary column (30 m, 0.25 mm, 0.25 µm, Agilent) in a Hewlett Packard 6850 gas chromatograph having a flame ionization detector. The conditions for the GLC analysis are as follows: The oven temperature is programmed to rise from 50° C. to 250° C. at a rate of 5° C./min and to finally be held for 10 min at 250° C.

Identification of the signals is performed by comparing the retention times with corresponding fatty acid standards (Sigma). The methodology is described, for example, in Napier and Michaelson, 2001, Lipids. 36(8):761-766; Sayanova et al., 2001, Journal of Experimental Botany. 52(360): 1581-1585, Sperling et al., 2001, Arch. Biochem. Biophys. 388(2):293-298 and Michaelson et al., 1998, FEBS Letters. 439(3):215-218.

Example 8

Production of Transgenic Plants a) Producing Transgenic Rape Plants (Altered According to Moloney et al., 1992, Plant Cell Reports, 8:238-242)

For generating transgenic rape plants, the binary vectors in *Agrobacterium tumefaciens* C58C1:pGV2260 or *Escherichia coli* are utilized (Deblaere et al, 1984, Nucl. Acids. Res. 13, 4777-4788). For the transformation of rape plants (Var. Drakkar, NPZ Norddeutsche Pflanzenzucht, Hohenlieth, Germany), a 1:50 dilution of an overnight culture of a positively transformed colony of *Agrobacteria* in Murashige-Skoog medium (Murashige and Skoog 1962 Physiol. Plant. 15, 473) with 3% sucrose (3MS medium) is used. To this end petioles or hypocotyledons of freshly germinated sterile rape plants (each on about 1 cm$^2$) are incubated with a 1:50 *Agrobacteria* dilution in a petri dish for 5-10 minutes. A 3-day co-incubation in the dark at 25° C. on 3MS medium with 0.8% Bacto agar follows. Cultivation is then performed with 16 hours light/8 hours darkness. In weekly intervals on MS medium with 500 mg/l Claforan (cefotaxime sodium), 50 mg/l kanamycin, 20 microM benzylaminopurine (BAP), incubation is then continued with 1.6 g/l glucose. Growing sprouts are transferred to MS medium containing 2% sucrose, 250 mg/l Claforan and 0.8% Bacto agar. In case no roots have developed after three weeks, 2-indole butyric acid as growth hormone is added to the medium for root development.

Regenerated sprouts are maintained on 2MS medium containing kanamycin and Claforan, then transferred to soil after root development, and after cultivation they were grown for two weeks in a climatic chamber or in a greenhouse, brought to blossom, and ripe seeds are harvested and examined for elongase expression such as for Δ-5 elongase or Δ-6 elongase activity by lipid analyses. Lines having increased contents of C$_{20}$ and C$_{22}$ polyunsaturated fatty acids can be identified in this manner.

b) Production of Transgenic Flax Plants

The production of transgenic flax plants can, for example, be carried out according to the method of Bell et al. (1999, In Vitro Cell. Dev. Biol.-Plant. 35(6):456-465) by particle bombardment. Transformations mediated by *Agrobacteria* can, for example, be generated according to Mlynarova et al. (1994), Plant Cell Report 13: 282-285.

Example 9

Lipid Extraction from Yeasts and Seeds

The effect of genetic modification in plants, fungi, algae, or ciliates on the production of a desired compound (like a fatty acid) can be determined by culturing the modified microorganisms or the modified plant under suitable conditions (like those previously described) and examining the medium and/ or the cellular components for the increased production of the desired product (i.e. of lipids or a fatty acid). Said analysis techniques are known to the person skilled in the art and comprise spectroscopy, thin layer chromatography, staining methods of various types, enzymatic and microbiological methods as well as analytical chromatography like high performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; chapter 11, p. 1-27, VCH: Weinheim; and Dechow, F. J. (1989) Separation and purification techniques in biotechnology, Noyes Publications).

Beside the methods mentioned in the above, plant lipids are extracted from plant material as has been described by Cahoon et al. (1999) Proc. Natl. Acad. Sci. USA 96 (22): 12935-12940, and Browse et al. (1986) Analytic Biochemistry 152:141-145. Qualitative and quantitative lipid or fatty acid analysis is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, repr. 1992, IX, 307 p. (Oily Press Lipid Library; 1); "Progress in Lipid Research, Oxford: Pergamon Press, 1 (1952)-16 (1977), entitled: Progress in the Chemistry of Fats and Other Lipids CODEN.

In addition in order to measure the final product of fermentation, it is also possible to analyze other components of the metabolic pathways, which are used for the production of the desired compound, like intermediate products and by-products, in order to determine the total efficiency of the production of the compound. The analysis methods comprise measuring the amount of nutrients in the medium (for example sugars, carbohydrates, nitrogen sources, phosphate and other ions), measuring the biomass composition and the growth, analyzing the production of conventional metabolites of the biosynthesis pathways and measuring gases that are generated during fermentation. Standard methods for said measurements are described in Applied Microbial Physiology; A Practical Approach, P. M. Rhodes und P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas-liquid chromatographic mass spectrometry; TAG, triacylglycerol; TLC, thin layer chromatography).

The presence of fatty acid products can unambiguously be detected by analyzing recombinant organisms according to standard analysis methods: GC, GC-MS or TLC, like repeatedly described by Christie and the references cited therein (1997, in: Advances on Lipid Methodology, 4$^{th}$ edition: Christie, Oily Press, Dundee, 119-169; 1998, Gaschromatographie-Massenspektrometrie-Verfahren, Lipide 33:343-353).

The material to be analyzed can be disrupted by ultrasonic treatment, grinding in a glass mill, liquid nitrogen and grinding or via other applicable methods. After disruption, the material has to be centrifuged. The sediment is resuspended in Aqua dist., heated for 10 min at 100° C., cooled down on ice and again centrifuged, followed by extraction in 0.5 M sulfuric acid in methanol containing 2% dimethoxypropane for 1 h at 90° C., which leads to hydrolyzed oil and lipid compounds resulting in transmethylated lipids. Said fatty acid methyl esters are extracted in petrol ether and finally subjected to a GC analysis using a capillary column (Chrompack, WCOT Fused Silica, CP-Wax-52 CB, 25 microm., 0.32 mm) at a temperature gradient between 170° C. and 240° C. for 20 min and 5 min at 240° C. The identity of the fatty acid methyl esters obtained has to be defined using standards available from commercial sources (i.e. Sigma).

In order to render it more accessible for an extraction, the plant material is first mechanically homogenized by mortaring.

It is then heated for 10 min to 100° C. and again sedimented after cooling down on ice. The cell sediment is hydrolyzed with 1 M methanolic sulfuric acid and 2% dimethoxypropane for 1 h at 90° C. and the lipids are transmethylated. The resulting fatty acid methyl esters (FAMEs) are extracted in petrol ether. The extracted FAMEs are analyzed by gas-liquid chromatography with a capillary column (Chrompack, WCOT Fused Silica, CP-Wax-52 CB, 25 m, 0.32 mm) and a temperature gradient from 170° C. to 240° C. in 20 min and for 5 min at 240° C. The identity of the fatty acid methyl esters is verified by comparison with corresponding FAME standards (Sigma). The identity and position of the double bond can be further analyzed by suitable chemical derivatization of the FAME mixtures, for example to form 4,4-dimethoxyoxazoline derivatives (Christie, 1998), via GC-MS.

EQUIVALENTS

By merely using routine experiments, the person skilled in the art is capable of recognizing or establishing many equivalents of the specific embodiments according to the present invention as described herein. Said equivalents are supposed to be comprised by the patent claims.

---

The invention claimed is:

1. A method for producing oils and/or lipids having a high content of polyunsaturated fatty acids containing at least two double bonds in a transgenic organism comprising:
   a) introducing at least one nucleic acid sequence coding for a polypeptide exhibiting a phospholipase A2 activity into an organism,
   b) cultivating the organism.

2. The method according to claim 1, characterized in that the oil and/or lipid is isolated from the transgenic organism.

3. The method according to claim 1, characterized in that the nucleic acid sequence coding for a polypeptide or a protein exhibiting phospholipase A2 activity is selected from the group consisting of:
   a) a nucleic acid sequence having the sequence depicted in SEQ ID NO: 1,
   b) a nucleic acid sequence which encodes the amino acid sequence depicted in SEQ ID NO: 2, and
   c) a derivative of the nucleic acid sequence depicted in SEQ ID NO: 1 coding for a polypeptide or a protein having at least 70% identity at the amino acid level to SEQ ID NO: 2 and exhibiting phospholipase A2 activity.

4. The method according to claim 1, characterized in that at least one nucleic acid sequence coding for a polypeptide or a protein exhibiting Δ-12 desaturase, Δ-9 elongase, Δ-8 desaturase, Δ-6 desaturase, Δ-6 elongase, Δ-5 desaturase, Δ-5 elongase, ω-3 desaturase, Δ-4 desaturase activity is additionally introduced into the organism.

5. The method according to claim 1, characterized in that the oil and/or lipid is selected from the group consisting of linoleic acid, γ-linolenic acid, stearidonic acid, dihomo-γ-linolenic acid, ω-3-eicosatetraenoic acid, arachidonic acid, eicosapentaenoic acid, ω-6-docosapentaenoic acid, ω-6-docosatetraenoic acid, ω-3-docosapentaenoic acid and docosahexaenoic acid.

6. The method according to claim 1, characterized in that the polyunsaturated fatty acids are isolated from the oil and/or lipid in the form of free fatty acids.

7. The method according to claim 6, characterized in that the free fatty acids are isolated at a concentration of at least 5% by weight, based on the total lipid content of the transgenic organism.

8. The method according to claim 1, characterized in that the transgenic organism is a transgenic microorganism or a transgenic plant.

9. The method according to claim 1, characterized in that the transgenic organism is an oil-producing plant, a vegetable plant, or an ornamental plant.

10. The method according to claim 1, characterized in that the transgenic organism is a transgenic plant selected from the group consisting of plant classes or families: Adelothecioideae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crythecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae and Prasinophyceae.

11. A method for producing an oil, lipid or fatty acid composition by mixing oil, lipids or fatty acids according to claim 1 with animal oil, lipids or fatty acids.

12. The method according to claim 1, wherein the at least one nucleic acid sequence coding for a polypeptide exhibiting a phospholipase A2 activity codes for a protein having at least 95% identity at the amino acid level to SEQ ID NO: 2 and exhibiting phospholipase A2 activity.

13. An isolated nucleic acid molecule comprising a nucleic acid sequence coding for a polypeptide or a protein exhibiting phospholipase A2 activity, characterized in that the nucleic acid sequence is selected from the group consisting of:
   a) a nucleic acid sequence having the sequence depicted in SEQ ID NO: 1,
   b) a nucleic acid sequence which encodes the amino acid sequence depicted in SEQ ID NO: 2, and
   c) a derivative of the nucleic acid sequence depicted in SEQ ID NO: 1, which codes for a polypeptide or a protein having at least 70% homology at the amino acid level to SEQ ID NO: 2 and exhibiting a phospholipase A2 activity.

14. The isolated nucleic acid molecule according to claim 13, wherein the nucleic acid sequence is originated from an alga, a fungus, a microorganism, a plant, or a non-human animal.

15. The isolated nucleic acid molecule according to claim 13, wherein the nucleic acid sequence is originated from the order Salmoniformes, the diatoms genera Thalassiosira or Crypthecodinium, the classes Prasinophyceae or Phycomycota, or the families Euglenaceae or Pythiaceae.

16. A polypeptide comprising an amino acid sequence encoded by the isolated nucleic acid molecule according to claim 13.

17. A gene construct containing the isolated nucleic acid molecule according to claim 13, wherein the nucleic acid molecule is functionally linked to one or more regulatory signals.

18. The Gene construct according to claim 17, characterized in that the gene construct contains at least one additional biosynthesis gene of the fatty acid or lipid metabolism selected from the group consisting of: acyl-CoA dehydrogenase(s), acyl-ACP [=acyl carrier protein] desaturase(s), acyl-ACP thioesterase(s), fatty acid acyltransferase(s), acyl-CoA: lysophospholipid acyltransferase(s), fatty acid synthase(s), fatty acid hydroxylase(s), acetyl-Coenzyme A carboxylase(s), acyl-Coenzyme A oxidase(s), fatty acid desaturase(s), fatty acid acetylenase(s), lipoxygenase(s), triacylglycerol lipase(s), allene oxide synthase(s), hydroperoxide lyases and fatty acid elongase(s).

19. The gene construct according to claim 17, characterized in that the gene construct contains at least one additional biosynthesis gene of the fatty acid or lipid metabolism selected from the group consisting of $\Delta$-4 desaturase, $\Delta$-5 desaturase, $\Delta$-6 desaturase, $\Delta$-8 desaturase, $\Delta$-9 desaturase, $\Delta$-12 desaturase, $\Delta$-6 elongase, $\Delta$-5 elongase and $\Delta$-9 elongase.

20. A vector containing the nucleic acid molecule according to claim 13.

21. A transgenic non-human organism containing at least one nucleic acid molecule according to claim 13.

22. The transgenic non-human organism according to claim 21, wherein the organism is a plant.

23. The isolated nucleic acid molecule according to claim 13, wherein the nucleic acid sequence codes for a protein having at least 95% identity at the amino acid level to SEQ ID NO: 2 and exhibiting phospholipase A2 activity.

\* \* \* \* \*

SEQUENCE LISTING

```
<160> NUMBER OF SEQ ID NOS: 152

<210> SEQ ID NO 1
<211> LENGTH: 2793
<212> TYPE: DNA
<213> ORGANISM: Ostreococcus tauri
<220> FEATURE:
<221> NAME/KEY: CDS
<222> LOCATION: (1)..(2793)
<223> OTHER INFORMATION: Phospholipase 2

<400> SEQUENCE: 1 atg ggc gtg tgt tcc tcc aag agc ggc gcc gcg ccc gag gcc cag gag        48
Met Gly Val Cys Ser Ser Lys Ser Gly Ala Ala Pro Glu Ala Gln Glu
1               5                   10                  15 acg gag ttt cgc ttg cgc aag acg gcg gat gga aga aga ttg ggc gac        96
Thr Glu Phe Arg Leu Arg Lys Thr Ala Asp Gly Arg Arg Leu Gly Asp
            20                  25                  30 gat tcg acg aag aac ctc agc gcg ttc gct gag gac agc gga atg tcg       144
Asp Ser Thr Lys Asn Leu Ser Ala Phe Ala Glu Asp Ser Gly Met Ser
        35                  40                  45 gtc ggg agc gaa cga gag gtg acg agg ggg gaa ccg atc gca tcg ctt       192
Val Gly Ser Glu Arg Glu Val Thr Arg Gly Glu Pro Ile Ala Ser Leu
    50                  55                  60 cga cct caa acc agg aat cag gag att tcg aaa aaa gac ttc aag acg       240
Arg Pro Gln Thr Arg Asn Gln Glu Ile Ser Lys Lys Asp Phe Lys Thr
65                  70                  75                  80
```

-continued

| | |
|---|---|
| aag aag aag aac gcg atc gcg gtg gag gac gac cag gtg ttg gaa gga<br>Lys Lys Lys Asn Ala Ile Ala Val Glu Asp Asp Gln Val Leu Glu Gly<br>                    85                        90                    95 | 288 |
| gac gat gac gac gtg tat cgc ttc gat cag tca ctg cta aac agt gct<br>Asp Asp Asp Asp Val Tyr Arg Phe Asp Gln Ser Leu Leu Asn Ser Ala<br>            100                  105                110 | 336 |
| cgg gcg gcg atg aac gag gac gag gac gcc gat caa aac cgt agc ctg<br>Arg Ala Ala Met Asn Glu Asp Glu Asp Ala Asp Gln Asn Arg Ser Leu<br>        115                    120                125 | 384 |
| ctt cga aga caa tcg atc gtg aag gct ccg aac cag acg gtc gcc aag<br>Leu Arg Arg Gln Ser Ile Val Lys Ala Pro Asn Gln Thr Val Ala Lys<br>130                    135                140 | 432 |
| cca ccc gtc gag ctg agc gag cgt ctc aaa agg tac gag gcc gaa cca<br>Pro Pro Val Glu Leu Ser Glu Arg Leu Lys Arg Tyr Glu Ala Glu Pro<br>145                    150                155                160 | 480 |
| aaa tta aag gcg aat gag tta ccg gtt tca tat ggt cca gaa tgg ctg<br>Lys Leu Lys Ala Asn Glu Leu Pro Val Ser Tyr Gly Pro Glu Trp Leu<br>                  165                170                175 | 528 |
| gca ccg ccg gat ata caa cga gag acg acg gtg aga aaa cca aaa aag<br>Ala Pro Pro Asp Ile Gln Arg Glu Thr Thr Val Arg Lys Pro Lys Lys<br>            180                  185                190 | 576 |
| tac tcc att ggc aac ctt gca aga ggt gat cat aag ttg gaa ccg acg<br>Tyr Ser Ile Gly Asn Leu Ala Arg Gly Asp His Lys Leu Glu Pro Thr<br>                195                200                205 | 624 |
| aat ttg acg gac aaa gac ttc tct gat tat gct ccc ggg aac ggg ccg<br>Asn Leu Thr Asp Lys Asp Phe Ser Asp Tyr Ala Pro Gly Asn Gly Pro<br>        210                    215                220 | 672 |
| tgg ttt aac ggt ccg ttc ccg agc atg atg gca tcg tca gca aag caa<br>Trp Phe Asn Gly Pro Phe Pro Ser Met Met Ala Ser Ser Ala Lys Gln<br>225                    230                235                240 | 720 |
| atg ggt tta gcg tac ggt aaa ttc tgc gta gtc ggt gtc atc acg ttg<br>Met Gly Leu Ala Tyr Gly Lys Phe Cys Val Val Gly Val Ile Thr Leu<br>                245                250                255 | 768 |
| ttt tgg gtg cca aac ttt ctt ctt tac cat agg ctg cta atg aac ggc<br>Phe Trp Val Pro Asn Phe Leu Leu Tyr His Arg Leu Leu Met Asn Gly<br>            260                  265                270 | 816 |
| acg ttt cag gca tat tcc agg ctc ctt tct gca atc tta tcg agc ctt<br>Thr Phe Gln Ala Tyr Ser Arg Leu Leu Ser Ala Ile Leu Ser Ser Leu<br>        275                    280                285 | 864 |
| ttt atg acg cga act gtg ctc aac atg aac atg gag ttg tgt cgc atg<br>Phe Met Thr Arg Thr Val Leu Asn Met Asn Met Glu Leu Cys Arg Met<br>290                    295                300 | 912 |
| ttc tgg cga ggt tca ata gtg aat tcg cag gtt atc tgc tcc ttg ata<br>Phe Trp Arg Gly Ser Ile Val Asn Ser Gln Val Ile Cys Ser Leu Ile<br>305                    310                315                320 | 960 |
| ggc gcg gtc ggc ttc ttc tgg caa act ctg gtc atc ttc acc gtt gga<br>Gly Ala Val Gly Phe Phe Trp Gln Thr Leu Val Ile Phe Thr Val Gly<br>                325                330                335 | 1008 |
| tgg ctg agc gac aat cgc ggt atc ttt tca ttc ctg atc gcc ttt ggt<br>Trp Leu Ser Asp Asn Arg Gly Ile Phe Ser Phe Leu Ile Ala Phe Gly<br>            340                  345                350 | 1056 |
| gtt ggt tgg ttt atc gtt tgg agg caa gat cag cgc cat gaa aag caa<br>Val Gly Trp Phe Ile Val Trp Arg Gln Asp Gln Arg His Glu Lys Gln<br>        355                    360                365 | 1104 |
| cag cgc atc agg aca gtg atg ggt gct ttc ctt gcg ttg gaa aaa gat<br>Gln Arg Ile Arg Thr Val Met Gly Ala Phe Leu Ala Leu Glu Lys Asp<br>            370                  375                380 | 1152 |
| gcg aag cac atg gcc caa ctc atg ggc tca ccg gtg gtt cgt aca aac<br>Ala Lys His Met Ala Gln Leu Met Gly Ser Pro Val Val Arg Thr Asn<br>385                    390                395                400 | 1200 |

```
gac atc caa tac atg aat gcg gcg ccc gtt tgg gcg aga tac cgc cca    1248
Asp Ile Gln Tyr Met Asn Ala Ala Pro Val Trp Ala Arg Tyr Arg Pro
            405                 410                 415 gat gag ctt gtt ccg tgg ctg aac aat ttc ttg aca cag gtc tgg ccc    1296
Asp Glu Leu Val Pro Trp Leu Asn Asn Phe Leu Thr Gln Val Trp Pro
        420                 425                 430 ttc tac aac aaa gcg gcg agc gag ctg gtt cgc gag atc gtt gag ccg    1344
Phe Tyr Asn Lys Ala Ala Ser Glu Leu Val Arg Glu Ile Val Glu Pro
                435                 440                 445 ttg atg gag caa tct cgc ccc tcc atg ttg aag agg ctg act ttc aag    1392
Leu Met Glu Gln Ser Arg Pro Ser Met Leu Lys Arg Leu Thr Phe Lys
450                 455                 460 cag ctc gat ttc ggc gaa aac cct ttc atg gtg cga agc gtc tca tat    1440
Gln Leu Asp Phe Gly Glu Asn Pro Phe Met Val Arg Ser Val Ser Tyr
465                 470                 475                 480 gtc ggg aaa aaa gcc gag gac aaa ggt atg agc ctt gat ata gat ttt    1488
Val Gly Lys Lys Ala Glu Asp Lys Gly Met Ser Leu Asp Ile Asp Phe
                485                 490                 495 gcc tgg gct gga agg tca aac atc gtt ctt gcg gca aaa acc cac ata    1536
Ala Trp Ala Gly Arg Ser Asn Ile Val Leu Ala Ala Lys Thr His Ile
            500                 505                 510 gga gca gac att aac atc gca gtt aaa gat ctt gag att tac acc aag    1584
Gly Ala Asp Ile Asn Ile Ala Val Lys Asp Leu Glu Ile Tyr Thr Lys
        515                 520                 525 ctc cgg gtg aca ctg aat ccc ctt gtg ccg ctg cca agc ccg ctt ggt    1632
Leu Arg Val Thr Leu Asn Pro Leu Val Pro Leu Pro Ser Pro Leu Gly
    530                 535                 540 ggt gtc gta att tct atg aca gag aga cct atc gtt gag ttt cac gta    1680
Gly Val Val Ile Ser Met Thr Glu Arg Pro Ile Val Glu Phe His Val
545                 550                 555                 560 gag tta ccg agt ggg ttg gat gtg ctc tac gcc gca att gac aag tgg    1728
Glu Leu Pro Ser Gly Leu Asp Val Leu Tyr Ala Ala Ile Asp Lys Trp
                565                 570                 575 ctc gag gag ttt gtc gcc ggt ctc ctt ggc gac atg ttt att cag ccc    1776
Leu Glu Glu Phe Val Ala Gly Leu Leu Gly Asp Met Phe Ile Gln Pro
            580                 585                 590 gag cgt ctg gtc ata ccg ttg agc ttc aat ttt gat cca atc gtc atg    1824
Glu Arg Leu Val Ile Pro Leu Ser Phe Asn Phe Asp Pro Ile Val Met
        595                 600                 605 ccg gac ggc gag gtg aag cca ttc aag tgg tac gac cat aac gtt ttg    1872
Pro Asp Gly Glu Val Lys Pro Phe Lys Trp Tyr Asp His Asn Val Leu
    610                 615                 620 cag ctg cgc aac act ggg gta ctc aag gta act gtt gtg cga gct gag    1920
Gln Leu Arg Asn Thr Gly Val Leu Lys Val Thr Val Val Arg Ala Glu
625                 630                 635                 640 aac gtt cca agc gcg gat ctc ttg tcc aag acg gat cca ttc gtg aag    1968
Asn Val Pro Ser Ala Asp Leu Leu Ser Lys Thr Asp Pro Phe Val Lys
                645                 650                 655 atg ttt gtc aag aaa cat ggg ttg caa gta aac acg acg acg att atg    2016
Met Phe Val Lys Lys His Gly Leu Gln Val Asn Thr Thr Thr Ile Met
            660                 665                 670 aac aac gaa gac cca gtc tgg aat gaa atc ttt tac att cca gtc gat    2064
Asn Asn Glu Asp Pro Val Trp Asn Glu Ile Phe Tyr Ile Pro Val Asp
        675                 680                 685 gat gtc gac ttg aga gtg ctc aag gtc gcc atg tac gat cac gac gta    2112
Asp Val Asp Leu Arg Val Leu Lys Val Ala Met Tyr Asp His Asp Val
    690                 695                 700 gat cct ctt agt agc gat gac aag ttg ggt gcc acg gaa gta cgc ata    2160
Asp Pro Leu Ser Ser Asp Asp Lys Leu Gly Ala Thr Glu Val Arg Ile
```

```
                705                 710                 715                 720
gac acg atc aaa gcc gcg aca gct gat ggg agt gaa caa gaa ctt tgg        2208
Asp Thr Ile Lys Ala Ala Thr Ala Asp Gly Ser Glu Gln Glu Leu Trp
            725                 730                 735 ctc gat ttc ccg gag caa gtc aag ggg aat gtg aaa aaa ccg ccc atg        2256
Leu Asp Phe Pro Glu Gln Val Lys Gly Asn Val Lys Lys Pro Pro Met
        740                 745                 750 aaa ctg ttg ctg aat gca cag ttc atc tcg ttc ggc agc gac atc gca        2304
Lys Leu Leu Leu Asn Ala Gln Phe Ile Ser Phe Gly Ser Asp Ile Ala
    755                 760                 765 caa aat atg ttc act ggt ctt ggg cta ctg tcg gtt cac gtg atc cgc        2352
Gln Asn Met Phe Thr Gly Leu Gly Leu Leu Ser Val His Val Ile Arg
770                 775                 780 ggc cga aat ttg caa cca atg gat tcg aat gga ttg tca gat cct tac        2400
Gly Arg Asn Leu Gln Pro Met Asp Ser Asn Gly Leu Ser Asp Pro Tyr
785                 790                 795                 800 gtt aag gtc aag gtg cca aag ttc acc ctt gat agt atg gac atg gac        2448
Val Lys Val Lys Val Pro Lys Phe Thr Leu Asp Ser Met Asp Met Asp
                805                 810                 815 aag ggc aaa ata ctg agg ggc aag aga ggt aag aag ggc aag aag aat        2496
Lys Gly Lys Ile Leu Arg Gly Lys Arg Gly Lys Lys Gly Lys Lys Asn
            820                 825                 830 gcg gaa gct cat gat tac acg gtt tat agc tca aag att cat tac aag        2544
Ala Glu Ala His Asp Tyr Thr Val Tyr Ser Ser Lys Ile His Tyr Lys
        835                 840                 845 aac ctg aat cca gag ttt aac gcc atg ttt gag ttc tct cct gca agt        2592
Asn Leu Asn Pro Glu Phe Asn Ala Met Phe Glu Phe Ser Pro Ala Ser
    850                 855                 860 gaa gac acg aag gtg tcg ata gag ctg ttt gac gtt gat tcg acg ttt        2640
Glu Asp Thr Lys Val Ser Ile Glu Leu Phe Asp Val Asp Ser Thr Phe
865                 870                 875                 880 ccg atg ggg act aag agt aaa ttc atg ggg aat ctt gaa gtg ccg att        2688
Pro Met Gly Thr Lys Ser Lys Phe Met Gly Asn Leu Glu Val Pro Ile
                885                 890                 895 tcg act atc att cac cac ggt gga tcg atg gag gcg agg ttt aaa gtt        2736
Ser Thr Ile Ile His His Gly Gly Ser Met Glu Ala Arg Phe Lys Val
            900                 905                 910 ggc aac gct aag tcg ggt gag cta gac atc gcg ttc aac tgg caa cca        2784
Gly Asn Ala Lys Ser Gly Glu Leu Asp Ile Ala Phe Asn Trp Gln Pro
        915                 920                 925 tac acg tga                                                            2793
Tyr Thr
    930

<210> SEQ ID NO 2
<211> LENGTH: 930
<212> TYPE: PRT
<213> ORGANISM: Ostreococcus tauri

<400> SEQUENCE: 2

Met Gly Val Cys Ser Ser Lys Ser Gly Ala Ala Pro Glu Ala Gln Glu
1               5                   10                  15

Thr Glu Phe Arg Leu Arg Lys Thr Ala Asp Gly Arg Arg Leu Gly Asp
            20                  25                  30

Asp Ser Thr Lys Asn Leu Ser Ala Phe Ala Glu Asp Ser Gly Met Ser
        35                  40                  45

Val Gly Ser Glu Arg Glu Val Thr Arg Gly Glu Pro Ile Ala Ser Leu
    50                  55                  60

Arg Pro Gln Thr Arg Asn Gln Glu Ile Ser Lys Lys Asp Phe Lys Thr
```

-continued

```
                65                  70                  75                  80
        Lys Lys Lys Asn Ala Ile Ala Val Glu Asp Asp Gln Val Leu Glu Gly
                            85                  90                  95

Asp Asp Asp Asp Val Tyr Arg Phe Asp Gln Ser Leu Leu Asn Ser Ala
                        100                 105                 110

Arg Ala Ala Met Asn Glu Asp Glu Asp Ala Asp Gln Asn Arg Ser Leu
                        115                 120                 125

Leu Arg Arg Gln Ser Ile Val Lys Ala Pro Asn Gln Thr Val Ala Lys
                    130                 135                 140

Pro Pro Val Glu Leu Ser Glu Arg Leu Lys Arg Tyr Glu Ala Glu Pro
        145                 150                 155                 160

Lys Leu Lys Ala Asn Glu Leu Pro Val Ser Tyr Gly Pro Glu Trp Leu
                        165                 170                 175

Ala Pro Pro Asp Ile Gln Arg Glu Thr Thr Val Arg Lys Pro Lys Lys
                        180                 185                 190

Tyr Ser Ile Gly Asn Leu Ala Arg Gly Asp His Lys Leu Glu Pro Thr
                    195                 200                 205

Asn Leu Thr Asp Lys Asp Phe Ser Asp Tyr Ala Pro Gly Asn Gly Pro
                210                 215                 220

Trp Phe Asn Gly Pro Phe Pro Ser Met Met Ala Ser Ser Ala Lys Gln
        225                 230                 235                 240

Met Gly Leu Ala Tyr Gly Lys Phe Cys Val Val Gly Val Ile Thr Leu
                        245                 250                 255

Phe Trp Val Pro Asn Phe Leu Leu Tyr His Arg Leu Leu Met Asn Gly
                    260                 265                 270

Thr Phe Gln Ala Tyr Ser Arg Leu Leu Ser Ala Ile Leu Ser Ser Leu
                    275                 280                 285

Phe Met Thr Arg Thr Val Leu Asn Met Asn Met Glu Leu Cys Arg Met
                290                 295                 300

Phe Trp Arg Gly Ser Ile Val Asn Ser Gln Val Ile Cys Ser Leu Ile
        305                 310                 315                 320

Gly Ala Val Gly Phe Phe Trp Gln Thr Leu Val Ile Phe Thr Val Gly
                        325                 330                 335

Trp Leu Ser Asp Asn Arg Gly Ile Phe Ser Phe Leu Ile Ala Phe Gly
                    340                 345                 350

Val Gly Trp Phe Ile Val Trp Arg Gln Asp Gln Arg His Glu Lys Gln
                    355                 360                 365

Gln Arg Ile Arg Thr Val Met Gly Ala Phe Leu Ala Leu Glu Lys Asp
                    370                 375                 380

Ala Lys His Met Ala Gln Leu Met Gly Ser Pro Val Val Arg Thr Asn
        385                 390                 395                 400

Asp Ile Gln Tyr Met Asn Ala Ala Pro Val Trp Ala Arg Tyr Arg Pro
                        405                 410                 415

Asp Glu Leu Val Pro Trp Leu Asn Asn Phe Leu Thr Gln Val Trp Pro
                    420                 425                 430

Phe Tyr Asn Lys Ala Ala Ser Glu Leu Val Arg Glu Ile Val Glu Pro
                    435                 440                 445

Leu Met Glu Gln Ser Arg Pro Ser Met Leu Lys Arg Leu Thr Phe Lys
                450                 455                 460

Gln Leu Asp Phe Gly Glu Asn Pro Phe Met Val Arg Ser Val Ser Tyr
        465                 470                 475                 480

Val Gly Lys Lys Ala Glu Asp Lys Gly Met Ser Leu Asp Ile Asp Phe
                        485                 490                 495
```

```
Ala Trp Ala Gly Arg Ser Asn Ile Val Leu Ala Ala Lys Thr His Ile
            500                 505                 510
Gly Ala Asp Ile Asn Ile Ala Val Lys Asp Leu Glu Ile Tyr Thr Lys
        515                 520                 525
Leu Arg Val Thr Leu Asn Pro Leu Val Pro Leu Pro Ser Pro Leu Gly
    530                 535                 540
Gly Val Val Ile Ser Met Thr Glu Arg Pro Ile Val Glu Phe His Val
545                 550                 555                 560
Glu Leu Pro Ser Gly Leu Asp Val Leu Tyr Ala Ala Ile Asp Lys Trp
                565                 570                 575
Leu Glu Glu Phe Val Ala Gly Leu Leu Gly Asp Met Phe Ile Gln Pro
            580                 585                 590
Glu Arg Leu Val Ile Pro Leu Ser Phe Asn Phe Asp Pro Ile Val Met
        595                 600                 605
Pro Asp Gly Glu Val Lys Pro Phe Lys Trp Tyr Asp His Asn Val Leu
    610                 615                 620
Gln Leu Arg Asn Thr Gly Val Leu Lys Val Thr Val Val Arg Ala Glu
625                 630                 635                 640
Asn Val Pro Ser Ala Asp Leu Leu Ser Lys Thr Asp Pro Phe Val Lys
                645                 650                 655
Met Phe Val Lys Lys His Gly Leu Gln Val Asn Thr Thr Thr Ile Met
            660                 665                 670
Asn Asn Glu Asp Pro Val Trp Asn Glu Ile Phe Tyr Ile Pro Val Asp
        675                 680                 685
Asp Val Asp Leu Arg Val Leu Lys Val Ala Met Tyr Asp His Asp Val
    690                 695                 700
Asp Pro Leu Ser Ser Asp Asp Lys Leu Gly Ala Thr Glu Val Arg Ile
705                 710                 715                 720
Asp Thr Ile Lys Ala Ala Thr Ala Asp Gly Ser Glu Gln Glu Leu Trp
                725                 730                 735
Leu Asp Phe Pro Glu Gln Val Lys Gly Asn Val Lys Lys Pro Pro Met
            740                 745                 750
Lys Leu Leu Leu Asn Ala Gln Phe Ile Ser Phe Gly Ser Asp Ile Ala
        755                 760                 765
Gln Asn Met Phe Thr Gly Leu Gly Leu Leu Ser Val His Val Ile Arg
    770                 775                 780
Gly Arg Asn Leu Gln Pro Met Asp Ser Asn Gly Leu Ser Asp Pro Tyr
785                 790                 795                 800
Val Lys Val Lys Val Pro Lys Phe Thr Leu Asp Ser Met Asp Met Asp
                805                 810                 815
Lys Gly Lys Ile Leu Arg Gly Lys Arg Gly Lys Lys Gly Lys Lys Asn
            820                 825                 830
Ala Glu Ala His Asp Tyr Thr Val Tyr Ser Ser Lys Ile His Tyr Lys
        835                 840                 845
Asn Leu Asn Pro Glu Phe Asn Ala Met Phe Glu Phe Ser Pro Ala Ser
    850                 855                 860
Glu Asp Thr Lys Val Ser Ile Glu Leu Phe Asp Val Asp Ser Thr Phe
865                 870                 875                 880
Pro Met Gly Thr Lys Ser Lys Phe Met Gly Asn Leu Glu Val Pro Ile
                885                 890                 895
Ser Thr Ile Ile His His Gly Gly Ser Met Glu Ala Arg Phe Lys Val
            900                 905                 910
```

```
Gly Asn Ala Lys Ser Gly Glu Leu Asp Ile Ala Phe Asn Trp Gln Pro
        915                 920                 925

Tyr Thr
    930

<210> SEQ ID NO 3
<211> LENGTH: 984
<212> TYPE: DNA
<213> ORGANISM: Ostreococcus tauri
<220> FEATURE:
<221> NAME/KEY: CDS
<222> LOCATION: (1)..(984)
<223> OTHER INFORMATION: Ketoacyl-CoA-Reduktase

<400> SEQUENCE: 3 atg ggc gcc ctg agc tat ctc ccg att ccc tac gtc cgc gcg ctg gtg      48
Met Gly Ala Leu Ser Tyr Leu Pro Ile Pro Tyr Val Arg Ala Leu Val
1               5                   10                  15 cgg gat acc gtc gtc gat gcg tgc gtc tcg cac gtc ttg gcg ctc tac      96
Arg Asp Thr Val Val Asp Ala Cys Val Ser His Val Leu Ala Leu Tyr
            20                  25                  30 ggc ctc gtc gcg ctg ttg acg tat tgg gtg cca aag gtg gcg gtg cag     144
Gly Leu Val Ala Leu Leu Thr Tyr Trp Val Pro Lys Val Ala Val Gln
        35                  40                  45 atg atg ccg agt cag gat tta aag aag aag tac gac gcg cag tgg gcg     192
Met Met Pro Ser Gln Asp Leu Lys Lys Lys Tyr Asp Ala Gln Trp Ala
    50                  55                  60 ctc gtc acc ggt ggg tcc acg gga atc gga cga tcg ttg gcg ttc gcg     240
Leu Val Thr Gly Gly Ser Thr Gly Ile Gly Arg Ser Leu Ala Phe Ala
65                  70                  75                  80 ctc gcg gaa caa ggg ctg aac gtc gcg gtg tgc gcg ctg gat gac gaa     288
Leu Ala Glu Gln Gly Leu Asn Val Ala Val Cys Ala Leu Asp Asp Glu
                85                  90                  95 cat ctg gag acg acg tgt cgg gcg ctg cgg gag aaa ttc ggc gcg acg     336
His Leu Glu Thr Thr Cys Arg Ala Leu Arg Glu Lys Phe Gly Ala Thr
            100                 105                 110 agc gag att cga aaa att gga tgt aat ctc ggc gat cag tcg ggg gcg     384
Ser Glu Ile Arg Lys Ile Gly Cys Asn Leu Gly Asp Gln Ser Gly Ala
        115                 120                 125 tac gtg gag acg atc tcg aag gcg ttg gag gac gtg gat gtg cag gtg     432
Tyr Val Glu Thr Ile Ser Lys Ala Leu Glu Asp Val Asp Val Gln Val
    130                 135                 140 gtg ttc aat aac gcc ggg ttc atg ctc acg ggc ttt ttc gat aag cag     480
Val Phe Asn Asn Ala Gly Phe Met Leu Thr Gly Phe Phe Asp Lys Gln
145                 150                 155                 160 ccg ttg gag aag ttg aac gcg aac aac gag tgc aac gcg acg agc gcg     528
Pro Leu Glu Lys Leu Asn Ala Asn Asn Glu Cys Asn Ala Thr Ser Ala
                165                 170                 175 atg cga atc acg cac gtc ttc gtg cga agg atg ttg gca aaa aaa ctg     576
Met Arg Ile Thr His Val Phe Val Arg Arg Met Leu Ala Lys Lys Leu
            180                 185                 190 aga ggg tgc gtt gtt ttc acc tcg agc gcg gcg gcg tgt caa ccc acg     624
Arg Gly Cys Val Val Phe Thr Ser Ser Ala Ala Ala Cys Gln Pro Thr
        195                 200                 205 ccg ttt tcg gcg atg tac ggg gcg acg aag gcg tac att tcg agt ttc     672
Pro Phe Ser Ala Met Tyr Gly Ala Thr Lys Ala Tyr Ile Ser Ser Phe
    210                 215                 220 gcc gcc aac atc ggc gtc gag tta aag tct cga gga atc gac gtg tgc     720
Ala Ala Asn Ile Gly Val Glu Leu Lys Ser Arg Gly Ile Asp Val Cys
225                 230                 235                 240 gcc gtg cat ccg agc ccg gtg gcg agt aac ttt tac gac aaa gcg cat     768
Ala Val His Pro Ser Pro Val Ala Ser Asn Phe Tyr Asp Lys Ala His
```

```
Ala Val His Pro Ser Pro Val Ala Ser Asn Phe Tyr Asp Lys Ala His
            245                 250                 255 aaa ttg gac tca ctc aac ttt ttc atg aac ttt gcg gtg aag ccg gag      816
Lys Leu Asp Ser Leu Asn Phe Phe Met Asn Phe Ala Val Lys Pro Glu
                260                 265                 270 gag tta ccg acg gag atg ttc cgc ccg atc ggt cgc gtc ttg tgg cac      864
Glu Leu Pro Thr Glu Met Phe Arg Pro Ile Gly Arg Val Leu Trp His
            275                 280                 285 gac gtc ggc ggc gtc gcc atc ggt ttc cgc atg ctc ctc aag ctc ttc      912
Asp Val Gly Gly Val Ala Ile Gly Phe Arg Met Leu Leu Lys Leu Phe
290                 295                 300 gac tac ggt ttc ttc gcg acg ctc atc tcg aga ttc gcc cac ctc atg      960
Asp Tyr Gly Phe Phe Ala Thr Leu Ile Ser Arg Phe Ala His Leu Met
305                 310                 315                 320 ggc gat tac aag aag aac gtg taa                                       984
Gly Asp Tyr Lys Lys Asn Val
            325
```

<210> SEQ ID NO 4
<211> LENGTH: 327
<212> TYPE: PRT
<213> ORGANISM: Ostreococcus tauri

<400> SEQUENCE: 4

```
Met Gly Ala Leu Ser Tyr Leu Pro Ile Pro Tyr Val Arg Ala Leu Val
1               5                   10                  15

Arg Asp Thr Val Val Asp Ala Cys Val Ser His Val Leu Ala Leu Tyr
            20                  25                  30

Gly Leu Val Ala Leu Leu Thr Tyr Trp Val Pro Lys Val Ala Val Gln
        35                  40                  45

Met Met Pro Ser Gln Asp Leu Lys Lys Lys Tyr Asp Ala Gln Trp Ala
    50                  55                  60

Leu Val Thr Gly Gly Ser Thr Gly Ile Gly Arg Ser Leu Ala Phe Ala
65                  70                  75                  80

Leu Ala Glu Gln Gly Leu Asn Val Ala Val Cys Ala Leu Asp Asp Glu
                85                  90                  95

His Leu Glu Thr Thr Cys Arg Ala Leu Arg Glu Lys Phe Gly Ala Thr
            100                 105                 110

Ser Glu Ile Arg Lys Ile Gly Cys Asn Leu Gly Asp Gln Ser Gly Ala
        115                 120                 125

Tyr Val Glu Thr Ile Ser Lys Ala Leu Glu Asp Val Asp Val Gln Val
    130                 135                 140

Val Phe Asn Asn Ala Gly Phe Met Leu Thr Gly Phe Phe Asp Lys Gln
145                 150                 155                 160

Pro Leu Glu Lys Leu Asn Ala Asn Asn Glu Cys Asn Ala Thr Ser Ala
                165                 170                 175

Met Arg Ile Thr His Val Phe Val Arg Arg Met Leu Ala Lys Lys Leu
            180                 185                 190

Arg Gly Cys Val Val Phe Thr Ser Ser Ala Ala Cys Gln Pro Thr
        195                 200                 205

Pro Phe Ser Ala Met Tyr Gly Ala Thr Lys Ala Tyr Ile Ser Ser Phe
    210                 215                 220

Ala Ala Asn Ile Gly Val Glu Leu Lys Ser Arg Gly Ile Asp Val Cys
225                 230                 235                 240

Ala Val His Pro Ser Pro Val Ala Ser Asn Phe Tyr Asp Lys Ala His
                245                 250                 255
```

```
Lys Leu Asp Ser Leu Asn Phe Phe Met Asn Phe Ala Val Lys Pro Glu
            260                 265                 270

Glu Leu Pro Thr Glu Met Phe Arg Pro Ile Gly Arg Val Leu Trp His
        275                 280                 285

Asp Val Gly Val Ala Ile Gly Phe Arg Met Leu Leu Lys Leu Phe
    290                 295                 300

Asp Tyr Gly Phe Phe Ala Thr Leu Ile Ser Arg Phe Ala His Leu Met
305                 310                 315                 320

Gly Asp Tyr Lys Lys Asn Val
            325

<210> SEQ ID NO 5
<211> LENGTH: 1092
<212> TYPE: DNA
<213> ORGANISM: Ostreococcus tauri
<220> FEATURE:
<221> NAME/KEY: CDS
<222> LOCATION: (1)..(1092)
<223> OTHER INFORMATION: Dehydratase

<400> SEQUENCE: 5 atg tcc acc cca ccc cat cca ccg ctc cgc gtc gag cgg cgt gga aac      48
Met Ser Thr Pro Pro His Pro Pro Leu Arg Val Glu Arg Arg Gly Asn
1               5                   10                  15 gcc cag ttc atc gtc ctc gac cgt ccg aga gcg cgt aac gcg tta acg      96
Ala Gln Phe Ile Val Leu Asp Arg Pro Arg Ala Arg Asn Ala Leu Thr
            20                  25                  30 tcg gac gtc atc gag cgt tta cac cgc gcg tac gcc gcg ggc gag gac     144
Ser Asp Val Ile Glu Arg Leu His Arg Ala Tyr Ala Ala Gly Glu Asp
        35                  40                  45 aat gcg acg ctc tgc gcg cac gtc ata ctc ggc gcg aac tct gga acg     192
Asn Ala Thr Leu Cys Ala His Val Ile Leu Gly Ala Asn Ser Gly Thr
    50                  55                  60 ttc tgc gcc gga ggg gac gtg cgc gcg gtt cgc gaa atg gtg ctg aag     240
Phe Cys Ala Gly Gly Asp Val Arg Ala Val Arg Glu Met Val Leu Lys
65                  70                  75                  80 aac gag cgg gac gcg gcg gtg ggc ttt ttc tcg aga gag ttc gcg ctg     288
Asn Glu Arg Asp Ala Ala Val Gly Phe Phe Ser Arg Glu Phe Ala Leu
                85                  90                  95 aac gcg cgc ttg gcg acg ctg aca aag ccg tcg gcg tgc gtg tgg aac     336
Asn Ala Arg Leu Ala Thr Leu Thr Lys Pro Ser Ala Cys Val Trp Asn
            100                 105                 110 gga agc gtc atg ggc ggt ggg gcg gga ttg agc tgt tac gcc ccg gtg     384
Gly Ser Val Met Gly Gly Gly Ala Gly Leu Ser Cys Tyr Ala Pro Val
        115                 120                 125 cgg gtg tcg acg gag aag acg gtt ttt gcg atg ccg gag tgc gcg atc     432
Arg Val Ser Thr Glu Lys Thr Val Phe Ala Met Pro Glu Cys Ala Ile
    130                 135                 140 ggg ctt tgg ccc gac gtg ggg gcg tcg tgg ttt ttg aga agg ttg tgc     480
Gly Leu Trp Pro Asp Val Gly Ala Ser Trp Phe Leu Arg Arg Leu Cys
145                 150                 155                 160 ggc ggc gcg acc ggg acg tgg ttg gcg ctc acg ggc gcg cgt gtt cgt     528
Gly Gly Ala Thr Gly Thr Trp Leu Ala Leu Thr Gly Ala Arg Val Arg
                165                 170                 175 gga aaa gcg tgc aag gct tta gga tta tcc acg cat cac gtc acg tgc     576
Gly Lys Ala Cys Lys Ala Leu Gly Leu Ser Thr His His Val Thr Cys
            180                 185                 190 gag tca tgg gat gcg gtg tgc gaa ccg atg gtt cga gcg ctc acg gtt     624
Glu Ser Trp Asp Ala Val Cys Glu Pro Met Val Arg Ala Leu Thr Val
        195                 200                 205
```

```
ggg gcg agc gcg gag gat tta gcg gcg tgc gcg gcg ggc gag acc    672
Gly Ala Ser Ala Glu Asp Leu Ala Ala Cys Ala Ala Gly Glu Thr
    210                 215                 220 tcg gcg gac gcg gcg gaa gac ggg tgc gac gag tac gcg acg acg gcg    720
Ser Ala Asp Ala Ala Glu Asp Gly Cys Asp Glu Tyr Ala Thr Thr Ala
225                 230                 235                 240 cgt ggg aag cgc gcg atc gag gag gtt ttc gga gat gaa tct cta tcg    768
Arg Gly Lys Arg Ala Ile Glu Glu Val Phe Gly Asp Glu Ser Leu Ser
                245                 250                 255 ttg agc ggg atc acg agc gaa atc gct cgc agg cgc gac gcg gca acg    816
Leu Ser Gly Ile Thr Ser Glu Ile Ala Arg Arg Arg Asp Ala Ala Thr
            260                 265                 270 gac gac gta gaa cga cga ttc ttc gcc gaa tcc gcc gag tcg ctc gca    864
Asp Asp Val Glu Arg Arg Phe Phe Ala Glu Ser Ala Glu Ser Leu Ala
        275                 280                 285 aag gcg tgc ccg acg agc ctc gag gtc acg ctc gag ctc atg cgt cgc    912
Lys Ala Cys Pro Thr Ser Leu Glu Val Thr Leu Glu Leu Met Arg Arg
    290                 295                 300 gcg cga ggg aaa agt ttg gag tgg agc ttg gcg acg gac aac gcg ttg    960
Ala Arg Gly Lys Ser Leu Glu Trp Ser Leu Ala Thr Asp Asn Ala Leu
305                 310                 315                 320 atc tcg cag ttc atc ttc gcc gac gat ttc aag cgc ggc gtc gac gcg   1008
Ile Ser Gln Phe Ile Phe Ala Asp Asp Phe Lys Arg Gly Val Asp Ala
                325                 330                 335 gtg ctc atc aca aaa gtc ggc gtc ccg ccc ccc gag gga tgg gcg ccg   1056
Val Leu Ile Thr Lys Val Gly Val Pro Pro Pro Glu Gly Trp Ala Pro
            340                 345                 350 acg cgt tcg ccc gct tcc ttc ttc tct cgc ttg taa                   1092
Thr Arg Ser Pro Ala Ser Phe Phe Ser Arg Leu
    355                 360
```

<210> SEQ ID NO 6
<211> LENGTH: 363
<212> TYPE: PRT
<213> ORGANISM: Ostreococcus tauri

<400> SEQUENCE: 6

```
Met Ser Thr Pro Pro His Pro Pro Leu Arg Val Glu Arg Arg Gly Asn
1               5                   10                  15

Ala Gln Phe Ile Val Leu Asp Arg Pro Arg Ala Arg Asn Ala Leu Thr
            20                  25                  30

Ser Asp Val Ile Glu Arg Leu His Arg Ala Tyr Ala Ala Gly Glu Asp
        35                  40                  45

Asn Ala Thr Leu Cys Ala His Val Ile Leu Gly Ala Asn Ser Gly Thr
    50                  55                  60

Phe Cys Ala Gly Gly Asp Val Arg Ala Val Arg Glu Met Val Leu Lys
65                  70                  75                  80

Asn Glu Arg Asp Ala Ala Val Gly Phe Phe Ser Arg Glu Phe Ala Leu
                85                  90                  95

Asn Ala Arg Leu Ala Thr Leu Thr Lys Pro Ser Ala Cys Val Trp Asn
            100                 105                 110

Gly Ser Val Met Gly Gly Gly Ala Gly Leu Ser Cys Tyr Ala Pro Val
        115                 120                 125

Arg Val Ser Thr Glu Lys Thr Val Phe Ala Met Pro Glu Cys Ala Ile
    130                 135                 140

Gly Leu Trp Pro Asp Val Gly Ala Ser Trp Phe Leu Arg Arg Leu Cys
145                 150                 155                 160

Gly Gly Ala Thr Gly Thr Trp Leu Ala Leu Thr Gly Ala Arg Val Arg
```

-continued

|   |   |   |   |   |   |   |   |   |   |   |   |
|---|---|---|---|---|---|---|---|---|---|---|---|
|   |   | 165 |   |   |   | 170 |   |   |   | 175 |   |
| Gly | Lys | Ala | Cys | Lys | Ala | Leu | Gly | Leu | Ser | Thr | His | His | Val | Thr | Cys |
|   |   |   | 180 |   |   |   |   | 185 |   |   |   | 190 |   |   |   |
| Glu | Ser | Trp | Asp | Ala | Val | Cys | Glu | Pro | Met | Val | Arg | Ala | Leu | Thr | Val |
|   |   | 195 |   |   |   |   | 200 |   |   |   |   | 205 |   |   |   |
| Gly | Ala | Ser | Ala | Glu | Asp | Leu | Ala | Ala | Cys | Ala | Ala | Ala | Gly | Glu | Thr |
|   | 210 |   |   |   |   | 215 |   |   |   |   | 220 |   |   |   |   |
| Ser | Ala | Asp | Ala | Ala | Glu | Asp | Gly | Cys | Asp | Glu | Tyr | Ala | Thr | Thr | Ala |
| 225 |   |   |   |   | 230 |   |   |   |   | 235 |   |   |   |   | 240 |
| Arg | Gly | Lys | Arg | Ala | Ile | Glu | Glu | Val | Phe | Gly | Asp | Glu | Ser | Leu | Ser |
|   |   |   | 245 |   |   |   |   | 250 |   |   |   |   | 255 |   |   |
| Leu | Ser | Gly | Ile | Thr | Ser | Glu | Ile | Ala | Arg | Arg | Arg | Asp | Ala | Ala | Thr |
|   |   | 260 |   |   |   |   | 265 |   |   |   |   | 270 |   |   |   |
| Asp | Asp | Val | Glu | Arg | Arg | Phe | Phe | Ala | Glu | Ser | Ala | Glu | Ser | Leu | Ala |
|   | 275 |   |   |   |   | 280 |   |   |   |   | 285 |   |   |   |   |
| Lys | Ala | Cys | Pro | Thr | Ser | Leu | Glu | Val | Thr | Leu | Glu | Leu | Met | Arg | Arg |
| 290 |   |   |   |   | 295 |   |   |   |   | 300 |   |   |   |   |   |
| Ala | Arg | Gly | Lys | Ser | Leu | Glu | Trp | Ser | Leu | Ala | Thr | Asp | Asn | Ala | Leu |
| 305 |   |   |   |   | 310 |   |   |   |   | 315 |   |   |   |   | 320 |
| Ile | Ser | Gln | Phe | Ile | Phe | Ala | Asp | Asp | Phe | Lys | Arg | Gly | Val | Asp | Ala |
|   |   |   |   | 325 |   |   |   |   | 330 |   |   |   |   | 335 |   |
| Val | Leu | Ile | Thr | Lys | Val | Gly | Val | Pro | Pro | Glu | Gly | Trp | Ala | Pro |   |
|   |   |   | 340 |   |   |   |   | 345 |   |   |   |   | 350 |   |   |
| Thr | Arg | Ser | Pro | Ala | Ser | Phe | Phe | Ser | Arg | Leu |   |   |   |   |   |
|   | 355 |   |   |   |   | 360 |   |   |   |   |   |   |   |   |   |

```
<210> SEQ ID NO 7
<211> LENGTH: 1171
<212> TYPE: DNA
<213> ORGANISM: Thraustochytrium
<220> FEATURE:
<221> NAME/KEY: gene
<222> LOCATION: (1)..(1171)
<223> OTHER INFORMATION: putative Dehydratase

<400> SEQUENCE: 7
acgagcgagg tgctgctcaa caagccgaag aagctcaacg cgctggacct ggagatggtg      60
cgcatcatca agcccaagta cgacgaatgg gtcggctccg gcaaggcgca gtgcgtgctc     120
atgcacggcg ccggcgagaa ggccttttgc gccggcggcg catcgcctc ggtgcgctcg      180 agcgcgctcg agggcggctc gctcgcagag gacttcttct acgaagagta tcagctcaac     240
taccgcattg ccacggcctt tgaccgctgc ggcatcgtcc aagttagctt ttgggatggc     300
atcaccatgg gcggcggcgt cggcctcagc ctgcacggca gatccgcgt cgccacggag      360 aagacgcttt cgccatgcc ggaaaccggc atcggcctct ccccggatgt cggcggcacc      420
tttgcgctct cccgcattc gggcggacct gagatcggca tgtacctcgc gctcacgggg      480
actcgcctcg gcgcggccga ctgcctctac gcgggcctca ctacgcacta cgtggccagc     540
gagaacgtcg acaaggtctg cgaaaagctc gccgcgtcca gtcggaccc ctcagccatt      600 gaggccgttc tgcgcgagtt cgcggcggac gcgccgccgc caagaaccc tgccatgggc      660 ctcgaggcgc gccacgaggc catcaaaaag tgctttagca tcagcgagtc cgtcgaggtt     720
atcctcgacc gtctcgaggc catggccgcc gacgaggccg ccgacaagga cgaccgcgcc     780
tgggccgagg cctcgcgcga tgccattcgt aaggcctcgc ccacctctgt gtgcctctcg     840
ttcgaagccg tgcgccgcca cgctggcgcc gacgtcgaca tcgccaaggc gctcaccaac     900
```

```
gagtaccgcc tcacgcagcg catctgcgtg ccggatggcg atttcttcga aggcgtccgc    960
gccgtcctcg tcgaccgaga ccagtctccc aagtggaaat ttgcttcggt cgaggacgtc   1020
cccgccgact tcatcgagag ccactttcag ccattgcctg actcgcatcc gcgcggcgat   1080
ctcagcctct cctaggctag gctagccgtt tgcggacttt agactctgct aatcacaagt   1140
ttactatgca gcgaaaaaaa aaaaaaaaaa a                                  1171
```

<210> SEQ ID NO 8
<211> LENGTH: 346
<212> TYPE: PRT
<213> ORGANISM: Thraustochytrium

<400> SEQUENCE: 8

```
Met Val Arg Ile Ile Lys Pro Lys Tyr Asp Glu Trp Val Gly Ser Gly
1               5                   10                  15

Lys Ala Gln Cys Val Leu Met His Gly Ala Gly Glu Lys Ala Phe Cys
            20                  25                  30

Ala Gly Gly Asp Ile Ala Ser Val Arg Ser Ser Ala Leu Glu Gly Gly
        35                  40                  45

Ser Leu Ala Glu Asp Phe Phe Tyr Glu Glu Tyr Gln Leu Asn Tyr Arg
    50                  55                  60

Ile Ala Thr Ala Phe Asp Arg Cys Gly Ile Val Gln Val Ser Phe Trp
65                  70                  75                  80

Asp Gly Ile Thr Met Gly Gly Gly Val Gly Leu Ser Leu His Gly Lys
                85                  90                  95

Ile Arg Val Ala Thr Glu Lys Thr Leu Phe Ala Met Pro Glu Thr Gly
            100                 105                 110

Ile Gly Leu Phe Pro Asp Val Gly Gly Thr Phe Ala Leu Ser Arg Ile
        115                 120                 125

Ser Gly Gly Pro Glu Ile Gly Met Tyr Leu Ala Leu Thr Gly Thr Arg
    130                 135                 140

Leu Gly Ala Ala Asp Cys Leu Tyr Ala Gly Leu Thr Thr His Tyr Val
145                 150                 155                 160

Ala Ser Glu Asn Val Asp Lys Val Cys Glu Lys Leu Ala Ala Ser Lys
                165                 170                 175

Ser Asp Pro Ser Ala Ile Glu Ala Val Leu Arg Glu Phe Ala Ala Asp
            180                 185                 190

Ala Pro Pro Pro Lys Asn Pro Ala Met Gly Leu Glu Ala Arg His Glu
        195                 200                 205

Ala Ile Lys Lys Cys Phe Ser Ile Ser Glu Ser Val Glu Val Ile Leu
    210                 215                 220

Asp Arg Leu Glu Ala Met Ala Ala Asp Glu Ala Ala Asp Lys Asp Asp
225                 230                 235                 240

Arg Ala Trp Ala Glu Ala Ser Arg Asp Ala Ile Arg Lys Ala Ser Pro
                245                 250                 255

Thr Ser Val Cys Leu Ser Phe Glu Ala Val Arg Arg His Ala Gly Ala
            260                 265                 270

Asp Val Asp Ile Ala Lys Ala Leu Thr Asn Glu Tyr Arg Leu Thr Gln
        275                 280                 285

Arg Ile Cys Val Pro Asp Gly Asp Phe Glu Gly Val Arg Ala Val
    290                 295                 300

Leu Val Asp Arg Asp Gln Ser Pro Lys Trp Lys Phe Ala Ser Val Glu
305                 310                 315                 320
```

```
Asp Val Pro Ala Asp Phe Ile Glu Ser His Phe Gln Pro Leu Pro Asp
                325                 330                 335

Ser His Pro Arg Gly Asp Leu Ser Leu Ser
            340                 345
```

```
<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
caccatgggc gtgtgttcct c                                           21

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
tcacgtgtat ggttgccagt tg                                          22

<210> SEQ ID NO 11
<211> LENGTH: 23
<212> TYPE: DNA
<213> ORGANISM: Artificial
<220> FEATURE:
<223> OTHER INFORMATION: Primer

<400> SEQUENCE: 11
caccatgggc gccctgagct atc                                         23

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
ttacacgttc ttcttgtaat                                             20

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
caccatgtcc accccacccc atccac                                      26

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ttacaagcga gagaagaagg                                             20
```

<210> SEQ ID NO 15
<211> LENGTH: 24
<212> TYPE: DNA
<213> ORGANISM: Artificial
<220> FEATURE:
<223> OTHER INFORMATION: Primer

<400> SEQUENCE: 15
caccatggtg cgcatcatca agcc                                              24

<210> SEQ ID NO 16
<211> LENGTH: 19
<212> TYPE: DNA
<213> ORGANISM: Artificial
<220> FEATURE:
<223> OTHER INFORMATION: Primer

<400> SEQUENCE: 16
ctaggagagg ctgagatcg                                                    19

<210> SEQ ID NO 17
<211> LENGTH: 60
<212> TYPE: DNA
<213> ORGANISM: Artificial
<220> FEATURE:
<223> OTHER INFORMATION: Primer

<400> SEQUENCE: 17
gtcgacccgc ggactagtgg gccctctaga cccgggggat ccggatctgc tggctatgaa       60

<210> SEQ ID NO 18
<211> LENGTH: 1266
<212> TYPE: DNA
<213> ORGANISM: Euglena gracilis
<220> FEATURE:
<221> NAME/KEY: CDS
<222> LOCATION: (1)..(1266)
<223> OTHER INFORMATION: delta-8-Desaturase

<400> SEQUENCE: 18

```
atg aag tca aag cgc caa gcg ctt ccc ctt aca att gat gga aca aca        48
Met Lys Ser Lys Arg Gln Ala Leu Pro Leu Thr Ile Asp Gly Thr Thr
1               5                   10                  15 tat gat gtg tct gcc tgg gtc aat ttc cac cct ggt ggt gcg gaa att        96
Tyr Asp Val Ser Ala Trp Val Asn Phe His Pro Gly Gly Ala Glu Ile
            20                  25                  30 ata gag aat tac caa gga agg gat gcc act gat gcc ttc atg gtt atg       144
Ile Glu Asn Tyr Gln Gly Arg Asp Ala Thr Asp Ala Phe Met Val Met
        35                  40                  45 cac tct caa gaa gcc ttc gac aag ctc aag cgc atg ccc aaa atc aat       192
His Ser Gln Glu Ala Phe Asp Lys Leu Lys Arg Met Pro Lys Ile Asn
    50                  55                  60 ccc agt tct gag ttg cca ccc cag gct gca gtg aat gaa gct caa gag       240
Pro Ser Ser Glu Leu Pro Pro Gln Ala Ala Val Asn Glu Ala Gln Glu
65                  70                  75                  80 gat ttc cgg aag ctc cga gaa gag ttg atc gca act ggc atg ttt gat       288
Asp Phe Arg Lys Leu Arg Glu Glu Leu Ile Ala Thr Gly Met Phe Asp
                85                  90                  95 gcc tcc ccc ctc tgg tac tca tac aaa atc agc acc aca ctg ggc ctt       336
Ala Ser Pro Leu Trp Tyr Ser Tyr Lys Ile Ser Thr Thr Leu Gly Leu
            100                 105                 110 gga gtg ctg ggt tat ttc ctg atg gtt cag tat cag atg tat ttc att       384
Gly Val Leu Gly Tyr Phe Leu Met Val Gln Tyr Gln Met Tyr Phe Ile
        115                 120                 125
```

| | | |
|---|---|---|
| ggg gca gtg ttg ctt ggg atg cac tat caa cag atg ggc tgg ctt tct<br>Gly Ala Val Leu Leu Gly Met His Tyr Gln Gln Met Gly Trp Leu Ser<br>130                             135                           140 | | 432 |
| cat gac att tgc cac cac cag act ttc aag aac cgg aac tgg aac aac<br>His Asp Ile Cys His His Gln Thr Phe Lys Asn Arg Asn Trp Asn Asn<br>145                         150                         155                     160 | | 480 |
| ctc gtg gga ctg gta ttt ggc aat ggt ctg caa ggt ttt tcc gtg aca<br>Leu Val Gly Leu Val Phe Gly Asn Gly Leu Gln Gly Phe Ser Val Thr<br>                       165                         170                     175 | | 528 |
| tgc tgg aag gac aga cac aat gca cat cat tcg gca acc aat gtt caa<br>Cys Trp Lys Asp Arg His Asn Ala His His Ser Ala Thr Asn Val Gln<br>                180                         185                         190 | | 576 |
| ggg cac gac cct gat att gac aac ctc ccc ctc tta gcc tgg tct gag<br>Gly His Asp Pro Asp Ile Asp Asn Leu Pro Leu Leu Ala Trp Ser Glu<br>             195                         200                         205 | | 624 |
| gat gac gtc aca cgg gcg tca ccg att tcc cgc aag ctc att cag ttc<br>Asp Asp Val Thr Arg Ala Ser Pro Ile Ser Arg Lys Leu Ile Gln Phe<br>210                             215                         220 | | 672 |
| cag cag tat tat ttc ttg gtc atc tgt atc ttg ttg cgg ttc att tgg<br>Gln Gln Tyr Tyr Phe Leu Val Ile Cys Ile Leu Leu Arg Phe Ile Trp<br>225                           230                        235                  240 | | 720 |
| tgt ttc cag agc gtg ttg acc gtg cgc agt ctg aag gac aga gat aac<br>Cys Phe Gln Ser Val Leu Thr Val Arg Ser Leu Lys Asp Arg Asp Asn<br>                       245                         250                     255 | | 768 |
| caa ttc tat cgc tct cag tat aag aag gag gcc att ggc ctc gcc ctg<br>Gln Phe Tyr Arg Ser Gln Tyr Lys Lys Glu Ala Ile Gly Leu Ala Leu<br>                260                         265                         270 | | 816 |
| cat tgg aca ttg aag gcc ctg ttc cac tta ttc ttt atg ccc agc atc<br>His Trp Thr Leu Lys Ala Leu Phe His Leu Phe Phe Met Pro Ser Ile<br>             275                         280                         285 | | 864 |
| ctc aca tcg ctg ttg gta ttt ttc gtt tcg gag ctg gtt ggc ggc ttc<br>Leu Thr Ser Leu Leu Val Phe Phe Val Ser Glu Leu Val Gly Gly Phe<br>290                             295                         300 | | 912 |
| ggc att gcg atc gtg gtg ttc atg aac cac tac cca ctg gag aag atc<br>Gly Ile Ala Ile Val Val Phe Met Asn His Tyr Pro Leu Glu Lys Ile<br>305                           310                         315                   320 | | 960 |
| ggg gac tcg gtc tgg gat ggc cat gga ttc tcg gtt ggc cag atc cat<br>Gly Asp Ser Val Trp Asp Gly His Gly Phe Ser Val Gly Gln Ile His<br>                       325                         330                     335 | | 1008 |
| gag acc atg aac att cgg cga ggg att atc aca gat tgg ttt ttc gga<br>Glu Thr Met Asn Ile Arg Arg Gly Ile Ile Thr Asp Trp Phe Phe Gly<br>             340                         345                         350 | | 1056 |
| ggc ttg aac tac cag atc gag cac cat ttg tgg ccg acc ctc cct cgc<br>Gly Leu Asn Tyr Gln Ile Glu His His Leu Trp Pro Thr Leu Pro Arg<br>355                           360                        365 | | 1104 |
| cac aac ctg aca gcg gtt agc tac cag gtg gaa cag ctg tgc cag aag<br>His Asn Leu Thr Ala Val Ser Tyr Gln Val Glu Gln Leu Cys Gln Lys<br>370                           375                         380 | | 1152 |
| cac aac ctg ccg tat cgg aac ccg ctg ccc cat gaa ggg ttg gtc atc<br>His Asn Leu Pro Tyr Arg Asn Pro Leu Pro His Glu Gly Leu Val Ile<br>385                           390                         395                   400 | | 1200 |
| ctg ctg cgc tat ctg gcg gtg ttc gcc cgg atg gcg gag aag caa ccc<br>Leu Leu Arg Tyr Leu Ala Val Phe Ala Arg Met Ala Glu Lys Gln Pro<br>                       405                         410                     415 | | 1248 |
| gcg ggg aag gct cta taa<br>Ala Gly Lys Ala Leu<br>             420 | | 1266 |

<210> SEQ ID NO 19
<211> LENGTH: 421

-continued

```
<212> TYPE: PRT
<213> ORGANISM: Euglena gracilis

<400> SEQUENCE: 19
```

| | | | | | | | | | | | | | | | |
|---|---|---|---|---|---|---|---|---|---|---|---|---|---|---|---|
| Met | Lys | Ser | Lys | Arg | Gln | Ala | Leu | Pro | Leu | Thr | Ile | Asp | Gly | Thr | Thr |
| 1 | | | | 5 | | | | | 10 | | | | | 15 | |
| Tyr | Asp | Val | Ser | Ala | Trp | Val | Asn | Phe | His | Pro | Gly | Gly | Ala | Glu | Ile |
| | | | 20 | | | | | 25 | | | | | 30 | | |
| Ile | Glu | Asn | Tyr | Gln | Gly | Arg | Asp | Ala | Thr | Asp | Ala | Phe | Met | Val | Met |
| | | | 35 | | | | | 40 | | | | | 45 | | |
| His | Ser | Gln | Glu | Ala | Phe | Asp | Lys | Leu | Lys | Arg | Met | Pro | Lys | Ile | Asn |
| | 50 | | | | | 55 | | | | | 60 | | | | |
| Pro | Ser | Ser | Glu | Leu | Pro | Pro | Gln | Ala | Ala | Val | Asn | Glu | Ala | Gln | Glu |
| 65 | | | | | 70 | | | | | 75 | | | | | 80 |
| Asp | Phe | Arg | Lys | Leu | Arg | Glu | Glu | Leu | Ile | Ala | Thr | Gly | Met | Phe | Asp |
| | | | | 85 | | | | | 90 | | | | | 95 | |
| Ala | Ser | Pro | Leu | Trp | Tyr | Ser | Tyr | Lys | Ile | Ser | Thr | Thr | Leu | Gly | Leu |
| | | | 100 | | | | | 105 | | | | | 110 | | |
| Gly | Val | Leu | Gly | Tyr | Phe | Leu | Met | Val | Gln | Tyr | Gln | Met | Tyr | Phe | Ile |
| | | 115 | | | | | 120 | | | | | 125 | | | |
| Gly | Ala | Val | Leu | Leu | Gly | Met | His | Tyr | Gln | Gln | Met | Gly | Trp | Leu | Ser |
| | 130 | | | | | 135 | | | | | 140 | | | | |
| His | Asp | Ile | Cys | His | His | Gln | Thr | Phe | Lys | Asn | Arg | Asn | Trp | Asn | Asn |
| 145 | | | | | 150 | | | | | 155 | | | | | 160 |
| Leu | Val | Gly | Leu | Val | Phe | Gly | Asn | Gly | Leu | Gln | Gly | Phe | Ser | Val | Thr |
| | | | | 165 | | | | | 170 | | | | | 175 | |
| Cys | Trp | Lys | Asp | Arg | His | Asn | Ala | His | His | Ser | Ala | Thr | Asn | Val | Gln |
| | | | 180 | | | | | 185 | | | | | 190 | | |
| Gly | His | Asp | Pro | Asp | Ile | Asp | Asn | Leu | Pro | Leu | Leu | Ala | Trp | Ser | Glu |
| | | 195 | | | | | 200 | | | | | 205 | | | |
| Asp | Asp | Val | Thr | Arg | Ala | Ser | Pro | Ile | Ser | Arg | Lys | Leu | Ile | Gln | Phe |
| 210 | | | | | 215 | | | | | 220 | | | | | |
| Gln | Gln | Tyr | Tyr | Phe | Leu | Val | Ile | Cys | Ile | Leu | Leu | Arg | Phe | Ile | Trp |
| 225 | | | | | 230 | | | | | 235 | | | | | 240 |
| Cys | Phe | Gln | Ser | Val | Leu | Thr | Val | Arg | Ser | Leu | Lys | Asp | Arg | Asp | Asn |
| | | | | 245 | | | | | 250 | | | | | 255 | |
| Gln | Phe | Tyr | Arg | Ser | Gln | Tyr | Lys | Lys | Glu | Ala | Ile | Gly | Leu | Ala | Leu |
| | | | 260 | | | | | 265 | | | | | 270 | | |
| His | Trp | Thr | Leu | Lys | Ala | Leu | Phe | His | Leu | Phe | Phe | Met | Pro | Ser | Ile |
| | | 275 | | | | | 280 | | | | | 285 | | | |
| Leu | Thr | Ser | Leu | Leu | Val | Phe | Phe | Val | Ser | Glu | Leu | Val | Gly | Gly | Phe |
| | 290 | | | | | 295 | | | | | 300 | | | | |
| Gly | Ile | Ala | Ile | Val | Val | Phe | Met | Asn | His | Tyr | Pro | Leu | Glu | Lys | Ile |
| 305 | | | | | 310 | | | | | 315 | | | | | 320 |
| Gly | Asp | Ser | Val | Trp | Asp | Gly | His | Gly | Phe | Ser | Val | Gly | Gln | Ile | His |
| | | | | 325 | | | | | 330 | | | | | 335 | |
| Glu | Thr | Met | Asn | Ile | Arg | Arg | Gly | Ile | Ile | Thr | Asp | Trp | Phe | Phe | Gly |
| | | | 340 | | | | | 345 | | | | | 350 | | |
| Gly | Leu | Asn | Tyr | Gln | Ile | Glu | His | His | Leu | Trp | Pro | Thr | Leu | Pro | Arg |
| | | 355 | | | | | 360 | | | | | 365 | | | |
| His | Asn | Leu | Thr | Ala | Val | Ser | Tyr | Gln | Val | Glu | Gln | Leu | Cys | Gln | Lys |
| | 370 | | | | | 375 | | | | | 380 | | | | |
| His | Asn | Leu | Pro | Tyr | Arg | Asn | Pro | Leu | Pro | His | Glu | Gly | Leu | Val | Ile |
| 385 | | | | | 390 | | | | | 395 | | | | | 400 |

```
Leu Leu Arg Tyr Leu Ala Val Phe Ala Arg Met Ala Glu Lys Gln Pro
            405                 410                 415
Ala Gly Lys Ala Leu
            420

<210> SEQ ID NO 20
<211> LENGTH: 777
<212> TYPE: DNA
<213> ORGANISM: Isochrysis galbana
<220> FEATURE:
<221> NAME/KEY: CDS
<222> LOCATION: (1)..(777)
<223> OTHER INFORMATION: delta-9-Elongase

<400> SEQUENCE: 20 atg gcc ctc gca aac gac gcg gga gag cgc atc tgg gcg gct gtg acc      48
Met Ala Leu Ala Asn Asp Ala Gly Glu Arg Ile Trp Ala Ala Val Thr
1               5                  10                  15 gac ccg gaa atc ctc att ggc acc ttc tcg tac ttg cta ctc aaa ccg      96
Asp Pro Glu Ile Leu Ile Gly Thr Phe Ser Tyr Leu Leu Leu Lys Pro
                20                  25                  30 ctg ctc cgc aat tcc ggg ctg gtg gat gag aag aag ggc gca tac agg     144
Leu Leu Arg Asn Ser Gly Leu Val Asp Glu Lys Lys Gly Ala Tyr Arg
            35                  40                  45 acg tcc atg atc tgg tac aac gtt ctg ctg gcg ctc ttc tct gcg ctg     192
Thr Ser Met Ile Trp Tyr Asn Val Leu Leu Ala Leu Phe Ser Ala Leu
        50                  55                  60 agc ttc tac gtg acg gcg acc gcc ctc ggc tgg gac tat ggt acg ggc     240
Ser Phe Tyr Val Thr Ala Thr Ala Leu Gly Trp Asp Tyr Gly Thr Gly
65                  70                  75                  80 gcg tgg ctg cgc agg caa acc ggc gac aca ccg cag ccg ctc ttc cag     288
Ala Trp Leu Arg Arg Gln Thr Gly Asp Thr Pro Gln Pro Leu Phe Gln
                85                  90                  95 tgc ccg tcc ccg gtt tgg gac tcg aag ctc ttc aca tgg acc gcc aag     336
Cys Pro Ser Pro Val Trp Asp Ser Lys Leu Phe Thr Trp Thr Ala Lys
            100                 105                 110 gca ttc tat tac tcc aag tac gtg gag tac ctc gac acg gcc tgg ctg     384
Ala Phe Tyr Tyr Ser Lys Tyr Val Glu Tyr Leu Asp Thr Ala Trp Leu
        115                 120                 125 agg gtc tcc ttt ctc cag gcc ttc cac cac ttt ggc gcg ccg tgg gat     432
Arg Val Ser Phe Leu Gln Ala Phe His His Phe Gly Ala Pro Trp Asp
    130                 135                 140 gtg tac ctc ggc att cgg ctg cac aac gag ggc gta tgg atc ttc atg     480
Val Tyr Leu Gly Ile Arg Leu His Asn Glu Gly Val Trp Ile Phe Met
145                 150                 155                 160 ttt ttc aac tcg ttc att cac acc atc atg tac acc tac tac ggc ctc     528
Phe Phe Asn Ser Phe Ile His Thr Ile Met Tyr Thr Tyr Tyr Gly Leu
                165                 170                 175 acc gcc gcc ggg tat aag ttc aag gcc aag ccg ctc atc acc gcg atg     576
Thr Ala Ala Gly Tyr Lys Phe Lys Ala Lys Pro Leu Ile Thr Ala Met
            180                 185                 190 cag atc tgc cag ttc gtg ggc ggc ttc ctg ttg gtc tgg gac tac atc     624
Gln Ile Cys Gln Phe Val Gly Gly Phe Leu Leu Val Trp Asp Tyr Ile
        195                 200                 205 aac gtc ccc tgc ttc aac tcg gac aaa ggg aag ttg ttc agc tgg gct     672
Asn Val Pro Cys Phe Asn Ser Asp Lys Gly Lys Leu Phe Ser Trp Ala
    210                 215                 220 ttc aac tat gca tac gtc ggc tcg gtc ttc ttg ctc ttc tgc cac ttt     720
Phe Asn Tyr Ala Tyr Val Gly Ser Val Phe Leu Leu Phe Cys His Phe
225                 230                 235                 240
```

| | | |
|---|---|---|
| ttc tac cag gac aac ttg gca acg aag aaa tcg gcc aag gcg ggc aag<br>Phe Tyr Gln Asp Asn Leu Ala Thr Lys Lys Ser Ala Lys Ala Gly Lys<br>245 250 255 | | 768 |
| cag ctc tag<br>Gln Leu | | 777 |

<210> SEQ ID NO 21
<211> LENGTH: 258
<212> TYPE: PRT
<213> ORGANISM: Isochrysis galbana

<400> SEQUENCE: 21

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Arg Val Ser Phe Leu Gln Ala Phe His His Phe Gly Ala Pro Trp Asp
    130                 135                 140

Val Tyr Leu Gly Ile Arg Leu His Asn Glu Gly Val Trp Ile Phe Met
145                 150                 155                 160

Phe Phe Asn Ser Phe Ile His Thr Ile Met Tyr Thr Tyr Tyr Gly Leu
                165                 170                 175

Thr Ala Ala Gly Tyr Lys Phe Lys Ala Lys Pro Leu Ile Thr Ala Met
            180                 185                 190

Gln Ile Cys Gln Phe Val Gly Gly Phe Leu Leu Val Trp Asp Tyr Ile
        195                 200                 205

Asn Val Pro Cys Phe Asn Ser Asp Lys Gly Lys Leu Phe Ser Trp Ala
    210                 215                 220

Phe Asn Tyr Ala Tyr Val Gly Ser Val Phe Leu Leu Phe Cys His Phe
225                 230                 235                 240

Phe Tyr Gln Asp Asn Leu Ala Thr Lys Lys Ser Ala Lys Ala Gly Lys
                245                 250                 255

Gln Leu
```

<210> SEQ ID NO 22
<211> LENGTH: 1410
<212> TYPE: DNA
<213> ORGANISM: Phaeodactylum tricornutum
<220> FEATURE:
<221> NAME/KEY: CDS
<222> LOCATION: (1)..(1410)
<223> OTHER INFORMATION: delta-5-Desaturase

<400> SEQUENCE: 22

| | | |
|---|---|---|
| atg gct ccg gat gcg gat aag ctt cga caa cgc cag acg act gcg gta<br>Met Ala Pro Asp Ala Asp Lys Leu Arg Gln Arg Gln Thr Thr Ala Val | | 48 |

| | | | | | | | | | | | | | | | | |
|---|---|---|---|---|---|---|---|---|---|---|---|---|---|---|---|---|
| gcg | aag | cac | aat | gct | gct | acc | ata | tcg | acg | cag | gaa | cgc | ctt | tgc | agt | 96 |
| Ala | Lys | His | Asn<br>20 | Ala | Ala | Thr | Ile | Ser<br>25 | Thr | Gln | Glu | Arg | Leu<br>30 | Cys | Ser | |
| ctg | tct | tcg | ctc | aaa | ggc | gaa | gaa | gtc | tgc | atc | gac | gga | atc | atc | tat | 144 |
| Leu | Ser | Ser<br>35 | Leu | Lys | Gly | Glu | Glu<br>40 | Val | Cys | Ile | Asp | Gly<br>45 | Ile | Ile | Tyr | |
| gac | ctc | caa | tca | ttc | gat | cat | ccc | ggg | ggt | gaa | acg | atc | aaa | atg | ttt | 192 |
| Asp | Leu<br>50 | Gln | Ser | Phe | Asp | His<br>55 | Pro | Gly | Gly | Glu | Thr<br>60 | Ile | Lys | Met | Phe | |
| ggt | ggc | aac | gat | gtc | act | gta | cag | tac | aag | atg | att | cac | ccg | tac | cat | 240 |
| Gly<br>65 | Gly | Asn | Asp | Val | Thr<br>70 | Val | Gln | Tyr | Lys | Met<br>75 | Ile | His | Pro | Tyr | His<br>80 | |
| acc | gag | aag | cat | ttg | gaa | aag | atg | aag | cgt | gtc | ggc | aag | gtg | acg | gat | 288 |
| Thr | Glu | Lys | His | Leu<br>85 | Glu | Lys | Met | Lys | Arg<br>90 | Val | Gly | Lys | Val | Thr<br>95 | Asp | |
| ttc | gtc | tgc | gag | tac | aag | ttc | gat | acc | gaa | ttt | gaa | cgc | gaa | atc | aaa | 336 |
| Phe | Val | Cys | Glu<br>100 | Tyr | Lys | Phe | Asp | Thr<br>105 | Glu | Phe | Glu | Arg | Glu<br>110 | Ile | Lys | |
| cga | gaa | gtc | ttc | aag | att | gtg | cga | cga | ggc | aag | gat | ttc | ggt | act | ttg | 384 |
| Arg | Glu | Val | Phe<br>115 | Lys | Ile | Val | Arg | Arg<br>120 | Gly | Lys | Asp | Phe | Gly<br>125 | Thr | Leu | |
| gga | tgg | ttc | ttc | cgt | gcg | ttt | tgc | tac | att | gcc | att | ttc | ttc | tac | ctg | 432 |
| Gly | Trp | Phe<br>130 | Phe | Arg | Ala | Phe | Cys<br>135 | Tyr | Ile | Ala | Ile | Phe<br>140 | Phe | Tyr | Leu | |
| cag | tac | cat | tgg | gtc | acc | acg | gga | acc | tct | tgg | ctg | ctg | gcc | gtg | gcc | 480 |
| Gln<br>145 | Tyr | His | Trp | Val | Thr<br>150 | Thr | Gly | Thr | Ser | Trp<br>155 | Leu | Leu | Ala | Val | Ala<br>160 | |
| tac | gga | atc | tcc | caa | gcg | atg | att | ggc | atg | aat | gtc | cag | cac | gat | gcc | 528 |
| Tyr | Gly | Ile | Ser | Gln<br>165 | Ala | Met | Ile | Gly | Met<br>170 | Asn | Val | Gln | His | Asp<br>175 | Ala | |
| aac | cac | ggg | gcc | acc | tcc | aag | cgt | ccc | tgg | gtc | aac | gac | atg | cta | ggc | 576 |
| Asn | His | Gly | Ala<br>180 | Thr | Ser | Lys | Arg | Pro<br>185 | Trp | Val | Asn | Asp | Met<br>190 | Leu | Gly | |
| ctc | ggt | gcg | gat | ttt | att | ggt | ggt | tcc | aag | tgg | ctc | tgg | cag | gaa | caa | 624 |
| Leu | Gly | Ala<br>195 | Asp | Phe | Ile | Gly | Gly<br>200 | Ser | Lys | Trp | Leu | Trp<br>205 | Gln | Glu | Gln | |
| cac | tgg | acc | cac | cac | gct | tac | acc | aat | cac | gcc | gag | atg | gat | ccc | gat | 672 |
| His | Trp<br>210 | Thr | His | His | Ala | Tyr<br>215 | Thr | Asn | His | Ala | Glu<br>220 | Met | Asp | Pro | Asp | |
| agc | ttt | ggt | gcc | gaa | cca | atg | ctc | cta | ttc | aac | gac | tat | ccc | ttg | gat | 720 |
| Ser<br>225 | Phe | Gly | Ala | Glu | Pro<br>230 | Met | Leu | Leu | Phe | Asn<br>235 | Asp | Tyr | Pro | Leu | Asp<br>240 | |
| cat | ccc | gct | cgt | acc | tgg | cta | cat | cgc | ttt | caa | gca | ttc | ttt | tac | atg | 768 |
| His | Pro | Ala | Arg | Thr<br>245 | Trp | Leu | His | Arg | Phe<br>250 | Gln | Ala | Phe | Phe | Tyr<br>255 | Met | |
| ccc | gtc | ttg | gct | gga | tac | tgg | ttg | tcc | gct | gtc | ttc | aat | cca | caa | att | 816 |
| Pro | Val | Leu | Ala | Gly<br>260 | Tyr | Trp | Leu | Ser | Ala<br>265 | Val | Phe | Asn | Pro | Gln<br>270 | Ile | |
| ctt | gac | ctc | cag | caa | cgc | ggc | gca | ctt | tcc | gtc | ggt | atc | cgt | ctc | gac | 864 |
| Leu | Asp | Leu | Gln | Gln<br>275 | Arg | Gly | Ala | Leu | Ser<br>280 | Val | Gly | Ile | Arg | Leu<br>285 | Asp | |
| aac | gct | ttc | att | cac | tcg | cga | cgc | aag | tat | gcg | gtt | ttc | tgg | cgg | gct | 912 |
| Asn | Ala | Phe | Ile<br>290 | His | Ser | Arg | Arg | Lys<br>295 | Tyr | Ala | Val | Phe | Trp<br>300 | Arg | Ala | |
| gtg | tac | att | gcg | gtg | aac | gtg | att | gct | ccg | ttt | tac | aca | aac | tcc | ggc | 960 |
| Val<br>305 | Tyr | Ile | Ala | Val | Asn<br>310 | Val | Ile | Ala | Pro | Phe<br>315 | Tyr | Thr | Asn | Ser | Gly<br>320 | |
| ctc | gaa | tgg | tcc | tgg | cgt | gtc | ttt | gga | aac | atc | atg | ctc | atg | ggt | gtg | 1008 |

-continued

```
Leu Glu Trp Ser Trp Arg Val Phe Gly Asn Ile Met Leu Met Gly Val
            325                 330                 335 gcg gaa tcg ctc gcg ctg gcg gtc ctg ttt tcg ttg tcg cac aat ttc      1056
Ala Glu Ser Leu Ala Leu Ala Val Leu Phe Ser Leu Ser His Asn Phe
            340                 345                 350 gaa tcc gcg gat cgc gat ccg acc gcc cca ctg aaa aag acg gga gaa      1104
Glu Ser Ala Asp Arg Asp Pro Thr Ala Pro Leu Lys Lys Thr Gly Glu
        355                 360                 365 cca gtc gac tgg ttc aag aca cag gtc gaa act tcc tgc act tac ggt      1152
Pro Val Asp Trp Phe Lys Thr Gln Val Glu Thr Ser Cys Thr Tyr Gly
    370                 375                 380 gga ttc ctt tcc ggt tgc ttc acg gga ggt ctc aac ttt cag gtt gaa      1200
Gly Phe Leu Ser Gly Cys Phe Thr Gly Gly Leu Asn Phe Gln Val Glu
385                 390                 395                 400 cac cac ttg ttc cca cgc atg agc agc gct tgg tat ccc tac att gcc      1248
His His Leu Phe Pro Arg Met Ser Ser Ala Trp Tyr Pro Tyr Ile Ala
                405                 410                 415 ccc aag gtc cgc gaa att tgc gcc aaa cac ggc gtc cac tac gcc tac      1296
Pro Lys Val Arg Glu Ile Cys Ala Lys His Gly Val His Tyr Ala Tyr
            420                 425                 430 tac ccg tgg atc cac caa aac ttt ctc tcc acc gtc cgc tac atg cac      1344
Tyr Pro Trp Ile His Gln Asn Phe Leu Ser Thr Val Arg Tyr Met His
        435                 440                 445 gcg gcc ggg acc ggt gcc aac tgg cgc cag atg gcc aga gaa aat ccc      1392
Ala Ala Gly Thr Gly Ala Asn Trp Arg Gln Met Ala Arg Glu Asn Pro
    450                 455                 460 ttg acc gga cgg gcg taa                                              1410
Leu Thr Gly Arg Ala
465

<210> SEQ ID NO 23
<211> LENGTH: 469
<212> TYPE: PRT
<213> ORGANISM: Phaeodactylum tricornutum

<400> SEQUENCE: 23

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175
```

```
Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 24
<211> LENGTH: 1344
<212> TYPE: DNA
<213> ORGANISM: Ceratodon purpureus
<220> FEATURE:
<221> NAME/KEY: CDS
<222> LOCATION: (1)..(1344)
<223> OTHER INFORMATION: delta-5-Desaturase

<400> SEQUENCE: 24 atg gta tta cga gag caa gag cat gag cca ttc ttc att aaa att gat     48
Met Val Leu Arg Glu Gln Glu His Glu Pro Phe Phe Ile Lys Ile Asp
1               5                   10                  15 gga aaa tgg tgt caa att gac gat gct gtc ctg aga tca cat cca ggt     96
Gly Lys Trp Cys Gln Ile Asp Asp Ala Val Leu Arg Ser His Pro Gly
            20                  25                  30 ggt agt gca att act acc tat aaa aat atg gat gcc act acc gta ttc    144
```

```
                Gly Ser Ala Ile Thr Thr Tyr Lys Asn Met Asp Ala Thr Thr Val Phe
                         35                  40                  45 cac aca ttc cat act ggt tct aaa gaa gcg tat caa tgg ctg aca gaa              192
His Thr Phe His Thr Gly Ser Lys Glu Ala Tyr Gln Trp Leu Thr Glu
         50                  55                  60 ttg aaa aaa gag tgc cct aca caa gaa cca gag atc cca gat att aag              240
Leu Lys Lys Glu Cys Pro Thr Gln Glu Pro Glu Ile Pro Asp Ile Lys
65                  70                  75                  80 gat gac cca atc aaa gga att gat gat gtg aac atg gga act ttc aat              288
Asp Asp Pro Ile Lys Gly Ile Asp Asp Val Asn Met Gly Thr Phe Asn
                         85                  90                  95 att tct gag aaa cga tct gcc caa ata aat aaa agt ttc act gat cta              336
Ile Ser Glu Lys Arg Ser Ala Gln Ile Asn Lys Ser Phe Thr Asp Leu
                 100                 105                 110 cgt atg cga gtt cgt gca gaa gga ctt atg gat gga tct cct ttg ttc              384
Arg Met Arg Val Arg Ala Glu Gly Leu Met Asp Gly Ser Pro Leu Phe
                 115                 120                 125 tac att aga aaa att ctt gaa aca atc ttc aca att ctt ttt gca ttc              432
Tyr Ile Arg Lys Ile Leu Glu Thr Ile Phe Thr Ile Leu Phe Ala Phe
        130                 135                 140 tac ctt caa tac cac aca tat tat ctt cca tca gct att cta atg gga              480
Tyr Leu Gln Tyr His Thr Tyr Tyr Leu Pro Ser Ala Ile Leu Met Gly
145                 150                 155                 160 gtt gcg tgg caa caa ttg gga tgg tta atc cat gaa ttc gca cat cat              528
Val Ala Trp Gln Gln Leu Gly Trp Leu Ile His Glu Phe Ala His His
                 165                 170                 175 cag ttg ttc aaa aac aga tac tac aat gat ttg gcc agc tat ttc gtt              576
Gln Leu Phe Lys Asn Arg Tyr Tyr Asn Asp Leu Ala Ser Tyr Phe Val
                 180                 185                 190 gga aac ttt tta caa gga ttc tca tct ggt ggt tgg aaa gag cag cac              624
Gly Asn Phe Leu Gln Gly Phe Ser Ser Gly Gly Trp Lys Glu Gln His
        195                 200                 205 aat gtg cat cac gca gcc aca aat gtt gtt gga cga gac gga gat ctt              672
Asn Val His His Ala Ala Thr Asn Val Val Gly Arg Asp Gly Asp Leu
210                 215                 220 gat tta gtc cca ttc tat gct aca gtg gca gaa cat ctc aac aat tat              720
Asp Leu Val Pro Phe Tyr Ala Thr Val Ala Glu His Leu Asn Asn Tyr
225                 230                 235                 240 tct cag gat tca tgg gtt atg act cta ttc aga tgg caa cat gtt cat              768
Ser Gln Asp Ser Trp Val Met Thr Leu Phe Arg Trp Gln His Val His
                 245                 250                 255 tgg aca ttc atg tta cca ttc ctc cgt ctc tcg tgg ctt ctt cag tca              816
Trp Thr Phe Met Leu Pro Phe Leu Arg Leu Ser Trp Leu Leu Gln Ser
        260                 265                 270 atc att ttt gtt agt cag atg cca act cat tat tat gac tat tac aga              864
Ile Ile Phe Val Ser Gln Met Pro Thr His Tyr Tyr Asp Tyr Tyr Arg
        275                 280                 285 aat act gcg att tat gaa cag gtt ggc ctc tct ttg cac tgg gct tgg              912
Asn Thr Ala Ile Tyr Glu Gln Val Gly Leu Ser Leu His Trp Ala Trp
        290                 295                 300 tca ttg ggt caa ttg tat ttc cta ccc gat tgg tca act aga ata atg              960
Ser Leu Gly Gln Leu Tyr Phe Leu Pro Asp Trp Ser Thr Arg Ile Met
305                 310                 315                 320 ttc ttc ctt gtt tct cat ctt gtt gga ggt ttc ctg ctc tct cat gta             1008
Phe Phe Leu Val Ser His Leu Val Gly Gly Phe Leu Leu Ser His Val
                 325                 330                 335 gtt act ttc aat cat tat tca gtg gag aag ttt gca ttg agc tcg aac             1056
Val Thr Phe Asn His Tyr Ser Val Glu Lys Phe Ala Leu Ser Ser Asn
                 340                 345                 350
```

-continued

```
atc atg tca aat tac gct tgt ctt caa atc atg acc aca aga aat atg    1104
Ile Met Ser Asn Tyr Ala Cys Leu Gln Ile Met Thr Thr Arg Asn Met
        355                 360                 365 aga cct gga aga ttc att gac tgg ctt tgg gga ggt ctt aac tat cag    1152
Arg Pro Gly Arg Phe Ile Asp Trp Leu Trp Gly Gly Leu Asn Tyr Gln
370                 375                 380 att gag cac cat ctt ttc cca acg atg cca cga cac aac ttg aac act    1200
Ile Glu His His Leu Phe Pro Thr Met Pro Arg His Asn Leu Asn Thr
385                 390                 395                 400 gtt atg cca ctt gtt aag gag ttt gca gca gca aat ggt tta cca tac    1248
Val Met Pro Leu Val Lys Glu Phe Ala Ala Ala Asn Gly Leu Pro Tyr
                405                 410                 415 atg gtc gac gat tat ttc aca gga ttc tgg ctt gaa att gag caa ttc    1296
Met Val Asp Asp Tyr Phe Thr Gly Phe Trp Leu Glu Ile Glu Gln Phe
            420                 425                 430 cga aat att gca aat gtt gct gct aaa ttg act aaa aag att gcc tag    1344
Arg Asn Ile Ala Asn Val Ala Ala Lys Leu Thr Lys Lys Ile Ala
        435                 440                 445

<210> SEQ ID NO 25
<211> LENGTH: 447
<212> TYPE: PRT
<213> ORGANISM: Ceratodon purpureus

<400> SEQUENCE: 25

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Ile Pro Asp Ile Lys
65                  70                  75                  80

Asp Asp Pro Ile Lys Gly Ile Asp Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
                165                 170                 175

Gln Leu Phe Lys Asn Arg Tyr Tyr Asn Asp Leu Ala Ser Tyr Phe Val
            180                 185                 190

Gly Asn Phe Leu Gln Gly Phe Ser Ser Gly Gly Trp Lys Glu Gln His
        195                 200                 205

Asn Val His His Ala Ala Thr Asn Val Val Gly Arg Asp Gly Asp Leu
    210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
                245                 250                 255
```

```
Trp Thr Phe Met Leu Pro Phe Leu Arg Leu Ser Trp Leu Leu Gln Ser
            260                 265                 270

Ile Ile Phe Val Ser Gln Met Pro Thr His Tyr Tyr Asp Tyr Tyr Arg
            275                 280                 285

Asn Thr Ala Ile Tyr Glu Gln Val Gly Leu Ser Leu His Trp Ala Trp
            290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Phe Leu Leu Ser His Val
                325                 330                 335

Val Thr Phe Asn His Tyr Ser Val Glu Lys Phe Ala Leu Ser Ser Asn
            340                 345                 350

Ile Met Ser Asn Tyr Ala Cys Leu Gln Ile Met Thr Thr Arg Asn Met
            355                 360                 365

Arg Pro Gly Arg Phe Ile Asp Trp Leu Trp Gly Gly Leu Asn Tyr Gln
            370                 375                 380

Ile Glu His His Leu Phe Pro Thr Met Pro Arg His Asn Leu Asn Thr
385                 390                 395                 400

Val Met Pro Leu Val Lys Glu Phe Ala Ala Ala Asn Gly Leu Pro Tyr
                405                 410                 415

Met Val Asp Asp Tyr Phe Thr Gly Phe Trp Leu Glu Ile Glu Gln Phe
            420                 425                 430

Arg Asn Ile Ala Asn Val Ala Ala Lys Leu Thr Lys Lys Ile Ala
            435                 440                 445

<210> SEQ ID NO 26
<211> LENGTH: 1443
<212> TYPE: DNA
<213> ORGANISM: Physcomitrella patens
<220> FEATURE:
<221> NAME/KEY: CDS
<222> LOCATION: (1)..(1443)
<223> OTHER INFORMATION: delta-5-Desaturase

<400> SEQUENCE: 26 atg gcg ccc cac tct gcg gat act gct ggg ctc gtg cct tct gac gaa      48
Met Ala Pro His Ser Ala Asp Thr Ala Gly Leu Val Pro Ser Asp Glu
1               5                   10                  15 ttg agg cta cga acg tcg aat tca aag ggt ccc gaa caa gag caa act      96
Leu Arg Leu Arg Thr Ser Asn Ser Lys Gly Pro Glu Gln Glu Gln Thr
            20                  25                  30 ttg aag aag tac acc ctt gaa gat gtc agc cgc cac aac acc cca gca     144
Leu Lys Lys Tyr Thr Leu Glu Asp Val Ser Arg His Asn Thr Pro Ala
        35                  40                  45 gat tgt tgg ttg gtg ata tgg ggc aaa gtc tac gat gtc aca agc tgg     192
Asp Cys Trp Leu Val Ile Trp Gly Lys Val Tyr Asp Val Thr Ser Trp
    50                  55                  60 att ccc aat cat ccg ggg ggc agt ctc atc cac gta aaa gca ggg cag     240
Ile Pro Asn His Pro Gly Gly Ser Leu Ile His Val Lys Ala Gly Gln
65                  70                  75                  80 gat tcc act cag ctt ttc gat tcc tat cac ccc ctt tat gtc agg aaa     288
Asp Ser Thr Gln Leu Phe Asp Ser Tyr His Pro Leu Tyr Val Arg Lys
                85                  90                  95 atg ctc gcg aag tac tgt att ggg gaa tta gta ccg tct gct ggt gat     336
Met Leu Ala Lys Tyr Cys Ile Gly Glu Leu Val Pro Ser Ala Gly Asp
            100                 105                 110 gac aag ttt aag aaa gca act ctg gag tat gca gat gcc gaa aat gaa     384
Asp Lys Phe Lys Lys Ala Thr Leu Glu Tyr Ala Asp Ala Glu Asn Glu
```

```
                    115                 120                 125
gat ttc tat ttg gtt gtg aag caa cga gtt gaa tct tat ttc aag agt      432
Asp Phe Tyr Leu Val Val Lys Gln Arg Val Glu Ser Tyr Phe Lys Ser
    130                 135                 140 aac aag ata aac ccc caa att cat cca cat atg atc ctg aag tca ttg      480
Asn Lys Ile Asn Pro Gln Ile His Pro His Met Ile Leu Lys Ser Leu
145                 150                 155                 160 ttc att ctt ggg gga tat ttc gcc agt tac tat tta gcg ttc ttc tgg      528
Phe Ile Leu Gly Gly Tyr Phe Ala Ser Tyr Tyr Leu Ala Phe Phe Trp
                165                 170                 175 tct tca agt gtc ctt gtt tct ttg ttt ttc gca ttg tgg atg ggg ttc      576
Ser Ser Ser Val Leu Val Ser Leu Phe Phe Ala Leu Trp Met Gly Phe
            180                 185                 190 ttc gca gcg gaa gtc ggc gtg tcg att caa cat gat gga aat cat ggt      624
Phe Ala Ala Glu Val Gly Val Ser Ile Gln His Asp Gly Asn His Gly
        195                 200                 205 tca tac act aaa tgg cgt ggc ttt gga tat atc atg gga gcc tcc cta      672
Ser Tyr Thr Lys Trp Arg Gly Phe Gly Tyr Ile Met Gly Ala Ser Leu
    210                 215                 220 gat cta gtc gga gcc agt agc ttc atg tgg aga cag caa cac gtt gtg      720
Asp Leu Val Gly Ala Ser Ser Phe Met Trp Arg Gln Gln His Val Val
225                 230                 235                 240 gga cat cac tcg ttt aca aat gtg gac aac tac gat cct gat att cgt      768
Gly His His Ser Phe Thr Asn Val Asp Asn Tyr Asp Pro Asp Ile Arg
                245                 250                 255 gtg aaa gat cca gat gtc agg agg gtt gcg acc aca caa cca aga caa      816
Val Lys Asp Pro Asp Val Arg Arg Val Ala Thr Thr Gln Pro Arg Gln
            260                 265                 270 tgg tat cat gcg tat cag cat atc tac ctg gca gta tta tat gga act      864
Trp Tyr His Ala Tyr Gln His Ile Tyr Leu Ala Val Leu Tyr Gly Thr
        275                 280                 285 cta gct ctt aag agt att ttt cta gat gat ttc ctt gcg tac ttc aca      912
Leu Ala Leu Lys Ser Ile Phe Leu Asp Asp Phe Leu Ala Tyr Phe Thr
    290                 295                 300 gga tca att ggc cct gtc aag gtg gcg aaa atg acc ccc ctg gag ttc      960
Gly Ser Ile Gly Pro Val Lys Val Ala Lys Met Thr Pro Leu Glu Phe
305                 310                 315                 320 aac atc ttc ttt cag gga aag ctg cta tat gcg ttc tac atg ttc gtg     1008
Asn Ile Phe Phe Gln Gly Lys Leu Leu Tyr Ala Phe Tyr Met Phe Val
                325                 330                 335 ttg cca tct gtg tac ggt gtt cac tcc gga gga act ttc ttg gca cta     1056
Leu Pro Ser Val Tyr Gly Val His Ser Gly Gly Thr Phe Leu Ala Leu
            340                 345                 350 tat gtg gct tct cag ctc att aca ggt tgg atg tta gct ttt ctt ttt     1104
Tyr Val Ala Ser Gln Leu Ile Thr Gly Trp Met Leu Ala Phe Leu Phe
        355                 360                 365 caa gta gca cat gtc gtg gat gat gtt gca ttt cct aca cca gaa ggt     1152
Gln Val Ala His Val Val Asp Asp Val Ala Phe Pro Thr Pro Glu Gly
    370                 375                 380 ggg aag gtg aag gga gga tgg gct gca atg cag gtt gca aca act acg     1200
Gly Lys Val Lys Gly Gly Trp Ala Ala Met Gln Val Ala Thr Thr Thr
385                 390                 395                 400 gat ttc agt cca cgc tca tgg ttc tgg ggt cat gtc tct gga gga tta     1248
Asp Phe Ser Pro Arg Ser Trp Phe Trp Gly His Val Ser Gly Gly Leu
                405                 410                 415 aac aac caa att gag cat cat ctg ttt cca gga gtg tgc cat gtt cat     1296
Asn Asn Gln Ile Glu His His Leu Phe Pro Gly Val Cys His Val His
            420                 425                 430 tat cca gcc att cag cct att gtc gag aag acg tgc aag gaa ttc gat     1344
```

```
Tyr Pro Ala Ile Gln Pro Ile Val Glu Lys Thr Cys Lys Glu Phe Asp
        435                 440                 445 gtg cct tat gta gcc tac cca act ttt tgg act gcg ttg aga gcc cac      1392
Val Pro Tyr Val Ala Tyr Pro Thr Phe Trp Thr Ala Leu Arg Ala His
450                 455                 460 ttt gcg cat ttg aaa aag gtt gga ttg aca gag ttt cgg ctc gat ggc      1440
Phe Ala His Leu Lys Lys Val Gly Leu Thr Glu Phe Arg Leu Asp Gly
465                 470                 475                 480 tga                                                                   1443

<210> SEQ ID NO 27
<211> LENGTH: 480
<212> TYPE: PRT
<213> ORGANISM: Physcomitrella patens

<400> SEQUENCE: 27

Met Ala Pro His Ser Ala Asp Thr Ala Gly Leu Val Pro Ser Asp Glu
1               5                   10                  15

Leu Arg Leu Arg Thr Ser Asn Ser Lys Gly Pro Glu Gln Glu Gln Thr
            20                  25                  30

Leu Lys Lys Tyr Thr Leu Glu Asp Val Ser Arg His Asn Thr Pro Ala
        35                  40                  45

Asp Cys Trp Leu Val Ile Trp Gly Lys Val Tyr Asp Val Thr Ser Trp
    50                  55                  60

Ile Pro Asn His Pro Gly Gly Ser Leu Ile His Val Lys Ala Gly Gln
65                  70                  75                  80

Asp Ser Thr Gln Leu Phe Asp Ser Tyr His Pro Leu Tyr Val Arg Lys
                85                  90                  95

Met Leu Ala Lys Tyr Cys Ile Gly Glu Leu Val Pro Ser Ala Gly Asp
            100                 105                 110

Asp Lys Phe Lys Lys Ala Thr Leu Glu Tyr Ala Asp Ala Glu Asn Glu
        115                 120                 125

Asp Phe Tyr Leu Val Val Lys Gln Arg Val Glu Ser Tyr Phe Lys Ser
    130                 135                 140

Asn Lys Ile Asn Pro Gln Ile His Pro His Met Ile Leu Lys Ser Leu
145                 150                 155                 160

Phe Ile Leu Gly Gly Tyr Phe Ala Ser Tyr Tyr Leu Ala Phe Phe Trp
                165                 170                 175

Ser Ser Ser Val Leu Val Ser Leu Phe Phe Ala Leu Trp Met Gly Phe
            180                 185                 190

Phe Ala Ala Glu Val Gly Val Ser Ile Gln His Asp Gly Asn His Gly
        195                 200                 205

Ser Tyr Thr Lys Trp Arg Gly Phe Gly Tyr Ile Met Gly Ala Ser Leu
    210                 215                 220

Asp Leu Val Gly Ala Ser Ser Phe Met Trp Arg Gln Gln His Val Val
225                 230                 235                 240

Gly His His Ser Phe Thr Asn Val Asp Asn Tyr Asp Pro Asp Ile Arg
                245                 250                 255

Val Lys Asp Pro Asp Val Arg Arg Val Ala Thr Thr Gln Pro Arg Gln
            260                 265                 270

Trp Tyr His Ala Tyr Gln His Ile Tyr Leu Ala Val Leu Tyr Gly Thr
        275                 280                 285

Leu Ala Leu Lys Ser Ile Phe Leu Asp Asp Phe Leu Ala Tyr Phe Thr
    290                 295                 300

Gly Ser Ile Gly Pro Val Lys Val Ala Lys Met Thr Pro Leu Glu Phe
```

```
                305                 310                 315                 320
Asn Ile Phe Phe Gln Gly Lys Leu Leu Tyr Ala Phe Tyr Met Phe Val
                    325                 330                 335

Leu Pro Ser Val Tyr Gly Val His Ser Gly Gly Thr Phe Leu Ala Leu
            340                 345                 350

Tyr Val Ala Ser Gln Leu Ile Thr Gly Trp Met Leu Ala Phe Leu Phe
                355                 360                 365

Gln Val Ala His Val Val Asp Val Ala Phe Pro Thr Pro Glu Gly
        370                 375                 380

Gly Lys Val Lys Gly Gly Trp Ala Ala Met Gln Val Ala Thr Thr Thr
385                 390                 395                 400

Asp Phe Ser Pro Arg Ser Trp Phe Trp Gly His Val Ser Gly Gly Leu
                405                 410                 415

Asn Asn Gln Ile Glu His His Leu Phe Pro Gly Val Cys His Val His
                420                 425                 430

Tyr Pro Ala Ile Gln Pro Ile Val Glu Lys Thr Cys Lys Glu Phe Asp
                435                 440                 445

Val Pro Tyr Val Ala Tyr Pro Thr Phe Trp Thr Ala Leu Arg Ala His
            450                 455                 460

Phe Ala His Leu Lys Lys Val Gly Leu Thr Glu Phe Arg Leu Asp Gly
465                 470                 475                 480

<210> SEQ ID NO 28
<211> LENGTH: 1320
<212> TYPE: DNA
<213> ORGANISM: Thraustochytrium
<220> FEATURE:
<221> NAME/KEY: CDS
<222> LOCATION: (1)..(1320)

<400> SEQUENCE: 28 atg ggc aag ggc agc gag ggc cgc agc gcg gcg cgc gag atg acg gcc      48
Met Gly Lys Gly Ser Glu Gly Arg Ser Ala Ala Arg Glu Met Thr Ala
1               5                   10                  15 gag gcg aac ggc gac aag cgg aaa acg att ctg atc gag ggc gtc ctg      96
Glu Ala Asn Gly Asp Lys Arg Lys Thr Ile Leu Ile Glu Gly Val Leu
                20                  25                  30 tac gac gcg acg aac ttt aag cac ccg ggc ggt tcg atc atc aac ttc     144
Tyr Asp Ala Thr Asn Phe Lys His Pro Gly Gly Ser Ile Ile Asn Phe
            35                  40                  45 ttg acc gag ggc gag gcc ggc gtg gac gcg acg cag gcg tac cgc gag     192
Leu Thr Glu Gly Glu Ala Gly Val Asp Ala Thr Gln Ala Tyr Arg Glu
        50                  55                  60 ttt cat cag cgg tcc ggc aag gcc gac aag tac ctc aag tcg ctg ccg     240
Phe His Gln Arg Ser Gly Lys Ala Asp Lys Tyr Leu Lys Ser Leu Pro
65                  70                  75                  80 aag ctg gat gcg tcc aag gtg gag tcg cgg ttc tcg gcc aaa gag cag     288
Lys Leu Asp Ala Ser Lys Val Glu Ser Arg Phe Ser Ala Lys Glu Gln
                85                  90                  95 gcg cgg cgc gac gcc atg acg cgc gac tac gcg gcc ttt cgc gag gag     336
Ala Arg Arg Asp Ala Met Thr Arg Asp Tyr Ala Ala Phe Arg Glu Glu
                100                 105                 110 ctc gtc gcc gag ggg tac ttt gac ccg tcg atc ccg cac atg att tac     384
Leu Val Ala Glu Gly Tyr Phe Asp Pro Ser Ile Pro His Met Ile Tyr
            115                 120                 125 cgc gtc gtg gag atc gtg gcg ctc ttc gcg ctc tcg ttc tgg ctc atg     432
Arg Val Val Glu Ile Val Ala Leu Phe Ala Leu Ser Phe Trp Leu Met
        130                 135                 140
```

```
tcc aag gcc tcg ccc acc tcg ctc gtg ctg ggc gtg gtg atg aac ggc      480
Ser Lys Ala Ser Pro Thr Ser Leu Val Leu Gly Val Val Met Asn Gly
145                 150                 155                 160 att gcg cag ggc cgc tgc ggc tgg gtc atg cac gag atg ggc cac ggg      528
Ile Ala Gln Gly Arg Cys Gly Trp Val Met His Glu Met Gly His Gly
                165                 170                 175 tcg ttc acg ggc gtc atc tgg ctc gac gac cgg atg tgc gag ttc ttc      576
Ser Phe Thr Gly Val Ile Trp Leu Asp Asp Arg Met Cys Glu Phe Phe
            180                 185                 190 tac ggc gtc ggc tgc ggc atg agc ggg cac tac tgg aag aac cag cac      624
Tyr Gly Val Gly Cys Gly Met Ser Gly His Tyr Trp Lys Asn Gln His
        195                 200                 205 agc aag cac cac gcc gcg ccc aac cgc ctc gag cac gat gtc gat ctc      672
Ser Lys His His Ala Ala Pro Asn Arg Leu Glu His Asp Val Asp Leu
    210                 215                 220 aac acg ctg ccc ctg gtc gcc ttt aac gag cgc gtc gtg cgc aag gtc      720
Asn Thr Leu Pro Leu Val Ala Phe Asn Glu Arg Val Val Arg Lys Val
225                 230                 235                 240 aag ccg gga tcg ctg ctg gcg ctc tgg ctg cgc gtg cag gcg tac ctc      768
Lys Pro Gly Ser Leu Leu Ala Leu Trp Leu Arg Val Gln Ala Tyr Leu
                245                 250                 255 ttt gcg ccc gtc tcg tgc ctg ctc atc ggc ctt ggc tgg acg ctc tac      816
Phe Ala Pro Val Ser Cys Leu Leu Ile Gly Leu Gly Trp Thr Leu Tyr
            260                 265                 270 ctg cac ccg cgc tac atg ctg cgc acc aag cgg cac atg gag ttc gtc      864
Leu His Pro Arg Tyr Met Leu Arg Thr Lys Arg His Met Glu Phe Val
        275                 280                 285 tgg atc ttc gcg cgc tac att ggc tgg ttc tcg ctc atg ggc gct ctc      912
Trp Ile Phe Ala Arg Tyr Ile Gly Trp Phe Ser Leu Met Gly Ala Leu
    290                 295                 300 ggc tac tcg ccg ggc acc tcg gtc ggg atg tac ctg tgc tcg ttc ggc      960
Gly Tyr Ser Pro Gly Thr Ser Val Gly Met Tyr Leu Cys Ser Phe Gly
305                 310                 315                 320 ctc ggc tgc att tac att ttc ctg cag ttc gcc gtc agc cac acg cac     1008
Leu Gly Cys Ile Tyr Ile Phe Leu Gln Phe Ala Val Ser His Thr His
                325                 330                 335 ctg ccg gtg acc aac ccg gag gac cag ctg cac tgg ctc gag tac gcg     1056
Leu Pro Val Thr Asn Pro Glu Asp Gln Leu His Trp Leu Glu Tyr Ala
            340                 345                 350 gcc gac cac acg gtg aac att agc acc aag tcc tgg ctc gtc acg tgg     1104
Ala Asp His Thr Val Asn Ile Ser Thr Lys Ser Trp Leu Val Thr Trp
        355                 360                 365 tgg atg tcg aac ctg aac ttt cag atc gag cac cac ctc ttc ccc acg     1152
Trp Met Ser Asn Leu Asn Phe Gln Ile Glu His His Leu Phe Pro Thr
    370                 375                 380 gcg ccg cag ttc cgc ttc aag gaa atc agt cct cgc gtc gag gcc ctc     1200
Ala Pro Gln Phe Arg Phe Lys Glu Ile Ser Pro Arg Val Glu Ala Leu
385                 390                 395                 400 ttc aag cgc cac aac ctc ccg tac tac gac ctg ccc tac acg agc gcg     1248
Phe Lys Arg His Asn Leu Pro Tyr Tyr Asp Leu Pro Tyr Thr Ser Ala
                405                 410                 415 gtc tcg acc acc ttt gcc aat ctt tat tcc gtc ggc cac tcg gtc ggc     1296
Val Ser Thr Thr Phe Ala Asn Leu Tyr Ser Val Gly His Ser Val Gly
            420                 425                 430 gcc gac acc aag aag cag gac tga                                     1320
Ala Asp Thr Lys Lys Gln Asp
        435

<210> SEQ ID NO 29
<211> LENGTH: 439
```

<212> TYPE: PRT
<213> ORGANISM: Thraustochytrium

<400> SEQUENCE: 29

```
Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
370                 375                 380

Ala Pro Gln Phe Arg Phe Lys Glu Ile Ser Pro Arg Val Glu Ala Leu
385                 390                 395                 400
```

```
Phe Lys Arg His Asn Leu Pro Tyr Tyr Asp Leu Pro Tyr Thr Ser Ala
                405                 410                 415
Val Ser Thr Thr Phe Ala Asn Leu Tyr Ser Val Gly His Ser Val Gly
            420                 425                 430
Ala Asp Thr Lys Lys Gln Asp
        435

<210> SEQ ID NO 30
<211> LENGTH: 1341
<212> TYPE: DNA
<213> ORGANISM: Mortierella alpina
<220> FEATURE:
<221> NAME/KEY: CDS
<222> LOCATION: (1)..(1341)
<223> OTHER INFORMATION: delta-5-Desaturase

<400> SEQUENCE: 30 atg gga acg gac caa gga aaa acc ttc acc tgg gaa gag ctg gcg gcc      48
Met Gly Thr Asp Gln Gly Lys Thr Phe Thr Trp Glu Glu Leu Ala Ala
1               5                   10                  15 cat aac acc aag gac gac cta ctc ttg gcc atc cgc ggc agg gtg tac      96
His Asn Thr Lys Asp Asp Leu Leu Leu Ala Ile Arg Gly Arg Val Tyr
                20                  25                  30 gat gtc aca aag ttc ttg agc cgc cat cct ggt gga gtg gac act ctc     144
Asp Val Thr Lys Phe Leu Ser Arg His Pro Gly Gly Val Asp Thr Leu
            35                  40                  45 ctc ctc gga gct ggc cga gat gtt act ccg gtc ttt gag atg tat cac     192
Leu Leu Gly Ala Gly Arg Asp Val Thr Pro Val Phe Glu Met Tyr His
        50                  55                  60 gcg ttt ggg gct gca gat gcc att atg aag aag tac tat gtc ggt aca     240
Ala Phe Gly Ala Ala Asp Ala Ile Met Lys Lys Tyr Tyr Val Gly Thr
65                  70                  75                  80 ctg gtc tcg aat gag ctg ccc atc ttc ccg gag cca acg gtg ttc cac     288
Leu Val Ser Asn Glu Leu Pro Ile Phe Pro Glu Pro Thr Val Phe His
                85                  90                  95 aaa acc atc aag acg aga gtc gag ggc tac ttt acg gat cgg aac att     336
Lys Thr Ile Lys Thr Arg Val Glu Gly Tyr Phe Thr Asp Arg Asn Ile
                100                 105                 110 gat ccc aag aat aga cca gag atc tgg gga cga tac gct ctt atc ttt     384
Asp Pro Lys Asn Arg Pro Glu Ile Trp Gly Arg Tyr Ala Leu Ile Phe
            115                 120                 125 gga tcc ttg atc gct tcc tac tac gcg cag ctc ttt gtg cct ttc gtt     432
Gly Ser Leu Ile Ala Ser Tyr Tyr Ala Gln Leu Phe Val Pro Phe Val
        130                 135                 140 gtc gaa cgc aca tgg ctt cag gtg gtg ttt gca atc atc atg gga ttt     480
Val Glu Arg Thr Trp Leu Gln Val Val Phe Ala Ile Ile Met Gly Phe
145                 150                 155                 160 gcg tgc gca caa gtc gga ctc aac cct ctt cat gat gcg tct cac ttt     528
Ala Cys Ala Gln Val Gly Leu Asn Pro Leu His Asp Ala Ser His Phe
                165                 170                 175 tca gtg acc cac aac ccc act gtc tgg aag att ctg gga gcc acg cac     576
Ser Val Thr His Asn Pro Thr Val Trp Lys Ile Leu Gly Ala Thr His
                180                 185                 190 gac ttt ttc aac gga gca tcg tac ctg gtg tgg atg tac caa cat atg     624
Asp Phe Phe Asn Gly Ala Ser Tyr Leu Val Trp Met Tyr Gln His Met
            195                 200                 205 ctc ggc cat cac ccc tac acc aac att gct gga gca gat ccc gac gtg     672
Leu Gly His His Pro Tyr Thr Asn Ile Ala Gly Ala Asp Pro Asp Val
        210                 215                 220 tcg acg tct gag ccc gat gtt cgt cgt atc aag ccc aac caa aag tgg     720
```

```
Ser Thr Ser Glu Pro Asp Val Arg Arg Ile Lys Pro Asn Gln Lys Trp
225                 230                 235                 240 ttt gtc aac cac atc aac cag cac atg ttt gtt cct ttc ctg tac gga      768
Phe Val Asn His Ile Asn Gln His Met Phe Val Pro Phe Leu Tyr Gly
                245                 250                 255 ctg ctg gcg ttc aag gtg cgc att cag gac atc aac att ttg tac ttt      816
Leu Leu Ala Phe Lys Val Arg Ile Gln Asp Ile Asn Ile Leu Tyr Phe
            260                 265                 270 gtc aag acc aat gac gct att cgt gtc aat ccc atc tcg aca tgg cac      864
Val Lys Thr Asn Asp Ala Ile Arg Val Asn Pro Ile Ser Thr Trp His
        275                 280                 285 act gtg atg ttc tgg ggc ggc aag gct ttc ttt gtc tgg tat cgc ctg      912
Thr Val Met Phe Trp Gly Gly Lys Ala Phe Phe Val Trp Tyr Arg Leu
    290                 295                 300 att gtt ccc ctg cag tat ctg ccc ctg ggc aag gtg ctg ctc ttg ttc      960
Ile Val Pro Leu Gln Tyr Leu Pro Leu Gly Lys Val Leu Leu Leu Phe
305                 310                 315                 320 acg gtc gcg gac atg gtg tcg tct tac tgg ctg gcg ctg acc ttc cag     1008
Thr Val Ala Asp Met Val Ser Ser Tyr Trp Leu Ala Leu Thr Phe Gln
                325                 330                 335 gcg aac cac gtt gtt gag gaa gtt cag tgg ccg ttg cct gac gag aac     1056
Ala Asn His Val Val Glu Glu Val Gln Trp Pro Leu Pro Asp Glu Asn
            340                 345                 350 ggg atc atc caa aag gac tgg gca gct atg cag gtc gag act acg cag     1104
Gly Ile Ile Gln Lys Asp Trp Ala Ala Met Gln Val Glu Thr Thr Gln
        355                 360                 365 gat tac gca cac gat tcg cac ctc tgg acc agc atc act ggc agc ttg     1152
Asp Tyr Ala His Asp Ser His Leu Trp Thr Ser Ile Thr Gly Ser Leu
    370                 375                 380 aac tac cag gct gtg cac cat ctg ttc ccc aac gtg tcg cag cac cat     1200
Asn Tyr Gln Ala Val His His Leu Phe Pro Asn Val Ser Gln His His
385                 390                 395                 400 tat ccc gat att ctg gcc atc atc aag aac acc tgc agc gag tac aag     1248
Tyr Pro Asp Ile Leu Ala Ile Ile Lys Asn Thr Cys Ser Glu Tyr Lys
                405                 410                 415 gtt cca tac ctt gtc aag gat acg ttt tgg caa gca ttt gct tca cat     1296
Val Pro Tyr Leu Val Lys Asp Thr Phe Trp Gln Ala Phe Ala Ser His
            420                 425                 430 ttg gag cac ttg cgt gtt ctt gga ctc cgt ccc aag gaa gag tag         1341
Leu Glu His Leu Arg Val Leu Gly Leu Arg Pro Lys Glu Glu
        435                 440                 445

<210> SEQ ID NO 31
<211> LENGTH: 446
<212> TYPE: PRT
<213> ORGANISM: Mortierella alpina

<400> SEQUENCE: 31

Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
```

-continued

```
                85                  90                  95
Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445

<210> SEQ ID NO 32
<211> LENGTH: 1344
<212> TYPE: DNA
<213> ORGANISM: Caenorhabditis elegans
<220> FEATURE:
<221> NAME/KEY: CDS
<222> LOCATION: (1)..(1344)
<223> OTHER INFORMATION: delta-5-Desaturase

<400> SEQUENCE: 32
```

```
atg gta tta cga gag caa gag cat gag cca ttc ttc att aaa att gat      48
Met Val Leu Arg Glu Gln Glu His Glu Pro Phe Phe Ile Lys Ile Asp
1               5                  10                  15 gga aaa tgg tgt caa att gac gat gct gtc ctg aga tca cat cca ggt      96
Gly Lys Trp Cys Gln Ile Asp Asp Ala Val Leu Arg Ser His Pro Gly
            20                  25                  30 ggt agt gca att act acc tat aaa aat atg gat gcc act acc gta ttc     144
Gly Ser Ala Ile Thr Thr Tyr Lys Asn Met Asp Ala Thr Thr Val Phe
        35                  40                  45 cac aca ttc cat act ggt tct aaa gaa gcg tat caa tgg ctg aca gaa     192
His Thr Phe His Thr Gly Ser Lys Glu Ala Tyr Gln Trp Leu Thr Glu
    50                  55                  60 ttg aaa aaa gag tgc cct aca caa gaa cca gag atc cca gat att aag     240
Leu Lys Lys Glu Cys Pro Thr Gln Glu Pro Glu Ile Pro Asp Ile Lys
65                  70                  75                  80 gat gac cca atc aaa gga att gat gat gtg aac atg gga act ttc aat     288
Asp Asp Pro Ile Lys Gly Ile Asp Asp Val Asn Met Gly Thr Phe Asn
                85                  90                  95 att tct gag aaa cga tct gcc caa ata aat aaa agt ttc act gat cta     336
Ile Ser Glu Lys Arg Ser Ala Gln Ile Asn Lys Ser Phe Thr Asp Leu
            100                 105                 110 cgt atg cga gtt cgt gca gaa gga ctt atg gat gga tct cct ttg ttc     384
Arg Met Arg Val Arg Ala Glu Gly Leu Met Asp Gly Ser Pro Leu Phe
        115                 120                 125 tac att aga aaa att ctt gaa aca atc ttc aca att ctt ttt gca ttc     432
Tyr Ile Arg Lys Ile Leu Glu Thr Ile Phe Thr Ile Leu Phe Ala Phe
    130                 135                 140 tac ctt caa tac cac aca tat tat ctt cca tca gct att cta atg gga     480
Tyr Leu Gln Tyr His Thr Tyr Tyr Leu Pro Ser Ala Ile Leu Met Gly
145                 150                 155                 160 gtt gcg tgg caa caa ttg gga tgg tta atc cat gaa ttc gca cat cat     528
Val Ala Trp Gln Gln Leu Gly Trp Leu Ile His Glu Phe Ala His His
                165                 170                 175 cag ttg ttc aaa aac aga tac tac aat gat ttg gcc agc tat ttc gtt     576
Gln Leu Phe Lys Asn Arg Tyr Tyr Asn Asp Leu Ala Ser Tyr Phe Val
            180                 185                 190 gga aac ttt tta caa gga ttc tca tct ggt ggt tgg aaa gag cag cac     624
Gly Asn Phe Leu Gln Gly Phe Ser Ser Gly Gly Trp Lys Glu Gln His
        195                 200                 205 aat gtg cat cac gca gcc aca aat gtt gtt gga cga gac gga gat ctt     672
Asn Val His His Ala Ala Thr Asn Val Val Gly Arg Asp Gly Asp Leu
    210                 215                 220 gat tta gtc cca ttc tat gct aca gtg gca gaa cat ctc aac aat tat     720
Asp Leu Val Pro Phe Tyr Ala Thr Val Ala Glu His Leu Asn Asn Tyr
225                 230                 235                 240 tct cag gat tca tgg gtt atg act cta ttc aga tgg caa cat gtt cat     768
Ser Gln Asp Ser Trp Val Met Thr Leu Phe Arg Trp Gln His Val His
                245                 250                 255 tgg aca ttc atg tta cca ttc ctc cgt ctc tcg tgg ctt ctt cag tca     816
Trp Thr Phe Met Leu Pro Phe Leu Arg Leu Ser Trp Leu Leu Gln Ser
            260                 265                 270 atc att ttt gtt agt cag atg cca act cat tat tat gac tat tac aga     864
Ile Ile Phe Val Ser Gln Met Pro Thr His Tyr Tyr Asp Tyr Tyr Arg
        275                 280                 285 aat act gcg att tat gaa cag gtt ggt ctc tct ttg cac tgg gct tgg     912
Asn Thr Ala Ile Tyr Glu Gln Val Gly Leu Ser Leu His Trp Ala Trp
    290                 295                 300 tca ttg ggt caa ttg tat ttc cta ccc gat tgg tca act aga ata atg     960
Ser Leu Gly Gln Leu Tyr Phe Leu Pro Asp Trp Ser Thr Arg Ile Met
```

```
                305                 310                 315                 320
ttc ttc ctt gtt tct cat ctt gtt gga ggt ttc ctg ctc tct cat gta     1008
Phe Phe Leu Val Ser His Leu Val Gly Gly Phe Leu Leu Ser His Val
                325                 330                 335 gtt act ttc aat cat tat tca gtg gag aag ttt gca ttg agc tcg aac     1056
Val Thr Phe Asn His Tyr Ser Val Glu Lys Phe Ala Leu Ser Ser Asn
            340                 345                 350 atc atg tca aat tac gct tgt ctt caa atc atg acc aca aga aat atg     1104
Ile Met Ser Asn Tyr Ala Cys Leu Gln Ile Met Thr Thr Arg Asn Met
            355                 360                 365 aga cct gga aga ttc att gac tgg ctt tgg gga ggt ctt aac tat cag     1152
Arg Pro Gly Arg Phe Ile Asp Trp Leu Trp Gly Gly Leu Asn Tyr Gln
        370                 375                 380 att gag cac cat ctt ttc cca acg atg cca cga cac aac ttg aac act     1200
Ile Glu His His Leu Phe Pro Thr Met Pro Arg His Asn Leu Asn Thr
385                 390                 395                 400 gtt atg cca ctt gtt aag gag ttt gca gca gca aat ggt tta cca tac     1248
Val Met Pro Leu Val Lys Glu Phe Ala Ala Ala Asn Gly Leu Pro Tyr
                405                 410                 415 atg gtc gac gat tat ttc aca gga ttc tgg ctt gaa att gag caa ttc     1296
Met Val Asp Asp Tyr Phe Thr Gly Phe Trp Leu Glu Ile Glu Gln Phe
            420                 425                 430 cga aat att gca aat gtt gct gct aaa ttg act aaa aag att gcc tag     1344
Arg Asn Ile Ala Asn Val Ala Ala Lys Leu Thr Lys Lys Ile Ala
        435                 440                 445

<210> SEQ ID NO 33
<211> LENGTH: 447
<212> TYPE: PRT
<213> ORGANISM: Caenorhabditis elegans

<400> SEQUENCE: 33

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ala Ile Leu Met Gly
145                 150                 155                 160

Val Ala Trp Gln Gln Leu Gly Trp Leu Ile His Glu Phe Ala His His
                165                 170                 175

Gln Leu Phe Lys Asn Arg Tyr Tyr Asn Asp Leu Ala Ser Tyr Phe Val
            180                 185                 190

Gly Asn Phe Leu Gln Gly Phe Ser Ser Gly Gly Trp Lys Glu Gln His
```

-continued

```
                195                 200                 205
Asn Val His His Ala Ala Thr Asn Val Val Gly Arg Asp Gly Asp Leu
    210                 215                 220
Asp Leu Val Pro Phe Tyr Ala Thr Val Ala Glu His Leu Asn Asn Tyr
225                 230                 235                 240
Ser Gln Asp Ser Trp Val Met Thr Leu Phe Arg Trp Gln His Val His
                245                 250                 255
Trp Thr Phe Met Leu Pro Phe Leu Arg Leu Ser Trp Leu Leu Gln Ser
            260                 265                 270
Ile Ile Phe Val Ser Gln Met Pro Thr His Tyr Tyr Asp Tyr Tyr Arg
        275                 280                 285
Asn Thr Ala Ile Tyr Glu Gln Val Gly Leu Ser Leu His Trp Ala Trp
    290                 295                 300
Ser Leu Gly Gln Leu Tyr Phe Leu Pro Asp Trp Ser Thr Arg Ile Met
305                 310                 315                 320
Phe Phe Leu Val Ser His Leu Val Gly Gly Phe Leu Leu Ser His Val
                325                 330                 335
Val Thr Phe Asn His Tyr Ser Val Glu Lys Phe Ala Leu Ser Ser Asn
            340                 345                 350
Ile Met Ser Asn Tyr Ala Cys Leu Gln Ile Met Thr Thr Arg Asn Met
        355                 360                 365
Arg Pro Gly Arg Phe Ile Asp Trp Leu Trp Gly Gly Leu Asn Tyr Gln
    370                 375                 380
Ile Glu His His Leu Phe Pro Thr Met Pro Arg His Asn Leu Asn Thr
385                 390                 395                 400
Val Met Pro Leu Val Lys Glu Phe Ala Ala Ala Asn Gly Leu Pro Tyr
                405                 410                 415
Met Val Asp Asp Tyr Phe Thr Gly Phe Trp Leu Glu Ile Glu Gln Phe
            420                 425                 430
Arg Asn Ile Ala Asn Val Ala Ala Lys Leu Thr Lys Lys Ile Ala
        435                 440                 445

<210> SEQ ID NO 34
<211> LENGTH: 606
<212> TYPE: DNA
<213> ORGANISM: Ostreococcus tauri
<220> FEATURE:
<221> NAME/KEY: CDS
<222> LOCATION: (1)..(606)
<223> OTHER INFORMATION: delta-5-Desaturase

<400> SEQUENCE: 34 atg tac ggt ttg cta tcg ctc aag tcg tgc ttc gtc gac gat ttc aac      48
Met Tyr Gly Leu Leu Ser Leu Lys Ser Cys Phe Val Asp Asp Phe Asn
1               5                   10                  15 gcc tac ttc tcc gga cgc atc ggc tgg gtc aag gtg atg aag ttc acc      96
Ala Tyr Phe Ser Gly Arg Ile Gly Trp Val Lys Val Met Lys Phe Thr
            20                  25                  30 cgc ggc gag gcg atc gca ttt tgg ggc acc aag ctc ttg tgg gcc gcg     144
Arg Gly Glu Ala Ile Ala Phe Trp Gly Thr Lys Leu Leu Trp Ala Ala
        35                  40                  45 tat tac ctc gcg ttg ccg cta aag atg tcg cat cgg ccg ctc gga gaa     192
Tyr Tyr Leu Ala Leu Pro Leu Lys Met Ser His Arg Pro Leu Gly Glu
    50                  55                  60 ctc ctc gca ctc tgg gcc gtc acc gag ttc gtc acc gga tgg ctg ttg     240
Leu Leu Ala Leu Trp Ala Val Thr Glu Phe Val Thr Gly Trp Leu Leu
65                  70                  75                  80
```

```
gcg ttc atg ttc caa gtc gcc cac gtc gtc ggc gag gtt cac ttc ttc        288
Ala Phe Met Phe Gln Val Ala His Val Val Gly Glu Val His Phe Phe
            85                  90                  95 acc ctc gac gcg aag aac cgc gtg aac ttg gga tgg gga gag gca cag        336
Thr Leu Asp Ala Lys Asn Arg Val Asn Leu Gly Trp Gly Glu Ala Gln
        100                 105                 110 ctc atg tcg agc gcg gat ttc gcc cac gga tcc aag ttt tgg acg cac        384
Leu Met Ser Ser Ala Asp Phe Ala His Gly Ser Lys Phe Trp Thr His
    115                 120                 125 ttc tcc gga ggc tta aac tac caa gtc gtc cac cat ctc ttc ccg ggc        432
Phe Ser Gly Gly Leu Asn Tyr Gln Val Val His His Leu Phe Pro Gly
130                 135                 140 gtc tgc cac gtg cac tat ccc gcg ctc gcg cca att att aag gcg gca        480
Val Cys His Val His Tyr Pro Ala Leu Ala Pro Ile Ile Lys Ala Ala
145                 150                 155                 160 gct gag aag cac ggc ctc cac tac cag att tac ccc acg ttt tgg tcc        528
Ala Glu Lys His Gly Leu His Tyr Gln Ile Tyr Pro Thr Phe Trp Ser
                165                 170                 175 gcc ctg cgc gcg cac ttc cgg cac ctc gcc aac gtc ggc cgc gcc gcg        576
Ala Leu Arg Ala His Phe Arg His Leu Ala Asn Val Gly Arg Ala Ala
            180                 185                 190 tac gta ccg tcc ctc caa acc gtc gga tga                                606
Tyr Val Pro Ser Leu Gln Thr Val Gly
        195                 200

<210> SEQ ID NO 35
<211> LENGTH: 201
<212> TYPE: PRT
<213> ORGANISM: Ostreococcus tauri

<400> SEQUENCE: 35

Met Tyr Gly Leu Leu Ser Leu Lys Ser Cys Phe Val Asp Asp Phe Asn
1               5                   10                  15

Ala Tyr Phe Ser Gly Arg Ile Gly Trp Val Lys Val Met Lys Phe Thr
            20                  25                  30

Arg Gly Glu Ala Ile Ala Phe Trp Gly Thr Lys Leu Leu Trp Ala Ala
        35                  40                  45

Tyr Tyr Leu Ala Leu Pro Leu Lys Met Ser His Arg Pro Leu Gly Glu
    50                  55                  60

Leu Leu Ala Leu Trp Ala Val Thr Glu Phe Val Thr Gly Trp Leu Leu
65                  70                  75                  80

Ala Phe Met Phe Gln Val Ala His Val Val Gly Glu Val His Phe Phe
                85                  90                  95

Thr Leu Asp Ala Lys Asn Arg Val Asn Leu Gly Trp Gly Glu Ala Gln
            100                 105                 110

Leu Met Ser Ser Ala Asp Phe Ala His Gly Ser Lys Phe Trp Thr His
        115                 120                 125

Phe Ser Gly Gly Leu Asn Tyr Gln Val Val His His Leu Phe Pro Gly
    130                 135                 140

Val Cys His Val His Tyr Pro Ala Leu Ala Pro Ile Ile Lys Ala Ala
145                 150                 155                 160

Ala Glu Lys His Gly Leu His Tyr Gln Ile Tyr Pro Thr Phe Trp Ser
                165                 170                 175

Ala Leu Arg Ala His Phe Arg His Leu Ala Asn Val Gly Arg Ala Ala
            180                 185                 190

Tyr Val Pro Ser Leu Gln Thr Val Gly
        195                 200
```

<210> SEQ ID NO 36
<211> LENGTH: 714
<212> TYPE: DNA
<213> ORGANISM: Ostreococcus tauri
<220> FEATURE:
<221> NAME/KEY: CDS
<222> LOCATION: (1)..(714)
<223> OTHER INFORMATION: delta-5-Desaturase

<400> SEQUENCE: 36

| atg | gtg | agc | cat | cac | tcg | tac | tgt | aac | gac | gcg | gat | ttg | gat | cag | gat | 48 |
|---|---|---|---|---|---|---|---|---|---|---|---|---|---|---|---|---|
| Met | Val | Ser | His | His | Ser | Tyr | Cys | Asn | Asp | Ala | Asp | Leu | Asp | Gln | Asp | |
| 1 | | | | 5 | | | | | 10 | | | | | 15 | | |

| gtg | tac | acc | gca | ctg | ccg | ctc | ctg | cgc | ctg | gac | cct | tct | cag | gag | ttg | 96 |
|---|---|---|---|---|---|---|---|---|---|---|---|---|---|---|---|---|
| Val | Tyr | Thr | Ala | Leu | Pro | Leu | Leu | Arg | Leu | Asp | Pro | Ser | Gln | Glu | Leu | |
| | | | 20 | | | | | 25 | | | | | 30 | | | |

| aag | tgg | ttt | cat | cga | tac | cag | gcg | ttt | tac | gcc | ccg | ctc | atg | tgg | ccg | 144 |
|---|---|---|---|---|---|---|---|---|---|---|---|---|---|---|---|---|
| Lys | Trp | Phe | His | Arg | Tyr | Gln | Ala | Phe | Tyr | Ala | Pro | Leu | Met | Trp | Pro | |
| | | | 35 | | | | | 40 | | | | | 45 | | | |

| ttt | ttg | tgg | ctc | gcg | gcg | cag | ttt | ggc | gac | gcg | cag | aac | atc | ctg | atc | 192 |
|---|---|---|---|---|---|---|---|---|---|---|---|---|---|---|---|---|
| Phe | Leu | Trp | Leu | Ala | Ala | Gln | Phe | Gly | Asp | Ala | Gln | Asn | Ile | Leu | Ile | |
| 50 | | | | | 55 | | | | | 60 | | | | | | |

| gac | cga | gcg | tcg | ccg | ggc | gtc | gcg | tac | aag | gga | ttg | atg | gcg | aac | gag | 240 |
|---|---|---|---|---|---|---|---|---|---|---|---|---|---|---|---|---|
| Asp | Arg | Ala | Ser | Pro | Gly | Val | Ala | Tyr | Lys | Gly | Leu | Met | Ala | Asn | Glu | |
| 65 | | | | | 70 | | | | | 75 | | | | | 80 | |

| gtc | gcg | ctg | tac | gtt | ctc | ggt | aag | gtt | tta | cac | ttt | ggt | ctt | ctc | ctc | 288 |
|---|---|---|---|---|---|---|---|---|---|---|---|---|---|---|---|---|
| Val | Ala | Leu | Tyr | Val | Leu | Gly | Lys | Val | Leu | His | Phe | Gly | Leu | Leu | Leu | |
| | | | | 85 | | | | | 90 | | | | | 95 | | |

| ggc | gtt | cct | gcg | tac | ttg | cac | gga | ttg | tcc | aac | gcg | atc | gtt | cca | ttc | 336 |
|---|---|---|---|---|---|---|---|---|---|---|---|---|---|---|---|---|
| Gly | Val | Pro | Ala | Tyr | Leu | His | Gly | Leu | Ser | Asn | Ala | Ile | Val | Pro | Phe |  |
| | | | 100 | | | | | 105 | | | | | 110 | | | |

| ttg | gcg | tac | ggc | gca | ttc | ggc | tcc | ttc | gtc | ctg | tgc | tgg | ttc | ttc | atc | 384 |
|---|---|---|---|---|---|---|---|---|---|---|---|---|---|---|---|---|
| Leu | Ala | Tyr | Gly | Ala | Phe | Gly | Ser | Phe | Val | Leu | Cys | Trp | Phe | Phe | Ile | |
| | | 115 | | | | | 120 | | | | | 125 | | | | |

| gtc | agc | cat | aac | ctc | gaa | gcg | ctg | aca | ccc | gtt | aac | ctt | aac | aag | tcc | 432 |
|---|---|---|---|---|---|---|---|---|---|---|---|---|---|---|---|---|
| Val | Ser | His | Asn | Leu | Glu | Ala | Leu | Thr | Pro | Val | Asn | Leu | Asn | Lys | Ser | |
| | 130 | | | | | 135 | | | | | 140 | | | | | |

| acg | aag | aac | gac | tgg | ggg | gcg | tgg | cag | atc | gag | aca | tcg | gcg | tct | tgg | 480 |
|---|---|---|---|---|---|---|---|---|---|---|---|---|---|---|---|---|
| Thr | Lys | Asn | Asp | Trp | Gly | Ala | Trp | Gln | Ile | Glu | Thr | Ser | Ala | Ser | Trp | |
| 145 | | | | | 150 | | | | | 155 | | | | | 160 | |

| ggc | aac | gcg | ttc | tgg | agc | ttc | ttc | tct | gga | ggt | ctg | aac | ctg | caa | atc | 528 |
|---|---|---|---|---|---|---|---|---|---|---|---|---|---|---|---|---|
| Gly | Asn | Ala | Phe | Trp | Ser | Phe | Phe | Ser | Gly | Gly | Leu | Asn | Leu | Gln | Ile | |
| | | | | 165 | | | | | 170 | | | | | 175 | | |

| gag | cac | cac | ctc | ttc | ccg | ggc | atg | gcg | cac | aac | ctg | tac | ccg | aag | atg | 576 |
|---|---|---|---|---|---|---|---|---|---|---|---|---|---|---|---|---|
| Glu | His | His | Leu | Phe | Pro | Gly | Met | Ala | His | Asn | Leu | Tyr | Pro | Lys | Met | |
| | | | 180 | | | | | 185 | | | | | 190 | | | |

| gtg | ccg | atc | atc | aag | gac | gag | tgt | gcg | aaa | gcg | ggc | gtt | cgc | tac | acc | 624 |
|---|---|---|---|---|---|---|---|---|---|---|---|---|---|---|---|---|
| Val | Pro | Ile | Ile | Lys | Asp | Glu | Cys | Ala | Lys | Ala | Gly | Val | Arg | Tyr | Thr | |
| | | 195 | | | | | 200 | | | | | 205 | | | | |

| ggt | tac | ggt | ggc | tac | acc | ggc | ctg | ctc | ccg | atc | acc | cgc | gac | atg | ttc | 672 |
|---|---|---|---|---|---|---|---|---|---|---|---|---|---|---|---|---|
| Gly | Tyr | Gly | Gly | Tyr | Thr | Gly | Leu | Leu | Pro | Ile | Thr | Arg | Asp | Met | Phe | |
| | 210 | | | | | 215 | | | | | 220 | | | | | |

| tcc | tac | ctc | cat | aag | tgt | ggc | cga | acg | gcg | aaa | cta | gcc | taa | | | 714 |
|---|---|---|---|---|---|---|---|---|---|---|---|---|---|---|---|---|
| Ser | Tyr | Leu | His | Lys | Cys | Gly | Arg | Thr | Ala | Lys | Leu | Ala | | | | |
| 225 | | | | | 230 | | | | | 235 | | | | | | |

<210> SEQ ID NO 37
<211> LENGTH: 237
<212> TYPE: PRT
<213> ORGANISM: Ostreococcus tauri

<400> SEQUENCE: 37

```
Met Val Ser His His Ser Tyr Cys Asn Asp Ala Asp Leu Asp Gln Asp
1               5                   10                  15

Val Tyr Thr Ala Leu Pro Leu Leu Arg Leu Asp Pro Ser Gln Glu Leu
            20                  25                  30

Lys Trp Phe His Arg Tyr Gln Ala Phe Tyr Ala Pro Leu Met Trp Pro
            35                  40                  45

Phe Leu Trp Leu Ala Ala Gln Phe Gly Asp Ala Gln Asn Ile Leu Ile
        50                  55                  60

Asp Arg Ala Ser Pro Gly Val Ala Tyr Lys Gly Leu Met Ala Asn Glu
65                  70                  75                  80

Val Ala Leu Tyr Val Leu Gly Lys Val Leu His Phe Gly Leu Leu Leu
                85                  90                  95

Gly Val Pro Ala Tyr Leu His Gly Leu Ser Asn Ala Ile Val Pro Phe
            100                 105                 110

Leu Ala Tyr Gly Ala Phe Gly Ser Phe Val Leu Cys Trp Phe Phe Ile
            115                 120                 125

Val Ser His Asn Leu Glu Ala Leu Thr Pro Val Asn Leu Asn Lys Ser
130                 135                 140

Thr Lys Asn Asp Trp Gly Ala Trp Gln Ile Glu Thr Ser Ala Ser Trp
145                 150                 155                 160

Gly Asn Ala Phe Trp Ser Phe Ser Gly Gly Leu Asn Leu Gln Ile
                165                 170                 175

Glu His His Leu Phe Pro Gly Met Ala His Asn Leu Tyr Pro Lys Met
            180                 185                 190

Val Pro Ile Ile Lys Asp Glu Cys Ala Lys Ala Gly Val Arg Tyr Thr
            195                 200                 205

Gly Tyr Gly Gly Tyr Thr Gly Leu Leu Pro Ile Thr Arg Asp Met Phe
            210                 215                 220

Ser Tyr Leu His Lys Cys Gly Arg Thr Ala Lys Leu Ala
225                 230                 235

<210> SEQ ID NO 38
<211> LENGTH: 1431
<212> TYPE: DNA
<213> ORGANISM: Thalassiosira pseudonana
<220> FEATURE:
<221> NAME/KEY: CDS
<222> LOCATION: (1)..(1431)
<223> OTHER INFORMATION: delta-5-Desaturase

<400> SEQUENCE: 38 atg ccc ccc aac gcc gat atc tcc cgc atc cgc aac cgc atc ccc acc      48
Met Pro Pro Asn Ala Asp Ile Ser Arg Ile Arg Asn Arg Ile Pro Thr
1               5                   10                  15 aaa aca ggt acc gtt gcc tct gcc gac aac aac gac ccc gcc acc caa      96
Lys Thr Gly Thr Val Ala Ser Ala Asp Asn Asn Asp Pro Ala Thr Gln
            20                  25                  30 tcc gtc cga acc ctc aaa tct ctc aag ggc aac gag gtc gtc atc aac     144
Ser Val Arg Thr Leu Lys Ser Leu Lys Gly Asn Glu Val Val Ile Asn
        35                  40                  45 ggc aca att tat gac att gct gac ttt gtc cat cct gga gga gag gtt     192
Gly Thr Ile Tyr Asp Ile Ala Asp Phe Val His Pro Gly Gly Glu Val
    50                  55                  60 gtc aag ttc ttt ggt ggg aat gat gtt act att cag tat aat atg att     240
Val Lys Phe Phe Gly Gly Asn Asp Val Thr Ile Gln Tyr Asn Met Ile
65                  70                  75                  80 cat ccg tat cat acg ggg aaa cat ctg gag aag atg aag gct gtt gga     288
```

-continued

```
                His Pro Tyr His Thr Gly Lys His Leu Glu Lys Met Lys Ala Val Gly
                                85                  90                  95 aag gtt gta gat tgg cag tcg gac tac aag ttc gac acc ccc ttt gaa            336
Lys Val Val Asp Trp Gln Ser Asp Tyr Lys Phe Asp Thr Pro Phe Glu
                100                 105                 110 cga gag atc aaa tca gaa gtg ttc aag atc gta cgt cgc ggg cgt gag            384
Arg Glu Ile Lys Ser Glu Val Phe Lys Ile Val Arg Arg Gly Arg Glu
            115                 120                 125 ttc ggc aca aca ggc tac ttc ctc cgt gcc ttt ttc tac atc gct ctc            432
Phe Gly Thr Thr Gly Tyr Phe Leu Arg Ala Phe Phe Tyr Ile Ala Leu
        130                 135                 140 ttc ttc acc atg caa tac act ttc gcc aca tgc acc acc ttc acc acc            480
Phe Phe Thr Met Gln Tyr Thr Phe Ala Thr Cys Thr Thr Phe Thr Thr
145                 150                 155                 160 tac gat cac tgg tat cag agt ggt gta ttc atc gca att gtg ttt ggt            528
Tyr Asp His Trp Tyr Gln Ser Gly Val Phe Ile Ala Ile Val Phe Gly
                165                 170                 175 att tca cag gca ttc att ggg ttg aat gtc cag cac gat gcc aat cac            576
Ile Ser Gln Ala Phe Ile Gly Leu Asn Val Gln His Asp Ala Asn His
                180                 185                 190 gga gct gcc agt aag cgt ccc tgg gtg aat gac ttg ttg gga ttt gga            624
Gly Ala Ala Ser Lys Arg Pro Trp Val Asn Asp Leu Leu Gly Phe Gly
            195                 200                 205 acg gat ttg att gga tct aac aaa tgg aat tgg atg gca cag cat tgg            672
Thr Asp Leu Ile Gly Ser Asn Lys Trp Asn Trp Met Ala Gln His Trp
        210                 215                 220 act cat cac gct tac act aac cat agt gag aag gat ccc gat agc ttc            720
Thr His His Ala Tyr Thr Asn His Ser Glu Lys Asp Pro Asp Ser Phe
225                 230                 235                 240 agc tcg gaa cct atg ttt gca ttc aat gac tat ccc att gga cac ccg            768
Ser Ser Glu Pro Met Phe Ala Phe Asn Asp Tyr Pro Ile Gly His Pro
                245                 250                 255 aag aga aag tgg tgg cat agg ttc cag gga ggg tac ttc ctc ttc atg            816
Lys Arg Lys Trp Trp His Arg Phe Gln Gly Gly Tyr Phe Leu Phe Met
                260                 265                 270 ctt gga ctt tac tgg ctc tcg act gta ttc aat ccg caa ttc att gat            864
Leu Gly Leu Tyr Trp Leu Ser Thr Val Phe Asn Pro Gln Phe Ile Asp
            275                 280                 285 ctt cgt caa cgt ggg gct cag tac gtc gga att caa atg gag aat gat            912
Leu Arg Gln Arg Gly Ala Gln Tyr Val Gly Ile Gln Met Glu Asn Asp
        290                 295                 300 ttc att gtc aag agg agg aag tac gcc gtt gca ttg agg atg atg tac            960
Phe Ile Val Lys Arg Arg Lys Tyr Ala Val Ala Leu Arg Met Met Tyr
305                 310                 315                 320 att tac ttg aac att gtc agc ccc ttc atg aac aat ggt ttg agc tgg           1008
Ile Tyr Leu Asn Ile Val Ser Pro Phe Met Asn Asn Gly Leu Ser Trp
                325                 330                 335 tct acc ttt gga atc atc atg ttg atg gga atc agc gag agt ctc act           1056
Ser Thr Phe Gly Ile Ile Met Leu Met Gly Ile Ser Glu Ser Leu Thr
            340                 345                 350 ctc agt gtg ctc ttc tcg ttg tct cac aac ttc atc aat tcg gat cgt           1104
Leu Ser Val Leu Phe Ser Leu Ser His Asn Phe Ile Asn Ser Asp Arg
        355                 360                 365 gat cct acg gct gac ttc aaa aag acc gga gaa caa gtg tgc tgg ttc           1152
Asp Pro Thr Ala Asp Phe Lys Lys Thr Gly Glu Gln Val Cys Trp Phe
370                 375                 380 aag tcg cag gtg gag act tcg tct acc tat ggg ggt ttt att tcc gga           1200
Lys Ser Gln Val Glu Thr Ser Ser Thr Tyr Gly Gly Phe Ile Ser Gly
385                 390                 395                 400
```

```
tgt ctt acg gga gga ctc aac ttt cag gtg gaa cat cat ctc ttt ccc    1248
Cys Leu Thr Gly Gly Leu Asn Phe Gln Val Glu His His Leu Phe Pro
            405                 410                 415 cgt atg agc agt gct tgg tat cct tac att gca cct acg gtt cgt gag    1296
Arg Met Ser Ser Ala Trp Tyr Pro Tyr Ile Ala Pro Thr Val Arg Glu
        420                 425                 430 gtt tgc aag aag cac ggg gtg aac tac gct tat tat cct tgg att ggg    1344
Val Cys Lys Lys His Gly Val Asn Tyr Ala Tyr Tyr Pro Trp Ile Gly
    435                 440                 445 cag aat ttg gta tca aca ttc aaa tac atg cat cgc gct ggt agt gga    1392
Gln Asn Leu Val Ser Thr Phe Lys Tyr Met His Arg Ala Gly Ser Gly
450                 455                 460 gcc aac tgg gag ctc aag ccg ttg tct gga agt gcc taa                1431
Ala Asn Trp Glu Leu Lys Pro Leu Ser Gly Ser Ala
465                 470                 475

<210> SEQ ID NO 39
<211> LENGTH: 476
<212> TYPE: PRT
<213> ORGANISM: Thalassiosira pseudonana

<400> SEQUENCE: 39

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asp Pro Ala Thr Gln
            20                  25                  30

Ser Val Arg Thr Leu Lys Ser Leu Lys Gly Asn Glu Val Val Ile Asn
        35                  40                  45

Gly Thr Ile Tyr Asp Ile Ala Asp Phe Val His Pro Gly Gly Glu Val
    50                  55                  60

Val Lys Phe Phe Gly Gly Asn Asp Val Thr Ile Gln Tyr Asn Met Ile
65                  70                  75                  80

His Pro Tyr His Thr Gly Lys His Leu Glu Lys Met Lys Ala Val Gly
                85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Tyr Ile Ala Leu
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175

Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
        195                 200                 205

Thr Asp Leu Ile Gly Ser Asn Lys Trp Asn Trp Met Ala Gln His Trp
    210                 215                 220

Thr His His Ala Tyr Thr Asn His Ser Glu Lys Asp Pro Asp Ser Phe
225                 230                 235                 240

Ser Ser Glu Pro Met Phe Ala Phe Asn Asp Tyr Pro Ile Gly His Pro
                245                 250                 255

Lys Arg Lys Trp Trp His Arg Phe Gln Gly Gly Tyr Phe Leu Phe Met
            260                 265                 270
```

```
Leu Gly Leu Tyr Trp Leu Ser Thr Val Phe Asn Pro Gln Phe Ile Asp
        275                 280                 285

Leu Arg Gln Arg Gly Ala Gln Tyr Val Gly Ile Gln Met Glu Asn Asp
        290                 295                 300

Phe Ile Val Lys Arg Arg Lys Tyr Ala Val Ala Leu Arg Met Met Tyr
305                 310                 315                 320

Ile Tyr Leu Asn Ile Val Ser Pro Phe Met Asn Asn Gly Leu Ser Trp
                325                 330                 335

Ser Thr Phe Gly Ile Ile Met Leu Met Gly Ile Ser Glu Ser Leu Thr
            340                 345                 350

Leu Ser Val Leu Phe Ser Leu Ser His Asn Phe Ile Asn Ser Asp Arg
        355                 360                 365

Asp Pro Thr Ala Asp Phe Lys Lys Thr Gly Glu Gln Val Cys Trp Phe
    370                 375                 380

Lys Ser Gln Val Glu Thr Ser Ser Thr Tyr Gly Gly Phe Ile Ser Gly
385                 390                 395                 400

Cys Leu Thr Gly Gly Leu Asn Phe Gln Val Glu His His Leu Phe Pro
                405                 410                 415

Arg Met Ser Ser Ala Trp Tyr Pro Tyr Ile Ala Pro Thr Val Arg Glu
            420                 425                 430

Val Cys Lys Lys His Gly Val Asn Tyr Ala Tyr Tyr Pro Trp Ile Gly
        435                 440                 445

Gln Asn Leu Val Ser Thr Phe Lys Tyr Met His Arg Ala Gly Ser Gly
    450                 455                 460

Ala Asn Trp Glu Leu Lys Pro Leu Ser Gly Ser Ala
465                 470                 475

<210> SEQ ID NO 40
<211> LENGTH: 1449
<212> TYPE: DNA
<213> ORGANISM: Thalassiosira pseudonana
<220> FEATURE:
<221> NAME/KEY: CDS
<222> LOCATION: (1)..(1449)
<223> OTHER INFORMATION: delta-5-Desaturase

<400> SEQUENCE: 40 atg cca ccc aac gcc gag gtc aaa aac ctc cgt tca cgt tcc atc cca    48
Met Pro Pro Asn Ala Glu Val Lys Asn Leu Arg Ser Arg Ser Ile Pro
1               5                  10                  15 acg aag aag tcc agt tca tcg tca tcc acc gcg aac gac gat ccg gct    96
Thr Lys Lys Ser Ser Ser Ser Ser Thr Ala Asn Asp Asp Pro Ala
            20                  25                  30 acc caa tcc acc tca cct gtg aac cga acc ctc aag tct ttg aat gga   144
Thr Gln Ser Thr Ser Pro Val Asn Arg Thr Leu Lys Ser Leu Asn Gly
        35                  40                  45 aac gaa ata gct att gac ggt gtc atc tat gat att gat ggc ttt gtc   192
Asn Glu Ile Ala Ile Asp Gly Val Ile Tyr Asp Ile Asp Gly Phe Val
    50                  55                  60 cat cct gga gga gag gtt att agc ttc ttt gga ggc aac gat gtg act   240
His Pro Gly Gly Glu Val Ile Ser Phe Phe Gly Gly Asn Asp Val Thr
65                  70                  75                  80 gta cag tac aaa atg att cat ccg tat cat aat agt aag cat ctc gag   288
Val Gln Tyr Lys Met Ile His Pro Tyr His Asn Ser Lys His Leu Glu
                85                  90                  95 aag atg aga gcc gtt gga aag att gca gac tac tcc aca gag tac aag   336
Lys Met Arg Ala Val Gly Lys Ile Ala Asp Tyr Ser Thr Glu Tyr Lys
            100                 105                 110
```

| | | |
|---|---|---|
| ttc gac aca ccc ttt gaa cga gag atc aaa tcc gaa gtg ttc aaa atc<br>Phe Asp Thr Pro Phe Glu Arg Glu Ile Lys Ser Glu Val Phe Lys Ile<br>115                  120                125 | 384 | |
| gtc cgt cga gga cgt gaa ttc ggt aca aca gga tat ttc ctc cgt gcc<br>Val Arg Arg Gly Arg Glu Phe Gly Thr Thr Gly Tyr Phe Leu Arg Ala<br>130                  135                140 | 432 | |
| ttc ttc tac att gct ctc ttc ttc acc atg caa tac acc ttc gcc aca<br>Phe Phe Tyr Ile Ala Leu Phe Phe Thr Met Gln Tyr Thr Phe Ala Thr<br>145                  150                155                160 | 480 | |
| tgc act acc ttc acc acc tac gat cat tgg tat caa agt ggt gta ttc<br>Cys Thr Thr Phe Thr Thr Tyr Asp His Trp Tyr Gln Ser Gly Val Phe<br>                  165                170                175 | 528 | |
| atc gcc att gtg ttt ggt atc tca caa gct ttc att ggg ttg aat gta<br>Ile Ala Ile Val Phe Gly Ile Ser Gln Ala Phe Ile Gly Leu Asn Val<br>                  180                185                190 | 576 | |
| caa cat gat gcc aat cac gga gct gct agc aaa cga cct tgg gtg aat<br>Gln His Asp Ala Asn His Gly Ala Ala Ser Lys Arg Pro Trp Val Asn<br>                195                200                205 | 624 | |
| gat ctc ctt gga tct gga gct gat ctc atc ggt gga tgc aaa tgg aac<br>Asp Leu Leu Gly Ser Gly Ala Asp Leu Ile Gly Gly Cys Lys Trp Asn<br>210                  215                220 | 672 | |
| tgg ttg gct cag cat tgg act cat cat gcg tat acc aat cac gct gat<br>Trp Leu Ala Gln His Trp Thr His His Ala Tyr Thr Asn His Ala Asp<br>225                  230                235                240 | 720 | |
| aaa gat cct gat agc ttt agt tcc gag ccg gtc ttc aac ttt aac gat<br>Lys Asp Pro Asp Ser Phe Ser Ser Glu Pro Val Phe Asn Phe Asn Asp<br>                  245                250                255 | 768 | |
| tat ccc att ggt cac ccc aaa aga aag tgg tgg cat agg ttc caa ggg<br>Tyr Pro Ile Gly His Pro Lys Arg Lys Trp Trp His Arg Phe Gln Gly<br>                  260                265                270 | 816 | |
| ctc tac ttc cta atc atg ctg agt ttc tat tgg gta tcg atg gta ttc<br>Leu Tyr Phe Leu Ile Met Leu Ser Phe Tyr Trp Val Ser Met Val Phe<br>                  275                280                285 | 864 | |
| aac cca caa gtt atc gac ctc cgt cat gct gga gct gcc tac gtt gga<br>Asn Pro Gln Val Ile Asp Leu Arg His Ala Gly Ala Ala Tyr Val Gly<br>290                  295                300 | 912 | |
| ttt cag atg gag aac gac ttt atc gtc aaa cgg aga aag tat gca atg<br>Phe Gln Met Glu Asn Asp Phe Ile Val Lys Arg Arg Lys Tyr Ala Met<br>305                  310                315                320 | 960 | |
| gca ctt cgt gca atg tac ttc tat ttc aac atc tat tgt ccg att gtc<br>Ala Leu Arg Ala Met Tyr Phe Tyr Phe Asn Ile Tyr Cys Pro Ile Val<br>                  325                330                335 | 1008 | |
| aac aat gga ttg act tgg tcg aca gtt gga atc atc ctc tta atg gga<br>Asn Asn Gly Leu Thr Trp Ser Thr Val Gly Ile Ile Leu Leu Met Gly<br>                  340                345                350 | 1056 | |
| gtt agc gaa agc ttc atg ctc tcc ggt cta ttc gta ctc tca cac aac<br>Val Ser Glu Ser Phe Met Leu Ser Gly Leu Phe Val Leu Ser His Asn<br>                  355                360                365 | 1104 | |
| ttt gaa aat tcc gaa cgt gat cct acc tct gag tat cgc aag act ggt<br>Phe Glu Asn Ser Glu Arg Asp Pro Thr Ser Glu Tyr Arg Lys Thr Gly<br>370                  375                380 | 1152 | |
| gag caa gta tgt tgg ttc aag tct caa gtg gag act tct tct acc tac<br>Glu Gln Val Cys Trp Phe Lys Ser Gln Val Glu Thr Ser Ser Thr Tyr<br>385                  390                395                400 | 1200 | |
| gga ggt atc gtt gct ggg tgt ctc act ggt gga ctc aac ttt caa gtg<br>Gly Gly Ile Val Ala Gly Cys Leu Thr Gly Gly Leu Asn Phe Gln Val<br>                  405                410                415 | 1248 | |
| gag cat cat ttg ttc ccg agg atg agc agt gct tgg tat cct ttc atc<br>Glu His His Leu Phe Pro Arg Met Ser Ser Ala Trp Tyr Pro Phe Ile<br>420                  425                430 | 1296 | |

```
gcg ccg aag gtt aga gag att tgt aag aag cat gga gtt aga tac gct    1344
Ala Pro Lys Val Arg Glu Ile Cys Lys Lys His Gly Val Arg Tyr Ala
    435                 440                 445 tac tat ccg tac atc tgg cag aac ttg cat tct acc gtg agt tac atg    1392
Tyr Tyr Pro Tyr Ile Trp Gln Asn Leu His Ser Thr Val Ser Tyr Met
450                 455                 460 cat ggg acg gga acg gga gct aga tgg gag ctt cag ccg ttg tct gga    1440
His Gly Thr Gly Thr Gly Ala Arg Trp Glu Leu Gln Pro Leu Ser Gly
465                 470                 475                 480 agg gcg tag                                                        1449
Arg Ala
```

<210> SEQ ID NO 41
<211> LENGTH: 482
<212> TYPE: PRT
<213> ORGANISM: Thalassiosira pseudonana

<400> SEQUENCE: 41

```
Met Pro Pro Asn Ala Glu Val Lys Asn Leu Arg Ser Arg Ser Ile Pro
1               5                   10                  15

Thr Lys Lys Ser Ser Ser Ser Ser Thr Ala Asn Asp Asp Pro Ala
            20                  25                  30

Thr Gln Ser Thr Ser Pro Val Asn Arg Thr Leu Lys Ser Leu Asn Gly
        35                  40                  45

Asn Glu Ile Ala Ile Asp Gly Val Ile Tyr Asp Ile Asp Gly Phe Val
    50                  55                  60

His Pro Gly Gly Glu Val Ile Ser Phe Phe Gly Gly Asn Asp Val Thr
65                  70                  75                  80

Val Gln Tyr Lys Met Ile His Pro Tyr His Asn Ser Lys His Leu Glu
                85                  90                  95

Lys Met Arg Ala Val Gly Lys Ile Ala Asp Tyr Ser Thr Glu Tyr Lys
            100                 105                 110

Phe Asp Thr Pro Phe Glu Arg Glu Ile Lys Ser Glu Val Phe Lys Ile
        115                 120                 125

Val Arg Arg Gly Arg Glu Phe Gly Thr Thr Gly Tyr Phe Leu Arg Ala
    130                 135                 140

Phe Phe Tyr Ile Ala Leu Phe Phe Thr Met Gln Tyr Thr Phe Ala Thr
145                 150                 155                 160

Cys Thr Thr Phe Thr Thr Tyr Asp His Trp Tyr Gln Ser Gly Val Phe
                165                 170                 175

Ile Ala Ile Val Phe Gly Ile Ser Gln Ala Phe Ile Gly Leu Asn Val
            180                 185                 190

Gln His Asp Ala Asn His Gly Ala Ala Ser Lys Arg Pro Trp Val Asn
        195                 200                 205

Asp Leu Leu Gly Ser Gly Ala Asp Leu Ile Gly Gly Cys Lys Trp Asn
    210                 215                 220

Trp Leu Ala Gln His Trp Thr His His Ala Tyr Thr Asn His Ala Asp
225                 230                 235                 240

Lys Asp Pro Asp Ser Phe Ser Ser Glu Pro Val Phe Asn Phe Asn Asp
                245                 250                 255

Tyr Pro Ile Gly His Pro Lys Arg Lys Trp Trp His Arg Phe Gln Gly
            260                 265                 270

Leu Tyr Phe Leu Ile Met Leu Ser Phe Tyr Trp Val Ser Met Val Phe
        275                 280                 285

Asn Pro Gln Val Ile Asp Leu Arg His Ala Gly Ala Ala Tyr Val Gly
```

-continued

```
                    290                 295                 300
Phe Gln Met Glu Asn Asp Phe Ile Val Lys Arg Lys Tyr Ala Met
305                 310                 315                 320

Ala Leu Arg Ala Met Tyr Phe Tyr Phe Asn Ile Tyr Cys Pro Ile Val
                325                 330                 335

Asn Asn Gly Leu Thr Trp Ser Thr Val Gly Ile Ile Leu Leu Met Gly
            340                 345                 350

Val Ser Glu Ser Phe Met Leu Ser Gly Leu Phe Val Leu Ser His Asn
        355                 360                 365

Phe Glu Asn Ser Glu Arg Asp Pro Thr Ser Glu Tyr Arg Lys Thr Gly
    370                 375                 380

Glu Gln Val Cys Trp Phe Lys Ser Gln Val Glu Thr Ser Ser Thr Tyr
385                 390                 395                 400

Gly Gly Ile Val Ala Gly Cys Leu Thr Gly Gly Leu Asn Phe Gln Val
                405                 410                 415

Glu His His Leu Phe Pro Arg Met Ser Ser Ala Trp Tyr Pro Phe Ile
            420                 425                 430

Ala Pro Lys Val Arg Glu Ile Cys Lys Lys His Gly Val Arg Tyr Ala
        435                 440                 445

Tyr Tyr Pro Tyr Ile Trp Gln Asn Leu His Ser Thr Val Ser Tyr Met
    450                 455                 460

His Gly Thr Gly Thr Gly Ala Arg Trp Glu Leu Gln Pro Leu Ser Gly
465                 470                 475                 480

Arg Ala

<210> SEQ ID NO 42
<211> LENGTH: 1683
<212> TYPE: DNA
<213> ORGANISM: Borago officinalis
<220> FEATURE:
<221> NAME/KEY: CDS
<222> LOCATION: (42)..(1388)
<223> OTHER INFORMATION: delta-6-Desaturase

<400> SEQUENCE: 42
tatctgccta ccctcccaaa gagagtagtc attttcatc a atg gct gct caa atc         56
                                             Met Ala Ala Gln Ile
                                             1               5 aag aaa tac att acc tca gat gaa ctc aag aac cac gat aaa ccc gga        104
Lys Lys Tyr Ile Thr Ser Asp Glu Leu Lys Asn His Asp Lys Pro Gly
            10                  15                  20 gat cta tgg atc tcg att caa ggg aaa gcc tat gat gtt tcg gat tgg        152
Asp Leu Trp Ile Ser Ile Gln Gly Lys Ala Tyr Asp Val Ser Asp Trp
        25                  30                  35 gtg aaa gac cat cca ggt ggc agc ttt ccc ttg aag agt ctt gct ggt        200
Val Lys Asp His Pro Gly Gly Ser Phe Pro Leu Lys Ser Leu Ala Gly
    40                  45                  50 caa gag gta act gat gca ttt gtt gca ttc cat cct gcc tct aca tgg        248
Gln Glu Val Thr Asp Ala Phe Val Ala Phe His Pro Ala Ser Thr Trp
55                  60                  65 aag aat ctt gat aag ttt ttc act ggg tat tat ctt aaa gat tac tct        296
Lys Asn Leu Asp Lys Phe Phe Thr Gly Tyr Tyr Leu Lys Asp Tyr Ser
70                  75                  80                  85 gtt tct gag gtt tct aaa gat tat agg aag ctt gtg ttt gag ttt tct        344
Val Ser Glu Val Ser Lys Asp Tyr Arg Lys Leu Val Phe Glu Phe Ser
                90                  95                  100 aaa atg ggt ttg tat gac aaa aaa ggt cat att atg ttt gca act ttg        392
Lys Met Gly Leu Tyr Asp Lys Lys Gly His Ile Met Phe Ala Thr Leu
```

-continued

```
                105                 110                 115
tgc ttt ata gca atg ctg ttt gct atg agt gtt tat ggg gtt ttg ttt     440
Cys Phe Ile Ala Met Leu Phe Ala Met Ser Val Tyr Gly Val Leu Phe
        120                 125                 130 tgt gag ggt gtt ttg gta cat ttg ttt tct ggg tgt ttg atg ggg ttt     488
Cys Glu Gly Val Leu Val His Leu Phe Ser Gly Cys Leu Met Gly Phe
    135                 140                 145 ctt tgg att cag agt ggt tgg att gga cat gat gct ggg cat tat atg     536
Leu Trp Ile Gln Ser Gly Trp Ile Gly His Asp Ala Gly His Tyr Met
150                 155                 160                 165 gta gtg tct gat tca agg ctt aat aag ttt atg ggt att ttt gct gca     584
Val Val Ser Asp Ser Arg Leu Asn Lys Phe Met Gly Ile Phe Ala Ala
                170                 175                 180 aat tgt ctt tca gga ata agt att ggt tgg tgg aaa tgg aac cat aat     632
Asn Cys Leu Ser Gly Ile Ser Ile Gly Trp Trp Lys Trp Asn His Asn
            185                 190                 195 gca cat cac att gcc tgt aat agc ctt gaa tat gac cct gat tta caa     680
Ala His His Ile Ala Cys Asn Ser Leu Glu Tyr Asp Pro Asp Leu Gln
        200                 205                 210 tat ata cca ttc ctt gtt gtg tct tcc aag ttt ttt ggt tca ctc acc     728
Tyr Ile Pro Phe Leu Val Val Ser Ser Lys Phe Phe Gly Ser Leu Thr
    215                 220                 225 tct cat ttc tat gag aaa agg ttg act ttt gac tct tta tca aga ttc     776
Ser His Phe Tyr Glu Lys Arg Leu Thr Phe Asp Ser Leu Ser Arg Phe
230                 235                 240                 245 ttt gta agt tat caa cat tgg aca ttt tac cct att atg tgt gct gct     824
Phe Val Ser Tyr Gln His Trp Thr Phe Tyr Pro Ile Met Cys Ala Ala
                250                 255                 260 agg ctc aat atg tat gta caa tct ctc ata atg ttg ttg acc aag aga     872
Arg Leu Asn Met Tyr Val Gln Ser Leu Ile Met Leu Leu Thr Lys Arg
            265                 270                 275 aat gtg tcc tat cga gct cag gaa ctc ttg gga tgc cta gtg ttc tcg     920
Asn Val Ser Tyr Arg Ala Gln Glu Leu Leu Gly Cys Leu Val Phe Ser
        280                 285                 290 att tgg tac ccg ttg ctt gtt tct tgt ttg cct aat tgg ggt gaa aga     968
Ile Trp Tyr Pro Leu Leu Val Ser Cys Leu Pro Asn Trp Gly Glu Arg
    295                 300                 305 att atg ttt gtt att gca agt tta tca gtg act gga atg caa caa gtt    1016
Ile Met Phe Val Ile Ala Ser Leu Ser Val Thr Gly Met Gln Gln Val
310                 315                 320                 325 cag ttc tcc ttg aac cac ttc tct tca agt gtt tat gtt gga aag cct    1064
Gln Phe Ser Leu Asn His Phe Ser Ser Ser Val Tyr Val Gly Lys Pro
                330                 335                 340 aaa ggg aat aat tgg ttt gag aaa caa acg gat ggg aca ctt gac att    1112
Lys Gly Asn Asn Trp Phe Glu Lys Gln Thr Asp Gly Thr Leu Asp Ile
            345                 350                 355 tct tgt cct cct tgg atg gat tgg ttt cat ggt gga ttg caa ttc caa    1160
Ser Cys Pro Pro Trp Met Asp Trp Phe His Gly Gly Leu Gln Phe Gln
        360                 365                 370 att gag cat cat ttg ttt ccc aag atg cct aga tgc aac ctt agg aaa    1208
Ile Glu His His Leu Phe Pro Lys Met Pro Arg Cys Asn Leu Arg Lys
    375                 380                 385 atc tcg ccc tac gtg atc gag tta tgc aag aaa cat aat ttg cct tac    1256
Ile Ser Pro Tyr Val Ile Glu Leu Cys Lys Lys His Asn Leu Pro Tyr
390                 395                 400                 405 aat tat gca tct ttc tcc aag gcc aat gaa atg aca ctc aga aca ttg    1304
Asn Tyr Ala Ser Phe Ser Lys Ala Asn Glu Met Thr Leu Arg Thr Leu
                410                 415                 420 agg aac aca gca ttg cag gct agg gat ata acc aag ccg ctc ccg aag    1352
```

```
Arg Asn Thr Ala Leu Gln Ala Arg Asp Ile Thr Lys Pro Leu Pro Lys
            425                 430                 435 aat ttg gta tgg gaa gct ctt cac act cat ggt taa aattaccctt         1398
Asn Leu Val Trp Glu Ala Leu His Thr His Gly
        440                 445 agttcatgta ataatttgag attatgtatc tcctatgttt gtgtcttgtc ttggttctac  1458
ttgttggagt cattgcaact tgtcttttat ggtttattag atgttttta  atatatttta  1518 gaggttttgc tttcatctcc attattgatg aataaggagt tgcatattgt caattgttgt  1578
gctcaatatc tgatattttg gaatgtactt tgtaccactg tgttttcagt tgaagctcat  1638
gtgtacttct atagactttg tttaaatggt tatgtcatgt tattt                  1683

<210> SEQ ID NO 43
<211> LENGTH: 448
<212> TYPE: PRT
<213> ORGANISM: Borago officinalis

<400> SEQUENCE: 43

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
    210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala Gln Glu Leu Leu Gly
        275                 280                 285
```

```
Cys Leu Val Phe Ser Ile Trp Tyr Pro Leu Leu Val Ser Cys Leu Pro
        290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Val
                325                 330                 335

Tyr Val Gly Lys Pro Lys Gly Asn Asn Trp Phe Glu Lys Gln Thr Asp
                340                 345                 350

Gly Thr Leu Asp Ile Ser Cys Pro Pro Trp Met Asp Trp Phe His Gly
                355                 360                 365

Gly Leu Gln Phe Gln Ile Glu His His Leu Phe Pro Lys Met Pro Arg
        370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
                420                 425                 430

Lys Pro Leu Pro Lys Asn Leu Val Trp Glu Ala Leu His Thr His Gly
        435                 440                 445

<210> SEQ ID NO 44
<211> LENGTH: 1563
<212> TYPE: DNA
<213> ORGANISM: Ceratodon purpureus
<220> FEATURE:
<221> NAME/KEY: CDS
<222> LOCATION: (1)..(1563)
<223> OTHER INFORMATION: delta-6-Desaturase

<400> SEQUENCE: 44 atg gtg tcc cag ggc ggc ggt ctc tcg cag ggt tcc att gaa gaa aac        48
Met Val Ser Gln Gly Gly Gly Leu Ser Gln Gly Ser Ile Glu Glu Asn
1               5                   10                  15 att gac gtt gag cac ttg gca acg atg ccc ctc gtc agt gac ttc cta        96
Ile Asp Val Glu His Leu Ala Thr Met Pro Leu Val Ser Asp Phe Leu
                20                  25                  30 aat gtc ctg gga acg act ttg ggc cag tgg agt ctt tcc act aca ttc       144
Asn Val Leu Gly Thr Thr Leu Gly Gln Trp Ser Leu Ser Thr Thr Phe
            35                  40                  45 gct ttc aag agg ctc acg act aag aaa cac agt tcg gac atc tcg gtg       192
Ala Phe Lys Arg Leu Thr Thr Lys Lys His Ser Ser Asp Ile Ser Val
        50                  55                  60 gag gca caa aaa gaa tcg gtt gcg cgg ggg cca gtt gag aat att tct       240
Glu Ala Gln Lys Glu Ser Val Ala Arg Gly Pro Val Glu Asn Ile Ser
65                  70                  75                  80 caa tcg gtt gcg cag ccc atc agg cgg agg tgg gtg cag gat aaa aag       288
Gln Ser Val Ala Gln Pro Ile Arg Arg Arg Trp Val Gln Asp Lys Lys
                85                  90                  95 ccg gtt act tac agc ctg aag gat gta gct tcg cac gat atg ccc cag       336
Pro Val Thr Tyr Ser Leu Lys Asp Val Ala Ser His Asp Met Pro Gln
                100                 105                 110 gac tgc tgg att ata atc aaa gag aag gtg tat gat gtg agc acc ttc       384
Asp Cys Trp Ile Ile Ile Lys Glu Lys Val Tyr Asp Val Ser Thr Phe
            115                 120                 125 gct gag cag cac cct gga ggc acg gtt atc aac acc tac ttc gga cga       432
Ala Glu Gln His Pro Gly Gly Thr Val Ile Asn Thr Tyr Phe Gly Arg
        130                 135                 140 gac gcc aca gat gtt ttc tct act ttc cac gca tcc acc tca tgg aag       480
```

```
Asp Ala Thr Asp Val Phe Ser Thr Phe His Ala Ser Thr Ser Trp Lys
145                 150                 155                 160 att ctt cag aat ttc tac atc ggg aac ctt gtt agg gag gag ccg act    528
Ile Leu Gln Asn Phe Tyr Ile Gly Asn Leu Val Arg Glu Glu Pro Thr
                    165                 170                 175 ttg gag ctg ctg aag gag tac aga gag ttg aga gcc ctt ttc ttg aga    576
Leu Glu Leu Leu Lys Glu Tyr Arg Glu Leu Arg Ala Leu Phe Leu Arg
                180                 185                 190 gaa cag ctt ttc aag agt tcc aaa tcc tac tac ctt ttc aag act ctc    624
Glu Gln Leu Phe Lys Ser Ser Lys Ser Tyr Tyr Leu Phe Lys Thr Leu
            195                 200                 205 ata aat gtt tcc att gtt gcc aca agc att gcg ata atc agt ctg tac    672
Ile Asn Val Ser Ile Val Ala Thr Ser Ile Ala Ile Ile Ser Leu Tyr
        210                 215                 220 aag tct tac cgg gcg gtt ctg tta tca gcc agt ttg atg ggc ttg ttt    720
Lys Ser Tyr Arg Ala Val Leu Leu Ser Ala Ser Leu Met Gly Leu Phe
225                 230                 235                 240 att caa cag tgc gga tgg ttg tct cac gat ttt cta cac cat cag gta    768
Ile Gln Gln Cys Gly Trp Leu Ser His Asp Phe Leu His His Gln Val
                    245                 250                 255 ttt gag aca cgc tgg ctc aat gac gtt gtt ggc tat gtg gtc ggc aac    816
Phe Glu Thr Arg Trp Leu Asn Asp Val Val Gly Tyr Val Val Gly Asn
                260                 265                 270 gtt gtt ctg gga ttc agt gtc tcg tgg tgg aag acc aag cac aac ctg    864
Val Val Leu Gly Phe Ser Val Ser Trp Trp Lys Thr Lys His Asn Leu
            275                 280                 285 cat cat gct gct ccg aat gaa tgc gac caa aag tac aca ccg att gat    912
His His Ala Ala Pro Asn Glu Cys Asp Gln Lys Tyr Thr Pro Ile Asp
        290                 295                 300 gag gat att gat act ctc ccc atc att gct tgg agt aaa gat ctc ttg    960
Glu Asp Ile Asp Thr Leu Pro Ile Ile Ala Trp Ser Lys Asp Leu Leu
305                 310                 315                 320 gcc act gtt gag agc aag acc atg ttg cga gtt ctt cag tac cag cac   1008
Ala Thr Val Glu Ser Lys Thr Met Leu Arg Val Leu Gln Tyr Gln His
                    325                 330                 335 cta ttc ttt ttg gtt ctt ttg acg ttt gcc cgg gcg agt tgg cta ttt   1056
Leu Phe Phe Leu Val Leu Leu Thr Phe Ala Arg Ala Ser Trp Leu Phe
                340                 345                 350 tgg agc gcg gcc ttc act ctc agg ccc gag ttg acc ctt ggc gag aag   1104
Trp Ser Ala Ala Phe Thr Leu Arg Pro Glu Leu Thr Leu Gly Glu Lys
            355                 360                 365 ctt ttg gag agg gga acg atg gct ttg cac tac att tgg ttt aat agt   1152
Leu Leu Glu Arg Gly Thr Met Ala Leu His Tyr Ile Trp Phe Asn Ser
        370                 375                 380 gtt gcg ttt tat ctg ctc ccc gga tgg aaa cca gtt gta tgg atg gtg   1200
Val Ala Phe Tyr Leu Leu Pro Gly Trp Lys Pro Val Val Trp Met Val
385                 390                 395                 400 gtc agc gag ctc atg tct ggt ttc ctg ctg gga tac gta ttt gta ctc   1248
Val Ser Glu Leu Met Ser Gly Phe Leu Leu Gly Tyr Val Phe Val Leu
                    405                 410                 415 agt cac aat gga atg gag gtg tac aat acg tca aag gac ttc gtg aat   1296
Ser His Asn Gly Met Glu Val Tyr Asn Thr Ser Lys Asp Phe Val Asn
                420                 425                 430 gcc cag att gca tcg act cgc gac atc aaa gca ggg gtg ttt aat gat   1344
Ala Gln Ile Ala Ser Thr Arg Asp Ile Lys Ala Gly Val Phe Asn Asp
            435                 440                 445 tgg ttc acc gga ggt ctc aac aga cag att gag cat cat cta ttt cca   1392
Trp Phe Thr Gly Gly Leu Asn Arg Gln Ile Glu His His Leu Phe Pro
        450                 455                 460
```

```
acg atg ccc agg cac aac ctt aat aaa att tct cct cac gtg gag act    1440
Thr Met Pro Arg His Asn Leu Asn Lys Ile Ser Pro His Val Glu Thr
465                 470                 475                 480 ttg tgc aag aag cat gga ctg gtc tac gaa gac gtg agc atg gct tcg    1488
Leu Cys Lys Lys His Gly Leu Val Tyr Glu Asp Val Ser Met Ala Ser
                485                 490                 495 ggc act tac cgg gtt ttg aaa aca ctt aag gac gtt gcc gat gct gct    1536
Gly Thr Tyr Arg Val Leu Lys Thr Leu Lys Asp Val Ala Asp Ala Ala
            500                 505                 510 tca cac cag cag ctt gct gcg agt tga                                1563
Ser His Gln Gln Leu Ala Ala Ser
            515                 520

<210> SEQ ID NO 45
<211> LENGTH: 520
<212> TYPE: PRT
<213> ORGANISM: Ceratodon purpureus

<400> SEQUENCE: 45

Met Val Ser Gln Gly Gly Leu Ser Gln Gly Ser Ile Glu Glu Asn
1               5                   10                  15

Ile Asp Val Glu His Leu Ala Thr Met Pro Leu Val Ser Asp Phe Leu
            20                  25                  30

Asn Val Leu Gly Thr Thr Leu Gly Gln Trp Ser Leu Ser Thr Thr Phe
        35                  40                  45

Ala Phe Lys Arg Leu Thr Thr Lys Lys His Ser Ser Asp Ile Ser Val
    50                  55                  60

Glu Ala Gln Lys Glu Ser Val Ala Arg Gly Pro Val Glu Asn Ile Ser
65                  70                  75                  80

Gln Ser Val Ala Gln Pro Ile Arg Arg Trp Val Gln Asp Lys Lys
                85                  90                  95

Pro Val Thr Tyr Ser Leu Lys Asp Val Ala Ser His Asp Met Pro Gln
            100                 105                 110

Asp Cys Trp Ile Ile Ile Lys Glu Lys Val Tyr Asp Val Ser Thr Phe
        115                 120                 125

Ala Glu Gln His Pro Gly Gly Thr Val Ile Asn Thr Tyr Phe Gly Arg
    130                 135                 140

Asp Ala Thr Asp Val Phe Ser Thr Phe His Ala Ser Thr Ser Trp Lys
145                 150                 155                 160

Ile Leu Gln Asn Phe Tyr Ile Gly Asn Leu Val Arg Glu Pro Thr
                165                 170                 175

Leu Glu Leu Leu Lys Glu Tyr Arg Glu Leu Arg Ala Leu Phe Leu Arg
            180                 185                 190

Glu Gln Leu Phe Lys Ser Ser Lys Ser Tyr Tyr Leu Phe Lys Thr Leu
        195                 200                 205

Ile Asn Val Ser Ile Val Ala Thr Ser Ile Ala Ile Ile Ser Leu Tyr
    210                 215                 220

Lys Ser Tyr Arg Ala Val Leu Leu Ser Ala Ser Leu Met Gly Leu Phe
225                 230                 235                 240

Ile Gln Gln Cys Gly Trp Leu Ser His Asp Phe Leu His Gln Val
                245                 250                 255

Phe Glu Thr Arg Trp Leu Asn Asp Val Val Gly Tyr Val Val Gly Asn
            260                 265                 270

Val Val Leu Gly Phe Ser Val Ser Trp Trp Lys Thr Lys His Asn Leu
        275                 280                 285

His His Ala Ala Pro Asn Glu Cys Asp Gln Lys Tyr Thr Pro Ile Asp
```

```
                290                 295                 300
Glu Asp Ile Asp Thr Leu Pro Ile Ile Ala Trp Ser Lys Asp Leu Leu
305                 310                 315                 320

Ala Thr Val Glu Ser Lys Thr Met Leu Arg Val Leu Gln Tyr Gln His
                325                 330                 335

Leu Phe Phe Leu Val Leu Leu Thr Phe Ala Arg Ala Ser Trp Leu Phe
            340                 345                 350

Trp Ser Ala Ala Phe Thr Leu Arg Pro Glu Leu Thr Leu Gly Glu Lys
                355                 360                 365

Leu Leu Glu Arg Gly Thr Met Ala Leu His Tyr Ile Trp Phe Asn Ser
370                 375                 380

Val Ala Phe Tyr Leu Leu Pro Gly Trp Lys Pro Val Val Trp Met Val
385                 390                 395                 400

Val Ser Glu Leu Met Ser Gly Phe Leu Leu Gly Tyr Val Phe Val Leu
                405                 410                 415

Ser His Asn Gly Met Glu Val Tyr Asn Thr Ser Lys Asp Phe Val Asn
            420                 425                 430

Ala Gln Ile Ala Ser Thr Arg Asp Ile Lys Ala Gly Val Phe Asn Asp
                435                 440                 445

Trp Phe Thr Gly Gly Leu Asn Arg Gln Ile Glu His Leu Phe Pro
450                 455                 460

Thr Met Pro Arg His Asn Leu Asn Lys Ile Ser Pro His Val Glu Thr
465                 470                 475                 480

Leu Cys Lys Lys His Gly Leu Val Tyr Glu Asp Val Ser Met Ala Ser
                485                 490                 495

Gly Thr Tyr Arg Val Leu Lys Thr Leu Lys Asp Val Ala Asp Ala Ala
                500                 505                 510

Ser His Gln Gln Leu Ala Ala Ser
            515                 520

<210> SEQ ID NO 46
<211> LENGTH: 1434
<212> TYPE: DNA
<213> ORGANISM: Phaeodactylum tricornutum
<220> FEATURE:
<221> NAME/KEY: CDS
<222> LOCATION: (1)..(1434)
<223> OTHER INFORMATION: delta-6-Desaturase

<400> SEQUENCE: 46 atg ggc aaa gga ggg gac gct cgg gcc tcg aag ggc tca acg gcg gct     48
Met Gly Lys Gly Gly Asp Ala Arg Ala Ser Lys Gly Ser Thr Ala Ala
1               5                   10                  15 cgc aag atc agt tgg cag gaa gtc aag acc cac gcg tct ccg gag gac     96
Arg Lys Ile Ser Trp Gln Glu Val Lys Thr His Ala Ser Pro Glu Asp
            20                  25                  30 gcc tgg atc att cac tcc aat aag gtc tac gac gtg tcc aac tgg cac    144
Ala Trp Ile Ile His Ser Asn Lys Val Tyr Asp Val Ser Asn Trp His
        35                  40                  45 gaa cat ccc gga ggc gcc gtc att ttc acg cac gcc ggt gac gac atg    192
Glu His Pro Gly Gly Ala Val Ile Phe Thr His Ala Gly Asp Asp Met
    50                  55                  60 acg gac att ttc gct gcc ttt cac gca ccc gga tcg cag tcg ctc atg    240
Thr Asp Ile Phe Ala Ala Phe His Ala Pro Gly Ser Gln Ser Leu Met
65                  70                  75                  80 aag aag ttc tac att ggc gaa ttg ctc ccg gaa acc acc ggc aag gag    288
Lys Lys Phe Tyr Ile Gly Glu Leu Leu Pro Glu Thr Thr Gly Lys Glu
                85                  90                  95
```

```
                                                        -continued ccg cag caa atc gcc ttt gaa aag ggc tac cgc gat ctg cgc tcc aaa      336
Pro Gln Gln Ile Ala Phe Glu Lys Gly Tyr Arg Asp Leu Arg Ser Lys
            100                 105                 110 ctc atc atg atg ggc atg ttc aag tcc aac aag tgg ttc tac gtc tac      384
Leu Ile Met Met Gly Met Phe Lys Ser Asn Lys Trp Phe Tyr Val Tyr
        115                 120                 125 aag tgc ctc agc aac atg gcc att tgg gcc gcc gcc tgt gct ctc gtc      432
Lys Cys Leu Ser Asn Met Ala Ile Trp Ala Ala Ala Cys Ala Leu Val
130                 135                 140 ttt tac tcg gac cgc ttc tgg gta cac ctg gcc agc gcc gtc atg ctg      480
Phe Tyr Ser Asp Arg Phe Trp Val His Leu Ala Ser Ala Val Met Leu
145                 150                 155                 160 gga aca ttc ttt cag cag tcg gga tgg ttg gca cac gac ttt ctg cac      528
Gly Thr Phe Phe Gln Gln Ser Gly Trp Leu Ala His Asp Phe Leu His
                165                 170                 175 cac cag gtc ttc acc aag cgc aag cac ggg gat ctc gga gga ctc ttt      576
His Gln Val Phe Thr Lys Arg Lys His Gly Asp Leu Gly Gly Leu Phe
            180                 185                 190 tgg ggg aac ctc atg cag ggt tac tcc gta cag tgg tgg aaa aac aag      624
Trp Gly Asn Leu Met Gln Gly Tyr Ser Val Gln Trp Trp Lys Asn Lys
        195                 200                 205 cac aac gga cac cac gcc gtc ccc aac ctc cac tgc tcc tcc gca gtc      672
His Asn Gly His His Ala Val Pro Asn Leu His Cys Ser Ser Ala Val
210                 215                 220 gcg caa gat ggg gac ccg gac atc gat acc atg ccc ctt ctc gcc tgg      720
Ala Gln Asp Gly Asp Pro Asp Ile Asp Thr Met Pro Leu Leu Ala Trp
225                 230                 235                 240 tcc gtc cag caa gcc cag tct tac cgg gaa ctc caa gcc gac gga aag      768
Ser Val Gln Gln Ala Gln Ser Tyr Arg Glu Leu Gln Ala Asp Gly Lys
                245                 250                 255 gat tcg ggt ttg gtc aag ttc atg atc cgt aac caa tcc tac ttt tac      816
Asp Ser Gly Leu Val Lys Phe Met Ile Arg Asn Gln Ser Tyr Phe Tyr
            260                 265                 270 ttt ccc atc ttg ttg ctc gcc cgc ctg tcg tgg ttg aac gag tcc ttc      864
Phe Pro Ile Leu Leu Leu Ala Arg Leu Ser Trp Leu Asn Glu Ser Phe
        275                 280                 285 aag tgc gcc ttt ggg ctt gga gct gcg tcg gag aac gct gct ctc gaa      912
Lys Cys Ala Phe Gly Leu Gly Ala Ala Ser Glu Asn Ala Ala Leu Glu
290                 295                 300 ctc aag gcc aag ggt ctt cag tac ccc ctt ttg gaa aag gct ggc atc      960
Leu Lys Ala Lys Gly Leu Gln Tyr Pro Leu Leu Glu Lys Ala Gly Ile
305                 310                 315                 320 ctg ctg cac tac gct tgg atg ctt aca gtt tcg tcc ggc ttt gga cgc     1008
Leu Leu His Tyr Ala Trp Met Leu Thr Val Ser Ser Gly Phe Gly Arg
                325                 330                 335 ttc tcg ttc gcg tac acc gca ttt tac ttt cta acc gcg acc gcg tcc     1056
Phe Ser Phe Ala Tyr Thr Ala Phe Tyr Phe Leu Thr Ala Thr Ala Ser
            340                 345                 350 tgt gga ttc ttg ctc gcc att gtc ttt ggc ctc ggc cac aac ggc atg     1104
Cys Gly Phe Leu Leu Ala Ile Val Phe Gly Leu Gly His Asn Gly Met
        355                 360                 365 gcc acc tac aat gcc gac gcc cgt ccg gac ttc tgg aag ctc caa gtc     1152
Ala Thr Tyr Asn Ala Asp Ala Arg Pro Asp Phe Trp Lys Leu Gln Val
370                 375                 380 acc acg act cgc aac gtc acg ggc gga cac ggt ttc ccc caa gcc ttt     1200
Thr Thr Thr Arg Asn Val Thr Gly Gly His Gly Phe Pro Gln Ala Phe
385                 390                 395                 400 gtc gac tgg ttc tgt ggt ggc ctc cag tac caa gtc gac cac cac tta     1248
Val Asp Trp Phe Cys Gly Gly Leu Gln Tyr Gln Val Asp His His Leu
```

-continued

```
                 405                 410                 415
ttc ccc agc ctg ccc cga cac aat ctg gcc aag aca cac gca ctg gtc    1296
Phe Pro Ser Leu Pro Arg His Asn Leu Ala Lys Thr His Ala Leu Val
            420                 425                 430 gaa tcg ttc tgc aag gag tgg ggt gtc cag tac cac gaa gcc gac ctt    1344
Glu Ser Phe Cys Lys Glu Trp Gly Val Gln Tyr His Glu Ala Asp Leu
        435                 440                 445 gtg gac ggg acc atg gaa gtc ttg cac cat ttg ggc agc gtg gcc ggc    1392
Val Asp Gly Thr Met Glu Val Leu His His Leu Gly Ser Val Ala Gly
    450                 455                 460 gaa ttc gtc gtg gat ttt gta cgc gat gga ccc gcc atg taa            1434
Glu Phe Val Val Asp Phe Val Arg Asp Gly Pro Ala Met
465                 470                 475
```

<210> SEQ ID NO 47
<211> LENGTH: 477
<212> TYPE: PRT
<213> ORGANISM: Phaeodactylum tricornutum

<400> SEQUENCE: 47

```
Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45

Glu His Pro Gly Gly Ala Val Ile Phe Thr His Ala Gly Asp Asp Met
    50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Ala Cys Ala Leu Val
    130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Gly Leu Phe
            180                 185                 190

Trp Gly Asn Leu Met Gln Gly Tyr Ser Val Gln Trp Trp Lys Asn Lys
        195                 200                 205

His Asn Gly His His Ala Val Pro Asn Leu His Cys Ser Ser Ala Val
    210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
            260                 265                 270

Phe Pro Ile Leu Leu Leu Ala Arg Leu Ser Trp Leu Asn Glu Ser Phe
        275                 280                 285
```

```
Lys Cys Ala Phe Gly Leu Gly Ala Ala Ser Glu Asn Ala Ala Leu Glu
    290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
                325                 330                 335

Phe Ser Phe Ala Tyr Thr Ala Tyr Phe Leu Thr Ala Thr Ala Ser
            340                 345                 350

Cys Gly Phe Leu Leu Ala Ile Val Phe Gly Leu Gly His Asn Gly Met
                355                 360                 365

Ala Thr Tyr Asn Ala Asp Ala Arg Pro Asp Phe Trp Lys Leu Gln Val
    370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
                405                 410                 415

Phe Pro Ser Leu Pro Arg His Asn Leu Ala Lys Thr His Ala Leu Val
            420                 425                 430

Glu Ser Phe Cys Lys Glu Trp Gly Val Gln Tyr His Glu Ala Asp Leu
    435                 440                 445

Val Asp Gly Thr Met Glu Val Leu His His Leu Gly Ser Val Ala Gly
    450                 455                 460

Glu Phe Val Val Asp Phe Val Arg Asp Gly Pro Ala Met
465                 470                 475

<210> SEQ ID NO 48
<211> LENGTH: 1578
<212> TYPE: DNA
<213> ORGANISM: Physcomitrelllla patens
<220> FEATURE:
<221> NAME/KEY: CDS
<222> LOCATION: (1)..(1578)
<223> OTHER INFORMATION: delta-6-Desaturase

<400> SEQUENCE: 48 atg gta ttc gcg ggc ggt gga ctt cag cag ggc tct ctc gaa gaa aac      48
Met Val Phe Ala Gly Gly Gly Leu Gln Gln Gly Ser Leu Glu Glu Asn
1               5                   10                  15 atc gac gtc gag cac att gcc agt atg tct ctc ttc agc gac ttc ttc      96
Ile Asp Val Glu His Ile Ala Ser Met Ser Leu Phe Ser Asp Phe Phe
                20                  25                  30 agt tat gtg tct tca act gtt ggt tcg tgg agc gta cac agt ata caa     144
Ser Tyr Val Ser Ser Thr Val Gly Ser Trp Ser Val His Ser Ile Gln
            35                  40                  45 cct ttg aag cgc ctg acg agt aag aag cgt gtt tcg gaa agc gct gcc     192
Pro Leu Lys Arg Leu Thr Ser Lys Lys Arg Val Ser Glu Ser Ala Ala
        50                  55                  60 gtg caa tgt ata tca gct gaa gtt cag aga aat tcg agt acc cag gga     240
Val Gln Cys Ile Ser Ala Glu Val Gln Arg Asn Ser Ser Thr Gln Gly
65                  70                  75                  80 act gcg gag gca ctc gca gaa tca gtc gtg aag ccc acg aga cga agg     288
Thr Ala Glu Ala Leu Ala Glu Ser Val Val Lys Pro Thr Arg Arg Arg
                85                  90                  95 tca tct cag tgg aag aag tcg aca cac ccc cta tca gaa gta gca gta     336
Ser Ser Gln Trp Lys Lys Ser Thr His Pro Leu Ser Glu Val Ala Val
            100                 105                 110 cac aac aag cca agc gat tgc tgg att gtt gta aaa aac aag gtg tat     384
His Asn Lys Pro Ser Asp Cys Trp Ile Val Val Lys Asn Lys Val Tyr
```

-continued

```
                115                 120                 125
gat gtt tcc aat ttt gcg gac gag cat ccc gga gga tca gtt att agt       432
Asp Val Ser Asn Phe Ala Asp Glu His Pro Gly Gly Ser Val Ile Ser
        130                 135                 140 act tat ttt gga cga gac ggc aca gat gtt ttc tct agt ttt cat gca       480
Thr Tyr Phe Gly Arg Asp Gly Thr Asp Val Phe Ser Ser Phe His Ala
145                 150                 155                 160 gct tct aca tgg aaa att ctt caa gac ttt tac att ggt gac gtg gag       528
Ala Ser Thr Trp Lys Ile Leu Gln Asp Phe Tyr Ile Gly Asp Val Glu
                165                 170                 175 agg gtg gag ccg act cca gag ctg ctg aaa gat ttc cga gaa atg aga       576
Arg Val Glu Pro Thr Pro Glu Leu Leu Lys Asp Phe Arg Glu Met Arg
        180                 185                 190 gct ctt ttc ctg agg gag caa ctt ttc aaa agt tcg aaa ttg tac tat       624
Ala Leu Phe Leu Arg Glu Gln Leu Phe Lys Ser Ser Lys Leu Tyr Tyr
195                 200                 205 gtt atg aag ctc ctc acg aat gtt gct att ttt gct gcg agc att gca       672
Val Met Lys Leu Leu Thr Asn Val Ala Ile Phe Ala Ala Ser Ile Ala
210                 215                 220 ata ata tgt tgg agc aag act att tca gcg gtt ttg gct tca gct tgt       720
Ile Ile Cys Trp Ser Lys Thr Ile Ser Ala Val Leu Ala Ser Ala Cys
225                 230                 235                 240 atg atg gct ctg tgt ttc caa cag tgc gga tgg cta tcc cat gat ttt       768
Met Met Ala Leu Cys Phe Gln Gln Cys Gly Trp Leu Ser His Asp Phe
                245                 250                 255 ctc cac aat cag gtg ttt gag aca cgc tgg ctt aat gaa gtt gtc ggg       816
Leu His Asn Gln Val Phe Glu Thr Arg Trp Leu Asn Glu Val Val Gly
        260                 265                 270 tat gtg atc ggc aac gcc gtt ctg ggg ttt agt aca ggg tgg tgg aag       864
Tyr Val Ile Gly Asn Ala Val Leu Gly Phe Ser Thr Gly Trp Trp Lys
275                 280                 285 gag aag cat aac ctt cat cat gct gct cca aat gaa tgc gat cag act       912
Glu Lys His Asn Leu His His Ala Ala Pro Asn Glu Cys Asp Gln Thr
290                 295                 300 tac caa cca att gat gaa gat att gat act ctc ccc ctc att gcc tgg       960
Tyr Gln Pro Ile Asp Glu Asp Ile Asp Thr Leu Pro Leu Ile Ala Trp
305                 310                 315                 320 agc aag gac ata ctg gcc aca gtt gag aat aag aca ttc ttg cga atc      1008
Ser Lys Asp Ile Leu Ala Thr Val Glu Asn Lys Thr Phe Leu Arg Ile
                325                 330                 335 ctc caa tac cag cat ctg ttc ttc atg ggt ctg tta ttt ttc gcc cgt      1056
Leu Gln Tyr Gln His Leu Phe Phe Met Gly Leu Leu Phe Phe Ala Arg
        340                 345                 350 ggt agt tgg ctc ttt tgg agc tgg aga tat acc tct aca gca gtg ctc      1104
Gly Ser Trp Leu Phe Trp Ser Trp Arg Tyr Thr Ser Thr Ala Val Leu
355                 360                 365 tca cct gtc gac agg ttg ttg gag aag gga act gtt ctg ttt cac tac      1152
Ser Pro Val Asp Arg Leu Leu Glu Lys Gly Thr Val Leu Phe His Tyr
370                 375                 380 ttt tgg ttc gtc ggg aca gcg tgc tat ctt ctc cct ggt tgg aag cca      1200
Phe Trp Phe Val Gly Thr Ala Cys Tyr Leu Leu Pro Gly Trp Lys Pro
385                 390                 395                 400 tta gta tgg atg gcg gtg act gag ctc atg tcc ggc atg ctg ctg ggc      1248
Leu Val Trp Met Ala Val Thr Glu Leu Met Ser Gly Met Leu Leu Gly
                405                 410                 415 ttt gta ttt gta ctt agc cac aat ggg atg gag gtt tat aat tcg tct      1296
Phe Val Phe Val Leu Ser His Asn Gly Met Glu Val Tyr Asn Ser Ser
        420                 425                 430 aaa gaa ttc gtg agt gca cag atc gta tcc aca cgg gat atc aaa gga      1344
```

```
Lys Glu Phe Val Ser Ala Gln Ile Val Ser Thr Arg Asp Ile Lys Gly
            435                 440                 445 aac ata ttc aac gac tgg ttc act ggt ggc ctt aac agg caa ata gag      1392
Asn Ile Phe Asn Asp Trp Phe Thr Gly Gly Leu Asn Arg Gln Ile Glu
        450                 455                 460 cat cat ctt ttc cca aca atg ccc agg cat aat tta aac aaa ata gca      1440
His His Leu Phe Pro Thr Met Pro Arg His Asn Leu Asn Lys Ile Ala
465                 470                 475                 480 cct aga gtg gag gtg ttc tgt aag aaa cac ggt ctg gtg tac gaa gac      1488
Pro Arg Val Glu Val Phe Cys Lys Lys His Gly Leu Val Tyr Glu Asp
                485                 490                 495 gta tct att gct acc ggc act tgc aag gtt ttg aaa gca ttg aag gaa      1536
Val Ser Ile Ala Thr Gly Thr Cys Lys Val Leu Lys Ala Leu Lys Glu
            500                 505                 510 gtc gcg gag gct gcg gca gag cag cat gct acc acc agt taa              1578
Val Ala Glu Ala Ala Ala Glu Gln His Ala Thr Thr Ser
        515                 520                 525

<210> SEQ ID NO 49
<211> LENGTH: 525
<212> TYPE: PRT
<213> ORGANISM: Physcomitrellla patens

<400> SEQUENCE: 49

Met Val Phe Ala Gly Gly Gly Leu Gln Gln Gly Ser Leu Glu Glu Asn
1               5                   10                  15

Ile Asp Val Glu His Ile Ala Ser Met Ser Leu Phe Ser Asp Phe Phe
                20                  25                  30

Ser Tyr Val Ser Ser Thr Val Gly Ser Trp Ser Val His Ser Ile Gln
            35                  40                  45

Pro Leu Lys Arg Leu Thr Ser Lys Lys Arg Val Ser Glu Ser Ala Ala
        50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Lys Asn Lys Val Tyr
        115                 120                 125

Asp Val Ser Asn Phe Ala Asp Glu His Pro Gly Gly Ser Val Ile Ser
        130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255
```

```
Leu His Asn Gln Val Phe Glu Thr Arg Trp Leu Asn Glu Val Val Gly
              260                 265                 270

Tyr Val Ile Gly Asn Ala Val Leu Gly Phe Ser Thr Gly Trp Trp Lys
          275                 280                 285

Glu Lys His Asn Leu His His Ala Ala Pro Asn Glu Cys Asp Gln Thr
      290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
              325                 330                 335

Leu Gln Tyr Gln His Leu Phe Phe Met Gly Leu Leu Phe Phe Ala Arg
          340                 345                 350

Gly Ser Trp Leu Phe Trp Ser Trp Arg Tyr Thr Ser Thr Ala Val Leu
      355                 360                 365

Ser Pro Val Asp Arg Leu Leu Glu Lys Gly Thr Val Leu Phe His Tyr
370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
              405                 410                 415

Phe Val Phe Val Leu Ser His Asn Gly Met Glu Val Tyr Asn Ser Ser
          420                 425                 430

Lys Glu Phe Val Ser Ala Gln Ile Val Ser Thr Arg Asp Ile Lys Gly
      435                 440                 445

Asn Ile Phe Asn Asp Trp Phe Thr Gly Gly Leu Asn Arg Gln Ile Glu
      450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
              485                 490                 495

Val Ser Ile Ala Thr Gly Thr Cys Lys Val Leu Lys Ala Leu Lys Glu
          500                 505                 510

Val Ala Glu Ala Ala Glu Gln His Ala Thr Thr Ser
      515                 520                 525

<210> SEQ ID NO 50
<211> LENGTH: 1332
<212> TYPE: DNA
<213> ORGANISM: Caenorhabditis elegans
<220> FEATURE:
<221> NAME/KEY: CDS
<222> LOCATION: (1)..(1332)
<223> OTHER INFORMATION: delta-6-Desaturase

<400> SEQUENCE: 50 atg gtc gtc gac aag aat gcc tcc ggg ctt cga atg aag gtc gat ggc      48
Met Val Val Asp Lys Asn Ala Ser Gly Leu Arg Met Lys Val Asp Gly
1               5                   10                  15 aaa tgg ctc tac ctt agc gag gaa ttg gtg aag aaa cat cca gga gga      96
Lys Trp Leu Tyr Leu Ser Glu Glu Leu Val Lys Lys His Pro Gly Gly
            20                  25                  30 gct gtt att gaa caa tat aga aat tcg gat gct act cat att ttc cac     144
Ala Val Ile Glu Gln Tyr Arg Asn Ser Asp Ala Thr His Ile Phe His
        35                  40                  45 gct ttc cac gaa gga tct tct cag gct tat aag caa ctt gac ctt ctg     192
Ala Phe His Glu Gly Ser Ser Gln Ala Tyr Lys Gln Leu Asp Leu Leu
    50                  55                  60
```

-continued

```
aaa aag cac gga gag cac gat gaa ttc ctt gag aaa caa ttg gaa aag      240
Lys Lys His Gly Glu His Asp Glu Phe Leu Glu Lys Gln Leu Glu Lys
 65              70                  75                  80 aga ctt gac aaa gtt gat atc aat gta tca gca tat gat gtc agt gtt      288
Arg Leu Asp Lys Val Asp Ile Asn Val Ser Ala Tyr Asp Val Ser Val
                 85                  90                  95 gca caa gaa aag aaa atg gtt gaa tca ttc gaa aaa cta cga cag aag      336
Ala Gln Glu Lys Lys Met Val Glu Ser Phe Glu Lys Leu Arg Gln Lys
            100                 105                 110 ctt cat gat gat gga tta atg aaa gca aat gaa aca tat ttc ctg ttt      384
Leu His Asp Asp Gly Leu Met Lys Ala Asn Glu Thr Tyr Phe Leu Phe
        115                 120                 125 aaa gcg att tca aca ctt tca att atg gca ttt gca ttt tat ctt cag      432
Lys Ala Ile Ser Thr Leu Ser Ile Met Ala Phe Ala Phe Tyr Leu Gln
    130                 135                 140 tat ctt gga tgg tat att act tct gca tgt tta tta gca ctt gca tgg      480
Tyr Leu Gly Trp Tyr Ile Thr Ser Ala Cys Leu Leu Ala Leu Ala Trp
145                 150                 155                 160 caa caa ttc gga tgg tta aca cat gag ttc tgc cat caa cag cca aca      528
Gln Gln Phe Gly Trp Leu Thr His Glu Phe Cys His Gln Gln Pro Thr
                165                 170                 175 aag aac aga cct ttg aat gat act att tct ttg ttc ttt ggt aat ttc      576
Lys Asn Arg Pro Leu Asn Asp Thr Ile Ser Leu Phe Phe Gly Asn Phe
            180                 185                 190 tta caa gga ttt tca aga gat tgg tgg aag gac aag cat aac act cat      624
Leu Gln Gly Phe Ser Arg Asp Trp Trp Lys Asp Lys His Asn Thr His
        195                 200                 205 cac gct gcc aca aat gta att gat cat gac ggt gat atc gac ttg gca      672
His Ala Ala Thr Asn Val Ile Asp His Asp Gly Asp Ile Asp Leu Ala
    210                 215                 220 cca ctt ttc gca ttt att cca gga gat ttg tgc aag tat aag gcc agc      720
Pro Leu Phe Ala Phe Ile Pro Gly Asp Leu Cys Lys Tyr Lys Ala Ser
225                 230                 235                 240 ttt gaa aaa gca att ctc aag att gta cca tat caa cat ctc tat ttc      768
Phe Glu Lys Ala Ile Leu Lys Ile Val Pro Tyr Gln His Leu Tyr Phe
                245                 250                 255 acc gca atg ctt cca atg ctc cgt ttc tca tgg act ggt cag tca gtt      816
Thr Ala Met Leu Pro Met Leu Arg Phe Ser Trp Thr Gly Gln Ser Val
            260                 265                 270 caa tgg gta ttc aaa gag aat caa atg gag tac aag gtc tat caa aga      864
Gln Trp Val Phe Lys Glu Asn Gln Met Glu Tyr Lys Val Tyr Gln Arg
        275                 280                 285 aat gca ttc tgg gag caa gca aca att gtt gga cat tgg gct tgg gta      912
Asn Ala Phe Trp Glu Gln Ala Thr Ile Val Gly His Trp Ala Trp Val
    290                 295                 300 ttc tat caa ttg ttc tta tta cca aca tgg cca ctt cgg gtt gct tat      960
Phe Tyr Gln Leu Phe Leu Leu Pro Thr Trp Pro Leu Arg Val Ala Tyr
305                 310                 315                 320 ttc att att tca caa atg gga gga ggc ctt ttg att gct cac gta gtc     1008
Phe Ile Ile Ser Gln Met Gly Gly Gly Leu Leu Ile Ala His Val Val
                325                 330                 335 act ttc aac cat aac tct gtt gat aag tat cca gcc aat tct cga att     1056
Thr Phe Asn His Asn Ser Val Asp Lys Tyr Pro Ala Asn Ser Arg Ile
            340                 345                 350 tta aac aac ttc gcc gct ctt caa att ttg acc aca cgc aac atg act     1104
Leu Asn Asn Phe Ala Ala Leu Gln Ile Leu Thr Thr Arg Asn Met Thr
        355                 360                 365 cca tct cca ttc att gat tgg ctt tgg ggt gga ctc aat tat cag atc     1152
Pro Ser Pro Phe Ile Asp Trp Leu Trp Gly Gly Leu Asn Tyr Gln Ile
    370                 375                 380
```

```
gag cac cac ttg ttc cca aca atg cca cgt tgc aat ctg aat gct tgc    1200
Glu His His Leu Phe Pro Thr Met Pro Arg Cys Asn Leu Asn Ala Cys
385                 390                 395                 400 gtg aaa tat gtg aaa gaa tgg tgc aaa gag aat aat ctt cct tac ctc    1248
Val Lys Tyr Val Lys Glu Trp Cys Lys Glu Asn Asn Leu Pro Tyr Leu
            405                 410                 415 gtc gat gac tac ttt gac gga tat gca atg aat ttg caa caa ttg aaa    1296
Val Asp Asp Tyr Phe Asp Gly Tyr Ala Met Asn Leu Gln Gln Leu Lys
        420                 425                 430 aat atg gct gag cac att caa gct aaa gct gcc taa                    1332
Asn Met Ala Glu His Ile Gln Ala Lys Ala Ala
            435                 440

<210> SEQ ID NO 51
<211> LENGTH: 443
<212> TYPE: PRT
<213> ORGANISM: Caenorhabditis elegans

<400> SEQUENCE: 51
```

Met Val Val Asp Lys Asn Ala Ser Gly Leu Arg Met Lys Val Asp Gly
1               5                   10                  15

Lys Trp Leu Tyr Leu Ser Glu Glu Leu Val Lys Lys His Pro Gly Gly
            20                  25                  30

Ala Val Ile Glu Gln Tyr Arg Asn Ser Asp Ala Thr His Ile Phe His
        35                  40                  45

Ala Phe His Glu Gly Ser Ser Gln Ala Tyr Lys Gln Leu Asp Leu Leu
    50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Gly Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys His Asn Thr His
        195                 200                 205

His Ala Ala Thr Asn Val Ile Asp His Asp Gly Asp Ile Asp Leu Ala
    210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285

```
Asn Ala Phe Trp Glu Gln Ala Thr Ile Val Gly His Trp Ala Trp Val
    290                 295                 300

Phe Tyr Gln Leu Phe Leu Leu Pro Thr Trp Pro Leu Arg Val Ala Tyr
305                 310                 315                 320

Phe Ile Ile Ser Gln Met Gly Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
370                 375                 380

Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Gln Leu Lys
            420                 425                 430

Asn Met Ala Glu His Ile Gln Ala Lys Ala Ala
        435                 440

<210> SEQ ID NO 52
<211> LENGTH: 1362
<212> TYPE: DNA
<213> ORGANISM: Primula farinosa
<220> FEATURE:
<221> NAME/KEY: CDS
<222> LOCATION: (1)..(1362)
<223> OTHER INFORMATION: delta-6-Desaturase

<400> SEQUENCE: 52 atg gct aac aaa tct cca cca aac ccc aaa aca ggt tac ata acc agc       48
Met Ala Asn Lys Ser Pro Pro Asn Pro Lys Thr Gly Tyr Ile Thr Ser
1               5                   10                  15 tca gac ctg aaa tcc cac aac aag gca ggt gac cta tgg ata tca atc       96
Ser Asp Leu Lys Ser His Asn Lys Ala Gly Asp Leu Trp Ile Ser Ile
            20                  25                  30 cac ggc caa gtc tac gac gtg tcc tct tgg gcc gcc ctt cat ccg ggg      144
His Gly Gln Val Tyr Asp Val Ser Ser Trp Ala Ala Leu His Pro Gly
        35                  40                  45 ggc act gcc cct ctc atg gcc ctt gca gga cac gac gtg acc gat gct      192
Gly Thr Ala Pro Leu Met Ala Leu Ala Gly His Asp Val Thr Asp Ala
    50                  55                  60 ttc ctc gcg tac cat ccc cct tcc act gcc cgt ctc ctc cct cct ctc      240
Phe Leu Ala Tyr His Pro Pro Ser Thr Ala Arg Leu Leu Pro Pro Leu
65                  70                  75                  80 tct acc aac ctc ctt ctt caa aac cac tcc gtc tcc ccc acc tcc tca      288
Ser Thr Asn Leu Leu Leu Gln Asn His Ser Val Ser Pro Thr Ser Ser
                85                  90                  95 gac tac cgc aaa ctc ctc gac aac ttc cat aaa cat ggc ctt ttc cgc      336
Asp Tyr Arg Lys Leu Leu Asp Asn Phe His Lys His Gly Leu Phe Arg
            100                 105                 110 gcc agg ggc cac act gct tac gcc acc ttc gtc ttc atg ata gcg atg      384
Ala Arg Gly His Thr Ala Tyr Ala Thr Phe Val Phe Met Ile Ala Met
        115                 120                 125 ttt cta atg agc gtg act gga gtc ctt tgc agc gac agt gcg tgg gtc      432
Phe Leu Met Ser Val Thr Gly Val Leu Cys Ser Asp Ser Ala Trp Val
    130                 135                 140 cat ttg gct agc ggc gga gca atg ggg ttc gcc tgg atc caa tgc gga      480
```

```
                    -continued

His Leu Ala Ser Gly Gly Ala Met Gly Phe Ala Trp Ile Gln Cys Gly
145                 150                 155                 160 tgg ata ggt cac gac tct ggg cat tac cgg att atg tct gac agg aaa      528
Trp Ile Gly His Asp Ser Gly His Tyr Arg Ile Met Ser Asp Arg Lys
                    165                 170                 175 tgg aac tgg ttc gcg caa atc cta agc aca aac tgc ctc cag ggg att      576
Trp Asn Trp Phe Ala Gln Ile Leu Ser Thr Asn Cys Leu Gln Gly Ile
                180                 185                 190 agt atc ggg tgg tgg aag tgg aac cat aat gcg cac cac atc gct tgc      624
Ser Ile Gly Trp Trp Lys Trp Asn His Asn Ala His His Ile Ala Cys
            195                 200                 205 aat agc ctg gat tac gac ccc gac ctc cag tat atc cct ttg ctc gtc      672
Asn Ser Leu Asp Tyr Asp Pro Asp Leu Gln Tyr Ile Pro Leu Leu Val
        210                 215                 220 gtc tcc ccc aag ttc ttc aac tcc ctt act tct cgt ttc tac gac aag      720
Val Ser Pro Lys Phe Phe Asn Ser Leu Thr Ser Arg Phe Tyr Asp Lys
225                 230                 235                 240 aag ctg aac ttc gac ggc gtg tcg agg ttt ctg gtt tgc tac cag cac      768
Lys Leu Asn Phe Asp Gly Val Ser Arg Phe Leu Val Cys Tyr Gln His
                    245                 250                 255 tgg acg ttt tat ccg gtc atg tgt gtc gct agg ctg aac atg ctc gcg      816
Trp Thr Phe Tyr Pro Val Met Cys Val Ala Arg Leu Asn Met Leu Ala
                260                 265                 270 cag tca ttt ata acg ctt ttc tcg agt agg gag gtg tgc cat agg gcg      864
Gln Ser Phe Ile Thr Leu Phe Ser Ser Arg Glu Val Cys His Arg Ala
            275                 280                 285 caa gag gtt ttc gga ctt gcc gtg ttt tgg gtt tgg ttt ccg ctt tta      912
Gln Glu Val Phe Gly Leu Ala Val Phe Trp Val Trp Phe Pro Leu Leu
        290                 295                 300 ctt tct tgt tta cct aat tgg ggc gag agg att atg ttt ttg ctt gcg      960
Leu Ser Cys Leu Pro Asn Trp Gly Glu Arg Ile Met Phe Leu Leu Ala
305                 310                 315                 320 agc tat tcc gtt acg ggg ata caa cac gtg cag ttc agc ttg aac cat     1008
Ser Tyr Ser Val Thr Gly Ile Gln His Val Gln Phe Ser Leu Asn His
                    325                 330                 335 ttt tct tcg gac gtc tat gtg ggc ccg cca gta ggt aat gac tgg ttc     1056
Phe Ser Ser Asp Val Tyr Val Gly Pro Pro Val Gly Asn Asp Trp Phe
                340                 345                 350 aag aaa cag act gcc ggg aca ctt aac ata tcg tgc ccg gcg tgg atg     1104
Lys Lys Gln Thr Ala Gly Thr Leu Asn Ile Ser Cys Pro Ala Trp Met
            355                 360                 365 gat tgg ttc cat ggc ggg tta cag ttt cag gtc gag cac cac ttg ttt     1152
Asp Trp Phe His Gly Gly Leu Gln Phe Gln Val Glu His His Leu Phe
        370                 375                 380 ccg cgg atg cct agg ggt cag ttt agg aag att tct cct ttt gtg agg     1200
Pro Arg Met Pro Arg Gly Gln Phe Arg Lys Ile Ser Pro Phe Val Arg
385                 390                 395                 400 gat ttg tgt aag aaa cac aac ttg cct tac aat atc gcg tct ttt act     1248
Asp Leu Cys Lys Lys His Asn Leu Pro Tyr Asn Ile Ala Ser Phe Thr
                    405                 410                 415 aaa gcg aat gtg ttt acg ctt aag acg ctg aga aat acg gcc att gag     1296
Lys Ala Asn Val Phe Thr Leu Lys Thr Leu Arg Asn Thr Ala Ile Glu
                420                 425                 430 gct cgg gac ctc tct aat ccg ctc cca aag aat atg gtg tgg gaa gct     1344
Ala Arg Asp Leu Ser Asn Pro Leu Pro Lys Asn Met Val Trp Glu Ala
            435                 440                 445 ctt aaa act ctc ggg tga                                             1362
Leu Lys Thr Leu Gly
        450
```

<210> SEQ ID NO 53
<211> LENGTH: 453
<212> TYPE: PRT
<213> ORGANISM: Primula farinosa

<400> SEQUENCE: 53

Met Ala Asn Lys Ser Pro Pro Asn Pro Lys Thr Gly Tyr Ile Thr Ser
1               5                   10                  15

Ser Asp Leu Lys Ser His Asn Lys Ala Gly Asp Leu Trp Ile Ser Ile
            20                  25                  30

His Gly Gln Val Tyr Asp Val Ser Ser Trp Ala Ala Leu His Pro Gly
        35                  40                  45

Gly Thr Ala Pro Leu Met Ala Leu Ala Gly His Asp Val Thr Asp Ala
    50                  55                  60

Phe Leu Ala Tyr His Pro Pro Ser Thr Ala Arg Leu Leu Pro Pro Leu
65                  70                  75                  80

Ser Thr Asn Leu Leu Leu Gln Asn His Ser Val Ser Pro Thr Ser Ser
                85                  90                  95

Asp Tyr Arg Lys Leu Leu Asp Asn Phe His Lys His Gly Leu Phe Arg
            100                 105                 110

Ala Arg Gly His Thr Ala Tyr Ala Thr Phe Val Phe Met Ile Ala Met
        115                 120                 125

Phe Leu Met Ser Val Thr Gly Val Leu Cys Ser Asp Ser Ala Trp Val
130                 135                 140

His Leu Ala Ser Gly Gly Ala Met Gly Phe Ala Trp Ile Gln Cys Gly
145                 150                 155                 160

Trp Ile Gly His Asp Ser Gly His Tyr Arg Ile Met Ser Asp Arg Lys
                165                 170                 175

Trp Asn Trp Phe Ala Gln Ile Leu Ser Thr Asn Cys Leu Gln Gly Ile
            180                 185                 190

Ser Ile Gly Trp Trp Lys Trp Asn His Asn Ala His His Ile Ala Cys
        195                 200                 205

Asn Ser Leu Asp Tyr Asp Pro Asp Leu Gln Tyr Ile Pro Leu Leu Val
    210                 215                 220

Val Ser Pro Lys Phe Phe Asn Ser Leu Thr Ser Arg Phe Tyr Asp Lys
225                 230                 235                 240

Lys Leu Asn Phe Asp Gly Val Ser Arg Phe Leu Val Cys Tyr Gln His
                245                 250                 255

Trp Thr Phe Tyr Pro Val Met Cys Val Ala Arg Leu Asn Met Leu Ala
            260                 265                 270

Gln Ser Phe Ile Thr Leu Phe Ser Ser Arg Glu Val Cys His Arg Ala
        275                 280                 285

Gln Glu Val Phe Gly Leu Ala Val Phe Trp Val Trp Phe Pro Leu Leu
    290                 295                 300

Leu Ser Cys Leu Pro Asn Trp Gly Glu Arg Ile Met Phe Leu Leu Ala
305                 310                 315                 320

Ser Tyr Ser Val Thr Gly Ile Gln His Val Gln Phe Ser Leu Asn His
                325                 330                 335

Phe Ser Ser Asp Val Tyr Val Gly Pro Pro Val Gly Asn Asp Trp Phe
            340                 345                 350

Lys Lys Gln Thr Ala Gly Thr Leu Asn Ile Ser Cys Pro Ala Trp Met
        355                 360                 365

Asp Trp Phe His Gly Gly Leu Gln Phe Gln Val Glu His His Leu Phe
    370                 375                 380

```
Pro Arg Met Pro Arg Gly Gln Phe Arg Lys Ile Ser Pro Phe Val Arg
385                 390                 395                 400

Asp Leu Cys Lys Lys His Asn Leu Pro Tyr Asn Ile Ala Ser Phe Thr
            405                 410                 415

Lys Ala Asn Val Phe Thr Leu Lys Thr Leu Arg Asn Thr Ala Ile Glu
            420                 425                 430

Ala Arg Asp Leu Ser Asn Pro Leu Pro Lys Asn Met Val Trp Glu Ala
            435                 440                 445

Leu Lys Thr Leu Gly
    450

<210> SEQ ID NO 54
<211> LENGTH: 1362
<212> TYPE: DNA
<213> ORGANISM: Primula vialii
<220> FEATURE:
<221> NAME/KEY: CDS
<222> LOCATION: (1)..(1362)
<223> OTHER INFORMATION: delta-6-Desaturase

<400> SEQUENCE: 54 atg gct aac aaa tct cca cca aac ccc aaa aca ggt tac att acc agc      48
Met Ala Asn Lys Ser Pro Pro Asn Pro Lys Thr Gly Tyr Ile Thr Ser
1               5                   10                  15 tca gac ctg aaa ggg cac aac aaa gca gga gac cta tgg ata tca atc      96
Ser Asp Leu Lys Gly His Asn Lys Ala Gly Asp Leu Trp Ile Ser Ile
                20                  25                  30 cac ggg gag gta tac gac gtg tcc tcg tgg gcc ggc ctt cac ccg ggg     144
His Gly Glu Val Tyr Asp Val Ser Ser Trp Ala Gly Leu His Pro Gly
            35                  40                  45 ggc agt gcc ccc ctc atg gcc ctc gca gga cac gac gta acc gac gct     192
Gly Ser Ala Pro Leu Met Ala Leu Ala Gly His Asp Val Thr Asp Ala
    50                  55                  60 ttt cta gcg tat cat cct cct tct acc gcc cgc ctc ctc cct ccc ctc     240
Phe Leu Ala Tyr His Pro Pro Ser Thr Ala Arg Leu Leu Pro Pro Leu
65                  70                  75                  80 tcc acc aac ctc ctc ctt caa aac cac tcc gtc tcc ccc acc tcc tct     288
Ser Thr Asn Leu Leu Leu Gln Asn His Ser Val Ser Pro Thr Ser Ser
                85                  90                  95 gac tac cgc aaa ctc ctc cac aac ttc cat aaa att ggt atg ttc cgc     336
Asp Tyr Arg Lys Leu Leu His Asn Phe His Lys Ile Gly Met Phe Arg
            100                 105                 110 gcc agg ggc cac act gct tac gcc acc ttc gtc atc atg ata gtg atg     384
Ala Arg Gly His Thr Ala Tyr Ala Thr Phe Val Ile Met Ile Val Met
    115                 120                 125 ttt cta acg agc gtg acc gga gtc ctt tgc agc gac agt gcg tgg gtc     432
Phe Leu Thr Ser Val Thr Gly Val Leu Cys Ser Asp Ser Ala Trp Val
130                 135                 140 cat ctg gct agc ggc gca gca atg ggg ttc gcc tgg atc cag tgc gga     480
His Leu Ala Ser Gly Ala Ala Met Gly Phe Ala Trp Ile Gln Cys Gly
145                 150                 155                 160 tgg ata ggt cac gac tct ggg cat tac cgg att atg tct gac agg aaa     528
Trp Ile Gly His Asp Ser Gly His Tyr Arg Ile Met Ser Asp Arg Lys
                165                 170                 175 tgg aac tgg ttc gcg cag gtc ctg agc aca aac tgc ctc cag ggg atc     576
Trp Asn Trp Phe Ala Gln Val Leu Ser Thr Asn Cys Leu Gln Gly Ile
            180                 185                 190 agt atc ggg tgg tgg aag tgg aac cat aac gcc cac cac att gct tgc     624
Ser Ile Gly Trp Trp Lys Trp Asn His Asn Ala His His Ile Ala Cys
    195                 200                 205
```

-continued

```
aat agc ctg gac tac gac ccc gac ctc cag tat atc cct ttg ctc gtg      672
Asn Ser Leu Asp Tyr Asp Pro Asp Leu Gln Tyr Ile Pro Leu Leu Val
210                 215                 220 gtc tcc ccc aag ttc ttc aac tcc ctt act tct cgt ttc tac gac aag      720
Val Ser Pro Lys Phe Phe Asn Ser Leu Thr Ser Arg Phe Tyr Asp Lys
225                 230                 235                 240 aag ctg aat ttc gac ggc gtg tca agg ttt ctg gtt tgc tac cag cac      768
Lys Leu Asn Phe Asp Gly Val Ser Arg Phe Leu Val Cys Tyr Gln His
                245                 250                 255 tgg acg ttt tat cca gtc atg tgt gtc gct agg cta aac atg atc gca      816
Trp Thr Phe Tyr Pro Val Met Cys Val Ala Arg Leu Asn Met Ile Ala
            260                 265                 270 cag tcg ttt ata acg ctt ttc tcg agc agg gag gtg ggt cat agg gcg      864
Gln Ser Phe Ile Thr Leu Phe Ser Ser Arg Glu Val Gly His Arg Ala
        275                 280                 285 caa gag att ttc gga ctt gct gtg ttt tgg gtt tgg ttt ccg ctc ctg      912
Gln Glu Ile Phe Gly Leu Ala Val Phe Trp Val Trp Phe Pro Leu Leu
    290                 295                 300 ctc tct tgc tta cct aat tgg agc gag agg att atg ttt ctg cta gcg      960
Leu Ser Cys Leu Pro Asn Trp Ser Glu Arg Ile Met Phe Leu Leu Ala
305                 310                 315                 320 agc tat tcc gtt acg ggg ata cag cac gtg cag ttc agc ttg aac cat     1008
Ser Tyr Ser Val Thr Gly Ile Gln His Val Gln Phe Ser Leu Asn His
                325                 330                 335 ttt tct tcg gac gtc tac gtg ggc ccg cca gta gct aac gac tgg ttc     1056
Phe Ser Ser Asp Val Tyr Val Gly Pro Pro Val Ala Asn Asp Trp Phe
            340                 345                 350 aag aaa cag act gct ggg aca ctt aac ata tcg tgc ccg gcg tgg atg     1104
Lys Lys Gln Thr Ala Gly Thr Leu Asn Ile Ser Cys Pro Ala Trp Met
        355                 360                 365 gac tgg ttc cat ggc ggg ttg cag ttt cag gtc gag cac cac ttg ttt     1152
Asp Trp Phe His Gly Gly Leu Gln Phe Gln Val Glu His His Leu Phe
    370                 375                 380 ccg cgg atg cct agg ggt cag ttt agg aag att tct cct ttt gtg agg     1200
Pro Arg Met Pro Arg Gly Gln Phe Arg Lys Ile Ser Pro Phe Val Arg
385                 390                 395                 400 gat ttg tgt aag aaa cac aac ttg cct tac aat atc gcg tct ttt act     1248
Asp Leu Cys Lys Lys His Asn Leu Pro Tyr Asn Ile Ala Ser Phe Thr
                405                 410                 415 aaa gca aac gtg ttg acg ctt aag acg ctg aga aat acg gcc att gag     1296
Lys Ala Asn Val Leu Thr Leu Lys Thr Leu Arg Asn Thr Ala Ile Glu
            420                 425                 430 gct cgg gac ctc tct aat ccg acc cca aag aat atg gtg tgg gaa gcc     1344
Ala Arg Asp Leu Ser Asn Pro Thr Pro Lys Asn Met Val Trp Glu Ala
        435                 440                 445 gtc cac aca cac ggc tag                                             1362
Val His Thr His Gly
    450

<210> SEQ ID NO 55
<211> LENGTH: 453
<212> TYPE: PRT
<213> ORGANISM: Primula vialii

<400> SEQUENCE: 55

Met Ala Asn Lys Ser Pro Pro Asn Pro Lys Thr Gly Tyr Ile Thr Ser
1               5                   10                  15

Ser Asp Leu Lys Gly His Asn Lys Ala Gly Asp Leu Trp Ile Ser Ile
            20                  25                  30
```

-continued

```
His Gly Glu Val Tyr Asp Val Ser Ser Trp Ala Gly Leu His Pro Gly
        35                  40                  45
Gly Ser Ala Pro Leu Met Ala Leu Ala Gly His Asp Val Thr Asp Ala
    50                  55                  60
Phe Leu Ala Tyr His Pro Pro Ser Thr Ala Arg Leu Leu Pro Pro Leu
65                  70                  75                  80
Ser Thr Asn Leu Leu Leu Gln Asn His Ser Val Ser Pro Thr Ser Ser
                85                  90                  95
Asp Tyr Arg Lys Leu Leu His Asn Phe His Lys Ile Gly Met Phe Arg
            100                 105                 110
Ala Arg Gly His Thr Ala Tyr Ala Thr Phe Val Ile Met Ile Val Met
            115                 120                 125
Phe Leu Thr Ser Val Thr Gly Val Leu Cys Ser Asp Ser Ala Trp Val
    130                 135                 140
His Leu Ala Ser Gly Ala Ala Met Gly Phe Ala Trp Ile Gln Cys Gly
145                 150                 155                 160
Trp Ile Gly His Asp Ser Gly His Tyr Arg Ile Met Ser Asp Arg Lys
                165                 170                 175
Trp Asn Trp Phe Ala Gln Val Leu Ser Thr Asn Cys Leu Gln Gly Ile
            180                 185                 190
Ser Ile Gly Trp Trp Lys Trp Asn His Asn Ala His His Ile Ala Cys
            195                 200                 205
Asn Ser Leu Asp Tyr Asp Pro Asp Leu Gln Tyr Ile Pro Leu Leu Val
    210                 215                 220
Val Ser Pro Lys Phe Phe Asn Ser Leu Thr Ser Arg Phe Tyr Asp Lys
225                 230                 235                 240
Lys Leu Asn Phe Asp Gly Val Ser Arg Phe Leu Val Cys Tyr Gln His
                245                 250                 255
Trp Thr Phe Tyr Pro Val Met Cys Val Ala Arg Leu Asn Met Ile Ala
            260                 265                 270
Gln Ser Phe Ile Thr Leu Phe Ser Ser Arg Glu Val Gly His Arg Ala
    275                 280                 285
Gln Glu Ile Phe Gly Leu Ala Val Phe Trp Val Trp Phe Pro Leu Leu
    290                 295                 300
Leu Ser Cys Leu Pro Asn Trp Ser Glu Arg Ile Met Phe Leu Leu Ala
305                 310                 315                 320
Ser Tyr Ser Val Thr Gly Ile Gln His Val Gln Phe Ser Leu Asn His
                325                 330                 335
Phe Ser Ser Asp Val Tyr Val Gly Pro Pro Val Ala Asn Asp Trp Phe
            340                 345                 350
Lys Lys Gln Thr Ala Gly Thr Leu Asn Ile Ser Cys Pro Ala Trp Met
            355                 360                 365
Asp Trp Phe His Gly Gly Leu Gln Phe Gln Val Glu His His Leu Phe
    370                 375                 380
Pro Arg Met Pro Arg Gly Gln Phe Arg Lys Ile Ser Pro Phe Val Arg
385                 390                 395                 400
Asp Leu Cys Lys Lys His Asn Leu Pro Tyr Asn Ile Ala Ser Phe Thr
                405                 410                 415
Lys Ala Asn Val Leu Thr Leu Lys Thr Leu Arg Asn Thr Ala Ile Glu
            420                 425                 430
Ala Arg Asp Leu Ser Asn Pro Thr Pro Lys Asn Met Val Trp Glu Ala
            435                 440                 445
Val His Thr His Gly
```

<210> SEQ ID NO 56
<211> LENGTH: 1371
<212> TYPE: DNA
<213> ORGANISM: Ostreococcus tauri
<220> FEATURE:
<221> NAME/KEY: CDS
<222> LOCATION: (1)..(1371)
<223> OTHER INFORMATION: delta-6-Desaturase

<400> SEQUENCE: 56

| | | | | | | | | | | | | | | | | |
|---|---|---|---|---|---|---|---|---|---|---|---|---|---|---|---|---|
| atg | tgc | gtg | gag | acg | gaa | aat | aac | gat | ggg | atc | ccc | acg | gtg | gag | atc | 48 |
| Met | Cys | Val | Glu | Thr | Glu | Asn | Asn | Asp | Gly | Ile | Pro | Thr | Val | Glu | Ile | |
| 1 | | | | 5 | | | | | 10 | | | | | 15 | | |
| gcg | ttc | gac | ggt | gag | cgc | gag | cgg | gcg | gag | gca | aac | gtg | aag | ctg | tcc | 96 |
| Ala | Phe | Asp | Gly | Glu | Arg | Glu | Arg | Ala | Glu | Ala | Asn | Val | Lys | Leu | Ser | |
| | | | 20 | | | | | 25 | | | | | 30 | | | |
| gcg | gag | aag | atg | gag | ccg | gcg | gcg | ctg | gcg | aag | acg | ttc | gcg | agg | cgg | 144 |
| Ala | Glu | Lys | Met | Glu | Pro | Ala | Ala | Leu | Ala | Lys | Thr | Phe | Ala | Arg | Arg | |
| | | 35 | | | | | 40 | | | | | 45 | | | | |
| tac | gtc | gtg | atc | gag | ggg | gtg | gag | tac | gat | gtg | acg | gat | ttt | aag | cac | 192 |
| Tyr | Val | Val | Ile | Glu | Gly | Val | Glu | Tyr | Asp | Val | Thr | Asp | Phe | Lys | His | |
| | 50 | | | | | 55 | | | | | 60 | | | | | |
| ccg | gga | gga | acg | gtt | att | ttc | tat | gcg | ttg | tca | aac | acc | ggg | gcg | gac | 240 |
| Pro | Gly | Gly | Thr | Val | Ile | Phe | Tyr | Ala | Leu | Ser | Asn | Thr | Gly | Ala | Asp | |
| 65 | | | | | 70 | | | | | 75 | | | | | 80 | |
| gcg | acg | gaa | gcg | ttc | aag | gag | ttt | cat | cat | cgg | tcg | aga | aag | gcg | agg | 288 |
| Ala | Thr | Glu | Ala | Phe | Lys | Glu | Phe | His | His | Arg | Ser | Arg | Lys | Ala | Arg | |
| | | | | 85 | | | | | 90 | | | | | 95 | | |
| aaa | gcc | ttg | gcg | gcg | ctc | ccg | tct | cga | ccg | gcc | aag | acg | gcc | aag | gtg | 336 |
| Lys | Ala | Leu | Ala | Ala | Leu | Pro | Ser | Arg | Pro | Ala | Lys | Thr | Ala | Lys | Val | |
| | | | 100 | | | | | 105 | | | | | 110 | | | |
| gac | gac | gcg | gag | atg | ctc | caa | gat | ttc | gcc | aag | tgg | cgg | aaa | gaa | ttg | 384 |
| Asp | Asp | Ala | Glu | Met | Leu | Gln | Asp | Phe | Ala | Lys | Trp | Arg | Lys | Glu | Leu | |
| | | 115 | | | | | 120 | | | | | 125 | | | | |
| gag | aga | gat | gga | ttc | ttc | aag | ccc | tct | ccg | gcg | cac | gtg | gcg | tat | cgc | 432 |
| Glu | Arg | Asp | Gly | Phe | Phe | Lys | Pro | Ser | Pro | Ala | His | Val | Ala | Tyr | Arg | |
| | 130 | | | | | 135 | | | | | 140 | | | | | |
| ttc | gcc | gag | ctc | gcg | gcg | atg | tac | gct | ctc | ggg | acg | tac | ctg | atg | tac | 480 |
| Phe | Ala | Glu | Leu | Ala | Ala | Met | Tyr | Ala | Leu | Gly | Thr | Tyr | Leu | Met | Tyr | |
| 145 | | | | | 150 | | | | | 155 | | | | | 160 | |
| gct | cga | tac | gtc | gtc | tcc | tcg | gtg | ctc | gtg | tac | gct | tgc | ttt | ttc | ggc | 528 |
| Ala | Arg | Tyr | Val | Val | Ser | Ser | Val | Leu | Val | Tyr | Ala | Cys | Phe | Phe | Gly | |
| | | | | 165 | | | | | 170 | | | | | 175 | | |
| gcc | cga | tgc | ggt | tgg | gtg | cag | cac | gag | ggc | gga | cac | agc | tcg | ctg | acg | 576 |
| Ala | Arg | Cys | Gly | Trp | Val | Gln | His | Glu | Gly | Gly | His | Ser | Ser | Leu | Thr | |
| | | | 180 | | | | | 185 | | | | | 190 | | | |
| ggc | aac | att | tgg | tgg | gac | aag | cgc | atc | cag | gcc | ttc | aca | gcc | ggg | ttc | 624 |
| Gly | Asn | Ile | Trp | Trp | Asp | Lys | Arg | Ile | Gln | Ala | Phe | Thr | Ala | Gly | Phe | |
| | | 195 | | | | | 200 | | | | | 205 | | | | |
| ggt | ctc | gcc | ggt | agc | ggc | gac | atg | tgg | aac | tcg | atg | cac | aac | aag | cat | 672 |
| Gly | Leu | Ala | Gly | Ser | Gly | Asp | Met | Trp | Asn | Ser | Met | His | Asn | Lys | His | |
| | 210 | | | | | 215 | | | | | 220 | | | | | |
| cac | gcg | acg | cct | caa | aag | gtt | cgt | cac | gac | atg | gat | ctg | gac | acc | acc | 720 |
| His | Ala | Thr | Pro | Gln | Lys | Val | Arg | His | Asp | Met | Asp | Leu | Asp | Thr | Thr | |
| 225 | | | | | 230 | | | | | 235 | | | | | 240 | |
| ccc | gcg | gtg | gcg | ttc | ttc | aac | acc | gcg | gtg | gaa | gac | aat | cgt | ccc | cgt | 768 |
| Pro | Ala | Val | Ala | Phe | Phe | Asn | Thr | Ala | Val | Glu | Asp | Asn | Arg | Pro | Arg | |
| | | | | 245 | | | | | 250 | | | | | 255 | | |
| ggc | ttt | agc | aag | tac | tgg | ttg | cgc | ctt | cag | gcg | tgg | acc | ttc | atc | ccc | 816 |

```
Gly Phe Ser Lys Tyr Trp Leu Arg Leu Gln Ala Trp Thr Phe Ile Pro
                260                 265                 270 gtg acg tcc ggc ttg gtg ctc ctt ttc tgg atg ttt ttc ctc cac ccc       864
Val Thr Ser Gly Leu Val Leu Leu Phe Trp Met Phe Phe Leu His Pro
            275                 280                 285 tcc aag gct ttg aag ggt ggc aag tac gaa gag ttg gtg tgg atg ctc       912
Ser Lys Ala Leu Lys Gly Gly Lys Tyr Glu Glu Leu Val Trp Met Leu
        290                 295                 300 gcc gcg cac gtc atc cgc acg tgg acg atc aag gcg gtg acc gga ttc       960
Ala Ala His Val Ile Arg Thr Trp Thr Ile Lys Ala Val Thr Gly Phe
305                 310                 315                 320 acc gcg atg cag tcc tac ggc tta ttt ttg gcg acg agc tgg gtg agc      1008
Thr Ala Met Gln Ser Tyr Gly Leu Phe Leu Ala Thr Ser Trp Val Ser
                325                 330                 335 ggc tgc tat ctg ttt gca cac ttc tcc acg tcg cac acg cac ctg gat      1056
Gly Cys Tyr Leu Phe Ala His Phe Ser Thr Ser His Thr His Leu Asp
            340                 345                 350 gtg gtg ccc gcg gac gag cat ctc tcc tgg gtt cga tac gcc gtc gat      1104
Val Val Pro Ala Asp Glu His Leu Ser Trp Val Arg Tyr Ala Val Asp
        355                 360                 365 cac acg atc gac atc gat ccg agt caa ggt tgg gtg aac tgg ttg atg      1152
His Thr Ile Asp Ile Asp Pro Ser Gln Gly Trp Val Asn Trp Leu Met
370                 375                 380 ggc tac ctc aac tgc caa gtc atc cac cac ctc ttt ccg agc atg ccg      1200
Gly Tyr Leu Asn Cys Gln Val Ile His His Leu Phe Pro Ser Met Pro
385                 390                 395                 400 cag ttc cgc cag ccc gag gta tct cgc cgc ttc gtc gcc ttt gcg aaa      1248
Gln Phe Arg Gln Pro Glu Val Ser Arg Arg Phe Val Ala Phe Ala Lys
                405                 410                 415 aag tgg aac ctc aac tac aag gtc atg acc tac gcc ggt gcg tgg aag      1296
Lys Trp Asn Leu Asn Tyr Lys Val Met Thr Tyr Ala Gly Ala Trp Lys
            420                 425                 430 gca acg ctc gga aac ctc gac aac gtg ggt aag cac tac tac gtg cac      1344
Ala Thr Leu Gly Asn Leu Asp Asn Val Gly Lys His Tyr Tyr Val His
        435                 440                 445 ggc caa cac tcc gga aag acg gcg taa                                  1371
Gly Gln His Ser Gly Lys Thr Ala
    450                 455

<210> SEQ ID NO 57
<211> LENGTH: 456
<212> TYPE: PRT
<213> ORGANISM: Ostreococcus tauri

<400> SEQUENCE: 57

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110
```

```
Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
    275                 280                 285

Ser Lys Ala Leu Lys Gly Gly Lys Tyr Glu Glu Leu Val Trp Met Leu
290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
    355                 360                 365

His Thr Ile Asp Ile Asp Pro Ser Gln Gly Trp Val Asn Trp Leu Met
370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His
    435                 440                 445

Gly Gln His Ser Gly Lys Thr Ala
    450                 455

<210> SEQ ID NO 58
<211> LENGTH: 1455
<212> TYPE: DNA
<213> ORGANISM: Thalassiosira pseudonana
<220> FEATURE:
<221> NAME/KEY: CDS
<222> LOCATION: (1)..(1455)
<223> OTHER INFORMATION: delta-6-Desaturase

<400> SEQUENCE: 58
```

-continued

| | |
|---|---|
| atg gga aaa gga gga gac gca gcc gca gct acc aag cgt agt gga gca<br>Met Gly Lys Gly Gly Asp Ala Ala Ala Thr Lys Arg Ser Gly Ala<br>1                          5                        10                      15 | 48 |
| ttg aaa ttg gcg gag aag ccg cag aag tac act tgg cag gag gtg aag<br>Leu Lys Leu Ala Glu Lys Pro Gln Lys Tyr Thr Trp Gln Glu Val Lys<br>               20                      25                      30 | 96 |
| aag cac atc acc ccc gac gat gcc tgg gta gtc cac caa aac aaa gtc<br>Lys His Ile Thr Pro Asp Asp Ala Trp Val Val His Gln Asn Lys Val<br>       35                      40                      45 | 144 |
| tac gac gtc tcc aac tgg tac gac cac ccc ggt gga gcc gtg gtg ttc<br>Tyr Asp Val Ser Asn Trp Tyr Asp His Pro Gly Gly Ala Val Val Phe<br>50                          55                      60 | 192 |
| acc cac gcc gga gac gac atg acg gac atc ttc gcc gcc ttc cac gcc<br>Thr His Ala Gly Asp Asp Met Thr Asp Ile Phe Ala Ala Phe His Ala<br>65                          70                      75                      80 | 240 |
| caa ggc tct cag gcc atg atg aag aag ttt tac att gga gat ttg att<br>Gln Gly Ser Gln Ala Met Met Lys Lys Phe Tyr Ile Gly Asp Leu Ile<br>                      85                      90                      95 | 288 |
| ccg gag agt gtg gag cat aag gat caa aga cag ttg gat ttc gag aag<br>Pro Glu Ser Val Glu His Lys Asp Gln Arg Gln Leu Asp Phe Glu Lys<br>                     100                    105                    110 | 336 |
| gga tat cgt gat tta cgg gcc aag ctt gtc atg atg ggg atg ttc aag<br>Gly Tyr Arg Asp Leu Arg Ala Lys Leu Val Met Met Gly Met Phe Lys<br>           115                    120                    125 | 384 |
| tcg agt aag atg tat tat gca tac aag tgc tcg ttc aat atg tgc atg<br>Ser Ser Lys Met Tyr Tyr Ala Tyr Lys Cys Ser Phe Asn Met Cys Met<br>      130                    135                    140 | 432 |
| tgg ttg gtg gcg gtg gcc atg gtg tac tac tcg gac agt ttg gca atg<br>Trp Leu Val Ala Val Ala Met Val Tyr Tyr Ser Asp Ser Leu Ala Met<br>145                        150                    155                    160 | 480 |
| cac att gga tcg gct ctc ttg ttg gga ttg ttc tgg cag cag tgt gga<br>His Ile Gly Ser Ala Leu Leu Leu Gly Leu Phe Trp Gln Gln Cys Gly<br>                     165                    170                    175 | 528 |
| tgg ctt gcg cac gac ttt ctt cac cac caa gtc ttt aag caa cga aag<br>Trp Leu Ala His Asp Phe Leu His His Gln Val Phe Lys Gln Arg Lys<br>           180                    185                    190 | 576 |
| tac gga gat ctc gtt ggc atc ttt tgg gga gat ctc atg cag ggg ttc<br>Tyr Gly Asp Leu Val Gly Ile Phe Trp Gly Asp Leu Met Gln Gly Phe<br>               195                    200                    205 | 624 |
| tcg atg cag tgg tgg aag aac aag cac aat ggc cac cat gct gtt ccc<br>Ser Met Gln Trp Trp Lys Asn Lys His Asn Gly His His Ala Val Pro<br>      210                    215                    220 | 672 |
| aac ttg cac aac tct tcc ttg gac agt cag gat ggt gat ccc gat att<br>Asn Leu His Asn Ser Ser Leu Asp Ser Gln Asp Gly Asp Pro Asp Ile<br>225                        230                    235                    240 | 720 |
| gat acc atg cca ctc ctt gct tgg agt ctc aag cag gct cag agt ttc<br>Asp Thr Met Pro Leu Leu Ala Trp Ser Leu Lys Gln Ala Gln Ser Phe<br>                   245                    250                    255 | 768 |
| aga gag atc aat aag gga aag gac agt acc ttc gtc aag tac gct atc<br>Arg Glu Ile Asn Lys Gly Lys Asp Ser Thr Phe Val Lys Tyr Ala Ile<br>           260                    265                    270 | 816 |
| aaa ttc cag gca ttc aca tac ttc ccc atc ctc ctc ttg gct cgc atc<br>Lys Phe Gln Ala Phe Thr Tyr Phe Pro Ile Leu Leu Leu Ala Arg Ile<br>           275                    280                    285 | 864 |
| tct tgg ttg aat gaa tcc ttc aaa act gca ttc gga ctc gga gct gcc<br>Ser Trp Leu Asn Glu Ser Phe Lys Thr Ala Phe Gly Leu Gly Ala Ala<br>      290                    295                    300 | 912 |
| tcg gag aat gcc aag ttg gag ttg gag aag cgt gga ctt cag tac cca<br>Ser Glu Asn Ala Lys Leu Glu Leu Glu Lys Arg Gly Leu Gln Tyr Pro<br>305                        310                    315                    320 | 960 |

-continued

```
ctt ttg gag aag ctt gga atc acc ctt cat tac act tgg atg ttc gtc      1008
Leu Leu Glu Lys Leu Gly Ile Thr Leu His Tyr Thr Trp Met Phe Val
            325                 330                 335 ctc tct tcc gga ttt gga agg tgg tct ctt cca tat tcc atc atg tat      1056
Leu Ser Ser Gly Phe Gly Arg Trp Ser Leu Pro Tyr Ser Ile Met Tyr
        340                 345                 350 ttc ttc act gcc aca tgc tcc tcg gga ctt ttc ctc gca ttg gtc ttt      1104
Phe Phe Thr Ala Thr Cys Ser Ser Gly Leu Phe Leu Ala Leu Val Phe
    355                 360                 365 gga ttg gga cac aac ggt atg tca gtg tac gat gcc acc acc cga cct      1152
Gly Leu Gly His Asn Gly Met Ser Val Tyr Asp Ala Thr Thr Arg Pro
370                 375                 380 gac ttc tgg caa ctc caa gtc acc act aca cgt aac atc att ggt gga      1200
Asp Phe Trp Gln Leu Gln Val Thr Thr Thr Arg Asn Ile Ile Gly Gly
385                 390                 395                 400 cac ggc att ccc caa ttc ttt gtg gat tgg ttc tgc ggt gga ttg caa      1248
His Gly Ile Pro Gln Phe Phe Val Asp Trp Phe Cys Gly Gly Leu Gln
            405                 410                 415 tac caa gtg gat cac cac ctc ttc ccc atg atg cct aga aac aat atc      1296
Tyr Gln Val Asp His His Leu Phe Pro Met Met Pro Arg Asn Asn Ile
        420                 425                 430 gcg aaa tgc cac aag ctt gtg gag tca ttc tgt aag gag tgg ggt gtg      1344
Ala Lys Cys His Lys Leu Val Glu Ser Phe Cys Lys Glu Trp Gly Val
    435                 440                 445 aag tac cat gag gcc gat atg tgg gat ggt acc gtg gaa gtg ttg caa      1392
Lys Tyr His Glu Ala Asp Met Trp Asp Gly Thr Val Glu Val Leu Gln
450                 455                 460 cat ctc tcc aag gtg tcg gat gat ttc ctt gtg gag atg gtg aag gat      1440
His Leu Ser Lys Val Ser Asp Asp Phe Leu Val Glu Met Val Lys Asp
465                 470                 475                 480 ttc cct gcc atg taa                                                  1455
Phe Pro Ala Met <210> SEQ ID NO 59
<211> LENGTH: 484
<212> TYPE: PRT
<213> ORGANISM: Thalassiosira pseudonana

<400> SEQUENCE: 59

Met Gly Lys Gly Gly Asp Ala Ala Ala Thr Lys Arg Ser Gly Ala
1               5                   10                  15

Leu Lys Leu Ala Glu Lys Pro Gln Lys Tyr Thr Trp Gln Glu Val Lys
            20                  25                  30

Lys His Ile Thr Pro Asp Asp Ala Trp Val Val His Gln Asn Lys Val
        35                  40                  45

Tyr Asp Val Ser Asn Trp Tyr Asp His Pro Gly Gly Ala Val Val Phe
    50                  55                  60

Thr His Ala Gly Asp Asp Met Thr Asp Ile Phe Ala Ala Phe His Ala
65                  70                  75                  80

Gln Gly Ser Gln Ala Met Met Lys Lys Phe Tyr Ile Gly Asp Leu Ile
                85                  90                  95

Pro Glu Ser Val Glu His Lys Asp Gln Arg Gln Leu Asp Phe Glu Lys
            100                 105                 110

Gly Tyr Arg Asp Leu Arg Ala Lys Leu Val Met Met Gly Met Phe Lys
        115                 120                 125

Ser Ser Lys Met Tyr Tyr Ala Tyr Lys Cys Ser Phe Asn Met Cys Met
    130                 135                 140
```

```
Trp Leu Val Ala Val Ala Met Val Tyr Tyr Ser Asp Ser Leu Ala Met
145                 150                 155                 160

His Ile Gly Ser Ala Leu Leu Gly Leu Phe Trp Gln Gln Cys Gly
            165                 170                 175

Trp Leu Ala His Asp Phe Leu His His Gln Val Phe Lys Gln Arg Lys
            180                 185                 190

Tyr Gly Asp Leu Val Gly Ile Phe Trp Gly Asp Leu Met Gln Gly Phe
            195                 200                 205

Ser Met Gln Trp Trp Lys Asn Lys His Asn Gly His His Ala Val Pro
        210                 215                 220

Asn Leu His Asn Ser Ser Leu Asp Ser Gln Asp Gly Asp Pro Asp Ile
225                 230                 235                 240

Asp Thr Met Pro Leu Leu Ala Trp Ser Leu Lys Gln Ala Gln Ser Phe
                245                 250                 255

Arg Glu Ile Asn Lys Gly Lys Asp Ser Thr Phe Val Lys Tyr Ala Ile
            260                 265                 270

Lys Phe Gln Ala Phe Thr Tyr Phe Pro Ile Leu Leu Leu Ala Arg Ile
        275                 280                 285

Ser Trp Leu Asn Glu Ser Phe Lys Thr Ala Phe Gly Leu Gly Ala Ala
        290                 295                 300

Ser Glu Asn Ala Lys Leu Glu Leu Glu Lys Arg Gly Leu Gln Tyr Pro
305                 310                 315                 320

Leu Leu Glu Lys Leu Gly Ile Thr Leu His Tyr Thr Trp Met Phe Val
                325                 330                 335

Leu Ser Ser Gly Phe Gly Arg Trp Ser Leu Pro Tyr Ser Ile Met Tyr
            340                 345                 350

Phe Phe Thr Ala Thr Cys Ser Ser Gly Leu Phe Leu Ala Leu Val Phe
        355                 360                 365

Gly Leu Gly His Asn Gly Met Ser Val Tyr Asp Ala Thr Thr Arg Pro
    370                 375                 380

Asp Phe Trp Gln Leu Gln Val Thr Thr Thr Arg Asn Ile Ile Gly Gly
385                 390                 395                 400

His Gly Ile Pro Gln Phe Phe Val Asp Trp Phe Cys Gly Gly Leu Gln
                405                 410                 415

Tyr Gln Val Asp His His Leu Phe Pro Met Met Pro Arg Asn Asn Ile
            420                 425                 430

Ala Lys Cys His Lys Leu Val Glu Ser Phe Cys Lys Glu Trp Gly Val
        435                 440                 445

Lys Tyr His Glu Ala Asp Met Trp Asp Gly Thr Val Glu Val Leu Gln
    450                 455                 460

His Leu Ser Lys Val Ser Asp Asp Phe Leu Val Glu Met Val Lys Asp
465                 470                 475                 480

Phe Pro Ala Met
```

<210> SEQ ID NO 60
<211> LENGTH: 873
<212> TYPE: DNA
<213> ORGANISM: Physcomitrella patens
<220> FEATURE:
<221> NAME/KEY: CDS
<222> LOCATION: (1)..(873)
<223> OTHER INFORMATION: delta-6-Elongase

<400> SEQUENCE: 60

```
atg gag gtc gtg gag aga ttc tac ggt gag ttg gat ggg aag gtc tcg      48
Met Glu Val Val Glu Arg Phe Tyr Gly Glu Leu Asp Gly Lys Val Ser
```

```
1               5                   10                  15
cag ggc gtg aat gca ttg ctg ggt agt ttt ggg gtg gag ttg acg gat      96
Gln Gly Val Asn Ala Leu Leu Gly Ser Phe Gly Val Glu Leu Thr Asp
            20                  25                  30 acg ccc act acc aaa ggc ttg ccc ctc gtt gac agt ccc aca ccc atc     144
Thr Pro Thr Thr Lys Gly Leu Pro Leu Val Asp Ser Pro Thr Pro Ile
        35                  40                  45 gtc ctc ggt gtt tct gta tac ttg act att gtc att gga ggg ctt ttg     192
Val Leu Gly Val Ser Val Tyr Leu Thr Ile Val Ile Gly Gly Leu Leu
    50                  55                  60 tgg ata aag gcc agg gat ctg aaa ccg cgc gcc tcg gag cca ttt ttg     240
Trp Ile Lys Ala Arg Asp Leu Lys Pro Arg Ala Ser Glu Pro Phe Leu
65                  70                  75                  80 ctc caa gct ttg gtg ctt gtg cac aac ctg ttc tgt ttt gcg ctc agt     288
Leu Gln Ala Leu Val Leu Val His Asn Leu Phe Cys Phe Ala Leu Ser
                85                  90                  95 ctg tat atg tgc gtg ggc atc gct tat cag gct att acc tgg cgg tac     336
Leu Tyr Met Cys Val Gly Ile Ala Tyr Gln Ala Ile Thr Trp Arg Tyr
            100                 105                 110 tct ctc tgg ggc aat gca tac aat cct aaa cat aaa gag atg gcg att     384
Ser Leu Trp Gly Asn Ala Tyr Asn Pro Lys His Lys Glu Met Ala Ile
        115                 120                 125 ctg gta tac ttg ttc tac atg tct aag tac gtg gaa ttc atg gat acc     432
Leu Val Tyr Leu Phe Tyr Met Ser Lys Tyr Val Glu Phe Met Asp Thr
    130                 135                 140 gtt atc atg ata ctg aag cgc agc acc agg caa ata agc ttc ctc cac     480
Val Ile Met Ile Leu Lys Arg Ser Thr Arg Gln Ile Ser Phe Leu His
145                 150                 155                 160 gtt tat cat cat tct tca att tcc ctc att tgg tgg gct att gct cat     528
Val Tyr His His Ser Ser Ile Ser Leu Ile Trp Trp Ala Ile Ala His
                165                 170                 175 cac gct cct ggc ggt gaa gca tat tgg tct gcg gct ctg aac tca gga     576
His Ala Pro Gly Gly Glu Ala Tyr Trp Ser Ala Ala Leu Asn Ser Gly
            180                 185                 190 gtg cat gtt ctc atg tat gcg tat tac ttc ttg gct gcc tgc ctt cga     624
Val His Val Leu Met Tyr Ala Tyr Tyr Phe Leu Ala Ala Cys Leu Arg
        195                 200                 205 agt agc cca aag tta aaa aat aag tac ctt ttt tgg ggc agg tac ttg     672
Ser Ser Pro Lys Leu Lys Asn Lys Tyr Leu Phe Trp Gly Arg Tyr Leu
    210                 215                 220 aca caa ttc caa atg ttc cag ttt atg ctg aac tta gtg cag gct tac     720
Thr Gln Phe Gln Met Phe Gln Phe Met Leu Asn Leu Val Gln Ala Tyr
225                 230                 235                 240 tac gac atg aaa acg aat gcg cca tat cca caa tgg ctg atc aag att     768
Tyr Asp Met Lys Thr Asn Ala Pro Tyr Pro Gln Trp Leu Ile Lys Ile
                245                 250                 255 ttg ttc tac tac atg atc tcg ttg ctg ttt ctt ttc ggc aat ttt tac     816
Leu Phe Tyr Tyr Met Ile Ser Leu Leu Phe Leu Phe Gly Asn Phe Tyr
            260                 265                 270 gta caa aaa tac atc aaa ccc tct gac gga aag caa aag gga gct aaa     864
Val Gln Lys Tyr Ile Lys Pro Ser Asp Gly Lys Gln Lys Gly Ala Lys
        275                 280                 285 act gag tga                                                         873
Thr Glu
    290

<210> SEQ ID NO 61
<211> LENGTH: 290
<212> TYPE: PRT
<213> ORGANISM: Physcomitrella patens
```

<400> SEQUENCE: 61

Met Glu Val Val Glu Arg Phe Tyr Gly Glu Leu Asp Gly Lys Val Ser
1               5                   10                  15
Gln Gly Val Asn Ala Leu Leu Gly Ser Phe Gly Val Glu Leu Thr Asp
            20                  25                  30
Thr Pro Thr Thr Lys Gly Leu Pro Leu Val Asp Ser Pro Thr Pro Ile
        35                  40                  45
Val Leu Gly Val Ser Val Tyr Leu Thr Ile Val Ile Gly Gly Leu Leu
    50                  55                  60
Trp Ile Lys Ala Arg Asp Leu Lys Pro Arg Ala Ser Glu Pro Phe Leu
65                  70                  75                  80
Leu Gln Ala Leu Val Leu Val His Asn Leu Phe Cys Phe Ala Leu Ser
                85                  90                  95
Leu Tyr Met Cys Val Gly Ile Ala Tyr Gln Ala Ile Thr Trp Arg Tyr
            100                 105                 110
Ser Leu Trp Gly Asn Ala Tyr Asn Pro Lys His Lys Glu Met Ala Ile
        115                 120                 125
Leu Val Tyr Leu Phe Tyr Met Ser Lys Tyr Val Glu Phe Met Asp Thr
    130                 135                 140
Val Ile Met Ile Leu Lys Arg Ser Thr Arg Gln Ile Ser Phe Leu His
145                 150                 155                 160
Val Tyr His His Ser Ser Ile Ser Leu Ile Trp Trp Ala Ile Ala His
                165                 170                 175
His Ala Pro Gly Gly Glu Ala Tyr Trp Ser Ala Ala Leu Asn Ser Gly
            180                 185                 190
Val His Val Leu Met Tyr Ala Tyr Tyr Phe Leu Ala Ala Cys Leu Arg
        195                 200                 205
Ser Ser Pro Lys Leu Lys Asn Lys Tyr Leu Phe Trp Gly Arg Tyr Leu
    210                 215                 220
Thr Gln Phe Gln Met Phe Gln Phe Met Leu Asn Leu Val Gln Ala Tyr
225                 230                 235                 240
Tyr Asp Met Lys Thr Asn Ala Pro Tyr Pro Gln Trp Leu Ile Lys Ile
                245                 250                 255
Leu Phe Tyr Tyr Met Ile Ser Leu Leu Phe Leu Phe Gly Asn Phe Tyr
            260                 265                 270
Val Gln Lys Tyr Ile Lys Pro Ser Asp Gly Lys Gln Lys Gly Ala Lys
        275                 280                 285
Thr Glu
    290

<210> SEQ ID NO 62
<211> LENGTH: 1049
<212> TYPE: DNA
<213> ORGANISM: Thraustochytrium
<220> FEATURE:
<221> NAME/KEY: CDS
<222> LOCATION: (43)..(858)
<223> OTHER INFORMATION: delta-6-Elongase

<400> SEQUENCE: 62
gaattcggca cgagagcgcg cggagcggag acctcggccg cg atg atg gag ccg       54
                                            Met Met Glu Pro
                                             1 ctc gac agg tac agg gcg ctg gcg gag ctc gcc gcg agg tac gcc agc     102
Leu Asp Arg Tyr Arg Ala Leu Ala Glu Leu Ala Ala Arg Tyr Ala Ser
 5              10                  15                  20

```
tcg gcg gcc ttc aag tgg caa gtc acg tac gac gcc aag gac agc ttc      150
Ser Ala Ala Phe Lys Trp Gln Val Thr Tyr Asp Ala Lys Asp Ser Phe
             25                  30                  35 gtc ggg ccc ctg gga atc cgg gag ccg ctc ggg ctg ctg gtg ggc tcc      198
Val Gly Pro Leu Gly Ile Arg Glu Pro Leu Gly Leu Leu Val Gly Ser
         40                  45                  50 gtg gtc ctc tac ctg agc ctg ctg gcc gtg gtc tac gcg ctg cgg aac      246
Val Val Leu Tyr Leu Ser Leu Leu Ala Val Val Tyr Ala Leu Arg Asn
             55                  60                  65 tac ctt ggc ggc ctc atg gcg ctc cgc agc gtg cat aac ctc ggg ctc      294
Tyr Leu Gly Gly Leu Met Ala Leu Arg Ser Val His Asn Leu Gly Leu
 70                  75                  80 tgc ctc ttc tcg ggc gcc gtg tgg atc tac acg agc tac ctc atg atc      342
Cys Leu Phe Ser Gly Ala Val Trp Ile Tyr Thr Ser Tyr Leu Met Ile
 85                  90                  95                 100 cag gat ggg cac ttt cgc agc ctc gag gcg gca acg tgc gag ccg ctc      390
Gln Asp Gly His Phe Arg Ser Leu Glu Ala Ala Thr Cys Glu Pro Leu
                105                 110                 115 aag cat ccg cac ttc cag ctc atc agc ttg ctc ttt gcg ctg tcc aag      438
Lys His Pro His Phe Gln Leu Ile Ser Leu Leu Phe Ala Leu Ser Lys
             120                 125                 130 atc tgg gag tgg ttc gac acg gtg ctc ctc atc gtc aag ggc aac aag      486
Ile Trp Glu Trp Phe Asp Thr Val Leu Leu Ile Val Lys Gly Asn Lys
             135                 140                 145 ctc cgc ttc ctg cac gtc ttg cac cac gcc acg acc ttt tgg ctc tac      534
Leu Arg Phe Leu His Val Leu His His Ala Thr Thr Phe Trp Leu Tyr
 150                 155                 160 gcc atc gac cac atc ttt ctc tcg tcc atc aag tac ggc gtc gcg gtc      582
Ala Ile Asp His Ile Phe Leu Ser Ser Ile Lys Tyr Gly Val Ala Val
165                 170                 175                 180 aat gct ttc atc cac acc gtc atg tac gcg cac tac ttc cgc cca ttc      630
Asn Ala Phe Ile His Thr Val Met Tyr Ala His Tyr Phe Arg Pro Phe
                185                 190                 195 ccg aag ggc ttg cgc ccg ctt att acg cag ttg cag atc gtc cag ttc      678
Pro Lys Gly Leu Arg Pro Leu Ile Thr Gln Leu Gln Ile Val Gln Phe
             200                 205                 210 att ttc agc atc ggc atc cat acc gcc att tac tgg cac tac gac tgc      726
Ile Phe Ser Ile Gly Ile His Thr Ala Ile Tyr Trp His Tyr Asp Cys
             215                 220                 225 gag ccg ctc gtg cat acc cac ttt tgg gaa tac gtc acg ccc tac ctt      774
Glu Pro Leu Val His Thr His Phe Trp Glu Tyr Val Thr Pro Tyr Leu
 230                 235                 240 ttc gtc gtg ccc ttc ctc atc ctc ttt ttc aat ttt tac ctg cag cag      822
Phe Val Val Pro Phe Leu Ile Leu Phe Phe Asn Phe Tyr Leu Gln Gln
245                 250                 255                 260 tac gtc ctc gcg ccc gca aaa acc aag aag gca tag ccacgtaaca          868
Tyr Val Leu Ala Pro Ala Lys Thr Lys Lys Ala
             265                 270 gtagaccagc agcgccgagg acgcgtgccg cgttatcgcg aagcacgaaa taaagaagat    928
catttgattc aacgaggcta cttgcggcca cgagaaaaaa aaaaaaaaaa aaaaaaaaaa    988
aaaaaaaaaa aaaaaaaaaa aaaaaaaaaa aaaaaaaaaa aaaaaaaaaa aaaaaaaaaa   1048
c                                                                   1049

<210> SEQ ID NO 63
<211> LENGTH: 271
<212> TYPE: PRT
<213> ORGANISM: Thraustochytrium
```

<400> SEQUENCE: 63

```
Met Met Glu Pro Leu Asp Arg Tyr Arg Ala Leu Ala Glu Leu Ala Ala
1               5                   10                  15

Arg Tyr Ala Ser Ser Ala Ala Phe Lys Trp Gln Val Thr Tyr Asp Ala
            20                  25                  30

Lys Asp Ser Phe Val Gly Pro Leu Gly Ile Arg Glu Pro Leu Gly Leu
            35                  40                  45

Leu Val Gly Ser Val Val Leu Tyr Leu Ser Leu Leu Ala Val Val Tyr
50                  55                  60

Ala Leu Arg Asn Tyr Leu Gly Gly Leu Met Ala Leu Arg Ser Val His
65                  70                  75                  80

Asn Leu Gly Leu Cys Leu Phe Ser Gly Ala Val Trp Ile Tyr Thr Ser
                85                  90                  95

Tyr Leu Met Ile Gln Asp Gly His Phe Arg Ser Leu Glu Ala Ala Thr
            100                 105                 110

Cys Glu Pro Leu Lys His Pro His Phe Gln Leu Ile Ser Leu Leu Phe
            115                 120                 125

Ala Leu Ser Lys Ile Trp Glu Trp Phe Asp Thr Val Leu Leu Ile Val
130                 135                 140

Lys Gly Asn Lys Leu Arg Phe Leu His Val Leu His His Ala Thr Thr
145                 150                 155                 160

Phe Trp Leu Tyr Ala Ile Asp His Ile Phe Leu Ser Ser Ile Lys Tyr
                165                 170                 175

Gly Val Ala Val Asn Ala Phe Ile His Thr Val Met Tyr Ala His Tyr
            180                 185                 190

Phe Arg Pro Phe Pro Lys Gly Leu Arg Pro Leu Ile Thr Gln Leu Gln
            195                 200                 205

Ile Val Gln Phe Ile Phe Ser Ile Gly Ile His Thr Ala Ile Tyr Trp
210                 215                 220

His Tyr Asp Cys Glu Pro Leu Val His Thr His Phe Trp Glu Tyr Val
225                 230                 235                 240

Thr Pro Tyr Leu Phe Val Val Pro Phe Leu Ile Leu Phe Phe Asn Phe
                245                 250                 255

Tyr Leu Gln Gln Tyr Val Leu Ala Pro Ala Lys Thr Lys Ala
            260                 265                 270
```

<210> SEQ ID NO 64
<211> LENGTH: 837
<212> TYPE: DNA
<213> ORGANISM: Phytophthora infestans
<220> FEATURE:
<221> NAME/KEY: CDS
<222> LOCATION: (1)..(837)
<223> OTHER INFORMATION: delta-6-Elongase

<400> SEQUENCE: 64

```
atg tcg act gag cta ctg cag agc tac tac gcg tgg gcc aac gcc acg      48
Met Ser Thr Glu Leu Leu Gln Ser Tyr Tyr Ala Trp Ala Asn Ala Thr
1               5                   10                  15 gag gcc aag ctg ctg gac tgg gtc gac cct gag ggc ggc tgg aag gtg      96
Glu Ala Lys Leu Leu Asp Trp Val Asp Pro Glu Gly Gly Trp Lys Val
            20                  25                  30 cat cct atg gca gac tac ccc cta gcc aac ttc tcc agc gtc tac gcc     144
His Pro Met Ala Asp Tyr Pro Leu Ala Asn Phe Ser Ser Val Tyr Ala
            35                  40                  45 atc tgc gtc gga tac ttg ctc ttc gta atc ttc ggc acg gcc ctg atg     192
Ile Cys Val Gly Tyr Leu Leu Phe Val Ile Phe Gly Thr Ala Leu Met
```

```
                50                  55                  60
aaa atg gga gtc ccc gcc atc aag acc agt cca tta cag ttt gtg tac      240
Lys Met Gly Val Pro Ala Ile Lys Thr Ser Pro Leu Gln Phe Val Tyr
 65                  70                  75                  80 aac ccc atc caa gtc att gcc tgc tct tat atg tgc gtg gag gcc gcc      288
Asn Pro Ile Gln Val Ile Ala Cys Ser Tyr Met Cys Val Glu Ala Ala
                 85                  90                  95 atc cag gcc tac cgc aac ggc tac acc gcc gcc ccg tgc aac gcc ttt      336
Ile Gln Ala Tyr Arg Asn Gly Tyr Thr Ala Ala Pro Cys Asn Ala Phe
            100                 105                 110 aag tcc gac gac ccc gtc atg ggc aac gtt ctg tac ctc ttc tat ctc      384
Lys Ser Asp Asp Pro Val Met Gly Asn Val Leu Tyr Leu Phe Tyr Leu
        115                 120                 125 tcc aag atg ctc gac ctg tgc gac aca gtc ttc att atc cta gga aag      432
Ser Lys Met Leu Asp Leu Cys Asp Thr Val Phe Ile Ile Leu Gly Lys
    130                 135                 140 aag tgg aaa cag ctt tcc atc ttg cac gtg tac cac cac ctt acc gtg      480
Lys Trp Lys Gln Leu Ser Ile Leu His Val Tyr His His Leu Thr Val
145                 150                 155                 160 ctt ttc gtc tac tat gtg acg ttc cgc gcc gct cag gac ggg gac tca      528
Leu Phe Val Tyr Tyr Val Thr Phe Arg Ala Ala Gln Asp Gly Asp Ser
                165                 170                 175 tat gct acc atc gtg ctc aac ggc ttc gtg cac acc atc atg tac act      576
Tyr Ala Thr Ile Val Leu Asn Gly Phe Val His Thr Ile Met Tyr Thr
            180                 185                 190 tac tac ttc gtc agc gcc cac acg cgc aac att tgg tgg aag aag tac      624
Tyr Tyr Phe Val Ser Ala His Thr Arg Asn Ile Trp Trp Lys Lys Tyr
        195                 200                 205 ctc acg cgc att cag ctt atc cag ttc gtg acc atg aac gtg cag ggc      672
Leu Thr Arg Ile Gln Leu Ile Gln Phe Val Thr Met Asn Val Gln Gly
    210                 215                 220 tac ctg acc tac tct cga cag tgc cca ggc atg cct cct aag gtg ccg      720
Tyr Leu Thr Tyr Ser Arg Gln Cys Pro Gly Met Pro Pro Lys Val Pro
225                 230                 235                 240 ctc atg tac ctt gtg tac gtg cag tca ctc ttc tgg ctc ttc atg aat      768
Leu Met Tyr Leu Val Tyr Val Gln Ser Leu Phe Trp Leu Phe Met Asn
                245                 250                 255 ttc tac att cgc gcg tac gtg ttc ggc ccc aag aaa ccg gcc gtg gag      816
Phe Tyr Ile Arg Ala Tyr Val Phe Gly Pro Lys Lys Pro Ala Val Glu
            260                 265                 270 gaa tcg aag aag aag ttg taa                                          837
Glu Ser Lys Lys Lys Leu
        275

<210> SEQ ID NO 65
<211> LENGTH: 278
<212> TYPE: PRT
<213> ORGANISM: Phytophthora infestans

<400> SEQUENCE: 65

Met Ser Thr Glu Leu Leu Gln Ser Tyr Tyr Ala Trp Ala Asn Ala Thr
  1               5                  10                  15

Glu Ala Lys Leu Leu Asp Trp Val Asp Pro Glu Gly Gly Trp Lys Val
             20                  25                  30

His Pro Met Ala Asp Tyr Pro Leu Ala Asn Phe Ser Ser Val Tyr Ala
         35                  40                  45

Ile Cys Val Gly Tyr Leu Leu Phe Val Ile Phe Gly Thr Ala Leu Met
     50                  55                  60

Lys Met Gly Val Pro Ala Ile Lys Thr Ser Pro Leu Gln Phe Val Tyr
```

-continued

```
              65                  70                  75                  80
Asn Pro Ile Gln Val Ile Ala Cys Ser Tyr Met Cys Val Glu Ala Ala
                    85                  90                  95

Ile Gln Ala Tyr Arg Asn Gly Tyr Thr Ala Ala Pro Cys Asn Ala Phe
                100                 105                 110

Lys Ser Asp Asp Pro Val Met Gly Asn Val Leu Tyr Leu Phe Tyr Leu
                115                 120                 125

Ser Lys Met Leu Asp Leu Cys Asp Thr Val Phe Ile Ile Leu Gly Lys
            130                 135                 140

Lys Trp Lys Gln Leu Ser Ile Leu His Val Tyr His His Leu Thr Val
145                 150                 155                 160

Leu Phe Val Tyr Val Thr Phe Arg Ala Ala Gln Asp Gly Asp Ser
                165                 170                 175

Tyr Ala Thr Ile Val Leu Asn Gly Phe Val His Thr Ile Met Tyr Thr
                180                 185                 190

Tyr Tyr Phe Val Ser Ala His Thr Arg Asn Ile Trp Trp Lys Lys Tyr
                195                 200                 205

Leu Thr Arg Ile Gln Leu Ile Gln Phe Val Thr Met Asn Val Gln Gly
            210                 215                 220

Tyr Leu Thr Tyr Ser Arg Gln Cys Pro Gly Met Pro Pro Lys Val Pro
225                 230                 235                 240

Leu Met Tyr Leu Val Tyr Gln Ser Leu Phe Trp Leu Phe Met Asn
                245                 250                 255

Phe Tyr Ile Arg Ala Tyr Val Phe Gly Pro Lys Lys Pro Ala Val Glu
                260                 265                 270

Glu Ser Lys Lys Lys Leu
            275
```

<210> SEQ ID NO 66
<211> LENGTH: 954
<212> TYPE: DNA
<213> ORGANISM: Mortierella alpina
<220> FEATURE:
<221> NAME/KEY: CDS
<222> LOCATION: (1)..(954)
<223> OTHER INFORMATION: delta-6-Elongase

<400> SEQUENCE: 66

```
atg gcc gcc gca atc ttg gac aag gtc aac ttc ggc att gat cag ccc        48
Met Ala Ala Ala Ile Leu Asp Lys Val Asn Phe Gly Ile Asp Gln Pro
1               5                   10                  15 ttc gga atc aag ctc gac acc tac ttt gct cag gcc tat gaa ctc gtc        96
Phe Gly Ile Lys Leu Asp Thr Tyr Phe Ala Gln Ala Tyr Glu Leu Val
            20                  25                  30 acc gga aag tcc atc gac tcc ttc gtc ttc cag gag ggc gtc acg cct       144
Thr Gly Lys Ser Ile Asp Ser Phe Val Phe Gln Glu Gly Val Thr Pro
        35                  40                  45 ctc tcg acc cag aga gag gtc gcc atg tgg act atc act tac ttc gtc       192
Leu Ser Thr Gln Arg Glu Val Ala Met Trp Thr Ile Thr Tyr Phe Val
    50                  55                  60 gtc atc ttt ggt ggc cgc cag atc atg aag agc cag gac gcc ttc aag       240
Val Ile Phe Gly Gly Arg Gln Ile Met Lys Ser Gln Asp Ala Phe Lys
65                  70                  75                  80 ctc aag ccc ctc ttc atc ctc cac aac ttc ctc ctg acg atc gcg tcc       288
Leu Lys Pro Leu Phe Ile Leu His Asn Phe Leu Leu Thr Ile Ala Ser
                85                  90                  95 gga tcg ctg ttg ctc ctg ttc atc gag aac ctg gtc ccc atc ctc gcc       336
Gly Ser Leu Leu Leu Leu Phe Ile Glu Asn Leu Val Pro Ile Leu Ala
```

```
                    100                 105                 110
aga aac gga ctt ttc tac gcc atc tgc gac gac ggt gcc tgg acc cag      384
Arg Asn Gly Leu Phe Tyr Ala Ile Cys Asp Asp Gly Ala Trp Thr Gln
            115                 120                 125 cgc ctc gag ctc ctc tac tac ctc aac tac ctg gtc aag tac tgg gag      432
Arg Leu Glu Leu Leu Tyr Tyr Leu Asn Tyr Leu Val Lys Tyr Trp Glu
130                 135                 140 ttg gcc gac acc gtc ttt ttg gtc ctc aag aag aag cct ctt gag ttc      480
Leu Ala Asp Thr Val Phe Leu Val Leu Lys Lys Lys Pro Leu Glu Phe
145                 150                 155                 160 ctg cac tac ttc cac cac tcg atg acc atg gtt ctc tgc ttt gtc cag      528
Leu His Tyr Phe His His Ser Met Thr Met Val Leu Cys Phe Val Gln
                165                 170                 175 ctt gga gga tac act tca gtg tcc tgg gtc cct att acc ctc aac ttg      576
Leu Gly Gly Tyr Thr Ser Val Ser Trp Val Pro Ile Thr Leu Asn Leu
            180                 185                 190 act gtc cac gtc ttc atg tac tac tac atg cgc tcc gct gcc ggt          624
Thr Val His Val Phe Met Tyr Tyr Tyr Met Arg Ser Ala Ala Gly
        195                 200                 205 gtt cgc atc tgg tgg aag cag tac ttg acc act ctc cag atc gtc cag      672
Val Arg Ile Trp Trp Lys Gln Tyr Leu Thr Thr Leu Gln Ile Val Gln
    210                 215                 220 ttc gtt ctt gac ctc gga ttc atc tac ttc tgc gcc tac acc tac ttc      720
Phe Val Leu Asp Leu Gly Phe Ile Tyr Phe Cys Ala Tyr Thr Tyr Phe
225                 230                 235                 240 gcc ttc acc tac ttc ccc tgg gct ccc aac gtc ggc aag tgc gcc ggt      768
Ala Phe Thr Tyr Phe Pro Trp Ala Pro Asn Val Gly Lys Cys Ala Gly
                245                 250                 255 acc gag ggt gct gct ctc ttt ggc tgc gga ctc ctc tcc agc tat ctc      816
Thr Glu Gly Ala Ala Leu Phe Gly Cys Gly Leu Leu Ser Ser Tyr Leu
            260                 265                 270 ttg ctc ttt atc aac ttc tac cgc att acc tac aat gcc aag gcc aag      864
Leu Leu Phe Ile Asn Phe Tyr Arg Ile Thr Tyr Asn Ala Lys Ala Lys
        275                 280                 285 gca gcc aag gag cgt gga agc aac ttt acc ccc aag act gtc aag tcc      912
Ala Ala Lys Glu Arg Gly Ser Asn Phe Thr Pro Lys Thr Val Lys Ser
    290                 295                 300 ggc gga tcg ccc aag aag ccc tcc aag agc aag cac atc taa              954
Gly Gly Ser Pro Lys Lys Pro Ser Lys Ser Lys His Ile
305                 310                 315

<210> SEQ ID NO 67
<211> LENGTH: 317
<212> TYPE: PRT
<213> ORGANISM: Mortierella alpina

<400> SEQUENCE: 67

Met Ala Ala Ala Ile Leu Asp Lys Val Asn Phe Gly Ile Asp Gln Pro
1               5                   10                  15

Phe Gly Ile Lys Leu Asp Thr Tyr Phe Ala Gln Ala Tyr Glu Leu Val
                20                  25                  30

Thr Gly Lys Ser Ile Asp Ser Phe Val Phe Gln Glu Gly Val Thr Pro
            35                  40                  45

Leu Ser Thr Gln Arg Glu Val Ala Met Trp Thr Ile Thr Tyr Phe Val
        50                  55                  60

Val Ile Phe Gly Gly Arg Gln Ile Met Lys Ser Gln Asp Ala Phe Lys
65                  70                  75                  80

Leu Lys Pro Leu Phe Ile Leu His Asn Phe Leu Leu Thr Ile Ala Ser
                85                  90                  95
```

```
Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
            115                 120                 125

Arg Leu Glu Leu Leu Tyr Tyr Leu Asn Tyr Leu Val Lys Tyr Trp Glu
130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
            195                 200                 205

Val Arg Ile Trp Trp Lys Gln Tyr Leu Thr Thr Leu Gln Ile Val Gln
            210                 215                 220

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
                245                 250                 255

Thr Glu Gly Ala Ala Leu Phe Gly Cys Gly Leu Leu Ser Ser Tyr Leu
            260                 265                 270

Leu Leu Phe Ile Asn Phe Tyr Arg Ile Thr Tyr Asn Ala Lys Ala Lys
            275                 280                 285

Ala Ala Lys Glu Arg Gly Ser Asn Phe Thr Pro Lys Thr Val Lys Ser
            290                 295                 300

Gly Gly Ser Pro Lys Lys Pro Ser Lys Ser Lys His Ile
305                 310                 315

<210> SEQ ID NO 68
<211> LENGTH: 957
<212> TYPE: DNA
<213> ORGANISM: Mortierella alpina
<220> FEATURE:
<221> NAME/KEY: CDS
<222> LOCATION: (1)..(957)
<223> OTHER INFORMATION: delta-6-Elongase

<400> SEQUENCE: 68 atg gag tcg att gcg cca ttc ctc cca tca aag atg ccg caa gat ctg     48
Met Glu Ser Ile Ala Pro Phe Leu Pro Ser Lys Met Pro Gln Asp Leu
1               5                   10                  15 ttt atg gac ctt gcc acc gct atc ggt gtc cgg gcc gcg ccc tat gtc     96
Phe Met Asp Leu Ala Thr Ala Ile Gly Val Arg Ala Ala Pro Tyr Val
                20                  25                  30 gat cct ctc gag gcc gcg ctg gtg gcc cag gcc gag aag tac atc ccc    144
Asp Pro Leu Glu Ala Ala Leu Val Ala Gln Ala Glu Lys Tyr Ile Pro
            35                  40                  45 acg att gtc cat cac acg cgt ggg ttc ctg gtc gcg gtg gag tcg cct    192
Thr Ile Val His His Thr Arg Gly Phe Leu Val Ala Val Glu Ser Pro
50                  55                  60 ttg gcc cgt gag ctg ccg ttg atg aac ccg ttc cac gtg ctg ttg atc    240
Leu Ala Arg Glu Leu Pro Leu Met Asn Pro Phe His Val Leu Leu Ile
65                  70                  75                  80 gtg ctc gct tat ttg gtc acg gtc ttt gtg ggc atg cag atc atg aag    288
Val Leu Ala Tyr Leu Val Thr Val Phe Val Gly Met Gln Ile Met Lys
                85                  90                  95
```

-continued

| | | |
|---|---|---|
| aac ttt gag cgg ttc gag gtc aag acg ttt tcg ctc ctg cac aac ttt<br>Asn Phe Glu Arg Phe Glu Val Lys Thr Phe Ser Leu Leu His Asn Phe<br>100                       105                     110 | 336 |
| tgt ctg gtc tcg atc agc gcc tac atg tgc ggt ggg atc ctg tac gag<br>Cys Leu Val Ser Ile Ser Ala Tyr Met Cys Gly Gly Ile Leu Tyr Glu<br>         115                        120                      125 | 384 |
| gct tat cag gcc aac tat gga ctg ttt gag aac gct gct gat cat acc<br>Ala Tyr Gln Ala Asn Tyr Gly Leu Phe Glu Asn Ala Ala Asp His Thr<br>        130                       135                     140 | 432 |
| ttc aag ggt ctt cct atg gcc aag atg atc tgg ctc ttc tac ttc tcc<br>Phe Lys Gly Leu Pro Met Ala Lys Met Ile Trp Leu Phe Tyr Phe Ser<br>145                       150                     155                    160 | 480 |
| aag atc atg gag ttt gtc gac acc atg atc atg gtc ctc aag aag aac<br>Lys Ile Met Glu Phe Val Asp Thr Met Ile Met Val Leu Lys Lys Asn<br>                    165                     170                     175 | 528 |
| aac cgc cag atc tcc ttc ttg cac gtt tac cac cac agc tcc atc ttc<br>Asn Arg Gln Ile Ser Phe Leu His Val Tyr His His Ser Ser Ile Phe<br>        180                       185                     190 | 576 |
| acc atc tgg tgg ttg gtc acc ttt gtt gca ccc aac ggt gaa gcc tac<br>Thr Ile Trp Trp Leu Val Thr Phe Val Ala Pro Asn Gly Glu Ala Tyr<br>         195                       200                     205 | 624 |
| ttc tct gct gcg ttg aac tcg ttc atc cat gtg atc atg tac ggc tac<br>Phe Ser Ala Ala Leu Asn Ser Phe Ile His Val Ile Met Tyr Gly Tyr<br>210                       215                     220 | 672 |
| tac ttc ttg tcg gcc ttg ggc ttc aag cag gtg tcg ttc atc aag ttc<br>Tyr Phe Leu Ser Ala Leu Gly Phe Lys Gln Val Ser Phe Ile Lys Phe<br>225                       230                     235                    240 | 720 |
| tac atc acg cgc tcg cag atg aca cag ttc tgc atg atg tcg gtc cag<br>Tyr Ile Thr Arg Ser Gln Met Thr Gln Phe Cys Met Met Ser Val Gln<br>                    245                     250                     255 | 768 |
| tct tcc tgg gac atg tac gcc atg aag gtc ctt ggc cgc ccc gga tac<br>Ser Ser Trp Asp Met Tyr Ala Met Lys Val Leu Gly Arg Pro Gly Tyr<br>        260                       265                     270 | 816 |
| ccc ttc ttc atc acg gct ctg ctt tgg ttc tac atg tgg acc atg ctc<br>Pro Phe Phe Ile Thr Ala Leu Leu Trp Phe Tyr Met Trp Thr Met Leu<br>275                       280                     285 | 864 |
| ggt ctc ttc tac aac ttt tac aga aag aac gcc aag ttg gcc aag cag<br>Gly Leu Phe Tyr Asn Phe Tyr Arg Lys Asn Ala Lys Leu Ala Lys Gln<br>        290                       295                     300 | 912 |
| gcc aag gcc gac gct gcc aag gag aag gca agg aag ttg cag taa<br>Ala Lys Ala Asp Ala Ala Lys Glu Lys Ala Arg Lys Leu Gln<br>305                       310                     315 | 957 |

```
<210> SEQ ID NO 69
<211> LENGTH: 318
<212> TYPE: PRT
<213> ORGANISM: Mortierella alpina

<400> SEQUENCE: 69
```

Met Glu Ser Ile Ala Pro Phe Leu Pro Ser Lys Met Pro Gln Asp Leu
1                   5                       10                      15

Phe Met Asp Leu Ala Thr Ala Ile Gly Val Arg Ala Ala Pro Tyr Val
                 20                      25                       30

Asp Pro Leu Glu Ala Ala Leu Val Ala Gln Ala Glu Lys Tyr Ile Pro
                    35                      40                       45

Thr Ile Val His His Thr Arg Gly Phe Leu Val Ala Val Glu Ser Pro
        50                       55                      60

Leu Ala Arg Glu Leu Pro Leu Met Asn Pro Phe His Val Leu Leu Ile
65                       70                       75                    80

```
Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Thr Met Val Leu Lys Lys Asn
                165                 170                 175

Asn Arg Gln Ile Ser Phe Leu His Val Tyr His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315
```

<210> SEQ ID NO 70
<211> LENGTH: 867
<212> TYPE: DNA
<213> ORGANISM: Caenorhabditis elegans
<220> FEATURE:
<221> NAME/KEY: CDS
<222> LOCATION: (1)..(867)
<223> OTHER INFORMATION: delta-6-Elongase

<400> SEQUENCE: 70

```
atg gct cag cat ccg ctc gtt caa cgg ctt ctc gat gtc aaa ttc gac      48
Met Ala Gln His Pro Leu Val Gln Arg Leu Leu Asp Val Lys Phe Asp
1               5                   10                  15 acg aaa cga ttt gtg gct att gct act cat ggg cca aag aat ttc cct      96
Thr Lys Arg Phe Val Ala Ile Ala Thr His Gly Pro Lys Asn Phe Pro
                20                  25                  30 gac gca gaa ggt cgc aag ttc ttt gct gat cac ttt gat gtt act att     144
Asp Ala Glu Gly Arg Lys Phe Phe Ala Asp His Phe Asp Val Thr Ile
            35                  40                  45 cag gct tca atc ctg tac atg gtc gtt gtg ttc gga aca aaa tgg ttc     192
Gln Ala Ser Ile Leu Tyr Met Val Val Val Phe Gly Thr Lys Trp Phe
        50                  55                  60 atg cgt aat cgt caa cca ttc caa ttg act att cca ctc aac atc tgg     240
Met Arg Asn Arg Gln Pro Phe Gln Leu Thr Ile Pro Leu Asn Ile Trp
65                  70                  75                  80 aat ttc atc ctc gcc gca ttt tcc atc gca gga gct gtc aaa atg acc     288
Asn Phe Ile Leu Ala Ala Phe Ser Ile Ala Gly Ala Val Lys Met Thr
```

```
                85                  90                  95
cca gag ttc ttt gga acc att gcc aac aaa gga att gtc gca tcc tac        336
Pro Glu Phe Phe Gly Thr Ile Ala Asn Lys Gly Ile Val Ala Ser Tyr
            100                 105                 110 tgc aaa gtg ttt gat ttc acg aaa gga gag aat gga tac tgg gtg tgg        384
Cys Lys Val Phe Asp Phe Thr Lys Gly Glu Asn Gly Tyr Trp Val Trp
            115                 120                 125 ctc ttc atg gct tcc aaa ctt ttc gaa ctt gtt gac acc atc ttc ttg        432
Leu Phe Met Ala Ser Lys Leu Phe Glu Leu Val Asp Thr Ile Phe Leu
        130                 135                 140 gtt ctc cgt aaa cgt cca ctc atg ttc ctt cac tgg tat cac cat att        480
Val Leu Arg Lys Arg Pro Leu Met Phe Leu His Trp Tyr His His Ile
145                 150                 155                 160 ctc acc atg atc tac gcc tgg tac tct cat cca ttg acc cca gga ttc        528
Leu Thr Met Ile Tyr Ala Trp Tyr Ser His Pro Leu Thr Pro Gly Phe
                165                 170                 175 aac aga tac gga att tat ctt aac ttt gtc gtc cac gcc ttc atg tac        576
Asn Arg Tyr Gly Ile Tyr Leu Asn Phe Val Val His Ala Phe Met Tyr
            180                 185                 190 tct tac tac ttc ctt cgc tcg atg aag att cgc gtg cca gga ttc atc        624
Ser Tyr Tyr Phe Leu Arg Ser Met Lys Ile Arg Val Pro Gly Phe Ile
        195                 200                 205 gcc caa gct atc aca tct ctt caa atc gtt caa ttc atc atc tct tgc        672
Ala Gln Ala Ile Thr Ser Leu Gln Ile Val Gln Phe Ile Ile Ser Cys
    210                 215                 220 gcc gtt ctt gct cat ctt ggt tat ctc atg cac ttc acc aat gcc aac        720
Ala Val Leu Ala His Leu Gly Tyr Leu Met His Phe Thr Asn Ala Asn
225                 230                 235                 240 tgt gat ttc gag cca tca gta ttc aag ctc gca gtt ttc atg gac aca        768
Cys Asp Phe Glu Pro Ser Val Phe Lys Leu Ala Val Phe Met Asp Thr
                245                 250                 255 aca tac ttg gct ctt ttc gtc aac ttc ttc ctc caa tca tat gtt ctc        816
Thr Tyr Leu Ala Leu Phe Val Asn Phe Phe Leu Gln Ser Tyr Val Leu
            260                 265                 270 cgc gga gga aaa gac aag tac aag gca gtg cca aag aag aag aac aac        864
Arg Gly Gly Lys Asp Lys Tyr Lys Ala Val Pro Lys Lys Lys Asn Asn
        275                 280                 285 taa                                                                    867

<210> SEQ ID NO 71
<211> LENGTH: 288
<212> TYPE: PRT
<213> ORGANISM: Caenorhabditis elegans

<400> SEQUENCE: 71

Met Ala Gln His Pro Leu Val Gln Arg Leu Leu Asp Val Lys Phe Asp
1               5                   10                  15

Thr Lys Arg Phe Val Ala Ile Ala Thr His Gly Pro Lys Asn Phe Pro
            20                  25                  30

Asp Ala Glu Gly Arg Lys Phe Phe Ala Asp His Phe Asp Val Thr Ile
        35                  40                  45

Gln Ala Ser Ile Leu Tyr Met Val Val Phe Gly Thr Lys Trp Phe
    50                  55                  60

Met Arg Asn Arg Gln Pro Phe Gln Leu Thr Ile Pro Leu Asn Ile Trp
65                  70                  75                  80

Asn Phe Ile Leu Ala Ala Phe Ser Ile Ala Gly Ala Val Lys Met Thr
                85                  90                  95

Pro Glu Phe Phe Gly Thr Ile Ala Asn Lys Gly Ile Val Ala Ser Tyr
```

-continued

```
            100                 105                 110
Cys Lys Val Phe Asp Phe Thr Lys Gly Glu Asn Gly Tyr Trp Val Trp
        115                 120                 125

Leu Phe Met Ala Ser Lys Leu Phe Glu Leu Val Asp Thr Ile Phe Leu
130                 135                 140

Val Leu Arg Lys Arg Pro Leu Met Phe Leu His Trp Tyr His His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val Val His Ala Phe Met Tyr
            180                 185                 190

Ser Tyr Tyr Phe Leu Arg Ser Met Lys Ile Arg Val Pro Gly Phe Ile
        195                 200                 205

Ala Gln Ala Ile Thr Ser Leu Gln Ile Val Gln Phe Ile Ile Ser Cys
    210                 215                 220

Ala Val Leu Ala His Leu Gly Tyr Leu Met His Phe Thr Asn Ala Asn
225                 230                 235                 240

Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
            260                 265                 270

Arg Gly Gly Lys Asp Lys Tyr Lys Ala Val Pro Lys Lys Asn Asn
        275                 280                 285
```

<210> SEQ ID NO 72
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: delta-6-Elongase

<400> SEQUENCE: 72

```
atg agt ggc tta cgt gca ccc aac ttt tta cac aga ttc tgg aca aag      48
Met Ser Gly Leu Arg Ala Pro Asn Phe Leu His Arg Phe Trp Thr Lys
1               5                  10                  15 tgg gac tac gcg att tcc aaa gtc gtc ttc acg tgt gcc gac agt ttt      96
Trp Asp Tyr Ala Ile Ser Lys Val Val Phe Thr Cys Ala Asp Ser Phe
            20                  25                  30 cag tgg gac atc ggg cca gtg agt tcg agt acg gcg cat tta ccc gcc     144
Gln Trp Asp Ile Gly Pro Val Ser Ser Ser Thr Ala His Leu Pro Ala
        35                  40                  45 att gaa tcc cct acc cca ctg gtg act agc ctc ttg ttc tac tta gtc     192
Ile Glu Ser Pro Thr Pro Leu Val Thr Ser Leu Leu Phe Tyr Leu Val
    50                  55                  60 aca gtt ttc ttg tgg tat ggt cgt tta acc agg agt tca gac aag aaa     240
Thr Val Phe Leu Trp Tyr Gly Arg Leu Thr Arg Ser Ser Asp Lys Lys
65                  70                  75                  80 att aga gag cct acg tgg tta aga aga ttc ata ata tgt cat aat gcg     288
Ile Arg Glu Pro Thr Trp Leu Arg Arg Phe Ile Ile Cys His Asn Ala
                85                  90                  95 ttc ttg ata gtc ctc agt ctt tac atg tgc ctt ggt tgt gtg gcc caa     336
Phe Leu Ile Val Leu Ser Leu Tyr Met Cys Leu Gly Cys Val Ala Gln
            100                 105                 110 gcg tat cag aat gga tat act tta tgg ggt aat gaa ttc aag gcc acg     384
Ala Tyr Gln Asn Gly Tyr Thr Leu Trp Gly Asn Glu Phe Lys Ala Thr
        115                 120                 125
```

```
gaa act cag ctt gct ctc tac att tac att ttt tac gta agt aaa ata      432
Glu Thr Gln Leu Ala Leu Tyr Ile Tyr Ile Phe Tyr Val Ser Lys Ile
130                 135                 140 tac gag ttt gta gat act tac att atg ctt ctc aag aat aac ttg cgg      480
Tyr Glu Phe Val Asp Thr Tyr Ile Met Leu Leu Lys Asn Asn Leu Arg
145                 150                 155                 160 caa gta agt ttc cta cac att tat cac cac agc acg att tcc ttt att      528
Gln Val Ser Phe Leu His Ile Tyr His His Ser Thr Ile Ser Phe Ile
                165                 170                 175 tgg tgg atc att gct cgg agg gct ccg ggt ggt gat gct tac ttc agc      576
Trp Trp Ile Ile Ala Arg Arg Ala Pro Gly Gly Asp Ala Tyr Phe Ser
            180                 185                 190 gcg gcc ttg aac tca tgg gta cac gtg tgc atg tac acc tat tat cta      624
Ala Ala Leu Asn Ser Trp Val His Val Cys Met Tyr Thr Tyr Tyr Leu
        195                 200                 205 tta tca acc ctt att gga aaa gaa gat cct aag cgt tcc aac tac ctt      672
Leu Ser Thr Leu Ile Gly Lys Glu Asp Pro Lys Arg Ser Asn Tyr Leu
210                 215                 220 tgg tgg ggt cgc cac cta acg caa atg cag atg ctt cag ttt ttc ttc      720
Trp Trp Gly Arg His Leu Thr Gln Met Gln Met Leu Gln Phe Phe Phe
225                 230                 235                 240 aac gta ctt caa gcg ttg tac tgc gct tcg ttc tct acg tat ccc aag      768
Asn Val Leu Gln Ala Leu Tyr Cys Ala Ser Phe Ser Thr Tyr Pro Lys
                245                 250                 255 ttt ttg tcc aaa att ctg ctc gtc tat atg atg agc ctt ctc ggc ttg      816
Phe Leu Ser Lys Ile Leu Leu Val Tyr Met Met Ser Leu Leu Gly Leu
            260                 265                 270 ttt ggg cat ttc tac tat tcc aag cac ata gca gca gct aag ctc cag      864
Phe Gly His Phe Tyr Tyr Ser Lys His Ile Ala Ala Ala Lys Leu Gln
        275                 280                 285 aaa aaa cag cag tga                                                  879
Lys Lys Gln Gln
    290
```

<210> SEQ ID NO 73
<211> LENGTH: 292
<212> TYPE: PRT
<213> ORGANISM: Ostreococcus tauri

<400> SEQUENCE: 73

```
Met Ser Gly Leu Arg Ala Pro Asn Phe Leu His Arg Phe Trp Thr Lys
1               5                   10                  15

Trp Asp Tyr Ala Ile Ser Lys Val Val Phe Thr Cys Ala Asp Ser Phe
            20                  25                  30

Gln Trp Asp Ile Gly Pro Val Ser Ser Thr Ala His Leu Pro Ala
        35                  40                  45

Ile Glu Ser Pro Thr Pro Leu Val Thr Ser Leu Leu Phe Tyr Leu Val
50                  55                  60

Thr Val Phe Leu Trp Tyr Gly Arg Leu Thr Arg Ser Ser Asp Lys Lys
65                  70                  75                  80

Ile Arg Glu Pro Thr Trp Leu Arg Arg Phe Ile Ile Cys His Asn Ala
                85                  90                  95

Phe Leu Ile Val Leu Ser Leu Tyr Met Cys Leu Gly Cys Val Ala Gln
            100                 105                 110

Ala Tyr Gln Asn Gly Tyr Thr Leu Trp Gly Asn Glu Phe Lys Ala Thr
        115                 120                 125

Glu Thr Gln Leu Ala Leu Tyr Ile Tyr Ile Phe Tyr Val Ser Lys Ile
130                 135                 140
```

-continued

```
Tyr Glu Phe Val Asp Thr Tyr Ile Met Leu Leu Lys Asn Asn Leu Arg
145                 150                 155                 160

Gln Val Ser Phe Leu His Ile Tyr His His Ser Thr Ile Ser Phe Ile
            165                 170                 175

Trp Trp Ile Ile Ala Arg Arg Ala Pro Gly Gly Asp Ala Tyr Phe Ser
                180                 185                 190

Ala Ala Leu Asn Ser Trp Val His Val Cys Met Tyr Thr Tyr Tyr Leu
            195                 200                 205

Leu Ser Thr Leu Ile Gly Lys Glu Asp Pro Lys Arg Ser Asn Tyr Leu
        210                 215                 220

Trp Trp Gly Arg His Leu Thr Gln Met Gln Met Leu Gln Phe Phe Phe
225                 230                 235                 240

Asn Val Leu Gln Ala Leu Tyr Cys Ala Ser Phe Ser Thr Tyr Pro Lys
                245                 250                 255

Phe Leu Ser Lys Ile Leu Leu Val Tyr Met Met Ser Leu Leu Gly Leu
            260                 265                 270

Phe Gly His Phe Tyr Tyr Ser Lys His Ile Ala Ala Ala Lys Leu Gln
        275                 280                 285

Lys Lys Gln Gln
    290

<210> SEQ ID NO 74
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: delta-6-Elongase

<400> SEQUENCE: 74 atg agt ggc tta cgt gca ccc aac ttt tta cac aga ttc tgg aca aag      48
Met Ser Gly Leu Arg Ala Pro Asn Phe Leu His Arg Phe Trp Thr Lys
1               5                   10                  15 tgg gac tac gcg att tcc aaa gtc gtc ttc acg tgt gcc gac agt ttt      96
Trp Asp Tyr Ala Ile Ser Lys Val Val Phe Thr Cys Ala Asp Ser Phe
            20                  25                  30 cag tgg gac atc ggg cca gtg agt tcg agt acg gcg cat tta ccc gcc     144
Gln Trp Asp Ile Gly Pro Val Ser Ser Ser Thr Ala His Leu Pro Ala
        35                  40                  45 att gaa tcc cct acc cca ctg gtg act agc ctc ttg ttc tac tta gtc     192
Ile Glu Ser Pro Thr Pro Leu Val Thr Ser Leu Leu Phe Tyr Leu Val
    50                  55                  60 aca gtt ttc ttg tgg tat ggt cgt tta acc agg agt tca gac aag aaa     240
Thr Val Phe Leu Trp Tyr Gly Arg Leu Thr Arg Ser Ser Asp Lys Lys
65                  70                  75                  80 att aga gag cct acg tgg tta aga aga ttc ata ata tgt cat aat gcg     288
Ile Arg Glu Pro Thr Trp Leu Arg Arg Phe Ile Ile Cys His Asn Ala
                85                  90                  95 ttc ttg ata gtc ctc agt ctt tac atg tgc ctt ggt tgt gtg gcc caa     336
Phe Leu Ile Val Leu Ser Leu Tyr Met Cys Leu Gly Cys Val Ala Gln
            100                 105                 110 gcg tat cag aat gga tat act tta tgg ggt aat gaa ttc aag gcc acg     384
Ala Tyr Gln Asn Gly Tyr Thr Leu Trp Gly Asn Glu Phe Lys Ala Thr
        115                 120                 125 gaa act cag ctt gct ctc tac att tac att ttt tac gta agt aaa ata     432
Glu Thr Gln Leu Ala Leu Tyr Ile Tyr Ile Phe Tyr Val Ser Lys Ile
    130                 135                 140 tac gag ttt gta gat act tac att atg ctt ctc aag aat aac ttg cgg     480
```

```
Tyr Glu Phe Val Asp Thr Tyr Ile Met Leu Leu Lys Asn Asn Leu Arg
145                 150                 155                 160 caa gta aga ttc cta cac act tat cac cac agc acg att tcc ttt att    528
Gln Val Arg Phe Leu His Thr Tyr His His Ser Thr Ile Ser Phe Ile
            165                 170                 175 tgg tgg atc att gct cgg agg gct ccg ggt ggt gat gct tac ttc agc    576
Trp Trp Ile Ile Ala Arg Arg Ala Pro Gly Gly Asp Ala Tyr Phe Ser
            180                 185                 190 gcg gcc ttg aac tca tgg gta cac gtg tgc atg tac acc tat tat cta    624
Ala Ala Leu Asn Ser Trp Val His Val Cys Met Tyr Thr Tyr Tyr Leu
            195                 200                 205 tta tca acc ctt att gga aaa gaa gat cct aag cgt tcc aac tac ctt    672
Leu Ser Thr Leu Ile Gly Lys Glu Asp Pro Lys Arg Ser Asn Tyr Leu
    210                 215                 220 tgg tgg ggt cgc cac cta acg caa atg cag atg ctt cag ttt ttc ttc    720
Trp Trp Gly Arg His Leu Thr Gln Met Gln Met Leu Gln Phe Phe Phe
225                 230                 235                 240 aac gta ctt caa gcg ttg tac tgc gct tcg ttc tct acg tat ccc aag    768
Asn Val Leu Gln Ala Leu Tyr Cys Ala Ser Phe Ser Thr Tyr Pro Lys
            245                 250                 255 ttt ttg tcc aaa att ctg ctc gtc tat atg atg agc ctt ctc ggc ttg    816
Phe Leu Ser Lys Ile Leu Leu Val Tyr Met Met Ser Leu Leu Gly Leu
            260                 265                 270 ttt ggg cat ttc tac tat tcc aag cac ata gca gca gct aag ctc cag    864
Phe Gly His Phe Tyr Tyr Ser Lys His Ile Ala Ala Ala Lys Leu Gln
            275                 280                 285 aaa aaa cag cag tga                                                879
Lys Lys Gln Gln
        290

<210> SEQ ID NO 75
<211> LENGTH: 292
<212> TYPE: PRT
<213> ORGANISM: Ostreococcus tauri

<400> SEQUENCE: 75

Met Ser Gly Leu Arg Ala Pro Asn Phe Leu His Arg Phe Trp Thr Lys
1               5                   10                  15

Trp Asp Tyr Ala Ile Ser Lys Val Val Phe Thr Cys Ala Asp Ser Phe
            20                  25                  30

Gln Trp Asp Ile Gly Pro Val Ser Ser Thr Ala His Leu Pro Ala
        35                  40                  45

Ile Glu Ser Pro Thr Pro Leu Val Thr Ser Leu Phe Tyr Leu Val
    50                  55                  60

Thr Val Phe Leu Trp Tyr Gly Arg Leu Thr Arg Ser Ser Asp Lys Lys
65                  70                  75                  80

Ile Arg Glu Pro Thr Trp Leu Arg Arg Phe Ile Ile Cys His Asn Ala
                85                  90                  95

Phe Leu Ile Val Leu Ser Leu Tyr Met Cys Leu Gly Cys Val Ala Gln
            100                 105                 110

Ala Tyr Gln Asn Gly Tyr Thr Leu Trp Gly Asn Glu Phe Lys Ala Thr
        115                 120                 125

Glu Thr Gln Leu Ala Leu Tyr Ile Tyr Ile Phe Tyr Val Ser Lys Ile
    130                 135                 140

Tyr Glu Phe Val Asp Thr Tyr Ile Met Leu Leu Lys Asn Asn Leu Arg
145                 150                 155                 160

Gln Val Arg Phe Leu His Thr Tyr His His Ser Thr Ile Ser Phe Ile
            165                 170                 175
```

```
Trp Trp Ile Ile Ala Arg Arg Ala Pro Gly Gly Asp Ala Tyr Phe Ser
            180                 185                 190

Ala Ala Leu Asn Ser Trp Val His Val Cys Met Tyr Thr Tyr Tyr Leu
        195                 200                 205

Leu Ser Thr Leu Ile Gly Lys Glu Asp Pro Lys Arg Ser Asn Tyr Leu
    210                 215                 220

Trp Trp Gly Arg His Leu Thr Gln Met Gln Met Leu Gln Phe Phe Phe
225                 230                 235                 240

Asn Val Leu Gln Ala Leu Tyr Cys Ala Ser Phe Ser Thr Tyr Pro Lys
                245                 250                 255

Phe Leu Ser Lys Ile Leu Leu Val Tyr Met Met Ser Leu Leu Gly Leu
            260                 265                 270

Phe Gly His Phe Tyr Tyr Ser Lys His Ile Ala Ala Lys Leu Gln
        275                 280                 285

Lys Lys Gln Gln
    290
```

<210> SEQ ID NO 76
<211> LENGTH: 993
<212> TYPE: DNA
<213> ORGANISM: Phaeodactylum tricornutum
<220> FEATURE:
<221> NAME/KEY: CDS
<222> LOCATION: (103)..(939)
<223> OTHER INFORMATION: delta-6-Elongase

<400> SEQUENCE: 76

```
ggtcttttgt ggtagctatc gtcatcacac gcaggtcgtt gctcactatc gtgatccgta    60
tattgaccgt gcacttgtgt aaaacagaga tatttcaaga gt atg atg gta cct       114
                                              Met Met Val Pro
                                                1 tca agt tat gac gag tat atc gtc atg gtc aac gac ctt ggc gac tct      162
Ser Ser Tyr Asp Glu Tyr Ile Val Met Val Asn Asp Leu Gly Asp Ser
  5                  10                  15                  20 att ctg agc tgg gcc gac cct gat cac tat cgt gga cat acc gag gga      210
Ile Leu Ser Trp Ala Asp Pro Asp His Tyr Arg Gly His Thr Glu Gly
             25                  30                  35 tgg gag ttc act gac ttt tct gct gct ttt agc att gcc gtc gcg tac      258
Trp Glu Phe Thr Asp Phe Ser Ala Ala Phe Ser Ile Ala Val Ala Tyr
         40                  45                  50 ctc ctg ttt gtc ttt gtt gga tct ctc att atg agt atg gga gtc ccc      306
Leu Leu Phe Val Phe Val Gly Ser Leu Ile Met Ser Met Gly Val Pro
     55                  60                  65 gca att gac cct tat ccg ctc aag ttt gtc tac aat gtt tca cag att      354
Ala Ile Asp Pro Tyr Pro Leu Lys Phe Val Tyr Asn Val Ser Gln Ile
 70                  75                  80 atg ctt tgt gct tac atg acc att gaa gcc agt ctt cta gct tat cgt      402
Met Leu Cys Ala Tyr Met Thr Ile Glu Ala Ser Leu Leu Ala Tyr Arg
 85                  90                  95                 100 aac ggc tac aca ttc tgg cct tgc aac gat tgg gac ttt gaa aag ccg      450
Asn Gly Tyr Thr Phe Trp Pro Cys Asn Asp Trp Asp Phe Glu Lys Pro
            105                 110                 115 cct atc gct aag ctc ctc tgg ctc ttt tac gtt tcc aaa att tgg gat      498
Pro Ile Ala Lys Leu Leu Trp Leu Phe Tyr Val Ser Lys Ile Trp Asp
        120                 125                 130 ttt tgg gac acc atc ttt att gtt ctc ggg aag aag tgg cgt caa ctt      546
Phe Trp Asp Thr Ile Phe Ile Val Leu Gly Lys Lys Trp Arg Gln Leu
    135                 140                 145
```

```
tcc ttc ctg cac gtc tac cat cac acc acc atc ttt ctc ttc tac tgg      594
Ser Phe Leu His Val Tyr His His Thr Thr Ile Phe Leu Phe Tyr Trp
    150                 155                 160 ttg aat gca cat gta aac ttt gat ggt gat att ttc ctc acc atc gtc      642
Leu Asn Ala His Val Asn Phe Asp Gly Asp Ile Phe Leu Thr Ile Val
165                 170                 175                 180 ttg aac ggt ttc atc cac acc gtc atg tac acg tac tac ttc att tgc      690
Leu Asn Gly Phe Ile His Thr Val Met Tyr Thr Tyr Tyr Phe Ile Cys
                185                 190                 195 atg cac acc aag gtc cca gag acc ggc aaa tcc ttg ccc att tgg tgg      738
Met His Thr Lys Val Pro Glu Thr Gly Lys Ser Leu Pro Ile Trp Trp
                    200                 205                 210 aaa tct agt ttg aca agc atg cag ctg gtg cag ttc atc acg atg atg      786
Lys Ser Ser Leu Thr Ser Met Gln Leu Val Gln Phe Ile Thr Met Met
                215                 220                 225 acg cag gct atc atg atc ttg tac aag ggc tgt gct gct ccc cat agc      834
Thr Gln Ala Ile Met Ile Leu Tyr Lys Gly Cys Ala Ala Pro His Ser
            230                 235                 240 cgg gtg gtg aca tcg tac ttg gtt tac att ttg tcg ctc ttt att ttg      882
Arg Val Val Thr Ser Tyr Leu Val Tyr Ile Leu Ser Leu Phe Ile Leu
245                 250                 255                 260 ttc gcc cag ttc ttt gtc agc tca tac ctc aag ccg aag aag aag aag      930
Phe Ala Gln Phe Phe Val Ser Ser Tyr Leu Lys Pro Lys Lys Lys Lys
                265                 270                 275 aca gct taa gcgaaatttg ggtctacgtt aaaacaatta cgttacaaaa               979
Thr Ala aaaaaaaaaa aaaa                                                       993

<210> SEQ ID NO 77
<211> LENGTH: 278
<212> TYPE: PRT
<213> ORGANISM: Phaeodactylum tricornutum

<400> SEQUENCE: 77

Met Met Val Pro Ser Ser Tyr Asp Glu Tyr Ile Val Met Val Asn Asp
1               5                   10                  15

Leu Gly Asp Ser Ile Leu Ser Trp Ala Asp Pro Asp His Tyr Arg Gly
            20                  25                  30

His Thr Glu Gly Trp Glu Phe Thr Asp Phe Ser Ala Ala Phe Ser Ile
        35                  40                  45

Ala Val Ala Tyr Leu Leu Phe Val Phe Val Gly Ser Leu Ile Met Ser
    50                  55                  60

Met Gly Val Pro Ala Ile Asp Pro Tyr Pro Leu Lys Phe Val Tyr Asn
65              70                  75                  80

Val Ser Gln Ile Met Leu Cys Ala Tyr Met Thr Ile Glu Ala Ser Leu
            85                  90                  95

Leu Ala Tyr Arg Asn Gly Tyr Thr Phe Trp Pro Cys Asn Asp Trp Asp
        100                 105                 110

Phe Glu Lys Pro Pro Ile Ala Lys Leu Leu Trp Leu Phe Tyr Val Ser
    115                 120                 125

Lys Ile Trp Asp Phe Trp Asp Thr Ile Phe Ile Val Leu Gly Lys Lys
130                 135                 140

Trp Arg Gln Leu Ser Phe Leu His Val Tyr His His Thr Thr Ile Phe
145                 150                 155                 160

Leu Phe Tyr Trp Leu Asn Ala His Val Asn Phe Asp Gly Asp Ile Phe
                165                 170                 175

Leu Thr Ile Val Leu Asn Gly Phe Ile His Thr Val Met Tyr Thr Tyr
```

```
                        180                 185                 190
Tyr Phe Ile Cys Met His Thr Lys Val Pro Glu Thr Gly Lys Ser Leu
            195                 200                 205

Pro Ile Trp Trp Lys Ser Ser Leu Thr Ser Met Gln Leu Val Gln Phe
        210                 215                 220

Ile Thr Met Met Thr Gln Ala Ile Met Ile Leu Tyr Lys Gly Cys Ala
225                 230                 235                 240

Ala Pro His Ser Arg Val Val Thr Ser Tyr Leu Val Tyr Ile Leu Ser
                245                 250                 255

Leu Phe Ile Leu Phe Ala Gln Phe Phe Val Ser Ser Tyr Leu Lys Pro
            260                 265                 270

Lys Lys Lys Lys Thr Ala
        275

<210> SEQ ID NO 78
<211> LENGTH: 1512
<212> TYPE: DNA
<213> ORGANISM: Thalassiosira pseudonana
<220> FEATURE:
<221> NAME/KEY: CDS
<222> LOCATION: (1)..(1512)
<223> OTHER INFORMATION: delta-4-Desaturase

<400> SEQUENCE: 78 atg tgc aac ggc aac ctc cca gca tcc acc gca cag ctc aag tcc acc       48
Met Cys Asn Gly Asn Leu Pro Ala Ser Thr Ala Gln Leu Lys Ser Thr
1               5                   10                  15 tcg aag ccc cag cag caa cat gag cat cgc acc atc tcc aag tcc gag       96
Ser Lys Pro Gln Gln Gln His Glu His Arg Thr Ile Ser Lys Ser Glu
            20                  25                  30 ctc gcc caa cac aac acg ccc aaa tca gca tgg tgt gcc gtc cac tcc      144
Leu Ala Gln His Asn Thr Pro Lys Ser Ala Trp Cys Ala Val His Ser
        35                  40                  45 act ccc gcc acc gac cca tcc cac tcc aac aac aaa caa cac gca cac      192
Thr Pro Ala Thr Asp Pro Ser His Ser Asn Asn Lys Gln His Ala His
    50                  55                  60 cta gtc ctc gac att acc gac ttt gcg tcc cgc cat cca ggg gga gac      240
Leu Val Leu Asp Ile Thr Asp Phe Ala Ser Arg His Pro Gly Gly Asp
65                  70                  75                  80 ctc atc ctc ctc gct tcc ggc aaa gac gcc tcg gtg ctg ttt gaa aca      288
Leu Ile Leu Leu Ala Ser Gly Lys Asp Ala Ser Val Leu Phe Glu Thr
                85                  90                  95 tac cat cca cgt gga gtt ccg acg tct ctc att caa aag ctg cag att      336
Tyr His Pro Arg Gly Val Pro Thr Ser Leu Ile Gln Lys Leu Gln Ile
            100                 105                 110 gga gtg atg gag gag gag gcg ttt cgg gat tcg ttt tac agt tgg act      384
Gly Val Met Glu Glu Glu Ala Phe Arg Asp Ser Phe Tyr Ser Trp Thr
        115                 120                 125 gat tct gac ttt tat act gtg ttg aag agg agg gtt gtg gag cgg ttg      432
Asp Ser Asp Phe Tyr Thr Val Leu Lys Arg Arg Val Val Glu Arg Leu
    130                 135                 140 gag gag agg ggg ttg gac agg agg gga tcg aaa gag att tgg atc aag      480
Glu Glu Arg Gly Leu Asp Arg Arg Gly Ser Lys Glu Ile Trp Ile Lys
145                 150                 155                 160 gct ttg ttc ttg ttg gtt gga ttt tgg tac tgt ttg tac aag atg tat      528
Ala Leu Phe Leu Leu Val Gly Phe Trp Tyr Cys Leu Tyr Lys Met Tyr
                165                 170                 175 act acg tcg gat atc gat cag tac ggt att gcc att gcc tat tct att      576
Thr Thr Ser Asp Ile Asp Gln Tyr Gly Ile Ala Ile Ala Tyr Ser Ile
            180                 185                 190
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gga | atg | gga | acc | ttt | gcg | gca | ttc | atc | ggc | acg | tgt | att | caa | cac | gat | 624 |
| Gly | Met | Gly | Thr | Phe | Ala | Ala | Phe | Ile | Gly | Thr | Cys | Ile | Gln | His | Asp | |
| | | 195 | | | | 200 | | | | 205 | | | | | | |
| gga | aat | cac | ggt | gca | ttc | gct | cag | aac | aag | tta | ctc | aac | aag | ttg | gct | 672 |
| Gly | Asn | His | Gly | Ala | Phe | Ala | Gln | Asn | Lys | Leu | Leu | Asn | Lys | Leu | Ala | |
| 210 | | | | | 215 | | | | | 220 | | | | | | |
| ggg | tgg | acg | ttg | gat | atg | att | ggt | gcg | agt | gcg | ttt | acg | tgg | gag | ctt | 720 |
| Gly | Trp | Thr | Leu | Asp | Met | Ile | Gly | Ala | Ser | Ala | Phe | Thr | Trp | Glu | Leu | |
| 225 | | | | | 230 | | | | | 235 | | | | | 240 | |
| cag | cac | atg | ctg | ggg | cat | cat | cca | tat | acg | aat | gtg | ttg | gat | ggg | gtg | 768 |
| Gln | His | Met | Leu | Gly | His | His | Pro | Tyr | Thr | Asn | Val | Leu | Asp | Gly | Val | |
| | | | | 245 | | | | | 250 | | | | | 255 | | |
| gag | gag | gag | agg | aag | gag | agg | ggg | gag | gat | gtt | gct | ttg | gaa | gaa | aag | 816 |
| Glu | Glu | Glu | Arg | Lys | Glu | Arg | Gly | Glu | Asp | Val | Ala | Leu | Glu | Glu | Lys | |
| | | | 260 | | | | | 265 | | | | | 270 | | | |
| gat | cag | gat | ttt | gaa | gtt | gcc | aca | tcc | gga | cga | tta | tat | cat | att | gat | 864 |
| Asp | Gln | Asp | Phe | Glu | Val | Ala | Thr | Ser | Gly | Arg | Leu | Tyr | His | Ile | Asp | |
| | | 275 | | | | 280 | | | | 285 | | | | | | |
| gcc | aat | gta | cgt | tat | ggt | tcg | gta | tgg | aat | gtc | atg | agg | ttt | tgg | gct | 912 |
| Ala | Asn | Val | Arg | Tyr | Gly | Ser | Val | Trp | Asn | Val | Met | Arg | Phe | Trp | Ala | |
| 290 | | | | | 295 | | | | | 300 | | | | | | |
| atg | aag | gtc | att | acg | atg | gga | tat | atg | atg | gga | tta | cca | atc | tac | ttt | 960 |
| Met | Lys | Val | Ile | Thr | Met | Gly | Tyr | Met | Met | Gly | Leu | Pro | Ile | Tyr | Phe | |
| 305 | | | | | 310 | | | | | 315 | | | | | 320 | |
| cat | gga | gta | ctg | agg | gga | gtt | gga | ttg | ttt | gtt | att | ggg | cat | ttg | gcg | 1008 |
| His | Gly | Val | Leu | Arg | Gly | Val | Gly | Leu | Phe | Val | Ile | Gly | His | Leu | Ala | |
| | | | | 325 | | | | | 330 | | | | | 335 | | |
| tgt | gga | gag | ttg | ttg | gcg | acg | atg | ttt | att | gtg | aat | cac | gtc | att | gag | 1056 |
| Cys | Gly | Glu | Leu | Leu | Ala | Thr | Met | Phe | Ile | Val | Asn | His | Val | Ile | Glu | |
| | | | 340 | | | | | 345 | | | | | 350 | | | |
| ggt | gtg | agt | tat | gga | acg | aag | gat | ttg | gtt | ggt | ggt | gcg | agt | cat | gta | 1104 |
| Gly | Val | Ser | Tyr | Gly | Thr | Lys | Asp | Leu | Val | Gly | Gly | Ala | Ser | His | Val | |
| | | 355 | | | | 360 | | | | 365 | | | | | | |
| gat | gag | aag | aag | att | gtc | aag | cca | acg | act | gta | ttg | gga | gat | aca | cca | 1152 |
| Asp | Glu | Lys | Lys | Ile | Val | Lys | Pro | Thr | Thr | Val | Leu | Gly | Asp | Thr | Pro | |
| 370 | | | | | 375 | | | | | 380 | | | | | | |
| atg | gta | aag | act | cgc | gag | gag | gca | ttg | aaa | agc | aac | agc | aat | aac | aac | 1200 |
| Met | Val | Lys | Thr | Arg | Glu | Glu | Ala | Leu | Lys | Ser | Asn | Ser | Asn | Asn | Asn | |
| 385 | | | | | 390 | | | | | 395 | | | | | 400 | |
| aag | aag | aag | gga | gag | aag | aac | tcg | gta | cca | tcc | gtt | cca | ttc | aac | gac | 1248 |
| Lys | Lys | Lys | Gly | Glu | Lys | Asn | Ser | Val | Pro | Ser | Val | Pro | Phe | Asn | Asp | |
| | | | | 405 | | | | | 410 | | | | | 415 | | |
| tgg | gca | gca | gtc | caa | tgc | cag | acc | tcc | gtg | aat | tgg | tct | cca | ggc | tca | 1296 |
| Trp | Ala | Ala | Val | Gln | Cys | Gln | Thr | Ser | Val | Asn | Trp | Ser | Pro | Gly | Ser | |
| | | | 420 | | | | | 425 | | | | | 430 | | | |
| tgg | ttc | tgg | aat | cac | ttt | tct | ggg | gga | ctc | tct | cat | cag | att | gag | cat | 1344 |
| Trp | Phe | Trp | Asn | His | Phe | Ser | Gly | Gly | Leu | Ser | His | Gln | Ile | Glu | His | |
| | | 435 | | | | 440 | | | | 445 | | | | | | |
| cac | ttg | ttc | ccc | agc | att | tgt | cat | aca | aac | tac | tgt | cat | atc | cag | gat | 1392 |
| His | Leu | Phe | Pro | Ser | Ile | Cys | His | Thr | Asn | Tyr | Cys | His | Ile | Gln | Asp | |
| 450 | | | | | 455 | | | | | 460 | | | | | | |
| gtt | gtg | gag | agt | acg | tgt | gct | gag | tac | gga | gtt | ccg | tat | cag | agt | gag | 1440 |
| Val | Val | Glu | Ser | Thr | Cys | Ala | Glu | Tyr | Gly | Val | Pro | Tyr | Gln | Ser | Glu | |
| 465 | | | | | 470 | | | | | 475 | | | | | 480 | |
| agt | aat | ttg | ttt | gtt | gct | tat | gga | aag | atg | att | agt | cat | ttg | aag | ttt | 1488 |
| Ser | Asn | Leu | Phe | Val | Ala | Tyr | Gly | Lys | Met | Ile | Ser | His | Leu | Lys | Phe | |
| | | | | 485 | | | | | 490 | | | | | 495 | | |
| ttg | ggt | aaa | gcc | aag | tgt | gag | tag | | | | | | | | | 1512 |
| Leu | Gly | Lys | Ala | Lys | Cys | Glu | | | | | | | | | | |

<210> SEQ ID NO 79
<211> LENGTH: 503
<212> TYPE: PRT
<213> ORGANISM: Thalassiosira pseudonana

<400> SEQUENCE: 79

```
Met Cys Asn Gly Asn Leu Pro Ala Ser Thr Ala Gln Leu Lys Ser Thr
1               5                   10                  15

Ser Lys Pro Gln Gln Gln His Glu His Arg Thr Ile Ser Lys Ser Glu
            20                  25                  30

Leu Ala Gln His Asn Thr Pro Lys Ser Ala Trp Cys Ala Val His Ser
        35                  40                  45

Thr Pro Ala Thr Asp Pro Ser His Ser Asn Asn Lys Gln His Ala His
    50                  55                  60

Leu Val Leu Asp Ile Thr Asp Phe Ala Ser Arg His Pro Gly Gly Asp
65                  70                  75                  80

Leu Ile Leu Leu Ala Ser Gly Lys Asp Ala Ser Val Leu Phe Glu Thr
                85                  90                  95

Tyr His Pro Arg Gly Val Pro Thr Ser Leu Ile Gln Lys Leu Gln Ile
            100                 105                 110

Gly Val Met Glu Glu Ala Phe Arg Asp Ser Phe Tyr Ser Trp Thr
        115                 120                 125

Asp Ser Asp Phe Tyr Thr Val Leu Lys Arg Arg Val Glu Arg Leu
    130                 135                 140

Glu Glu Arg Gly Leu Asp Arg Arg Gly Ser Lys Glu Ile Trp Ile Lys
145                 150                 155                 160

Ala Leu Phe Leu Leu Val Gly Phe Trp Tyr Cys Leu Tyr Lys Met Tyr
                165                 170                 175

Thr Thr Ser Asp Ile Asp Gln Tyr Gly Ile Ala Ile Ala Tyr Ser Ile
            180                 185                 190

Gly Met Gly Thr Phe Ala Ala Phe Ile Gly Thr Cys Ile Gln His Asp
        195                 200                 205

Gly Asn His Gly Ala Phe Ala Gln Asn Lys Leu Leu Asn Lys Leu Ala
    210                 215                 220

Gly Trp Thr Leu Asp Met Ile Gly Ala Ser Ala Phe Thr Trp Glu Leu
225                 230                 235                 240

Gln His Met Leu Gly His His Pro Tyr Thr Asn Val Leu Asp Gly Val
                245                 250                 255

Glu Glu Glu Arg Lys Glu Arg Gly Glu Asp Val Ala Leu Glu Glu Lys
            260                 265                 270

Asp Gln Asp Phe Glu Val Ala Thr Ser Gly Arg Leu Tyr His Ile Asp
    275                 280                 285

Ala Asn Val Arg Tyr Gly Ser Val Trp Asn Val Met Arg Phe Trp Ala
    290                 295                 300

Met Lys Val Ile Thr Met Gly Tyr Met Met Gly Leu Pro Ile Tyr Phe
305                 310                 315                 320

His Gly Val Leu Arg Gly Val Gly Leu Phe Val Ile Gly His Leu Ala
                325                 330                 335

Cys Gly Glu Leu Leu Ala Thr Met Phe Ile Val Asn His Val Ile Glu
            340                 345                 350

Gly Val Ser Tyr Gly Thr Lys Asp Leu Val Gly Gly Ala Ser His Val
    355                 360                 365
```

```
Asp Glu Lys Lys Ile Val Lys Pro Thr Thr Val Leu Gly Asp Thr Pro
    370                 375                 380

Met Val Lys Thr Arg Glu Glu Ala Leu Lys Ser Asn Ser Asn Asn Asn
385                 390                 395                 400

Lys Lys Lys Gly Glu Lys Asn Ser Val Pro Ser Val Pro Phe Asn Asp
                405                 410                 415

Trp Ala Val Gln Cys Gln Thr Ser Val Asn Trp Ser Pro Gly Ser
            420                 425                 430

Trp Phe Trp Asn His Phe Ser Gly Gly Leu Ser His Gln Ile Glu His
        435                 440                 445

His Leu Phe Pro Ser Ile Cys His Thr Asn Tyr Cys His Ile Gln Asp
    450                 455                 460

Val Val Glu Ser Thr Cys Ala Glu Tyr Gly Val Pro Tyr Gln Ser Glu
465                 470                 475                 480

Ser Asn Leu Phe Val Ala Tyr Gly Lys Met Ile Ser His Leu Lys Phe
                485                 490                 495

Leu Gly Lys Ala Lys Cys Glu
            500

<210> SEQ ID NO 80
<211> LENGTH: 1626
<212> TYPE: DNA
<213> ORGANISM: Euglena gracilis
<220> FEATURE:
<221> NAME/KEY: CDS
<222> LOCATION: (1)..(1626)
<223> OTHER INFORMATION: delta-4-Desaturase

<400> SEQUENCE: 80 atg ttg gtg ctg ttt ggc aat ttc tat gtc aag caa tac tcc caa aag      48
Met Leu Val Leu Phe Gly Asn Phe Tyr Val Lys Gln Tyr Ser Gln Lys
1               5                   10                  15 aac ggc aag ccg gag aac gga gcc acc cct gag aac gga gcg aag ccg      96
Asn Gly Lys Pro Glu Asn Gly Ala Thr Pro Glu Asn Gly Ala Lys Pro
            20                  25                  30 caa cct tgc gag aac ggc acg gtg gaa aag cga gag aat gac acc gcc     144
Gln Pro Cys Glu Asn Gly Thr Val Glu Lys Arg Glu Asn Asp Thr Ala
        35                  40                  45 aac gtt cgg ccc acc cgt cca gct gga ccc ccg ccg gcc acg tac tac     192
Asn Val Arg Pro Thr Arg Pro Ala Gly Pro Pro Pro Ala Thr Tyr Tyr
    50                  55                  60 gac tcc ctg gca gtg tcg ggg cag ggc aag gag cgg ctg ttc acc acc     240
Asp Ser Leu Ala Val Ser Gly Gln Gly Lys Glu Arg Leu Phe Thr Thr
65                  70                  75                  80 gat gag gtg agg cgg cac atc ctc ccc acc gat ggc tgg ctg acg tgc     288
Asp Glu Val Arg Arg His Ile Leu Pro Thr Asp Gly Trp Leu Thr Cys
                85                  90                  95 cac gaa gga gtc tac gat gtc act gat ttc ctt gcc aag cac cct ggt     336
His Glu Gly Val Tyr Asp Val Thr Asp Phe Leu Ala Lys His Pro Gly
            100                 105                 110 ggc ggt gtc atc acg ctg ggc ctt gga agg gac tgc aca atc ctc atc     384
Gly Gly Val Ile Thr Leu Gly Leu Gly Arg Asp Cys Thr Ile Leu Ile
        115                 120                 125 gag tca tac cac cct gct ggg cgc ccg gac aag gtg atg gag aag tac     432
Glu Ser Tyr His Pro Ala Gly Arg Pro Asp Lys Val Met Glu Lys Tyr
    130                 135                 140 cgc att ggt acg ctg cag gac ccc aag acg ttc tat gct tgg gga gag     480
Arg Ile Gly Thr Leu Gln Asp Pro Lys Thr Phe Tyr Ala Trp Gly Glu
145                 150                 155                 160
```

| | | |
|---|---|---|
| tcc gat ttc tac cct gag ttg aag cgc cgg gcc ctt gca agg ctg aag<br>Ser Asp Phe Tyr Pro Glu Leu Lys Arg Arg Ala Leu Ala Arg Leu Lys<br>                     165                     170                     175 | | 528 |
| gag gct ggt cag gcg cgg cgc ggc ctt ggg gtg aag gcc ctc ctg<br>Glu Ala Gly Gln Ala Arg Arg Gly Gly Leu Gly Val Lys Ala Leu Leu<br>                     180                     185                     190 | | 576 |
| gtg ctc acc ctc ttc ttc gtg tcg tgg tac atg tgg gtg gcc cac aag<br>Val Leu Thr Leu Phe Phe Val Ser Trp Tyr Met Trp Val Ala His Lys<br>                195                     200                     205 | | 624 |
| tcc ttc ctc tgg gcc gcc gtc tgg ggc ttc gcc ggc tcc cac gtc ggg<br>Ser Phe Leu Trp Ala Ala Val Trp Gly Phe Ala Gly Ser His Val Gly<br>       210                     215                     220 | | 672 |
| ctg agc atc cag cac gat ggc aac cac ggc gcg ttc agc cgc aac aca<br>Leu Ser Ile Gln His Asp Gly Asn His Gly Ala Phe Ser Arg Asn Thr<br>225                     230                     235                     240 | | 720 |
| ctg gtg aac cgc ctg gcg ggg tgg ggc atg gac ttg atc ggc gcg tcg<br>Leu Val Asn Arg Leu Ala Gly Trp Gly Met Asp Leu Ile Gly Ala Ser<br>                     245                     250                     255 | | 768 |
| tcc acg gtg tgg gag tac cag cac gtc atc ggc cac cac cag tac acc<br>Ser Thr Val Trp Glu Tyr Gln His Val Ile Gly His His Gln Tyr Thr<br>                     260                     265                     270 | | 816 |
| aac ctc gtg tcg gac acg cta ttc agt ctg cct gag aac gat ccg gac<br>Asn Leu Val Ser Asp Thr Leu Phe Ser Leu Pro Glu Asn Asp Pro Asp<br>                275                     280                     285 | | 864 |
| gtc ttc tcc agc tac ccg ctg atg cgc atg cac ccg gat acg gcg tgg<br>Val Phe Ser Ser Tyr Pro Leu Met Arg Met His Pro Asp Thr Ala Trp<br>       290                     295                     300 | | 912 |
| cag ccg cac cac cgc ttc cag cac ctg ttc gcg ttc cca ctg ttc gcc<br>Gln Pro His His Arg Phe Gln His Leu Phe Ala Phe Pro Leu Phe Ala<br>305                     310                     315                     320 | | 960 |
| ctg atg aca atc agc aag gtg ctg acc agc gat ttc gct gtc tgc ctc<br>Leu Met Thr Ile Ser Lys Val Leu Thr Ser Asp Phe Ala Val Cys Leu<br>                     325                     330                     335 | | 1008 |
| agc atg aag aag ggg tcc atc gac tgc tcc tcc agg ctc gtc cca ctg<br>Ser Met Lys Lys Gly Ser Ile Asp Cys Ser Ser Arg Leu Val Pro Leu<br>                     340                     345                     350 | | 1056 |
| gag ggg cag ctg ctg ttc tgg ggg gcc aag ctg gcg aac ttc ctg ttg<br>Glu Gly Gln Leu Leu Phe Trp Gly Ala Lys Leu Ala Asn Phe Leu Leu<br>                355                     360                     365 | | 1104 |
| cag att gtg ttg cca tgc tac ctc cac ggg aca gct atg ggc ctg gcc<br>Gln Ile Val Leu Pro Cys Tyr Leu His Gly Thr Ala Met Gly Leu Ala<br>       370                     375                     380 | | 1152 |
| ctc ttc tct gtt gct cac ctt gtg tcg ggg gag tac ctc gcg atc tgc<br>Leu Phe Ser Val Ala His Leu Val Ser Gly Glu Tyr Leu Ala Ile Cys<br>385                     390                     395                     400 | | 1200 |
| ttc atc atc aac cac atc agc gag tct tgt gag ttt atg aat aca agc<br>Phe Ile Ile Asn His Ile Ser Glu Ser Cys Glu Phe Met Asn Thr Ser<br>                     405                     410                     415 | | 1248 |
| ttt caa acc gcc gcc cgg agg aca gag atg ctt cag gca gca cat cag<br>Phe Gln Thr Ala Ala Arg Arg Thr Glu Met Leu Gln Ala Ala His Gln<br>                     420                     425                     430 | | 1296 |
| gca gcg gag gcc aag aag gtg aag ccc acc cct cca ccg aac gat tgg<br>Ala Ala Glu Ala Lys Lys Val Lys Pro Thr Pro Pro Pro Asn Asp Trp<br>                     435                     440                     445 | | 1344 |
| gct gtg aca cag gtc caa tgc tgc gtg aat tgg aga tca ggt ggc gtg<br>Ala Val Thr Gln Val Gln Cys Cys Val Asn Trp Arg Ser Gly Gly Val<br>       450                     455                     460 | | 1392 |
| ttg gcc aat cac ctc tct gga ggc ttg aac cac cag atc gag cat cat<br>Leu Ala Asn His Leu Ser Gly Gly Leu Asn His Gln Ile Glu His His<br>465                     470                     475                     480 | | 1440 |

```
ctg ttc ccc agc atc tcg cat gcc aac tac ccc acc atc gcc cct gtt    1488
Leu Phe Pro Ser Ile Ser His Ala Asn Tyr Pro Thr Ile Ala Pro Val
            485                 490                 495 gtg aag gag gtg tgc gag gag tac ggg ttg ccg tac aag aat tac gtc    1536
Val Lys Glu Val Cys Glu Glu Tyr Gly Leu Pro Tyr Lys Asn Tyr Val
                500                 505                 510 acg ttc tgg gat gca gtc tgt ggc atg gtt cag cac ctc cgg ttg atg    1584
Thr Phe Trp Asp Ala Val Cys Gly Met Val Gln His Leu Arg Leu Met
            515                 520                 525 ggt gct cca ccg gtg cca acg aac ggg gac aaa aag tca taa            1626
Gly Ala Pro Pro Val Pro Thr Asn Gly Asp Lys Lys Ser
            530                 535                 540

<210> SEQ ID NO 81
<211> LENGTH: 541
<212> TYPE: PRT
<213> ORGANISM: Euglena gracilis

<400> SEQUENCE: 81

Met Leu Val Leu Phe Gly Asn Phe Tyr Val Lys Gln Tyr Ser Gln Lys
1               5                   10                  15

Asn Gly Lys Pro Glu Asn Gly Ala Thr Pro Glu Asn Gly Ala Lys Pro
            20                  25                  30

Gln Pro Cys Glu Asn Gly Thr Val Glu Lys Arg Glu Asn Asp Thr Ala
        35                  40                  45

Asn Val Arg Pro Thr Arg Pro Ala Gly Pro Pro Ala Thr Tyr Tyr
    50                  55                  60

Asp Ser Leu Ala Val Ser Gly Gln Gly Lys Glu Arg Leu Phe Thr Thr
65                  70                  75                  80

Asp Glu Val Arg Arg His Ile Leu Pro Thr Asp Gly Trp Leu Thr Cys
                85                  90                  95

His Glu Gly Val Tyr Asp Val Thr Asp Phe Leu Ala Lys His Pro Gly
            100                 105                 110

Gly Gly Val Ile Thr Leu Gly Leu Gly Arg Asp Cys Thr Ile Leu Ile
        115                 120                 125

Glu Ser Tyr His Pro Ala Gly Arg Pro Asp Lys Val Met Glu Lys Tyr
    130                 135                 140

Arg Ile Gly Thr Leu Gln Asp Pro Lys Thr Phe Tyr Ala Trp Gly Glu
145                 150                 155                 160

Ser Asp Phe Tyr Pro Glu Leu Lys Arg Arg Ala Leu Ala Arg Leu Lys
                165                 170                 175

Glu Ala Gly Gln Ala Arg Arg Gly Gly Leu Gly Val Lys Ala Leu Leu
            180                 185                 190

Val Leu Thr Leu Phe Phe Val Ser Trp Tyr Met Trp Val Ala His Lys
        195                 200                 205

Ser Phe Leu Trp Ala Ala Val Trp Gly Phe Ala Gly Ser His Val Gly
    210                 215                 220

Leu Ser Ile Gln His Asp Gly Asn His Gly Ala Phe Ser Arg Asn Thr
225                 230                 235                 240

Leu Val Asn Arg Leu Ala Gly Trp Gly Met Asp Leu Ile Gly Ala Ser
                245                 250                 255

Ser Thr Val Trp Glu Tyr Gln His Val Ile Gly His His Gln Tyr Thr
            260                 265                 270

Asn Leu Val Ser Asp Thr Leu Phe Ser Leu Pro Glu Asn Asp Pro Asp
        275                 280                 285
```

```
Val Phe Ser Ser Tyr Pro Leu Met Arg Met His Pro Asp Thr Ala Trp
    290                 295                 300

Gln Pro His His Arg Phe Gln His Leu Phe Ala Phe Pro Leu Phe Ala
305                 310                 315                 320

Leu Met Thr Ile Ser Lys Val Leu Thr Ser Asp Phe Ala Val Cys Leu
                325                 330                 335

Ser Met Lys Lys Gly Ser Ile Asp Cys Ser Ser Arg Leu Val Pro Leu
            340                 345                 350

Glu Gly Gln Leu Leu Phe Trp Gly Ala Lys Leu Ala Asn Phe Leu Leu
        355                 360                 365

Gln Ile Val Leu Pro Cys Tyr Leu His Gly Thr Ala Met Gly Leu Ala
    370                 375                 380

Leu Phe Ser Val Ala His Leu Val Ser Gly Glu Tyr Leu Ala Ile Cys
385                 390                 395                 400

Phe Ile Ile Asn His Ile Ser Glu Ser Cys Glu Phe Met Asn Thr Ser
                405                 410                 415

Phe Gln Thr Ala Ala Arg Arg Thr Glu Met Leu Gln Ala Ala His Gln
            420                 425                 430

Ala Ala Glu Ala Lys Lys Val Lys Pro Thr Pro Pro Asn Asp Trp
        435                 440                 445

Ala Val Thr Gln Val Gln Cys Cys Val Asn Trp Arg Ser Gly Val
    450                 455                 460

Leu Ala Asn His Leu Ser Gly Gly Leu Asn His Gln Ile Glu His His
465                 470                 475                 480

Leu Phe Pro Ser Ile Ser His Ala Asn Tyr Pro Thr Ile Ala Pro Val
                485                 490                 495

Val Lys Glu Val Cys Glu Glu Tyr Gly Leu Pro Tyr Lys Asn Tyr Val
            500                 505                 510

Thr Phe Trp Asp Ala Val Cys Gly Met Val Gln His Leu Arg Leu Met
        515                 520                 525

Gly Ala Pro Pro Val Pro Thr Asn Gly Asp Lys Lys Ser
    530                 535                 540

<210> SEQ ID NO 82
<211> LENGTH: 1548
<212> TYPE: DNA
<213> ORGANISM: Thraustochytrium
<220> FEATURE:
<221> NAME/KEY: CDS
<222> LOCATION: (1)..(1548)
<223> OTHER INFORMATION: delta-4-Desaturase

<400> SEQUENCE: 82 atg acg gtc ggg ttt gac gaa acg gtg act atg gac acg gtc cgc aac      48
Met Thr Val Gly Phe Asp Glu Thr Val Thr Met Asp Thr Val Arg Asn
1               5                   10                  15 cac aac atg ccg gac gac gcc tgg tgc gcg atc cac ggc acc gtg tac      96
His Asn Met Pro Asp Asp Ala Trp Cys Ala Ile His Gly Thr Val Tyr
            20                  25                  30 gac atc acc aag ttc agc aag gtg cac ccc ggc ggg gac atc atc atg     144
Asp Ile Thr Lys Phe Ser Lys Val His Pro Gly Gly Asp Ile Ile Met
        35                  40                  45 ctg gcc gct ggc aag gag gcc acc atc ctg ttc gag acc tac cac atc     192
Leu Ala Ala Gly Lys Glu Ala Thr Ile Leu Phe Glu Thr Tyr His Ile
    50                  55                  60 aag ggc gtc ccg gac gcg gtg ctg cgc aag tac aag gtc ggc aag ctc     240
Lys Gly Val Pro Asp Ala Val Leu Arg Lys Tyr Lys Val Gly Lys Leu
65                  70                  75                  80
```

```
ccc cag ggc aag aag ggc gaa acg agc cac atg ccc acc ggg ctc gac        288
Pro Gln Gly Lys Lys Gly Glu Thr Ser His Met Pro Thr Gly Leu Asp
                85                  90                  95 tcg gcc tcc tac tac tcg tgg gac agc gag ttt tac agg gtc ctc cgc        336
Ser Ala Ser Tyr Tyr Ser Trp Asp Ser Glu Phe Tyr Arg Val Leu Arg
            100                 105                 110 gag cgc gtc gcc aag aag ctg gcc gag ccc ggc ctc atg cag cgc gcg        384
Glu Arg Val Ala Lys Lys Leu Ala Glu Pro Gly Leu Met Gln Arg Ala
        115                 120                 125 cgc atg gag ctc tgg gcc aag gcg atc ttc ctc ctg gca ggt ttc tgg        432
Arg Met Glu Leu Trp Ala Lys Ala Ile Phe Leu Leu Ala Gly Phe Trp
130                 135                 140 ggc tcc ctt tac gcc atg tgc gtg cta gac ccg cac ggc ggt gcc atg        480
Gly Ser Leu Tyr Ala Met Cys Val Leu Asp Pro His Gly Gly Ala Met
145                 150                 155                 160 gta gcc gcc gtt acg ctc ggc gtg ttc gct gcc ttt gtc gga act tgc        528
Val Ala Ala Val Thr Leu Gly Val Phe Ala Ala Phe Val Gly Thr Cys
                165                 170                 175 atc cag cac gac ggc agc cac ggc gcc ttc tcc aag tcg cga ttc atg        576
Ile Gln His Asp Gly Ser His Gly Ala Phe Ser Lys Ser Arg Phe Met
            180                 185                 190 aac aag gcg gcg ggc tgg acc ctc gac atg atc ggc gcg agt gcg atg        624
Asn Lys Ala Ala Gly Trp Thr Leu Asp Met Ile Gly Ala Ser Ala Met
        195                 200                 205 acc tgg gag atg cag cac gtt ctt ggc cac cac ccg tac acc aac ctc        672
Thr Trp Glu Met Gln His Val Leu Gly His His Pro Tyr Thr Asn Leu
210                 215                 220 atc gag atg gag aac ggt ttg gcc aag gtc aag ggc gcc gac gtc gac        720
Ile Glu Met Glu Asn Gly Leu Ala Lys Val Lys Gly Ala Asp Val Asp
225                 230                 235                 240 ccg aag aag gtc gac cag gag agc gac ccg gac gtc ttc agt acg tac        768
Pro Lys Lys Val Asp Gln Glu Ser Asp Pro Asp Val Phe Ser Thr Tyr
                245                 250                 255 ccg atg ctt cgc ctg cac ccg tgg cac cgc cag cgg ttt tac cac aag        816
Pro Met Leu Arg Leu His Pro Trp His Arg Gln Arg Phe Tyr His Lys
            260                 265                 270 ttc cag cac ctg tac gcc ccg ttt atc ttt ggg tct atg acg att aac        864
Phe Gln His Leu Tyr Ala Pro Phe Ile Phe Gly Ser Met Thr Ile Asn
        275                 280                 285 aag gtg att tcc cag gat gtc ggg gtt gtg ctg cgc aag cgc ctg ttc        912
Lys Val Ile Ser Gln Asp Val Gly Val Val Leu Arg Lys Arg Leu Phe
290                 295                 300 cag atc gac gcc aac tgc cgg tat ggc agc ccc tgg tac gtg gcc cgc        960
Gln Ile Asp Ala Asn Cys Arg Tyr Gly Ser Pro Trp Tyr Val Ala Arg
305                 310                 315                 320 ttc tgg atc atg aag ctc ctc acc acg ctc tac atg gtg gcg ctt ccc       1008
Phe Trp Ile Met Lys Leu Leu Thr Thr Leu Tyr Met Val Ala Leu Pro
                325                 330                 335 atg tac atg cag ggg cct gct cag ggc ttg aag ctt ttc ttc atg gcc       1056
Met Tyr Met Gln Gly Pro Ala Gln Gly Leu Lys Leu Phe Phe Met Ala
            340                 345                 350 cac ttc acc tgc gga gag gtc ctc gcc acc atg ttt att gtc aac cac       1104
His Phe Thr Cys Gly Glu Val Leu Ala Thr Met Phe Ile Val Asn His
        355                 360                 365 atc atc gag ggc gtc agc tac gct tcc aag gac gcg gtc aag ggc gtc       1152
Ile Ile Glu Gly Val Ser Tyr Ala Ser Lys Asp Ala Val Lys Gly Val
370                 375                 380 atg gct ccg ccg cgc act gtg cac ggt gtc acc ccg atg cag gtg acg       1200
Met Ala Pro Pro Arg Thr Val His Gly Val Thr Pro Met Gln Val Thr
```

-continued

```
                385                 390                 395                 400
caa aag gcg ctc agt gcg gcc gag tcg gcc aag tcg gac gcc gac aag        1248
Gln Lys Ala Leu Ser Ala Ala Glu Ser Ala Lys Ser Asp Ala Asp Lys
                405                 410                 415 acg acc atg atc ccc ctc aac gac tgg gcc gct gtg cag tgc cag acc        1296
Thr Thr Met Ile Pro Leu Asn Asp Trp Ala Ala Val Gln Cys Gln Thr
            420                 425                 430 tct gtg aac tgg gct gtc ggg tcg tgg ttt tgg aac cac ttt tcg ggc        1344
Ser Val Asn Trp Ala Val Gly Ser Trp Phe Trp Asn His Phe Ser Gly
        435                 440                 445 ggc ctc aac cac cag att gag cac cac tgc ttc ccc caa aac ccc cac        1392
Gly Leu Asn His Gln Ile Glu His His Cys Phe Pro Gln Asn Pro His
    450                 455                 460 acg gtc aac gtc tac atc tcg ggc atc gtc aag gag acc tgc gaa gaa        1440
Thr Val Asn Val Tyr Ile Ser Gly Ile Val Lys Glu Thr Cys Glu Glu
465                 470                 475                 480 tac ggc gtg ccg tac cag gct gag atc agc ctc ttc tct gcc tat ttc        1488
Tyr Gly Val Pro Tyr Gln Ala Glu Ile Ser Leu Phe Ser Ala Tyr Phe
                485                 490                 495 aag atg ctg tcg cac ctc cgc acg ctc ggc aac gag gac ctc acg gcc        1536
Lys Met Leu Ser His Leu Arg Thr Leu Gly Asn Glu Asp Leu Thr Ala
            500                 505                 510 tgg tcc acg tga                                                         1548
Trp Ser Thr
        515

<210> SEQ ID NO 83
<211> LENGTH: 515
<212> TYPE: PRT
<213> ORGANISM: Thraustochytrium

<400> SEQUENCE: 83

Met Thr Val Gly Phe Asp Glu Thr Val Thr Met Asp Thr Val Arg Asn
1               5                   10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
        35                  40                  45

Leu Ala Ala Gly Lys Glu Ala Thr Ile Leu Phe Glu Thr Tyr His Ile
    50                  55                  60

Lys Gly Val Pro Asp Ala Val Leu Arg Lys Tyr Lys Val Gly Lys Leu
65                  70                  75                  80

Pro Gln Gly Lys Lys Gly Glu Thr Ser His Met Pro Thr Gly Leu Asp
            85                  90                  95

Ser Ala Ser Tyr Tyr Ser Trp Asp Ser Glu Phe Tyr Arg Val Leu Arg
        100                 105                 110

Glu Arg Val Ala Lys Lys Leu Ala Glu Pro Gly Leu Met Gln Arg Ala
    115                 120                 125

Arg Met Glu Leu Trp Ala Lys Ala Ile Phe Leu Leu Ala Gly Phe Trp
130                 135                 140

Gly Ser Leu Tyr Ala Met Cys Val Leu Asp Pro His Gly Gly Ala Met
145                 150                 155                 160

Val Ala Ala Val Thr Leu Gly Val Phe Ala Phe Val Gly Thr Cys
            165                 170                 175

Ile Gln His Asp Gly Ser His Gly Ala Phe Ser Lys Ser Arg Phe Met
        180                 185                 190

Asn Lys Ala Ala Gly Trp Thr Leu Asp Met Ile Gly Ala Ser Ala Met
```

```
                    195                 200                 205
Thr Trp Glu Met Gln His Val Leu Gly His His Pro Tyr Thr Asn Leu
    210                 215                 220

Ile Glu Met Glu Asn Gly Leu Ala Lys Val Lys Gly Ala Asp Val Asp
225                 230                 235                 240

Pro Lys Lys Val Asp Gln Glu Ser Asp Pro Asp Val Phe Ser Thr Tyr
                245                 250                 255

Pro Met Leu Arg Leu His Pro Trp His Arg Gln Arg Phe Tyr His Lys
                260                 265                 270

Phe Gln His Leu Tyr Ala Pro Phe Ile Phe Gly Ser Met Thr Ile Asn
            275                 280                 285

Lys Val Ile Ser Gln Asp Val Gly Val Val Leu Arg Lys Arg Leu Phe
    290                 295                 300

Gln Ile Asp Ala Asn Cys Arg Tyr Gly Ser Pro Trp Tyr Val Ala Arg
305                 310                 315                 320

Phe Trp Ile Met Lys Leu Leu Thr Thr Leu Tyr Met Val Ala Leu Pro
                325                 330                 335

Met Tyr Met Gln Gly Pro Ala Gln Gly Leu Lys Leu Phe Phe Met Ala
                340                 345                 350

His Phe Thr Cys Gly Glu Val Leu Ala Thr Met Phe Ile Val Asn His
            355                 360                 365

Ile Ile Glu Gly Val Ser Tyr Ala Ser Lys Asp Ala Val Lys Gly Val
    370                 375                 380

Met Ala Pro Pro Arg Thr Val His Gly Val Thr Pro Met Gln Val Thr
385                 390                 395                 400

Gln Lys Ala Leu Ser Ala Ala Glu Ser Ala Lys Ser Asp Ala Asp Lys
                405                 410                 415

Thr Thr Met Ile Pro Leu Asn Asp Trp Ala Ala Val Gln Cys Gln Thr
                420                 425                 430

Ser Val Asn Trp Ala Val Gly Ser Trp Phe Trp Asn His Phe Ser Gly
            435                 440                 445

Gly Leu Asn His Gln Ile Glu His His Cys Phe Pro Gln Asn Pro His
    450                 455                 460

Thr Val Asn Val Tyr Ile Ser Gly Ile Val Lys Glu Thr Cys Glu Glu
465                 470                 475                 480

Tyr Gly Val Pro Tyr Gln Ala Glu Ile Ser Leu Phe Ser Ala Tyr Phe
                485                 490                 495

Lys Met Leu Ser His Leu Arg Thr Leu Gly Asn Glu Asp Leu Thr Ala
                500                 505                 510

Trp Ser Thr
        515

<210> SEQ ID NO 84
<211> LENGTH: 1611
<212> TYPE: DNA
<213> ORGANISM: Ostreococcus tauri
<220> FEATURE:
<221> NAME/KEY: CDS
<222> LOCATION: (1)..(1611)
<223> OTHER INFORMATION: delta-4-Desaturase

<400> SEQUENCE: 84 atg tac ctc gga cgc ggc cgt ctc gag agc ggg acg acg cga ggg atg        48
Met Tyr Leu Gly Arg Gly Arg Leu Glu Ser Gly Thr Thr Arg Gly Met
1               5                   10                  15 atg cgg acg cac gcg cgg cga ccg tcg acg acg tcg aat ccg tgc gcg        96
```

```
Met Arg Thr His Ala Arg Arg Pro Ser Thr Thr Ser Asn Pro Cys Ala
            20                  25                  30 cgg tca cgc gtg cgt aag acg acg gag cga tcg ctc gcg cga gtg cga       144
Arg Ser Arg Val Arg Lys Thr Thr Glu Arg Ser Leu Ala Arg Val Arg
        35                  40                  45 cga tcg acg agt gag aag gga agc gcg ctc gtg ctc gag cga gag agc       192
Arg Ser Thr Ser Glu Lys Gly Ser Ala Leu Val Leu Glu Arg Glu Ser
50                  55                  60 gaa cgg gag aag gag gag gga ggg aaa gcg cga gcg gag gga ttg cga       240
Glu Arg Glu Lys Glu Glu Gly Gly Lys Ala Arg Ala Glu Gly Leu Arg
65                  70                  75                  80 ttc caa cgc ccg gac gtc gcc gcg ccg ggg gga gcg gat cct tgg aac       288
Phe Gln Arg Pro Asp Val Ala Ala Pro Gly Gly Ala Asp Pro Trp Asn
                85                  90                  95 gac gag aag tgg aca aag acc aag tgg acg gta ttc aga gac gtc gcg       336
Asp Glu Lys Trp Thr Lys Thr Lys Trp Thr Val Phe Arg Asp Val Ala
            100                 105                 110 tac gat ctc gat cct ttc ttc gct cga cac ccc gga gga gac tgg ctc       384
Tyr Asp Leu Asp Pro Phe Phe Ala Arg His Pro Gly Gly Asp Trp Leu
        115                 120                 125 ctg aac ttg gcc gtg gga cga gac tgc acc gcg ctc atc gaa tcc tat       432
Leu Asn Leu Ala Val Gly Arg Asp Cys Thr Ala Leu Ile Glu Ser Tyr
130                 135                 140 cac ttg cga cca gag gtg gcg acg gct cgt ttc aga atg ctg ccc aaa       480
His Leu Arg Pro Glu Val Ala Thr Ala Arg Phe Arg Met Leu Pro Lys
145                 150                 155                 160 ctc gag gat ttt ccc gtc gag gcc gtg ccc aag tcc ccg aga ccg aac       528
Leu Glu Asp Phe Pro Val Glu Ala Val Pro Lys Ser Pro Arg Pro Asn
                165                 170                 175 gat tcg ccg tta tac aac aac att cgc aac cga gtc cgc gaa gag ctc       576
Asp Ser Pro Leu Tyr Asn Asn Ile Arg Asn Arg Val Arg Glu Glu Leu
            180                 185                 190 ttc cca gag gag gga aag aat atg cac aga cag ggc ggc gac cac ggc       624
Phe Pro Glu Glu Gly Lys Asn Met His Arg Gln Gly Gly Asp His Gly
        195                 200                 205 gac ggt gac gat tct ggg ttt cgc cgc ctt ttg ctt atg ccg tgt acc       672
Asp Gly Asp Asp Ser Gly Phe Arg Arg Leu Leu Leu Met Pro Cys Thr
210                 215                 220 tat tcc ctt ccg ggg gtt cct ttc cgg ctg cct cct cgg gtc tcg cgg       720
Tyr Ser Leu Pro Gly Val Pro Phe Arg Leu Pro Pro Arg Val Ser Arg
225                 230                 235                 240 ggg cgt gga ttg gtc tca cga ttc agg cac tgc gcc aac cac ggc gcg       768
Gly Arg Gly Leu Val Ser Arg Phe Arg His Cys Ala Asn His Gly Ala
                245                 250                 255 atg tct cct tcg ccg gcc gtt aac ggc gtc ctc ggt ttg acg aac gat       816
Met Ser Pro Ser Pro Ala Val Asn Gly Val Leu Gly Leu Thr Asn Asp
            260                 265                 270 ctc atc ggc ggc tcg tcc ttg atg tgg aga tat cac cac caa gtc agc       864
Leu Ile Gly Gly Ser Ser Leu Met Trp Arg Tyr His His Gln Val Ser
        275                 280                 285 cac cac att cat tgc aac gac aac gcc atg gat caa gac gtg tac acg       912
His His Ile His Cys Asn Asp Asn Ala Met Asp Gln Asp Val Tyr Thr
290                 295                 300 gcg atg cca tta ttg cgt ttc gac gct cgc cgg ccc aag tcc tgg tac       960
Ala Met Pro Leu Leu Arg Phe Asp Ala Arg Arg Pro Lys Ser Trp Tyr
305                 310                 315                 320 cat cgc ttc cag cag tgg tac atg ttt tta gcg ttc ccg ttg ttg cag      1008
His Arg Phe Gln Gln Trp Tyr Met Phe Leu Ala Phe Pro Leu Leu Gln
                325                 330                 335
```

| | | | | | | | | | | | | | | | | |
|---|---|---|---|---|---|---|---|---|---|---|---|---|---|---|---|---|
| gtt | gcc | ttc | caa | gtc | gga | gac | att | gcc | gca | ctg | ttc | acg | cgt | gat | acc | 1056 |
| Val | Ala | Phe | Gln | Val | Gly | Asp | Ile | Ala | Ala | Leu | Phe | Thr | Arg | Asp | Thr | |
| | | | 340 | | | | | 345 | | | | | 350 | | | |
| gaa | ggc | gct | aag | ctt | cac | ggg | gcg | acg | acg | tgg | gag | ctt | acc | acg | gtt | 1104 |
| Glu | Gly | Ala | Lys | Leu | His | Gly | Ala | Thr | Thr | Trp | Glu | Leu | Thr | Thr | Val | |
| | 355 | | | | | 360 | | | | | 365 | | | | | |
| gtc | ctc | ggt | aag | att | gtg | cac | ttc | ggt | ctt | ttg | ttg | ggg | ccg | ttg | atg | 1152 |
| Val | Leu | Gly | Lys | Ile | Val | His | Phe | Gly | Leu | Leu | Leu | Gly | Pro | Leu | Met | |
| 370 | | | | | 375 | | | | | 380 | | | | | | |
| aac | cac | gcg | gtg | agt | tct | gtt | ttg | ctg | ggg | atc | gtc | ggt | ttc | atg | gcg | 1200 |
| Asn | His | Ala | Val | Ser | Ser | Val | Leu | Leu | Gly | Ile | Val | Gly | Phe | Met | Ala | |
| 385 | | | | | 390 | | | | | 395 | | | | | 400 | |
| tgc | caa | ggt | ata | gtt | ctg | gcg | tgc | acg | ttt | gct | gtg | agt | cac | aat | gtc | 1248 |
| Cys | Gln | Gly | Ile | Val | Leu | Ala | Cys | Thr | Phe | Ala | Val | Ser | His | Asn | Val | |
| | | | | 405 | | | | | 410 | | | | | 415 | | |
| gcg | gag | gcg | aag | ata | cct | gag | gac | acc | gga | gga | gaa | gcc | tgg | gag | aga | 1296 |
| Ala | Glu | Ala | Lys | Ile | Pro | Glu | Asp | Thr | Gly | Gly | Glu | Ala | Trp | Glu | Arg | |
| | | | 420 | | | | | 425 | | | | | 430 | | | |
| gat | tgg | ggt | gtc | cag | cag | ttg | gtg | act | agc | gcc | gac | tgg | ggt | gga | aag | 1344 |
| Asp | Trp | Gly | Val | Gln | Gln | Leu | Val | Thr | Ser | Ala | Asp | Trp | Gly | Gly | Lys | |
| | 435 | | | | | 440 | | | | | 445 | | | | | |
| ata | ggt | aac | ttc | ttc | acg | ggt | ggc | ctc | aac | ttg | caa | gtt | gag | cac | cac | 1392 |
| Ile | Gly | Asn | Phe | Phe | Thr | Gly | Gly | Leu | Asn | Leu | Gln | Val | Glu | His | His | |
| 450 | | | | | 455 | | | | | 460 | | | | | | |
| ttg | ttt | ccg | gcg | att | tgc | ttc | gtc | cac | tac | ccg | gac | atc | gcg | aag | atc | 1440 |
| Leu | Phe | Pro | Ala | Ile | Cys | Phe | Val | His | Tyr | Pro | Asp | Ile | Ala | Lys | Ile | |
| 465 | | | | | 470 | | | | | 475 | | | | | 480 | |
| gtg | aag | gaa | gaa | gcg | gcc | aag | ctc | aac | atc | cct | tac | gcg | tct | tac | agg | 1488 |
| Val | Lys | Glu | Glu | Ala | Ala | Lys | Leu | Asn | Ile | Pro | Tyr | Ala | Ser | Tyr | Arg | |
| | | | | 485 | | | | | 490 | | | | | 495 | | |
| act | ctt | cct | ggt | att | ttc | gtc | caa | ttc | tgg | aga | ttt | atg | aag | gac | atg | 1536 |
| Thr | Leu | Pro | Gly | Ile | Phe | Val | Gln | Phe | Trp | Arg | Phe | Met | Lys | Asp | Met | |
| | | | 500 | | | | | 505 | | | | | 510 | | | |
| ggc | acg | gct | gag | caa | att | ggt | gaa | gtt | cca | ttg | ccg | aag | att | ccc | aac | 1584 |
| Gly | Thr | Ala | Glu | Gln | Ile | Gly | Glu | Val | Pro | Leu | Pro | Lys | Ile | Pro | Asn | |
| | 515 | | | | | 520 | | | | | 525 | | | | | |
| ccg | cag | ctc | gcg | ccg | aag | ctc | gct | tag | | | | | | | | 1611 |
| Pro | Gln | Leu | Ala | Pro | Lys | Leu | Ala | | | | | | | | | |
| | 530 | | | | | 535 | | | | | | | | | | |

<210> SEQ ID NO 85
<211> LENGTH: 536
<212> TYPE: PRT
<213> ORGANISM: Ostreococcus tauri

<400> SEQUENCE: 85

Met Tyr Leu Gly Arg Gly Arg Leu Glu Ser Gly Thr Thr Arg Gly Met
1               5                   10                  15

Met Arg Thr His Ala Arg Arg Pro Ser Thr Thr Ser Asn Pro Cys Ala
            20                  25                  30

Arg Ser Arg Val Arg Lys Thr Thr Glu Arg Ser Leu Ala Arg Val Arg
        35                  40                  45

Arg Ser Thr Ser Glu Lys Gly Ser Ala Leu Val Leu Glu Arg Glu Ser
    50                  55                  60

Glu Arg Glu Lys Glu Glu Gly Gly Lys Ala Arg Ala Glu Gly Leu Arg
65                  70                  75                  80

Phe Gln Arg Pro Asp Val Ala Ala Pro Gly Gly Ala Asp Pro Trp Asn
                85                  90                  95

Asp Glu Lys Trp Thr Lys Thr Lys Trp Thr Val Phe Arg Asp Val Ala

-continued

```
            100                 105                 110
Tyr Asp Leu Asp Pro Phe Phe Ala Arg His Pro Gly Gly Asp Trp Leu
        115                 120                 125

Leu Asn Leu Ala Val Gly Arg Asp Cys Thr Ala Leu Ile Glu Ser Tyr
130                 135                 140

His Leu Arg Pro Glu Val Ala Thr Ala Arg Phe Arg Met Leu Pro Lys
145                 150                 155                 160

Leu Glu Asp Phe Pro Val Ala Val Pro Lys Ser Pro Arg Pro Asn
                165                 170                 175

Asp Ser Pro Leu Tyr Asn Asn Ile Arg Asn Arg Val Arg Glu Glu Leu
            180                 185                 190

Phe Pro Glu Glu Gly Lys Asn Met His Arg Gln Gly Gly Asp His Gly
        195                 200                 205

Asp Gly Asp Asp Ser Gly Phe Arg Arg Leu Leu Leu Met Pro Cys Thr
    210                 215                 220

Tyr Ser Leu Pro Gly Val Pro Phe Arg Leu Pro Pro Arg Val Ser Arg
225                 230                 235                 240

Gly Arg Gly Leu Val Ser Arg Phe Arg His Cys Ala Asn His Gly Ala
                245                 250                 255

Met Ser Pro Ser Pro Ala Val Asn Gly Val Leu Gly Leu Thr Asn Asp
            260                 265                 270

Leu Ile Gly Gly Ser Ser Leu Met Trp Arg Tyr His His Gln Val Ser
        275                 280                 285

His His Ile His Cys Asn Asp Asn Ala Met Asp Gln Asp Val Tyr Thr
    290                 295                 300

Ala Met Pro Leu Leu Arg Phe Asp Ala Arg Arg Pro Lys Ser Trp Tyr
305                 310                 315                 320

His Arg Phe Gln Gln Trp Tyr Met Phe Leu Ala Phe Pro Leu Leu Gln
                325                 330                 335

Val Ala Phe Gln Val Gly Asp Ile Ala Ala Leu Phe Thr Arg Asp Thr
            340                 345                 350

Glu Gly Ala Lys Leu His Gly Ala Thr Thr Trp Glu Leu Thr Thr Val
        355                 360                 365

Val Leu Gly Lys Ile Val His Phe Gly Leu Leu Leu Gly Pro Leu Met
    370                 375                 380

Asn His Ala Val Ser Ser Val Leu Leu Gly Ile Val Gly Phe Met Ala
385                 390                 395                 400

Cys Gln Gly Ile Val Leu Ala Cys Thr Phe Ala Val Ser His Asn Val
                405                 410                 415

Ala Glu Ala Lys Ile Pro Glu Asp Thr Gly Gly Glu Ala Trp Glu Arg
            420                 425                 430

Asp Trp Gly Val Gln Gln Leu Val Thr Ser Ala Asp Trp Gly Gly Lys
        435                 440                 445

Ile Gly Asn Phe Phe Thr Gly Gly Leu Asn Leu Gln Val Glu His His
    450                 455                 460

Leu Phe Pro Ala Ile Cys Phe Val His Tyr Pro Asp Ile Ala Lys Ile
465                 470                 475                 480

Val Lys Glu Glu Ala Ala Lys Leu Asn Ile Pro Tyr Ala Ser Tyr Arg
                485                 490                 495

Thr Leu Pro Gly Ile Phe Val Gln Phe Trp Arg Phe Met Lys Asp Met
            500                 505                 510

Gly Thr Ala Glu Gln Ile Gly Glu Val Pro Leu Pro Lys Ile Pro Asn
        515                 520                 525
```

```
Pro Gln Leu Ala Pro Lys Leu Ala
    530                 535

<210> SEQ ID NO 86
<211> LENGTH: 960
<212> TYPE: DNA
<213> ORGANISM: Thalassiosira pseudonana
<220> FEATURE:
<221> NAME/KEY: CDS
<222> LOCATION: (1)..(960)
<223> OTHER INFORMATION: delta-5-Elongase

<400> SEQUENCE: 86 atg gtg ttg tac aat gtg gcg caa gtg ctg ctc aat ggg tgg acg gtg        48
Met Val Leu Tyr Asn Val Ala Gln Val Leu Leu Asn Gly Trp Thr Val
1               5                   10                  15 tat gcg att gtg gat gcg gtg atg aat aga gac cat ccg ttt att gga        96
Tyr Ala Ile Val Asp Ala Val Met Asn Arg Asp His Pro Phe Ile Gly
            20                  25                  30 agt aga agt ttg gtt ggg gcg gcg ttg cat agt ggg agc tcg tat gcg       144
Ser Arg Ser Leu Val Gly Ala Ala Leu His Ser Gly Ser Ser Tyr Ala
        35                  40                  45 gtg tgg gtt cat tat tgt gat aag tat ttg gag ttc ttt gat acg tat       192
Val Trp Val His Tyr Cys Asp Lys Tyr Leu Glu Phe Phe Asp Thr Tyr
    50                  55                  60 ttt atg gtg ttg agg ggg aaa atg gac cag atg gta ctt ggt gaa gtt       240
Phe Met Val Leu Arg Gly Lys Met Asp Gln Met Val Leu Gly Glu Val
65                  70                  75                  80 ggt ggc agt gtg tgg tgt ggc gtt gga tat atg gat atg gag aag atg       288
Gly Gly Ser Val Trp Cys Gly Val Gly Tyr Met Asp Met Glu Lys Met
                85                  90                  95 ata cta ctc agc ttt gga gtg cat cgg tct gct cag gga acg ggg aag       336
Ile Leu Leu Ser Phe Gly Val His Arg Ser Ala Gln Gly Thr Gly Lys
            100                 105                 110 gct ttc acc aac aac gtt acc aat cca cat ctc acg ctt cca cct cat       384
Ala Phe Thr Asn Asn Val Thr Asn Pro His Leu Thr Leu Pro Pro His
        115                 120                 125 tct aca aaa aca aaa aaa cag gtc tcc ttc ctc cac atc tac cac cac       432
Ser Thr Lys Thr Lys Lys Gln Val Ser Phe Leu His Ile Tyr His His
    130                 135                 140 acg acc ata gcg tgg gca tgg tgg atc gcc ctc cgc ttc tcc ccc ggt       480
Thr Thr Ile Ala Trp Ala Trp Trp Ile Ala Leu Arg Phe Ser Pro Gly
145                 150                 155                 160 gga gac att tac ttc ggg gca ctc ctc aac tcc atc atc cac gtc ctc       528
Gly Asp Ile Tyr Phe Gly Ala Leu Leu Asn Ser Ile Ile His Val Leu
                165                 170                 175 atg tat tcc tac tac gcc ctt gcc cta ctc aag gtc agt tgt cca tgg       576
Met Tyr Ser Tyr Tyr Ala Leu Ala Leu Leu Lys Val Ser Cys Pro Trp
            180                 185                 190 aaa cga tac ctg act caa gct caa tta ttg caa ttc aca agt gtg gtg       624
Lys Arg Tyr Leu Thr Gln Ala Gln Leu Leu Gln Phe Thr Ser Val Val
        195                 200                 205 gtt tat acg ggg tgt acg ggt tat act cat tac tat cat acg aag cat       672
Val Tyr Thr Gly Cys Thr Gly Tyr Thr His Tyr Tyr His Thr Lys His
    210                 215                 220 gga gcg gat gag aca cag cct agt tta gga acg tat tat ttc tgt tgt       720
Gly Ala Asp Glu Thr Gln Pro Ser Leu Gly Thr Tyr Tyr Phe Cys Cys
225                 230                 235                 240 gga gtg cag gtg ttt gag atg gtt agt ttg ttt gta ctc ttt tcc atc       768
Gly Val Gln Val Phe Glu Met Val Ser Leu Phe Val Leu Phe Ser Ile
                245                 250                 255
```

```
ttt tat aaa cga tcc tat tcg aag aag aac aag tca gga gga aag gat    816
Phe Tyr Lys Arg Ser Tyr Ser Lys Lys Asn Lys Ser Gly Gly Lys Asp
        260                 265                 270 agc aag aag aat gat gat ggg aat aat gag gat caa tgt cac aag gct    864
Ser Lys Lys Asn Asp Asp Gly Asn Asn Glu Asp Gln Cys His Lys Ala
        275                 280                 285 atg aag gat ata tcg gag ggt gcg aag gag gtt gtg ggg cat gca gcg    912
Met Lys Asp Ile Ser Glu Gly Ala Lys Glu Val Val Gly His Ala Ala
        290                 295                 300 aag gat gct gga aag ttg gtg gct acg aga gta agg tgt aag gtg taa    960
Lys Asp Ala Gly Lys Leu Val Ala Thr Arg Val Arg Cys Lys Val
305                 310                 315

<210> SEQ ID NO 87
<211> LENGTH: 319
<212> TYPE: PRT
<213> ORGANISM: Thalassiosira pseudonana

<400> SEQUENCE: 87

Met Val Leu Tyr Asn Val Ala Gln Val Leu Leu Asn Gly Trp Thr Val
1               5                   10                  15

Tyr Ala Ile Val Asp Ala Val Met Asn Arg Asp His Pro Phe Ile Gly
            20                  25                  30

Ser Arg Ser Leu Val Gly Ala Ala Leu His Ser Gly Ser Ser Tyr Ala
        35                  40                  45

Val Trp Val His Tyr Cys Asp Lys Tyr Leu Glu Phe Phe Asp Thr Tyr
    50                  55                  60

Phe Met Val Leu Arg Gly Lys Met Asp Gln Met Val Leu Gly Glu Val
65                  70                  75                  80

Gly Gly Ser Val Trp Cys Gly Val Gly Tyr Met Asp Met Glu Lys Met
                85                  90                  95

Ile Leu Leu Ser Phe Gly Val His Arg Ser Ala Gln Gly Thr Gly Lys
            100                 105                 110

Ala Phe Thr Asn Asn Val Thr Asn Pro His Leu Thr Leu Pro Pro His
        115                 120                 125

Ser Thr Lys Thr Lys Lys Gln Val Ser Phe Leu His Ile Tyr His His
    130                 135                 140

Thr Thr Ile Ala Trp Ala Trp Trp Ile Ala Leu Arg Phe Ser Pro Gly
145                 150                 155                 160

Gly Asp Ile Tyr Phe Gly Ala Leu Leu Asn Ser Ile Ile His Val Leu
                165                 170                 175

Met Tyr Ser Tyr Tyr Ala Leu Ala Leu Leu Lys Val Ser Cys Pro Trp
            180                 185                 190

Lys Arg Tyr Leu Thr Gln Ala Gln Leu Leu Gln Phe Thr Ser Val Val
        195                 200                 205

Val Tyr Thr Gly Cys Thr Gly Tyr Thr His Tyr His Thr Lys His
    210                 215                 220

Gly Ala Asp Glu Thr Gln Pro Ser Leu Gly Thr Tyr Tyr Phe Cys Cys
225                 230                 235                 240

Gly Val Gln Val Phe Glu Met Val Ser Leu Phe Val Leu Phe Ser Ile
                245                 250                 255

Phe Tyr Lys Arg Ser Tyr Ser Lys Lys Asn Lys Ser Gly Gly Lys Asp
            260                 265                 270

Ser Lys Lys Asn Asp Asp Gly Asn Asn Glu Asp Gln Cys His Lys Ala
        275                 280                 285
```

```
Met Lys Asp Ile Ser Glu Gly Ala Lys Glu Val Val Gly His Ala Ala
            290                 295                 300
Lys Asp Ala Gly Lys Leu Val Ala Thr Arg Val Arg Cys Lys Val
305                 310                 315

<210> SEQ ID NO 88
<211> LENGTH: 819
<212> TYPE: DNA
<213> ORGANISM: Thalassiosira pseudonana
<220> FEATURE:
<221> NAME/KEY: CDS
<222> LOCATION: (1)..(819)
<223> OTHER INFORMATION: delta-5-Elongase

<400> SEQUENCE: 88 atg gac gcc tac aac gct gca atg gat aag atc ggt gcc gcc atc atc      48
Met Asp Ala Tyr Asn Ala Ala Met Asp Lys Ile Gly Ala Ala Ile Ile
1               5                   10                  15 gat tgg tct gat ccc gat gga aag ttc cgt gcc gat aga gag gac tgg      96
Asp Trp Ser Asp Pro Asp Gly Lys Phe Arg Ala Asp Arg Glu Asp Trp
            20                  25                  30 tgg ctc tgc gac ttc cgt agc gcc atc acc atc gcc ctc atc tac atc     144
Trp Leu Cys Asp Phe Arg Ser Ala Ile Thr Ile Ala Leu Ile Tyr Ile
        35                  40                  45 gcc ttc gtc atc ctc ggt tcc gcc gtc atg caa tcc ctc ccc gca atg     192
Ala Phe Val Ile Leu Gly Ser Ala Val Met Gln Ser Leu Pro Ala Met
    50                  55                  60 gat ccc tac ccc atc aaa ttc ctc tac aac gtc tcc caa atc ttc ctt     240
Asp Pro Tyr Pro Ile Lys Phe Leu Tyr Asn Val Ser Gln Ile Phe Leu
65                  70                  75                  80 tgt gcc tac atg act gtc gag gcg gga ttt ttg gcc tac cgc aat gga     288
Cys Ala Tyr Met Thr Val Glu Ala Gly Phe Leu Ala Tyr Arg Asn Gly
                85                  90                  95 tat acc gtc atg cct tgc aat cat ttc aat gtg aat gat cct ccc gtg     336
Tyr Thr Val Met Pro Cys Asn His Phe Asn Val Asn Asp Pro Pro Val
            100                 105                 110 gcg aat ctt ctt tgg ttg ttt tat att tcc aag gtg tgg gac ttt tgg     384
Ala Asn Leu Leu Trp Leu Phe Tyr Ile Ser Lys Val Trp Asp Phe Trp
        115                 120                 125 gat acc att ttc att gtg ttg ggg aag aag tgg cgt caa tta tct ttc     432
Asp Thr Ile Phe Ile Val Leu Gly Lys Lys Trp Arg Gln Leu Ser Phe
    130                 135                 140 ttg cat gta tac cat cac acc acc atc ttt cta ttc tat tgg ctg aat     480
Leu His Val Tyr His His Thr Thr Ile Phe Leu Phe Tyr Trp Leu Asn
145                 150                 155                 160 gcc aat gtc ttg tac gat ggt gac atc ttc ctt acc atc ttg ctc aat     528
Ala Asn Val Leu Tyr Asp Gly Asp Ile Phe Leu Thr Ile Leu Leu Asn
                165                 170                 175 gga ttc atc cac acg gtg atg tac acg tat tac ttc atc tgt atg cat     576
Gly Phe Ile His Thr Val Met Tyr Thr Tyr Tyr Phe Ile Cys Met His
            180                 185                 190 acc aaa gat tcc aag acg ggc aag agt ctt cct ata tgg tgg aag tcg     624
Thr Lys Asp Ser Lys Thr Gly Lys Ser Leu Pro Ile Trp Trp Lys Ser
        195                 200                 205 agt ttg acg gcg ttt cag ttg ttg caa ttc act atc atg atg agt cag     672
Ser Leu Thr Ala Phe Gln Leu Leu Gln Phe Thr Ile Met Met Ser Gln
    210                 215                 220 gct acc tac ctt gtc ttc cac ggg tgt gat aag gtg tcg ctt cgt atc     720
Ala Thr Tyr Leu Val Phe His Gly Cys Asp Lys Val Ser Leu Arg Ile
225                 230                 235                 240 acg att gtg tac ttt gtg tcc ctt ttg agt ttg ttc ttc ctt ttt gct     768
Thr Ile Val Tyr Phe Val Ser Leu Leu Ser Leu Phe Phe Leu Phe Ala
```

```
Thr Ile Val Tyr Phe Val Ser Leu Leu Ser Leu Phe Leu Phe Ala
            245                 250                 255 cag ttc ttt gtg caa tca tac atg gca ccc aaa aag aag aag agt gct      816
Gln Phe Phe Val Gln Ser Tyr Met Ala Pro Lys Lys Lys Lys Ser Ala
            260                 265                 270 tag                                                                  819
```

<210> SEQ ID NO 89
<211> LENGTH: 272
<212> TYPE: PRT
<213> ORGANISM: Thalassiosira pseudonana

<400> SEQUENCE: 89

```
Met Asp Ala Tyr Asn Ala Ala Met Asp Lys Ile Gly Ala Ala Ile Ile
1               5                   10                  15

Asp Trp Ser Asp Pro Asp Gly Lys Phe Arg Ala Asp Arg Glu Asp Trp
            20                  25                  30

Trp Leu Cys Asp Phe Arg Ser Ala Ile Thr Ile Ala Leu Ile Tyr Ile
        35                  40                  45

Ala Phe Val Ile Leu Gly Ser Ala Val Met Gln Ser Leu Pro Ala Met
    50                  55                  60

Asp Pro Tyr Pro Ile Lys Phe Leu Tyr Asn Val Ser Gln Ile Phe Leu
65                  70                  75                  80

Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Ser Leu Leu Ser Leu Phe Leu Phe Ala
                245                 250                 255

Gln Phe Phe Val Gln Ser Tyr Met Ala Pro Lys Lys Lys Lys Ser Ala
            260                 265                 270
```

<210> SEQ ID NO 90
<211> LENGTH: 936
<212> TYPE: DNA
<213> ORGANISM: Crypthecodinium cohnii
<220> FEATURE:
<221> NAME/KEY: CDS
<222> LOCATION: (1)..(936)
<223> OTHER INFORMATION: delta-5-Elongase

<400> SEQUENCE: 90

```
atg tct gcc ttc atg act ctc cca cag gct ctc tcc gat gtg acc tcg      48
Met Ser Ala Phe Met Thr Leu Pro Gln Ala Leu Ser Asp Val Thr Ser
1               5                   10                  15 gcc ttg gtc acg ctg gga aag gat gtc tcc agc cct tca gct ttt caa      96
Ala Leu Val Thr Leu Gly Lys Asp Val Ser Ser Pro Ser Ala Phe Gln
                20                  25                  30 gct gtc act ggc ttc tgc agg gag cag tgg ggg att ccg aca gta ttc     144
Ala Val Thr Gly Phe Cys Arg Glu Gln Trp Gly Ile Pro Thr Val Phe
            35                  40                  45 tgc ctg ggc tac ttg gcc atg gtc tac gcg gcc aga aga ccc ctc ccg     192
Cys Leu Gly Tyr Leu Ala Met Val Tyr Ala Ala Arg Arg Pro Leu Pro
50                  55                  60 cag cac ggc tac atg gtt gcg gtg gac cgt tgc ttc gct gct tgg aac     240
Gln His Gly Tyr Met Val Ala Val Asp Arg Cys Phe Ala Ala Trp Asn
65                  70                  75                  80 ttg gct ctc tct gtc ttc agc act tgg ggc ttc tac cac atg gct gtc     288
Leu Ala Leu Ser Val Phe Ser Thr Trp Gly Phe Tyr His Met Ala Val
                85                  90                  95 ggg ctc tac aac atg aca gag acg agg ggc ttg caa ttc acc atc tgc     336
Gly Leu Tyr Asn Met Thr Glu Thr Arg Gly Leu Gln Phe Thr Ile Cys
                100                 105                 110 ggt tcg act ggg gag ctc gtg cag aac ctt cag act ggc cca acc gct     384
Gly Ser Thr Gly Glu Leu Val Gln Asn Leu Gln Thr Gly Pro Thr Ala
            115                 120                 125 ctg gcg ctc tgc ctc ttc tgc ttc agc aag atc ccc gag ttg atg gac     432
Leu Ala Leu Cys Leu Phe Cys Phe Ser Lys Ile Pro Glu Leu Met Asp
130                 135                 140 acg gtg ttt ctc atc ctg aag gcc aag aag gtc cgc ttc ttg cag tgg     480
Thr Val Phe Leu Ile Leu Lys Ala Lys Lys Val Arg Phe Leu Gln Trp
145                 150                 155                 160 tac cac cat gcc aca gtc atg ctc ttc tgt tgg ctc gcc ctc gcg acg     528
Tyr His His Ala Thr Val Met Leu Phe Cys Trp Leu Ala Leu Ala Thr
                165                 170                 175 gag tac act cct ggc ttg tgg ttt gcg gcg acg aac tac ttc gtg cac     576
Glu Tyr Thr Pro Gly Leu Trp Phe Ala Ala Thr Asn Tyr Phe Val His
                180                 185                 190 tcc atc atg tac atg tac ttc ttc ctc atg acc ttc aag tcg gcc gcg     624
Ser Ile Met Tyr Met Tyr Phe Phe Leu Met Thr Phe Lys Ser Ala Ala
                195                 200                 205 aag gtg gtg aag ccc atc gcc cct ctc atc aca gtt atc cag att gct     672
Lys Val Val Lys Pro Ile Ala Pro Leu Ile Thr Val Ile Gln Ile Ala
                210                 215                 220 cag atg gtc tgg ggc ctc atc gtc aac ggc atc gcc atc acc acc ttc     720
Gln Met Val Trp Gly Leu Ile Val Asn Gly Ile Ala Ile Thr Thr Phe
225                 230                 235                 240 ttc acg act ggt gcc tgc cag atc cag tct gtg act gtg tat tcg gcc     768
Phe Thr Thr Gly Ala Cys Gln Ile Gln Ser Val Thr Val Tyr Ser Ala
                245                 250                 255 atc atc atg tac gct tcg tac ttc tac ctg ttc tcc cag ctc ttc ttc     816
Ile Ile Met Tyr Ala Ser Tyr Phe Tyr Leu Phe Ser Gln Leu Phe Phe
                260                 265                 270 gag gcc cat ggt gcc gct ggc aag aac aag aag aag ttg acc cgc gag     864
Glu Ala His Gly Ala Ala Gly Lys Asn Lys Lys Lys Leu Thr Arg Glu
                275                 280                 285 ctc tct cga aaa atc tcg gag gct ctc ctg aac acc ggt gac gag gtt     912
Leu Ser Arg Lys Ile Ser Glu Ala Leu Leu Asn Thr Gly Asp Glu Val
            290                 295                 300 tcc aag cac ctg aag gtg aat tga                                     936
Ser Lys His Leu Lys Val Asn
```

<210> SEQ ID NO 91
<211> LENGTH: 311
<212> TYPE: PRT
<213> ORGANISM: Crypthecodinium cohnii

<400> SEQUENCE: 91

```
Met Ser Ala Phe Met Thr Leu Pro Gln Ala Leu Ser Asp Val Thr Ser
1               5                   10                  15

Ala Leu Val Thr Leu Gly Lys Asp Val Ser Pro Ser Ala Phe Gln
            20                  25                  30

Ala Val Thr Gly Phe Cys Arg Glu Gln Trp Gly Ile Pro Thr Val Phe
        35                  40                  45

Cys Leu Gly Tyr Leu Ala Met Val Tyr Ala Ala Arg Arg Pro Leu Pro
    50                  55                  60

Gln His Gly Tyr Met Val Ala Val Asp Arg Cys Phe Ala Ala Trp Asn
65                  70                  75                  80

Leu Ala Leu Ser Val Phe Ser Thr Trp Gly Phe Tyr His Met Ala Val
                85                  90                  95

Gly Leu Tyr Asn Met Thr Glu Thr Arg Gly Leu Gln Phe Thr Ile Cys
            100                 105                 110

Gly Ser Thr Gly Glu Leu Val Gln Asn Leu Gln Thr Gly Pro Thr Ala
        115                 120                 125

Leu Ala Leu Cys Leu Phe Cys Phe Ser Lys Ile Pro Glu Leu Met Asp
    130                 135                 140

Thr Val Phe Leu Ile Leu Lys Ala Lys Lys Val Arg Phe Leu Gln Trp
145                 150                 155                 160

Tyr His His Ala Thr Val Met Leu Phe Cys Trp Leu Ala Leu Ala Thr
                165                 170                 175

Glu Tyr Thr Pro Gly Leu Trp Phe Ala Ala Thr Asn Tyr Phe Val His
            180                 185                 190

Ser Ile Met Tyr Met Tyr Phe Phe Leu Met Thr Phe Lys Ser Ala Ala
        195                 200                 205

Lys Val Val Lys Pro Ile Ala Pro Leu Ile Thr Val Ile Gln Ile Ala
    210                 215                 220

Gln Met Val Trp Gly Leu Ile Val Asn Gly Ile Ala Ile Thr Thr Phe
225                 230                 235                 240

Phe Thr Thr Gly Ala Cys Gln Ile Gln Ser Val Thr Val Tyr Ser Ala
                245                 250                 255

Ile Ile Met Tyr Ala Ser Tyr Phe Tyr Leu Phe Ser Gln Leu Phe Phe
            260                 265                 270

Glu Ala His Gly Ala Ala Gly Lys Asn Lys Lys Leu Thr Arg Glu
        275                 280                 285

Leu Ser Arg Lys Ile Ser Glu Ala Leu Leu Asn Thr Gly Asp Glu Val
    290                 295                 300

Ser Lys His Leu Lys Val Asn
305                 310
```

<210> SEQ ID NO 92
<211> LENGTH: 927
<212> TYPE: DNA
<213> ORGANISM: Crypthecodinium cohnii
<220> FEATURE:
<221> NAME/KEY: CDS
<222> LOCATION: (1)..(927)
<223> OTHER INFORMATION: delta-5-Elongase

<400> SEQUENCE: 92

| | | | | | | | | | | | | | | | | |
|---|---|---|---|---|---|---|---|---|---|---|---|---|---|---|---|---|
| atg | gct | tcc | tac | caa | caa | gca | ttc | tcc | gaa | ttg | gct | aga | gct | ttg | tcc | 48 |
| Met | Ala | Ser | Tyr | Gln | Gln | Ala | Phe | Ser | Glu | Leu | Ala | Arg | Ala | Leu | Ser | |
| 1 | | | | 5 | | | | | 10 | | | | | 15 | | |

| act | ttg | aac | cac | gac | ttc | tcc | agc | gtc | gag | cca | ttc | aaa | gtc | gtg | acg | 96 |
|---|---|---|---|---|---|---|---|---|---|---|---|---|---|---|---|---|
| Thr | Leu | Asn | His | Asp | Phe | Ser | Ser | Val | Glu | Pro | Phe | Lys | Val | Val | Thr | |
| | | | 20 | | | | | 25 | | | | | 30 | | | |

| cag | ttc | tgc | agg | gac | cag | tgg | gcg | atc | ccg | aca | gtc | ttt | tgc | atc | ggt | 144 |
|---|---|---|---|---|---|---|---|---|---|---|---|---|---|---|---|---|
| Gln | Phe | Cys | Arg | Asp | Gln | Trp | Ala | Ile | Pro | Thr | Val | Phe | Cys | Ile | Gly | |
| | | 35 | | | | | 40 | | | | | 45 | | | | |

| tac | ttg | gca | atg | gtc | tac | gcc | acg | cga | aga | cct | atc | gcg | aag | cac | ccc | 192 |
|---|---|---|---|---|---|---|---|---|---|---|---|---|---|---|---|---|
| Tyr | Leu | Ala | Met | Val | Tyr | Ala | Thr | Arg | Arg | Pro | Ile | Ala | Lys | His | Pro | |
| 50 | | | | | 55 | | | | | 60 | | | | | | |

| tac | atg | tct | ctc | gtg | gat | cgc | tgc | ttt | gcg | gcc | tgg | aac | ttg | ggc | ctc | 240 |
|---|---|---|---|---|---|---|---|---|---|---|---|---|---|---|---|---|
| Tyr | Met | Ser | Leu | Val | Asp | Arg | Cys | Phe | Ala | Ala | Trp | Asn | Leu | Gly | Leu | |
| 65 | | | | 70 | | | | | 75 | | | | | 80 | | |

| tcg | ctc | ttc | agt | tgc | tgg | ggc | ttc | tac | cac | atg | gca | gtg | gga | ctc | tcc | 288 |
|---|---|---|---|---|---|---|---|---|---|---|---|---|---|---|---|---|
| Ser | Leu | Phe | Ser | Cys | Trp | Gly | Phe | Tyr | His | Met | Ala | Val | Gly | Leu | Ser | |
| | | | 85 | | | | | 90 | | | | | 95 | | | |

| cac | acc | act | tgg | aat | ttc | ggg | ctc | cag | ttc | acc | atc | tgc | ggc | agc | acc | 336 |
|---|---|---|---|---|---|---|---|---|---|---|---|---|---|---|---|---|
| His | Thr | Thr | Trp | Asn | Phe | Gly | Leu | Gln | Phe | Thr | Ile | Cys | Gly | Ser | Thr | |
| | | 100 | | | | | 105 | | | | | 110 | | | | |

| acg | gag | ctt | gtg | aat | ggc | ttc | cag | aag | ggc | ccg | gcg | gcc | ctc | gcc | ctc | 384 |
|---|---|---|---|---|---|---|---|---|---|---|---|---|---|---|---|---|
| Thr | Glu | Leu | Val | Asn | Gly | Phe | Gln | Lys | Gly | Pro | Ala | Ala | Leu | Ala | Leu | |
| | | 115 | | | | | 120 | | | | | 125 | | | | |

| atc | ctg | ttc | tgc | ttc | tcc | aag | atc | ccg | gag | ttg | ggc | gac | acc | gtc | ttc | 432 |
|---|---|---|---|---|---|---|---|---|---|---|---|---|---|---|---|---|
| Ile | Leu | Phe | Cys | Phe | Ser | Lys | Ile | Pro | Glu | Leu | Gly | Asp | Thr | Val | Phe | |
| 130 | | | | | 135 | | | | | 140 | | | | | | |

| ttg | atc | ttg | aag | gga | aag | aag | gtc | cgc | ttc | ttg | cag | tgg | tac | cac | cac | 480 |
|---|---|---|---|---|---|---|---|---|---|---|---|---|---|---|---|---|
| Leu | Ile | Leu | Lys | Gly | Lys | Lys | Val | Arg | Phe | Leu | Gln | Trp | Tyr | His | His | |
| 145 | | | | | 150 | | | | | 155 | | | | | 160 | |

| acg | acc | gtg | atg | ctc | ttc | tgt | tgg | atg | gcc | ttg | gcg | act | gag | tac | act | 528 |
|---|---|---|---|---|---|---|---|---|---|---|---|---|---|---|---|---|
| Thr | Thr | Val | Met | Leu | Phe | Cys | Trp | Met | Ala | Leu | Ala | Thr | Glu | Tyr | Thr | |
| | | | | 165 | | | | | 170 | | | | | 175 | | |

| cct | gga | ttg | tgg | ttc | gcg | gcc | acg | aac | tac | ttc | gtg | cac | tcc | atc | atg | 576 |
|---|---|---|---|---|---|---|---|---|---|---|---|---|---|---|---|---|
| Pro | Gly | Leu | Trp | Phe | Ala | Ala | Thr | Asn | Tyr | Phe | Val | His | Ser | Ile | Met | |
| | | | 180 | | | | | 185 | | | | | 190 | | | |

| tac | atg | tac | ttc | ttc | ctc | atg | acc | ttc | aag | acg | gcc | gcc | ggc | atc | atc | 624 |
|---|---|---|---|---|---|---|---|---|---|---|---|---|---|---|---|---|
| Tyr | Met | Tyr | Phe | Phe | Leu | Met | Thr | Phe | Lys | Thr | Ala | Ala | Gly | Ile | Ile | |
| | | 195 | | | | | 200 | | | | | 205 | | | | |

| aag | ccc | atc | gcg | cct | ctc | atc | acc | atc | cag | atc | tcc | cag | atg | gtc | | 672 |
|---|---|---|---|---|---|---|---|---|---|---|---|---|---|---|---|---|
| Lys | Pro | Ile | Ala | Pro | Leu | Ile | Thr | Ile | Ile | Gln | Ile | Ser | Gln | Met | Val | |
| | 210 | | | | | 215 | | | | | 220 | | | | | |

| tgg | ggc | ttg | gtc | gtg | aac | gcc | atc | gcc | gtc | ggc | acc | ttc | ttc | acc | aca | 720 |
|---|---|---|---|---|---|---|---|---|---|---|---|---|---|---|---|---|
| Trp | Gly | Leu | Val | Val | Asn | Ala | Ile | Ala | Val | Gly | Thr | Phe | Phe | Thr | Thr | |
| 225 | | | | | 230 | | | | | 235 | | | | | 240 | |

| ggc | aac | tgc | cag | atc | cag | gca | gtg | aca | gtc | tac | tcc | gcc | atc | gtg | atg | 768 |
|---|---|---|---|---|---|---|---|---|---|---|---|---|---|---|---|---|
| Gly | Asn | Cys | Gln | Ile | Gln | Ala | Val | Thr | Val | Tyr | Ser | Ala | Ile | Val | Met | |
| | | | | 245 | | | | | 250 | | | | | 255 | | |

| tac | gcc | tcc | tac | ttc | tac | ctc | ttc | ggc | cag | ctc | ttc | ttc | gag | gcc | cag | 816 |
|---|---|---|---|---|---|---|---|---|---|---|---|---|---|---|---|---|
| Tyr | Ala | Ser | Tyr | Phe | Tyr | Leu | Phe | Gly | Gln | Leu | Phe | Phe | Glu | Ala | Gln | |
| | | | 260 | | | | | 265 | | | | | 270 | | | |

| ggt | tcg | gct | gga | aag | gac | aag | aag | aag | ttg | gcc | cga | gag | ctg | agc | cga | 864 |
|---|---|---|---|---|---|---|---|---|---|---|---|---|---|---|---|---|
| Gly | Ser | Ala | Gly | Lys | Asp | Lys | Lys | Lys | Leu | Ala | Arg | Glu | Leu | Ser | Arg | |
| | | 275 | | | | | 280 | | | | | 285 | | | | |

| aag | gtc | tcg | cgg | gct | ctc | aca | gca | acg | ggc | gaa | gag | gtg | tcg | aag | cac | 912 |
|---|---|---|---|---|---|---|---|---|---|---|---|---|---|---|---|---|
| Lys | Val | Ser | Arg | Ala | Leu | Thr | Ala | Thr | Gly | Glu | Glu | Val | Ser | Lys | His | |
| | 290 | | | | | 295 | | | | | 300 | | | | | |

```
atg aag gtg aat tga                                                      927
Met Lys Val Asn
305

<210> SEQ ID NO 93
<211> LENGTH: 308
<212> TYPE: PRT
<213> ORGANISM: Crypthecodinium cohnii

<400> SEQUENCE: 93

Met Ala Ser Tyr Gln Gln Ala Phe Ser Glu Leu Ala Arg Ala Leu Ser
1               5                   10                  15

Thr Leu Asn His Asp Phe Ser Ser Val Glu Pro Phe Lys Val Val Thr
            20                  25                  30

Gln Phe Cys Arg Asp Gln Trp Ala Ile Pro Thr Val Phe Cys Ile Gly
        35                  40                  45

Tyr Leu Ala Met Val Tyr Ala Thr Arg Arg Pro Ile Ala Lys His Pro
    50                  55                  60

Tyr Met Ser Leu Val Asp Arg Cys Phe Ala Ala Trp Asn Leu Gly Leu
65                  70                  75                  80

Ser Leu Phe Ser Cys Trp Gly Phe Tyr His Met Ala Val Gly Leu Ser
                85                  90                  95

His Thr Thr Trp Asn Phe Gly Leu Gln Phe Thr Ile Cys Gly Ser Thr
            100                 105                 110

Thr Glu Leu Val Asn Gly Phe Gln Lys Gly Pro Ala Ala Leu Ala Leu
        115                 120                 125

Ile Leu Phe Cys Phe Ser Lys Ile Pro Glu Leu Gly Asp Thr Val Phe
    130                 135                 140

Leu Ile Leu Lys Gly Lys Lys Val Arg Phe Leu Gln Trp Tyr His His
145                 150                 155                 160

Thr Thr Val Met Leu Phe Cys Trp Met Ala Leu Ala Thr Glu Tyr Thr
                165                 170                 175

Pro Gly Leu Trp Phe Ala Ala Thr Asn Tyr Phe Val His Ser Ile Met
            180                 185                 190

Tyr Met Tyr Phe Phe Leu Met Thr Phe Lys Thr Ala Ala Gly Ile Ile
        195                 200                 205

Lys Pro Ile Ala Pro Leu Ile Thr Ile Gln Ile Ser Gln Met Val
    210                 215                 220

Trp Gly Leu Val Val Asn Ala Ile Ala Val Gly Thr Phe Phe Thr Thr
225                 230                 235                 240

Gly Asn Cys Gln Ile Gln Ala Val Thr Val Tyr Ser Ala Ile Val Met
                245                 250                 255

Tyr Ala Ser Tyr Phe Tyr Leu Phe Gly Gln Leu Phe Phe Glu Ala Gln
            260                 265                 270

Gly Ser Ala Gly Lys Asp Lys Lys Leu Ala Arg Glu Leu Ser Arg
        275                 280                 285

Lys Val Ser Arg Ala Leu Thr Ala Thr Gly Glu Glu Val Ser Lys His
    290                 295                 300

Met Lys Val Asn
305

<210> SEQ ID NO 94
<211> LENGTH: 795
<212> TYPE: DNA
<213> ORGANISM: Oncorhynchus mykiss
<220> FEATURE:
<221> NAME/KEY: CDS
```

-continued

<220> LOCATION: (1)..(795)
<223> OTHER INFORMATION: delta-5-Elongase

<400> SEQUENCE: 94

```
atg gct tca aca tgg caa agc gtt cag tcc atg cgc cag tgg att tta      48
Met Ala Ser Thr Trp Gln Ser Val Gln Ser Met Arg Gln Trp Ile Leu
1               5                   10                  15 gag aat gga gat aaa agg aca gac cca tgg cta ctg gtc tac tcc cct      96
Glu Asn Gly Asp Lys Arg Thr Asp Pro Trp Leu Leu Val Tyr Ser Pro
            20                  25                  30 atg cca gtg gcc att ata ttc ctc ctc tat ctt ggt gtg gtc tgg gct     144
Met Pro Val Ala Ile Ile Phe Leu Leu Tyr Leu Gly Val Val Trp Ala
        35                  40                  45 ggg ccc aag ctg atg aaa cgc agg gaa cca gtt gat ctc aag gct gta     192
Gly Pro Lys Leu Met Lys Arg Arg Glu Pro Val Asp Leu Lys Ala Val
    50                  55                  60 ctc att gtc tac aac ttc gcc atg gtc tgc ctg tct gtc tac atg ttc     240
Leu Ile Val Tyr Asn Phe Ala Met Val Cys Leu Ser Val Tyr Met Phe
65                  70                  75                  80 cat gag ttc ttg gtc acg tcc ttg ctg tct aac tac agt tac ctg tgt     288
His Glu Phe Leu Val Thr Ser Leu Leu Ser Asn Tyr Ser Tyr Leu Cys
                85                  90                  95 caa cct gtg gat tac agc act agt cca ctg gcg atg agg atg gcc aaa     336
Gln Pro Val Asp Tyr Ser Thr Ser Pro Leu Ala Met Arg Met Ala Lys
            100                 105                 110 gta tgc tgg tgg ttt ttc ttc tcc aag gtc ata gaa ttg gct gac acg     384
Val Cys Trp Trp Phe Phe Phe Ser Lys Val Ile Glu Leu Ala Asp Thr
        115                 120                 125 gtg ttc ttc atc ctg agg aag aag aac agt cag ctg act ttc ctg cat     432
Val Phe Phe Ile Leu Arg Lys Lys Asn Ser Gln Leu Thr Phe Leu His
    130                 135                 140 gtc tat cac cat ggc acc atg atc ttc aac tgg tgg gca ggg gtc aag     480
Val Tyr His His Gly Thr Met Ile Phe Asn Trp Trp Ala Gly Val Lys
145                 150                 155                 160 tat ctg gct gga ggc caa tcg ttc ttc atc ggc ctg ctc aat acc ttt     528
Tyr Leu Ala Gly Gly Gln Ser Phe Phe Ile Gly Leu Leu Asn Thr Phe
                165                 170                 175 gtg cac atc gtg atg tac tct tac tac gga ctg gct gcc ctg ggg cct     576
Val His Ile Val Met Tyr Ser Tyr Tyr Gly Leu Ala Ala Leu Gly Pro
            180                 185                 190 cac acg cag aag tac tta tgg tgg aag cgc tat ctg acc tca ctg cag     624
His Thr Gln Lys Tyr Leu Trp Trp Lys Arg Tyr Leu Thr Ser Leu Gln
        195                 200                 205 ctg ctc cag ttt gtc ctg ttg acc act cac act ggc tac aac ctc ttc     672
Leu Leu Gln Phe Val Leu Leu Thr Thr His Thr Gly Tyr Asn Leu Phe
    210                 215                 220 act gag tgt gac ttc ccg gac tcc atg aac gct gtg gtg ttt gcc tac     720
Thr Glu Cys Asp Phe Pro Asp Ser Met Asn Ala Val Val Phe Ala Tyr
225                 230                 235                 240 tgt gtc agt ctc att gct ctc ttc agc aac ttc tac tat cag agc tac     768
Cys Val Ser Leu Ile Ala Leu Phe Ser Asn Phe Tyr Tyr Gln Ser Tyr
                245                 250                 255 ctc aac agg aag agc aag aag aca taa                                  795
Leu Asn Arg Lys Ser Lys Lys Thr
            260
```

<210> SEQ ID NO 95
<211> LENGTH: 264
<212> TYPE: PRT
<213> ORGANISM: Oncorhynchus mykiss -continued

```
<400> SEQUENCE: 95

Met Ala Ser Thr Trp Gln Ser Val Gln Ser Met Arg Gln Trp Ile Leu
1               5                   10                  15

Glu Asn Gly Asp Lys Arg Thr Asp Pro Trp Leu Leu Val Tyr Ser Pro
            20                  25                  30

Met Pro Val Ala Ile Ile Phe Leu Leu Tyr Leu Gly Val Val Trp Ala
        35                  40                  45

Gly Pro Lys Leu Met Lys Arg Arg Glu Pro Val Asp Leu Lys Ala Val
    50                  55                  60

Leu Ile Val Tyr Asn Phe Ala Met Val Cys Leu Ser Val Tyr Met Phe
65                  70                  75                  80

His Glu Phe Leu Val Thr Ser Leu Leu Ser Asn Tyr Ser Tyr Leu Cys
                85                  90                  95

Gln Pro Val Asp Tyr Ser Thr Ser Pro Leu Ala Met Arg Met Ala Lys
            100                 105                 110

Val Cys Trp Trp Phe Phe Phe Ser Lys Val Ile Glu Leu Ala Asp Thr
        115                 120                 125

Val Phe Phe Ile Leu Arg Lys Lys Asn Ser Gln Leu Thr Phe Leu His
    130                 135                 140

Val Tyr His His Gly Thr Met Ile Phe Asn Trp Trp Ala Gly Val Lys
145                 150                 155                 160

Tyr Leu Ala Gly Gly Gln Ser Phe Phe Ile Gly Leu Leu Asn Thr Phe
                165                 170                 175

Val His Ile Val Met Tyr Ser Tyr Tyr Gly Leu Ala Ala Leu Gly Pro
            180                 185                 190

His Thr Gln Lys Tyr Leu Trp Trp Lys Arg Tyr Leu Thr Ser Leu Gln
        195                 200                 205

Leu Leu Gln Phe Val Leu Leu Thr Thr His Thr Gly Tyr Asn Leu Phe
    210                 215                 220

Thr Glu Cys Asp Phe Pro Asp Ser Met Asn Ala Val Val Phe Ala Tyr
225                 230                 235                 240

Cys Val Ser Leu Ile Ala Leu Phe Ser Asn Phe Tyr Tyr Gln Ser Tyr
                245                 250                 255

Leu Asn Arg Lys Ser Lys Lys Thr
            260

<210> SEQ ID NO 96
<211> LENGTH: 885
<212> TYPE: DNA
<213> ORGANISM: Oncorhynchus mykiss
<220> FEATURE:
<221> NAME/KEY: CDS
<222> LOCATION: (1)..(885)
<223> OTHER INFORMATION: delta-5-Elongase

<400> SEQUENCE: 96 atg gag act ttt aat tat aaa cta aac atg tac ata gac tca tgg atg       48
Met Glu Thr Phe Asn Tyr Lys Leu Asn Met Tyr Ile Asp Ser Trp Met
1               5                   10                  15 ggt ccc aga gat gag cgg gta cag gga tgg ctg ctt ctg gac aac tac       96
Gly Pro Arg Asp Glu Arg Val Gln Gly Trp Leu Leu Leu Asp Asn Tyr
            20                  25                  30 cct cca acc ttt gca cta aca gtc atg tac ctg ctg atc gta tgg atg      144
Pro Pro Thr Phe Ala Leu Thr Val Met Tyr Leu Leu Ile Val Trp Met
        35                  40                  45 ggg ccc aag tac atg aga cac aga cag ccg gtg tct tgc cgg ggt ctc      192
Gly Pro Lys Tyr Met Arg His Arg Gln Pro Val Ser Cys Arg Gly Leu
```

```
ctc ttg gtc tac aat ctg ggc ctc acg atc ttg tcc ttc tat atg ttc      240
Leu Leu Val Tyr Asn Leu Gly Leu Thr Ile Leu Ser Phe Tyr Met Phe
 65              70                  75                  80 tat gag atg gtg tct gct gtg tgg cac ggg gat tat aac ttc ttt tgc      288
Tyr Glu Met Val Ser Ala Val Trp His Gly Asp Tyr Asn Phe Phe Cys
                 85                  90                  95 caa gac aca cac agt gca gga gaa acc gat acc aag atc ata aat gtg      336
Gln Asp Thr His Ser Ala Gly Glu Thr Asp Thr Lys Ile Ile Asn Val
            100                 105                 110 ctg tgg tgg tac tac ttc tcc aag ctc ata gag ttt atg gat acc ttc      384
Leu Trp Trp Tyr Tyr Phe Ser Lys Leu Ile Glu Phe Met Asp Thr Phe
        115                 120                 125 ttc ttc atc ctg cgg aag aac aac cat caa atc acg ttt ctg cac atc      432
Phe Phe Ile Leu Arg Lys Asn Asn His Gln Ile Thr Phe Leu His Ile
    130                 135                 140 tac cac cat gct agc atg ctc aac atc tgg tgg ttc gtc atg aac tgg      480
Tyr His His Ala Ser Met Leu Asn Ile Trp Trp Phe Val Met Asn Trp
145                 150                 155                 160 gtg ccc tgt ggt cac tcc tac ttt ggt gcc tcc ctg aac agc ttc atc      528
Val Pro Cys Gly His Ser Tyr Phe Gly Ala Ser Leu Asn Ser Phe Ile
                165                 170                 175 cat gtc ctg atg tac tct tac tat ggg ctc tct gct gtc ccg gcc ttg      576
His Val Leu Met Tyr Ser Tyr Tyr Gly Leu Ser Ala Val Pro Ala Leu
            180                 185                 190 cgg ccc tat cta tgg tgg aag aaa tac atc aca caa gta cag ctg att      624
Arg Pro Tyr Leu Trp Trp Lys Lys Tyr Ile Thr Gln Val Gln Leu Ile
        195                 200                 205 cag ttc ttt ttg acc atg tcc cag acg ata tgt gca gtc att tgg cca      672
Gln Phe Phe Leu Thr Met Ser Gln Thr Ile Cys Ala Val Ile Trp Pro
    210                 215                 220 tgt gat ttc ccc aga ggg tgg ctg tat ttc cag ata ttc tat gtc atc      720
Cys Asp Phe Pro Arg Gly Trp Leu Tyr Phe Gln Ile Phe Tyr Val Ile
225                 230                 235                 240 aca ctt att gcc ctt ttc tca aac ttc tac att cag act tac aag aaa      768
Thr Leu Ile Ala Leu Phe Ser Asn Phe Tyr Ile Gln Thr Tyr Lys Lys
                245                 250                 255 cac ctt gtt tca caa aag aag gag tat cat cag aat ggc tct gtt gct      816
His Leu Val Ser Gln Lys Lys Glu Tyr His Gln Asn Gly Ser Val Ala
            260                 265                 270 tca ttg aat ggc cat gtg aat ggg gtg aca ccc acg gaa acc att aca      864
Ser Leu Asn Gly His Val Asn Gly Val Thr Pro Thr Glu Thr Ile Thr
        275                 280                 285 cac agg aaa gtg agg ggg gac                                          885
His Arg Lys Val Arg Gly Asp
    290                 295
```

<210> SEQ ID NO 97
<211> LENGTH: 295
<212> TYPE: PRT
<213> ORGANISM: Oncorhynchus mykiss

<400> SEQUENCE: 97

```
Met Glu Thr Phe Asn Tyr Lys Leu Asn Met Tyr Ile Asp Ser Trp Met
1               5                   10                  15

Gly Pro Arg Asp Glu Arg Val Gln Gly Trp Leu Leu Leu Asp Asn Tyr
            20                  25                  30

Pro Pro Thr Phe Ala Leu Thr Val Met Tyr Leu Leu Ile Val Trp Met
        35                  40                  45
```

-continued

```
Gly Pro Lys Tyr Met Arg His Arg Gln Pro Val Ser Cys Arg Gly Leu
 50                  55                  60

Leu Leu Val Tyr Asn Leu Gly Leu Thr Ile Leu Ser Phe Tyr Met Phe
 65                  70                  75                  80

Tyr Glu Met Val Ser Ala Val Trp His Gly Asp Tyr Asn Phe Phe Cys
                 85                  90                  95

Gln Asp Thr His Ser Ala Gly Glu Thr Asp Thr Lys Ile Ile Asn Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Phe Leu His Ile
130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Ser Leu Asn Ser Phe Ile
                165                 170                 175

His Val Leu Met Tyr Ser Tyr Tyr Gly Leu Ser Ala Val Pro Ala Leu
            180                 185                 190

Arg Pro Tyr Leu Trp Trp Lys Lys Tyr Ile Thr Gln Val Gln Leu Ile
        195                 200                 205

Gln Phe Phe Leu Thr Met Ser Gln Thr Ile Cys Ala Val Ile Trp Pro
210                 215                 220

Cys Asp Phe Pro Arg Gly Trp Leu Tyr Phe Gln Ile Phe Tyr Val Ile
225                 230                 235                 240

Thr Leu Ile Ala Leu Phe Ser Asn Phe Tyr Ile Gln Thr Tyr Lys Lys
                245                 250                 255

His Leu Val Ser Gln Lys Lys Glu Tyr His Gln Asn Gly Ser Val Ala
            260                 265                 270

Ser Leu Asn Gly His Val Asn Gly Val Thr Pro Thr Glu Thr Ile Thr
        275                 280                 285

His Arg Lys Val Arg Gly Asp
290                 295

<210> SEQ ID NO 98
<211> LENGTH: 6753
<212> TYPE: DNA
<213> ORGANISM: Oncorhynchus mykiss
<220> FEATURE:
<221> NAME/KEY: CDS
<222> LOCATION: (513)..(1397)
<223> OTHER INFORMATION: delta-5-Elongase

<400> SEQUENCE: 98
acggattaga agccgccgag cgggtgacag ccctccgaag gaagactctc ctccgtgcgt      60
cctcgtcctc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agcctatttt ctggggtaat taatcagcga agcgatgatt tttgatctat     300
taacagatat ataaatgcaa aaactgcatt aaccacttta actaatactt tcaacatttt     360
cggtttgtat tacttcttat tcaaatgtaa taaaagtatc aacaaaaaat tgttaatata     420
cctctatact ttaacgtcaa ggagaaaaaa ccccggatcg gactactagc agctgtaata     480
cgactcacta tagggaatat taagcttaca ta atg gag act ttt aat tat aaa     533
                                    Met Glu Thr Phe Asn Tyr Lys
                                     1               5
```

```
cta aac atg tac ata gac tca tgg atg ggt ccc aga gat gag cgg gta        581
Leu Asn Met Tyr Ile Asp Ser Trp Met Gly Pro Arg Asp Glu Arg Val
         10                  15                  20 cag gga tgg ctg ctt ctg gac aac tac cct cca acc ttt gca cta aca        629
Gln Gly Trp Leu Leu Leu Asp Asn Tyr Pro Pro Thr Phe Ala Leu Thr
 25                  30                  35 gtc atg tac ctg ctg atc gta tgg atg ggg ccc aag tac atg aga cac        677
Val Met Tyr Leu Leu Ile Val Trp Met Gly Pro Lys Tyr Met Arg His
 40                  45                  50                  55 aga cag ccg gtg tct tgc cgg ggt ctc ctc ttg gtc tac aat ctg ggc        725
Arg Gln Pro Val Ser Cys Arg Gly Leu Leu Leu Val Tyr Asn Leu Gly
                 60                  65                  70 ctc acg atc ttg tcc ttc tat atg ttc tat gag atg gtg tct gct gtg        773
Leu Thr Ile Leu Ser Phe Tyr Met Phe Tyr Glu Met Val Ser Ala Val
         75                  80                  85 tgg cac ggg gat tat aac ttc ttt tgc caa gac aca cac agt gca gga        821
Trp His Gly Asp Tyr Asn Phe Phe Cys Gln Asp Thr His Ser Ala Gly
             90                  95                 100 gaa acc gat acc aag atc ata aat gtg ctg tgg tgg tac tac ttc tcc        869
Glu Thr Asp Thr Lys Ile Ile Asn Val Leu Trp Trp Tyr Tyr Phe Ser
105                 110                 115 aag ctc ata gag ttt atg gat acc ttc ttc ttc atc ctg cgg aag aac        917
Lys Leu Ile Glu Phe Met Asp Thr Phe Phe Phe Ile Leu Arg Lys Asn
120                 125                 130                 135 aac cat caa atc acg ttt ctg cac atc tac cac cat gct agc atg ctc        965
Asn His Gln Ile Thr Phe Leu His Ile Tyr His His Ala Ser Met Leu
             140                 145                 150 aac atc tgg tgg ttc gtc atg aac tgg gtg ccc tgt ggt cac tcc tac       1013
Asn Ile Trp Trp Phe Val Met Asn Trp Val Pro Cys Gly His Ser Tyr
         155                 160                 165 ttt ggt gcc tcc ctg aac agc ttc atc cat gtc ctg atg tac tct tac       1061
Phe Gly Ala Ser Leu Asn Ser Phe Ile His Val Leu Met Tyr Ser Tyr
170                 175                 180 tat ggg ctc tct gct gtc ccg gcc ttg cgg ccc tat cta tgg tgg aag       1109
Tyr Gly Leu Ser Ala Val Pro Ala Leu Arg Pro Tyr Leu Trp Trp Lys
185                 190                 195 aaa tac atc aca caa gta cag ctg att cag ttc ttt ttg acc atg tcc       1157
Lys Tyr Ile Thr Gln Val Gln Leu Ile Gln Phe Phe Leu Thr Met Ser
200                 205                 210                 215 cag acg ata tgt gca gtc att tgg cca tgt gat ttc ccc aga ggg tgg       1205
Gln Thr Ile Cys Ala Val Ile Trp Pro Cys Asp Phe Pro Arg Gly Trp
             220                 225                 230 ctg tat ttc cag ata ttc tat gtc atc aca ctt att gcc ctt ttc tca       1253
Leu Tyr Phe Gln Ile Phe Tyr Val Ile Thr Leu Ile Ala Leu Phe Ser
         235                 240                 245 aac ttc tac att cag act tac aag aaa cac ctt gtt tca caa aag aag       1301
Asn Phe Tyr Ile Gln Thr Tyr Lys Lys His Leu Val Ser Gln Lys Lys
     250                 255                 260 gag tat cat cag aat ggc tct gtt gct tca ttg aat ggc cat gtg aat       1349
Glu Tyr His Gln Asn Gly Ser Val Ala Ser Leu Asn Gly His Val Asn
265                 270                 275 ggg gtg aca ccc acg gaa acc att aca cac agg aaa gtg agg ggg gac       1397
Gly Val Thr Pro Thr Glu Thr Ile Thr His Arg Lys Val Arg Gly Asp
280                 285                 290                 295 tgaaggatcc actagtaacg gccgccagtg tgctggaatt ctgcagatat ccagcacagt    1457
ggcggccgct cgagtctaga gggcccttcg aaggtaagcc tatccctaac cctctcctcg    1517
gtctcgattc tacgcgtacc ggtcatcatc accatcacca ttgagtttaa acccgctgat   1577
```

```
cctagagggc cgcatcatgt aattagttat gtcacgctta cattcacgcc ctccccccac   1637
atccgctcta accgaaaagg aaggagttag acaacctgaa gtctaggtcc ctatttattt   1697
ttttatagtt atgttagtat taagaacgtt atttatattt caaattttc ttttttttct   1757 gtacagacgc gtgtacgcat gtaacattat actgaaaacc ttgcttgaga aggttttggg   1817
acgctcgaag gctttaattt gcaagctgcg gccctgcatt aatgaatcgg ccaacgcgcg   1877
gggagaggcg gtttgcgtat tgggcgctct tccgcttcct cgctcactga ctcgctgcgc   1937
tcggtcgttc ggctgcggcg agcggtatca gctcactcaa aggcggtaat acggttatcc   1997
acagaatcag gggataacgc aggaaagaac atgtgagcaa aaggccagca aaagcccagg   2057
aaccgtaaaa aggccgcgtt gctggcgttt ttccataggc tccgcccccc tgacgagcat   2117
cacaaaaatc gacgctcaag tcagaggtgg cgaaacccga caggactata agataccag    2177 gcgtttcccc ctggaagctc cctcgtgcgc tctcctgttc cgaccctgcc gcttaccgga   2237
tacctgtccg cctttctccc ttcgggaagc gtggcgcttt ctcatagctc acgctgtagg   2297
tatctcagtt cggtgtaggt cgttcgctcc aagctgggct gtgtgcacga accccccgtt   2357
cagcccgacc gctgcgcctt atccggtaac tatcgtcttg agtccaaccc ggtaagacac   2417
gacttatcgc cactggcagc agccactggt aacaggatta gcagagcgag gtatgtaggc   2477
ggtgctacag agttcttgaa gtggtggcct aactacggct acactagaag gacagtattt   2537
ggtatctgcg ctctgctgaa gccagttacc ttcggaaaaa gagttggtag ctcttgatcc   2597
ggcaaacaaa ccaccgctgg tagcggtggt ttttttgttt gcaagcagca gattacgcgc   2657 agaaaaaag gatctcaaga agatcctttg atcttttcta cggggtctga cgctcagtgg    2717
aacgaaaact cacgttaagg gattttggtc atgagattat caaaaaggat cttcacctag   2777
atccttttaa attaaaaatg aagttttaaa tcaatctaaa gtatatatga gtaaacttgg   2837
tctgacagtt accaatgctt aatcagtgag gcacctatct cagcgatctg tctatttcgt   2897
tcatccatag ttgcctgact ccccgtcgtg tagataacta cgatacggga gcgcttacca   2957
tctggcccca gtgctgcaat gataccgcga gacccacgct caccggctcc agatttatca   3017
gcaataaacc agccagccgg aagggccgag cgcagaagtg gtcctgcaac tttatccgcc   3077
tccatccagt ctattaattg ttgccgggaa gctagagtaa gtagttcgcc agttaatagt   3137
ttgcgcaacg ttgttgccat tgctacaggc atcgtggtgt cacgctcgtc gtttggtatg   3197
gcttcattca gctccggttc caacgatcca aggcgagtta catgatcccc catgttgtgc   3257
aaaaaagcgg ttagctcctt cggtcctccg atcgttgtca gaagtaagtt ggccgcagtg   3317
ttatcactca tggttatggc agcactgcat aattctctta ctgtcatgcc atccgtaaga   3377
tgcttttctg tgactggtga gtactcaacc aagtcattct gagaatagtg tatgcggcga   3437
ccgagttgct cttgcccggc gtcaacacgg gataataccg cgccacatag cagaactta    3497 aaagtgctca tcattggaaa acgttcttcg ggcgaaaac tctcaaggat cttaccgctg    3557
ttgagatcca gttcgatgta acccactcgt gcacccaact gatcttcagc atcttttact   3617
ttcaccagcg tttctgggtg agcaaaaaca ggaaggcaaa atgccgcaaa aaagggaata   3677
agggcgacac ggaaatgttg aatactcata ctcttccttt ttcaatatta ttgaagcatt   3737
tatcagggtt attgtctcat gagcggatac atatttgaat gtatttagaa aaataaacaa   3797
ataggggttc cgcgcacatt tccccgaaaa gtgccacctg acgtctaaga aaccattatt   3857
atcatgacat taacctataa aaataggcgt atcacgaggc cctttcgtct tcaagaaatt   3917
cggtcgaaaa aagaaaagga gagggccaag agggagggca ttggtgacta ttgagcacgt   3977
```

```
gagtatacgt gattaagcac acaaaggcag cttggagtat gtctgttatt aatttcacag    4037
gtagttctgg tccattggtg aaagtttgcg gcttgcagag cacagaggcc gcagaatgtg    4097
ctctagattc cgatgctgac ttgctgggta ttatatgtgt gcccaataga aagagaacaa    4157
ttgacccggt tattgcaagg aaaatttcaa gtcttgtaaa agcatataaa aatagttcag    4217
gcactccgaa atacttggtt ggcgtgtttc gtaatcaacc taaggaggat gttttggctc    4277
tggtcaatga ttacggcatt gatatcgtcc aactgcacgg agatgagtcg tggcaagaat    4337
accaagagtt cctcggtttg ccagttatta aaagactcgt atttccaaaa gactgcaaca    4397
tactactcag tgcagcttca cagaaacctc attcgtttat tcccttgttt gattcagaag    4457
caggtgggac aggtgaactt ttggattgga actcgatttc tgactgggtt ggaaggcaag    4517
agagccccga gagcttacat tttatgttag ctggtggact gacgccagaa aatgttggtg    4577
atgcgcttag attaaatggc gttattggtg ttgatgtaag cggaggtgtg gagacaaatg    4637
gtgtaaaaga ctctaacaaa atagcaaatt tcgtcaaaaa tgctaagaaa taggttatta    4697
ctgagtagta tttatttaag tattgtttgt gcacttgccc tagcttatcg atgataagct    4757
gtcaaagatg agaattaatt ccacggacta tagactatac tagatactcc gtctactgta    4817
cgatacactt ccgctcaggt ccttgtcctt taacgaggcc ttaccactct tttgttactc    4877
tattgatcca gctcagcaaa ggcagtgtga tctaagattc tatcttcgcg atgtagtaaa    4937
actagctaga ccgagaaaga gactagaaat gcaaaaggca cttctacaat ggctgccatc    4997
attattatcc gatgtgacgc tgcagcttct caatgatatt cgaatacgct ttgaggagat    5057
acagcctaat atccgacaaa ctgttttaca gatttacgat cgtacttgtt acccatcatt    5117
gaattttgaa catccgaacc tgggagtttt ccctgaaaca gatagtatat ttgaacctgt    5177
ataataatat atagtctagc ctttacggaa agacaatgta tgtatttcgg ttcctggaga    5237
aactattgca tctattgcat aggtaatctt gcacgtcgca tccccggttc attttctgcg    5297
tttccatctt gcacttcaat agcatatctt tgttaacgaa gcatctgtgc ttcattttgt    5357
agaacaaaaa tgcaacgcga gagcgctaat ttttcaaaca aagaatctga gctgcatttt    5417
tacagaacag aaatgcaacg cgaaagcgct attttaccaa cgaagaatct gtgcttcatt    5477
tttgtaaaac aaaaatgcaa cgcgacgaga gcgctaattt ttcaaacaaa gaatctgagc    5537
tgcatttttta cagaacagaa atgcaacgcg agagcgctat tttaccaaca aagaatctat    5597
acttcttttt tgttctacaa aaatgcatcc cgagagcgct attttttctaa caaagcatct    5657
tagattactt tttttctcct ttgtgcgctc tataatgcag tctcttgata acttttttgca    5717
ctgtaggtcc gttaaggtta gaagaaggct actttggtgt ctattttctc ttccataaaa    5777
aaagcctgac tccacttccc gcgtttactg attactagcg aagctgcggg tgcatttttt    5837
caagataaag gcatcccccga ttatattcta taccgatgtg gattgcgcat actttgtgaa    5897
cagaaagtga tagcgttgat gattcttcat tggtcagaaa attatgaacg gtttcttcta    5957
ttttgtctct atatactacg tataggaaat gtttacattt tcgtattgtt ttcgattcac    6017
tctatgaata gttcttacta caattttttt gtctaaagag taatactaga gataaacata    6077
aaaaatgtag aggtcgagtt tagatgcaag ttcaaggagc gaaaggtgga tgggtaggtt    6137
atatagggat atagcacaga gatatatagc aaagagatac ttttgagcaa tgtttgtgga    6197
agcggtattc gcaatgggaa gctccacccc ggttgataat cagaaaagcc ccaaaaacag    6257
gaagattgta taagcaaata tttaaattgt aaacgttaat attttgttaa aattcgcgtt    6317
```

```
aaattttttgt taaatcagct cattttttaa cgaatagccc gaaatcggca aaatcccctta    6377 taaatcaaaa gaatagaccg agatagggtt gagtgttgtt ccagtttcca acaagagtcc    6437
actattaaag aacgtggact ccaacgtcaa agggcgaaaa aggtctctatc agggcgatgg    6497 cccactacgt gaaccatcac cctaatcaag ttttttgggg tcgaggtgcc gtaaagcagt    6557
aaatcggaag ggtaaacgga tgcccccatt tagagcttga cggggaaagc cggcgaacgt    6617
ggcgagaaag gaagggaaga aagcgaaagg agcgggggct agggcggtgg gaagtgtagg    6677
ggtcacgctg ggcgtaaacca ccacacccgc cgcgcttaat ggggcgctac agggcgcgtg    6737
gggatgatcc actagt                                                    6753
```

<210> SEQ ID NO 99
<211> LENGTH: 295
<212> TYPE: PRT
<213> ORGANISM: Oncorhynchus mykiss

<400> SEQUENCE: 99

```
Met Glu Thr Phe Asn Tyr Lys Leu Asn Met Tyr Ile Asp Ser Trp Met
1               5                   10                  15

Gly Pro Arg Asp Glu Arg Val Gln Gly Trp Leu Leu Leu Asp Asn Tyr
            20                  25                  30

Pro Pro Thr Phe Ala Leu Thr Val Met Tyr Leu Leu Ile Val Trp Met
        35                  40                  45

Gly Pro Lys Tyr Met Arg His Arg Gln Pro Val Ser Cys Arg Gly Leu
    50                  55                  60

Leu Leu Val Tyr Asn Leu Gly Leu Thr Ile Leu Ser Phe Tyr Met Phe
65                  70                  75                  80

Tyr Glu Met Val Ser Ala Val Trp His Gly Asp Tyr Asn Phe Phe Cys
                85                  90                  95

Gln Asp Thr His Ser Ala Gly Glu Thr Asp Thr Lys Ile Ile Asn Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Phe Leu His Ile
    130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Ser Leu Asn Ser Phe Ile
                165                 170                 175

His Val Leu Met Tyr Ser Tyr Tyr Gly Leu Ser Ala Val Pro Ala Leu
            180                 185                 190

Arg Pro Tyr Leu Trp Trp Lys Lys Tyr Ile Thr Gln Val Gln Leu Ile
        195                 200                 205

Gln Phe Phe Leu Thr Met Ser Gln Thr Ile Cys Ala Val Ile Trp Pro
    210                 215                 220

Cys Asp Phe Pro Arg Gly Trp Leu Tyr Phe Gln Ile Phe Tyr Val Ile
225                 230                 235                 240

Thr Leu Ile Ala Leu Phe Ser Asn Phe Tyr Ile Gln Thr Tyr Lys Lys
                245                 250                 255

His Leu Val Ser Gln Lys Lys Glu Tyr His Gln Asn Gly Ser Val Ala
            260                 265                 270

Ser Leu Asn Gly His Val Asn Gly Val Thr Pro Thr Glu Thr Ile Thr
        275                 280                 285

His Arg Lys Val Arg Gly Asp
```

<210> SEQ ID NO 100
<211> LENGTH: 6645
<212> TYPE: DNA
<213> ORGANISM: Oncorhynchus mykiss
<220> FEATURE:
<221> NAME/KEY: CDS
<222> LOCATION: (513)..(1304)
<223> OTHER INFORMATION: delta-5-Elongase

<400> SEQUENCE: 100

```
acggattaga agccgccgag cgggtgacag ccctccgaag gaagactctc ctccgtgcgt      60
cctcgtcctc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcatt aaccacttta actaatactt tcaacatttt     360
cggtttgtat tacttcttat tcaaatgtaa taaaagtatc aacaaaaaat tgttaatata     420
cctctatact ttaacgtcaa ggagaaaaaa ccccggatcg gactactagc agctgtaata     480
cgactcacta tagggaatat taagcttaca ta atg gct tca aca tgg caa agc      533
                                   Met Ala Ser Thr Trp Gln Ser
                                     1               5
```

| | | | | | | | | | | | | | | | | |
|---|---|---|---|---|---|---|---|---|---|---|---|---|---|---|---|---|
| gtt | cag | tcc | atg | cgc | cag | tgg | att | tta | gag | aat | gga | gat | aaa | agg | aca | 581 |
| Val | Gln | Ser | Met | Arg | Gln | Trp | Ile | Leu | Glu | Asn | Gly | Asp | Lys | Arg | Thr | |
| | 10 | | | | 15 | | | | | 20 | | | | | | |

| gac | cca | tgg | cta | ctg | gtc | tac | tcc | cct | atg | cca | gtg | gcc | att | ata | ttc | 629 |
|---|---|---|---|---|---|---|---|---|---|---|---|---|---|---|---|---|
| Asp | Pro | Trp | Leu | Leu | Val | Tyr | Ser | Pro | Met | Pro | Val | Ala | Ile | Ile | Phe | |
| 25 | | | | | 30 | | | | | 35 | | | | | | |

| ctc | ctc | tat | ctt | ggt | gtg | gtc | tgg | gct | ggg | ccc | aag | ctg | atg | aaa | cgc | 677 |
|---|---|---|---|---|---|---|---|---|---|---|---|---|---|---|---|---|
| Leu | Leu | Tyr | Leu | Gly | Val | Val | Trp | Ala | Gly | Pro | Lys | Leu | Met | Lys | Arg | |
| 40 | | | | 45 | | | | | 50 | | | | | 55 | | |

| agg | gaa | cca | gtt | gat | ctc | aag | gct | gta | ctc | att | gtc | tac | aac | ttc | gcc | 725 |
|---|---|---|---|---|---|---|---|---|---|---|---|---|---|---|---|---|
| Arg | Glu | Pro | Val | Asp | Leu | Lys | Ala | Val | Leu | Ile | Val | Tyr | Asn | Phe | Ala | |
| | | | | 60 | | | | | 65 | | | | | 70 | | |

| atg | gtc | tgc | ctg | tct | gtc | tac | atg | ttc | cat | gag | ttc | ttg | gtc | acg | tcc | 773 |
|---|---|---|---|---|---|---|---|---|---|---|---|---|---|---|---|---|
| Met | Val | Cys | Leu | Ser | Val | Tyr | Met | Phe | His | Glu | Phe | Leu | Val | Thr | Ser | |
| | | 75 | | | | | 80 | | | | | 85 | | | | |

| ttg | ctg | tct | aac | tac | agt | tac | ctg | tgt | caa | cct | gtg | gat | tac | agc | act | 821 |
|---|---|---|---|---|---|---|---|---|---|---|---|---|---|---|---|---|
| Leu | Leu | Ser | Asn | Tyr | Ser | Tyr | Leu | Cys | Gln | Pro | Val | Asp | Tyr | Ser | Thr | |
| | | | 90 | | | | | 95 | | | | | 100 | | | |

| agt | cca | ctg | gcg | atg | agg | atg | gcc | aaa | gta | tgc | tgg | tgg | ttt | ttc | ttc | 869 |
|---|---|---|---|---|---|---|---|---|---|---|---|---|---|---|---|---|
| Ser | Pro | Leu | Ala | Met | Arg | Met | Ala | Lys | Val | Cys | Trp | Trp | Phe | Phe | Phe | |
| | 105 | | | | | 110 | | | | | 115 | | | | | |

| tcc | aag | gtc | ata | gaa | ttg | gct | gac | acg | gtg | ttc | ttc | atc | ctg | agg | aag | 917 |
|---|---|---|---|---|---|---|---|---|---|---|---|---|---|---|---|---|
| Ser | Lys | Val | Ile | Glu | Leu | Ala | Asp | Thr | Val | Phe | Phe | Ile | Leu | Arg | Lys | |
| 120 | | | | | 125 | | | | | 130 | | | | | 135 | |

| aag | aac | agt | cag | ctg | act | ttc | ctg | cat | gtc | tat | cac | cat | ggc | acc | atg | 965 |
|---|---|---|---|---|---|---|---|---|---|---|---|---|---|---|---|---|
| Lys | Asn | Ser | Gln | Leu | Thr | Phe | Leu | His | Val | Tyr | His | His | Gly | Thr | Met | |
| | | | | 140 | | | | | 145 | | | | | 150 | | |

| atc | ttc | aac | tgg | tgg | gca | ggg | gtc | aag | tat | ctg | gct | gga | ggc | caa | tcg | 1013 |
|---|---|---|---|---|---|---|---|---|---|---|---|---|---|---|---|---|
| Ile | Phe | Asn | Trp | Trp | Ala | Gly | Val | Lys | Tyr | Leu | Ala | Gly | Gly | Gln | Ser | |
| | | | | 155 | | | | | 160 | | | | | 165 | | |

| ttc | ttc | atc | ggc | ctg | ctc | aat | acc | ttt | gtg | cac | atc | gtg | atg | tac | tct | 1061 |
|---|---|---|---|---|---|---|---|---|---|---|---|---|---|---|---|---|
| Phe | Phe | Ile | Gly | Leu | Leu | Asn | Thr | Phe | Val | His | Ile | Val | Met | Tyr | Ser | |
| | | | 170 | | | | | 175 | | | | | 180 | | | |

| tac | tac | gga | ctg | gct | gcc | ctg | ggg | cct | cac | acg | cag | aag | tac | tta | tgg | 1109 |
|---|---|---|---|---|---|---|---|---|---|---|---|---|---|---|---|---|

```
Tyr Tyr Gly Leu Ala Ala Leu Gly Pro His Thr Gln Lys Tyr Leu Trp
    185                 190                 195 tgg aag cgc tat ctg acc tca ctg cag ctg ctc cag ttt gtc ctg ttg      1157
Trp Lys Arg Tyr Leu Thr Ser Leu Gln Leu Leu Gln Phe Val Leu Leu
200                 205                 210                 215 acc act cac act ggc tac aac ctc ttc act gag tgt gac ttc ccg gac      1205
Thr Thr His Thr Gly Tyr Asn Leu Phe Thr Glu Cys Asp Phe Pro Asp
                220                 225                 230 tcc atg aac gct gtg gtg ttt gcc tac tgt gtc agt ctc att gct ctc      1253
Ser Met Asn Ala Val Val Phe Ala Tyr Cys Val Ser Leu Ile Ala Leu
            235                 240                 245 ttc agc aac ttc tac tat cag agc tac ctc aac agg aag agc aag aag      1301
Phe Ser Asn Phe Tyr Tyr Gln Ser Tyr Leu Asn Arg Lys Ser Lys Lys
        250                 255                 260 aca taaggatcca ctagtaacgg ccgccagtgt gctggaattc tgcagatatc           1354
Thr catcacactg gcggccgctc gagcatgcat ctagagggcc gcatcatgta attagttatg    1414
tcacgcttac attcacgccc tccccccaca tccgctctaa ccgaaaagga aggagttaga    1474
caacctgaag tctaggtccc tatttatttt tttatagtta tgttagtatt aagaacgtta    1534
tttatatttc aaattttct tttttttctg tacagacgcg tgtacgcatg taacattata    1594
ctgaaaacct tgcttgagaa ggttttggga cgctcgaagg ctttaatttg cggccctgca    1654
ttaatgaatc ggccaacgcg cggggagagg cggtttgcgt attgggcgct cttccgcttc    1714
ctcgctcact gactcgctgc gctcggtcgt tcggctgcgg cgagcggtat cagctcactc    1774
aaaggcggta atacggttat ccacagaatc aggggataac gcaggaaaga acatgtgagc    1834
aaaaggccag caaaagccca ggaaccgtaa aaaggccgcg ttgctggcgt ttttccatag    1894
gctccgcccc cctgacgagc atcacaaaaa tcgacgctca agtcagaggt ggcgaaaccc    1954
gacaggacta taaagatacc aggcgtttcc cctggaagc tccctcgtgc gctctcctgt    2014
tccgaccctg ccgcttaccg gatacctgtc cgcctttctc ccttcgggaa gcgtggcgct    2074
ttctcatagc tcacgctgta ggtatctcag ttcggtgtag gtcgttcgct ccaagctggg    2134
ctgtgtgcac gaaccccccg ttcagcccga ccgctgcgcc ttatccggta actatcgtct    2194
tgagtccaac ccggtaagac acgacttatc gccactggca gcagccactg gtaacaggat    2254
tagcagagcg aggtatgtag gcggtgctac agagttcttg aagtggtggc ctaactacgg    2314
ctacactaga aggacagtat ttggtatctg cgctctgctg aagccagtta ccttcggaaa    2374
aagagttggt agctcttgat ccggcaaaca accaccgct ggtagcggtg ttttttttgt    2434
ttgcaagcag cagattacgc gcagaaaaaa aggatctcaa gaagatcctt tgatcttttc    2494 tacgggtct gacgctcagt ggaacgaaaa ctcacgttaa gggattttgg tcatgagatt    2554
atcaaaaagg atcttcacct agatcctttt aaattaaaaa tgaagtttta aatcaatcta    2614
aagtatatat gagtaaactt ggtctgacag ttaccaatgc ttaatcagtg aggcacctat    2674
ctcagcgatc tgtctatttc gttcatccat agttgcctga ctccccgtcg tgtagataac    2734
tacgatacgg gagcgcttac catctggccc cagtgctgca atgataccgc gagacccacg    2794
ctcaccggct ccagatttat cagcaataaa ccagccagcc ggaagggccg agcgcagaag    2854
tggtcctgca actttatccg cctccattca gtctattaat tgttgccggg aagctagagt    2914
aagtagttcg ccagttaata gtttgcgcaa cgttgttggc attgctacag gcatcgtggt    2974
gtcactctcg tcgtttggta tggcttcatt cagctccggt tcccaacgat caaggcgagt    3034
tacatgatcc cccatgttgt gcaaaaaagc ggttagctcc ttcggtcctc cgatcgttgt    3094
```

```
cagaagtaag ttggccgcag tgttatcact catggttatg gcagcactgc ataattctct    3154
tactgtcatg ccatccgtaa gatgcttttc tgtgactggt gagtactcaa ccaagtcatt    3214
ctgagaatag tgtatgcggc gaccgagttg ctcttgcccg gcgtcaatac gggataatag    3274
tgtatcacat agcagaactt taaaagtgct catcattgga aaacgttctt cggggcgaaa    3334
actctcaagg atcttaccgc tgttgagatc cagttcgatg taacccactc gtgcacccaa    3394
ctgatcttca gcatctttta cttttaccag cgtttctggg tgagcaaaaa caggaaggca    3454
aaatgccgca aaaagggaa taagggcgac acggaaatgt tgaatactca tactcttcct    3514
ttttcaatgg gtaataactg atataattaa attgaagctc taatttgtga gtttagtata    3574 catgcatttta cttataatac agttttttag ttttgctggc cgcatcttct caaatatgct    3634
tcccagcctg cttttctgta acgttcaccc tctaccttag catcccttcc ctttgcaaat    3694
agtcctcttc aacaataat aatgtcagat cctgtagaga ccacatcatc cacggttcta    3754
tactgttgac ccaatgcgtc tcccttgtca tctaaaccca caccgggtgt cataatcaac    3814
caatcgtaac cttcatctct tccacccatg tctctttgag caataaagcc gataacaaaa    3874
tctttgtcgc tcttcgcaat gtcaacagta cccttagtat attctccagt agatagggag    3934
cccttgcatg acaattctgc taacatcaaa aggcctctag gttcctttgt tacttcttct    3994
gccgcctgct tcaaaccgct aacaatacct gggcccacca caccgtgtgc attcgtaatg    4054
tctgcccatt ctgctattct gtatacaccc gcagagtact gcaatttgac tgtattacca    4114
atgtcagcaa attttctgtc ttcgaagagt aaaaaattgt acttggcgga taatgccttt    4174
agcggcttaa ctgtgccctc catggaaaaa tcagtcaaga tatccacatg tgttttagt    4234 aaacaaattt tgggacctaa tgcttcaact aactccagta attccttggt ggtacgaaca    4294
tccaatgaag cacacaagtt tgtttgcttt tcgtgcatga tattaaatag cttggcagca    4354
acaggactag gatgagtagc agcacgttcc ttatatgtag ctttcgacat gatttatctt    4414
cgtttcctgc aggttttttgt tctgtgcagt tgggttaaga atactgggca atttcatgtt    4474
tcttcaacac tacatatgcg tatatatacc aatctaagtc tgtgctcctt ccttcgttct    4534
tccttctgtt cggagattac cgaatcaaaa aaatttcaaa gaaaccgaaa tcaaaaaaaa    4594
gaataaaaaa aaaatgatga attgaattga aaagctagct tatcgatgat aagctgtcaa    4654
agatgagaat taattccacg gactatagac tatactagat actccgtcta ctgtacgata    4714
cacttccgct caggtccttg tccttttaacg aggccttacc actctttttgt tactctattg    4774 atccagctca gcaaaggcag tgtgatctaa gattctatct tcgcgatgta gtaaaactag    4834
ctagaccgag aaagagacta gaaatgcaaa aggcacttct acaatggctg ccatcattat    4894
tatccgatgt gacgctgcag cttctcaatg atattcgaat acgctttgag gagatacagc    4954
ctaatatccg acaaactgtt ttacagattt acgatcgtac ttgttaccca tcattgaatt    5014
ttgaacatcc gaacctggga gttttccctg aaacagatag tatatttgaa cctgtataat    5074
aatatatagt ctagcgcttt acggaagaca atgtatgtat ttcggttcct ggagaaacta    5134
ttgcatctat tgcataggta atcttgcacg tcgcatcccc ggttcatttt ctgcgtttcc    5194
atcttgcact tcaatagcat atctttgtta acgaagcatc tgtgcttcat tttgtagaac    5254
aaaaatgcaa cgcgagagcg ctaattttc aaacaaagaa tctgagctgc attttttacag    5314 aacagaaatg caacgcgaaa gcgctatttt accaacgaag aatctgtgct tcattttttgt    5374 aaaacaaaaa tgcaacgcga cgagagcgct aattttttcaa acaaagaatc tgagctgcat    5434
```

-continued

```
ttttacagaa cagaaatgca acgcgagagc gctattttac caacaaagaa tctatacttc   5494 tttttttgttc tacaaaaatg catcccgaga gcgctatttt tctaacaaag catcttagat   5554 tactttttttt ctcctttgtg cgctctataa tgcagtctct tgataacttt ttgcactgta   5614
ggtccgttaa ggttagaaga aggctacttt ggtgtctatt ttctcttcca taaaaaaagc   5674
ctgactccac ttcccgcgtt tactgattac tagcgaagct gcgggtgcat ttttcaaga    5734 taaaggcatc cccgattata ttctataccg atgtggattg cgcatacttt gtgaacagaa   5794
agtgatagcg ttgatgattc ttcattggtc agaaaattat gaacggtttc ttctattttg   5854
tctctatata ctacgtatag gaaatgttta cattttcgta ttgttttcga ttcactctat   5914
gaatagttct tactacaatt ttttgtcta aagagtaata ctagagataa acataaaaaa    5974
tgtagaggtc gagtttagat gcaagttcaa ggagcgaaag gtggatgggt aggttatata   6034
gggatatagc acagagatat atagcaaaga gatacttttg agcaatgttt gtggaagcgg   6094
tattcgcaat gggaagctcc accccggttg ataatcagaa aagccccaaa acaggaaga   6154 ttgtataagc aaatatttaa attgtaaacg ttaatatttt gttaaaattc gcgttaaatt   6214
tttgttaaat cagctcattt tttaacgaat agcccgaaat cggcaaaatc ccttataaat   6274
caaaagaata gaccgagata gggttgagtg ttgttccagt ttccaacaag agtccactat   6334 taagaacgt  ggactccaac gtcaaagggc gaaaagggt ctatcagggc gatgccccac     6394
tacgtgaacc atcaccctaa tcaagttttt tggggtcgag gtgccgtaaa gcagtaaatc   6454
ggaagggtaa acgatgcccc ccatttagag cttgacgggg aaagccggcg aacgtggcga   6514
gaaaggaagg gaagaaagcg aaaggagcgg gggctagggc ggtgggaagt gtagggtca    6574 cgctgggcgt aaccaccaca cccgccgcgc ttaatggggc gctacagggc gcgtggggat   6634
gatccactag t                                                        6645
```

```
<210> SEQ ID NO 101
<211> LENGTH: 264
<212> TYPE: PRT
<213> ORGANISM: Oncorhynchus mykiss

<400> SEQUENCE: 101

Met Ala Ser Thr Trp Gln Ser Val Gln Ser Met Arg Gln Trp Ile Leu
1               5                   10                  15

Glu Asn Gly Asp Lys Arg Thr Asp Pro Trp Leu Leu Val Tyr Ser Pro
            20                  25                  30

Met Pro Val Ala Ile Ile Phe Leu Leu Tyr Leu Gly Val Val Trp Ala
        35                  40                  45

Gly Pro Lys Leu Met Lys Arg Arg Glu Pro Val Asp Leu Lys Ala Val
    50                  55                  60

Leu Ile Val Tyr Asn Phe Ala Met Val Cys Leu Ser Val Tyr Met Phe
65                  70                  75                  80

His Glu Phe Leu Val Thr Ser Leu Leu Ser Asn Tyr Ser Tyr Leu Cys
                85                  90                  95

Gln Pro Val Asp Tyr Ser Thr Ser Pro Leu Ala Met Arg Met Ala Lys
            100                 105                 110

Val Cys Trp Trp Phe Phe Phe Ser Lys Val Ile Glu Leu Ala Asp Thr
        115                 120                 125

Val Phe Phe Ile Leu Arg Lys Lys Asn Ser Gln Leu Thr Phe Leu His
    130                 135                 140

Val Tyr His His Gly Thr Met Ile Phe Asn Trp Trp Ala Gly Val Lys
145                 150                 155                 160
```

```
Tyr Leu Ala Gly Gly Gln Ser Phe Phe Ile Gly Leu Leu Asn Thr Phe
            165                 170                 175

Val His Ile Val Met Tyr Ser Tyr Tyr Gly Leu Ala Ala Leu Gly Pro
            180                 185                 190

His Thr Gln Lys Tyr Leu Trp Trp Lys Arg Tyr Leu Thr Ser Leu Gln
            195                 200                 205

Leu Leu Gln Phe Val Leu Leu Thr Thr His Thr Gly Tyr Asn Leu Phe
            210                 215                 220

Thr Glu Cys Asp Phe Pro Asp Ser Met Asn Ala Val Val Phe Ala Tyr
225                 230                 235                 240

Cys Val Ser Leu Ile Ala Leu Phe Ser Asn Phe Tyr Tyr Gln Ser Tyr
                245                 250                 255

Leu Asn Arg Lys Ser Lys Lys Thr
            260

<210> SEQ ID NO 102
<211> LENGTH: 1077
<212> TYPE: DNA
<213> ORGANISM: Thalassiosira pseudonana
<220> FEATURE:
<221> NAME/KEY: CDS
<222> LOCATION: (1)..(1077)
<223> OTHER INFORMATION: delta-5-Elongase

<400> SEQUENCE: 102 atg tgc tca tca ccg ccg tca caa tcc aaa aca aca tcc ctc cta gca      48
Met Cys Ser Ser Pro Pro Ser Gln Ser Lys Thr Thr Ser Leu Leu Ala
1               5                   10                  15 cgg tac acc acc gcc gcc ctc ctc ctc acc ctc aca aca tgg tgc          96
Arg Tyr Thr Thr Ala Ala Leu Leu Leu Thr Leu Thr Thr Trp Cys
            20                  25                  30 cac ttc gcc ttc cca gcc gcc acc gcc aca ccc ggc ctc acc gcc gaa     144
His Phe Ala Phe Pro Ala Ala Thr Ala Thr Pro Gly Leu Thr Ala Glu
                35                  40                  45 atg cac tcc tac aaa gtc cca ctc ggt ctc acc gta ttc tac ctg ctg     192
Met His Ser Tyr Lys Val Pro Leu Gly Leu Thr Val Phe Tyr Leu Leu
    50                  55                  60 agt cta ccg tca cta aag tac gtt acg gac aac tac ctt gcc aaa aag     240
Ser Leu Pro Ser Leu Lys Tyr Val Thr Asp Asn Tyr Leu Ala Lys Lys
65                  70                  75                  80 tat gat atg aag tca ctc cta acg gaa tca atg gtg ttg tac aat gtg     288
Tyr Asp Met Lys Ser Leu Leu Thr Glu Ser Met Val Leu Tyr Asn Val
                85                  90                  95 gcg caa gtg ctg ctc aat ggg tgg acg gtg tat gcg att gtg gat gcg     336
Ala Gln Val Leu Leu Asn Gly Trp Thr Val Tyr Ala Ile Val Asp Ala
            100                 105                 110 gtg atg aat aga gac cat ccg ttt att gga agt aga agt ttg gtt ggg     384
Val Met Asn Arg Asp His Pro Phe Ile Gly Ser Arg Ser Leu Val Gly
        115                 120                 125 gcg gcg ttg cat agt ggg agc tcg tat gcg gtg tgg gtt cat tat tgt     432
Ala Ala Leu His Ser Gly Ser Ser Tyr Ala Val Trp Val His Tyr Cys
    130                 135                 140 gat aag tat ttg gag ttc ttt gat acg tat ttt atg gtg ttg agg ggg     480
Asp Lys Tyr Leu Glu Phe Phe Asp Thr Tyr Phe Met Val Leu Arg Gly
145                 150                 155                 160 aaa atg gac cag gtc tcc ttc ctc cac atc tac cac cac acg acc ata     528
Lys Met Asp Gln Val Ser Phe Leu His Ile Tyr His His Thr Thr Ile
                165                 170                 175 gcg tgg gca tgg tgg atc gcc ctc cgc ttc tcc ccc ggt gga gac att     576
```

```
Ala Trp Ala Trp Trp Ile Ala Leu Arg Phe Ser Pro Gly Gly Asp Ile
            180                 185                 190 tac ttc ggg gca ctc ctc aac tcc atc atc cac gtc ctc atg tat tcc      624
Tyr Phe Gly Ala Leu Leu Asn Ser Ile Ile His Val Leu Met Tyr Ser
        195                 200                 205 tac tac gcc ctt gcc cta ctc aag gtc agt tgt cca tgg aaa cga tac      672
Tyr Tyr Ala Leu Ala Leu Leu Lys Val Ser Cys Pro Trp Lys Arg Tyr
    210                 215                 220 ctg act caa gct caa tta ttg caa ttc aca agt gtg gtg gtt tat acg      720
Leu Thr Gln Ala Gln Leu Leu Gln Phe Thr Ser Val Val Val Tyr Thr
225                 230                 235                 240 ggg tgt acg ggt tat act cat tac tat cat acg aag cat gga gcg gat      768
Gly Cys Thr Gly Tyr Thr His Tyr Tyr His Thr Lys His Gly Ala Asp
                245                 250                 255 gag aca cag cct agt tta gga acg tat tat ttc tgt tgt gga gtg cag      816
Glu Thr Gln Pro Ser Leu Gly Thr Tyr Tyr Phe Cys Cys Gly Val Gln
            260                 265                 270 gtg ttt gag atg gtt agt ttg ttt gta ctc ttt tcc atc ttt tat aaa      864
Val Phe Glu Met Val Ser Leu Phe Val Leu Phe Ser Ile Phe Tyr Lys
        275                 280                 285 cga tcc tat tcg aag aag aac aag tca gga gga aag gat agc aag aag      912
Arg Ser Tyr Ser Lys Lys Asn Lys Ser Gly Gly Lys Asp Ser Lys Lys
    290                 295                 300 aat gat gat ggg aat aat gag gat caa tgt cac aag gct atg aag gat      960
Asn Asp Asp Gly Asn Asn Glu Asp Gln Cys His Lys Ala Met Lys Asp
305                 310                 315                 320 ata tcg gag ggt gcg aag gag gtt gtg ggg cat gca gcg aag gat gct     1008
Ile Ser Glu Gly Ala Lys Glu Val Val Gly His Ala Ala Lys Asp Ala
                325                 330                 335 gga aag ttg gtg gct acg gcg agt aag gct gta aag agg aag gga act     1056
Gly Lys Leu Val Ala Thr Ala Ser Lys Ala Val Lys Arg Lys Gly Thr
            340                 345                 350 cgt gtt act ggt gcc atg tag                                         1077
Arg Val Thr Gly Ala Met
        355

<210> SEQ ID NO 103
<211> LENGTH: 358
<212> TYPE: PRT
<213> ORGANISM: Thalassiosira pseudonana

<400> SEQUENCE: 103

Met Cys Ser Ser Pro Ser Gln Ser Lys Thr Thr Ser Leu Leu Ala
1               5                   10                  15

Arg Tyr Thr Thr Ala Ala Leu Leu Leu Thr Leu Thr Thr Trp Cys
            20                  25                  30

His Phe Ala Phe Pro Ala Ala Thr Ala Thr Pro Gly Leu Thr Ala Glu
        35                  40                  45

Met His Ser Tyr Lys Val Pro Leu Gly Leu Thr Val Phe Tyr Leu Leu
    50                  55                  60

Ser Leu Pro Ser Leu Lys Tyr Val Thr Asp Asn Tyr Leu Ala Lys Lys
65                  70                  75                  80

Tyr Asp Met Lys Ser Leu Leu Thr Glu Ser Met Val Leu Tyr Asn Val
                85                  90                  95

Ala Gln Val Leu Leu Asn Gly Trp Thr Val Tyr Ala Ile Val Asp Ala
            100                 105                 110

Val Met Asn Arg Asp His Pro Phe Ile Gly Ser Arg Ser Leu Val Gly
        115                 120                 125
```

```
Ala Ala Leu His Ser Gly Ser Ser Tyr Ala Val Trp Val His Tyr Cys
    130                 135                 140

Asp Lys Tyr Leu Glu Phe Phe Asp Thr Tyr Phe Met Val Leu Arg Gly
145                 150                 155                 160

Lys Met Asp Gln Val Ser Phe Leu His Ile Tyr His His Thr Thr Ile
                165                 170                 175

Ala Trp Ala Trp Trp Ile Ala Leu Arg Phe Ser Pro Gly Gly Asp Ile
            180                 185                 190

Tyr Phe Gly Ala Leu Leu Asn Ser Ile Ile His Val Leu Met Tyr Ser
        195                 200                 205

Tyr Tyr Ala Leu Ala Leu Leu Lys Val Ser Cys Pro Trp Lys Arg Tyr
    210                 215                 220

Leu Thr Gln Ala Gln Leu Leu Gln Phe Thr Ser Val Val Val Tyr Thr
225                 230                 235                 240

Gly Cys Thr Gly Tyr Thr His Tyr Tyr His Thr Lys His Gly Ala Asp
                245                 250                 255

Glu Thr Gln Pro Ser Leu Gly Thr Tyr Tyr Phe Cys Cys Gly Val Gln
            260                 265                 270

Val Phe Glu Met Val Ser Leu Pro Val Leu Phe Ser Ile Phe Tyr Lys
        275                 280                 285

Arg Ser Tyr Ser Lys Lys Asn Lys Ser Gly Gly Lys Asp Ser Lys Lys
    290                 295                 300

Asn Asp Asp Gly Asn Asn Glu Asp Gln Cys His Lys Ala Met Lys Asp
305                 310                 315                 320

Ile Ser Glu Gly Ala Lys Glu Val Val Gly His Ala Ala Lys Asp Ala
                325                 330                 335

Gly Lys Leu Val Ala Thr Ala Ser Lys Ala Val Lys Arg Lys Gly Thr
            340                 345                 350

Arg Val Thr Gly Ala Met
        355

<210> SEQ ID NO 104
<211> LENGTH: 933
<212> TYPE: DNA
<213> ORGANISM: Thalassiosira pseudonana
<220> FEATURE:
<221> NAME/KEY: CDS
<222> LOCATION: (1)..(933)
<223> OTHER INFORMATION: delta-5-Elongase

<400> SEQUENCE: 104 atg cac tcc tac aaa gtc cca ctc ggt ctc acc gta ttc tac ctg ctg      48
Met His Ser Tyr Lys Val Pro Leu Gly Leu Thr Val Phe Tyr Leu Leu
1               5                   10                  15 agt cta ccg tca cta aag tac gtt acg gac aac tac ctt gcc aaa aag      96
Ser Leu Pro Ser Leu Lys Tyr Val Thr Asp Asn Tyr Leu Ala Lys Lys
            20                  25                  30 tat gat atg aag tca ctc cta acg gaa tca atg gtg ttg tac aat gtg     144
Tyr Asp Met Lys Ser Leu Leu Thr Glu Ser Met Val Leu Tyr Asn Val
        35                  40                  45 gcg caa gtg ctg ctc aat ggg tgg acg gta tat gcg att gtg gat gcg     192
Ala Gln Val Leu Leu Asn Gly Trp Thr Val Tyr Ala Ile Val Asp Ala
    50                  55                  60 gtg atg aat aga gac cat ccg ttt att gga agt aga agt ttg gtt ggg     240
Val Met Asn Arg Asp His Pro Phe Ile Gly Ser Arg Ser Leu Val Gly
65                  70                  75                  80 gcg gcg ttg cat agt ggg agc tcg tat gcg gtg tgg gtt cat tat tgt     288
Ala Ala Leu His Ser Gly Ser Ser Tyr Ala Val Trp Val His Tyr Cys
```

-continued

```
              85                  90                  95
gat aag tat ttg gag ttc ttt gat acg tat ttt atg gtg ttg agg ggg       336
Asp Lys Tyr Leu Glu Phe Phe Asp Thr Tyr Phe Met Val Leu Arg Gly
            100                 105                 110 aaa atg gac cag gtc tcc ttc ctc cac atc tac cac cac acg acc ata       384
Lys Met Asp Gln Val Ser Phe Leu His Ile Tyr His His Thr Thr Ile
                115                 120                 125 gcg tgg gca tgg tgg atc gcc ctc cgc ttc tcc ccc ggt gga gac att       432
Ala Trp Ala Trp Trp Ile Ala Leu Arg Phe Ser Pro Gly Gly Asp Ile
130                 135                 140 tac ttc ggg gca ctc ctc aac tcc atc atc cac gtc ctc atg tat tcc       480
Tyr Phe Gly Ala Leu Leu Asn Ser Ile Ile His Val Leu Met Tyr Ser
145                 150                 155                 160 tac tac gcc ctt gcc cta ctc aag gtc agt tgt cca tgg aaa cga tac       528
Tyr Tyr Ala Leu Ala Leu Leu Lys Val Ser Cys Pro Trp Lys Arg Tyr
                165                 170                 175 ctg act caa gct caa tta ttg caa ttc aca agt gtg gtg gtt tat acg       576
Leu Thr Gln Ala Gln Leu Leu Gln Phe Thr Ser Val Val Val Tyr Thr
            180                 185                 190 ggg tgt acg ggt tat act cat tac tat cat acg aag cat gga gcg gat       624
Gly Cys Thr Gly Tyr Thr His Tyr Tyr His Thr Lys His Gly Ala Asp
        195                 200                 205 gag aca cag cct agt tta gga acg tat tat ttc tgt tgt gga gtg cag       672
Glu Thr Gln Pro Ser Leu Gly Thr Tyr Tyr Phe Cys Cys Gly Val Gln
    210                 215                 220 gtg ttt gag atg gtt agt ttg ttt gta ctc ttt tcc atc ttt tat aaa       720
Val Phe Glu Met Val Ser Leu Phe Val Leu Phe Ser Ile Phe Tyr Lys
225                 230                 235                 240 cga tcc tat tcg aag aag aac aag tca gga gga aag gat agc aag aag       768
Arg Ser Tyr Ser Lys Lys Asn Lys Ser Gly Gly Lys Asp Ser Lys Lys
                245                 250                 255 aat gat gat ggg aat aat gag gat caa tgt cac aag gct atg aag gat       816
Asn Asp Asp Gly Asn Asn Glu Asp Gln Cys His Lys Ala Met Lys Asp
            260                 265                 270 ata tcg gag ggt gcg aag gag gtt gtg ggg cat gca gcg aag gat gct       864
Ile Ser Glu Gly Ala Lys Glu Val Val Gly His Ala Ala Lys Asp Ala
        275                 280                 285 gga aag ttg gtg gct acg gcg agt aag gct gta aag agg aag gga act       912
Gly Lys Leu Val Ala Thr Ala Ser Lys Ala Val Lys Arg Lys Gly Thr
    290                 295                 300 cgt gtt act ggt gcc atg tag                                            933
Arg Val Thr Gly Ala Met
305                 310

<210> SEQ ID NO 105
<211> LENGTH: 310
<212> TYPE: PRT
<213> ORGANISM: Thalassiosira pseudonana

<400> SEQUENCE: 105

Met His Ser Tyr Lys Val Pro Leu Gly Leu Thr Val Phe Tyr Leu Leu
1               5                   10                  15

Ser Leu Pro Ser Leu Lys Tyr Val Thr Asp Asn Tyr Leu Ala Lys Lys
                20                  25                  30

Tyr Asp Met Lys Ser Leu Leu Thr Glu Ser Met Val Leu Tyr Asn Val
            35                  40                  45

Ala Gln Val Leu Leu Asn Gly Trp Thr Val Tyr Ala Ile Val Asp Ala
        50                  55                  60

Val Met Asn Arg Asp His Pro Phe Ile Gly Ser Arg Ser Leu Val Gly
```

```
                65                  70                  75                  80
Ala Ala Leu His Ser Gly Ser Ser Tyr Ala Val Trp Val His Tyr Cys
                        85                  90                  95

Asp Lys Tyr Leu Glu Phe Phe Asp Thr Tyr Phe Met Val Leu Arg Gly
                100                 105                 110

Lys Met Asp Gln Val Ser Phe Leu His Ile Tyr His His Thr Thr Ile
                115                 120                 125

Ala Trp Ala Trp Trp Ile Ala Leu Arg Phe Ser Pro Gly Gly Asp Ile
    130                 135                 140

Tyr Phe Gly Ala Leu Leu Asn Ser Ile Ile His Val Leu Met Tyr Ser
145                 150                 155                 160

Tyr Tyr Ala Leu Ala Leu Leu Lys Val Ser Cys Pro Trp Lys Arg Tyr
                165                 170                 175

Leu Thr Gln Ala Gln Leu Leu Gln Phe Thr Ser Val Val Tyr Thr
                180                 185                 190

Gly Cys Thr Gly Tyr Thr His Tyr Tyr His Thr Lys His Gly Ala Asp
                195                 200                 205

Glu Thr Gln Pro Ser Leu Gly Thr Tyr Tyr Phe Cys Cys Gly Val Gln
    210                 215                 220

Val Phe Glu Met Val Ser Leu Phe Val Leu Phe Ser Ile Phe Tyr Lys
225                 230                 235                 240

Arg Ser Tyr Ser Lys Lys Asn Lys Ser Gly Lys Asp Ser Lys Lys
                245                 250                 255

Asn Asp Asp Gly Asn Asn Glu Asp Gln Cys His Lys Ala Met Lys Asp
                260                 265                 270

Ile Ser Glu Gly Ala Lys Glu Val Val Gly His Ala Ala Lys Asp Ala
    275                 280                 285

Gly Lys Leu Val Ala Thr Ala Ser Lys Ala Val Lys Arg Lys Gly Thr
    290                 295                 300

Arg Val Thr Gly Ala Met
305                 310

<210> SEQ ID NO 106
<211> LENGTH: 933
<212> TYPE: DNA
<213> ORGANISM: Thalassiosira pseudonana
<220> FEATURE:
<221> NAME/KEY: CDS
<222> LOCATION: (1)..(933)
<223> OTHER INFORMATION: delta-5-Elongase

<400> SEQUENCE: 106 atg cac tcc tac aaa gtc cca ctc ggt ctc acc gta ttc tac ctg ctg     48
Met His Ser Tyr Lys Val Pro Leu Gly Leu Thr Val Phe Tyr Leu Leu
1               5                   10                  15 agt cta ccg tca cta aag tac gtt acg gac aac tac ctt gcc aaa aag     96
Ser Leu Pro Ser Leu Lys Tyr Val Thr Asp Asn Tyr Leu Ala Lys Lys
                20                  25                  30 tat gat atg aag tca ctc cta acg gaa tca atg gtg ttg tac aat gtg    144
Tyr Asp Met Lys Ser Leu Leu Thr Glu Ser Met Val Leu Tyr Asn Val
            35                  40                  45 gcg caa gtg ctg ctc aat ggg tgg acg gtg tat gcg att gtg gat gcg    192
Ala Gln Val Leu Leu Asn Gly Trp Thr Val Tyr Ala Ile Val Asp Ala
        50                  55                  60 gtg atg aat aga gac cat ccg ttt att gga agt aga agt ttg gtt ggg    240
Val Met Asn Arg Asp His Pro Phe Ile Gly Ser Arg Ser Leu Val Gly
65                  70                  75                  80
```

```
gcg gcg ttg cat agt ggg agc tcg tat gcg gtg tgg gtt cat tat tgt      288
Ala Ala Leu His Ser Gly Ser Ser Tyr Ala Val Trp Val His Tyr Cys
             85                  90                  95 gat aag tat ttg gag ttc ttt gat acg tat ttt atg gtg ttg agg ggg      336
Asp Lys Tyr Leu Glu Phe Phe Asp Thr Tyr Phe Met Val Leu Arg Gly
            100                 105                 110 aaa atg gac cag gtc tcc ttc ctc cac atc tac cac cac acg acc ata      384
Lys Met Asp Gln Val Ser Phe Leu His Ile Tyr His His Thr Thr Ile
        115                 120                 125 gcg tgg gca tgg tgg atc gcc ctc cgc ttc tcc ccc ggt gga gac att      432
Ala Trp Ala Trp Trp Ile Ala Leu Arg Phe Ser Pro Gly Gly Asp Ile
    130                 135                 140 tac ttc ggg gca ctc ctc aac tcc atc atc cac gtc ctc atg tat tcc      480
Tyr Phe Gly Ala Leu Leu Asn Ser Ile Ile His Val Leu Met Tyr Ser
145                 150                 155                 160 tac tac gcc ctt gcc cta ctc aag gtc agt tgt cca tgg aaa cga tac      528
Tyr Tyr Ala Leu Ala Leu Leu Lys Val Ser Cys Pro Trp Lys Arg Tyr
                165                 170                 175 ctg act caa gct caa tta ttg caa ttc aca agt gtg gtg gtt tat acg      576
Leu Thr Gln Ala Gln Leu Leu Gln Phe Thr Ser Val Val Val Tyr Thr
            180                 185                 190 ggg tgt acg ggt tat act cat tac tat cat acg aag cat gga gcg gat      624
Gly Cys Thr Gly Tyr Thr His Tyr Tyr His Thr Lys His Gly Ala Asp
        195                 200                 205 gag aca cag cct agt tta gga acg tat tat ttc tgt tgt gga gtg cag      672
Glu Thr Gln Pro Ser Leu Gly Thr Tyr Tyr Phe Cys Cys Gly Val Gln
    210                 215                 220 gtg ttt gag atg gtt agt ttg ttt gta ctc ttt tcc atc ttt tat aaa      720
Val Phe Glu Met Val Ser Leu Phe Val Leu Phe Ser Ile Phe Tyr Lys
225                 230                 235                 240 cga tcc tat tcg aag aag aac aag tca gga gga aag gat agc aag aag      768
Arg Ser Tyr Ser Lys Lys Asn Lys Ser Gly Gly Lys Asp Ser Lys Lys
                245                 250                 255 aat gat gat ggg aat aat gag gat caa tgt cac aag gct atg aag gat      816
Asn Asp Asp Gly Asn Asn Glu Asp Gln Cys His Lys Ala Met Lys Asp
            260                 265                 270 ata tcg gag ggt gcg aag gag gtt gtg ggg cat gca gcg aag gat gct      864
Ile Ser Glu Gly Ala Lys Glu Val Val Gly His Ala Ala Lys Asp Ala
        275                 280                 285 gga aag ttg gtg gct acg gcg agt aag gct gta aag agg aag gga act      912
Gly Lys Leu Val Ala Thr Ala Ser Lys Ala Val Lys Arg Lys Gly Thr
    290                 295                 300 cgt gtt act ggt gcc atg tag                                          933
Arg Val Thr Gly Ala Met
305                 310

<210> SEQ ID NO 107
<211> LENGTH: 310
<212> TYPE: PRT
<213> ORGANISM: Thalassiosira pseudonana

<400> SEQUENCE: 107

Met His Ser Tyr Lys Val Pro Leu Gly Leu Thr Val Phe Tyr Leu Leu
1               5                   10                  15

Ser Leu Pro Ser Leu Lys Tyr Val Thr Asp Asn Tyr Leu Ala Lys Lys
            20                  25                  30

Tyr Asp Met Lys Ser Leu Leu Thr Glu Ser Met Val Leu Tyr Asn Val
        35                  40                  45

Ala Gln Val Leu Leu Asn Gly Trp Thr Val Tyr Ala Ile Val Asp Ala
    50                  55                  60
```

-continued

```
Val Met Asn Arg Asp His Pro Phe Ile Gly Ser Arg Ser Leu Val Gly
65                  70                  75                  80

Ala Ala Leu His Ser Gly Ser Ser Tyr Ala Val Trp Val His Tyr Cys
                85                  90                  95

Asp Lys Tyr Leu Glu Phe Asp Thr Tyr Phe Met Val Leu Arg Gly
            100                 105                 110

Lys Met Asp Gln Val Ser Phe Leu His Ile Tyr His Thr Thr Ile
            115                 120                 125

Ala Trp Ala Trp Trp Ile Ala Leu Arg Phe Ser Pro Gly Gly Asp Ile
    130                 135                 140

Tyr Phe Gly Ala Leu Leu Asn Ser Ile Ile His Val Leu Met Tyr Ser
145                 150                 155                 160

Tyr Tyr Ala Leu Ala Leu Leu Lys Val Ser Cys Pro Trp Lys Arg Tyr
                165                 170                 175

Leu Thr Gln Ala Gln Leu Leu Gln Phe Thr Ser Val Val Tyr Thr
            180                 185                 190

Gly Cys Thr Gly Tyr Thr His Tyr Tyr His Thr Lys His Gly Ala Asp
    195                 200                 205

Glu Thr Gln Pro Ser Leu Gly Thr Tyr Tyr Phe Cys Cys Gly Val Gln
    210                 215                 220

Val Phe Glu Met Val Ser Leu Phe Val Leu Phe Ser Ile Phe Tyr Lys
225                 230                 235                 240

Arg Ser Tyr Ser Lys Lys Asn Lys Ser Gly Gly Lys Asp Ser Lys Lys
                245                 250                 255

Asn Asp Asp Gly Asn Asn Glu Asp Gln Cys His Lys Ala Met Lys Asp
            260                 265                 270

Ile Ser Glu Gly Ala Lys Glu Val Gly His Ala Ala Lys Asp Ala
    275                 280                 285

Gly Lys Leu Val Ala Thr Ala Ser Lys Ala Val Lys Arg Lys Gly Thr
    290                 295                 300

Arg Val Thr Gly Ala Met
305                 310

<210> SEQ ID NO 108
<211> LENGTH: 825
<212> TYPE: DNA
<213> ORGANISM: Thraustochytrium aureum
<220> FEATURE:
<221> NAME/KEY: CDS
<222> LOCATION: (1)..(825)
<223> OTHER INFORMATION: delta-5-Elongase

<400> SEQUENCE: 108 atg acg agc aac atg agc gcg tgg ggc gtc gcc gtc gac cag acg cag    48
Met Thr Ser Asn Met Ser Ala Trp Gly Val Ala Val Asp Gln Thr Gln
1               5                   10                  15 cag gtc gtc gac cag atc atg ggc ggc gcc gag ccg tac aag ctg aca    96
Gln Val Val Asp Gln Ile Met Gly Gly Ala Glu Pro Tyr Lys Leu Thr
            20                  25                  30 gaa ggg cgc atg acg aac gtc gag acg atg ctg gcg atc gag tgc ggc   144
Glu Gly Arg Met Thr Asn Val Glu Thr Met Leu Ala Ile Glu Cys Gly
        35                  40                  45 tac gcc gcc atg ctg ctg ttc ctg acc ccg atc atg aag cag gcc gag   192
Tyr Ala Ala Met Leu Leu Phe Leu Thr Pro Ile Met Lys Gln Ala Glu
    50                  55                  60 aag ccc ttc gag ctc aag tcc ttc aag ctc gcc cac aac ctg ttc ctg   240
Lys Pro Phe Glu Leu Lys Ser Phe Lys Leu Ala His Asn Leu Phe Leu
```

```
                65                  70                  75                  80
ttc gtc ctg tcc gcc tac atg tgc ctc gag acc gtc cgc cag gcc tac         288
Phe Val Leu Ser Ala Tyr Met Cys Leu Glu Thr Val Arg Gln Ala Tyr
                    85                  90                  95 ctt gcg ggc tac tcg gtg ttc ggc aac gac atg gag aag ggc agc gag         336
Leu Ala Gly Tyr Ser Val Phe Gly Asn Asp Met Glu Lys Gly Ser Glu
            100                 105                 110 ccg cac gcg cac ggc atg gcc caa atc gtg tgg atc ttt tac gtg tcc         384
Pro His Ala His Gly Met Ala Gln Ile Val Trp Ile Phe Tyr Val Ser
        115                 120                 125 aag gcg tac gag ttc gtg gac acg ctg atc atg atc ctg tgc aaa aag         432
Lys Ala Tyr Glu Phe Val Asp Thr Leu Ile Met Ile Leu Cys Lys Lys
    130                 135                 140 ttc aac cag gtc tcc gtc ctg cac gtg tac cac cac gcc acc atc ttt         480
Phe Asn Gln Val Ser Val Leu His Val Tyr His His Ala Thr Ile Phe
145                 150                 155                 160 gct atc tgg ttt atg atc gcc aag tac gcc ccg ggc ggc gac gca tac         528
Ala Ile Trp Phe Met Ile Ala Lys Tyr Ala Pro Gly Gly Asp Ala Tyr
                165                 170                 175 ttt agc gtc atc ctg aac tcg ttc gtg cac acc gtc atg tac gcg tac         576
Phe Ser Val Ile Leu Asn Ser Phe Val His Thr Val Met Tyr Ala Tyr
            180                 185                 190 tac ttc ttc tcg tcg cag ggc ttc ggg ttc gtc aag ccg atc aag ccg         624
Tyr Phe Phe Ser Ser Gln Gly Phe Gly Phe Val Lys Pro Ile Lys Pro
        195                 200                 205 tac atc acc tcg ctg cag atg acg cag ttc atg gcg atg ctc gtg cag         672
Tyr Ile Thr Ser Leu Gln Met Thr Gln Phe Met Ala Met Leu Val Gln
    210                 215                 220 tcg ctg tac gac tac ctt tac ccg tgc gac tac ccg cag ggg ctc gtc         720
Ser Leu Tyr Asp Tyr Leu Tyr Pro Cys Asp Tyr Pro Gln Gly Leu Val
225                 230                 235                 240 aag ctc ctc ggc gtg tac atg ctc acc ctg ctt gcg ctc ttc ggc aac         768
Lys Leu Leu Gly Val Tyr Met Leu Thr Leu Leu Ala Leu Phe Gly Asn
                245                 250                 255 ttt ttc gtg cag agc tac ctc aag aag tcg aac aag ccc aag gcc aag         816
Phe Phe Val Gln Ser Tyr Leu Lys Lys Ser Asn Lys Pro Lys Ala Lys
            260                 265                 270 tcg gcc taa                                                              825
Ser Ala <210> SEQ ID NO 109
<211> LENGTH: 274
<212> TYPE: PRT
<213> ORGANISM: Thraustochytrium aureum

<400> SEQUENCE: 109

Met Thr Ser Asn Met Ser Ala Trp Gly Val Ala Val Asp Gln Thr Gln
1               5                   10                  15

Gln Val Val Asp Gln Ile Met Gly Gly Ala Glu Pro Tyr Lys Leu Thr
            20                  25                  30

Glu Gly Arg Met Thr Asn Val Glu Thr Met Leu Ala Ile Glu Cys Gly
        35                  40                  45

Tyr Ala Ala Met Leu Leu Phe Leu Thr Pro Ile Met Lys Gln Ala Glu
    50                  55                  60

Lys Pro Phe Glu Leu Lys Ser Phe Lys Leu Ala His Asn Leu Phe Leu
65                  70                  75                  80

Phe Val Leu Ser Ala Tyr Met Cys Leu Glu Thr Val Arg Gln Ala Tyr
                85                  90                  95
```

-continued

```
Leu Ala Gly Tyr Ser Val Phe Gly Asn Asp Met Glu Lys Gly Ser Glu
                100                 105                 110

Pro His Ala His Gly Met Ala Gln Ile Val Trp Ile Phe Tyr Val Ser
            115                 120                 125

Lys Ala Tyr Glu Phe Val Asp Thr Leu Ile Met Ile Leu Cys Lys Lys
        130                 135                 140

Phe Asn Gln Val Ser Val Leu His Val Tyr His Ala Thr Ile Phe
145                 150                 155                 160

Ala Ile Trp Phe Met Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Ser Leu Gln Met Thr Gln Phe Met Ala Met Leu Val Gln
    210                 215                 220

Ser Leu Tyr Asp Tyr Leu Tyr Pro Cys Asp Tyr Pro Gln Gly Leu Val
225                 230                 235                 240

Lys Leu Leu Gly Val Tyr Met Leu Thr Leu Leu Ala Leu Phe Gly Asn
                245                 250                 255

Phe Phe Val Gln Ser Tyr Leu Lys Lys Ser Asn Lys Pro Lys Ala Lys
            260                 265                 270

Ser Ala
```

<210> SEQ ID NO 110
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta-5-Elongase

<400> SEQUENCE: 110

```
atg agc gcc tcc ggt gcg ctg ctg ccc gcg atc gcg ttc gcc gcg tac    48
Met Ser Ala Ser Gly Ala Leu Leu Pro Ala Ile Ala Phe Ala Ala Tyr
1               5                  10                  15 gcg tac gcg acg tac gcc tac gcc ttt gag tgg tcg cac gcg aat ggc    96
Ala Tyr Ala Thr Tyr Ala Tyr Ala Phe Glu Trp Ser His Ala Asn Gly
            20                  25                  30 atc gac aac gtc gac gcg cgc gag tgg atc ggt gcg ctg tcg ttg agg   144
Ile Asp Asn Val Asp Ala Arg Glu Trp Ile Gly Ala Leu Ser Leu Arg
        35                  40                  45 ctc ccg gcg atc gcg acg acg atg tac ctg ttg ttc tgc ctg gtc gga   192
Leu Pro Ala Ile Ala Thr Thr Met Tyr Leu Leu Phe Cys Leu Val Gly
    50                  55                  60 ccg agg ttg atg gcg aag cgc gag gcg ttc gac ccg aag ggg ttc atg   240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtc ctc ggg   288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca   336
Met Phe Ala Arg Glu Ile Ser Gly Leu Gly Gln Pro Val Trp Gly Ser
            100                 105                 110 acc atg ccg tgg agc gat aga aaa tcg ttt aag atc ctc ctc ggg gtg   384
Thr Met Pro Trp Ser Asp Arg Lys Ser Phe Lys Ile Leu Leu Gly Val
        115                 120                 125
```

```
tgg ttg cac tac aac aac caa tat ttg gag cta ttg gac act gtg ttc    432
Trp Leu His Tyr Asn Asn Gln Tyr Leu Glu Leu Leu Asp Thr Val Phe
    130                 135                 140 atg gtt gcg cgc aag aag acg aag cag ttg agc ttc ttg cac gtt tat    480
Met Val Ala Arg Lys Lys Thr Lys Gln Leu Ser Phe Leu His Val Tyr
145                 150                 155                 160 cat cac gcc ctg ttg atc tgg gcg tgg tgg ttg gtg tgt cac ttg atg    528
His His Ala Leu Leu Ile Trp Ala Trp Trp Leu Val Cys His Leu Met
                165                 170                 175 gcc acg aac gat tgt atc gat gcc tac ttc ggc gcg gcg tgc aac tcg    576
Ala Thr Asn Asp Cys Ile Asp Ala Tyr Phe Gly Ala Ala Cys Asn Ser
            180                 185                 190 ttc att cac atc gtg atg tac tcg tat tat ctc atg tcg gcg ctc ggc    624
Phe Ile His Ile Val Met Tyr Ser Tyr Tyr Leu Met Ser Ala Leu Gly
        195                 200                 205 att cga tgc ccg tgg aag cga tac atc acc cag gct caa atg ctc caa    672
Ile Arg Cys Pro Trp Lys Arg Tyr Ile Thr Gln Ala Gln Met Leu Gln
    210                 215                 220 ttc gtc att gtc ttc gcg cac gcc gtg ttc gtg ctg cgt cag aag cac    720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg    768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg    816
Leu Val Leu Phe Gly Asn Phe Tyr Leu Lys Ala Tyr Ser Asn Lys Ser
            260                 265                 270 cgc ggc gac ggc gcg agt tcc gtg aaa cca gcc gag acc acg cgc gcg    864
Arg Gly Asp Gly Ala Ser Ser Val Lys Pro Ala Glu Thr Thr Arg Ala
        275                 280                 285 ccc agc gtg cga cgc acg cga tct cga aaa att gac taa                903
Pro Ser Val Arg Arg Thr Arg Ser Arg Lys Ile Asp
    290                 295                 300

<210> SEQ ID NO 111
<211> LENGTH: 300
<212> TYPE: PRT
<213> ORGANISM: Ostreococcus tauri

<400> SEQUENCE: 111

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
                20                  25                  30

Ile Asp Asn Val Asp Ala Arg Glu Trp Ile Gly Ala Leu Ser Leu Arg
            35                  40                  45

Leu Pro Ala Ile Ala Thr Thr Met Tyr Leu Leu Phe Cys Leu Val Gly
        50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
            115                 120                 125

Trp Leu His Tyr Asn Asn Gln Tyr Leu Glu Leu Leu Asp Thr Val Phe
        130                 135                 140
```

```
Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Leu Met Ser Ala Leu Gly
        195                 200                 205

Ile Arg Cys Pro Trp Lys Arg Tyr Ile Thr Gln Ala Gln Met Leu Gln
        210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
        290                 295                 300

<210> SEQ ID NO 112
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: delta-6-Elongase

<400> SEQUENCE: 112 atg agt ggc tta cgt gca ccc aac ttt tta cac aga ttc tgg aca aag      48
Met Ser Gly Leu Arg Ala Pro Asn Phe Leu His Arg Phe Trp Thr Lys
1               5                   10                  15 tgg gac tac gcg att tcc aaa gtc gtc ttc acg tgt gcc gac agt ttt      96
Trp Asp Tyr Ala Ile Ser Lys Val Val Phe Thr Cys Ala Asp Ser Phe
            20                  25                  30 cag tgg gac atc ggg cca gtg agt tcg agt acg gcg cat tta ccc gcc     144
Gln Trp Asp Ile Gly Pro Val Ser Ser Ser Thr Ala His Leu Pro Ala
        35                  40                  45 att gaa tcc cct acc cca ctg gtg act agc ctc ttg ttc tac tta gtc     192
Ile Glu Ser Pro Thr Pro Leu Val Thr Ser Leu Leu Phe Tyr Leu Val
    50                  55                  60 aca gtt ttc ttg tgg tat ggt cgt tta acc agg agt tca gac aag aaa     240
Thr Val Phe Leu Trp Tyr Gly Arg Leu Thr Arg Ser Ser Asp Lys Lys
65                  70                  75                  80 att aga gag cct acg tgg tta aga aga ttc ata ata tgt cat aat gcg     288
Ile Arg Glu Pro Thr Trp Leu Arg Arg Phe Ile Ile Cys His Asn Ala
                85                  90                  95 ttc ttg ata gtc ctc agt ctt tac atg tgc ctt ggt tgt gtg gcc caa     336
Phe Leu Ile Val Leu Ser Leu Tyr Met Cys Leu Gly Cys Val Ala Gln
            100                 105                 110 gcg tat cag aat gga tat act tta tgg ggt aat gaa ttc aag gcc acg     384
Ala Tyr Gln Asn Gly Tyr Thr Leu Trp Gly Asn Glu Phe Lys Ala Thr
        115                 120                 125 gaa act cag ctt gct ctc tac att tac att ttt tac gta agt aaa ata     432
Glu Thr Gln Leu Ala Leu Tyr Ile Tyr Ile Phe Tyr Val Ser Lys Ile
    130                 135                 140 tac gag ttt gta gat act tac att atg ctt ctc aag aat aac ttg cgg     480
```

```
Tyr Glu Phe Val Asp Thr Tyr Ile Met Leu Leu Lys Asn Asn Leu Arg
145                 150                 155                 160 caa gta agt ttc cta cac att tat cac cac agc acg att tcc ttt att    528
Gln Val Ser Phe Leu His Ile Tyr His His Ser Thr Ile Ser Phe Ile
                165                 170                 175 tgg tgg atc att gct cgg agg gct ccg ggt ggt gat gct tac ttc agc    576
Trp Trp Ile Ile Ala Arg Arg Ala Pro Gly Gly Asp Ala Tyr Phe Ser
            180                 185                 190 gcg gcc ttg aac tca tgg gta cac gtg tgc atg tac acc tat tat cta    624
Ala Ala Leu Asn Ser Trp Val His Val Cys Met Tyr Thr Tyr Tyr Leu
        195                 200                 205 tta tca acc ctt att gga aaa gaa gat cct aag cgt tcc aac tac ctt    672
Leu Ser Thr Leu Ile Gly Lys Glu Asp Pro Lys Arg Ser Asn Tyr Leu
    210                 215                 220 tgg tgg ggt cgc cac cta acg caa atg cag atg ctt cag ttt ttc ttc    720
Trp Trp Gly Arg His Leu Thr Gln Met Gln Met Leu Gln Phe Phe Phe
225                 230                 235                 240 aac gta ctt caa gcg ttg tac tgc gct tcg ttc tct acg tat ccc aag    768
Asn Val Leu Gln Ala Leu Tyr Cys Ala Ser Phe Ser Thr Tyr Pro Lys
                245                 250                 255 ttt ttg tcc aaa att ctg ctc gtc tat atg atg agc ctt ctc ggc ttg    816
Phe Leu Ser Lys Ile Leu Leu Val Tyr Met Met Ser Leu Leu Gly Leu
            260                 265                 270 ttt ggg cat ttc tac tat tcc aag cac ata gca gca gct aag ctc cag    864
Phe Gly His Phe Tyr Tyr Ser Lys His Ile Ala Ala Ala Lys Leu Gln
        275                 280                 285 aaa aaa cag cag tga                                                879
Lys Lys Gln Gln
    290

<210> SEQ ID NO 113
<211> LENGTH: 292
<212> TYPE: PRT
<213> ORGANISM: Ostreococcus tauri

<400> SEQUENCE: 113

Met Ser Gly Leu Arg Ala Pro Asn Phe Leu His Arg Phe Trp Thr Lys
1               5                   10                  15

Trp Asp Tyr Ala Ile Ser Lys Val Val Phe Thr Cys Ala Asp Ser Phe
            20                  25                  30

Gln Trp Asp Ile Gly Pro Val Ser Ser Thr Ala His Leu Pro Ala
        35                  40                  45

Ile Glu Ser Pro Thr Pro Leu Val Thr Ser Leu Leu Phe Tyr Leu Val
    50                  55                  60

Thr Val Phe Leu Trp Tyr Gly Arg Leu Thr Arg Ser Ser Asp Lys Lys
65                  70                  75                  80

Ile Arg Glu Pro Thr Trp Leu Arg Arg Phe Ile Ile Cys His Asn Ala
                85                  90                  95

Phe Leu Ile Val Leu Ser Leu Tyr Met Cys Leu Gly Cys Val Ala Gln
            100                 105                 110

Ala Tyr Gln Asn Gly Tyr Thr Leu Trp Gly Asn Glu Phe Lys Ala Thr
        115                 120                 125

Glu Thr Gln Leu Ala Leu Tyr Ile Tyr Ile Phe Tyr Val Ser Lys Ile
    130                 135                 140

Tyr Glu Phe Val Asp Thr Tyr Ile Met Leu Leu Lys Asn Asn Leu Arg
145                 150                 155                 160

Gln Val Ser Phe Leu His Ile Tyr His His Ser Thr Ile Ser Phe Ile
                165                 170                 175
```

```
Trp Trp Ile Ile Ala Arg Arg Ala Pro Gly Gly Asp Ala Tyr Phe Ser
            180                 185                 190

Ala Ala Leu Asn Ser Trp Val His Val Cys Met Tyr Thr Tyr Tyr Leu
            195                 200                 205

Leu Ser Thr Leu Ile Gly Lys Glu Asp Pro Lys Arg Ser Asn Tyr Leu
            210                 215                 220

Trp Trp Gly Arg His Leu Thr Gln Met Gln Met Leu Gln Phe Phe Phe
225                 230                 235                 240

Asn Val Leu Gln Ala Leu Tyr Cys Ala Ser Phe Ser Thr Tyr Pro Lys
                245                 250                 255

Phe Leu Ser Lys Ile Leu Leu Val Tyr Met Met Ser Leu Leu Gly Leu
            260                 265                 270

Phe Gly His Phe Tyr Tyr Ser Lys His Ile Ala Ala Lys Leu Gln
            275                 280                 285

Lys Lys Gln Gln
        290

<210> SEQ ID NO 114
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta-5-Elongase

<400> SEQUENCE: 114 atg agc gcc tcc ggt gcg ctg ctg ccc gcg atc gcg tcc gcc gcg tac      48
Met Ser Ala Ser Gly Ala Leu Leu Pro Ala Ile Ala Ser Ala Ala Tyr
1               5                   10                  15 gcg tac gcg acg tac gcc tac gcc ttt gag tgg tcg cac gcg aat ggc      96
Ala Tyr Ala Thr Tyr Ala Tyr Ala Phe Glu Trp Ser His Ala Asn Gly
                20                  25                  30 atc gac aac gtc gac gcg cgc gag tgg atc ggt gcg ctg tcg ttg agg     144
Ile Asp Asn Val Asp Ala Arg Glu Trp Ile Gly Ala Leu Ser Leu Arg
            35                  40                  45 ctc ccg gcg atc gcg acg acg atg tac ctg ttg ttc tgc ctg gtc gga     192
Leu Pro Ala Ile Ala Thr Thr Met Tyr Leu Leu Phe Cys Leu Val Gly
        50                  55                  60 ccg agg ttg atg gcg aag cgc gag gcg ttc gac ccg aag ggg ttc atg     240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtg ctc ggg     288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca     336
Met Phe Ala Arg Glu Ile Ser Gly Leu Gly Gln Pro Val Trp Gly Ser
                100                 105                 110 acc atg ccg tgg agc gat aga aaa tcg ttt aag atc ctc ctc ggg gtg     384
Thr Met Pro Trp Ser Asp Arg Lys Ser Phe Lys Ile Leu Leu Gly Val
            115                 120                 125 tgg ttg cac tac aac aac aaa tat ttg gag cta ttg gac act gtg ttc     432
Trp Leu His Tyr Asn Asn Lys Tyr Leu Glu Leu Leu Asp Thr Val Phe
        130                 135                 140 atg gtt gcg cgc aag aag acg aag cag ttg agc ttc ttg cac gtt tat     480
Met Val Ala Arg Lys Lys Thr Lys Gln Leu Ser Phe Leu His Val Tyr
145                 150                 155                 160 cat cac gcc ctg ttg atc tgg gcg tgg tgg ttg gtg tgt cac ttg atg     528
His His Ala Leu Leu Ile Trp Ala Trp Trp Leu Val Cys His Leu Met
                165                 170                 175
```

```
                    165                 170                 175
gcc acg aac gat tgt atc gat gcc tac ttc ggc gcg gcg tgc aac tcg      576
Ala Thr Asn Asp Cys Ile Asp Ala Tyr Phe Gly Ala Ala Cys Asn Ser
            180                 185                 190 ttc att cac atc gtg atg tac tcg tat tat ctc atg tcg gcg ctc ggc      624
Phe Ile His Ile Val Met Tyr Ser Tyr Tyr Leu Met Ser Ala Leu Gly
        195                 200                 205 att cga tgc ccg tgg aag cga tac atc acc cag gct caa atg ctc caa      672
Ile Arg Cys Pro Trp Lys Arg Tyr Ile Thr Gln Ala Gln Met Leu Gln
    210                 215                 220 ttc gtc att gtc ttc gcg cac gcc gtg ttc gtg ctg cgt cag aag cac      720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg      768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg      816
Leu Val Leu Phe Gly Asn Phe Tyr Leu Lys Ala Tyr Ser Asn Lys Ser
            260                 265                 270 cgc ggc gac ggc gcg agt tcc gtg aaa cca gcc gag acc acg cgc gcg      864
Arg Gly Asp Gly Ala Ser Ser Val Lys Pro Ala Glu Thr Thr Arg Ala
        275                 280                 285 ccc agc gtg cga cgc acg cga tct cga aaa att gac taa                  903
Pro Ser Val Arg Arg Thr Arg Ser Arg Lys Ile Asp
    290                 295                 300

<210> SEQ ID NO 115
<211> LENGTH: 300
<212> TYPE: PRT
<213> ORGANISM: Ostreococcus tauri

<400> SEQUENCE: 115

Met Ser Ala Ser Gly Ala Leu Leu Pro Ala Ile Ala Ser Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
            85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
```

```
                195                 200                 205
Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
                275                 280                 285

Pro Ser Val Arg Arg Thr Arg Ser Arg Lys Ile Asp
    290                 295                 300

<210> SEQ ID NO 116
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta-5-Elongase

<400> SEQUENCE: 116
```

| | | | | | | | | | | | | | | | | |
|---|---|---|---|---|---|---|---|---|---|---|---|---|---|---|---|---|
| atg | agc | gcc | tcc | ggt | gcg | ctg | ctg | ccc | gcg | atc | gcg | ttc | gcc | gcg | tac | 48 |
| Met | Ser | Ala | Ser | Gly | Ala | Leu | Leu | Pro | Ala | Ile | Ala | Phe | Ala | Ala | Tyr | |
| 1 | | | | 5 | | | | | 10 | | | | | 15 | | |
| gcg | tac | gcg | acg | tac | gcc | tac | gcc | ttt | gag | tgg | tcg | cac | gcg | aat | ggc | 96 |
| Ala | Tyr | Ala | Thr | Tyr | Ala | Tyr | Ala | Phe | Glu | Trp | Ser | His | Ala | Asn | Gly | |
| | | | 20 | | | | | 25 | | | | | 30 | | | |
| atc | gac | aac | gtc | gac | gcg | cgc | gag | tgg | atc | ggt | gcg | ctg | tcg | ttg | agg | 144 |
| Ile | Asp | Asn | Val | Asp | Ala | Arg | Glu | Trp | Ile | Gly | Ala | Leu | Ser | Leu | Arg | |
| | | 35 | | | | | 40 | | | | | 45 | | | | |
| ctc | ccg | gcg | atc | gcg | acg | acg | atg | tac | ctg | ttg | ttc | tgc | ctg | gtc | gga | 192 |
| Leu | Pro | Ala | Ile | Ala | Thr | Thr | Met | Tyr | Leu | Leu | Phe | Cys | Leu | Val | Gly | |
| | 50 | | | | | 55 | | | | | 60 | | | | | |
| ccg | agg | ttg | atg | gcg | aag | cgc | gag | gcg | ttc | gac | ccg | aag | ggg | ttc | atg | 240 |
| Pro | Arg | Leu | Met | Ala | Lys | Arg | Glu | Ala | Phe | Asp | Pro | Lys | Gly | Phe | Met | |
| 65 | | | | | 70 | | | | | 75 | | | | | 80 | |
| ctg | gcg | tac | aat | gcg | tat | cag | acg | gcg | ttc | aac | gtc | gtc | gtg | ctc | ggg | 288 |
| Leu | Ala | Tyr | Asn | Ala | Tyr | Gln | Thr | Ala | Phe | Asn | Val | Val | Val | Leu | Gly | |
| | | | | 85 | | | | | 90 | | | | | 95 | | |
| atg | ttc | gcg | cga | gag | atc | tcg | ggg | ctg | ggg | cag | ccc | gtg | tgg | ggg | tca | 336 |
| Met | Phe | Ala | Arg | Glu | Ile | Ser | Gly | Leu | Gly | Gln | Pro | Val | Trp | Gly | Ser | |
| | | | 100 | | | | | 105 | | | | | 110 | | | |
| acc | atg | ccg | tgg | agc | gat | aga | aaa | tcg | ttt | aag | atc | ctc | ctc | ggg | gtg | 384 |
| Thr | Met | Pro | Trp | Ser | Asp | Arg | Lys | Ser | Phe | Lys | Ile | Leu | Leu | Gly | Val | |
| | | 115 | | | | | 120 | | | | | 125 | | | | |
| tgg | ttg | cac | tac | aac | aac | aaa | tat | ttg | gag | cta | ttg | gac | act | gtg | ttc | 432 |
| Trp | Leu | His | Tyr | Asn | Asn | Lys | Tyr | Leu | Glu | Leu | Leu | Asp | Thr | Val | Phe | |
| | 130 | | | | | 135 | | | | | 140 | | | | | |
| atg | gtt | gcg | cgc | aag | aag | acg | aag | cag | ttg | agc | ttc | ttg | cac | gtt | tat | 480 |
| Met | Val | Ala | Arg | Lys | Lys | Thr | Lys | Gln | Leu | Ser | Phe | Leu | His | Val | Tyr | |
| 145 | | | | | 150 | | | | | 155 | | | | | 160 | |
| cat | cac | gcc | ctg | ttg | atc | tgg | gcg | tgg | tgg | ttg | gtg | tgt | cac | ttg | atg | 528 |
| His | His | Ala | Leu | Leu | Ile | Trp | Ala | Trp | Trp | Leu | Val | Cys | His | Leu | Met | |
| | | | | 165 | | | | | 170 | | | | | 175 | | |
| gcc | acg | aac | gat | tgt | atc | gat | gcc | tac | ttc | ggc | gcg | gcg | tgc | aac | tcg | 576 |
| Ala | Thr | Asn | Asp | Cys | Ile | Asp | Ala | Tyr | Phe | Gly | Ala | Ala | Cys | Asn | Ser | |
| | | | 180 | | | | | 185 | | | | | 190 | | | |

```
ttc att cac atc gtg atg tac tcg tat tat ctc atg tcg gcg ctc ggc    624
Phe Ile His Ile Val Met Tyr Ser Tyr Tyr Leu Met Ser Ala Leu Gly
        195                 200                 205 att cga tgc ccg tgg aag cga tac atc acc cag gct caa atg ctc caa    672
Ile Arg Cys Pro Trp Lys Arg Tyr Ile Thr Gln Ala Gln Met Leu Gln
    210                 215                 220 ttc gtc att gtc ttc gcg cac gcc gtg ttc gtg ctg cgt cag aag cac    720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg    768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg    816
Leu Val Leu Phe Gly Asn Phe Tyr Leu Lys Ala Tyr Ser Asn Lys Ser
            260                 265                 270 cgc ggc gac ggc gcg agt tcc gtg aaa cca gcc gag acc acg cgc gcg    864
Arg Gly Asp Gly Ala Ser Ser Val Lys Pro Ala Glu Thr Thr Arg Ala
        275                 280                 285 ccc agc gtg cga cgc acg cga tct cga aaa att gac taa                903
Pro Ser Val Arg Arg Thr Arg Ser Arg Lys Ile Asp
    290                 295                 300

<210> SEQ ID NO 117
<211> LENGTH: 300
<212> TYPE: PRT
<213> ORGANISM: Ostreococcus tauri

<400> SEQUENCE: 117

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
            85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220
```

```
Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
            245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
        275                 280                 285

Pro Ser Val Arg Arg Thr Arg Ser Arg Lys Ile Asp
    290                 295                 300

<210> SEQ ID NO 118
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta-5-Elongase

<400> SEQUENCE: 118
```

| | | | | | | | | | | | | | | | | |
|---|---|---|---|---|---|---|---|---|---|---|---|---|---|---|---|---|
| atg | agc | gcc | tcc | ggt | gcg | ctg | ctg | ccc | gcg | atc | gcg | tcc | gcc | gcg | tac | 48 |
| Met | Ser | Ala | Ser | Gly | Ala | Leu | Leu | Pro | Ala | Ile | Ala | Ser | Ala | Ala | Tyr | |
| 1 | | | | 5 | | | | | 10 | | | | | 15 | | |
| gcg | tac | gcg | acg | tac | gcc | tac | gcc | ttt | gag | tgg | tcg | cac | gcg | aat | ggc | 96 |
| Ala | Tyr | Ala | Thr | Tyr | Ala | Tyr | Ala | Phe | Glu | Trp | Ser | His | Ala | Asn | Gly | |
| | | | 20 | | | | | 25 | | | | | 30 | | | |
| atc | gac | aac | gtc | gac | gcg | cgc | gag | tgg | atc | ggt | gcg | ctg | tcg | ttg | agg | 144 |
| Ile | Asp | Asn | Val | Asp | Ala | Arg | Glu | Trp | Ile | Gly | Ala | Leu | Ser | Leu | Arg | |
| | | 35 | | | | | 40 | | | | | 45 | | | | |
| ctc | ccg | gcg | atc | gcg | acg | acg | atg | tac | ctg | ttg | ttc | tgc | ctg | gtc | gga | 192 |
| Leu | Pro | Ala | Ile | Ala | Thr | Thr | Met | Tyr | Leu | Leu | Phe | Cys | Leu | Val | Gly | |
| | 50 | | | | | 55 | | | | | 60 | | | | | |
| ccg | agg | ttg | atg | gcg | aag | cgc | gag | gcg | ttc | gac | ccg | aag | ggg | ttc | atg | 240 |
| Pro | Arg | Leu | Met | Ala | Lys | Arg | Glu | Ala | Phe | Asp | Pro | Lys | Gly | Phe | Met | |
| 65 | | | | | 70 | | | | | 75 | | | | | 80 | |
| ctg | gcg | tac | aat | gcg | tat | cag | acg | gcg | ttc | aac | gtc | gtc | gtg | ctc | ggg | 288 |
| Leu | Ala | Tyr | Asn | Ala | Tyr | Gln | Thr | Ala | Phe | Asn | Val | Val | Val | Leu | Gly | |
| | | | | 85 | | | | | 90 | | | | | 95 | | |
| atg | ttc | gcg | cga | gag | atc | tcg | ggg | ctg | ggg | cag | ccc | gtg | tgg | ggg | tca | 336 |
| Met | Phe | Ala | Arg | Glu | Ile | Ser | Gly | Leu | Gly | Gln | Pro | Val | Trp | Gly | Ser | |
| | | | 100 | | | | | 105 | | | | | 110 | | | |
| acc | atg | ccg | tgg | agc | gat | aga | aaa | tcg | ttt | aag | atc | ctc | ctc | ggg | gtg | 384 |
| Thr | Met | Pro | Trp | Ser | Asp | Arg | Lys | Ser | Phe | Lys | Ile | Leu | Leu | Gly | Val | |
| | | 115 | | | | | 120 | | | | | 125 | | | | |
| tgg | ttg | cac | tac | aac | aac | caa | tat | ttg | gag | cta | ttg | gac | act | gtg | ttc | 432 |
| Trp | Leu | His | Tyr | Asn | Asn | Gln | Tyr | Leu | Glu | Leu | Leu | Asp | Thr | Val | Phe | |
| | 130 | | | | | 135 | | | | | 140 | | | | | |
| atg | gtt | gcg | cgc | aag | aag | acg | aag | cag | ttg | agc | ttc | ttg | cac | gtt | tat | 480 |
| Met | Val | Ala | Arg | Lys | Lys | Thr | Lys | Gln | Leu | Ser | Phe | Leu | His | Val | Tyr | |
| 145 | | | | | 150 | | | | | 155 | | | | | 160 | |
| cat | cac | gcc | ctg | ttg | atc | tgg | gcg | tgg | tgg | ttg | gtg | tgt | cac | ttg | atg | 528 |
| His | His | Ala | Leu | Leu | Ile | Trp | Ala | Trp | Trp | Leu | Val | Cys | His | Leu | Met | |
| | | | | 165 | | | | | 170 | | | | | 175 | | |
| gcc | acg | aac | gat | tgt | atc | gat | gcc | tac | ttc | ggc | gcg | gcg | tgc | aac | tcg | 576 |
| Ala | Thr | Asn | Asp | Cys | Ile | Asp | Ala | Tyr | Phe | Gly | Ala | Ala | Cys | Asn | Ser | |
| | | | 180 | | | | | 185 | | | | | 190 | | | |
| ttc | att | cac | atc | gtg | atg | tac | tcg | tat | tat | ctc | atg | tcg | gcg | ctc | ggc | 624 |
| Phe | Ile | His | Ile | Val | Met | Tyr | Ser | Tyr | Tyr | Leu | Met | Ser | Ala | Leu | Gly | |
| | | | 195 | | | | | 200 | | | | | 205 | | | |

```
att cga tgc ccg tgg aag cga tac atc acc cag gct caa atg ctc caa      672
Ile Arg Cys Pro Trp Lys Arg Tyr Ile Thr Gln Ala Gln Met Leu Gln
    210                 215                 220 ttc gtc att gtc ttc gcg cac gcc gtg ttc gtg ctg cgt cag aag cac      720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg      768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg      816
Leu Val Leu Phe Gly Asn Phe Tyr Leu Lys Ala Tyr Ser Asn Lys Ser
            260                 265                 270 cgc ggc gac ggc gcg agt tcc gtg aaa cca gcc gag acc acg cgc gcg      864
Arg Gly Asp Gly Ala Ser Ser Val Lys Pro Ala Glu Thr Thr Arg Ala
        275                 280                 285 ccc agc gtg cga cgc acg cga tct cga aaa att gac taa                  903
Pro Ser Val Arg Arg Thr Arg Ser Arg Lys Ile Asp
    290                 295                 300

<210> SEQ ID NO 119
<211> LENGTH: 300
<212> TYPE: PRT
<213> ORGANISM: Ostreococcus tauri

<400> SEQUENCE: 119

Met Ser Ala Ser Gly Ala Leu Leu Pro Ala Ile Ala Ser Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Val Leu Gly
                85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Gln Tyr Leu Glu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255
```

```
Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
        275                 280                 285

Pro Ser Val Arg Arg Thr Arg Ser Arg Lys Ile Asp
    290                 295                 300

<210> SEQ ID NO 120
<211> LENGTH: 831
<212> TYPE: DNA
<213> ORGANISM: Thraustochytrium sp.
<220> FEATURE:
<221> NAME/KEY: CDS
<222> LOCATION: (1)..(831)
<223> OTHER INFORMATION: delta-5-Elongase

<400> SEQUENCE: 120 atg gac gtc gtc gag cag caa tgg cgc cgc ttc gtg gac gcc gtg gac      48
Met Asp Val Val Glu Gln Gln Trp Arg Arg Phe Val Asp Ala Val Asp
1               5                   10                  15 aac gga atc gtg gag ttc atg gag cat gag aag ccc aac aag ctg aac      96
Asn Gly Ile Val Glu Phe Met Glu His Glu Lys Pro Asn Lys Leu Asn
            20                  25                  30 gag ggc aag ctc ttc acc tcg acc gag gag atg atg gcg ctt atc gtc     144
Glu Gly Lys Leu Phe Thr Ser Thr Glu Glu Met Met Ala Leu Ile Val
        35                  40                  45 ggc tac ctg gcg ttc gtg gtc ctc ggg tcc gcc ttc atg aag gcc ttt     192
Gly Tyr Leu Ala Phe Val Val Leu Gly Ser Ala Phe Met Lys Ala Phe
    50                  55                  60 gtc gat aag cct ttc gag ctc aag ttc ctc aag ctc gtg cac aac atc     240
Val Asp Lys Pro Phe Glu Leu Lys Phe Leu Lys Leu Val His Asn Ile
65                  70                  75                  80 ttc ctc acc ggt ctg tcc atg tac atg gcc acc gag tgc gcg cgc cag     288
Phe Leu Thr Gly Leu Ser Met Tyr Met Ala Thr Glu Cys Ala Arg Gln
                85                  90                  95 gca tac ctc ggc ggc tac aag ctc ttt ggc aac ccg atg gag aag ggc     336
Ala Tyr Leu Gly Gly Tyr Lys Leu Phe Gly Asn Pro Met Glu Lys Gly
            100                 105                 110 acc gag tcg cac gcc ccg ggc atg gcc aac atc atc tac atc ttc tac     384
Thr Glu Ser His Ala Pro Gly Met Ala Asn Ile Ile Tyr Ile Phe Tyr
        115                 120                 125 gtg agc aag ttc ctc gaa ttc ctc gac acc gtc ttc atg atc ctc ggc     432
Val Ser Lys Phe Leu Glu Phe Leu Asp Thr Val Phe Met Ile Leu Gly
    130                 135                 140 aag aag tgg aag cag ctc agc ttt ctc cac gtc tac cac cac gcg agc     480
Lys Lys Trp Lys Gln Leu Ser Phe Leu His Val Tyr His His Ala Ser
145                 150                 155                 160 atc agc ttc atc tgg ggc atc atc gcc cgc ttc gcg ccc ggt ggc gac     528
Ile Ser Phe Ile Trp Gly Ile Ile Ala Arg Phe Ala Pro Gly Gly Asp
                165                 170                 175 gcc tac ttc tct acc atc ctc aac agc agc gtg cat gtc gtg ctc tac     576
Ala Tyr Phe Ser Thr Ile Leu Asn Ser Ser Val His Val Val Leu Tyr
            180                 185                 190 ggc tac tac gcc tcg acc acc ctc ggc tac acc ttc atg cgc ccg ctg     624
Gly Tyr Tyr Ala Ser Thr Thr Leu Gly Tyr Thr Phe Met Arg Pro Leu
        195                 200                 205 cgc ccg tac att acc acc att cag ctc acg cag ttc atg gcc atg gtc     672
Arg Pro Tyr Ile Thr Thr Ile Gln Leu Thr Gln Phe Met Ala Met Val
    210                 215                 220 gtc cag tcc gtc tat gac tac tac aac ccc tgc gac tac ccg cag ccc     720
```

```
Val Gln Ser Val Tyr Asp Tyr Asn Pro Cys Asp Tyr Pro Gln Pro
225                 230                 235                 240 ctc gtc aag ctg ctc ttc tgg tac atg ctc acc atg ctc ggc ctc ttc      768
Leu Val Lys Leu Leu Phe Trp Tyr Met Leu Thr Met Leu Gly Leu Phe
            245                 250                 255 ggc aac ttc ttc gtg cag cag tac ctc aag ccc aag gcg ccc aag aag      816
Gly Asn Phe Phe Val Gln Gln Tyr Leu Lys Pro Lys Ala Pro Lys Lys
        260                 265                 270 cag aag acc atc taa                                                  831
Gln Lys Thr Ile
        275

<210> SEQ ID NO 121
<211> LENGTH: 276
<212> TYPE: PRT
<213> ORGANISM: Thraustochytrium sp.

<400> SEQUENCE: 121

Met Asp Val Val Glu Gln Gln Trp Arg Arg Phe Val Asp Ala Val Asp
1               5                   10                  15

Asn Gly Ile Val Glu Phe Met Glu His Glu Lys Pro Asn Lys Leu Asn
            20                  25                  30

Glu Gly Lys Leu Phe Thr Ser Thr Glu Glu Met Met Ala Leu Ile Val
        35                  40                  45

Gly Tyr Leu Ala Phe Val Val Leu Gly Ser Ala Phe Met Lys Ala Phe
    50                  55                  60

Val Asp Lys Pro Phe Glu Leu Lys Phe Leu Lys Leu Val His Asn Ile
65                  70                  75                  80

Phe Leu Thr Gly Leu Ser Met Tyr Met Ala Thr Glu Cys Ala Arg Gln
                85                  90                  95

Ala Tyr Leu Gly Gly Tyr Lys Leu Phe Gly Asn Pro Met Glu Lys Gly
            100                 105                 110

Thr Glu Ser His Ala Pro Gly Met Ala Asn Ile Ile Tyr Ile Phe Tyr
        115                 120                 125

Val Ser Lys Phe Leu Glu Phe Leu Asp Thr Val Phe Met Ile Leu Gly
    130                 135                 140

Lys Lys Trp Lys Gln Leu Ser Phe Leu His Val Tyr His His Ala Ser
145                 150                 155                 160

Ile Ser Phe Ile Trp Gly Ile Ile Ala Arg Phe Ala Pro Gly Gly Asp
                165                 170                 175

Ala Tyr Phe Ser Thr Ile Leu Asn Ser Ser Val His Val Val Leu Tyr
            180                 185                 190

Gly Tyr Tyr Ala Ser Thr Thr Leu Gly Tyr Thr Phe Met Arg Pro Leu
        195                 200                 205

Arg Pro Tyr Ile Thr Thr Ile Gln Leu Thr Gln Phe Met Ala Met Val
    210                 215                 220

Val Gln Ser Val Tyr Asp Tyr Asn Pro Cys Asp Tyr Pro Gln Pro
225                 230                 235                 240

Leu Val Lys Leu Leu Phe Trp Tyr Met Leu Thr Met Leu Gly Leu Phe
            245                 250                 255

Gly Asn Phe Phe Val Gln Gln Tyr Leu Lys Pro Lys Ala Pro Lys Lys
        260                 265                 270

Gln Lys Thr Ile
        275

<210> SEQ ID NO 122
```

-continued

```
<211> LENGTH: 1077
<212> TYPE: DNA
<213> ORGANISM: Thalassiosira pseudonana
<220> FEATURE:
<221> NAME/KEY: CDS
<222> LOCATION: (1)..(1077)
<223> OTHER INFORMATION: delta-5-Elongase

<400> SEQUENCE: 122 atg tgc tca cca ccg ccg tca caa tcc aaa aca aca tcc ctc cta gca        48
Met Cys Ser Pro Pro Pro Ser Gln Ser Lys Thr Thr Ser Leu Leu Ala
1               5                   10                  15 cgg tac acc acc gcc gcc ctc ctc ctc acc ctc aca acg tgg tgc            96
Arg Tyr Thr Thr Ala Ala Leu Leu Leu Thr Leu Thr Thr Trp Cys
            20                  25                  30 cac ttc gcc ttc cca gcc gcc acc gcc aca ccc ggc ctc acc gcc gaa       144
His Phe Ala Phe Pro Ala Ala Thr Ala Thr Pro Gly Leu Thr Ala Glu
        35                  40                  45 atg cac tcc tac aaa gtc cca ctc ggt ctc acc gta ttc tac ctg ctg       192
Met His Ser Tyr Lys Val Pro Leu Gly Leu Thr Val Phe Tyr Leu Leu
50                  55                  60 agt cta ccg tca cta aag tac gtt acg gac aac tac ctt gcc aaa aag       240
Ser Leu Pro Ser Leu Lys Tyr Val Thr Asp Asn Tyr Leu Ala Lys Lys
65                  70                  75                  80 tat gat atg aag tca ctc ctg acg gaa tca atg gtg ttg tac aat gtg       288
Tyr Asp Met Lys Ser Leu Leu Thr Glu Ser Met Val Leu Tyr Asn Val
                85                  90                  95 gcg caa gtg ctg ctc aat ggg tgg acg gtg tat gcg att gtg gat gcg       336
Ala Gln Val Leu Leu Asn Gly Trp Thr Val Tyr Ala Ile Val Asp Ala
            100                 105                 110 gtg atg aat aga gac cat cct ttt att gga agt aga agt ttg gtt ggg       384
Val Met Asn Arg Asp His Pro Phe Ile Gly Ser Arg Ser Leu Val Gly
        115                 120                 125 gcg gcg ttg cat agt ggg agc tcg tat gcg gtg tgg gtt cat tat tgt       432
Ala Ala Leu His Ser Gly Ser Ser Tyr Ala Val Trp Val His Tyr Cys
130                 135                 140 gat aag tat ttg gag ttc ttt gat acg tat ttt atg gtg ttg agg ggg       480
Asp Lys Tyr Leu Glu Phe Phe Asp Thr Tyr Phe Met Val Leu Arg Gly
145                 150                 155                 160 aaa atg gac cag gtc tcc ttc ctc cac atc tac cac cac acg acc ata       528
Lys Met Asp Gln Val Ser Phe Leu His Ile Tyr His His Thr Thr Ile
                165                 170                 175 gcg tgg gca tgg tgg atc gcc ctc cgc ttc tcc ccc ggc gga gac att       576
Ala Trp Ala Trp Trp Ile Ala Leu Arg Phe Ser Pro Gly Gly Asp Ile
            180                 185                 190 tac ttc ggg gca ctc ctc aac tcc atc atc cac gtc ctc atg tat tcc       624
Tyr Phe Gly Ala Leu Leu Asn Ser Ile Ile His Val Leu Met Tyr Ser
        195                 200                 205 tac tac gcc ctt gcc cta ctc aag gtc agt tgt cca tgg aaa cga tac       672
Tyr Tyr Ala Leu Ala Leu Leu Lys Val Ser Cys Pro Trp Lys Arg Tyr
210                 215                 220 ttg act caa gct caa tta ttg caa ttc aca agt gtg gtg gtt tat acg       720
Leu Thr Gln Ala Gln Leu Leu Gln Phe Thr Ser Val Val Val Tyr Thr
225                 230                 235                 240 ggg tgt acg ggt tat act cat tac tat cat acg aag cat gga gcg gat       768
Gly Cys Thr Gly Tyr Thr His Tyr Tyr His Thr Lys His Gly Ala Asp
                245                 250                 255 gag aca cag cct agt tta gga acg tat tat ttc tgt tgt gga gtg cag       816
Glu Thr Gln Pro Ser Leu Gly Thr Tyr Tyr Phe Cys Cys Gly Val Gln
            260                 265                 270 gtg ttt gag atg gtt agt ttg ttt gta ctc ttt tcc atc ttt tat aaa       864
Val Phe Glu Met Val Ser Leu Phe Val Leu Phe Ser Ile Phe Tyr Lys
```

```
Val Phe Glu Met Val Ser Leu Phe Val Leu Phe Ser Ile Phe Tyr Lys
            275                 280                 285 cga tcc tat tcg aag aag aac aag tca gga gga aag gat agc aag aag       912
Arg Ser Tyr Ser Lys Lys Asn Lys Ser Gly Gly Lys Asp Ser Lys Lys
    290                 295                 300 aat gat gat ggg aat aat gag gat caa tgt cac aag gct atg aag gat       960
Asn Asp Asp Gly Asn Asn Glu Asp Gln Cys His Lys Ala Met Lys Asp
305                 310                 315                 320 ata tcg gag ggt gcg aag gag gtt gtg ggg cat gca gcg aag gat gct      1008
Ile Ser Glu Gly Ala Lys Glu Val Val Gly His Ala Ala Lys Asp Ala
                325                 330                 335 gga aag ttg gtg gct acg gcg agt aag gct gta aag agg aag gga act      1056
Gly Lys Leu Val Ala Thr Ala Ser Lys Ala Val Lys Arg Lys Gly Thr
            340                 345                 350 cgt gtt act ggt gcc atg tag                                          1077
Arg Val Thr Gly Ala Met
            355

<210> SEQ ID NO 123
<211> LENGTH: 358
<212> TYPE: PRT
<213> ORGANISM: Thalassiosira pseudonana

<400> SEQUENCE: 123

Met Cys Ser Pro Pro Ser Gln Ser Lys Thr Thr Ser Leu Leu Ala
1               5                   10                  15

Arg Tyr Thr Thr Ala Ala Leu Leu Leu Leu Thr Leu Thr Thr Trp Cys
            20                  25                  30

His Phe Ala Phe Pro Ala Ala Thr Ala Thr Pro Gly Leu Thr Ala Glu
        35                  40                  45

Met His Ser Tyr Lys Val Pro Leu Gly Leu Thr Val Phe Tyr Leu Leu
    50                  55                  60

Ser Leu Pro Ser Leu Lys Tyr Val Thr Asp Asn Tyr Leu Ala Lys Lys
65                  70                  75                  80

Tyr Asp Met Lys Ser Leu Leu Thr Glu Ser Met Val Leu Tyr Asn Val
                85                  90                  95

Ala Gln Val Leu Leu Asn Gly Trp Thr Val Tyr Ala Ile Val Asp Ala
            100                 105                 110

Val Met Asn Arg Asp His Pro Phe Ile Gly Ser Arg Ser Leu Val Gly
        115                 120                 125

Ala Ala Leu His Ser Gly Ser Ser Tyr Ala Val Trp Val His Tyr Cys
    130                 135                 140

Asp Lys Tyr Leu Glu Phe Phe Asp Thr Tyr Phe Met Val Leu Arg Gly
145                 150                 155                 160

Lys Met Asp Gln Val Ser Phe Leu His Ile Tyr His His Thr Thr Ile
                165                 170                 175

Ala Trp Ala Trp Trp Ile Ala Leu Arg Phe Ser Pro Gly Gly Asp Ile
            180                 185                 190

Tyr Phe Gly Ala Leu Leu Asn Ser Ile Ile His Val Leu Met Tyr Ser
        195                 200                 205

Tyr Tyr Ala Leu Ala Leu Leu Lys Val Ser Cys Pro Trp Lys Arg Tyr
    210                 215                 220

Leu Thr Gln Ala Gln Leu Leu Gln Phe Thr Ser Val Val Val Tyr Thr
225                 230                 235                 240

Gly Cys Thr Gly Tyr Thr His Tyr Tyr His Thr Lys His Gly Ala Asp
                245                 250                 255
```

-continued

```
Glu Thr Gln Pro Ser Leu Gly Thr Tyr Tyr Phe Cys Cys Gly Val Gln
            260                 265                 270

Val Phe Glu Met Val Ser Leu Phe Val Leu Phe Ser Ile Phe Tyr Lys
        275                 280                 285

Arg Ser Tyr Ser Lys Lys Asn Lys Ser Gly Gly Lys Asp Ser Lys Lys
    290                 295                 300

Asn Asp Asp Gly Asn Asn Glu Asp Gln Cys His Lys Ala Met Lys Asp
305                 310                 315                 320

Ile Ser Glu Gly Ala Lys Glu Val Val Gly His Ala Ala Lys Asp Ala
                325                 330                 335

Gly Lys Leu Val Ala Thr Ala Ser Lys Ala Val Lys Arg Lys Gly Thr
            340                 345                 350

Arg Val Thr Gly Ala Met
            355
```

```
<210> SEQ ID NO 124
<211> LENGTH: 903
<212> TYPE: DNA
<213> ORGANISM: Ostreococcus tauri
<220> FEATURE:
<221> NAME/KEY: CDS
<222> LOCATION: (1)..(903)
<223> OTHER INFORMATION: delta-5-Elongase

<400> SEQUENCE: 124
```

```
atg agc gcc tcc ggt gcg ctg ctg ccc gcg atc gcg ttc gcc gcg tac       48
Met Ser Ala Ser Gly Ala Leu Leu Pro Ala Ile Ala Phe Ala Ala Tyr
1               5                   10                  15 gcg tac gcg acg tac gcc tac gcc ttt gag tgg tcg cac gcg aat ggc       96
Ala Tyr Ala Thr Tyr Ala Tyr Ala Phe Glu Trp Ser His Ala Asn Gly
            20                  25                  30 atc gac aac gtc gac gcg cgc gag tgg atc ggt gcg ctg tcg ttg agg      144
Ile Asp Asn Val Asp Ala Arg Glu Trp Ile Gly Ala Leu Ser Leu Arg
        35                  40                  45 ctc ccg gcg atc gcg acg acg atg tac ctg ttg ttc tgc ctg gtc gga      192
Leu Pro Ala Ile Ala Thr Thr Met Tyr Leu Leu Phe Cys Leu Val Gly
    50                  55                  60 ccg agg ttg atg gcg aag cgc gag gcg ttc gac ccg aag ggg ttc atg      240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtg ctc ggg      288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca      336
Met Phe Ala Arg Glu Ile Ser Gly Leu Gly Gln Pro Val Trp Gly Ser
            100                 105                 110 acc atg ccg tgg agc gat aga aaa tcg ttt aag atc ctc ctc ggg gtg      384
Thr Met Pro Trp Ser Asp Arg Lys Ser Phe Lys Ile Leu Leu Gly Val
        115                 120                 125 tgg ttg cac tac aac aac aaa tat ttg gag cta ttg gac act gtg ttc      432
Trp Leu His Tyr Asn Asn Lys Tyr Leu Glu Leu Leu Asp Thr Val Phe
    130                 135                 140 atg gtt gcg cgc aag aag acg aag cag ttg agc ttc ttg cac gtt tat      480
Met Val Ala Arg Lys Lys Thr Lys Gln Leu Ser Phe Leu His Val Tyr
145                 150                 155                 160 cat cac gcc ctg ttg atc tgg gcg tgg tgg ttg gtg tgt cac ttg atg      528
His His Ala Leu Leu Ile Trp Ala Trp Trp Leu Val Cys His Leu Met
                165                 170                 175 gcc acg aac gat tgt atc gat gcc tac ttc ggc gcg gcg tgc aac tcg      576
Ala Thr Asn Asp Cys Ile Asp Ala Tyr Phe Gly Ala Ala Cys Asn Ser
```

-continued

| | |
|---|---|
| ttc att cac atc gtg atg tac tcg tat tat ctc atg tcg gcg ctc ggc<br>Phe Ile His Ile Val Met Tyr Ser Tyr Tyr Leu Met Ser Ala Leu Gly<br>        195                  200                  205 | 624 |
| att cga tgc ccg tgg aag cga tac atc acc cag gct caa atg ctc caa<br>Ile Arg Cys Pro Trp Lys Arg Tyr Ile Thr Gln Ala Gln Met Leu Gln<br>210                  215                  220 | 672 |
| ttc gtc att gtc ttc gcg cac gcc gtg ttc gtg ctg cgt cag aag cac<br>Phe Val Ile Val Phe Ala His Ala Val Phe Val Leu Arg Gln Lys His<br>225                  230                  235                  240 | 720 |
| tgc ccg gtc acc ctt cct tgg gcg caa atg ttc gtc atg acg aac atg<br>Cys Pro Val Thr Leu Pro Trp Ala Gln Met Phe Val Met Thr Asn Met<br>        245                  250                  255 | 768 |
| ctc gtg ctc ttc ggg aac ttc tac ctc aag gcg tac tcg aac aag tcg<br>Leu Val Leu Phe Gly Asn Phe Tyr Leu Lys Ala Tyr Ser Asn Lys Ser<br>            260                  265                  270 | 816 |
| cgc ggc gac ggc gcg agt tcc gtg aaa cca gcc gag acc acg cgc gcg<br>Arg Gly Asp Gly Ala Ser Ser Val Lys Pro Ala Glu Thr Thr Arg Ala<br>275                  280                  285 | 864 |
| ccc agc gtg cga cgc acg cga tct cga aaa att gac taa<br>Pro Ser Val Arg Arg Thr Arg Ser Arg Lys Ile Asp<br>        290                  295                  300 | 903 |

<210> SEQ ID NO 125
<211> LENGTH: 300
<212> TYPE: PRT
<213> ORGANISM: Ostreococcus tauri

<400> SEQUENCE: 125

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
                20                  25                  30

Ile Asp Asn Val Asp Ala Arg Glu Trp Ile Gly Ala Leu Ser Leu Arg
            35                  40                  45

Leu Pro Ala Ile Ala Thr Thr Met Tyr Leu Leu Phe Cys Leu Val Gly
        50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
                100                 105                 110

Thr Met Pro Trp Ser Asp Arg Lys Ser Phe Lys Ile Leu Leu Gly Val
            115                 120                 125

Trp Leu His Tyr Asn Asn Lys Tyr Leu Glu Leu Leu Asp Thr Val Phe
        130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
                180                 185                 190

Phe Ile His Ile Val Met Tyr Ser Tyr Tyr Leu Met Ser Ala Leu Gly
            195                 200                 205

Ile Arg Cys Pro Trp Lys Arg Tyr Ile Thr Gln Ala Gln Met Leu Gln
        210                 215                 220

```
Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
            245                 250                 255

Leu Val Leu Phe Gly Asn Phe Tyr Leu Lys Ala Tyr Ser Asn Lys Ser
        260                 265                 270

Arg Gly Asp Gly Ala Ser Ser Val Lys Pro Ala Glu Thr Thr Arg Ala
    275                 280                 285

Pro Ser Val Arg Arg Thr Arg Ser Arg Lys Ile Asp
    290                 295                 300

<210> SEQ ID NO 126
<211> LENGTH: 909
<212> TYPE: DNA
<213> ORGANISM: Xenopus laevis
<220> FEATURE:
<221> NAME/KEY: CDS
<222> LOCATION: (1)..(909)
<223> OTHER INFORMATION: delta-5-Elongase

<400> SEQUENCE: 126 atg gcc ttc aag gag ctc aca tca agg gca gtg ctc ctg tat gat gaa      48
Met Ala Phe Lys Glu Leu Thr Ser Arg Ala Val Leu Leu Tyr Asp Glu
1               5                   10                  15 tgg att aaa gat gct gat cct agg gtt gaa gac tgg cca ctc atg tcc      96
Trp Ile Lys Asp Ala Asp Pro Arg Val Glu Asp Trp Pro Leu Met Ser
            20                  25                  30 tct cct atc cta caa acc atc atc atc ggc gct tac atc tac ttt gtc     144
Ser Pro Ile Leu Gln Thr Ile Ile Ile Gly Ala Tyr Ile Tyr Phe Val
        35                  40                  45 aca tca ttg ggc cca agg atc atg gag aac agg aag ccg ttt gct ctg     192
Thr Ser Leu Gly Pro Arg Ile Met Glu Asn Arg Lys Pro Phe Ala Leu
    50                  55                  60 aag gag atc atg gca tgt tac aac tta ttc atg gtt ctg ttt tct gtg     240
Lys Glu Ile Met Ala Cys Tyr Asn Leu Phe Met Val Leu Phe Ser Val
65                  70                  75                  80 tac atg tgc tat gag ttt ctc atg tcg ggc tgg gct act gga tat tcc     288
Tyr Met Cys Tyr Glu Phe Leu Met Ser Gly Trp Ala Thr Gly Tyr Ser
                85                  90                  95 ttt aga tgt gac att gtt gac tac tct cag tca cct cag gcg tta cgg     336
Phe Arg Cys Asp Ile Val Asp Tyr Ser Gln Ser Pro Gln Ala Leu Arg
            100                 105                 110 atg gcc tgg acc tgc tgg ctc ttc tat ttt tca aag ttc att gaa tta     384
Met Ala Trp Thr Cys Trp Leu Phe Tyr Phe Ser Lys Phe Ile Glu Leu
        115                 120                 125 tta gac act gtt ttc ttt gtg ctg cgt aag aag aac agc cag att aca     432
Leu Asp Thr Val Phe Phe Val Leu Arg Lys Lys Asn Ser Gln Ile Thr
    130                 135                 140 ttc ctg cac gtc tat cac cac tcc att atg cct tgg acg tgg tgg ttt     480
Phe Leu His Val Tyr His His Ser Ile Met Pro Trp Thr Trp Trp Phe
145                 150                 155                 160 gga gtc aaa ttt gct cca ggt ggt ttg ggc aca ttc cat gca ctg gtg     528
Gly Val Lys Phe Ala Pro Gly Gly Leu Gly Thr Phe His Ala Leu Val
                165                 170                 175 aac tgt gtg gtc cat gtt atc atg tac agc tac tac ggc ctg tca gcc     576
Asn Cys Val Val His Val Ile Met Tyr Ser Tyr Tyr Gly Leu Ser Ala
            180                 185                 190 ttg ggg cct gcc tac cag aag tac ctg tgg tgg aaa aag tac atg acg     624
Leu Gly Pro Ala Tyr Gln Lys Tyr Leu Trp Trp Lys Lys Tyr Met Thr
        195                 200                 205
```

```
tct atc caa ctg acc cag ttc ttg atg gtt act ttt cac atc ggc cag      672
Ser Ile Gln Leu Thr Gln Phe Leu Met Val Thr Phe His Ile Gly Gln
    210                 215                 220 ttc ttc ttc atg gag aat tgc ccg tac cag tat ccc gtc ttc ttg tat      720
Phe Phe Phe Met Glu Asn Cys Pro Tyr Gln Tyr Pro Val Phe Leu Tyr
225                 230                 235                 240 gtc att tgg ctg tac ggg ttc gtt ttc tta atc ttg ttc ctc aac ttc      768
Val Ile Trp Leu Tyr Gly Phe Val Phe Leu Ile Leu Phe Leu Asn Phe
                245                 250                 255 tgg ttc cac gct tac atc aaa gga cag agg ctg ccg aaa gcc gtc caa      816
Trp Phe His Ala Tyr Ile Lys Gly Gln Arg Leu Pro Lys Ala Val Gln
        260                 265                 270 aat ggc cac tgc aag aac aac aac aac caa gaa aac act tgg tgc aag      864
Asn Gly His Cys Lys Asn Asn Asn Asn Gln Glu Asn Thr Trp Cys Lys
            275                 280                 285 aac aaa aac cag aaa aac ggt gca ttg aaa agc aaa aac cat tga          909
Asn Lys Asn Gln Lys Asn Gly Ala Leu Lys Ser Lys Asn His
290                 295                 300
```

<210> SEQ ID NO 127
<211> LENGTH: 302
<212> TYPE: PRT
<213> ORGANISM: Xenopus laevis

<400> SEQUENCE: 127

```
Met Ala Phe Lys Glu Leu Thr Ser Arg Ala Val Leu Leu Tyr Asp Glu
1               5                   10                  15

Trp Ile Lys Asp Ala Asp Pro Arg Val Glu Asp Trp Pro Leu Met Ser
                20                  25                  30

Ser Pro Ile Leu Gln Thr Ile Ile Ile Gly Ala Tyr Ile Tyr Phe Val
            35                  40                  45

Thr Ser Leu Gly Pro Arg Ile Met Glu Asn Arg Lys Pro Phe Ala Leu
        50                  55                  60

Lys Glu Ile Met Ala Cys Tyr Asn Leu Phe Met Val Leu Phe Ser Val
65                  70                  75                  80

Tyr Met Cys Tyr Glu Phe Leu Met Ser Gly Trp Ala Thr Gly Tyr Ser
                85                  90                  95

Phe Arg Cys Asp Ile Val Asp Tyr Ser Gln Ser Pro Gln Ala Leu Arg
            100                 105                 110

Met Ala Trp Thr Cys Trp Leu Phe Tyr Phe Ser Lys Phe Ile Glu Leu
        115                 120                 125

Leu Asp Thr Val Phe Phe Val Leu Arg Lys Lys Asn Ser Gln Ile Thr
130                 135                 140

Phe Leu His Val Tyr His His Ser Ile Met Pro Trp Thr Trp Trp Phe
145                 150                 155                 160

Gly Val Lys Phe Ala Pro Gly Gly Leu Gly Thr Phe His Ala Leu Val
                165                 170                 175

Asn Cys Val Val His Val Ile Met Tyr Ser Tyr Tyr Gly Leu Ser Ala
            180                 185                 190

Leu Gly Pro Ala Tyr Gln Lys Tyr Leu Trp Trp Lys Lys Tyr Met Thr
        195                 200                 205

Ser Ile Gln Leu Thr Gln Phe Leu Met Val Thr Phe His Ile Gly Gln
    210                 215                 220

Phe Phe Phe Met Glu Asn Cys Pro Tyr Gln Tyr Pro Val Phe Leu Tyr
225                 230                 235                 240

Val Ile Trp Leu Tyr Gly Phe Val Phe Leu Ile Leu Phe Leu Asn Phe
```

```
                    245                 250                 255
Trp Phe His Ala Tyr Ile Lys Gly Gln Arg Leu Pro Lys Ala Val Gln
            260                 265                 270

Asn Gly His Cys Lys Asn Asn Asn Gln Glu Asn Thr Trp Cys Lys
        275                 280                 285

Asn Lys Asn Gln Lys Asn Gly Ala Leu Lys Ser Lys Asn His
    290                 295                 300

<210> SEQ ID NO 128
<211> LENGTH: 870
<212> TYPE: DNA
<213> ORGANISM: Ciona intestinalis
<220> FEATURE:
<221> NAME/KEY: CDS
<222> LOCATION: (1)..(870)
<223> OTHER INFORMATION: delta-5-Elongase

<400> SEQUENCE: 128
```

| | | | | | | | | | | | | | | | | |
|---|---|---|---|---|---|---|---|---|---|---|---|---|---|---|---|---|
| atg | gac | gta | ctt | cat | cgt | ttc | tta | gga | ttc | tac | gaa | tgg | acg | ctg | act | 48 |
| Met | Asp | Val | Leu | His | Arg | Phe | Leu | Gly | Phe | Tyr | Glu | Trp | Thr | Leu | Thr | |
| 1 | | | | 5 | | | | | 10 | | | | | 15 | | |
| ttc | gcg | gac | ccc | cga | gtg | gca | aaa | tgg | cct | tta | ata | gaa | aac | ccc | ctt | 96 |
| Phe | Ala | Asp | Pro | Arg | Val | Ala | Lys | Trp | Pro | Leu | Ile | Glu | Asn | Pro | Leu | |
| | | 20 | | | | | 25 | | | | | 30 | | | | |
| cct | aca | att | gct | att | gtg | ttg | ctg | tac | ctg | gcg | ttt | gtt | ctg | tat | att | 144 |
| Pro | Thr | Ile | Ala | Ile | Val | Leu | Leu | Tyr | Leu | Ala | Phe | Val | Leu | Tyr | Ile | |
| | 35 | | | | | 40 | | | | | 45 | | | | | |
| ggg | ccg | cgt | ttt | atg | cga | aaa | aga | gca | cca | gtt | gac | ttt | ggt | tta | ttc | 192 |
| Gly | Pro | Arg | Phe | Met | Arg | Lys | Arg | Ala | Pro | Val | Asp | Phe | Gly | Leu | Phe | |
| 50 | | | | | 55 | | | | | 60 | | | | | | |
| ctc | cct | gga | tat | aac | ttt | gct | ttg | gtt | gca | tta | aat | tat | tat | atc | ctg | 240 |
| Leu | Pro | Gly | Tyr | Asn | Phe | Ala | Leu | Val | Ala | Leu | Asn | Tyr | Tyr | Ile | Leu | |
| 65 | | | | | 70 | | | | | 75 | | | | | 80 | |
| caa | gaa | gtg | gtc | act | ggg | agt | tat | ggg | gct | ggg | tat | gat | ttg | gtt | tgc | 288 |
| Gln | Glu | Val | Val | Thr | Gly | Ser | Tyr | Gly | Ala | Gly | Tyr | Asp | Leu | Val | Cys | |
| | | | | 85 | | | | | 90 | | | | | 95 | | |
| aca | cca | ctt | cga | agt | gat | tcc | tac | gat | ccc | aat | gaa | atg | aag | gtt | gca | 336 |
| Thr | Pro | Leu | Arg | Ser | Asp | Ser | Tyr | Asp | Pro | Asn | Glu | Met | Lys | Val | Ala | |
| | | | 100 | | | | | 105 | | | | | 110 | | | |
| aac | gct | gta | tgg | tgg | tat | tat | gta | tcc | aag | ata | ata | gag | ttg | ttt | gat | 384 |
| Asn | Ala | Val | Trp | Trp | Tyr | Tyr | Val | Ser | Lys | Ile | Ile | Glu | Leu | Phe | Asp | |
| | | 115 | | | | | 120 | | | | | 125 | | | | |
| act | gtg | ttg | ttc | act | cta | cgc | aaa | cga | gac | cga | caa | gta | act | ttc | ctt | 432 |
| Thr | Val | Leu | Phe | Thr | Leu | Arg | Lys | Arg | Asp | Arg | Gln | Val | Thr | Phe | Leu | |
| | 130 | | | | | 135 | | | | | 140 | | | | | |
| cat | gtt | tat | cac | cat | tct | acc | atg | ccc | ctg | ttg | tgg | tgg | att | ggg | gca | 480 |
| His | Val | Tyr | His | His | Ser | Thr | Met | Pro | Leu | Leu | Trp | Trp | Ile | Gly | Ala | |
| 145 | | | | | 150 | | | | | 155 | | | | | 160 | |
| aag | tgg | gtg | cct | ggt | ggg | caa | tca | ttt | gtt | ggc | atc | ata | ctg | aac | tcc | 528 |
| Lys | Trp | Val | Pro | Gly | Gly | Gln | Ser | Phe | Val | Gly | Ile | Ile | Leu | Asn | Ser | |
| | | | | 165 | | | | | 170 | | | | | 175 | | |
| agt | gtt | cat | gtt | atc | atg | tat | acg | tac | tat | gga | ttg | tca | gcc | ttg | ggg | 576 |
| Ser | Val | His | Val | Ile | Met | Tyr | Thr | Tyr | Tyr | Gly | Leu | Ser | Ala | Leu | Gly | |
| | | | 180 | | | | | 185 | | | | | 190 | | | |
| cct | cac | atg | cag | aag | ttt | cta | tgg | tgg | aag | aaa | tat | atc | aca | atg | ttg | 624 |
| Pro | His | Met | Gln | Lys | Phe | Leu | Trp | Trp | Lys | Lys | Tyr | Ile | Thr | Met | Leu | |
| | | 195 | | | | | 200 | | | | | 205 | | | | |
| caa | ctg | gtt | caa | ttt | gtt | ctt | gcc | atc | tac | cat | act | gct | cga | tca | ttg | 672 |
| Gln | Leu | Val | Gln | Phe | Val | Leu | Ala | Ile | Tyr | His | Thr | Ala | Arg | Ser | Leu | |
| | 210 | | | | | 215 | | | | | 220 | | | | | |

```
tac gtt aaa tgt ccc tcg cct gtt tgg atg cac tgg gca ctt atc ttg      720
Tyr Val Lys Cys Pro Ser Pro Val Trp Met His Trp Ala Leu Ile Leu
225                 230                 235                 240 tac gct ttc tca ttc att ttg ctt ttc tca aac ttc tac atg cat gcc      768
Tyr Ala Phe Ser Phe Ile Leu Leu Phe Ser Asn Phe Tyr Met His Ala
                245                 250                 255 tat atc aag aaa tca aga aaa ggg aaa gag aat ggc agt cga gga aaa      816
Tyr Ile Lys Lys Ser Arg Lys Gly Lys Glu Asn Gly Ser Arg Gly Lys
            260                 265                 270 ggt ggt gta agt aat gga aag gaa aag ctg cac gct aat ggt aaa acc      864
Gly Gly Val Ser Asn Gly Lys Glu Lys Leu His Ala Asn Gly Lys Thr
                275                 280                 285 gat taa                                                               870
Asp
```

<210> SEQ ID NO 129
<211> LENGTH: 289
<212> TYPE: PRT
<213> ORGANISM: Ciona intestinalis

<400> SEQUENCE: 129

Met Asp Val Leu His Arg Phe Leu Gly Phe Tyr Glu Trp Thr Leu Thr
1               5                   10                  15

Phe Ala Asp Pro Arg Val Ala Lys Trp Pro Leu Ile Glu Asn Pro Leu
            20                  25                  30

Pro Thr Ile Ala Ile Val Leu Leu Tyr Leu Ala Phe Val Leu Tyr Ile
        35                  40                  45

Gly Pro Arg Phe Met Arg Lys Arg Ala Pro Val Asp Phe Gly Leu Phe
    50                  55                  60

Leu Pro Gly Tyr Asn Phe Ala Leu Val Ala Leu Asn Tyr Tyr Ile Leu
65                  70                  75                  80

Gln Glu Val Val Thr Gly Ser Tyr Gly Ala Gly Tyr Asp Leu Val Cys
                85                  90                  95

Thr Pro Leu Arg Ser Asp Ser Tyr Asp Pro Asn Glu Met Lys Val Ala
            100                 105                 110

Asn Ala Val Trp Trp Tyr Tyr Val Ser Lys Ile Ile Glu Leu Phe Asp
        115                 120                 125

Thr Val Leu Phe Thr Leu Arg Lys Arg Asp Arg Gln Val Thr Phe Leu
130                 135                 140

His Val Tyr His His Ser Thr Met Pro Leu Leu Trp Trp Ile Gly Ala
145                 150                 155                 160

Lys Trp Val Pro Gly Gly Gln Ser Phe Val Gly Ile Ile Leu Asn Ser
                165                 170                 175

Ser Val His Val Ile Met Tyr Thr Tyr Tyr Gly Leu Ser Ala Leu Gly
            180                 185                 190

Pro His Met Gln Lys Phe Leu Trp Trp Lys Lys Tyr Ile Thr Met Leu
        195                 200                 205

Gln Leu Val Gln Phe Val Leu Ala Ile Tyr His Thr Ala Arg Ser Leu
    210                 215                 220

Tyr Val Lys Cys Pro Ser Pro Val Trp Met His Trp Ala Leu Ile Leu
225                 230                 235                 240

Tyr Ala Phe Ser Phe Ile Leu Leu Phe Ser Asn Phe Tyr Met His Ala
                245                 250                 255

Tyr Ile Lys Lys Ser Arg Lys Gly Lys Glu Asn Gly Ser Arg Gly Lys
            260                 265                 270

Gly Gly Val Ser Asn Gly Lys Glu Lys Leu His Ala Asn Gly Lys Thr

-continued

```
                275                 280                 285
Asp

<210> SEQ ID NO 130
<211> LENGTH: 789
<212> TYPE: DNA
<213> ORGANISM: Euglena gracilis
<220> FEATURE:
<221> NAME/KEY: CDS
<222> LOCATION: (1)..(789)
<223> OTHER INFORMATION: delta-5-Elongase

<400> SEQUENCE: 130 atg ctg ggg gcc atc gcg gac gtc gtg ctc cgg ggg ccc gcc gca ttc      48
Met Leu Gly Ala Ile Ala Asp Val Val Leu Arg Gly Pro Ala Ala Phe
 1               5                  10                  15 cac tgg gac cct gcc acc acc ccg ctc gca tcg atc gtc agc ccc tgt      96
His Trp Asp Pro Ala Thr Thr Pro Leu Ala Ser Ile Val Ser Pro Cys
             20                  25                  30 gtg gcc tcc gtg gcg tac ctg ggg gcc atc ggg ctg ctg aag cgc cgc     144
Val Ala Ser Val Ala Tyr Leu Gly Ala Ile Gly Leu Leu Lys Arg Arg
         35                  40                  45 act gga ccg gag gtc cgc tcc aag ccc ttc gag ctg cta cac aac ggg     192
Thr Gly Pro Glu Val Arg Ser Lys Pro Phe Glu Leu Leu His Asn Gly
     50                  55                  60 ctg ctg gtg ggc tgg tcc ctc gtg gtg ctg ctc ggg acg ctg tac ggc     240
Leu Leu Val Gly Trp Ser Leu Val Val Leu Leu Gly Thr Leu Tyr Gly
 65                  70                  75                  80 gcg ttc cag cgc gtg cag gag gac ggc cgg ggg gtg cag gcc ctc ctg     288
Ala Phe Gln Arg Val Gln Glu Asp Gly Arg Gly Val Gln Ala Leu Leu
                 85                  90                  95 tgc acc cag cgg cca cca tct cag atc tgg gac ggc ccg gtg ggg tac     336
Cys Thr Gln Arg Pro Pro Ser Gln Ile Trp Asp Gly Pro Val Gly Tyr
            100                 105                 110 ttc acg tac ctc ttc tac ctc gcg aag tac tgg gag ctg gcg gac act     384
Phe Thr Tyr Leu Phe Tyr Leu Ala Lys Tyr Trp Glu Leu Ala Asp Thr
        115                 120                 125 gtc atc ctc gcc ctc cgc cag aag ccc acc atc ccc ctc cac gtc tac     432
Val Ile Leu Ala Leu Arg Gln Lys Pro Thr Ile Pro Leu His Val Tyr
    130                 135                 140 cat cac gcc gtc atg ctg ttc atc gtg tgg tcg tgg ttc gcg cac ccc     480
His His Ala Val Met Leu Phe Ile Val Trp Ser Trp Phe Ala His Pro
145                 150                 155                 160 tgg ctc gag ggg agc tgg tgg tgc tcc ctg gtc aac tct ttc atc cac     528
Trp Leu Glu Gly Ser Trp Trp Cys Ser Leu Val Asn Ser Phe Ile His
                165                 170                 175 acg gtg atg tac tcg tac tac acc ctg acg gtg gtt ggc atc aac cct     576
Thr Val Met Tyr Ser Tyr Tyr Thr Leu Thr Val Val Gly Ile Asn Pro
            180                 185                 190 tgg tgg aag aag tgg atg acc acc atg cag atc atc cag ttc atc acg     624
Trp Trp Lys Lys Trp Met Thr Thr Met Gln Ile Ile Gln Phe Ile Thr
        195                 200                 205 ggc tgc gtg tac gtc atg gcg ttc ttc ggc cta tat tat gcc ggg gcg     672
Gly Cys Val Tyr Val Met Ala Phe Phe Gly Leu Tyr Tyr Ala Gly Ala
    210                 215                 220 ggc tgc acc tcc aac gtg tac act gcc tgg ttc tcg atg ggg gtc aac     720
Gly Cys Thr Ser Asn Val Tyr Thr Ala Trp Phe Ser Met Gly Val Asn
225                 230                 235                 240 ctc agc ttt ctg tgg ctc ttc gct ctt ttc ttc cgc cgg tca tac agc     768
Leu Ser Phe Leu Trp Leu Phe Ala Leu Phe Phe Arg Arg Ser Tyr Ser
                245                 250                 255
```

```
aaa cct agc cgg aag gag tag                                      789
Lys Pro Ser Arg Lys Glu
        260

<210> SEQ ID NO 131
<211> LENGTH: 262
<212> TYPE: PRT
<213> ORGANISM: Euglena gracilis

<400> SEQUENCE: 131

Met Leu Gly Ala Ile Ala Asp Val Val Leu Arg Gly Pro Ala Ala Phe
1               5                   10                  15

His Trp Asp Pro Ala Thr Thr Pro Leu Ala Ser Ile Val Ser Pro Cys
            20                  25                  30

Val Ala Ser Val Ala Tyr Leu Gly Ala Ile Gly Leu Leu Lys Arg Arg
        35                  40                  45

Thr Gly Pro Glu Val Arg Ser Lys Pro Phe Glu Leu Leu His Asn Gly
    50                  55                  60

Leu Leu Val Gly Trp Ser Leu Val Val Leu Gly Thr Leu Tyr Gly
65                  70                  75                  80

Ala Phe Gln Arg Val Gln Glu Asp Gly Arg Gly Val Gln Ala Leu Leu
                85                  90                  95

Cys Thr Gln Arg Pro Pro Ser Gln Ile Trp Asp Gly Pro Val Gly Tyr
            100                 105                 110

Phe Thr Tyr Leu Phe Tyr Leu Ala Lys Tyr Trp Glu Leu Ala Asp Thr
        115                 120                 125

Val Ile Leu Ala Leu Arg Gln Lys Pro Thr Ile Pro Leu His Val Tyr
    130                 135                 140

His His Ala Val Met Leu Phe Ile Val Trp Ser Trp Phe Ala His Pro
145                 150                 155                 160

Trp Leu Glu Gly Ser Trp Trp Cys Ser Leu Val Asn Ser Phe Ile His
                165                 170                 175

Thr Val Met Tyr Ser Tyr Tyr Thr Leu Thr Val Gly Ile Asn Pro
            180                 185                 190

Trp Trp Lys Lys Trp Met Thr Thr Met Gln Ile Ile Gln Phe Ile Thr
        195                 200                 205

Gly Cys Val Tyr Val Met Ala Phe Phe Gly Leu Tyr Tyr Ala Gly Ala
    210                 215                 220

Gly Cys Thr Ser Asn Val Tyr Thr Ala Trp Phe Ser Met Gly Val Asn
225                 230                 235                 240

Leu Ser Phe Leu Trp Leu Phe Ala Leu Phe Phe Arg Arg Ser Tyr Ser
                245                 250                 255

Lys Pro Ser Arg Lys Glu
        260

<210> SEQ ID NO 132
<211> LENGTH: 789
<212> TYPE: DNA
<213> ORGANISM: Euglena gracilis
<220> FEATURE:
<221> NAME/KEY: CDS
<222> LOCATION: (1)..(789)
<223> OTHER INFORMATION: delta-5-Elongase

<400> SEQUENCE: 132 atg ctg ggg gcc atc gcg gac gtc gtg ctc cgg ggg ccc gcc gca ttc    48
Met Leu Gly Ala Ile Ala Asp Val Val Leu Arg Gly Pro Ala Ala Phe
1               5                   10                  15
```

```
cac tgg gac cct gcc acc acc ccg ctc gca tcg atc gtc agc ccc tgt        96
His Trp Asp Pro Ala Thr Thr Pro Leu Ala Ser Ile Val Ser Pro Cys
         20                  25                  30 gtg gcc tcc gtg gcg tac ctg ggg gcc atc ggg ctg ctg aag cgc cgc       144
Val Ala Ser Val Ala Tyr Leu Gly Ala Ile Gly Leu Leu Lys Arg Arg
             35                  40                  45 act gga ccg gag gtc cgc tcc aag ccc ttc gag ctg cta cac aac ggg       192
Thr Gly Pro Glu Val Arg Ser Lys Pro Phe Glu Leu Leu His Asn Gly
 50                  55                  60 ctg ctg gtg ggc tgg tcc ctc gtg gtg ctg ctc ggg acg ctg tac ggc       240
Leu Leu Val Gly Trp Ser Leu Val Val Leu Leu Gly Thr Leu Tyr Gly
 65                  70                  75                  80 gcg tac cag cgc gtg cag gag gac ggc cgg ggg gtg cag gcc ctg ctg       288
Ala Tyr Gln Arg Val Gln Glu Asp Gly Arg Gly Val Gln Ala Leu Leu
                 85                  90                  95 tgc acc cag cgg cca cca tct cag atc tgg gac ggc ccg gtg ggg tac       336
Cys Thr Gln Arg Pro Pro Ser Gln Ile Trp Asp Gly Pro Val Gly Tyr
            100                 105                 110 ttc acg tac ctt ttc tac ctc gcg aag tac tgg gag ctg gtg gac act       384
Phe Thr Tyr Leu Phe Tyr Leu Ala Lys Tyr Trp Glu Leu Val Asp Thr
        115                 120                 125 gtc atc ctc gcc ctc cgc cag aag ccc acc atc ccc ctc cac gtc tac       432
Val Ile Leu Ala Leu Arg Gln Lys Pro Thr Ile Pro Leu His Val Tyr
130                 135                 140 cat cac gcc gtc atg ctg ttc att gtg tgg tcg tgg ttc gcg cac ccc       480
His His Ala Val Met Leu Phe Ile Val Trp Ser Trp Phe Ala His Pro
145                 150                 155                 160 tgg ctc gag ggg agc tgg tgg tgc tcc ctg gtc aac tct ttc atc cac       528
Trp Leu Glu Gly Ser Trp Trp Cys Ser Leu Val Asn Ser Phe Ile His
                165                 170                 175 acg gtg atg tac tcg tat tac acc ctg acg gtg gtt ggc atc aac cct       576
Thr Val Met Tyr Ser Tyr Tyr Thr Leu Thr Val Val Gly Ile Asn Pro
            180                 185                 190 tgg tgg aag aag tgg atg acc acc atg cag atc atc cag ttc atc acg       624
Trp Trp Lys Lys Trp Met Thr Thr Met Gln Ile Ile Gln Phe Ile Thr
        195                 200                 205 ggc tgc gtg tac gtc acg gcg ttc ttc ggc cta tac tat gcc ggg gcg       672
Gly Cys Val Tyr Val Thr Ala Phe Phe Gly Leu Tyr Tyr Ala Gly Ala
210                 215                 220 ggc tgc acc tcc aac gtg tac act gcc tgg ttc tcg atg ggg gtc aac       720
Gly Cys Thr Ser Asn Val Tyr Thr Ala Trp Phe Ser Met Gly Val Asn
225                 230                 235                 240 ctc agc ttt ctg tgg ctc ttc gct ctt ttc ttc cgc cgg tcg tac agc       768
Leu Ser Phe Leu Trp Leu Phe Ala Leu Phe Phe Arg Arg Ser Tyr Ser
                245                 250                 255 aaa cct agc cgg aag gag tag                                           789
Lys Pro Ser Arg Lys Glu
            260

<210> SEQ ID NO 133
<211> LENGTH: 262
<212> TYPE: PRT
<213> ORGANISM: Euglena gracilis

<400> SEQUENCE: 133

Met Leu Gly Ala Ile Ala Asp Val Val Leu Arg Gly Pro Ala Ala Phe
1               5                   10                  15

His Trp Asp Pro Ala Thr Thr Pro Leu Ala Ser Ile Val Ser Pro Cys
            20                  25                  30
```

```
Val Ala Ser Val Ala Tyr Leu Gly Ala Ile Gly Leu Leu Lys Arg Arg
            35                  40                  45

Thr Gly Pro Glu Val Arg Ser Lys Pro Phe Glu Leu Leu His Asn Gly
        50                  55                  60

Leu Leu Val Gly Trp Ser Leu Val Val Leu Leu Gly Thr Leu Tyr Gly
65                  70                  75                  80

Ala Tyr Gln Arg Val Gln Glu Asp Gly Arg Gly Val Gln Ala Leu Leu
                85                  90                  95

Cys Thr Gln Arg Pro Pro Ser Gln Ile Trp Asp Gly Pro Val Gly Tyr
            100                 105                 110

Phe Thr Tyr Leu Phe Tyr Leu Ala Lys Tyr Trp Glu Leu Val Asp Thr
        115                 120                 125

Val Ile Leu Ala Leu Arg Gln Lys Pro Thr Ile Pro Leu His Val Tyr
130                 135                 140

His His Ala Val Met Leu Phe Ile Val Trp Ser Trp Phe Ala His Pro
145                 150                 155                 160

Trp Leu Glu Gly Ser Trp Trp Cys Ser Leu Val Asn Ser Phe Ile His
                165                 170                 175

Thr Val Met Tyr Ser Tyr Tyr Thr Leu Thr Val Gly Ile Asn Pro
            180                 185                 190

Trp Trp Lys Lys Trp Met Thr Thr Met Gln Ile Ile Gln Phe Ile Thr
        195                 200                 205

Gly Cys Val Tyr Val Thr Ala Phe Phe Gly Leu Tyr Tyr Ala Gly Ala
    210                 215                 220

Gly Cys Thr Ser Asn Val Tyr Thr Ala Trp Phe Ser Met Gly Val Asn
225                 230                 235                 240

Leu Ser Phe Leu Trp Leu Phe Ala Leu Phe Arg Arg Ser Tyr Ser
                245                 250                 255

Lys Pro Ser Arg Lys Glu
            260
```

<210> SEQ ID NO 134
<211> LENGTH: 897
<212> TYPE: DNA
<213> ORGANISM: Arabidopsis thaliana
<220> FEATURE:
<221> NAME/KEY: CDS
<222> LOCATION: (1)..(897)
<223> OTHER INFORMATION: delta-5-Elongase

<400> SEQUENCE: 134

```
atg gca tct gtt tac tcc acc cta acc tac tgg ctc gtc cac cac ccc     48
Met Ala Ser Val Tyr Ser Thr Leu Thr Tyr Trp Leu Val His His Pro
1               5                   10                  15 tac att gcc aac ttc acg tgg acc gaa ggt gaa aca cta ggc tcc acc     96
Tyr Ile Ala Asn Phe Thr Trp Thr Glu Gly Glu Thr Leu Gly Ser Thr
            20                  25                  30 gtt ttc ttt gtc ttt gtc gtc gtc tcc ctt tac ctc tcc gcc aca ttc    144
Val Phe Phe Val Phe Val Val Val Ser Leu Tyr Leu Ser Ala Thr Phe
        35                  40                  45 ctc ctc cga tac acc gtc gat tca ctc ccc aca ctc ggt ccc cgc att    192
Leu Leu Arg Tyr Thr Val Asp Ser Leu Pro Thr Leu Gly Pro Arg Ile
    50                  55                  60 ctc aaa cca atc aca gcc gtt cac agc ctc att ctc ttc ctc ctc tcc    240
Leu Lys Pro Ile Thr Ala Val His Ser Leu Ile Leu Phe Leu Leu Ser
65                  70                  75                  80 tta acc atg gcc gtt ggt tgc act ctc tcc cta atc tct tcc tcg gac    288
Leu Thr Met Ala Val Gly Cys Thr Leu Ser Leu Ile Ser Ser Ser Asp
```

```
                 85                  90                  95
ccg aag gcg cgt ctc ttc gac gcc gtt tgt ttc ccc ctc gac gtg aaa      336
Pro Lys Ala Arg Leu Phe Asp Ala Val Cys Phe Pro Leu Asp Val Lys
            100                 105                 110 cct aag gga ccg ctt ttc ttt tgg gct caa gtc ttt tac ctc tcg aag      384
Pro Lys Gly Pro Leu Phe Phe Trp Ala Gln Val Phe Tyr Leu Ser Lys
        115                 120                 125 atc ctt gag ttc gta gac aca ctt ctc atc ata ctc aac aaa tca atc      432
Ile Leu Glu Phe Val Asp Thr Leu Leu Ile Ile Leu Asn Lys Ser Ile
    130                 135                 140 caa cgg ctc tcg ttc ctc cac gtc tac cac cac gca acg gtt gtg att      480
Gln Arg Leu Ser Phe Leu His Val Tyr His His Ala Thr Val Val Ile
145                 150                 155                 160 ttg tgc tac ctc tgg tta cga aca cgt caa tcg atg ttt cct gtt ggg      528
Leu Cys Tyr Leu Trp Leu Arg Thr Arg Gln Ser Met Phe Pro Val Gly
                165                 170                 175 ctc gtg ttg aac tcg acg gtc cat gtg att atg tac ggg tac tat ttc      576
Leu Val Leu Asn Ser Thr Val His Val Ile Met Tyr Gly Tyr Tyr Phe
            180                 185                 190 ctc tgc gct atc gga tcg agg ccc aag tgg aag aag ttg gtg acg aat      624
Leu Cys Ala Ile Gly Ser Arg Pro Lys Trp Lys Lys Leu Val Thr Asn
        195                 200                 205 ttt caa atg gtt cag ttt gct ttc ggc atg ggg tta gga gcc gct tgg      672
Phe Gln Met Val Gln Phe Ala Phe Gly Met Gly Leu Gly Ala Ala Trp
    210                 215                 220 atg ctc cca gag cat tat ttc ggg tcg ggt tgc gcc ggg att tgg aca      720
Met Leu Pro Glu His Tyr Phe Gly Ser Gly Cys Ala Gly Ile Trp Thr
225                 230                 235                 240 gtt tat ttc aat ggt gtg ttt act gct tct cta ttg gct ctc ttc tac      768
Val Tyr Phe Asn Gly Val Phe Thr Ala Ser Leu Leu Ala Leu Phe Tyr
                245                 250                 255 aac ttc cac tcc aag aac tat gag aag act aca acg tcg cct ttg tat      816
Asn Phe His Ser Lys Asn Tyr Glu Lys Thr Thr Thr Ser Pro Leu Tyr
            260                 265                 270 aag atc gaa tcc ttt ata ttt att cac gga gag agg tgg gca aat aaa      864
Lys Ile Glu Ser Phe Ile Phe Ile His Gly Glu Arg Trp Ala Asn Lys
        275                 280                 285 gcg att aca tta ttt tcc aag aaa aac gat taa                          897
Ala Ile Thr Leu Phe Ser Lys Lys Asn Asp
    290                 295

<210> SEQ ID NO 135
<211> LENGTH: 298
<212> TYPE: PRT
<213> ORGANISM: Arabidopsis thaliana

<400> SEQUENCE: 135

Met Ala Ser Val Tyr Ser Thr Leu Thr Tyr Trp Leu Val His His Pro
1               5                   10                  15

Tyr Ile Ala Asn Phe Thr Trp Thr Glu Gly Glu Thr Leu Gly Ser Thr
            20                  25                  30

Val Phe Phe Val Phe Val Val Ser Leu Tyr Leu Ser Ala Thr Phe
        35                  40                  45

Leu Leu Arg Tyr Thr Val Asp Ser Leu Pro Thr Leu Gly Pro Arg Ile
    50                  55                  60

Leu Lys Pro Ile Thr Ala Val His Ser Leu Ile Leu Phe Leu Leu Ser
65                  70                  75                  80

Leu Thr Met Ala Val Gly Cys Thr Leu Ser Leu Ile Ser Ser Ser Asp
                85                  90                  95
```

```
Pro Lys Ala Arg Leu Phe Asp Ala Val Cys Phe Pro Leu Asp Val Lys
            100                 105                 110

Pro Lys Gly Pro Leu Phe Phe Trp Ala Gln Val Phe Tyr Leu Ser Lys
            115                 120                 125

Ile Leu Glu Phe Val Asp Thr Leu Leu Ile Ile Leu Asn Lys Ser Ile
130                 135                 140

Gln Arg Leu Ser Phe Leu His Val Tyr His Ala Thr Val Val Ile
145                 150                 155                 160

Leu Cys Tyr Leu Trp Leu Arg Thr Arg Gln Ser Met Phe Pro Val Gly
                165                 170                 175

Leu Val Leu Asn Ser Thr Val His Val Ile Met Tyr Gly Tyr Tyr Phe
                180                 185                 190

Leu Cys Ala Ile Gly Ser Arg Pro Lys Trp Lys Lys Leu Val Thr Asn
                195                 200                 205

Phe Gln Met Val Gln Phe Ala Phe Gly Met Gly Leu Gly Ala Ala Trp
            210                 215                 220

Met Leu Pro Glu His Tyr Phe Gly Ser Gly Cys Ala Gly Ile Trp Thr
225                 230                 235                 240

Val Tyr Phe Asn Gly Val Phe Thr Ala Ser Leu Leu Ala Leu Phe Tyr
                245                 250                 255

Asn Phe His Ser Lys Asn Tyr Glu Lys Thr Thr Thr Ser Pro Leu Tyr
            260                 265                 270

Lys Ile Glu Ser Phe Ile Phe Ile His Gly Glu Arg Trp Ala Asn Lys
            275                 280                 285

Ala Ile Thr Leu Phe Ser Lys Lys Asn Asp
            290                 295

<210> SEQ ID NO 136
<211> LENGTH: 837
<212> TYPE: DNA
<213> ORGANISM: Arabidopsis thaliana
<220> FEATURE:
<221> NAME/KEY: CDS
<222> LOCATION: (1)..(837)
<223> OTHER INFORMATION: delta-5-Elongase

<400> SEQUENCE: 136 atg gca tca att tac tcc tct tta acc tac tgg ctc gtt aac cac ccc      48
Met Ala Ser Ile Tyr Ser Ser Leu Thr Tyr Trp Leu Val Asn His Pro
1               5                  10                  15 tac atc tcc aat ttt act tgg atc gaa ggt gaa acc cta ggc tcc acc      96
Tyr Ile Ser Asn Phe Thr Trp Ile Glu Gly Glu Thr Leu Gly Ser Thr
                20                  25                  30 gtc ttt ttc gta tcc gtc gta gtc tcc gtt tac ctc tcc gcc acg ttc     144
Val Phe Phe Val Ser Val Val Val Ser Val Tyr Leu Ser Ala Thr Phe
            35                  40                  45 ctc ctc cga tcc gcc atc gat tca ctc cca tca ctc agt cca cgt atc     192
Leu Leu Arg Ser Ala Ile Asp Ser Leu Pro Ser Leu Ser Pro Arg Ile
        50                  55                  60 ctc aaa ccg atc aca gcc gtc cac agc cta atc ctc tgt ctc ctc tcc     240
Leu Lys Pro Ile Thr Ala Val His Ser Leu Ile Leu Cys Leu Leu Ser
65                  70                  75                  80 tta gtc atg gcc gtc ggt tgc act ctc tca ata acc tca tct cac gcg     288
Leu Val Met Ala Val Gly Cys Thr Leu Ser Ile Thr Ser Ser His Ala
                85                  90                  95 tct tca gat ccg atg gcg cgt ttc ctt cac gcg att tgc ttt ccc gtc     336
Ser Ser Asp Pro Met Ala Arg Phe Leu His Ala Ile Cys Phe Pro Val
            100                 105                 110
```

```
gac gtt aaa cct aac gga ccg ctt ttc ttc tgg gct caa gtc ttc tac    384
Asp Val Lys Pro Asn Gly Pro Leu Phe Phe Trp Ala Gln Val Phe Tyr
        115                 120                 125 ctc tcg aag atc ctc gag ttc gga gac acg atc ctc atc ata ctc ggc    432
Leu Ser Lys Ile Leu Glu Phe Gly Asp Thr Ile Leu Ile Ile Leu Gly
130                 135                 140 aaa tca atc caa cgg cta tcc ttc ctc cac gtg tac cac cac gcg acg    480
Lys Ser Ile Gln Arg Leu Ser Phe Leu His Val Tyr His His Ala Thr
145                 150                 155                 160 gtt gtg gtc atg tgt tat ctc tgg ctc cga act cgc caa tcg atg ttt    528
Val Val Val Met Cys Tyr Leu Trp Leu Arg Thr Arg Gln Ser Met Phe
                165                 170                 175 ccg att gcg ctc gtg acg aat tcg acg gta cac gtc atc atg tac ggt    576
Pro Ile Ala Leu Val Thr Asn Ser Thr Val His Val Ile Met Tyr Gly
            180                 185                 190 tac tac ttc ctc tgc gcc gtt gga tcg agg ccc aag tgg aag aga ttg    624
Tyr Tyr Phe Leu Cys Ala Val Gly Ser Arg Pro Lys Trp Lys Arg Leu
        195                 200                 205 gtg acg gat tgt cag att gtt cag ttt gtt ttc agt ttc ggg tta tcc    672
Val Thr Asp Cys Gln Ile Val Gln Phe Val Phe Ser Phe Gly Leu Ser
210                 215                 220 ggt tgg atg ctc cga gag cac tta ttc ggg tcg ggt tgc acc ggg att    720
Gly Trp Met Leu Arg Glu His Leu Phe Gly Ser Gly Cys Thr Gly Ile
225                 230                 235                 240 tgg gga tgg tgt ttc aac gct gca ttt aat gct tct ctt ttg gct ctc    768
Trp Gly Trp Cys Phe Asn Ala Ala Phe Asn Ala Ser Leu Leu Ala Leu
                245                 250                 255 ttt tcc aac ttc cat tca aag aat tat gtc aag aag cca acg aga gag    816
Phe Ser Asn Phe His Ser Lys Asn Tyr Val Lys Lys Pro Thr Arg Glu
            260                 265                 270 gat ggc aaa aaa agc gat tag                                        837
Asp Gly Lys Lys Ser Asp
        275

<210> SEQ ID NO 137
<211> LENGTH: 278
<212> TYPE: PRT
<213> ORGANISM: Arabidopsis thaliana

<400> SEQUENCE: 137

Met Ala Ser Ile Tyr Ser Ser Leu Thr Tyr Trp Leu Val Asn His Pro
1               5                   10                  15

Tyr Ile Ser Asn Phe Thr Trp Ile Glu Gly Glu Thr Leu Gly Ser Thr
            20                  25                  30

Val Phe Phe Val Ser Val Val Ser Val Tyr Leu Ser Ala Thr Phe
        35                  40                  45

Leu Leu Arg Ser Ala Ile Asp Ser Leu Pro Ser Leu Ser Pro Arg Ile
    50                  55                  60

Leu Lys Pro Ile Thr Ala Val His Ser Leu Ile Leu Cys Leu Leu Ser
65                  70                  75                  80

Leu Val Met Ala Val Gly Cys Thr Leu Ser Ile Thr Ser Ser His Ala
                85                  90                  95

Ser Ser Asp Pro Met Ala Arg Phe Leu His Ala Ile Cys Phe Pro Val
            100                 105                 110

Asp Val Lys Pro Asn Gly Pro Leu Phe Phe Trp Ala Gln Val Phe Tyr
        115                 120                 125

Leu Ser Lys Ile Leu Glu Phe Gly Asp Thr Ile Leu Ile Ile Leu Gly
    130                 135                 140
```

```
Lys Ser Ile Gln Arg Leu Ser Phe Leu His Val Tyr His Ala Thr
145                 150                 155                 160

Val Val Val Met Cys Tyr Leu Trp Leu Arg Thr Arg Gln Ser Met Phe
                165                 170                 175

Pro Ile Ala Leu Val Thr Asn Ser Thr Val His Val Ile Met Tyr Gly
            180                 185                 190

Tyr Tyr Phe Leu Cys Ala Val Gly Ser Arg Pro Lys Trp Lys Arg Leu
        195                 200                 205

Val Thr Asp Cys Gln Ile Val Gln Phe Val Phe Ser Phe Gly Leu Ser
210                 215                 220

Gly Trp Met Leu Arg Glu His Leu Phe Gly Ser Gly Cys Thr Gly Ile
225                 230                 235                 240

Trp Gly Trp Cys Phe Asn Ala Ala Phe Asn Ala Ser Leu Leu Ala Leu
                245                 250                 255

Phe Ser Asn Phe His Ser Lys Asn Tyr Val Lys Lys Pro Thr Arg Glu
                260                 265                 270

Asp Gly Lys Lys Ser Asp
        275
```

<210> SEQ ID NO 138
<211> LENGTH: 1086
<212> TYPE: DNA
<213> ORGANISM: Phytophthora infestans
<220> FEATURE:
<221> NAME/KEY: CDS
<222> LOCATION: (1)..(1086)
<223> OTHER INFORMATION: omega-3-Desaturase

<400> SEQUENCE: 138

```
atg gcg acg aag gag gcg tat gtg ttc ccc act ctg acg gag atc aag        48
Met Ala Thr Lys Glu Ala Tyr Val Phe Pro Thr Leu Thr Glu Ile Lys
1               5                   10                  15 cgg tcg cta cct aaa gac tgt ttc gag gct tcg gtg cct ctg tcg ctc        96
Arg Ser Leu Pro Lys Asp Cys Phe Glu Ala Ser Val Pro Leu Ser Leu
            20                  25                  30 tac tac acc gtg cgt tgt ctg gtg atc gcg gtg gct cta acc ttc ggt       144
Tyr Tyr Thr Val Arg Cys Leu Val Ile Ala Val Ala Leu Thr Phe Gly
        35                  40                  45 ctc aac tac gct cgc gct ctg ccc gag gtc gag agc ttc tgg gct ctg       192
Leu Asn Tyr Ala Arg Ala Leu Pro Glu Val Glu Ser Phe Trp Ala Leu
    50                  55                  60 gac gcc gca ctc tgc acg ggc tac atc ttg ctg cag ggc atc gtg ttc       240
Asp Ala Ala Leu Cys Thr Gly Tyr Ile Leu Leu Gln Gly Ile Val Phe
65                  70                  75                  80 tgg ggc ttc ttc acg gtg ggc cac gat gcc ggc cac ggc gcc ttc tcg       288
Trp Gly Phe Phe Thr Val Gly His Asp Ala Gly His Gly Ala Phe Ser
                85                  90                  95 cgc tac cac ctg ctt aac ttc gtg gtg ggc act ttc atg cac tcg ctc       336
Arg Tyr His Leu Leu Asn Phe Val Val Gly Thr Phe Met His Ser Leu
            100                 105                 110 atc ctc acg ccc ttc gag tcg tgg aag ctc acg cac cgt cac cac cac       384
Ile Leu Thr Pro Phe Glu Ser Trp Lys Leu Thr His Arg His His His
        115                 120                 125 aag aac acg ggc aac att gac cgt gac gag gtc ttc tac ccg caa cgc       432
Lys Asn Thr Gly Asn Ile Asp Arg Asp Glu Val Phe Tyr Pro Gln Arg
    130                 135                 140 aag gcc gac gac cac ccg ctg tct cgc aac ctg att ctg gcg ctc ggg       480
Lys Ala Asp Asp His Pro Leu Ser Arg Asn Leu Ile Leu Ala Leu Gly
145                 150                 155                 160
```

-continued

```
gca gcg tgg ctc gcc tat ttg gtc gag ggc ttc cct cct cgt aag gtc      528
Ala Ala Trp Leu Ala Tyr Leu Val Glu Gly Phe Pro Pro Arg Lys Val
            165                 170                 175 aac cac ttc aac ccg ttc gag cct ctg ttc gtg cgt cag gtc tca gct      576
Asn His Phe Asn Pro Phe Glu Pro Leu Phe Val Arg Gln Val Ser Ala
            180                 185                 190 gtg gta atc tct ctt ctc gcc cac ttc ttc gtg gcc gga ctc tcc atc      624
Val Val Ile Ser Leu Leu Ala His Phe Phe Val Ala Gly Leu Ser Ile
            195                 200                 205 tat ctg agc ctc cag ctg ggc ctt aag acg atg gca atc tac tac tat      672
Tyr Leu Ser Leu Gln Leu Gly Leu Lys Thr Met Ala Ile Tyr Tyr Tyr
    210                 215                 220 gga cct gtt ttt gtg ttc ggc agc atg ctg gtc att acc acc ttc cta      720
Gly Pro Val Phe Val Phe Gly Ser Met Leu Val Ile Thr Thr Phe Leu
225                 230                 235                 240 cac cac aat gat gag gag acc cca tgg tac gcc gac tcg gag tgg acg      768
His His Asn Asp Glu Glu Thr Pro Trp Tyr Ala Asp Ser Glu Trp Thr
                245                 250                 255 tac gtc aag ggc aac ctc tcg tcc gtg gac cga tcg tac ggc gcg ctc      816
Tyr Val Lys Gly Asn Leu Ser Ser Val Asp Arg Ser Tyr Gly Ala Leu
            260                 265                 270 att gac aac ctg agc cac aac atc ggc acg cac cag atc cac cac ctt      864
Ile Asp Asn Leu Ser His Asn Ile Gly Thr His Gln Ile His His Leu
    275                 280                 285 ttc cct atc att ccg cac tac aaa ctc aag aaa gcc act gcg gcc ttc      912
Phe Pro Ile Ile Pro His Tyr Lys Leu Lys Lys Ala Thr Ala Ala Phe
290                 295                 300 cac cag gct ttc cct gag ctc gtg cgc aag agc gac gag cca att atc      960
His Gln Ala Phe Pro Glu Leu Val Arg Lys Ser Asp Glu Pro Ile Ile
305                 310                 315                 320 aag gct ttc ttc cgg gtt gga cgt ctc tac gca aac tac ggc gtt gtg     1008
Lys Ala Phe Phe Arg Val Gly Arg Leu Tyr Ala Asn Tyr Gly Val Val
                325                 330                 335 gac cag gag gcg aag ctc ttc acg cta aag gaa gcc aag gcg gcg acc     1056
Asp Gln Glu Ala Lys Leu Phe Thr Leu Lys Glu Ala Lys Ala Ala Thr
            340                 345                 350 gag gcg gcg gcc aag acc aag tcc acg taa                             1086
Glu Ala Ala Ala Lys Thr Lys Ser Thr
            355                 360

<210> SEQ ID NO 139
<211> LENGTH: 361
<212> TYPE: PRT
<213> ORGANISM: Phytophthora infestans

<400> SEQUENCE: 139

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95
```

```
Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
            355                 360

<210> SEQ ID NO 140
<211> LENGTH: 1257
<212> TYPE: DNA
<213> ORGANISM: Thalassiosira pseudonana
<220> FEATURE:
<221> NAME/KEY: CDS
<222> LOCATION: (1)..(1257)
<223> OTHER INFORMATION: omega-3-Desaturase

<400> SEQUENCE: 140 atg tac aga tta aca tcc acc ttc ctc atc gca ttg gca ttc tcc tcc       48
Met Tyr Arg Leu Thr Ser Thr Phe Leu Ile Ala Leu Ala Phe Ser Ser
1               5                   10                  15 tcc atc aat gcc ttc tct cca caa cgg cca cca cgt act atc acc aaa       96
Ser Ile Asn Ala Phe Ser Pro Gln Arg Pro Pro Arg Thr Ile Thr Lys
            20                  25                  30 agt aaa gtc caa agc acc gtg cta ccc ata ccg acc aag gat gat ctg      144
Ser Lys Val Gln Ser Thr Val Leu Pro Ile Pro Thr Lys Asp Asp Leu
        35                  40                  45 aac ttt ctc caa cca caa ctc gat gag aat gat ctc tac ctc gac gat      192
Asn Phe Leu Gln Pro Gln Leu Asp Glu Asn Asp Leu Tyr Leu Asp Asp
    50                  55                  60
```

-continued

```
gtc aac act cca cca aga gca ggt acc atc atg aag atg ttg ccg aag    240
Val Asn Thr Pro Pro Arg Ala Gly Thr Ile Met Lys Met Leu Pro Lys
 65              70                  75                  80 gaa acg ttc aac att gat aca gca act tca ttg ggt tac ttt ggt atg    288
Glu Thr Phe Asn Ile Asp Thr Ala Thr Ser Leu Gly Tyr Phe Gly Met
                 85                  90                  95 gat atg gca gcg gtt gta tcg tcc atg acg ttg cta aat gct att gta    336
Asp Met Ala Ala Val Val Ser Ser Met Thr Leu Leu Asn Ala Ile Val
            100                 105                 110 act tcg gat cag tac cat gct ctt cca ctt cct ctc caa gca gca aca    384
Thr Ser Asp Gln Tyr His Ala Leu Pro Leu Pro Leu Gln Ala Ala Thr
        115                 120                 125 gtg att ccc ttt cag cta ttg gct ggg ttc gcc atg tgg tgt atg tgg    432
Val Ile Pro Phe Gln Leu Leu Ala Gly Phe Ala Met Trp Cys Met Trp
    130                 135                 140 tgc att gga cac gat gct gga cat tct act gtt tcg aag aca aag tgg    480
Cys Ile Gly His Asp Ala Gly His Ser Thr Val Ser Lys Thr Lys Trp
145                 150                 155                 160 atc aac cga gtc gtt ggt gaa gtg gct cat tct gtt gtt tgt ctc acg    528
Ile Asn Arg Val Val Gly Glu Val Ala His Ser Val Val Cys Leu Thr
                165                 170                 175 ccg ttc gtg cct tgg cag atg tcg cat agg aaa cac cat ttg aat cac    576
Pro Phe Val Pro Trp Gln Met Ser His Arg Lys His His Leu Asn His
            180                 185                 190 aat cat att gaa aag gac tac tct cat aag tgg tac agt cgc gac gag    624
Asn His Ile Glu Lys Asp Tyr Ser His Lys Trp Tyr Ser Arg Asp Glu
        195                 200                 205 ttt gat gat atc cca caa ctc tat aag aca ttt ggc tac aac cca aga    672
Phe Asp Asp Ile Pro Gln Leu Tyr Lys Thr Phe Gly Tyr Asn Pro Arg
    210                 215                 220 atg atg caa ctt cca ttc ctc tac ttc atg tat ctt gca ttg gga att    720
Met Met Gln Leu Pro Phe Leu Tyr Phe Met Tyr Leu Ala Leu Gly Ile
225                 230                 235                 240 cca gat ggt ggg cat gtt gtg ttc tac gga aga atg tgg gaa gga gtg    768
Pro Asp Gly Gly His Val Val Phe Tyr Gly Arg Met Trp Glu Gly Val
                245                 250                 255 tca ttg cag aag aag ttt gat gct gct att tct gtg gcc gta tca tgt    816
Ser Leu Gln Lys Lys Phe Asp Ala Ala Ile Ser Val Ala Val Ser Cys
            260                 265                 270 gca act gct gga tcg ctt tgg atg aat atg ggt aca gca gac ttc acg    864
Ala Thr Ala Gly Ser Leu Trp Met Asn Met Gly Thr Ala Asp Phe Thr
        275                 280                 285 gtg gta tgc atg gtt cct tgg cta gtt cta tcg tgg tgg ctc ttc atg    912
Val Val Cys Met Val Pro Trp Leu Val Leu Ser Trp Trp Leu Phe Met
    290                 295                 300 gta aca tac ctt cag cat cat tca gaa gac gga aag cta tac act gat    960
Val Thr Tyr Leu Gln His His Ser Glu Asp Gly Lys Leu Tyr Thr Asp
305                 310                 315                 320 gaa acg ttt aca ttt gaa aag gga gcc ttc gag acc gtg gat cgt tcg   1008
Glu Thr Phe Thr Phe Glu Lys Gly Ala Phe Glu Thr Val Asp Arg Ser
                325                 330                 335 tac ggc aag ttg atc aac cga atg tcg cat cac atg atg gac ggt cac   1056
Tyr Gly Lys Leu Ile Asn Arg Met Ser His His Met Met Asp Gly His
            340                 345                 350 gtg gtg cac cac ttg ttc ttt gaa cgt gta cct cac tac aga tta gag   1104
Val Val His His Leu Phe Phe Glu Arg Val Pro His Tyr Arg Leu Glu
        355                 360                 365 gca gct acc gaa gct ctt gtg aaa gga atg gat gaa acg gga cag aaa   1152
Ala Ala Thr Glu Ala Leu Val Lys Gly Met Asp Glu Thr Gly Gln Lys
    370                 375                 380
```

```
cat ttg tac aaa tac att gat act cct gat ttc aat gcc gag att gtc        1200
His Leu Tyr Lys Tyr Ile Asp Thr Pro Asp Phe Asn Ala Glu Ile Val
385                 390                 395                 400 aac gga ttt cgc gac aat tgg ttc ctt gtt gaa gag gag aac atc aaa        1248
Asn Gly Phe Arg Asp Asn Trp Phe Leu Val Glu Glu Glu Asn Ile Lys
                405                 410                 415 agg gag tag                                                            1257
Arg Glu
```

<210> SEQ ID NO 141
<211> LENGTH: 418
<212> TYPE: PRT
<213> ORGANISM: Thalassiosira pseudonana

<400> SEQUENCE: 141

```
Met Tyr Arg Leu Thr Ser Thr Phe Leu Ile Ala Leu Ala Phe Ser Ser
1               5                   10                  15

Ser Ile Asn Ala Phe Ser Pro Gln Arg Pro Pro Arg Thr Ile Thr Lys
                20                  25                  30

Ser Lys Val Gln Ser Thr Val Leu Pro Ile Pro Thr Lys Asp Asp Leu
            35                  40                  45

Asn Phe Leu Gln Pro Gln Leu Asp Glu Asn Asp Leu Tyr Leu Asp Asp
        50                  55                  60

Val Asn Thr Pro Pro Arg Ala Gly Thr Ile Met Lys Met Leu Pro Lys
65                  70                  75                  80

Glu Thr Phe Asn Ile Asp Thr Ala Thr Ser Leu Gly Tyr Phe Gly Met
                85                  90                  95

Asp Met Ala Ala Val Val Ser Ser Met Thr Leu Leu Asn Ala Ile Val
            100                 105                 110

Thr Ser Asp Gln Tyr His Ala Leu Pro Leu Pro Leu Gln Ala Ala Thr
        115                 120                 125

Val Ile Pro Phe Gln Leu Leu Ala Gly Phe Ala Met Trp Cys Met Trp
130                 135                 140

Cys Ile Gly His Asp Ala Gly His Ser Thr Val Ser Lys Thr Lys Trp
145                 150                 155                 160

Ile Asn Arg Val Val Gly Glu Val Ala His Ser Val Val Cys Leu Thr
                165                 170                 175

Pro Phe Val Pro Trp Gln Met Ser His Arg Lys His His Leu Asn His
            180                 185                 190

Asn His Ile Glu Lys Asp Tyr Ser His Lys Trp Tyr Ser Arg Asp Glu
        195                 200                 205

Phe Asp Asp Ile Pro Gln Leu Tyr Lys Thr Phe Gly Tyr Asn Pro Arg
    210                 215                 220

Met Met Gln Leu Pro Phe Leu Tyr Phe Met Tyr Leu Ala Leu Gly Ile
225                 230                 235                 240

Pro Asp Gly Gly His Val Val Phe Tyr Gly Arg Met Trp Glu Gly Val
                245                 250                 255

Ser Leu Gln Lys Lys Phe Asp Ala Ala Ile Ser Val Ala Val Ser Cys
            260                 265                 270

Ala Thr Ala Gly Ser Leu Trp Met Asn Met Gly Thr Ala Asp Phe Thr
        275                 280                 285

Val Val Cys Met Val Pro Trp Leu Val Leu Ser Trp Trp Leu Phe Met
    290                 295                 300

Val Thr Tyr Leu Gln His His Ser Glu Asp Gly Lys Leu Tyr Thr Asp
305                 310                 315                 320
```

```
Glu Thr Phe Thr Phe Glu Lys Gly Ala Phe Glu Thr Val Asp Arg Ser
            325                 330                 335
Tyr Gly Lys Leu Ile Asn Arg Met Ser His His Met Met Asp Gly His
        340                 345                 350
Val Val His His Leu Phe Phe Glu Arg Val Pro His Tyr Arg Leu Glu
        355                 360                 365
Ala Ala Thr Glu Ala Leu Val Lys Gly Met Asp Glu Thr Gly Gln Lys
        370                 375                 380
His Leu Tyr Lys Tyr Ile Asp Thr Pro Asp Phe Asn Ala Glu Ile Val
385                 390                 395                 400
Asn Gly Phe Arg Asp Asn Trp Phe Leu Val Glu Glu Asn Ile Lys
                405                 410                 415
Arg Glu

<210> SEQ ID NO 142
<211> LENGTH: 1086
<212> TYPE: DNA
<213> ORGANISM: Ostreococcus tauri
<220> FEATURE:
<221> NAME/KEY: CDS
<222> LOCATION: (1)..(1086)
<223> OTHER INFORMATION: delta-12-Desaturase

<400> SEQUENCE: 142
```

| | | | | | | | | | | | | | | | | |
|---|---|---|---|---|---|---|---|---|---|---|---|---|---|---|---|---|
| atg | cag | gag | ggg | gtg | cga | aac | att | ccg | aac | gag | tgc | ttt | gag | acg | gga | 48 |
| Met | Gln | Glu | Gly | Val | Arg | Asn | Ile | Pro | Asn | Glu | Cys | Phe | Glu | Thr | Gly | |
| 1 | | | | 5 | | | | 10 | | | | 15 | | | | |
| cat | ctt | gaa | aga | ccc | tgg | cgt | tcc | ggc | cgg | tgt | ggg | cgc | gat | ccc | ggt | 96 |
| His | Leu | Glu | Arg | Pro | Trp | Arg | Ser | Gly | Arg | Cys | Gly | Arg | Asp | Pro | Gly | |
| | | 20 | | | | 25 | | | | 30 | | | | | | |
| tcg | aat | tgg | ggc | gct | ggc | ttc | cgc | ttt | ttt | tcg | ctc | aag | ggg | ttt | tgg | 144 |
| Ser | Asn | Trp | Gly | Ala | Gly | Phe | Arg | Phe | Phe | Ser | Leu | Lys | Gly | Phe | Trp | |
| | | 35 | | | | 40 | | | | 45 | | | | | | |
| tgg | ccg | gcg | tgg | tgg | gcg | tac | gcg | ttc | gtg | acg | ggg | acg | gcg | gcc | act | 192 |
| Trp | Pro | Ala | Trp | Trp | Ala | Tyr | Ala | Phe | Val | Thr | Gly | Thr | Ala | Ala | Thr | |
| | 50 | | | | 55 | | | | 60 | | | | | | | |
| ggg | tgt | tgg | gtc | gcc | gcg | cac | gag | tgc | ggg | cac | ggc | gcg | ttc | agc | gat | 240 |
| Gly | Cys | Trp | Val | Ala | Ala | His | Glu | Cys | Gly | His | Gly | Ala | Phe | Ser | Asp | |
| 65 | | | | 70 | | | | 75 | | | | 80 | | | | |
| aac | aag | acg | ttg | caa | gat | gcg | gtt | gga | tac | gtg | ttg | cac | tcg | ttg | ctc | 288 |
| Asn | Lys | Thr | Leu | Gln | Asp | Ala | Val | Gly | Tyr | Val | Leu | His | Ser | Leu | Leu | |
| | | | 85 | | | | 90 | | | | 95 | | | | | |
| ttg | gtg | ccg | tac | ttt | tct | tgg | cag | cga | tca | cac | gcg | gtg | cat | cac | tcg | 336 |
| Leu | Val | Pro | Tyr | Phe | Ser | Trp | Gln | Arg | Ser | His | Ala | Val | His | His | Ser | |
| | | | 100 | | | | 105 | | | | 110 | | | | | |
| agg | acg | aat | cac | gtt | ctt | gag | ggc | gag | acg | cac | gtg | ccg | gcg | cgc | ttg | 384 |
| Arg | Thr | Asn | His | Val | Leu | Glu | Gly | Glu | Thr | His | Val | Pro | Ala | Arg | Leu | |
| | | 115 | | | | 120 | | | | 125 | | | | | | |
| ggg | acg | gaa | gac | gcc | aac | gtc | gtg | ttc | aag | ctt | cgc | gaa | ttg | atc | ggt | 432 |
| Gly | Thr | Glu | Asp | Ala | Asn | Val | Val | Phe | Lys | Leu | Arg | Glu | Leu | Ile | Gly | |
| | 130 | | | | 135 | | | | 140 | | | | | | | |
| gaa | ggg | ccg | ttc | acg | ttt | ttc | aac | ctc | gtc | ggc | gtc | ttc | gcg | ctc | gga | 480 |
| Glu | Gly | Pro | Phe | Thr | Phe | Phe | Asn | Leu | Val | Gly | Val | Phe | Ala | Leu | Gly | |
| 145 | | | | 150 | | | | 155 | | | | 160 | | | | |
| tgg | ccg | att | tac | ttg | ctc | acc | ggc | gcg | agc | gga | ccg | gtg | cgc | ggt | | 528 |
| Trp | Pro | Ile | Tyr | Leu | Leu | Thr | Gly | Ala | Ser | Gly | Gly | Pro | Val | Arg | Gly | |
| | | | 165 | | | | 170 | | | | 175 | | | | | |
| aac | acg | aac | cac | ttc | tta | ccc | ttc | atg | ggc | gag | aaa | ggt | aag | cac | gcg | 576 |
| Asn | Thr | Asn | His | Phe | Leu | Pro | Phe | Met | Gly | Glu | Lys | Gly | Lys | His | Ala | |

-continued

```
                180                 185                 190
ctg ttc ccg ggt aag tgg gcg aag aag gtg tgg cag tct gac atc ggc    624
Leu Phe Pro Gly Lys Trp Ala Lys Lys Val Trp Gln Ser Asp Ile Gly
        195                 200                 205 gtt gtt gcc gtc ctg ggc gcg ctc gcg gct tgg gcg gcg cac agc ggg    672
Val Val Ala Val Leu Gly Ala Leu Ala Ala Trp Ala Ala His Ser Gly
    210                 215                 220 att gcc aca gtg atg gca ctc tac gtc ggc ccg tac atg gtg acc aac    720
Ile Ala Thr Val Met Ala Leu Tyr Val Gly Pro Tyr Met Val Thr Asn
225                 230                 235                 240 ttt tgg ctc gtc ttg tac acg tgg tta cag cac acc gac gtt gac gtg    768
Phe Trp Leu Val Leu Tyr Thr Trp Leu Gln His Thr Asp Val Asp Val
                245                 250                 255 ccg cac ttc gag ggc gac gat tgg aac ttg gtc aag ggg gca ttc atg    816
Pro His Phe Glu Gly Asp Asp Trp Asn Leu Val Lys Gly Ala Phe Met
            260                 265                 270 acg atc gat cgc ccg tac ggc cca gtt ttt gat ttc ttg cac cac cgc    864
Thr Ile Asp Arg Pro Tyr Gly Pro Val Phe Asp Phe Leu His His Arg
        275                 280                 285 atc ggc agc acg cac gtc gcg cac cac atc aac aca cca ttc ccg cat    912
Ile Gly Ser Thr His Val Ala His His Ile Asn Thr Pro Phe Pro His
    290                 295                 300 tac aag gct caa atg gcg acg gat gcg cta aag gag gcg tat ccc gac    960
Tyr Lys Ala Gln Met Ala Thr Asp Ala Leu Lys Glu Ala Tyr Pro Asp
305                 310                 315                 320 ctc tac ctt tac gat cca act ccg atc gcg acc gct acg tgg cgc gtg    1008
Leu Tyr Leu Tyr Asp Pro Thr Pro Ile Ala Thr Ala Thr Trp Arg Val
                325                 330                 335 ggg agc aag tgc atc gcc gtc gtg aag aag gga gac gaa tgg gtg ttc    1056
Gly Ser Lys Cys Ile Ala Val Val Lys Lys Gly Asp Glu Trp Val Phe
            340                 345                 350 acg gat aag caa ctc ccg gtc gcg gcg tga                            1086
Thr Asp Lys Gln Leu Pro Val Ala Ala
        355                 360

<210> SEQ ID NO 143
<211> LENGTH: 361
<212> TYPE: PRT
<213> ORGANISM: Ostreococcus tauri

<400> SEQUENCE: 143

Met Gln Glu Gly Val Arg Asn Ile Pro Asn Glu Cys Phe Glu Thr Gly
1               5                   10                  15

His Leu Glu Arg Pro Trp Arg Ser Arg Cys Gly Arg Asp Pro Gly
            20                  25                  30

Ser Asn Trp Gly Ala Gly Phe Arg Phe Ser Leu Lys Gly Phe Trp
        35                  40                  45

Trp Pro Ala Trp Trp Ala Tyr Ala Phe Val Thr Gly Thr Ala Ala Thr
    50                  55                  60

Gly Cys Trp Val Ala Ala His Glu Cys Gly His Gly Ala Phe Ser Asp
65                  70                  75                  80

Asn Lys Thr Leu Gln Asp Ala Val Gly Tyr Val Leu His Ser Leu Leu
                85                  90                  95

Leu Val Pro Tyr Phe Ser Trp Gln Arg Ser His Ala Val His His Ser
            100                 105                 110

Arg Thr Asn His Val Leu Glu Gly Glu Thr His Val Pro Ala Arg Leu
        115                 120                 125

Gly Thr Glu Asp Ala Asn Val Val Phe Lys Leu Arg Glu Leu Ile Gly
```

-continued

```
             130                 135                 140
Glu Gly Pro Phe Thr Phe Asn Leu Val Gly Val Phe Ala Leu Gly
145                 150                 155                 160

Trp Pro Ile Tyr Leu Leu Thr Gly Ala Ser Gly Gly Pro Val Arg Gly
                165                 170                 175

Asn Thr Asn His Phe Leu Pro Phe Met Gly Glu Lys Gly Lys His Ala
            180                 185                 190

Leu Phe Pro Gly Lys Trp Ala Lys Val Trp Gln Ser Asp Ile Gly
        195                 200                 205

Val Val Ala Val Leu Gly Ala Leu Ala Ala Trp Ala Ala His Ser Gly
210                 215                 220

Ile Ala Thr Val Met Ala Leu Tyr Val Gly Pro Tyr Met Val Thr Asn
225                 230                 235                 240

Phe Trp Leu Val Leu Tyr Thr Trp Leu Gln His Thr Asp Val Asp Val
                245                 250                 255

Pro His Phe Glu Gly Asp Asp Trp Asn Leu Val Lys Gly Ala Phe Met
            260                 265                 270

Thr Ile Asp Arg Pro Tyr Gly Pro Val Phe Asp Phe Leu His His Arg
        275                 280                 285

Ile Gly Ser Thr His Val Ala His His Ile Asn Thr Pro Phe Pro His
        290                 295                 300

Tyr Lys Ala Gln Met Ala Thr Asp Ala Leu Lys Glu Ala Tyr Pro Asp
305                 310                 315                 320

Leu Tyr Leu Tyr Asp Pro Thr Pro Ile Ala Thr Ala Thr Trp Arg Val
                325                 330                 335

Gly Ser Lys Cys Ile Ala Val Val Lys Lys Gly Asp Glu Trp Val Phe
            340                 345                 350

Thr Asp Lys Gln Leu Pro Val Ala Ala
        355                 360

<210> SEQ ID NO 144
<211> LENGTH: 1305
<212> TYPE: DNA
<213> ORGANISM: Thalassiosira pseudonana
<220> FEATURE:
<221> NAME/KEY: CDS
<222> LOCATION: (1)..(1305)
<223> OTHER INFORMATION: delta-12-Desaturase

<400> SEQUENCE: 144 atg gga aag gga gga aga tca gta acc cgc gct caa aca gca gaa aag      48
Met Gly Lys Gly Gly Arg Ser Val Thr Arg Ala Gln Thr Ala Glu Lys
1               5                   10                  15 tca gca cac acc atc caa acc ttc acc gac ggc cga tgg gtc tcc ccc      96
Ser Ala His Thr Ile Gln Thr Phe Thr Asp Gly Arg Trp Val Ser Pro
            20                  25                  30 tac aac ccc ctc gca aaa gat gca cct gaa ctc ccc tcc aag ggt gaa     144
Tyr Asn Pro Leu Ala Lys Asp Ala Pro Glu Leu Pro Ser Lys Gly Glu
        35                  40                  45 atc aag gcg gtc atc ccc aaa gag tgc ttc gaa cga agc tac ctc cac     192
Ile Lys Ala Val Ile Pro Lys Glu Cys Phe Glu Arg Ser Tyr Leu His
    50                  55                  60 tcc atg tac ttc gtc ctc cgt gac acc gtc atg gcc gtg gcc tgc gcc     240
Ser Met Tyr Phe Val Leu Arg Asp Thr Val Met Ala Val Ala Cys Ala
65                  70                  75                  80 tac atc gcc cac tca acg ctc tcc acc gat att ccc tcc gag tta ctg     288
Tyr Ile Ala His Ser Thr Leu Ser Thr Asp Ile Pro Ser Glu Leu Leu
                85                  90                  95
```

-continued

```
agc gtg gac gca ctc aaa tgg ttc ctc gga tgg aac acc tac gcc ttt        336
Ser Val Asp Ala Leu Lys Trp Phe Leu Gly Trp Asn Thr Tyr Ala Phe
            100                 105                 110 tgg atg ggg tgc att ctc acc gga cac tgg gtc cta gcc cat gaa tgt        384
Trp Met Gly Cys Ile Leu Thr Gly His Trp Val Leu Ala His Glu Cys
        115                 120                 125 gga cat ggt gca ttc tct ccc tct cag acg ttt aat gac ttt tgg ggg        432
Gly His Gly Ala Phe Ser Pro Ser Gln Thr Phe Asn Asp Phe Trp Gly
    130                 135                 140 ttc att atg cat cag gcg gtg ttg gtt ccg tat ttc gcc tgg cag tac        480
Phe Ile Met His Gln Ala Val Leu Val Pro Tyr Phe Ala Trp Gln Tyr
145                 150                 155                 160 tct cat gcg aag cat cat cga cgt acc aac aac att atg gat ggg gag        528
Ser His Ala Lys His His Arg Arg Thr Asn Asn Ile Met Asp Gly Glu
                165                 170                 175 agc cat gtg ccc aat atc gcc aag gaa atg gga ttg aac gag aag aat        576
Ser His Val Pro Asn Ile Ala Lys Glu Met Gly Leu Asn Glu Lys Asn
            180                 185                 190 gag cgc agt gga gga tat gcc gcc att cat gag gct att gga gat gga        624
Glu Arg Ser Gly Gly Tyr Ala Ala Ile His Glu Ala Ile Gly Asp Gly
        195                 200                 205 ccc ttt gcg atg ttt caa atc ttt gct cac ttg gtg atc ggg tgg cct        672
Pro Phe Ala Met Phe Gln Ile Phe Ala His Leu Val Ile Gly Trp Pro
    210                 215                 220 att tac ttg atg gga ttt gct tcc act gga cgt ctc ggt cag gat ggg        720
Ile Tyr Leu Met Gly Phe Ala Ser Thr Gly Arg Leu Gly Gln Asp Gly
225                 230                 235                 240 aag gaa ctt cag gct gga gag atc atc gac cat tac cgt cct tgg agt        768
Lys Glu Leu Gln Ala Gly Glu Ile Ile Asp His Tyr Arg Pro Trp Ser
                245                 250                 255 aag atg ttc ccc acc aag ttg cga ttc aaa att gct ctt tcg aca ctt        816
Lys Met Phe Pro Thr Lys Leu Arg Phe Lys Ile Ala Leu Ser Thr Leu
            260                 265                 270 gga gtg att gcc gcc tgg gtt ggg ttg tac ttt gct gca caa gag tat        864
Gly Val Ile Ala Ala Trp Val Gly Leu Tyr Phe Ala Ala Gln Glu Tyr
        275                 280                 285 gga gtc ttg ccc gtg gtt ctt tgg tac att ggc cca ctc atg tgg aat        912
Gly Val Leu Pro Val Val Leu Trp Tyr Ile Gly Pro Leu Met Trp Asn
    290                 295                 300 cag gcg tgg ctt gtg ctc tac act tgg ctt cag cac aat gat ccc tcc        960
Gln Ala Trp Leu Val Leu Tyr Thr Trp Leu Gln His Asn Asp Pro Ser
305                 310                 315                 320 gtg cct caa tat gga agt gac gaa tgg aca tgg gtc aag gga gct ttg       1008
Val Pro Gln Tyr Gly Ser Asp Glu Trp Thr Trp Val Lys Gly Ala Leu
                325                 330                 335 tcg acg att gat cgc ccg tat ggt atc ttt gac ttc ttc cat cac aag       1056
Ser Thr Ile Asp Arg Pro Tyr Gly Ile Phe Asp Phe Phe His His Lys
            340                 345                 350 att gga agc act cac gta gct cat cat ttg ttc cac gag atg cca ttt       1104
Ile Gly Ser Thr His Val Ala His His Leu Phe His Glu Met Pro Phe
        355                 360                 365 tac aag gcg gat gtg gct act gcg tcg atc aag ggt ttc ttg gag ccg       1152
Tyr Lys Ala Asp Val Ala Thr Ala Ser Ile Lys Gly Phe Leu Glu Pro
    370                 375                 380 aag gga ctt tac aac tat gat cca acg cct tgg tat gtg gcc atg tgg       1200
Lys Gly Leu Tyr Asn Tyr Asp Pro Thr Pro Trp Tyr Val Ala Met Trp
385                 390                 395                 400 agg gtg gcc aag act tgt cat tat att gag gat gtg gat gga gtt cag       1248
Arg Val Ala Lys Thr Cys His Tyr Ile Glu Asp Val Asp Gly Val Gln
```

```
                    405                 410                 415
tat tat aag agt ttg gag gat gtg cct ttg aag aag gat gcc aag aag     1296
Tyr Tyr Lys Ser Leu Glu Asp Val Pro Leu Lys Lys Asp Ala Lys Lys
            420                 425                 430 tct gat tag                                                         1305
Ser Asp
```

<210> SEQ ID NO 145
<211> LENGTH: 434
<212> TYPE: PRT
<213> ORGANISM: Thalassiosira pseudonana

<400> SEQUENCE: 145

```
Met Gly Lys Gly Gly Arg Ser Val Thr Arg Ala Gln Thr Ala Glu Lys
1               5                   10                  15

Ser Ala His Thr Ile Gln Thr Phe Thr Asp Gly Arg Trp Val Ser Pro
            20                  25                  30

Tyr Asn Pro Leu Ala Lys Asp Ala Pro Glu Leu Pro Ser Lys Gly Glu
        35                  40                  45

Ile Lys Ala Val Ile Pro Lys Glu Cys Phe Glu Arg Ser Tyr Leu His
    50                  55                  60

Ser Met Tyr Phe Val Leu Arg Asp Thr Val Met Ala Val Ala Cys Ala
65                  70                  75                  80

Tyr Ile Ala His Ser Thr Leu Ser Thr Asp Ile Pro Ser Glu Leu Leu
                85                  90                  95

Ser Val Asp Ala Leu Lys Trp Phe Leu Gly Trp Asn Thr Tyr Ala Phe
            100                 105                 110

Trp Met Gly Cys Ile Leu Thr Gly His Trp Val Leu Ala His Glu Cys
        115                 120                 125

Gly His Gly Ala Phe Ser Pro Ser Gln Thr Phe Asn Asp Phe Trp Gly
    130                 135                 140

Phe Ile Met His Gln Ala Val Leu Val Pro Tyr Phe Ala Trp Gln Tyr
145                 150                 155                 160

Ser His Ala Lys His His Arg Arg Thr Asn Asn Ile Met Asp Gly Glu
                165                 170                 175

Ser His Val Pro Asn Ile Ala Lys Glu Met Gly Leu Asn Glu Lys Asn
            180                 185                 190

Glu Arg Ser Gly Gly Tyr Ala Ala Ile His Glu Ala Ile Gly Asp Gly
        195                 200                 205

Pro Phe Ala Met Phe Gln Ile Phe Ala His Leu Val Ile Gly Trp Pro
    210                 215                 220

Ile Tyr Leu Met Gly Phe Ala Ser Thr Gly Arg Leu Gly Gln Asp Gly
225                 230                 235                 240

Lys Glu Leu Gln Ala Gly Glu Ile Ile Asp His Tyr Arg Pro Trp Ser
                245                 250                 255

Lys Met Phe Pro Thr Lys Leu Arg Phe Lys Ile Ala Leu Ser Thr Leu
            260                 265                 270

Gly Val Ile Ala Ala Trp Val Gly Leu Tyr Phe Ala Ala Gln Glu Tyr
        275                 280                 285

Gly Val Leu Pro Val Val Leu Trp Tyr Ile Gly Pro Leu Met Trp Asn
    290                 295                 300

Gln Ala Trp Leu Val Leu Tyr Thr Trp Leu Gln His Asn Asp Pro Ser
305                 310                 315                 320

Val Pro Gln Tyr Gly Ser Asp Glu Trp Thr Trp Val Lys Gly Ala Leu
                325                 330                 335
```

```
Ser Thr Ile Asp Arg Pro Tyr Gly Ile Phe Asp Phe His His Lys
            340                 345                 350

Ile Gly Ser Thr His Val Ala His His Leu Phe His Glu Met Pro Phe
        355                 360                 365

Tyr Lys Ala Asp Val Ala Thr Ala Ser Ile Lys Gly Phe Leu Glu Pro
    370                 375                 380

Lys Gly Leu Tyr Asn Tyr Asp Pro Thr Pro Trp Tyr Val Ala Met Trp
385                 390                 395                 400

Arg Val Ala Lys Thr Cys His Tyr Ile Glu Asp Val Asp Gly Val Gln
                405                 410                 415

Tyr Tyr Lys Ser Leu Glu Asp Val Pro Leu Lys Lys Asp Ala Lys Lys
            420                 425                 430

Ser Asp

<210> SEQ ID NO 146
<211> LENGTH: 806
<212> TYPE: PRT
<213> ORGANISM: Homo sapiens

<400> SEQUENCE: 146

Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Glu Gly Gln Leu Ile Leu Phe Gln
        35                  40                  45

Asn Thr Pro Asn Arg Thr Trp Asp Cys Val Leu Val Asn Pro Arg Asn
    50                  55                  60

Ser Gln Ser Gly Phe Arg Leu Phe Gln Leu Glu Leu Glu Ala Asp Ala
65              70                  75                  80

Leu Val Asn Phe His Gln Tyr Ser Ser Gln Leu Leu Pro Phe Tyr Glu
                85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
        115                 120                 125

Leu Gly Ile Arg Glu Cys Phe His His Ser Arg Ile Ile Ser Cys Ala
    130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
        195                 200                 205

Ala Val Ala Gly Leu Asn Gln Val Asn Asn Gly Leu Thr Pro Leu
    210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
            260                 265                 270
```

```
Ser Met Asp Ser Ser Gln Ile His Ser Lys Asp Pro Arg Tyr Gly Ala
        275                 280                 285

Ser Pro Leu His Trp Ala Lys Asn Ala Glu Met Ala Arg Met Leu Leu
        290                 295                 300

Lys Arg Gly Cys Asn Val Asn Ser Thr Ser Ser Ala Gly Asn Thr Ala
305                 310                 315                 320

Leu His Val Ala Val Met Arg Asn Arg Phe Asp Cys Ala Ile Val Leu
                325                 330                 335

Leu Thr His Gly Ala Asn Ala Asp Ala Arg Gly Glu His Gly Asn Thr
                340                 345                 350

Pro Leu His Leu Ala Met Ser Lys Asp Asn Val Glu Met Ile Lys Ala
        355                 360                 365

Leu Ile Val Phe Gly Ala Glu Val Asp Thr Pro Asn Asp Phe Gly Glu
        370                 375                 380

Thr Pro Thr Phe Leu Ala Ser Lys Ile Gly Arg Leu Val Thr Arg Lys
385                 390                 395                 400

Ala Ile Leu Thr Leu Leu Arg Thr Val Gly Ala Glu Tyr Cys Phe Pro
                405                 410                 415

Pro Ile His Gly Val Pro Ala Glu Gln Gly Ser Ala Ala Pro His His
                420                 425                 430

Pro Phe Ser Leu Glu Arg Ala Gln Pro Pro Ile Ser Leu Asn Asn
        435                 440                 445

Leu Glu Leu Gln Asp Leu Met His Ile Ser Arg Ala Arg Lys Pro Ala
        450                 455                 460

Phe Ile Leu Gly Ser Met Arg Asp Glu Lys Arg Thr His Asp His Leu
465                 470                 475                 480

Leu Cys Leu Asp Gly Gly Val Lys Gly Leu Ile Ile Gln Leu
                485                 490                 495

Leu Ile Ala Ile Glu Lys Ala Ser Gly Val Ala Thr Lys Asp Leu Phe
                500                 505                 510

Asp Trp Val Ala Gly Thr Ser Thr Gly Gly Ile Leu Ala Leu Ala Ile
        515                 520                 525

Leu His Ser Lys Ser Met Ala Tyr Met Arg Gly Met Tyr Phe Arg Met
        530                 535                 540

Lys Asp Glu Val Phe Arg Gly Ser Arg Pro Tyr Glu Ser Gly Pro Leu
545                 550                 555                 560

Glu Glu Phe Leu Lys Arg Glu Phe Gly Glu His Thr Lys Met Thr Asp
                565                 570                 575

Val Arg Lys Pro Lys Val Met Leu Thr Gly Thr Leu Ser Asp Arg Gln
                580                 585                 590

Pro Ala Glu Leu His Leu Phe Arg Asn Tyr Asp Ala Pro Glu Thr Val
        595                 600                 605

Arg Glu Pro Arg Phe Asn Gln Asn Val Asn Leu Arg Pro Pro Ala Gln
        610                 615                 620

Pro Ser Asp Gln Leu Val Trp Arg Ala Ala Arg Ser Ser Gly Ala Ala
625                 630                 635                 640

Pro Thr Tyr Phe Arg Pro Asn Gly Arg Phe Leu Asp Gly Gly Leu Leu
                645                 650                 655

Ala Asn Asn Pro Thr Leu Asp Ala Met Thr Glu Ile His Glu Tyr Asn
                660                 665                 670

Gln Asp Leu Ile Arg Lys Gly Gln Ala Asn Lys Val Lys Lys Leu Ser
        675                 680                 685
```

```
Ile Val Val Ser Leu Gly Thr Gly Arg Ser Pro Gln Val Pro Val Thr
    690                 695                 700

Cys Val Asp Val Phe Arg Pro Ser Asn Pro Trp Glu Leu Ala Lys Thr
705                 710                 715                 720

Val Phe Gly Ala Lys Glu Leu Gly Lys Met Val Val Asp Cys Cys Thr
                725                 730                 735

Asp Pro Asp Gly Arg Ala Val Asp Arg Ala Arg Ala Trp Cys Glu Met
                740                 745                 750

Val Gly Ile Gln Tyr Phe Arg Leu Asn Pro Gln Leu Gly Thr Asp Ile
            755                 760                 765

Met Leu Asp Glu Val Ser Asp Thr Val Leu Val Asn Ala Leu Trp Glu
    770                 775                 780

Thr Glu Val Tyr Ile Tyr Glu His Arg Glu Glu Phe Gln Lys Leu Ile
785                 790                 795                 800

His Leu Leu Leu Ser Pro
                805

<210> SEQ ID NO 147
<211> LENGTH: 347
<212> TYPE: PRT
<213> ORGANISM: Saccharomyces cerevisiae

<400> SEQUENCE: 147

Met Thr Phe Met Gln Gln Leu Gln Glu Ala Gly Glu Arg Phe Arg Cys
1               5                   10                  15

Ile Asn Gly Leu Leu Trp Val Val Phe Gly Leu Gly Val Leu Lys Cys
            20                  25                  30

Thr Thr Leu Ser Leu Arg Phe Leu Ala Leu Ile Phe Asp Leu Phe Leu
        35                  40                  45

Leu Pro Ala Val Asn Phe Asp Lys Tyr Gly Ala Lys Thr Gly Lys Tyr
    50                  55                  60

Cys Ala Ile Thr Gly Ala Ser Asp Gly Ile Lys Glu Phe Ala Arg
65                  70                  75                  80

Gln Met Ala Lys Arg Gly Phe Asn Leu Val Leu Ile Ser Arg Thr Gln
                85                  90                  95

Ser Lys Leu Glu Ala Leu Gln Lys Glu Leu Glu Asp Gln His His Val
            100                 105                 110

Val Val Lys Ile Leu Ala Ile Asp Ile Ala Glu Asp Lys Glu Ser Asn
        115                 120                 125

Tyr Glu Ser Ile Lys Glu Leu Cys Ala Gln Leu Pro Ile Thr Val Leu
    130                 135                 140

Val Asn Asn Val Gly Gln Ser His Ser Ile Pro Val Pro Phe Leu Glu
145                 150                 155                 160

Thr Glu Glu Lys Glu Leu Arg Asn Ile Ile Thr Ile Asn Asn Thr Ala
                165                 170                 175

Thr Leu Leu Ile Thr Gln Ile Ile Ala Pro Lys Ile Val Glu Thr Val
            180                 185                 190

Lys Ala Glu Asn Lys Lys Ser Gly Thr Arg Gly Leu Ile Leu Thr Met
        195                 200                 205

Gly Ser Phe Gly Gly Leu Ile Pro Thr Pro Leu Leu Ala Thr Tyr Ser
    210                 215                 220

Gly Ser Lys Ser Phe Leu Gln Gly Trp Ser Asn Ser Leu Ala Gly Glu
225                 230                 235                 240

Leu Ser Lys Asp Ala Ile Asp Val Glu Leu Ile Ile Ser Tyr Leu Val
                245                 250                 255
```

```
Thr Ser Ser Met Ser Lys Ile Arg Arg Ser Ser Leu Met Ile Pro Asn
            260                 265                 270

Pro Gln Gln Phe Val Lys Ser Thr Leu Arg Ser Val Gly Arg Arg Cys
        275                 280                 285

Gly Ser Gln Glu Arg Tyr Ala Thr Met Thr Pro Tyr Trp Ala His Ala
        290                 295                 300

Val Tyr Gln Phe Val Ile Thr Glu Thr Phe Gly Val Tyr Ser Lys Ile
305                 310                 315                 320

Val Asn Ser Ile Asn Tyr Ser Phe His Lys Ser Ile Arg Ile Arg Ala
                325                 330                 335

Leu Lys Lys Ala Ala Arg Gln Val Lys Lys Glu
                340                 345

<210> SEQ ID NO 148
<211> LENGTH: 500
<212> TYPE: PRT
<213> ORGANISM: Saccharomyces cerevisiae

<400> SEQUENCE: 148

Met Leu Arg Asn Thr Leu Lys Cys Ala Gln Leu Ser Ser Lys Tyr Gly
1               5                   10                  15

Phe Lys Thr Thr Thr Arg Thr Phe Met Thr Thr Gln Pro Gln Leu Asn
            20                  25                  30

Val Thr Asp Ala Pro Pro Val Leu Phe Thr Val Gln Asp Thr Ala Arg
        35                  40                  45

Val Ile Thr Leu Asn Arg Pro Lys Lys Leu Asn Ala Leu Asn Ala Glu
    50                  55                  60

Met Ser Glu Ser Met Phe Lys Thr Leu Asn Glu Tyr Ala Lys Ser Asp
65                  70                  75                  80

Thr Thr Asn Leu Val Ile Leu Lys Ser Ser Asn Arg Pro Arg Ser Phe
                85                  90                  95

Cys Ala Gly Gly Asp Val Ala Thr Val Ala Ile Phe Asn Phe Asn Lys
            100                 105                 110

Glu Phe Ala Lys Ser Ile Lys Phe Phe Thr Asp Glu Tyr Ser Leu Asn
        115                 120                 125

Phe Gln Ile Ala Thr Tyr Leu Lys Pro Ile Val Thr Phe Met Asp Gly
    130                 135                 140

Ile Thr Met Gly Gly Gly Val Gly Leu Ser Ile His Thr Pro Phe Arg
145                 150                 155                 160

Ile Ala Thr Glu Asn Thr Lys Trp Ala Met Pro Glu Met Asp Ile Gly
                165                 170                 175

Phe Phe Pro Asp Val Gly Ser Thr Phe Ala Leu Pro Arg Ile Val Thr
            180                 185                 190

Leu Ala Asn Ser Asn Ser Gln Met Ala Leu Tyr Leu Cys Leu Thr Gly
        195                 200                 205

Glu Val Val Thr Gly Ala Asp Ala Tyr Met Leu Gly Leu Ala Ser His
    210                 215                 220

Tyr Val Ser Ser Glu Asn Leu Asp Ala Leu Gln Lys Arg Leu Gly Glu
225                 230                 235                 240

Ile Ser Pro Pro Phe Asn Asn Asp Pro Gln Ser Ala Tyr Phe Phe Gly
                245                 250                 255

Met Val Asn Glu Ser Ile Asp Glu Phe Val Ser Pro Leu Pro Lys Asp
            260                 265                 270

Tyr Val Phe Lys Tyr Ser Asn Glu Lys Leu Asn Val Ile Glu Ala Cys
```

-continued

```
                275                 280                 285
Phe Asn Leu Ser Lys Asn Gly Thr Ile Glu Asp Ile Met Asn Asn Leu
            290                 295                 300
Arg Gln Tyr Glu Gly Ser Ala Glu Gly Lys Ala Phe Ala Gln Glu Ile
305                 310                 315                 320
Lys Thr Lys Leu Leu Thr Lys Ser Pro Ser Ser Leu Gln Ile Ala Leu
                325                 330                 335
Arg Leu Val Gln Glu Asn Ser Arg Asp His Ile Glu Ser Ala Ile Lys
            340                 345                 350
Arg Asp Leu Tyr Thr Ala Ala Asn Met Cys Met Asn Gln Asp Ser Leu
        355                 360                 365
Val Glu Phe Ser Glu Ala Thr Lys His Lys Leu Ile Asp Lys Gln Arg
    370                 375                 380
Val Pro Tyr Pro Trp Thr Lys Lys Glu Gln Leu Phe Val Ser Gln Leu
385                 390                 395                 400
Thr Ser Ile Thr Ser Pro Lys Pro Ser Leu Pro Met Ser Leu Leu Arg
                405                 410                 415
Asn Thr Ser Asn Val Thr Trp Thr Gln Tyr Pro Tyr His Ser Lys Tyr
            420                 425                 430
Gln Leu Pro Thr Glu Gln Glu Ile Ala Ala Tyr Ile Glu Lys Arg Thr
        435                 440                 445
Asn Asp Asp Thr Gly Ala Lys Val Thr Glu Arg Glu Val Leu Asn His
    450                 455                 460
Phe Ala Asn Val Ile Pro Ser Arg Arg Gly Lys Leu Gly Ile Gln Ser
465                 470                 475                 480
Leu Cys Lys Ile Val Cys Glu Arg Lys Cys Glu Glu Val Asn Asp Gly
                485                 490                 495
Leu Arg Trp Lys
            500

<210> SEQ ID NO 149
<211> LENGTH: 6
<212> TYPE: PRT
<213> ORGANISM: Artificial sequence
<220> FEATURE:
<223> OTHER INFORMATION: Consensus sequence

<400> SEQUENCE: 149

Phe Cys Ala Gly Gly Asp
1               5

<210> SEQ ID NO 150
<211> LENGTH: 9
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 150

Phe Phe Xaa Xaa Glu Phe Xaa Leu Asn
1               5
```

```
-continued

<210> SEQ ID NO 151
<211> LENGTH: 7
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is any amino acid

<400> SEQUENCE: 151

Thr Xaa Phe Ala Met Pro Glu
1               5

<210> SEQ ID NO 152
<211> LENGTH: 7
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Thr or Ser
<220> FEATURE:
<221> NAME/KEY: MISC_FEATURE
<222> LOCATION: (7)..(7)
<223> OTHER INFORMATION: Xaa is Phe or Trp

<400> SEQUENCE: 152

Pro Asp Val Gly Xaa Xaa Xaa
1               5
```